US007820671B2

(12) United States Patent
Babine et al.

(10) Patent No.: US 7,820,671 B2
(45) Date of Patent: Oct. 26, 2010

(54) PEPTIDOMIMETIC PROTEASE INHIBITORS

(75) Inventors: Robert Edward Babine, Carlsbad, CA (US); Shu Hui Chen, Thousand Oaks, CA (US); Ivan Collado, Madrid (ES); Cristina Garcia-Paredes, Madrid (ES); John Irvin Glass, Germantown, MD (US); Deqi Guo, Carmel, IN (US); Ling Jin, Indianapolis, IN (US); Jason Eric Lamar, Indianapolis, IN (US); Raymond Samuel Parker, III, Doylestown, PA (US); Nancy June Snyder, Lizton, IN (US); Xicheng David Sun, Broomfied, CO (US); Mark Joseph Tebbe, Zionsville, IN (US); Frantz Victor, Indianapolis, IN (US); Q. May Wang, Indianapolis, IN (US); Yvonne Yee Mai Yip, Indianapolis, IN (US); Robert B. Perni, Marlborough, MA (US); Luc Farmer, Foxborough, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1274 days.

(21) Appl. No.: 10/344,112

(22) PCT Filed: Aug. 31, 2001

(86) PCT No.: PCT/US01/26008

§ 371 (c)(1),
(2), (4) Date: Dec. 17, 2004

(87) PCT Pub. No.: WO02/18369

PCT Pub. Date: Mar. 7, 2002

(65) Prior Publication Data

US 2005/0197299 A1   Sep. 8, 2005

Related U.S. Application Data

(60) Provisional application No. 60/229,398, filed on Aug. 31, 2000, provisional application No. 60/277,641, filed on Mar. 21, 2001.

(51) Int. Cl.
*A61K 31/497* (2006.01)
*C07D 241/02* (2006.01)
(52) U.S. Cl. ..................... 514/252.1; 544/406
(58) Field of Classification Search ............ None
See application file for complete search history.

(56) References Cited

U.S. PATENT DOCUMENTS

| 4,499,082 A | 2/1985 | Shenvi et al. |
| 4,720,484 A | 1/1988 | Vincent et al. |
| 4,880,780 A | 11/1989 | Trainor et al. |
| 5,053,519 A | 10/1991 | Teetz |
| 5,231,084 A | 7/1993 | Hock |
| 5,371,072 A | 12/1994 | Webb et al. |
| 5,384,410 A | 1/1995 | Kettner |
| 5,468,858 A | 11/1995 | Berlin et al. |
| 5,484,801 A | 1/1996 | Al-Razzak et al. |
| 5,496,927 A | 3/1996 | Kolb et al. |
| 5,502,061 A | 3/1996 | Hui et al. |
| 5,559,158 A | 9/1996 | Al-Razzak et al. |
| 5,610,193 A | 3/1997 | Al-Razzak et al. |
| 5,656,600 A | 8/1997 | Abelman et al. |
| 5,656,627 A | 8/1997 | Bemis et al. |
| 5,672,582 A | 9/1997 | Veber et al. |
| 5,716,929 A | 2/1998 | Bemis et al. |
| 5,725,878 A | 3/1998 | Al-Razzak et al. |
| 5,736,520 A | 4/1998 | Bey |
| 5,756,466 A | 5/1998 | Bemis et al. |

(Continued)

FOREIGN PATENT DOCUMENTS

DE          3211676         10/1983

(Continued)

OTHER PUBLICATIONS

Arasappan et al., Bioorg. Med. Chem. Lett., 15 (2005), 4180-4184.*
Chawla et al., "Challenges in Polymorphism of Pharmaceuticals", CRIPS vol. 5, No. 1, Jan.-Mar. 2004 (4 Pages.*
Newman et al., "Solid-state analysis of the active pharmaceutical ingredient in drug products", DDT vol. 8, No. 19, Oct. 2003, p. 898-905.*
PCT International Search Report dated May 2, 2002, International Application No. PCT/US01/26008.
Original Information Disclosure Statement dated May 14, 2003, for information.

(Continued)

*Primary Examiner*—Golam M. M. Shameem
*Assistant Examiner*—Sun Jae Y Loewe
(74) *Attorney, Agent, or Firm*—Honigman, Miller, Schwartz and Cohn; Jonathan P. O'Brien; Kathryn D. Soulier

(57) ABSTRACT

The present invention relates to peptidomimetic compounds useful as protease inhibitors, particularly as serine protease inhibitors and more particularly as hepatitis C NS3 protease inhibitors; intermediates thereto; their preparation including novel steroselective processes to intermediates. The invention is also directed to pharmaceutical compositions and to methods for using the compounds for inhibiting HCV protease or treating a patient suffering from an HCV infection or physiological condition related to the infection. Also provided are pharmaceutical combinations comprising, in addition to one or more HCV serine protease inhibitors, one or more interferons exhibiting anti-HCV activity and/or one or more compounds having anti HCV activity and a pharmaceutically acceptable carrier, and methods for treating or preventing a HCV infection in a patient using the compositions. The present invention is also directed to a kit or pharmaceutical pack for treating or preventing HCV infection in a patient.

8 Claims, 14 Drawing Sheets

U.S. PATENT DOCUMENTS

| | | |
|---|---|---|
| 5,760,029 A | 6/1998 | Jadhav et al. |
| 5,807,876 A | 9/1998 | Armistead et al. |
| 5,847,135 A | 12/1998 | Bemis et al. |
| 5,849,866 A | 12/1998 | Kolb et al. |
| 5,861,267 A | 1/1999 | Su |
| 5,866,684 A | 2/1999 | Attwood |
| 5,948,436 A | 9/1999 | Al-Razzak et al. |
| 5,973,111 A | 10/1999 | Bemis et al. |
| 5,990,276 A | 11/1999 | Zhang et al. |
| 6,018,020 A | 1/2000 | Attwood et al. |
| 6,025,147 A | 2/2000 | Bemis et al. |
| 6,025,516 A | 2/2000 | Ramaswamy et al. |
| 6,037,157 A | 3/2000 | Norbeck |
| 6,046,195 A | 4/2000 | Haworth et al. |
| 6,054,472 A | 4/2000 | Armistead et al. |
| 6,060,469 A | 5/2000 | Baker et al. |
| 6,103,711 A | 8/2000 | Bemis et al. |
| 6,117,639 A | 9/2000 | Germann et al. |
| 6,130,315 A | 10/2000 | Kolb |
| 6,143,715 A | 11/2000 | Llinas-Brunet et al. |
| 6,153,579 A | 11/2000 | Kim et al. |
| 6,172,077 B1 | 1/2001 | Curtis et al. |
| 6,183,121 B1 | 2/2001 | Kim et al. |
| 6,211,338 B1 | 4/2001 | Malcolm et al. |
| 6,225,320 B1 | 5/2001 | Kulagowski et al. |
| 6,251,583 B1 | 6/2001 | Zhang et al. |
| 6,265,380 B1 | 7/2001 | Tung et al. |
| 6,268,207 B1 | 7/2001 | Bailey |
| 6,274,613 B1 | 8/2001 | Plant et al. |
| 6,303,287 B1 | 10/2001 | Kim et al. |
| 6,323,180 B1 | 11/2001 | Llinas-Brunet et al. |
| 6,329,417 B1 | 12/2001 | Llinas-Brunet et al. |
| 6,344,465 B1 | 2/2002 | Armistead et al. |
| 6,348,608 B1 | 2/2002 | Plant et al. |
| 6,399,771 B1 | 6/2002 | Plant et al. |
| 6,410,531 B1 | 6/2002 | Llinas-Brunet et al. |
| 6,420,380 B2 | 7/2002 | Llinas-Brunet et al. |
| 6,420,522 B1 | 7/2002 | Bemis |
| 6,498,178 B2 | 12/2002 | Stamos et al. |
| 6,528,276 B1 | 3/2003 | Germann et al. |
| 6,534,523 B1 | 3/2003 | Linas-Brunet et al. |
| 6,541,496 B1 | 4/2003 | Armistead et al. |
| 6,548,555 B1 | 4/2003 | Curatolo et al. |
| 6,608,027 B1 | 8/2003 | Tsantrizos et al. |
| 6,608,067 B1 | 8/2003 | Tung et al. |
| 6,617,309 B2 | 9/2003 | Tung et al. |
| 6,653,127 B1 | 11/2003 | Malcolm et al. |
| 6,653,295 B2 | 11/2003 | Glunz et al. |
| 6,699,855 B2 | 3/2004 | Zhang et al. |
| 6,727,366 B2 | 4/2004 | Han et al. |
| 6,767,991 B1 | 7/2004 | Llinas-Brunet et al. |
| 6,774,212 B2 | 8/2004 | Han |
| 6,800,434 B2 | 10/2004 | Saksena et al. |
| 6,824,769 B2 | 11/2004 | Chaturvedi et al. |
| 6,833,442 B2 | 12/2004 | Shibasaki et al. |
| 6,838,475 B2 | 1/2005 | Arasappan et al. |
| 6,846,802 B2 | 1/2005 | Chen et al. |
| 6,846,806 B2 | 1/2005 | Priestley |
| 6,867,284 B1 | 3/2005 | Matassa et al. |
| 6,872,805 B2 | 3/2005 | Campbell et al. |
| 6,909,000 B2 | 6/2005 | Farmer et al. |
| 6,911,428 B2 | 6/2005 | Zhu et al. |
| 6,914,122 B2 | 7/2005 | Venkatraman et al. |
| 6,919,423 B2 | 7/2005 | Llinas-Brunet |
| 6,939,692 B2 | 9/2005 | Bathe et al. |
| 6,939,854 B2 | 9/2005 | Priestley |
| 7,012,066 B2 | 3/2006 | Saksena et al. |
| 7,034,178 B2 | 4/2006 | Faber et al. |
| 7,091,184 B2 | 8/2006 | Llinas-Brunet et al. |
| 7,105,302 B2 | 9/2006 | Bathe et al. |
| 7,109,172 B2 | 9/2006 | Britt et al. |
| 7,119,073 B2 | 10/2006 | Colarusso et al. |
| 7,122,627 B2 | 10/2006 | Priestley |
| 7,169,760 B2 | 1/2007 | Saksena et al. |
| 7,208,600 B2 | 4/2007 | Cottrell et al. |
| 7,241,796 B2 | 7/2007 | Farmer et al. |
| 7,244,721 B2 | 7/2007 | Saksena et al. |
| 7,250,520 B2 | 7/2007 | Wallace |
| 7,273,885 B2 | 9/2007 | Pitlik et al. |
| 7,288,624 B2 | 10/2007 | Bemis et al. |
| 7,365,092 B2 | 4/2008 | Cottrell et al. |
| 7,371,372 B2 | 5/2008 | Chaturvedi et al. |
| 7,378,422 B2 | 5/2008 | Perni et al. |
| 7,381,827 B2 | 6/2008 | Tanoury et al. |
| 7,388,017 B2 | 6/2008 | Tung et al. |
| 7,504,378 B2 | 3/2009 | Llinas-Brunet et al. |
| 7,592,316 B2 | 9/2009 | Njoroge et al. |
| 2002/0016294 A1 | 2/2002 | Venkatraman et al. |
| 2002/0016442 A1 | 2/2002 | Llinas-brunet et al. |
| 2002/0032175 A1 | 3/2002 | Tung et al. |
| 2002/0037998 A1 | 3/2002 | Llinas-Brunet et al. |
| 2002/0042046 A1 | 4/2002 | Kim et al. |
| 2002/0045729 A1 | 4/2002 | Kerres et al. |
| 2002/0065248 A1 | 5/2002 | Zhang et al. |
| 2002/0068702 A1 | 6/2002 | Lim-Wilby et al. |
| 2002/0102235 A1 | 8/2002 | Arasappan et al. |
| 2002/0107181 A1 | 8/2002 | Chen et al. |
| 2002/0111378 A1 | 8/2002 | Stamos et al. |
| 2002/0123468 A1 | 9/2002 | Han |
| 2002/0142449 A1 | 10/2002 | Kwong et al. |
| 2002/0147160 A1 | 10/2002 | Bhat et al. |
| 2002/0160962 A1 | 10/2002 | Saksena et al. |
| 2002/0177725 A1 | 11/2002 | Priestley et al. |
| 2002/0183249 A1 | 12/2002 | Taylor et al. |
| 2002/0187488 A1 | 12/2002 | Lin et al. |
| 2003/0008828 A1 | 1/2003 | Priestley et al. |
| 2003/0019752 A1 | 1/2003 | Ross et al. |
| 2003/0036501 A1 | 2/2003 | Saksena et al. |
| 2003/0064962 A1 | 4/2003 | Glunz et al. |
| 2003/0068369 A1 | 4/2003 | McAllister et al. |
| 2003/0083467 A1 | 5/2003 | Germann et al. |
| 2003/0100768 A1 | 5/2003 | Han et al. |
| 2003/0144257 A1 | 7/2003 | Biggadike et al. |
| 2003/0153788 A1 | 8/2003 | Kobayashi et al. |
| 2003/0181363 A1 | 9/2003 | Llinas-Brunet et al. |
| 2003/0186895 A1 | 10/2003 | Llinas-Brunet et al. |
| 2003/0186952 A1 | 10/2003 | Crew et al. |
| 2003/0187018 A1 | 10/2003 | Llinas-Brunet et al. |
| 2003/0191067 A1 | 10/2003 | Llinas-Brunet et al. |
| 2003/0195362 A1 | 10/2003 | Kempf et al. |
| 2003/0216325 A1 | 11/2003 | Saksena et al. |
| 2003/0236242 A1 | 12/2003 | Perni et al. |
| 2004/0006237 A1 | 1/2004 | Dolitzky et al. |
| 2004/0018986 A1 | 1/2004 | Pitlik et al. |
| 2004/0048774 A1 | 3/2004 | Saunders et al. |
| 2004/0058982 A1 | 3/2004 | Harris et al. |
| 2004/0067901 A1 | 4/2004 | Bhat et al. |
| 2004/0072788 A1 | 4/2004 | Bhat et al. |
| 2004/0077600 A1 | 4/2004 | Tung et al. |
| 2004/0082574 A1 | 4/2004 | Wang et al. |
| 2004/0105820 A1 | 6/2004 | Weers et al. |
| 2004/0110747 A1 | 6/2004 | Altman |
| 2004/0142876 A1 | 7/2004 | Colarusso et al. |
| 2004/0171626 A1 | 9/2004 | Beaulieu et al. |
| 2004/0180815 A1 | 9/2004 | Nakajima et al. |
| 2004/0186125 A1 | 9/2004 | Poupart et al. |
| 2004/0224900 A1 | 11/2004 | Bailey et al. |
| 2004/0229817 A1 | 11/2004 | Duggal et al. |
| 2004/0229818 A1 | 11/2004 | Llinas-Brunet |
| 2004/0266731 A1 | 12/2004 | Tung et al. |
| 2005/0020503 A1 | 1/2005 | Llinas-Brunet et al. |
| 2005/0049220 A1 | 3/2005 | Stuyver |
| 2005/0059606 A1 | 3/2005 | Saksena et al. |
| 2005/0062522 A1 | 3/2005 | Haider et al. |

| Pub. No. | Date | Inventor |
|---|---|---|
| 2005/0080005 A1 | 4/2005 | Llinas-Brunet et al. |
| 2005/0080017 A1 | 4/2005 | Cottrell et al. |
| 2005/0090450 A1 | 4/2005 | Farmer et al. |
| 2005/0107304 A1 | 5/2005 | Britt et al. |
| 2005/0112093 A1 | 5/2005 | Ette et al. |
| 2005/0119189 A1 | 6/2005 | Cottrell et al. |
| 2005/0119318 A1 | 6/2005 | Hudyma et al. |
| 2005/0120398 A1 | 6/2005 | Kalkeri et al. |
| 2005/0136400 A1 | 6/2005 | Lin et al. |
| 2005/0137139 A1 | 6/2005 | Perni et al. |
| 2005/0153877 A1 | 7/2005 | Miao et al. |
| 2005/0187165 A1 | 8/2005 | Scola et al. |
| 2005/0187192 A1 | 8/2005 | Fleming et al. |
| 2005/0192212 A1 | 9/2005 | Llinas-Brunet et al. |
| 2005/0197299 A1 | 9/2005 | Babine |
| 2005/0197301 A1 | 9/2005 | Njoroge et al. |
| 2005/0215486 A1 | 9/2005 | Cottrell et al. |
| 2005/0222236 A1 | 10/2005 | Tsantrizos et al. |
| 2005/0249702 A1 | 11/2005 | Njoroge et al. |
| 2005/0287514 A1 | 12/2005 | Byrn |
| 2006/0003317 A1 | 1/2006 | Perni et al. |
| 2006/0003942 A1 | 1/2006 | Tung et al. |
| 2006/0046956 A1 | 3/2006 | Sannigrahi et al. |
| 2006/0089385 A1 | 4/2006 | Cui et al. |
| 2006/0205672 A1 | 9/2006 | Saksena et al. |
| 2006/0211629 A1 | 9/2006 | Britt et al. |
| 2007/0087973 A1 | 4/2007 | Tanoury et al. |
| 2007/0105781 A1 | 5/2007 | Lyons et al. |
| 2007/0161789 A1 | 7/2007 | Cottrell et al. |
| 2007/0179167 A1 | 8/2007 | Cottrell et al. |
| 2007/0191381 A1 | 8/2007 | Tung |
| 2007/0212683 A1 | 9/2007 | Connelly |
| 2007/0218012 A1 | 9/2007 | Bittorf et al. |
| 2007/0218138 A1 | 9/2007 | Bittorf et al. |
| 2007/0225297 A1 | 9/2007 | Perni et al. |
| 2007/0231262 A1 | 10/2007 | Lin et al. |
| 2007/0243166 A1 | 10/2007 | Llinas-Brunet et al. |
| 2007/0244334 A1 | 10/2007 | Tanoury et al. |
| 2007/0292933 A1 | 12/2007 | Pitlik et al. |
| 2008/0045480 A1 | 2/2008 | Farmer et al. |
| 2008/0070972 A1 | 3/2008 | Kadiyala et al. |
| 2008/0125376 A1 | 5/2008 | Cottrell et al. |
| 2008/0167480 A1 | 7/2008 | Wallace |
| 2008/0311079 A1 | 12/2008 | Perni et al. |
| 2009/0022688 A1 | 1/2009 | Farmer et al. |
| 2009/0143312 A1 | 6/2009 | Tung et al. |
| 2009/0191555 A1 | 7/2009 | Lin et al. |
| 2009/0247468 A1 | 10/2009 | Bittorf et al. |

FOREIGN PATENT DOCUMENTS

| | | |
|---|---|---|
| EP | 0417721 | 3/1991 |
| EP | 0675112 | 10/1995 |
| JP | 09124691 | 5/1997 |
| WO | WO 92/12140 | 7/1992 |
| WO | WO 93/25574 | 12/1993 |
| WO | WO 94/14436 | 4/1995 |
| WO | WO 95/09614 | 4/1995 |
| WO | WO 97/17364 | 5/1997 |
| WO | WO 97/40028 | 10/1997 |
| WO | WO 97/43310 | 11/1997 |
| WO | WO 98/13365 | 4/1998 |
| WO | WO 98 17679 A | 4/1998 |
| WO | WO 98/22496 | 5/1998 |
| WO | WO 98/40381 | 9/1998 |
| WO | WO 98/46630 | 10/1998 |
| WO | WO 99 07733 A | 2/1999 |
| WO | WO 99 07734 A | 2/1999 |
| WO | WO 99/38888 | 8/1999 |
| WO | WO 99/50230 | 10/1999 |
| WO | WO 99/64442 | 12/1999 |
| WO | WO 00 09543 A | 2/2000 |
| WO | WO 00 09558 A | 2/2000 |
| WO | WO 00/09588 | 2/2000 |
| WO | WO 00/23421 | 4/2000 |
| WO | WO 00/31129 | 6/2000 |
| WO | WO 00/56331 | 9/2000 |
| WO | WO 00/59929 | 10/2000 |
| WO | WO 01/02424 | 1/2001 |
| WO | WO 01/07407 | 2/2001 |
| WO | WO 02/18369 | 3/2001 |
| WO | WO 01/32691 | 5/2001 |
| WO | WO 01/40262 A1 | 6/2001 |
| WO | WO-01/40266 | 6/2001 |
| WO | WO 01/58929 | 8/2001 |
| WO | WO 01/64678 | 9/2001 |
| WO | WO 01/74768 | 10/2001 |
| WO | WO 01/77113 | 10/2001 |
| WO | WO 01/81325 | 11/2001 |
| WO | WO 02/07761 | 1/2002 |
| WO | WO 02/08187 | 1/2002 |
| WO | WO 02/08198 | 1/2002 |
| WO | WO 02/08244 A2 | 1/2002 |
| WO | WO 02/08251 | 1/2002 |
| WO | WO 02/08256 | 1/2002 |
| WO | WO 02/48116 | 6/2002 |
| WO | WO 02/48157 | 6/2002 |
| WO | WO 02/48172 | 6/2002 |
| WO | WO 02/060926 | 8/2002 |
| WO | WO 02/079234 | 10/2002 |
| WO | WO 03/003804 | 1/2003 |
| WO | WO 03/006490 | 1/2003 |
| WO | WO 03/020298 | 3/2003 |
| WO | WO 03/062228 | 7/2003 |
| WO | WO 03/062265 | 7/2003 |
| WO | WO 03/064416 | 8/2003 |
| WO | WO 03/064456 | 8/2003 |
| WO | WO 03/087092 | 10/2003 |
| WO | WO 2004/026896 | 4/2004 |
| WO | WO 2004/030670 | 4/2004 |
| WO | WO 2004/032827 | 4/2004 |
| WO | WO 2004/037855 | 5/2004 |
| WO | WO 2004/039833 | 5/2004 |
| WO | WO 2004/072243 | 8/2004 |
| WO | WO 2004/089974 | 10/2004 |
| WO | WO 2004/092161 | 10/2004 |
| WO | WO 2004/093798 | 11/2004 |
| WO | WO 2004/094452 | 11/2004 |
| WO | WO 2004/103996 | 12/2004 |
| WO | WO 2004/113365 | 12/2004 |
| WO | WO 2005/007681 | 1/2005 |
| WO | WO 2005/010029 | 2/2005 |
| WO | WO 2005/021584 | 3/2005 |
| WO | WO 2005/028501 | 3/2005 |
| WO | WO 2005/028502 | 3/2005 |
| WO | WO 2005/030796 | 4/2005 |
| WO | WO 2005/037214 | 4/2005 |
| WO | WO 2005/037860 | 4/2005 |
| WO | WO 2005/042570 | 5/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/058821 | 6/2005 |
| WO | WO 2005/070955 | 8/2005 |
| WO | WO 2005/073195 | 8/2005 |
| WO | WO 2005/073216 | 8/2005 |
| WO | WO 2005/077969 | 8/2005 |
| WO | WO 2005/085242 | 9/2005 |
| WO | WO 2005/085275 | 9/2005 |
| WO | WO 2005/087721 | 9/2005 |
| WO | WO 2005/087725 | 9/2005 |
| WO | WO 2005/087731 | 9/2005 |
| WO | WO 2005/095403 | 10/2005 |
| WO | WO 2005/113581 | 12/2005 |
| WO | WO 2005/123076 | 12/2005 |

| WO | WO 2006/000085 | 1/2006 |
| WO | WO 2006/007448 | 1/2006 |
| WO | WO 2006/007700 | 1/2006 |
| WO | WO 2006/007708 | 1/2006 |
| WO | WO 2007/016589 | 2/2007 |
| WO | WO 2007/025307 | 3/2007 |
| WO | WO 2008/106058 A2 | 9/2008 |

OTHER PUBLICATIONS

Patent Abstracts of Japan, vol. 1997, No. 09, Sep. 30, 1997.
Bergmeier, S.C., et al., "Synthesis of Bicyclic Proline Analogs Using a Formal 3+2 ! Intramolecular Aziridine-Allylsilane Cycloaddition Reaction", Tetrahedron, Elsevier Science Publishers, Amsterdam, NL, vol. 55, No. 26, Jun. 25, 1999, pp. 8025-8038.
Collado, I., et al., "Stereocontrolled Synthesis of 4-Substituted (+/−) Kainic Acids", Journal of Roganic Chemistry, vol. 63, 1998, pp. 1995-2001.
Blankley, C.J., et al., "Synthesis and Structure-Activity Relationships of Potent new Angiotensin Converting Enzyme Inhibitors Containing Saturated Bicyclic Amino Acids", Journal of Medicinal Chemistry, vol. 30, 1987, pp. 992-998.
Yasuda, M., et al., "Synthesis of Conformationally Defined Glutamic Acids Analogues from Readily Available Diels-Alder Adducts", Chemical and Pharmaceutical Bulletin, 1995, pp. 1318-1324.
Esch, P.M., et al., "Reductive Cyclization of Carbon-Centered Glycine Radicals; A Novel Synthetic Route to Cyclic alpha-Amino Acids", Tetrahedron, vol. 48, No. 22, 1992, pp. 4659-4676.
Udding, J. H., et al., "Transition Metal-Catalyzed Chlorine Transfer Cyclizations of Carbon-Centered Glycine Radicals; A Novel Synthetic Route to Cyclic alpha-Amino Acids", Tetrahedron, 1994, pp. 1907-1918.
Sagnard, Isabelle, et al., "Enantioslective Synthesis of Cyclopropane alpha-Amino Acids: Synthesis of N-Boc-cis-(2S, 3R, 4S)-3,4-Methanoproline and N-Boc-(2S, 3R, 4S)-3,4-Methanoglutamic Acid," Tetrahedron Letters, vol. 36, No. 18, May 1, 1995, pp. 3149-4039.
Kim, J. L., et al., "Hepatitis C virus NS3 RNA helicase domain with a bound oligonucleotide: the crystal structure provides insights into the mode of unwinding," Structure. Jan. 15, 1998;6(1):89-100.
Kwong, A.D., et al., "Structure and function of hepatitis C virus NS3 helicase," Top Microbiol Immunol. 2000, 242:171-96.
Kwong, A.D., et al., "Hepatitis C virus NS3/4A protease," Antiviral Res. 1998; 40:1-18.
Kwong, A.D., et al., "Hepatitis C virus NS3/4A protease," Antiviral Res. 1999;41:67-84.
Lin, C., et al, "Structure-based mutagenesis study of hepatitis C virus NS3 helicase," J Virol. Oct. 1999;73(10):8798-807.
Kim, J.L., et al., "Broad-spectrum antiviral activity of the IMP dehydrogenase inhibitor VX-497: a comparison with ribavirin and demonstration of antiviral additivity with alpha interferon," Antimicrob Agents Chemother., Apr. 2000;44(4): 859-66.
Kim, J.L., et al., "Crystal structure of the hepatitis C virus NS3 protease domain complexed with a synthetic NS4A cofactor peptide," Cell. Oct. 18, 1996;87(2):343-55. Erratum in: Cell Apr. 4, 1997;89(1):159.
Morgenstern, K.A., et al, "Polynucleotide modulation of the protease, nucleoside triphosphatase, and helicase activities of a hepatitis C virus NS3-NS4A complex isolated from transfected COS cells,". J Virol. May 1997;71(5):3767-75.
Perni, R. B., "NS3•4A protease as a target for interfering with hepatitis C virus replication," Drug News Perspect., Mar. 13, 2000(2):69-77.
Avolio, S., "Inhibitors of hepatitis C virus NS3/4A: a-Ketoamide based macrocyclic inhibitors," Bioorganic & Medicinal Chemistry Letters (2009), 19, pp. 2295-2298.
Blair, W., "5th Antiviral Drug Discovery and Development Summit," Expert opinion on investigational drugs (2004), 13(8), pp. 1065-1069.
Chen, S., "Discovery of Small-Molecule Inhibitors of HCV NS3-4A Protease as Potential Therapeutic Agents against HCV Infection," Current Medicinal Chemistry (2005), 12(20), pp. 2317-2342.

Chen, S., "P1 and P1' Optimization of [3,4]-Bicycloproline P2 Incorporated Tetrapeptidyl a-ketoamide Based HCV Protease Inhibitors," Letters in Drug Design and Discovery (2005), 2(2), pp. 118-123.
Farmer, L., "Inhibitors of Hepatitis C Virus NS3-4A Protease: P2 Proline Variants," Letters in Drug Design and Discovery (2005), 2, pp. 497-502.
Johansson, P., "Potent inhibitors of the hepatitis C virus NS3 protease: Use of a novel P2 cyclopentane-derived template," Bioorganic & Medicinal Chemistry (2006), 14, pp. 5136-5151.
Kalkeri, G., "Expression of HCV Protease in the Liver of Mice Results in Liver Injury Which can be Inhibited by VX-950, A Vertex HCV Protease Inhibitor," AALSD Abstracts, Hepatology (2004), 40(4), Suppl. 1, pp. 281A.
McLaren, R., "Infrared observations of circumstellar ammonia in OH/IR supergiants," Astrophysical Journal (1980), 240(3, Pt. 2), pp. L159-L163.
Perni, R., "The Design of Inhibitors of the HCV NS3-4A Protease: The Identification of a Clinical Development Candidate, VX-950," ACS National Medicinal Chemistry Symposium, Madison, WI, Jun. 2004.
Perni, R., "Inhibitors of hepatitis C virus NS3-4A protease. Effect of P4 capping groups on inhibitory potency and pharmacokinetics," Bioorganic & Medicinal Chemistry Letters (2007), 17, pp. 3406-3411.
Perni, R., "Properties and Preclinical Profile of VX-950, An Orally Bioavailable Inhibitor of the Hepatitis C Virus (HCV) Protease and a Potential Anti-HCV Therapeutic," 10th International Symposium on Hepatitis C and Related Viruses, Kyoto, Japan, Dec. 2-6, 2003.
Perni, R., "Toward Smaller HCV NS3-4A Protease Inhibitors: 3-Substituted Proline-based Tripeptide Scaffolds," Abstracts of Papers, 229th ACS National Meeting, San Diego, CA, United States, Mar. 13-17, 2005, MEDI-350.
Yao, N., "Molecular views of viral polyprotein processing revealed by the crystal structure of the hepatitis C virus bifunctional protease-helicase," Structure (1999), 7(11), pp. 1353-1363.
Perni, R., "The Importance of Backbone Hydrogen Bonds in Binding a Tetrapeptide Scaffold to the HCV NS3-4A Protease," American Chemical Society's 229th National Meeting, San Diego, CA, Mar. 13-17, 2005.
Akahoshi, F., "Chymase Inhibitors and their Therapeutic Potential", Drugs of the Future, 27(8) (2009), pp. 765-770.
Anonymous, VPI internet press release Sep. 7, 2004.
Anonymous, Newsrx internet article, May 31, 2004.
Arasappan, "Hepatitis C Virus NS3-4A Serine Protease Inhibitors: SAR of P2 Moiety with Improved Potency," Bioorg. & Med. Chem. Let., vol. 15, (2005), pp. 4180-4184.
Bastos, M., "Inhibitors of Human Heart Chymase Based on a Peptide Library", Proc. Natl. Acad. Sci. USA, vol. 92 (1995), pp. 6738-6742.
Beak, P., "Complex Induced Proximity Effects: Enantioselective Syntheses Based on Asymmetric Deprotonations of N-Boc.". . J. Amer. Chem. Soc., vol. 116 (1994), pp. 3231-3239.
Behrens, C. "Selective Transformations of 2,3-Epoxy Alcohols and Related Derivatives. Strategies for Nucleophilic Attack at . . . ":, J. Org.Chem., vol. 50 (1985), pp. 5696-5704.
Cacciola, J., "The Synthesis of Lysine α-Ketoamide Thrombin Inhibitors via an Epoxy Amide Ring Opening", Tetrahedron Let., vol. 38, No. 33 (1997), pp. 5741-5744.
Chen, "Synthesis and Eval. of Tripeptidyl [alpha]-Ketoamides as Human Rhinovirus 3C Protease Inhibitors", Bioorg. & Med. Chem. Letters, vol. 13, No. 20 (2003), pp. 3531-3536.
Cheng, W. "Stereoselective Synthesis of Unnatural Spiroisoxazolinoproline-Based Amino Acids and Derivatives", J. Org. Chem., (2002), pp. 5673-5677.
Davis, G. "Future Options for the Management of Hepatitis C", Seminars in Liver Disease, vol. 19, Supp. 1 (1999), pp. 103-112.
Dunsdon, R., "Solid Phase Synthesis of Aminoboronic Acids: Potent Inhibitors of the Hepatitis C Virus NS3 Proteinase", Bioorganic & Medicinal Chemistry Letters, 10 (2000), pp. 1577-1579.
Elemes, Synthesis of enantiopure α-deuterated Boc-L-amino acids, J. Chem. Soc., Perkin Trans., vol. 1 (1995), pp. 537-540.
Forestier, Current status of subjects receiving peg-interferon-alfa-2a (PEG-IFN) and ribavirin (RBV) after a 14-day study of the hepatitis C protease inhibitor telaprevir (VX-950), with PEG-IFN, Hepatology, vol. 44, Supp. 2 (2006), p. 614A.

Freireich, E. "Quantitative Comparison of Toxicity of Anticancer Agents in Mouse, Rat, Hamster, Dog, Monkey and Man", Cancer Chemother. Rep., vol. 50, (1966) pp. 219-244.

Gallagher, D., "Complex-Induced Proximity Effects: Evidence for a Prelithiation Complex and a Rate-Determining Deprotonation . . . ",J. Org. Chem., vol. 60 (1995), pp. 7092-7093.

Gallagher, D., "Chiral Organolithium Complexes: The Effect of Ligand Structure on the Enantioselective Deprotonation of Boc . . . ", J. Org. Chem., vol. 60 (1995) pp. 8148-8154.

Garrison, "Novel 3, 7-Diheterabicyclo(3.3.1) nonanes that Possess Predominant Class III Antiarrhythmic Activity in 1-4 day Post . . . " J. Med. Chem, vol. 39, No. 13 (1996), pp. 2559-2570.

Golina, S., "Vulcanisation of Poly(diethyl-n-butylamino) Phosphazenes", Internat'l Polymer Science & Tech., vol. 18, No. 3 (1991), pp. T20-T22.

Han, W., "α-Ketoamides, α-Ketoesters and α-Diketones as HCV NS3 Protease Inhibitors", Bioorganic & Medicinal Chemistry Letters 10 (2000), pp. 711-713.

Janssen, H.L.A., "Suicide Associated with Alfa-Interferon Therapy for Chronic Viral Hepatitis", J. Hepatol., 21 (1994), pp. 241-243.

Johnansson, a., "Acyl Sulfonamides as Potent Protease Inhibitors of the Hepatitis C Virus Full-Length NS3 (Protease-Helicase/NTPase): A comparative Study of Different C-Terminals", Bioorganic & Medicinal Chemistry, 11 (2003), pp. 2551-2568.

Kakei, H., "Catalytic Asymmetric Epoxidation of α, β-Unsaturated Esters Using an Yttrium-Biphenyldiol Complex", J. Am. Chem. Soc., vol. 127 (2005), pp. 8962-8963.

Kamandi, E., "Die Synthese von β-Phenyl-Isoserinen Durch Ammonolyse von β-Phenyl-Glycidestern, I.", Archiv de Pharmazie, vol. 307 No. 11 (1974), pp. 871-878.

Kao, J.H., "Efficacy of Consensus Interferon in the Treatment of Chronic Hepatitis", J. Gastroenterol. Hepatol., 15 (2000), pp. 1418-1423.

Kerrick, S., "Asymmetric Deprotonations: Enantioselective Syntheses of 2-Substituted (tert-Butoxycarbonyl) pyrrolldines", J. Amer. Chem. Soc., vol. 113 (1991), pp. 9703-9710.

Kieffer, Genetic Heterogeneity in the HCV Ns3 Protease of Untreated Genotype 1 Patients Has Little Effect on the Sensitivity of the VX-950, 12th Internal'l Conf. on Hep. C Virus and Related Viruses, Montreal, Canada, Oct. 2-6, 2005.

Kieffer, Genetic heterogeneity in the HCV NS3 protease of untreated genotype 1 patents has little effect on the sensitivity to VX-950, Hepatology 2005; 42: 537A.

Kieffer, Wild-type HCV NS3 protease re-emerges during follow-up after 14 days of dosing with VX-950 in patients with genotype 1 HCV, Journal of Hepatology, vol. 44 Supp. 2, Apr. 2006, p. S7.

Kieffer, Combination of Telaprevir (VX-950) and Peg-IFN-alfa Supresses Both Wild-type Virus and Resistance Variants in HCV Genotype 1-Infected Patients in a 14-day Phase 1b study, Hepatology 44, Supp.2 (2006), p. 222A.

Kino, R., "Remarkable effect of tris(4-fluorophenyl)phosphine oxide on the stabilization of chiral lanthanum complex catalysts . . . ", Org. Bio. Chem., 2 (2004), pp. 1822-1824.

Kwong, VX-950: An Orally Bioavailable Inhibitor of the HCV ns3-4A Protease; a potential HCV therapeutic, 5th Antivir. Drug Discovery and Development Summit, Cherry Hill, NJ, Mar. 29-30, 2004.

Kwong, HCV Protease Inhibitors: Activity and Resistance, 13th Conference on Retroviruses and Opp. Infections (CROI), Denver, Co, Feb. 5-8, 2006.

Kwong, Beyond interferon and ribavirin: Antiviral therapies for hepatitis C virus, Drug Discovery Today: Therapeutic Strategies, vol. 3 (2006), pp. 211-220.

Kwong, VX-950: A Novel HCV Protease Inhibitor, HepDART 2005, Big island, Hawaii, Dec. 12-15, 2005.

Lamar, "Novel P4 Truncated Tripeptidyl Alpha-Ketoamides as HCV Protease Inhibitors," Bio. & Med. Chem. Let, vol. 14 No. 1 (2004), pp. 263-266.

Laplante, S., "NMR Line-Broadening and Transferred NOESY as a Medicinal Chemistry Tool for Studying Inhibitors of the Hepatitis C Virus NS3 Protease Domain", Bioorganic & Medicinal Chemistry Letters, 10 (2000), pp. 2271-2274.

Lawitz, 28 Days of the Hepatitis C Protease Inhibitor Telaprevir (VX-950), in Combination with Peginterferon-alfa-2a and Ribavirin, is well-tolerated and demonstrates robust antiviral effects, 12th Internat'l Symposium on Viral Hepatitis and Liver Disease (ISVHLD), Paris, France, Jul. 1-5, 2006.

Lawitz, 28 Days of the Hepatitis C Protease Inhibitor VX-950, in Combination With PEG-Interferon-ALFA-2a and Ribavirin, is well-tolerated and demonstrates robust antiviral effects, Gastroenterology, vol. 131, Issue 3, Sep. 2006, pp. 950-951.

Lehmann, Über die chemischen and biologischen Eigenschaften einiger α-Aminoketone, Helvetica Chimica Acta., vol. 33 (1950), pp. 1217-1226.

Lin, Combination of a Hepatitis C Virus NS3-4A Protease Inhibitor with IFN-α Synergistically Inhibits Viral RNA Replication and Facilitates Viral RNA Clearance in Replicon Cells, Antimicrob. Agents Chemo. 2004; 48: 4784-4792.

Lin, VX-950, a novel hepatitis C virus (HCV) NS3-4A protease inhibitor, exhibits potent antiviral activities in HCV replicon cells, Antimicrob. Agents Chemother. May 2006; 50 (5): 1813-1822.

Lin, VX-950: a tight-binding HCV protease inhibitor with a superior sustained inhibitory response in HCV replicon cells, Hepatology 2003; 38:222A.

Lin, Discovery and Development of VX-985, a Novel, Covalent, and Reversible Inhibitor of Hepatitis C Virus NS3-4A Serine Protease, Infectious Disorders—Drug Targets, vol. 6, No. 1, Mar. 2006, pp. 3-16.

Lin, In vitro resistance studies of hepatitis C virus serine protease inhibitors, VX-950 and BILN 2061: structural analysis indicates different resistance mechanisms, J. Biol. Chem. Apr. 23, 2004(17):17508-14. Epub Feb. 6, 2004.

Llinàs-Brunet, M., "Highly Potent and Selective Peptide-Based Inhibitors of the Hepatitis C Virus Serine Protease: Towards Smaller Inhibitors", Bioorganic & Medicinal Chemistry Letters, 10 (2000), pp. 2267-2270.

Llinàs-Brunet, M., "Peptide-Based Inhibitors of the Hepatitis C Virus Serine Protease", Bioorganic & Medicinal Chemistry Letters, 8 (1998), pp. 1713-1718.

Llinàs-Brunet, M., "Studies on the C-Terminal of Hexapeptide Inhibitors of the Hepatitis C virus Serine Protease", Bioorganic & Medicinal Chemistry Letters, 8 (1998), pp. 2719-2724.

Marigo, M., "Asymmetric Organocatalytic Epoxidation of α,β-Unsaturated Aldehydes with Hydrogen Peroxide", J. Am. Chem. Soc., vol. 127, No. 19 (2005), pp. 6964-6965.

Markland, W., "Broad-Spectrum Antiviral Activity of the IMP Dehydrogenase Inhibitor VX-497: a Compsrison with Ribavirin and Demonstration of Antiviral Additivity with Alph Interferon", Antimicrob. Ag. Chem., vol. 44, No. 4 (2000), pp. 859-866.

Mehdi, The Inbibition of Human Neutrophil Elastase and Cathepsin G by Peptidyl 1,2-Dicarbonyl Derivatives, Biochem & Biophys. Res. Comm., vol. 166, No. 2 (1990), pp. 595-660.

Monn, "A Concise, Stereocontrolled Thiazolium Ylide Approach to Kainic Acid", J. Organic Chem., vol. 59, No. 10 (1994), pp. 2773-2778.

Moradpour, "Current and Evolving Therapies for Hepatitis C," Eur. J. Gastroenterol. Hepatol., vol. 11 (1999), pp. 1199-1202.

Perni, Preclinical Profile of VX-950, a Potent, Selective, and Orally Bioavailable Inhibitor of Hepatitis C Virus NS3-4A Serine Protease, Antimicrob. Agents Chemo., vol. 50, No. 3, Mar. 2006, pp. 899-909.

Perni, VX-950: The Discovery of an Inhibitor of the Hepatitis C NS3-4A Protease and Potential Hepatitis C Virus Therapeutic, Hepatology 2003; 28:624A.

Perni, R.B., "Inhibitors of Hepatitis C Virus NS3-4A Protease 1. Non-Charged Tetrapeptide Variants", Bioorganic & Medicinal Chemistry Letters, 13 (2003), pp. 4059-4063.

Perni, R.B., "Inhibitors of Hepatitis C Virus NS3-4A Protease 2. Warhead SAR and Optimization", Bioorganic & Medicinal Chemistry Letters, 14 (2004), pp. 1441-1446.

Perni, R.B., "Inhibitors of Hepatitis C Virus NS3-4A Part 3: P2 Proline Variants", Bioorganic & Medicinal Chemistry Letters, 14 (2004), pp. 1939-1942.

Pippel, "Complex Induced Proximity Effects: Steroselective Carbon-Carbon Bond Formation in Chiral Auxiliary Mediated β-Lithiation- Substitution Sequences of β-Substituted Secondary Carboxamides," Journal of Organic Chemistry, vol. 63 (1998), pp. 2-3.

Poliakov, A., "Structure-Activity Relationships for the Selectivity of Hepatitis C Virus NS3 Protease Inhibitors", Biochimica et Biophysica Acta, 1672 (2004), pp. 51-59.

Ramachandran, Anti-viral activity of VX-950 resolves expression of an HCV-associated gene signature, Journal of Hepatology, vol. 44, Supp. 2, Apr. 2006, p. S223.

Reesink, "Initial Results of A Pahse 1B, Multiple-Dose Study of VX-950, A Hepatitis C Virus Protease Inhibitor," Gastroenterology, vol. 128, No. 4, Supp. 2, Apr. 2005, p. A696, A697.

Reesink, Rapid decline of viral RNA in hepatitis C patients treated with VX-950; a phase 1 b, placebo-controlled randomized study, Gastroenterology. Oct. 2006; vol. 131, No. 4: pp. 997-1002.

Reesink, "Final Results of a Phase 1B, Multiple-Dose Study of VX-950, A Hepatitis C Virus Protease Inhibitor," Hepatology, vol. 42, No. 4, Supp. 1, Oct. 2005, pp. 234A-235A & 56th Annual Meeting of The American Association for the Study of Liver Diseases, San Francisco, CA, Nov. 11-15, 2005, ISSN: 0270-9139.

Reesink, Initial results of a 14-day study of the hepatitis C virus inhibitor protease VX-950, in combination with peginterferon-alpha-2a, Journal of Hepatology, vol. 44, Supp. 2, Apr. 2006, p. S272.

Renault, P.F., "Side Effects of Alpha Interferon", Seminars in Liver disease, 9 (1989), pp. 273-277.

Rodriguez-Torres, Current status of subjects receiving peginterferon alpha-2a (PEG-IFN) and ribavirin (RBV) follow-on therapy after 28-day treatment with the hepatitis C protease inhibitor telaprevir (VX-950), with PEG-IFN and RBV, Hepatology, vol. 44, Supp. 2 (2006), p. 532A.

Schneider, Changed Phosphodiesterase Selectivity and Enhanced in vitro Efficacy by Selective Deuteration of Sildenafil, Arzneimittel-Forschung (Drug Res.), vol. 57, No. 6 (2007), pp. 293-298, Editio Cantor Verlag. Aulendorf (Germany).

Schneider, Enhanced Plasma Concentration by Selective Deuteration of Rofecoxib in rats, Arzneimittel-Forschung (Drug Res.), vol. 56, No. 4, pp. 295-300 (2006), Editio cantor Verlag, Aulendorf (Germany).

Taber, Asymmetric Nucleophilic Epoxidation, Org. Chem. Highlights, Nov. 22, 2004. URL: http//www.organic-chemistry.org/Highlights/2004/22November.shtm.

Taliani, A Continuous Assay of Hepatitis C Virus Protease Based on Resonance Energy Transfer Depsipeptide Substrates,: Anal. Biochem., vol. 240 (1996), pp. 60-67.

Tan, "Strategies for Hepatitis C Therapeutic Invention: Now and Next," Current Opinion in Pharmacology, Elsevier Science Publishers, NL, vol. 4, No. 5, Oct. 2004, pp. 465-470.

Tazulakhova, E.B., "Russian Experience in Screening, Analysis and Clinical Application of Novel Interferon Inducers", J. Interferon Cytokine Res., 21 (2001), pp. 65-73.

Thomson, Hepatitis C virus NS3-4A protease inhibitors: countering viral subversion in vitro and showing promise in the clinic, Curr. Opin. Drug Discov. Devel. Sep. 2006; vol. 9, No. 5, pp. 606-617.

Toom, "Microwave-Assisted Raney Nickel Reduction of Bispidinone Thioketals to N, N'-Dialkylbispidines", Synthesis, vol. 12 (2006), pp. 2064-2068.

Vishweshwar, Pharmaceutical Co-Crystals, J. Pharm. Sci., vol. 95, No. 3 (2006), pp. 499-516, XP000244334, ISSN: 0022-3549 1520-6017, p. 502, pp. 510-511.

Walker, M.A., "Hepatitis C Virus: An Overview of Current Approaches and Progress", DDT, 4 (1999), pp. 518-529.

Wang, Asymmetric Epoxidation of trans-β-Methylstyrene and 1-Phenylcyclohexene using a D-fructose-Derived Ketone: (R,R)-trans-β-Methylstyrene Oxide and (R,R)-1-Phenylcyclohexene Oxide, Org. Syntheses, vol. 80 (2003), p. 9.

Weiland, O., "Interferon Therapy in Chronic Hepatitis C Virus Infection", FEMS Microiol. Rev., 14 (1994), pp. 279-288.

Yip, "Discovery of a Novel Bicycloproline P2 Bearing Peptidyl .alpha.-Ketoamide LY514962 as HCV Protease Inhibitor", Bio. & Med. Chem. Let., vol. 14, No. 1 (2004), pp. 251-256.

Yip, "P4 and P1' Optimization of Bicycloproline P2 Bearing Tetrapeptidyl Alpha-Ketoamides as HCV Protease Inhibitors", Bio. & Med. Chem. Let., vol. 14, No. 9 (2004), pp. 5007-5011.

ISR dated Nov. 16, 2007 from PCT/US07/64294.

ISR from PCT/US05/039240.

ISR dated Dec. 27, 2007 from PCT/US2006/032481.

ISR from PCT/US06/0033770.

ISR dated Aug. 3, 2007 from PCT/US2007/0044995.

ISR dated Jul. 23, 2007 from PCT/US2007/006320.

* cited by examiner

A

Ribavirin Alone

B

Interferon alpha-2B Alone

US 7,820,671 B2

PEPTIDOMIMETIC PROTEASE INHIBITORS

RELATED APPLICATIONS

This is the national phase application, under 35 USC 371, for PCT/US01/26008, filed 31 Aug. 2001, which claims the priority of U.S. provisional applications No. 60/229,398, filed 31 Aug. 2000 and No. 60/277,641, filed Mar. 21 2001.

PARTIES TO A JOINT RESEARCH AGREEMENT

In compliance with 37 C.F.R. §1.71(g)(1), disclosure is herein made that the claimed invention was made pursuant to a Joint Research Agreement as defined in 35 U.S.C. §103(c)(3), that was in effect on or before the date the claimed invention was made, and as a result of activities undertaken within the scope of the Joint Research Agreement, by or on the behalf of Vertex Pharmaceuticals Incorporated and Eli Lilly and Company.

SEQUENCE LISTING

Incorporated herein by reference is a Sequence Listing named "00-131 US Seq List_ST25.txt" created on Dec. 14, 2009, which is 2,881 bytes. The sequence listing does not include any new matter which goes beyond the disclosure of the application as filed.

This invention is directed to peptidomimetic compounds and intermediates thereto, their preparation including stereoselective synthetic processes to intermediates, pharmaceutical compositions containing the peptidomimetic compounds, and the use of the peptidomimetic compounds or compositions thereof as protease inhibitors, particularly as serine protease inhibitors, and more particularly as hepatitis C virus ("HCV") NS3 protease inhibitors. The peptidomimetic compounds, as HCV NS3 protease inhibitors, are particularly useful in interfering with the life cycle of the hepatitis C virus and in treating or preventing an HCV infection or physiological conditions associated therewith. The present invention is also directed to methods of combination therapy for inhibiting HCV replication in cells, or for treating or preventing an HCV infection in patients using the peptidomimetic compounds or pharmaceutical compositions, or kits and pharmaceutical packs therefor. According to the present invention included as pharmaceutical compositions are those comprising an inhibitor of HCV serine protease in combination with an interferon having anti-HCV activity; an inhibitor of HCV serine protease in combination with a compound, other than an interferon, having anti-HCV activity; or an inhibitor of HCV serine protease in combination with both an interferon having anti-HCV activity and a compound, other than an interferon, having anti-HCV activity. Further the present invention is directed to stereoselective methods for preparing chiral bicycloprolinate intermediates useful in the synthesis of the peptidomimetic compounds.

BACKGROUND OF THE INVENTION

Infection by the HCV is a compelling human medical problem and is now recognized as the causative agent for most cases of non-A, non-B hepatitis.

The HCV is thought to infect chronically 3% of the world's population [A. Alberti et al., "Natural History of Hepatitis C," *J. Hepatology*, 31, (Suppl. 1), 17-24 (1999)]. In the United States alone the infection rate is 1.8% or 3.9 million people [M. J. Alter, "Hepatitis C Virus Infection in the United States," *J. Hepatology*, 31, (Suppl. 1), 88-91 (1999)]. Of all patients infected over 70% develop a chronic infection that is believed to be a major cause of cirrhosis and hepatocellular carcinoma. [D. Lavanchy, "Global Surveillance and Control of Hepatitis C," *J. Viral Hepatitis*, 6, 35-47 (1999)]

The replication of the HCV encompasses genomic encoding a polyprotein of 3010-3033 amino acids [Q.-L. Choo, et al., "Genetic Organization and Diversity of the Hepatitis C Virus", *Proc. Natl. Acad. Sci. USA*, 88, 2451-2455 (1991); N. Kato et al., "Molecular Cloning of the Human Hepatitis C Virus Genome Prom Japanese Patients with Non-A, Non-B Hepatitis", *Proc. Natl. Acad. Sci. USA*, 87, 9524-9528 (1990); A. Takamizawa et al., "Structure and Organization of the Hepatitis C Virus Genome Isolated From Human Carriers", *J. Virol.*, 65, 1105-1113 (1991)]. The HCV nonstructural (NS) proteins are presumed to provide the essential catalytic machinery for viral replication. The NS proteins are derived by proteolytic cleavage of the polyprotein [R. Bartenschlager et al., "Nonstructural Protein 3 of the Hepatitis C Virus Encodes a Serine-Type Proteinase Required for Cleavage at the NS3/4 and NS4/5 Junctions", *J. Virol.*, 67, 3835-3844 (1993); A. Grakoui et al. "Characterization of the Hepatitis C Virus-Encoded Serine Proteinase: Determination of Proteinase-Dependent Polyprotein Cleavage Sites", *J. Virol.*, 67, 2832-2843 (1993); A. Grakoui et al., Expression and Identification of Hepatitis C Virus Polyprotein Cleavage Products", *J. Virol.*, 67, 1385-1395 (1993); L. Tomei et al., "NS3 is a serine protease required for processing of hepatitis C virus polyprotein", *J. Virol.*, 67, 4017-4026 (1993)]. In fact, it is the first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", J. Virol., 68, 8147-8157 (1994)].

The HCV NS protein 3 (NS3) contains a serine protease activity that helps in the processing of the majority of the viral enzymes, and thus is considered essential for viral replication and infectivity. The essentiality of the NS3 protease was inferred from the fact that mutations in the yellow fever virus NS3 protease decreases viral infectivity [T. J. Chambers et al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, 8898-8902 (1990)]. More recently, it was demonstrated that mutations at the active site of the HCV NS3 protease could completely abolish the HCV infection in a chimpanzee model [C. M. Rice et al. "Hepatitis C virus-encoded enzymatic activities and conserved RNA elements in the 3'-nontranslated region are essential for virus replication in vivo." *J. Virol.*, 74(4) 2046-51 (2000)]. The HCV NS3 serine protease is also considered essential for viral replication as it and its associated cofactor, NS4A, help in the processing of all of the viral enzymes. This processing appears to be analogous to that carried out by the human immunodeficiency virus ("HIV") aspartyl protease. In addition, the demonstrated use of HIV protease inhibitors as potent antiviral agents in man demonstrates that interrupting a protease protein processing stage in the viral life cycle does result in therapeutically active agents. Consequently, the protease enzyme is an attractive target for drug discovery.

Several potential HCV protease inhibitors have been described. PCT Publications Numbers WO 00/09558, WO 00/09543, WO 99/64442, WO 99/07733, WO 99107734, WO 99/50230, WO98/46630, WO 98/17679 and WO 97/43310, U.S. Pat. No. 5,990,276, M. Llinás-Brunet et al., *Bioorg. Med. Chem. Lett.*, 8, 1713-1718 (1998), W. Han et al., *Bioorg. Med. Chem. Lett.*, 10, 711-713 (2000), R. Dunsdon et al., *Bioorg.*

Med. Chem. Lett., 10, 1571-1579 (2000), M. Llinás-Brunet et al., Bioorg. Med. Chem. Lett., 10, 2267-2270 (2000), and S. LaPlante et al., Bioorg. Med. Chem. Lett., 10, 2271-2274 (2000) each describe potential HCV NS3 protease inhibitors. Unfortunately, there are no serine protease inhibitors available currently as anti-HCV agents.

In fact, there are no anti-HCV therapies except interferon-α, interferon-α/ribavirin combination and more recently pegylated inteferon-α. The sustained response rates for the interferon-α therapies and interferon-α/ribavirin however tend to be low (<50%) and the side effects exhibited by the therapies tend to be significant and severe [M. A. Walker, "Hepatitis C Virus: an Overview of Current Approaches and Progress," DDT, 4, 518-529 (1999); D. Moradpour et al., "Current and Evolving Therapies for Hepatitis C," Eur. J. Gastroenterol. Hepatol., 11, 1199-1202 (1999); H. L. A. Janssen et al., "Suicide Associated with Alfa-Interferon Therapy for Chronic Viral Hepatitis," J. Hepatol., 21, 241-243 (1994); and P. F. Renault et al., "Side effects of alpha interferon", Seminars in Liver Disease 9, 273-277, (1989)]. Furthermore, the interferon therapies only induce long term remission in only a fraction (~25%) of cases [O. Weiland, "Interferon Therapy in Chronic Hepatitis C Virus Infection", FEMS Microbiol. Rev., 14, 279-288(1994)]. The aforesaid problems with the interferon-α therapies has even led to the development and clinical study of pegylated derivatized interferon-α compounds as improved anti-HCV therapeutics.

In view of the current situation regarding anti-HCV therapeutics, it is clear that there is a need for more effective and better tolerated therapies.

Furthermore, synthesis of complex peptidomimetic compounds has long been hampered by the nonstereoselective nature of most synthetic organic processes. It is well known that the therapeutic activity of enantiomers of peptidomimetic compounds varies widely. It is therefore of great benefit to provide such stereospecific synthetic processes.

Previous attempts to synthesize chirally specific bicycloprolinate intermediates, useful in the synthesis of the present therapeutic peptidomimetic protease inhibitors have suffered from being non enatioselective, or diasteroselective, or long encompassing synthetic pathways, or being unsuitable for preparing large quantities of product. Thus, there is also a need for a means of preparing large quantities of bicycloprolinates in a diastereoselective manner and enantiomerically enriched form.

SUMMARY OF THE INVENTION

The present invention relates to a peptidomimetic compound of formula 1

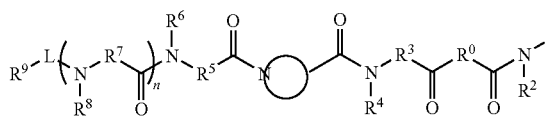

wherein:
$R^0$ is a bond or difluoromethylene;
$R^1$ is hydrogen, optionally substituted aliphatic group, optionally substituted cyclic group or optionally substituted aromatic group;
$R^2$ and $R^9$ are each independently optionally substituted aliphatic group, optionally substituted cyclic group or optionally substituted aromatic group;

$R^3$, $R^5$ and $R^7$ are each independently (optionally substituted aliphatic group, optionally substituted cyclic group or optionally substituted aromatic group)(optionally substituted methylene or optionally substituted ethylene), optionally substituted (1,1- or 1,2-)cycloalkylene or optionally substituted (1,1- or 1,2-)heterocyclylene;
$R^4$, $R^6$, $R^8$ and $R^{10}$ are each independently hydrogen or optionally substituted aliphatic group;

is substituted monocyclic azaheterocyclyl or optionally substituted multicyclic azaheterocyclyl, or optionally substituted multicyclic azaheterocyclenyl wherein the unsaturatation is in the ring distal to the ring bearing the $R^9$-L-(N($R^8$)—$R^7$—C(O)—)$_n$N($R^6$)—$R^5$—C(O)—N moiety and to which the —C(O)—N($R^4$)—$R^3$—C(O)C(O)N$R^2R^1$ moiety is attached;
L is —C(O)—, —OC(O)—, —NR$^{10}$C(O)—, —S(O)$_2$—, or —NR$^{10}$S(O)$_2$—; and
n is 0 or 1, or
a pharmaceutically acceptable salt or prodrug thereof, or a solvate of such a compound, its salt or its prodrug, provided when

is substituted

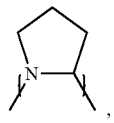

, then L is —OC(O)— and $R^9$ is optionally substituted aliphatic, or at least one of $R^3$, $R^5$ and $R^7$ is (optionally substituted aliphatic group, optionally substituted cyclic group or optionally substituted aromatic group)(optionally substituted ethanediyl), or $R^4$ is optionally substituted aliphatic.

This inventions also provides a compound having the structural formula:

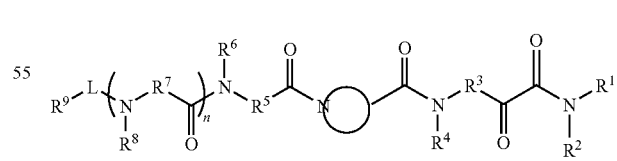

wherein:
$R^1$ is hydrogen, optionally substituted aliphatic group, optionally substituted cyclic group or optionally substituted aromatic group;
$R^2$ and $R^9$ are each independently optionally substituted aliphatic group, optionally substituted cyclic group or optionally substituted aromatic group;

$R^3$, $R^5$ and $R^7$ are each independently (optionally substituted aliphatic group, optionally substituted cyclic group or optionally substituted aromatic group)(optionally substituted methanediyl or optionally substituted ethanediyl);

$R^4$, $R^6$, $R^8$ and $R^{10}$ are each independently is hydrogen or optionally substituted aliphatic group;

is substituted monocyclic azaheterocyclyl or optionally substituted multicyclic azaheterocyclyl, or optionally substituted multicyclic azaheterocyclenyl wherein the unsaturatation is in the ring distal to the ring bearing the $R^9$-L-(N($R^8$)—$R^7$—C(O)—)$_n$N($R^6$)—$R^5$—C(O)—N moiety and to which the —C(O)—N($R^4$)—$R^3$—C(O)C(O)N$R^2R^1$ moiety is attached;

L is —C(O)—, —OC(O)—, —N$R^{10}$C(O)—, —S(O)$_2$—, or —N$R^{10}$S(O)$_2$—; and n is 0 or 1, or a pharmaceutically acceptable salt or prodrug thereof, or a solvate of such a compound, its salt or its prodrug, provided when

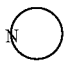

is substituted

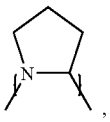

then L is —C(O)— and $R^9$ is optionally substituted aliphatic, or at least one of $R^3$, $R^5$ and $R^7$ is (optionally substituted aliphatic group, optionally substituted cyclic group or optionally substituted aromatic group)(optionally substituted ethanediyl), or $R^4$ is optionally substituted aliphatic.

The invention is also directed to a pharmaceutical composition comprising a compound of formula 1, and method for using the compound of formula 1 for inhibiting HCV protease, or treating or preventing an HCV infection in patients or physiological condition related to the infection.

The invention is also directed to a stereoselective process for preparing a chiral bicycloprolinate compound that is an intermediate useful in preparing a compound of formula 1. The synthetic process comprises the steps of:

(a) cleaving and cyclizing a compound of formula 24

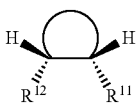

(24)

wherein:

is optionally substituted cycloalkyl or optionally substituted fused arylcycloalkyl;

$R^{11}$ is —CO$_2R^{13}$;

$R^{12}$ is an iminic glycinimide adduct;

$R^{13}$ is acid protecting group or optionally substituted aliphatic group;

under cleaving and cyclizing conditions to form a compound of formula 25

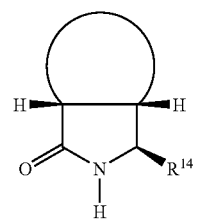

(25)

wherein:

$R^{14}$ is —CONR$^{15}R^{15}$, —CN;

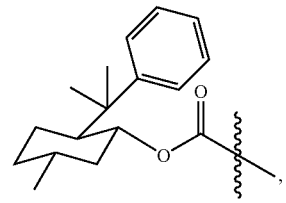

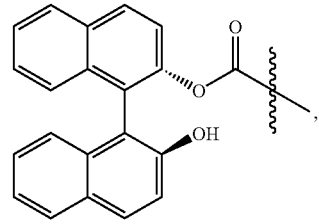

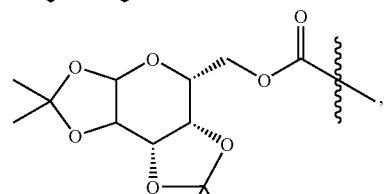

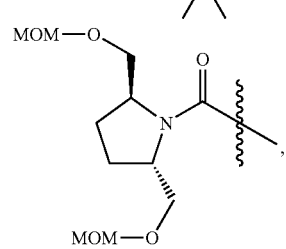

-continued

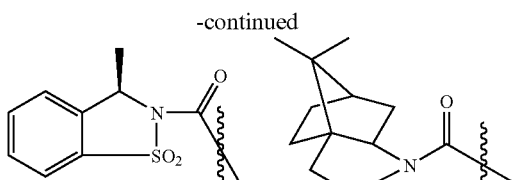

,

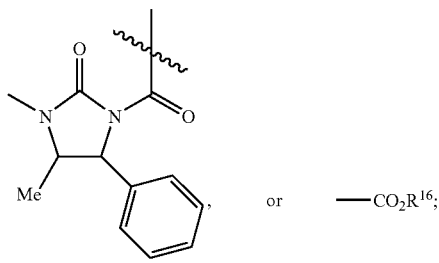

, or —CO$_2$R$^{16}$;

R$^{15}$ is optionally substituted aliphatic group;

R$^{16}$ is acid protecting group, optionally substituted aryl, or optionally substituted aliphatic group; and (b) protecting the nitrogen of the lactam moiety in the compound of formula 25 with an amide protecting group to form a compound of formula 26

(26)

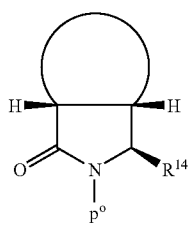

wherein:

p$^o$ is amide protecting group;

R$^{14}$ is as described herein; and (c) reducing the compound of formula 26 under reducing conditions to form a compound of formula 27

(27)

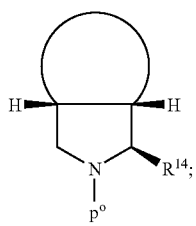

wherein:

p$^o$ and R$^{14}$ are as described herein; and (d) deprotecting the compound of formula 27 under deprotecting conditions to form a compound of formula 28

(28)

wherein:

R$^{14}$ is as described herein.

The invention is also directed to the above synthetic process further comprising the step wherein the compound of formula 24 is prepared by effecting a Michael addition with an iminic glycinimide compound on a compound of formula 29

(29)

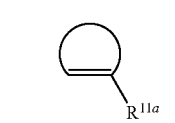

wherein:

is optionally substituted cycloalkenyl or optionally substituted fused arylcycloalkenyl;

R$^{11}$ is —CO$_2$R$^{13}$;

wherein:

the compound of formula 29 may be prepared by esterifying a compound of formula 29a (29a)

$\bigcirc$—R$^{11a}$ wherein:

$\bigcirc$ is optionally substituted cycloalkenyl or optionally substituted fused arylcycloalkenyl;

R$^{11a}$ is —CHO, —COR$^{15}$, —C≡N, or —CONR$^{15}$R$^{15}$; and

R$^{15}$ is as described herein.

Notably, one skilled in the art would know that conversion of ketones to esters may be accomplished, for example, by a Bayer-Villiger reaction. Conversion of nitrites and amides to esters may be accomplished, for example, by aqueous hydrolysis followed by further esterification. Conversion of aldehydes to esters may be accomplished, for example, by oxidation of the aldehyde followed by esterification.

Another aspect of the invention is a compound of formula 1 wherein the substituents are selected from a combination of preferred or particular embodiments as defined herein.

Another aspect of the invention is a compound of formulae 24-29 wherein the substituents are selected from a combination of preferred or particular embodiments as defined herein.

Another aspect of the invention are pharmaceutical compositions comprising, in addition to one or more HCV serine protease inhibitors, one or more interferons or compounds that induce the production of interferons that exhibit anti-HCV activity and/or one or more compounds having anti HCV activity, including immunomodulatory compounds such as immunostimulatory cytokines exhibiting HCV antiviral activity, and a pharmaceutically acceptable carrier.

Another aspect of the invention are methods of treating or preventing a HCV infection in a patient in need thereof, comprising administering to said patient a pharmaceutically effective amount of a combination of one or more HCV serine protease inhibitors; one or more interferons or compounds that induce the production of an inteferon that exhibit anti-HCV activity; and/or one or more compounds having anti-HCV activity, including immunomodulatory compounds such as immunostimulatory cytokines exhibiting HCV antiviral activity.

The invention is also directed to the use of one or more HCV serine protease inhibitors in combination with one or more interferons or compounds that induce the production of an inteferon that exhibit anti-HCV activity and/or one or more compounds having anti-HCV activity, including immunomodulatory compounds such as immunostimulatory cytokines exhibiting HCV antiviral activity, to prepare a medicament for treating or preventing a HCV infection in a patient in need thereof.

The present invention is also directed to a kit or pharmaceutical pack for treating or preventing HCV infection in a patient, wherein the kit or pharmaceutical pack comprises a plurality of separate containers, wherein at least one of said containers contains one or more HCV serine protease inhibitors (alone or in combination with a pharmaceutically acceptable carrier or diluent), at least another of said containers contains one or more interferons or compounds that induce the production of an inteferon that exhibit anti-HCV activity, (alone or in combination with a pharmaceutically acceptable carrier or diluent) and, optionally, at least another of said containers contains one or more compounds having anti-HCV activity (alone or in combination with a pharmaceutically acceptable carrier or diluent), including immunomodulatory compounds such as immunostimulatory cytokines exhibiting HCV antiviral activity.

The amount of the HCV serine protease inhibitor(s), interferon(s), or anti-HCV compound(s) in any of the foregoing applications can be a pharmaceutically effective amount, a subclinical anti-HCV effective amount, or combinations thereof, so long as the final combination of HCV serine protease inhibitor(s), interferon(s), or compounds that induce the production of an interferon that exhibit anti-HCV activity, and/or anti-HCV compound(s) comprises a pharmaceutically effective amount of compounds that is effective in treating or preventing HCV infection in a patient.

BRIEF DESCRIPTION OF THE DRAWINGS

The above and other aspects, features, and advantages of the present invention will be better understood from the following detailed description taken in conjunction with the accompanying drawings, all of which are given by way of illustration only, and are not limitative of the present invention, in which.

Figure 1:
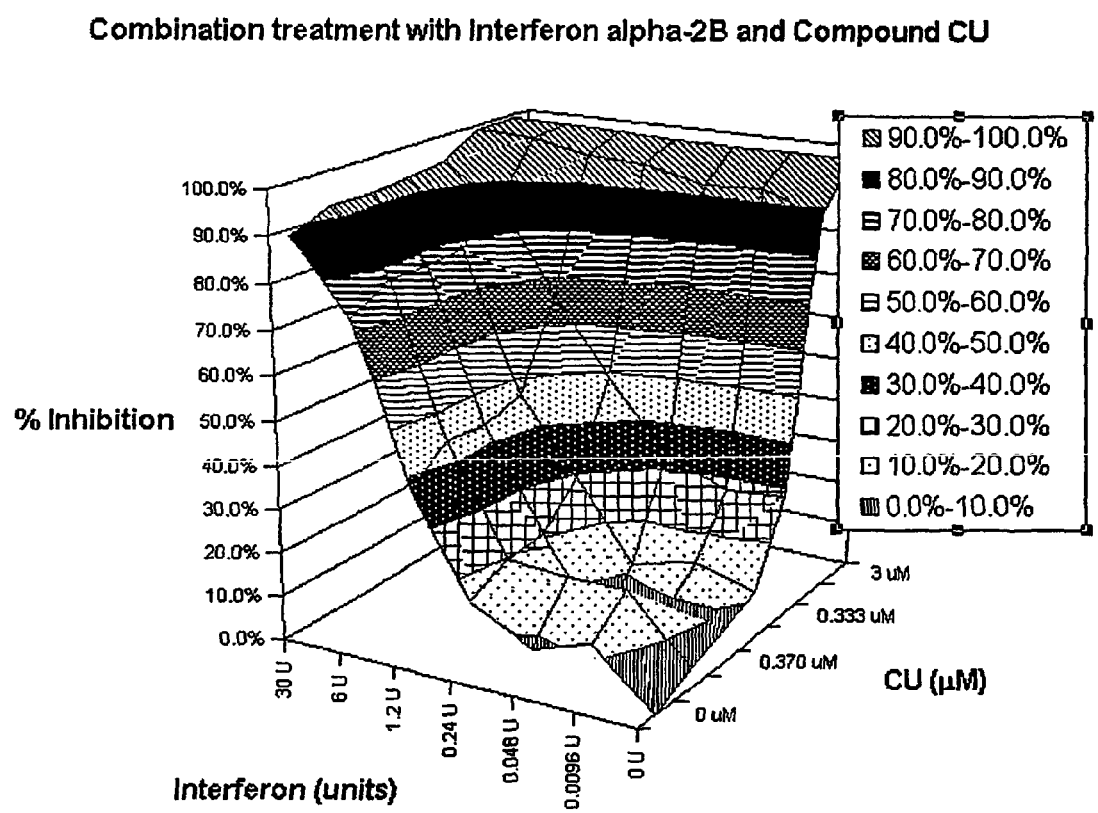
FIG. 1 shows the inhibition of HCV replicon RNA accumulation after 48 hour treatment of replicon-containing cells with Compound CU and interferon-alpha 2B, individually or in combination.

Ribavirin alone or (B) interferon alpha-2B alone. In both panels, the measured inhibition as well as the inhibition corrected for cytotoxicity of the compounds is shown.

DETAILED DESCRIPTION OF THE INVENTION

The contents of each of the patent documents and other references cited herein are herein incorporated by reference in their entirety.

As used above, and throughout the description of the invention, the following abbreviations, unless otherwise indicated, shall be understood to have the following meanings:—

| Designation | Reagent or Fragment |
|---|---|
| ACN | acetonitrile |
| AIBN | 2,2'-azobisisobutyronitrile |
| BOC or Boc | tert-butyl carbamate |
| BOP | benzotriazol-1-yl-oxytris (dimethylamino)phosphonium hexafluorophosphate |
| n-Bu₃SnH | tri-n-butyltin hydride |
| t-Bu | tert-butyl |
| Cbz | benzyl carbamate |
| chiral PTC | chiral phase transfer catalyst |

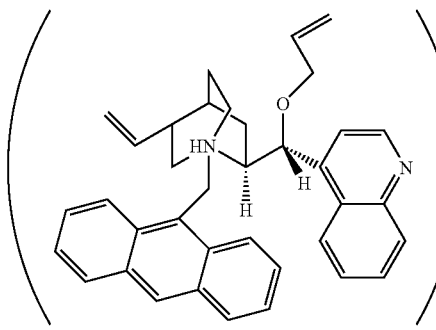

| DAST | (diethylamino)sulfur trifluoride (Et₂NSF₃) |
|---|---|
| DCC | dicyclocarbodiimide |
| DCM | dichloromethane (CH₂Cl₂) |
| DIBAL-H | Diisobutylaluminum hydride |
| DIC | 1,3-diisopropylcarbodiimide |
| DIPEA | diisopropylethylamine |
| DMAP | 4-(N,N-dimethylamino)pyridine |
| DMP reagent | Dess-Martin Periodinane reagent |

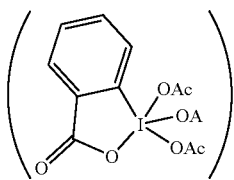

| DMF | dimethylformamide |
|---|---|
| DMSO | dimethylsulfoxide |
| EA | elemental analysis |
| EDCI | 1-ethyl-3-(3-dimethylaminopropyl) carbodiimide HCl |
| eq | equivalent(s) |
| Et | ethyl |
| Et₂O | diethyl ether |
| EtOH | ethanol |
| EtOAc | ethyl acetate |
| Et₃Si | triethylsilane |
| FMOC | 9-fluorenylmethoxycarbonyl |

-continued

| Designation | Reagent or Fragment |
|---|---|
| H-Chg-OH | (structure shown) |
| HOAt | 1-hydroxy-7-azabensotriazole |
| HOBT | 1-hydroxybenztriazole |
| HOSu | N-hydroxysuccinamide |
| HPLC | high performance liquid chromatography |
| LAH | lithium aluminum anhydride |
| Me | methyl |
| MeI | methyliodide |
| MeOH | methanol |
| MeOC(O)Cl | methyl chloroformate |
| MOMCl | methoxymethylchloride |
| MOM | methoxymethyl |
| MS | mass spectroscopy |
| NaBH₄ | sodium borohydride |
| Na₂C₄H₄O₆ | sodium tartrate |
| NMP | N-methyl pyrrolidinone |
| NMR | nuclear magnetic resonance |
| P- | Polymer bond |
| PyBOP | benzotriazole-1-yl-oxytris-pyrrolidino-phosphonium hexafluorophosphate |
| TBD | 1,5,7-triazabicyclo[4.4.0]-dec-5-ene |
| RP-HPLC | reverse phase - high pressure liquid chromatography |
| TBSCl | tert-butyldimethylsilyl chloride |
| TCA | trichloroacetic acid |
| TFA | trifluoroacetic acid |
| Tf₂O | triflate anhydride |
| THF | tetrahydrofuran |
| THP | tetrahydropyran |
| TLC | thin layer chromatography |

As used above, and throughout the description of the invention, the following terms, unless otherwise indicated, shall be understood to have the following meanings:—

"Acid bioisostere" means a group which has chemical and physical similarities producing broadly similar biological properties to a carboxy group (see Lipinski, Annual Reports in Medicinal Chemistry, "Bioisosterism In Drug Design" 21, 283 (1986); Yun, Hwahak Sekye, "Application Of Bioisosterism To New Drug Design" 33, 576-579, (1993); Zhao, Huaxue Tongbao, "Bioisosteric Replacement And Development Of Lead Compounds In Drug Design" 34-38, (1995); Graham, Theochem, "Theoretical Studies Applied To Drug Design:ab initio Electronic Distributions In Bioisosteres" 343, 105-109, (1995)). Exemplary acid bioisosteres include —C(O)—NHOH, —C(O)—CH₂OH, —C(O)—CH₂SH, —C(O)—NH—CN, sulpho, phosphono, alkylsulphonylcarbamoyl, tetrazolyl, arylsulphonylcarbamoyl, N-methoxycarbamoyl, heteroarylsulphonylcarbamoyl, 3-hydroxy-3-cyclobutene-1,2-dione, 3,5-dioxo-1,2,4-oxadiazolidinyl or hydroxyheteroaryl such as 3-hydroxyisoxazolyl, 3-hydoxy-1-methylpyrazolyl and the like.

"Acidic functional group" means a moiety bearing an acidic hydrogen. Exemplary acid functional groups include carboxyl (—C(O)OH), —C(O)—NHOH, —C(O)—CH₂OH, —C(O)—CH₂SH, —C(O)—NH—CN, sulpho, phosphono, alkylsulphonylcarbamoyl, tetrazolyl, arylsulphonylcarbamoyl, N-methoxycarbamoyl, heteroarylsulphonylcarbamoyl, 3-hydroxy-3-cyclobutene-1,2-dione, 3,5-dioxo-1,2,4-oxadiazolidinyl or hydroxyheteroaryl such as 3-hydroxyisoxazolyl, 3-hydoxy-1-methylpyrazolyl, imidazolyl, mercapto, and the like, and an appropriate hydroxy such as an aromatic hydroxy, e.g., hydroxyphenyl.

"Acid protecting group" means an easily removable group that is known in the art to protect an acidic hydrogen of a carboxyl group against undesirable reaction during synthetic procedures, e.g., to block or protect the acid functionality while the reactions involving other functional sites of the compound are carried out, and to be selectively removable. Such acid protecting groups are well known to those skilled in the art, having been extensively used in the protection of carboxyl groups, as described in U.S. Pat. Nos. 3,840,556 and 3,719,667, the disclosures of which are hereby incorporated herein by reference. For suitable acid protecting groups, see T. W. Green and P. G. M. Wuts in "Protective Groups in Organic Chemistry" John Wiley and Sons, 1991, Acid protecting group also includes hydrogenation labile acid protecting group as defined herein. Exemplary acid protecting groups include esters such as substituted and unsubstituted $C_{1-8}$ lower alkyl, e.g., methyl, ethyl, t-butyl, methoxymethyl, methylthiomethyl, 2,2,2-trichloroethyl and the like, tetrahydropyranyl, substituted and unsubstituted phenylalkyl such as benzyl and substituted derivatives thereof such as alkoxybenzyl or nitrobenzyl groups and the like, cinnamyl, dialkylaminoalkyl, e.g., dimethylaminoethyl and the like, trimethylsilyl, substituted and unsubstituted amides and hydrazides, e.g., amides and hydrazides of N,N-dimethylamine, 7-nitroindole, hydrazine, N-phenylhydrazine and the like, acyloxyalkyl groups such as pivaloyloxymethyl or propionyloxymethyl and the like, aroyloxyalkyl such as benzoyloxyethyl and the like, alkoxycarbonylalkyl such as methoxycarbonylmethyl, cyclohexyloxycarbonylmethyl and the like, alkoxycarbonyloxyalkyl such as t-butyloxycarbonyloxymethyl and the like, alkoxycarbonylaminoalkyl such as t-butyloxycarbonylaminomethyl and the like, alkylaminocarbonylaminoalkyl, such as methylaminocarbonylaminomethyl and the like, acylaminoalkyl such as acetylaminomethyl and the like, heterocyclylcarbonyloxyalkyl such as 4-methylpiperazinyl-carbonyloxymethyl and the like, dialkylaminocarbonylalkyl such as dimethylaminocarbonyl-methyl and the like, (5-(lower alkyl)-2-oxo-1,3-dioxolen-4-yl)alkyl such as (5-t-butyl-2-oxo-1,3-dioxolen-4-yl)methyl and the like, and (5-phenyl-2-oxo-1,3-dioxolen-4-yl)alkyl such as (5-phenyl-2-oxo-1,3-dioxolen-4-yl) methyl and the like.

"Acid labile amine protecting group" means an amine protecting group as defined herein which is readily removed by treatment with acid while remaining relatively stable to other reagents. A preferred acid labile amine protecting group is BOC.

"Aliphatic" means alkyl, alkenyl or alkynyl as defined herein.

"Aliphatic group substituent(s)" mean substituents attached to an aliphatic group as defined herein inclusive of aryl, heteroaryl, hydroxy, alkoxy, cyclyloxy, aryloxy, heteroaryloxy, acyl or its thioxo analogue, cyclylcarbonyl or its thioxo analogue, aroyl or its thioxo analogue, heteroaroyl or its thioxo analogue, acyloxy, cyclylcarbonyloxy, aroyloxy, heteroaroyloxy, halo, nitro, cyano, carboxy (acid), —C(O)—NHOH, —C(O)—CH$_2$OH, —C(O)—CH$_2$SH, —C(O)—NH—CN, sulpho, phosphono, alkylsulphonylcarbamoyl, tetrazolyl, arylsulphonylcarbamoyl, N-methoxycarbamoyl, heteroarylsulphonylcarbamoyl, 3-hydroxy-3-cyclobutene-1,2-dione, 3,5-dioxo-1,2,4-oxadiazolidinyl or hydroxyheteroaryl such as 3-hydroxyisoxazolyl, 3-hydoxy-1-methylpyrazolyl, alkoxycarbonyl, cyclyloxycarbonyl, aryloxycarbonyl, heteroaryloxycarbonyl, alkylsulfonyl, cyclylsulfonyl, arylsulfonyl, heteroarylsulfonyl, alkylsulfinyl, cyclylsulfinyl, arylsulfinyl, heteroarylsulfinyl, alkylthio, cyclylthio, arylthio, heteroarylthio, cyclyl, aryldiazo, heteroaryldiazo, thiol, methylene (H$_2$C=), oxo (O=), thioxo (S=), $Y^1Y^2N—$, $Y^1Y^2NC(O)—$, $Y^1Y^2NC(O)O—$, $Y^1Y^2NC(O)NY^3—$, $Y^1Y^2NSO_2—$, or $Y^3SO_2NY^1—$ wherein $R^2$ is as defined herein, $Y^1$ and $Y^2$ are independently hydrogen, alkyl, aryl or heteroaryl, and $Y^3$ is alkyl, cycloalkyl aryl or heteroaryl, or for where the substituent is $Y^1Y^2N—$, then one of $Y^1$ and $Y^2$ may be acyl, cyclylcarbonyl, aroyl, heteroaroyl, alkoxycarbonyl, cyclyloxycarbonyl, aryloxycarbonyl or heteroaryloxycarbonyl, as defined herein and the other of $Y^1$ and $Y^2$ is as defined previously, or for where the substituent is $Y^1Y^2NC(O)—$, $Y^1Y^2NC(O)O—$, $Y^1Y^2NC(O)NY^3—$ or $Y^1Y^2NSO_2—$, $Y^1$ and $Y^2$ may also be taken together with the N atom through which $Y^1$ and $Y^2$ are linked to form a 4 to 7 membered azaheterocyclyl or azaheterocyclenyl. Acidic/amide aliphatic group substituents are carboxy (acid), —C(O)—NHOH, —C(O)—CH$_2$OH, —C(O)—CH$_2$SH, —C(O)—NH—CN, sulpho, phosphono, alkylsulphonylcarbamoyl, tetrazolyl, arylsulphonylcarbamoyl, N-methoxycarbamoyl, heteroarylsulphonylcarbamoyl, 3-hydroxy-3-cyclobutene-1,2-dione, 3,5-dioxo-1,2,4-oxadiazolidinyl or hydroxyheteroaryl such as 3-hydroxyisoxazolyl, 3-hydoxy-1-methylpyrazolyl and $Y^1Y^2NCO—$. Non-acidic polar aliphatic group substituents are hydroxy, oxo (O=), thioxo (S=), acyl or its thioxo analogue, cyclylcarbonyl or its thioxo analogue, aroyl or its thioxo analogue, heteroaroyl or its thioxo analogue, alkoxycarbonyl, cyclyloxycarbonyl, aryloxycarbonyl, heteroaryloxycarbonyl, acyloxy, cyclylcarbonyloxy, aroyloxy, heteroaroyloxy, alkylsulfonyl, cyclylsulfonyl, arylsulfonyl, heteroarylsulfonyl, alkylsulfinyl, cyclylsulfinyl, arylsulfinyl, heteroarylsulfinyl, thiol, $Y^1Y^2N—$, $Y^1Y^2NC(O)—$, $Y^1Y^2NC(O)O—$, $Y^1Y^2NC(O)NY^3—$ or $Y^1Y^2NSO_2—$. Exemplary aliphatic groups bearing an aliphatic group substituent include methoxymethoxy, methoxyethoxy, ethoxyethoxy, (methoxy-, benzyloxy-, phenoxy-, or ethoxy-)carbonyl(methyl or ethyl), benzyloxycarbonyl, pyridylmethyloxy-carbonylmethyl, methoxyethyl, ethoxymethyl, n-butoxymethyl, cyclopentylmethyloxyethyl, phenoxypropyl, phenoxyallyl, trifluoromethyl, cyclopropylmethyl, cyclopentylmethyl, carboxy(methyl or ethyl), 2-phenethenyl, benzyloxy, 1- or 2-naphthyl-methoxy, 4-pyridyl-methyloxy, benzyloxyethyl, 3-benzyloxyallyl, 4-pyridylmethyl-oxyethyl, 4-pyridylmethyl-oxyallyl, benzyl, 2-phenethyl, naphthylmethyl, styryl, 4-phenyl-1,3-pentadienyl, phenyl-propynyl, 3-phenylbut-2-ynyl, pyrid-3-ylacetylenyl and quinolin-3-ylacetylenyl, 4-pyridyl-ethynyl, 4-pyridylvinyl, thienylethenyl, pyridylethenyl, imidazolylethenyl, pyrazinylethenyl, pyridylpentenyl, pyridylhexenyl and pyridylheptenyl, thienyl-methyl, pyridylmethyl, imidazolylmethyl, pyrazinylmethyl, tetrahydropyranylmethyl, tetrahydropyranyl-methyloxymethyl, and the like.

"Acyl" means an H—CO— or (aliphatic or cyclyl)-CO— group wherein the aliphatic group is as herein described. Preferred acyls contain a lower alkyl. Exemplary acyl groups include formyl, acetyl, propanoyl, 2-methylpropanoyl, butanoyl, palmitoyl, acryloyl, propynoyl, cyclohexylcarbonyl, and the like.

"Alkenoyl" means an alkenyl-CO— group wherein alkenyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain that may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl, decenyl, and the like. "Substituted alkenyl" means an alkenyl group as defined above which is substituted with one or more "aliphatic group substituents" (preferably 1 to 3) which may be the same or different and are as defined herein. Exemplary alkenyl alphatic group substituents include halo or cycloalkyl groups "Alkenyloxy" means an alkenyl-O— group wherein the alkenyl group is as herein described. Exemplary alkenyloxy groups include allyloxy, 3-butenyloxy, and the like.

"Alkoxy" means an alkyl-O— group wherein the alkyl group is as herein described. Exemplary alkoxy groups include methoxy, ethoxy, n-propoxy, i-propoxy, n-butoxy, heptoxy, and the like.

"Alkoxycarbonyl" means an alkyl-O—CO— group, wherein the alkyl group is as herein defined. Exemplary alkoxycarbonyl groups include methoxycarbonyl, ethoxycarbonyl, t-butyloxycarbonyl, and the like.

"Alkyl" means an aliphatic hydrocarbon group which may be straight or branched having about 1 to about 20 carbon atoms in the chain. Preferred alkyl groups have 1 to about 12 carbon atoms in the chain, more preferred is lower alkyl as defined herein. Branched means that one or more lower alkyl groups such as methyl, ethyl or propyl are attached to a linear alkyl chain. "Lower alkyl" means about 1 to about 4 carbon atoms in the chain that may be straight or branched. "Substituted alkyl" means an alkyl group as defined above which is substituted with one or more "aliphatic group substituents" (preferably 1 to 3) which may be the same or different, and are as defined herein.

"Alkylsulfinyl" means an alkyl-SO— group wherein the alkyl group is as defined above. Preferred groups are those wherein the alkyl group is lower alkyl.

"Alkylsulfonyl" means an alkyl-$SO_2$-group wherein the Alkyl group is as defined above. Preferred groups are those wherein the Alkyl group is lower alkyl.

"Alkylsulphonylcarbamoyl" means an alkyl-$SO_2$—NH—C(=O)— group wherein the alkyl group is as herein described. Preferred alkylsulphonylcarbamoyl groups are those wherein the alkyl group is lower alkyl.

"Alkylthio" means an alkyl-S— group wherein the alkyl group is as herein described. Exemplary alkylthio groups include methylthio, ethylthio, i-propylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Branched means that one or more lower alkyl groups such as methyl, ethyl or propyl are attached to a linear alkynyl chain. "Lower alkynyl" means about 2 to about 4 carbon atoms in the chain that may be straight or branched. The alkynyl group may be substituted by one or more halo. Exemplary alkynyl groups include ethynyl, propynyl, n-butynyl, 2-butynyl, 3-methylbutynyl, n-pentynyl, heptynyl, octynyl, decynyl, and the like. "Substituted alkynyl" means alkynyl as defined above which is substituted with one or more "aliphatic group substituents" (preferably 1 to 3) which may be the same or different, and are as defined herein.

"Amine protecting group" means an easily removable group that is known in the art to protect a nitrogen moiety of an amino or amide group against undesirable reaction during synthetic procedures and to be selectively removable. The use of amine/amide protecting groups is well known in the art for protecting groups against undesirable reactions during a synthetic procedure and many such protecting groups are known, for example, T. W. Greene and P. G. M. Wuts, Protective Groups in Organic Synthesis, 2nd edition, John Wiley & Sons, New York (1991), incorporated herein by reference. Amine/amide protecting group also includes "acid labile amine/amide protecting group" and "hydrogenation labile amine/amide protecting group". Exemplary amine/amide protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxy-carbonyl, 9-fluorenylmethoxycarbonyl, 2,2,2-trifluoroethoxycarbonyl, 2-trimethylsilylethoxy-carbonyl, vinyloxycarbonyl, allyloxycarbonyl, t-butyloxycarbonyl (BOC), 1,1-dimethyl-propynyloxycarbonyl, benzyloxycarbonyl (CBZ), p-nitrobenzyloxycarbonyl, 2,4-dichloro-benzyloxycarbonyl, and the like.

"Amide protecting group" means an easily removable group that is known in the art to protect a nitrogen moiety of an amide group against undesirable reaction during synthetic procedures and to be selectively removable after its conversion to the amine. The use of amide protecting groups is well known in the art for protecting groups against undesirable reactions during a synthetic procedure and many such protecting groups are known, for example, T. W. Greene and P. G. M. Wuts, Protective Groups in Organic Synthesis, 2nd edition, John Wiley & Sons, New York (1991), incorporated herein by reference. Amide protecting group also includes "acid labile amide protecting group" and "hydrogenation labile amide protecting group". Exemplary amide protecting groups are o-nitrocinnamoyl, picolinoyl, aminocaproyl, benzoyl and the like, and acyloxy including methoxy-carbonyl, 9-fluorenylmethoxycarbonyl, 2,2,2-trifluoroethoxycarbonyl, 2-trimethylsilylethoxy-carbonyl, vinyloxycarbonyl, allyloxycarbonyl, t-butyloxycarbonyl (BOC), 1,1-dimethyl-propynyloxycarbonyl, benzyloxycarbonyl (CBZ), p-nitrobenzyloxycarbonyl, 2,4-dichloro-benzyloxycarbonyl, and the like.

"Amino acid" means an amino acid selected from the group consisting of natural and unnatural amino acids as defined herein. Amino acid is also meant to include -amino acids having L or D stereochemistry at the α-carbon. Preferred amino acids are those possessing an α-amino group. The amino acids may be neutral, positive or negative depending on the substituents in the side chain. "Neutral amino acid" means an amino acid containing uncharged side chain substituents. Exemplary neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Exemplary positive amino acids include lysine, arginine and histidine. "Negative amino acid" means an amino acid in which the side chain substituents bear a net negative charge at physiological pH. Exemplary negative amino acids include aspartic acid and glutamic acid. Preferred amino acids are α-amino acids. Exemplary natural amino acids are isoleucine, proline, phenylalanine, tryptophan, methionine, glycine, serine, threonine, cysteine, tyrosine, asparagine, glutamine, lysine, arginine, histidine, aspartic acid and glutamic acid. Unnatural amino acid" means an amino acid for which there is no nucleic acid codon. Exemplary unnatural amino acids include, for example, the D-isomers of the natural α-amino acids as indicated above; Aib (aminobutyric acid), βAib (3-amino-isobutyric acid), Nva (norvaline), β-Ala, Aad (2-aminoadipic acid), βAad (3-aminoadipic acid), Abu (2-aminobutyric acid), Gaba (γ-aminobutyric acid), Acp (6-aminocaproic acid), Dbu (2,4-diaminobutryic acid), α-aminopimelic acid, TMSA (trimethylsilyl-Ala), aIle (allo-isoleucine), Nle (norleucine), tert-Leu, Cit (citrulline), Orn, Dpm (2,2'-diaminopimelic acid), Dpr (2,3-diaminopropionic acid), α- or β- Nal, Cha (cyclohexyl-Ala), hydroxyproline, Sar (sarcosine), and the like; cyclic amino acids; $N^a$-alkylated amino acids such as MeGly ($N^a$-methylglycine), EtGly ($N^a$-ethylglycine) and EtAsn ($N^a$-ethylasparagine); and amino acids in which the α-carbon bears two side-chain substituents. The names of natural and unnatural amino acids and residues thereof used herein follow the naming conventions suggested by the IUPAC Commission on the Nomenclature of Organic Chemistry and the IUPAC-IUB Commission on Biochemical Nomenclature as set out in "Nomenclature of a-Amino Acids (Recommendations, 1974)" Biochemistry, 14(2), (1975). To the extent that the names and abbreviations of amino acids and residues thereof employed in this specification and appended claims differ from those noted, differing names and abbreviations will be made clear.

"Amino acid protecting group" mean a group that protects an acid or amine moiety of the amino acid or other reactive moiety on the side chain of an amino acid, e.g., hydroxy or thiol. For examples of "corresponding protected derivatives" of amino acid side chains, see T. W. Green and P. G. M. Wuts in "Protective Groups in Organic Chemistry" John Wiley and Sons, 1991. Protecting groups for an acid group in an amino acid are described herein, for example in the sections "acidic functional group" and "hydrogenation labile acid protecting group". Protecting groups for an amine group in an amino acid are described herein, for example in the sections "amine protecting group", "acid labile amine protecting group" and "hydrogenation labile amine protecting group".

"Amino acid residue" means the individual amino acid units incorporated into the compound of the invention.

"Amino acid side chain" means the substituent found on the carbon between the amino and carboxy groups in α-amino acids. Exemplary •-amino acid side chains include isopropyl, methyl, and carboxymethyl for valine, alanine, and aspartic acid, respectively.

"Amino acid equivalent" means an amino acid that may be substituted for another amino acid in the peptides according to the invention without any appreciable loss of function. In making such changes, substitutions of like amino acids are made on the basis of relative similarity of side chain substituents, for example regarding size, charge, hydrophilicity, hydropathicity and hydrophobicity as described herein.

"Aromatic group" means aryl or heteroaryl as defined herein. Exemplary aromatic groups include phenyl, halo substituted phenyl, azaheteroaryl, and the like.

"Aroyl" means an aryl-CO— group wherein the aryl group is as herein described. Exemplary aroyl groups include benzoyl, 1- and 2-naphthoyl, and the like.

"Aryl" means an aromatic monocyclic or multicyclic ring system of about 6 to about 14 carbon atoms, preferably of about 6 to about 10 carbon atoms. Encompassed by aryl are fused arylcycloalkenyl, fused arylcycloalkyl, fused arylheterocyclenyl and fused arylheterocyclyl as defined herein when bonded through the aryl moiety thereof. The aryl is optionally substituted with one or more "ring group substituents" which may be the same or different, and are as defined herein. Exemplary aryl groups include phenyl or naphthyl, or phenyl substituted or naphthyl substituted. "Substituted aryl" means an aryl group as defined above which is substituted with one or more "ring group substituents" (preferably 1 to 3) which may be the same or different and are as defined herein.

"Aryldiazo" means an aryl-diazo- group wherein the aryl and diazo groups are as defined herein.

"Arylene" means an optionally substituted 1,2-, 1,3-, 1,4-, bivalent aryl group, wherein the aryl group is as defined herein. Exemplary arylene groups include optionally substituted phenylene, naphthylene and indanylene. A particular arylene is optionally substituted phenylene. "Substituted arylene" means an arylene group as defined above which is substituted with one or more "ring group substituents" (preferably 1 to 3) which may be the same or different and are as defined herein.

"Aryloxy" means an aryl-O— group wherein the aryl group is as defined herein. Exemplary aryloxy groups include phenoxy and 2-naphthyloxy.

"Aryloxycarbonyl" means an aryl-O—CO— group wherein the aryl group is as defined herein. Exemplary aryloxycarbonyl groups include phenoxycarbonyl and naphthoxycarbonyl.

"Arylsulfonyl" means an aryl-SO$_2$— group wherein the aryl group is as defined herein.

"Arylsulphonylcarbamoyl" means an aryl-SO$_2$—NH—C (=O)— group wherein the aryl group is as herein described. An exemplary arylsulphonylcarbamoyl group is phenylsulphonylcarbamoyl.

"Arylsulfinyl" means an aryl-SO— group wherein the aryl group is as defined herein.

"Arylthio" means an aryl-S— group wherein the aryl group is as herein described. Exemplary arylthio groups include phenylthio and naphthylthio.

"Basic nitrogen atom" means a $sp^2$ or $sp^3$ hybridized nitrogen atom having a non-bonded pair of electrons which is capable of being protonated. Exemplary basic nitrogen atoms include optionally substituted imino, optionally substituted amino and optionally substituted amidino groups.

"Carboxy" means an HO(O)C— (carboxylic acid) group.

"Coupling agent" means a compound that reacts with the hydroxyl moiety of a carboxy moiety thereby rendering it susceptible to nucleophilic attack. Exemplary coupling agents include DIC, EDCI, DCC, and the like.

"Cycloalkenyl" means a non-aromatic mono- or multicyclic ring system of about 3 to about 10 carbon atoms, preferably of about 5 to about 10 carbon atoms, and which contains at least one carbon-carbon double bond. Encompassed by cycloalkenyl are fused arylcycloalkenyl and fused heteroarylcycloalkenyl as defined herein when bonded through the cycloalkenyl moiety thereof. Preferred ring sizes of rings of the ring system include about 5 to about 6 ring atoms; and such preferred ring sizes are also referred to as "lower". "Substituted cycloalkenyl" means an cycloalkyenyl group as defined above which is substituted with one or more "ring group substituents" (preferably 1 to 3) which may be the same or different and are as defined herein. Exemplary monocyclic cycloalkenyl include cyclopentenyl, cyclohexenyl, cycloheptenyl, and the like. An exemplary multicyclic cycloalkenyl is norbornylenyl.

"Cycloalkyl" means a non-aromatic mono- or multicyclic ring system of about 3 to about 10 carbon atoms, preferably of about 5 to about 10 carbon atoms. Preferred ring sizes of rings of the ring system include about 5 to about 6 ring atoms; and such preferred ring sizes are also referred to as "lower". Encompassed by cycloalkyl are fused arylcycloalkyl and fused heteroarylcycloalkyl as defined herein when bonded through the cycloalkyl moiety thereof. "Substituted cycloalkyl" means a cycloalkyl group as defined above which is substituted with one or more "ring group substituents"

(preferably 1 to 3) which may be the same or different and are as defined herein. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

"Cycloalkylene" means a bivalent cycloalkyl group as defined herein having about 4 to about 8 carbon atoms. Preferred ring sizes of the cycloalkylene include about 5 to about 6 ring atoms; and such preferred ring sizes are also referred to as "lower". The points of binding on the cycloalkylene group include 1,1-, 1,2-, 1,3-, or 1,4-binding patterns, and where applicable the stereochemical relationship of the points of binding is either cis or trans. Exemplary cycloalkylene groups include (1,1-, 1,2- or 1,3-)cyclohexylene and (1,1- or 1,2-)cyclopentylene. "Substituted cycloalkylene" means an cycloalkylene group as defined above which is substituted with one or more "ring group substituents" (preferably 1 to 3) which may be the same or different and are as defined herein "Cyclic" or "Cyclyl" means cycloalkyl, cycloalkenyl, heterocyclyl or heterocyclenyl as defined herein. The term "lower" as used in connection with the term cyclic is the same as noted herein regarding the cycloalkyl, cycloalkenyl, heterocyclyl or heterocyclenyl.

"Cyclyloxy" means a cyclyl-O— group wherein the cyclyl group is as herein described. Exemplary cycloalkoxy groups include cyclopentyloxy, cyclohexyloxy, quinuclidyloxy, pentamethylenesulfideoxy, tetrahydropyranyloxy, tetrahydrothiophenyloxy, pyrrolidinyloxy, tetrahydrofuranyloxy or 7-oxabicyclo[2.2.1]heptanyloxy, hydroxytetrahydropyranyloxy, hydroxy-7-oxabicyclo[2.2.1]heptanyloxy, and the like.

"Cyclylsulfinyl" means a cyclyl-S(O)— group wherein the cyclyl group is as herein described.

"Cyclylsulfonyl" means a cyclyl-S(O)$_2$— group wherein the cyclyl group is as herein described.

"Cyclylthio" means a cyclyl-S— group wherein the cyclyl group is as herein described.

"Diazo" means a bivalent —N=N— radical.

"Displaceable moiety" means a group that where associated with L as defined herein is subject to being displaced by nucleophilic attack by a mono- or di-substituted amine moiety with or without the presence of an agent that facilitates said attack, e.g., coupling agent. Exemplary displaceable moieties include hydroxy, aliphatic oxy, halo, N-oxysuccinimide, acyloxy, and the like.

"Effective amount" is means an amount of a compound/composition according to the present invention effective in producing the desired therapeutic effect.

"Fused arylcycloalkenyl" means a fused aryl and cycloalkenyl as defined herein. Preferred fused arylcycloalkenyls are those wherein the aryl thereof is phenyl and the cycloalkenyl consists of about 5 to about 6 ring atoms. A fused arylcycloalkenyl as a variable may be bonded through any atom of the ring system thereof capable of such. "Substituted fused arylcycloalkenyl" means a fused arylcycloalkenyl group as defined above which is substituted with one or more "ring group substituents" (preferably 1 to 3) which may be the same or different and are as defined herein. Exemplary fused arylcycloalkenyl include 1,2-dihydronaphthylene, indene, and the like.

"Fused arylcycloalkyl" means a fused aryl and cycloalkyl as defined herein. Preferred fused arylcycloalkyls are those wherein the aryl thereof is phenyl and the cycloalkyl consists of about 5 to about 6 ring atoms. A fused arylcycloalkyl as a variable may be bonded through any atom of the ring system thereof capable of such. "Substituted fused arylcycloalkyl" means a fused arylcycloalkyl group as defined above which is substituted with one or more "ring group substituents" (preferably 1 to 3) which may be the same or different and are as defined herein. Exemplary fused arylcycloalkyl includes 1,2,3,4tetrahydro-naphthylene, and the like.

"Fused arylheterocyclenyl" means a fused aryl and heterocyclenyl as defined herein. Preferred fused arylheterocyclenyls are those wherein the aryl thereof is phenyl and the heterocyclenyl consists of about 5 to about 6 ring atoms. A fused arylheterocyclenyl as a variable may be bonded through any atom of the ring system thereof capable of such. The designation of the aza, oxa or thia as a prefix before heterocyclenyl portion of the fused arylheterocyclenyl define that at least a nitrogen, oxygen or sulfur atom is present, respectively, as a ring atom. "Substituted fused arylheterocyclenyl" means a fused arylheterocyclenyl group as defined above which is substituted with one or more "ring group substituents" (preferably 1 to 3) which may be the same or different and are as defined herein. The nitrogen atom of a fused arylheterocyclenyl may be a basic nitrogen atom. The nitrogen or sulfur atom of the heterocyclenyl portion of the fused arylheterocyclenyl may also be optionally oxidized to the corresponding N-oxide, S-oxide or S,S-dioxide. Exemplary fused arylheterocyclenyl include 3H-indolinyl, 1H-2-oxoquinolyl, 2H-1-oxoisoquinolyl, 1,2-di-hydroquinolinyl, 3,4-dihydroquinolinyl, 1,2-dihydroisoquinolinyl, 3,4-dihydroisoquinolinyl, and the like.

"Fused arylheterocyclyl" means a fused aryl and heterocyclyl as defined herein. Preferred fused arylheterocyclyls are those wherein the aryl thereof is phenyl and the heterocyclyl consists of about 5 to about 6 ring atoms. A fused arylheterocyclyl as a variable may be bonded through any atom of the ring system thereof capable of such. The designation of the aza, oxa or thia as a prefix before heterocyclyl portion of the fused arylheterocyclyl define that at least a nitrogen, oxygen or sulfur atom is present, respectively, as a ring atom. "Substituted fused arylheterocyclyl" means a fused arylheterocyclyl group as defined above which is substituted with one or more "ring group substituents" (preferably 1 to 3) which may be the same or different and are as defined herein. The nitrogen atom of a fused arylheterocyclyl may be a basic nitrogen atom. The nitrogen or sulfur atom of the heterocyclyl portion of the fused arylheterocyclyl may also be optionally oxidized to the corresponding N-oxide, S-oxide or S,S-dioxide. Exemplary fused arylheterocyclyl ring systems include indolinyl, 1,2,3,4-tetrahydroisoquinoline, 1,2,3,4-tetrahydroquinoline, 1H-2,3-dihydroisoindol-2-yl, 2,3-dihydrobenz[f]isoindol-2-yl, 1,2,3,4-tetrahydrobenz[g]-isoquinolin-2-yl, and the like.

"Fused heteroarylcycloalkenyl" means a fused heteroaryl and cycloalkenyl as defined herein. Preferred fused heteroarylcycloalkenyls are those wherein the heteroaryl thereof is phenyl and the cycloalkenyl consists of about 5 to about 6 ring atoms. A fused heteroaryl-cycloalkenyl as a variable may be bonded through any atom of the ring system thereof capable of such. The designation of the aza, oxa or thia as a prefix before heteroaryl portion of the fused heteroarylcycloalkenyl define that at least a nitrogen, oxygen or sulfur atom is present, respectively, as a ring atom "Substituted fused heteroarylcycloalkenyl" means a fused heteroarylcycloalkyenyl group as defined above which is substituted with one or more "ring group substituents" (preferably 1 to 30 which may be the same or different and are as defined herein. The nitrogen atom of a fused heteroarylcycloalkenyl may be a basic nitrogen atom. The nitrogen atom of the heteroaryl portion of the fused heteroarylcycloalkenyl may also be optionally oxidized to the corresponding N-oxide. Exemplary fused heteroarylcyclo-alkenyl include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-di-hydrobenzoxazolyl, and the like.

"Fused heteroarylcycloalkyl" means a fused heteroaryl and cycloalkyl as defined herein. Preferred fused heteroarylcycloalkyls are those wherein the heteroaryl thereof consists of about 5 to about 6 ring atoms and the cycloalkyl consists of about 5 to about 6 ring atoms. A fused heteroarylcycloalkyl as a variable may be bonded through any atom of the ring system thereof capable of such. The designation of the aza, oxa or thia as a prefix before heteroaryl portion of the fused heteroarylcycloalkyl define that at least a nitrogen, oxygen or sulfur atom is present, respectively, as a ring atom. "Substituted fused heteroarylcycloalkyl" means a fused heteroarylcycloalkyl group as defined above which is substituted with one or more "ring group substituents" (preferably 1 to 3) which may be the same or different and are as defined herein. The nitrogen atom of a fused heteroarylcycloalkyl may be a basic nitrogen atom. The nitrogen atom of the heteroaryl portion of the fused heteroarylcycloalkyl may also be optionally oxidized to the corresponding N-oxide. Exemplary fused heteroarylcycloalkyl include 5,6,7,8-tetrahydroquinolinyl, 5,6,7,8-tetra-hydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like.

"Fused heteroarylheterocyclenyl" means a fused heteroaryl and heterocyclenyl as defined herein. Preferred fused heteroarylheterocyclenyls are those wherein the heteroaryl thereof consists of about 5 to about 6 ring atoms and the heterocyclenyl consists of about 5 to about 6 ring atoms. A fused heteroarylheterocyclenyl as a variable may be bonded through any atom of the ring system thereof capable of such. The designation of the aza, oxa or thia as a prefix before the heteroaryl or heterocyclenyl portion of the fused heteroaryl-hetero-cyclenyl define that at least a nitrogen, oxygen or sulfur atom is present, respectively, as a ring atom. "Substituted fused heteroarylheterocyclenyl" means a fused heteroarylheterocyclenyl group as defined above which is substituted with one or more "ring group substituents" (preferably 1 to 3) which may be the same or different and are as defined herein. The nitrogen atom of a fused heteroarylazaheterocyclenyl may be a basic nitrogen atom. The nitrogen or sulfur atom of the heteroaryl portion of the fused heteroarylheterocyclyl may also be optionally oxidized to the corresponding N-oxide. The nitrogen or sulfur atom of the heteroaryl or heterocyclyl portion of the fused heteroarylheterocyclyl may also be optionally oxidized to the corresponding N-oxide, S-oxide or S,S-dioxide. Exemplary fused heteroarylheterocyclenyl include 7,8-dihydro[1,7] naphthyridinyl, 1,2-dihydro[2,7]-naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyrdinyl, 1,2-dihydro-2,6-naphthyridinyl, and the like.

"Fused heteroarylheterocyclyl" means a fused heteroaryl and heterocyclyl as defined herein. Preferred fused heteroarylheterocyclyls are those wherein the heteroaryl thereof consists of about 5 to about 6 ring atoms and the heterocyclyl consists of about 5 to about 6 ring atoms. A fused heteroarylheterocyclyl as a variable may be bonded through any atom of the ring system thereof capable of such. The designation of the aza, oxa or thia as a prefix before the heteroaryl or heterocyclyl portion of the fused heteroarylheterocyclyl define that at least a nitrogen, oxygen or sulfur atom is present, respectively, as a ring atom. "Substituted fused heteroarylheterocyclyl" means a fused heteroarylheterocyclyl group as defined above which is substituted with one or more "ring group substituents" (preferably 1 to 3) which may be the same or different and are as defined herein The nitrogen atom of a fused heteroarylheterocyclyl may be a basic nitrogen atom. The nitrogen or sulfur atom of the heteroaryl portion of the fused heteroarylheterocyclyl may also be optionally oxidized to the corresponding N-oxide. The nitrogen or sulfur atom of the heteroaryl or heterocyclyl portion of the fused heteroarylheterocyclyl may also be optionally oxidized to the corresponding N-oxide, S-oxide or S,S-dioxide. Exemplary fused heteroarylheterocyclyl include 2,3-dihydro-1H pyrrol[3,4-b]quinolin-2-yl, 1,2,3,4-tetrahydrobenz [b][1,7]naphthyridin-2-yl, 1,2,3,4-tetrahydrobenz [b][1,6]naphthyridin-2-yl, 1,2,3,4-tetra-hydro -9H-pyrido[3,4-b]indol-2yl, 1,2,3,4-tetrahydro-9H-pyrido[4,3-b]indol-2yl, 2,3-dihydro-1H-pyrrolo[3,4-b]indol-2-yl, 1H-2,3,4,5-tetrahydroazepino[3,4-b]indol-2-yl, 1H-2,3,4,5-tetra-hydroazepino [4,3-b]indol-3-yl, 1H-2,3,4,5-tetrahydroazepino[4,5-b]indol-2 yl, 5,6,7,8-tetra-hydro [1,7]napthyridyl, 1,2,3,4-tetrhydro[2,7] naphthyridyl, 2,3-dihydro[1,4]dioxino[2,3-b]pyridyl, 2,3-dihydro-[1,4]dioxino[2,3-b]pyridyl, 3,4-dihydro-2H-1-oxa [4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]-napthyridinyl, 1,2,3,4-tetrahydro[1,6] napthyridinyl, 1,2,3,4-tetrahydro[1,7]naphthyridinyl, 1,2,3,4-tetrahydro[1,8]napthyridinyl, 1,2,3,4-tetra-hydro[2,6] napthyridinyl, and the like.

"Halo" means fluoro, chloro, bromo, or iodo. Preferred are fluoro, chloro or bromo, and more preferred are fluoro or chloro.

"Heteroaroyl" means an heteroaryl-CO— group wherein the heteroaryl group is as herein described. Exemplary heteroaroyl groups include thiophenoyl, nicotinoyl, pyrrol-2-ylcarbonyl, 1- and 2-naphthoyl, pyridinoyl, and the like."

"Heteroaryl" means an aromatic monocyclic or multicyclic ring system of about 5 to about 14 carbon atoms, preferably about 5 to about 10 carbon atoms, in which one or more of the carbon atoms in the ring system is/are hetero element(s) other than carbon, for example nitrogen, oxygen or sulfur. Preferably the ring system includes 1 to 3 heteroatoms. Preferred ring sizes of rings of the ring system include about 5 to about 6 ring atoms. Encompassed by heteroaryl are fused heteroarylcycloalkenyl, fused heteroarylcycloalkyl, fused heteroarylheterocyclenyl and fused heteroarylheterocyclyl as defined herein when bonded through the heteroaryl moiety thereof. "Substituted heteroaryl" means a heteroaryl group as defined above which is substituted with one or more "ring group substituents" (preferably 1 to 3) which may be the same or different and are as defined herein. The designation of the aza, oxa or thia as a prefix before heteroaryl define that at least a nitrogen, oxygen or sulfur atom is present, respectively, as a ring atom. A nitrogen atom of an heteroaryl may be a basic nitrogen atom and may also be optionally oxidized to the corresponding N-oxide. Exemplary heteroaryl and substituted heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a] pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindolyl, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl, triazolyl, and the like. A preferred heteroaryl group is pyrazinyl.

"Heteroaryldiazo" means an heteroaryl-azo-group wherein the heteroaryl and azo groups are as defined herein.

"Heteroaryldiyl" means a bivalent radical derived from a heteroaryl, wherein the heteroaryl is as described herein. An exemplary heteroaryldiyl radical is optionally substituted pyridinediyl.

"Heteroarylsulphonylcarbamoyl" means a heteroaryl-SO$_2$—NH—C(=O)— group wherein the heteroaryl group is as herein described.

"Heterocyclenyl" means a non-aromatic monocyclic or multicyclic hydrocarbon ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Preferably, the ring includes 1 to 3 heteroatoms. Preferred ring sizes of rings of the ring system include about 5 to about 6 ring atoms; and such preferred ring sizes are also referred to as "lower". Encompassed by heterocyclenyl are fused arylheterocyclenyl and fused heteroarylheterocyclenyl as defined herein when bonded through the heterocyclenyl moiety thereof. The designation of the aza, oxa or thia as a prefix before heterocyclenyl define that at least a nitrogen, oxygen or sulfur atom is present, respectively, as a ring atom. "Substituted heterocyclenyl" means a heterocyclenyl group as defined above which is substituted with one or more "ring group substituents" (preferably 1 to 3) which may be the same or different and are as defined herein. The nitrogen atom of an heterocyclenyl may be a basic nitrogen atom. The nitrogen or sulfur atom of the heterocyclenyl may also be optionally oxidized to the corresponding N-oxide, S-oxide or S,S-dioxide. Exemplary monocyclic azaheterocyclenyl groups include 1,2,3,4-tetrahydrohydropyridine, 1,2-dihydropyridyl, 1,4-dihydropyridyl, 1,2,3,6-tetra-hydropyridine, 1,4,5,6-tetrahydro-pyrimidine, 2-pyrrolinyl, 3-pyrrolinyl, 2-imidazolinyl, 2-pyrazolinyl, and the like. Exemplary oxaheterocyclenyl groups include 3,4-dihydro-2H-pyran, dihydrofuranyl, and fluorodihydro-furanyl. An exemplary multicyclic oxaheterocyclenyl group is 7-oxabicyclo[2.2.1] heptenyl. Exemplary monocyclic thiaheterocyclenyl rings include dihydrothiophenyl and dihydrothiopyranyl.

"Heterocyclyl" means a non-aromatic saturated monocyclic or multicyclic ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur. Preferably, the ring system contains from 1 to 3 heteroatoms. Preferred ring sizes of rings of the ring system include about 5 to about 6 ring atoms; and such preferred ring sizes are also referred to as "lower". Encompassed by heterocyclyl are fused arylheterocyclyl and fused heteroarylheterocyclyl as defined herein when bonded through the heterocyclyl moiety thereof. The designation of the aza, oxa or thia as a prefix before heterocyclyl define that at least a nitrogen, oxygen or sulfur atom is present respectively as a ring atom. "Substituted heterocyclyl" means a heterocyclyl group as defined above which is substituted with one or more "ring group substituents" (preferably 1 to 3) which may be the same or different and are as defined herein The nitrogen atom of an heterocyclyl may be a basic nitrogen atom. The nitrogen or sulfur atom of the heterocyclyl may also be optionally oxidized to the corresponding N-oxide, S-oxide or S,S-dioxide. Exemplary monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

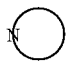

as substituted monocyclic azaheterocyclyl is substituted directly or through a linker by at least one substituent that is, or encompasses, or is substituted by an aromatic group as defined herein; for example aryl, heteroaryl, aryloxy, heteroaryloxy, aroyl or its thioxo analogue, heteroaroyl or its thioxo analogue, aroyloxy, heteroaroyloxy, aryloxycarbonyl, heteroaryloxycarbonyl, arylsulfonyl, heteroarylsulfonyl, arylsulfinyl, heteroarylsulfinyl, arylthio, heteroarylthio, aryldiazo, heteroaryldiazo, Y$^1$Y$^2$N—, Y$^1$Y$^2$NC(O)—, Y$^1$Y$^2$NC(O)O—, Y$^1$Y$^2$NC(O)NY$^3$— or Y$^1$Y$^2$NSO$_2$— wherein at least one of Y$^1$ and Y$^2$ is, encompasses or is substituted by an aryl or heteroaryl moiety. Preferred linkers include —C(O)—, —OC(O)—, lower alkyl, lower alkoxy, lower alkenyl, —O—, —S—, —C(O)C(O)—, —S(O)—, —S(O)$_2$—, —NR$^{80}$—, where R$^{80}$ is hydrogen, alkyl, cycloalkyl, aryl, aralkyl, heterocyclyl or heteroaryl. Particularly preferred linkers are —C(O)— and —OC(O)—. "Substituted multicyclic azaheterocyclyl" means a multicyclic azaheterocyclyl group as defined above which is substituted with one or more "ring group substituents" (preferably 1 to 3) which may be the same or different and are as defined herein. "Substituted multicyclic azaheterocyclenyl" means a multicyclic azaheterocyclenyl group as defined above which is substituted with one or more "ring group substituents" (preferably 1 to 3) which may be the same or different and are as defined herein.

"Heterocyclylene" means a bivalent heterocyclyl group as defined herein having about 4 to about 8 carbon atoms. Preferred ring sizes of the heterocyclylene include about 5 to about 6 ring atoms; and such preferred ring sizes are also referred to as "lower". The points of binding on the cycloalkylene group include 1,1-, 1,2-, 1,3-, or 1,4-binding patterns, and where applicable the stereochemical relationship of the points of binding is either cis or trans. Exemplary heterocyclylene groups include (1,1-, 1,2- or 1,3-)piperidinylene and (1,1- or 1,2-)tetrahydrofuranylene. "Substituted heterocyclylene" means a heterocyclylene group as defined above which is substituted with one or more "ring group substituents" (preferably 1 to 3) which may be the same or different and are as defined herein.

"Hydrate" means a solvate wherein the solvent molecule(s) is/are H$_2$O.

"Hydrogenation labile amine protecting group" means an amine protecting group as defined herein which is readily removed by hydrogenation while remaining relatively stable to other reagents. A preferred hydrogenation labile amine protecting group is Cbz.

"Hydrogenation labile acid protecting group" means an acid protecting group as defined herein which is readily removed by hydrogenation while remaining relatively stable to other reagents. A preferred hydrogenation labile acid protecting group is benzyl.

"Hygroscopicity" means sorption, implying an acquired amount or state of water sufficient to affect the physical or chemical properties of the substance (Eds. J. Swarbrick and J. C. Boylan, Encyclopedia of Pharmaceutical Technology, 10, 33).

"Iminic glycinimide derivative" means an iminic Schiff base of a glycine that is useful in the synthesis of of α-amino acids, both natural and unnatural. The iminic ester functionality may contain one or more assymetric centers that may aid in stereoinduction during the bond formating process. In addition, these iminic glycinimide derivatives may be incorporated onto polymeric supports to facilitate combinatorial synthesis. Iminic glycinimide derivatives may be prepared by condensing a glycine ester with the appropropriate ketone in the presence of an acid catalyst. The reaction is facilitated by the removal of water. Iminic glycinimide derivatives are well known in the art for use in Michael Addition synthetic procedures, for example as disclosed by Guillena, G., et al., *J. Org. Chem.* 2000, 65, 7310-7322, herein incorporated by reference. Particular examples of iminic glycinimide derivatives according to the invention include one selected from the group of formulae

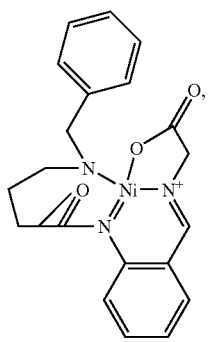

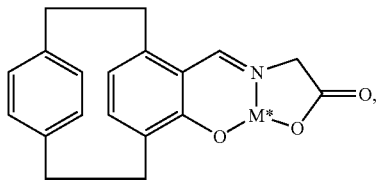

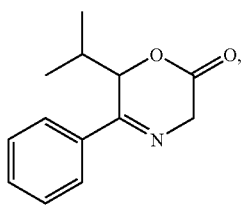 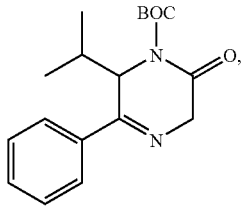

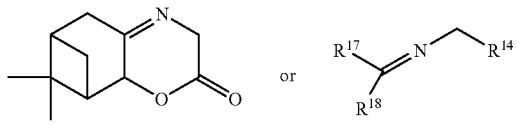

wherein:

M* is a transition metal, preferably CU, more preferably $CU^{II}$.

$R^{14}$ is  —$CO_2R^{16}$,  —CN,

-continued

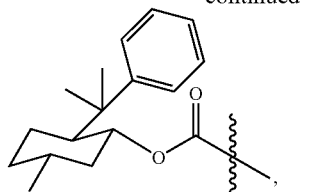

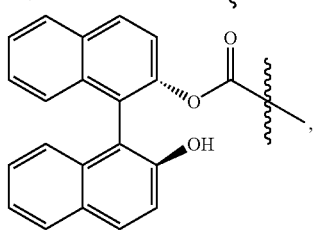

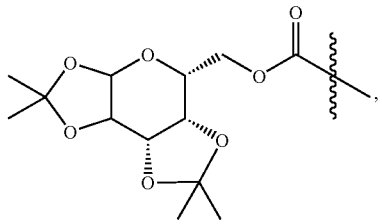

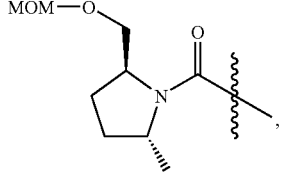

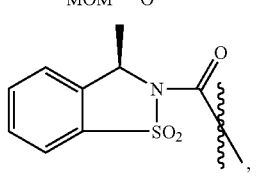 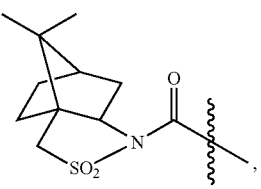

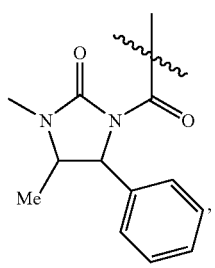  or  —$CONR^{15}R^{15}$;

$R^{15}$ is optionally substituted aliphatic group;

$R^{16}$ is acid protecting group, optionally substituted aryl, or optionally substituted aliphatic group;

$R^{17}$ is optionally substituted aryl, optionally substituted aliphatic group,

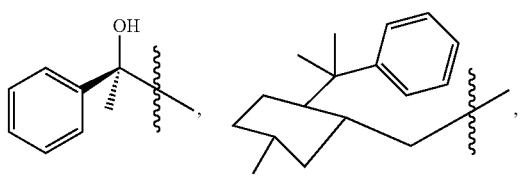

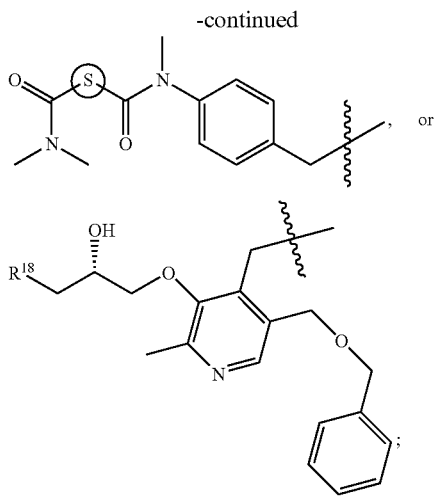, or

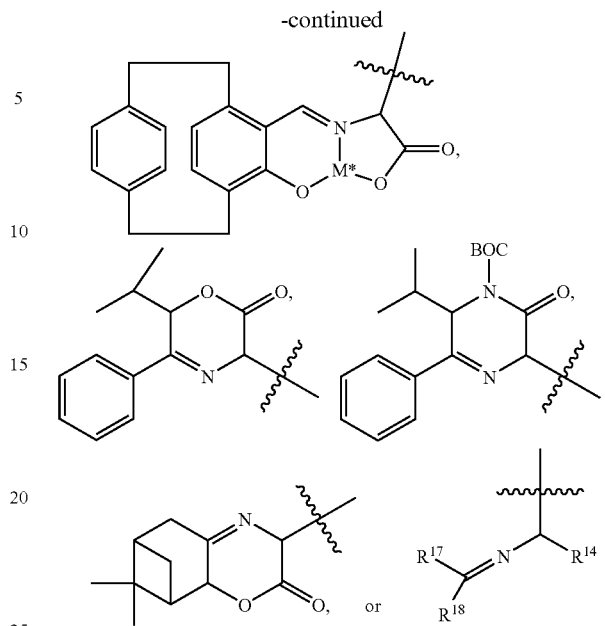

R[18] is hydrogen, alkyl, or alkylthio; or optionally substituted aryl;

R[17] and R[18] taken together with the carbon to which R[17] and R[18] are attached

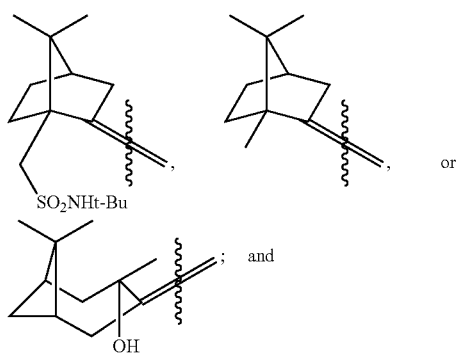; and

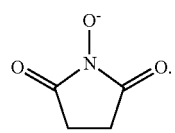 is a solid phase.

"Iminic glycinimide derivative adduct" means the resulting compound where an α-hydrogen to the nitrogen and carbonyl moiety of the Schiff base portion is removed and used to form an attachment for the bond formation thereto. Particular examples of iminic glycinimide derivative adducts according to the invention include one selected from the group of formulae

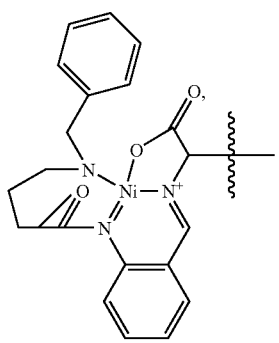

wherein:

R[14], R[17], and R[18] are defined as described in the definition of iminic glycinimide derivative herein.

"N-oxysuccinimide" means a moiety of the following structure

"N-oxide" means a moiety of the following structure

O=N⁺(O⁻)

"Patient" includes both human and other mammals.

"Peptidomimetic" mean a polymer encompassing amino acid residues joined together through amide bonds.

"Pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Exemplary esters include formates, acetates, propionates, butyrates, acrylates, ethylsuccinates, and the like.

"Pharmaceutically acceptable prodrugs" as used herein refers to those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. Functional groups that may be rapidly transformed, by metabolic cleavage, in vivo form a class of groups reactive with the carboxyl group of the compounds of this invention. They include, but are not limited to such groups as alkanoyl (such as acetyl, propanoyl, butanoyl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds of this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion is provided in Design of Prodrugs, H. Bundgaard, ed., Elsevier (1985); Methods in Enzymology; K. Widder et al, Ed., Academic Press, 42, 309-396 (1985); A Textbook of Drug Design and Developement, Krogsgaard-Larsen and H. Bandaged, ed., Chapter 5; "Design and Applications of Prodrugs" 113-191 (1991); Advanced Drug Delivery Reviews, H. Bundgard, 8, 1-38, (1992); J. Pharm. Sci., 77, 285 (1988); Chem. Pharm Bull., N. Nakeya et al, 32, 692 (1984); Pro-drugs as Novel Delivery Systems, T. Higuchi and V. Stella, 14 A.C.S. Symposium Series, and Bioreversible Carriers in Drug Design, E. B. Roche, ed., American Pharmaceutical Association and Pergamon Press, 1987, which are incorporated herein by reference.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinateslaurylsulphonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

"Ring group substituents" mean substituents attached to aromatic or non-aromatic ring systems inclusive of aryl, heteroaryl, hydroxy, alkoxy, cyclyloxy, aryloxy, heteroaryloxy, acyl or its thioxo analogue, cyclylcarbonyl or its thioxo analogue, aroyl or its thioxo analogue, heteroaroyl or its thioxo analogue, acyloxy, cyclylcarbonyloxy, aroyloxy, heteroaroyloxy, halo, nitro, cyano, carboxy (acid), —C(O)—NHOH, —C(O)—CH$_2$OH, —C(O)—CH$_2$SH, —C(O)—NH—CN, sulpho, phosphono, alkylsulphonylcarbamoyl, tetrazolyl, arylsulphonylcarbamoyl, N-methoxycarbamoyl, heteroarylsulphonylcarbamoyl, 3-hydroxy-3-cyclobutene-1,2-dione, 3,5-dioxo-1,2,4-oxadiazolidinyl or hydroxyheteroaryl such as 3-hydroxyisoxazolyl, 3-hydoxy-1-methylpyrazoly, alkoxycarbonyl, cyclyloxycarbonyl, aryloxycarbonyl, heteroaryloxycarbonyl, alkylsulfonyl, cyclylsulfonyl, arylsulfonyl, heteroarylsulfonyl, alkylsulfinyl, cyclylsulfinyl, arylsulfinyl, heteroarylsulfinyl, alkylthio, cyclylthio, arylthio, heteroarylthio, cyclyl, aryldiazo, heteroaryldiazo, thiol, $Y^1Y^2N—$, $Y^1Y^2NC(O)—$, $Y^1Y^2NC(O)O—$, $Y^1Y^2NC(O)NY^3—$ or $Y^1Y^2NSO_2—$, wherein $Y^1$, $Y^2$ and $Y^3$ are independently hydrogen, alkyl, aryl or heteroaryl, of for where the substituent is $Y^1Y^2N—$, then one of $Y^1$ and $Y^2$ may be acyl, cyclylcarbonyl, aroyl, heteroaroyl, alkoxycarbonyl, cyclyloxycarbonyl, aryloxycarbonyl or heteroaryloxycarbonyl, as defined herein and the other of $Y^1$ and $Y^2$ is as defined previously, or for where the substituent is $Y^1Y^2NC(O)—$, $Y^1Y^2NC(O)O—$, $Y^1Y^2NC(O)NY^3—$ or $Y^1Y^2NSO_2—$, $Y^1$ and $Y^2$ may also be taken together with the N atom through which $Y^1$ and $Y^2$ are linked to form a 4 to 7 membered azaheterocyclyl or azaheterocyclenyl. When a ring system is saturated or partially saturated, the "ring group substituents" further include, methylene (H$_2$C=), oxo (O=) and thioxo (S=). Acidic/amide ring group substituents are carboxy (acid), —C(O)—NHOH, —C(O)—CH$_2$OH, —C(O)—CH$_2$SH, —C(O)—NH—CN, sulpho, phosphono, alkylsulphonylcarbamoyl, tetrazolyl, arylsulphonylcarbamoyl, N-methoxycarbamoyl, heteroarylsulphonylcarbamoyl, 3-hydroxy-3-cyclobutene-1, 2-dione, 3,5-dioxo-1,2,4-oxadiazolidinyl or hydroxyheteroaryl such as 3-hydroxyisoxazolyl, 3-hydoxy-1-methylpyrazoly and $Y^1Y^2NCO—$. Non-acidic polar ring group substituents are hydroxy, oxo (O=), thioxo (S=), acyl or its thioxo analogue, cyclylcarbonyl or its thioxo analogue, aroyl or its thioxo analogue, heteroaroyl or its thioxo analogue, alkoxycarbonyl, cyclyloxycarbonyl, aryloxycarbonyl, heteroaryloxycarbonyl, acyloxy, cyclylcarbonyloxy, aroyloxy, heteroaroyloxy, alkylsulfonyl, cyclylsulfonyl, arylsulfonyl, heteroarylsulfonyl, alkylsulfinyl, cyclylsulfinyl, arylsulfinyl, heteroarylsulfinyl, thiol, $Y^1Y^2N—$, $Y^1Y^2NC(O)—$, $Y^1Y^2NC(O)O—$, $Y^1Y^2NC(O)NY^3—$ or $Y^1Y^2NSO_2$.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

Embodiments

With reference to inventions described herein, below are particular and preferred embodiments are related thereto.

A particular embodiment according to the invention is where $R^0$ is a bond.

Another particular embodiment according to the invention is where $R^0$ is difluoromethylene.

A particular embodiment according to the invention is where $R^1$ is hydrogen or optionally substituted lower aliphatic group.

Another particular embodiment according to the invention is where $R^1$ is hydrogen or lower alkyl.

A preferred embodiment according to the invention is where $R^1$ is hydrogen.

A particular embodiment according to the invention is where $R^2$ is optionally substituted lower aliphatic group or optionally substituted monocyclic group.

Another particular embodiment according to the invention is where $R^2$ is optionally substituted lower alkyl, optionally substituted lower alkenyl or optionally substituted monocyclic cycloalkyl.

Further particular embodiment according to the invention is where $R^2$ is carboxymethyl, 1-carboxy-2-phenylethyl, cyclopropyl, cyclobutyl, 1-cyclohexylethyl, 1-phenylethyl, but-2-yl, 1-pyrid4-ylethyl, propen-3-yl or 3-methylbut-2-yl; more preferred cyclopropyl.

A particular embodiment according to the invention is where $R^3$ is optionally substituted lower aliphatic group methylene.

Another particular embodiment according to the invention is where $R^3$ is optionally halo substituted lower (alkyl or alkenyl)methylene.

A preferred embodiment according to the invention is where $R^3$ is propylmethylene, 2,2-difluoroethylmethylene, 2,2,2-trifluoromethylene or propen-3-ylmethylene; more preferred $R^3$ is propylmethylene or 2,2-difluoroethylmethylene; further preferred $R^3$ is propylmethylene.

A particular embodiment according to the invention is where $R^4$ is hydrogen or optionally substituted lower aliphatic group.

Another particular embodiment according to the invention is where $R^4$ is hydrogen or lower alkyl.

A preferred embodiment according to the invention is where $R^4$ is hydrogen.

A particular embodiment according to the invention is where $R^5$ is optionally substituted lower aliphatic group methylene.

Another particular embodiment according to the invention is where $R^5$ is optionally (phenyl, carboxy, carboxamido or alkoxycarbonyl) substituted lower (alkyl or alkenyl) methylene.

A preferred embodiment according to the invention is where $R^5$ is methylmethylene, isopropylmethylene, t-butylmethylene, but-2-ylmethylene, butylmethylene, benzylmethylene, 3-methylbutylmethylene, 2-methylpropyl-methylene, carboxymethylmethylene, carboxamidomethylmethylene, benzyloxycarbonylmethylmethylene, benzyloxycarbonylpropylmethylene, or phenylpropen-3-ylmethylene; more preferred $R^5$ is isopropylmethylene or t-butyl-methylene.

A particular embodiment according to the invention is where $R^6$ is hydrogen or optionally substituted lower aliphatic group.

Another particular embodiment according to the invention is where $R^6$ is hydrogen or lower alkyl.

A preferred embodiment according to the invention is where $R^6$ is hydrogen.

A particular embodiment according to the invention is where $R^7$ is optionally substituted lower aliphatic group methylene, optionally substituted lower cyclic group methylene or optionally substituted monocyclic (aryl or heteroaryl) methylene.

Another particular embodiment according to the invention is where $R^7$ is optionally substituted lower alkylmethylene, optionally substituted lower cycloalkylmethylene or optional substituted phenylmethylene.

A preferred embodiment according to the invention is where $R^7$ is methylmethylene, isopropylmethylene, n-propylmethylene, phenylmethylene, cyclohexylmethylene, cyclopentylmethylene, t-butylmethylene, s-butylmethylene, cyclohexylmethylmethylene, or phenylmethylmethylene; more preferred is isopropylmethylene, cyclohexylmethylene, cyclopentylmethylene, t-butylmethylene or s-butylmethylene.

A preferred embodiment according to the invention is also wherein each of $R^3$, $R^5$, and $R^7$ is mono substituted methylene.

A preferred embodiment according to the invention is also wherein $R^3$ is mono substituted methylene and has an (S) configuration on the carbon attached to the —C(O)—$R^0$—C(O)—$NR^1R^2$ moiety.

A particular embodiment according to the invention is where $R^8$ is hydrogen or optionally substituted lower aliphatic group.

Another particular embodiment according to the invention is where $R^8$ is hydrogen or lower alkyl.

A preferred embodiment according to the invention is where $R^8$ is hydrogen.

A particular embodiment according to the invention is where $R^9$ is optionally substituted lower aliphatic group or optionally substituted monocyclic aromatic group.

Another particular embodiment according to the invention is where $R^9$ is optionally substituted lower alkyl or optionally substituted monocyclic heteroaryl.

Another particular embodiment according to the invention is where $R^9$ is optionally (carboxy, (loweralkyl)SO$_2$NH—, (lower alkyl)HNCO—, hydroxy, phenyl, heteroaryl, or (lower alkyl)OC(O)NH—)-substituted lower alkyl, or optionally substituted monocyclic heteroaryl.

A further preferred embodiment according to the invention is where $R^9$ is lower alkyl substituted by (mono- or di-)MeOC(O)NH—; more preferred is 1,2-di(MeOC(O)NH)ethyl or 1-(MeOC(O)NH)ethyl.

A preferred embodiment according to the invention is where $R^9$ is (carboxy, (lower allyl)HNCO— or tetrazolyl) substituted lower alkyl; more preferred 3-carboxypropyl, 2-tetrazol-5ylpropyl, 3-(N-methylcarboxamido)propyl or 3-carboxy-2,2-dimethylpropyl; further preferred is 3-carboxypropyl, 2-tetrazol-5ylpropyl or 3-(N-methylcarboxamido)propyl.

Another preferred embodiment according to the invention is where $R^9$ is optionally substituted lower alkyl; more preferred is 1-hydroxy-2-phenylethyl, methyl, isopropyl or t-butyl; further preferred is methyl, isopropyl or t-butyl.

Another preferred embodiment according to the invention is where $R^9$ is selected from the group consisting of

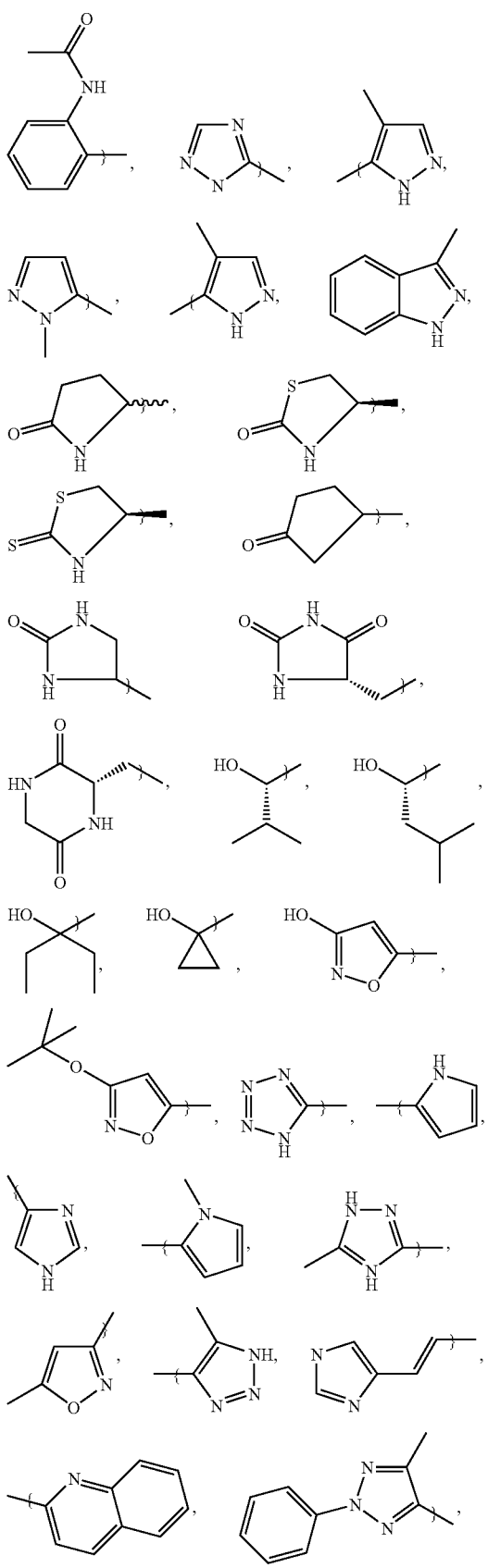

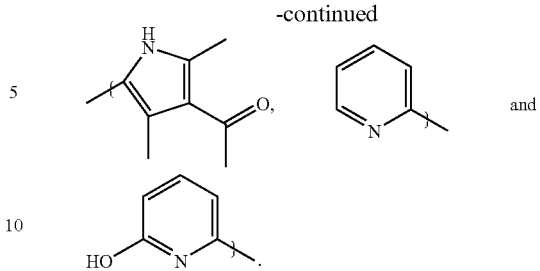

Yet another preferred embodiment according to the invention is where $R^9$ is pyrazinyl.

A particular embodiment according to the invention is where $R^{10}$ is hydrogen or optionally substituted lower aliphatic group.

Another particular embodiment according to the invention is where $R^{10}$ is hydrogen or lower alkyl.

A preferred embodiment according to the invention is where $R^{10}$ is hydrogen.

A preferred embodiment according to the invention is where

as a substituted monocyclic azaheterocyclyl is substituted pyrrolidinyl.

A preferred embodiment according to the invention is where

as a substituted monocyclic azaheterocyclyl is optionally substituted

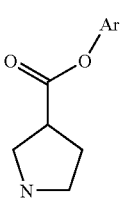

or optionally substituted

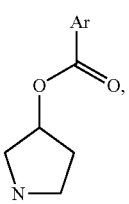

wherein Ar is R² that comprises an aromatic moiety; more preferred is optionally substituted

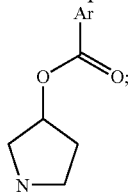

further preferred is optionally substituted


Further preferred optionally substituted

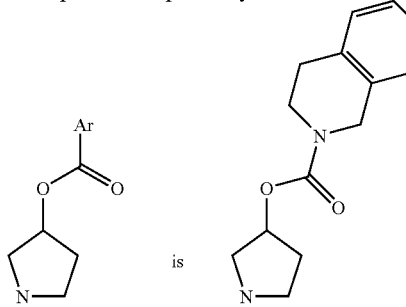

is or

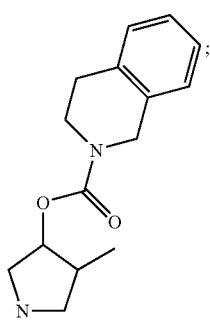

;

yet further preferred

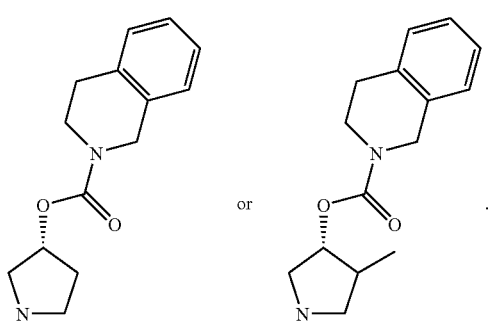

or

.

Another preferred embodiment according to the invention is where

as an optionally substituted multicyclic azaheterocyclyl is optionally substituted

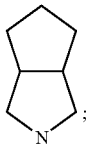

;

more preferred is optionally substituted

.

Particular substituents for

are hydroxy, fluoro or oxo.

Another preferred embodiment according to the invention is where

as an optionally substituted multicyclic azaheterocyclenyl is optionally substituted

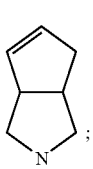

;

more preferred is

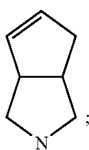

further preferred is

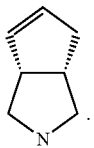

Another preferred embodiment according to the invention is where

as an optionally substituted multicyclic azaheterocyclenyl is optionally substituted

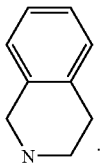

A preferred embodiment according to the invention is where the —C(O)—N(R⁴)—R³—C(O)RºC(O)NR²R¹ moiety attached to

is attached a carbon a to the nitrogen atom.

A preferred embodiment according to the invention is where L is —C(O)— or —OC(O)—.

A preferred embodiment according to the invention is where n is 0.

Another preferred embodiment according to the invention is where n is 1.

A preferred embodiment according to the invention is where $R^{11}$ is —CO$_2$R$^{13}$.

A preferred embodiment according to the invention is where

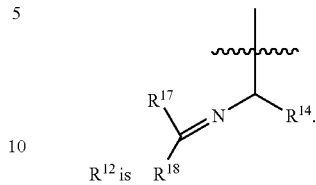

A particular embodiment according to the invention is where $R^{13}$ is an optionally substituted aliphatic group.

Another particular embodiment according to the invention is where $R^{13}$ is an alkyl group.

A preferred embodiment according to the invention is where $R^{13}$ is lower alkyl.

Another preferred embodiment according to the invention is where $R^{13}$ is methyl.

A preferred embodiment according to the invention is where $R^{14}$ is —CO$_2$R$^{16}$.

A particular embodiment according to the invention is where $R^{15}$ is alkyl.

A preferred embodiment according to the invention is where $R^{15}$ is lower alkyl.

A preferred embodiment according to the invention is where $R^{15}$ is methyl.

A particular embodiment according to the invention is where $R^{16}$ is optionally substituted aliphatic.

Another particular embodiment according to the invention is where $R^{16}$ is alkyl.

A preferred embodiment according to the invention is where $R^{16}$ is lower alkyl.

A preferred embodiment according to the invention is where $R^{16}$ is t-Bu.

A particular embodiment according to the invention is where $R^{17}$ is optionally substituted aryl.

A preferred embodiment according to the invention is where $R^{17}$ is phenyl.

A particular embodiment according to the invention is where $R^{18}$ is optionally substituted aryl.

A preferred embodiment according to the invention is where $R^{18}$ is phenyl.

A particular embodiment according to the invention is where $p^0$ is selected from the group consisting of BOC, CBz, and —CO$_2$alkyl.

A preferred embodiment according to the invention is where $p^0$ is BOC.

It is to be understood that this invention covers all appropriate combinations of the particular and preferred groupings referred to herein.

Particular compounds according to the invention are selected from the group of compounds A-FH consecutively consisting of

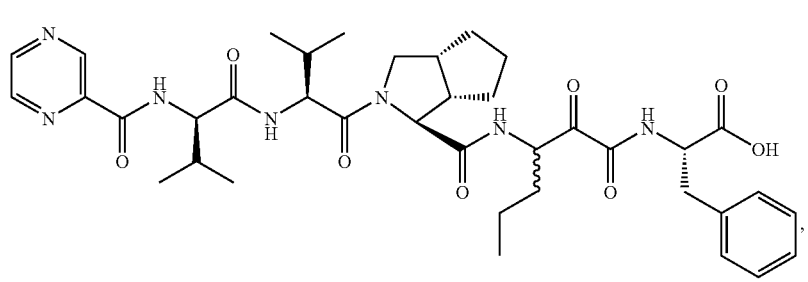
A
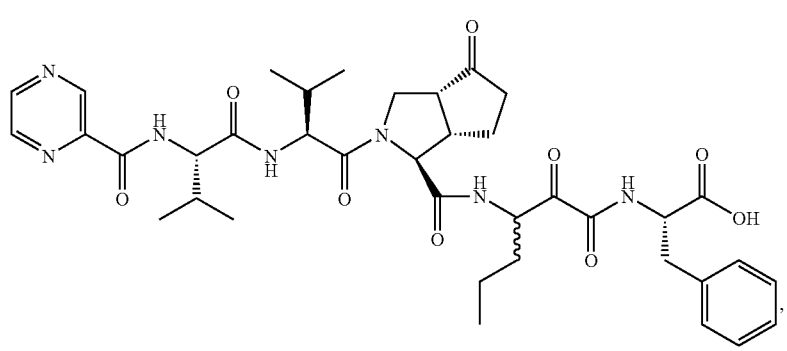
B
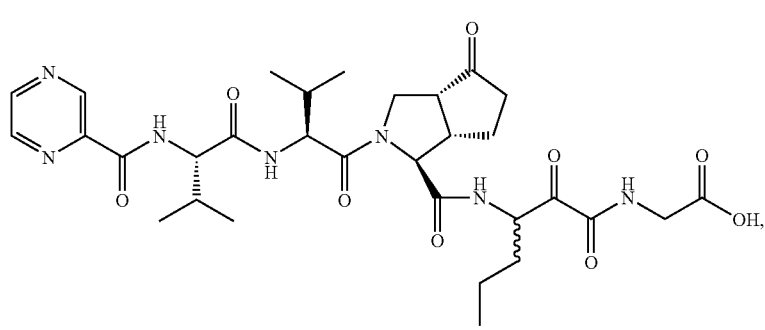
C
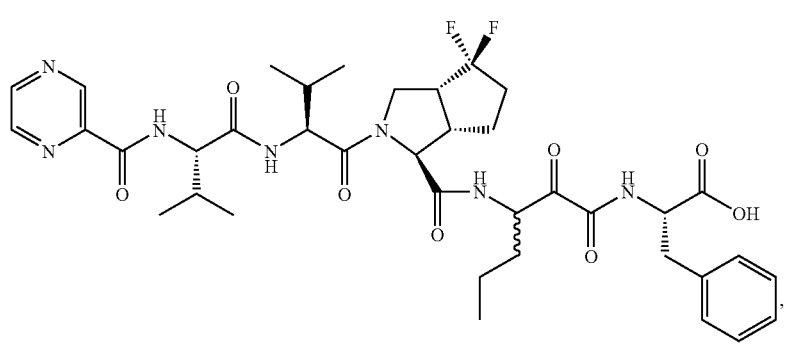
D
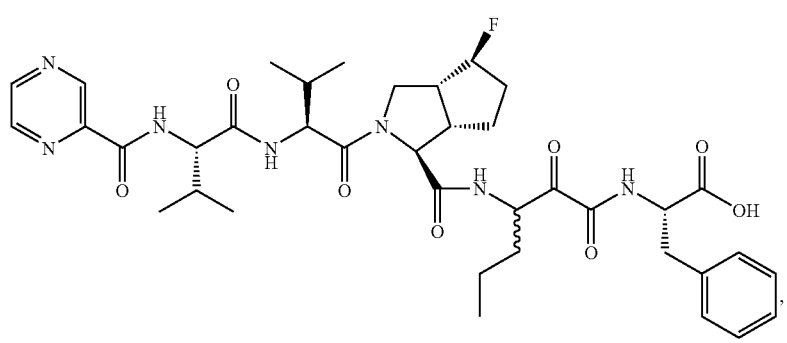
E

-continued
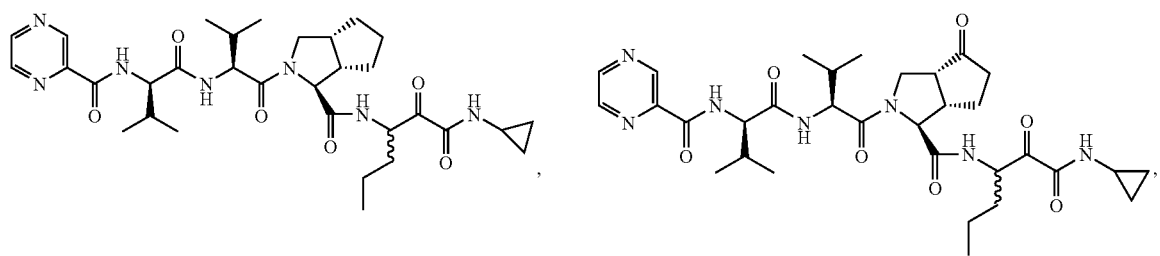
F
G
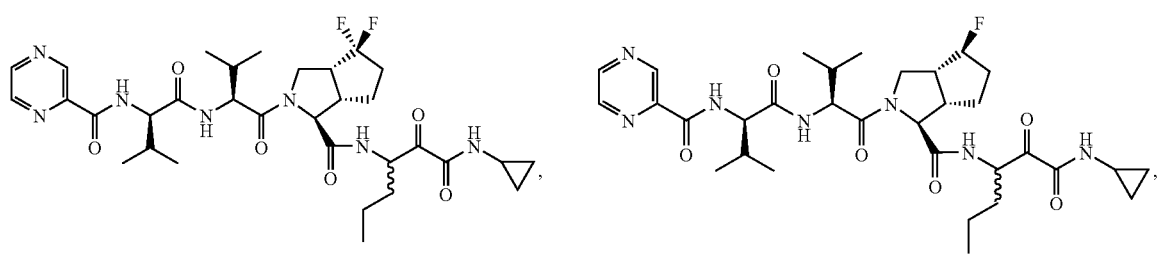
H
I
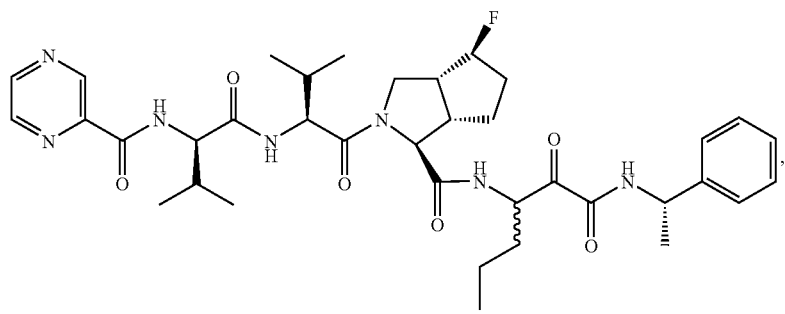
J
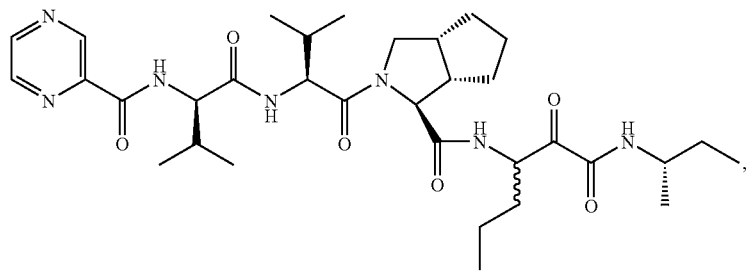
K
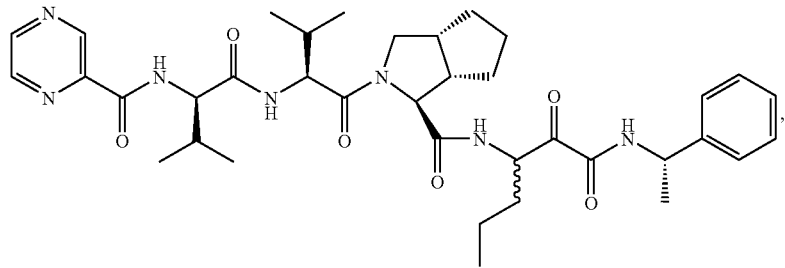
L

-continued
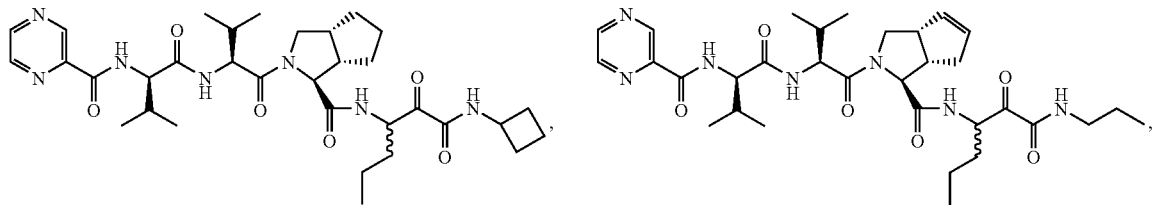
M
N
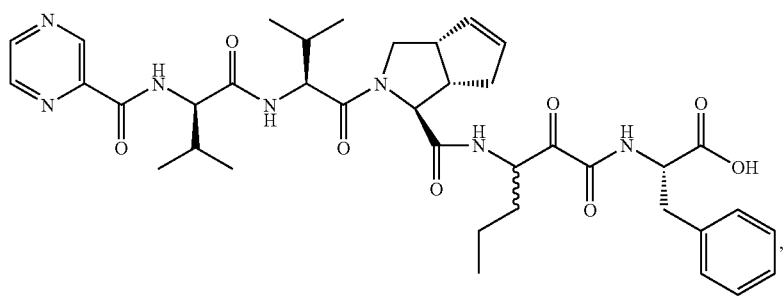
O
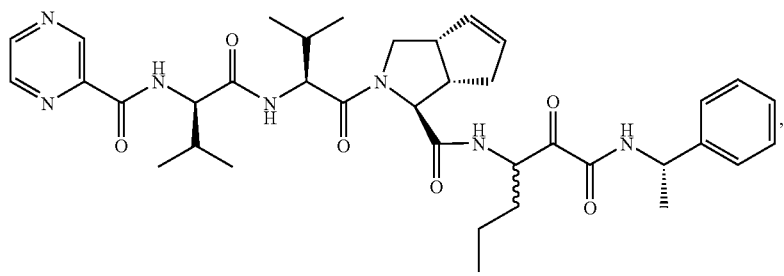
P
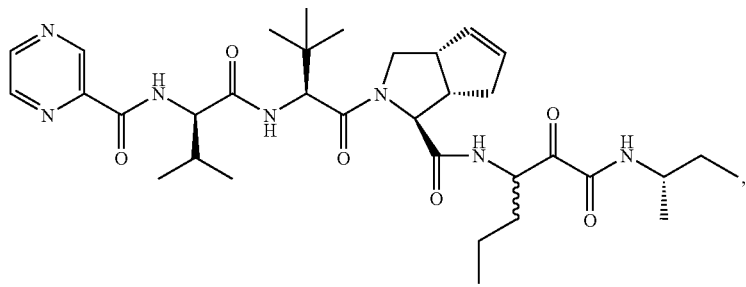
Q
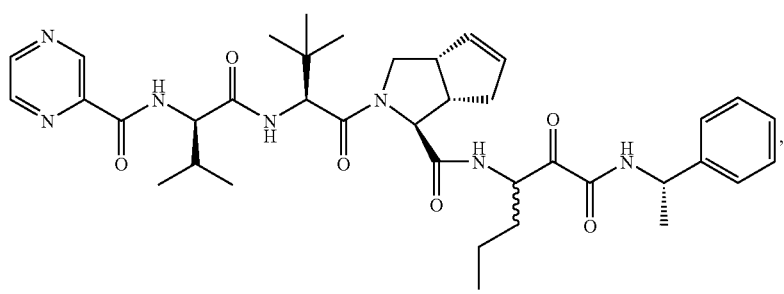
R

S
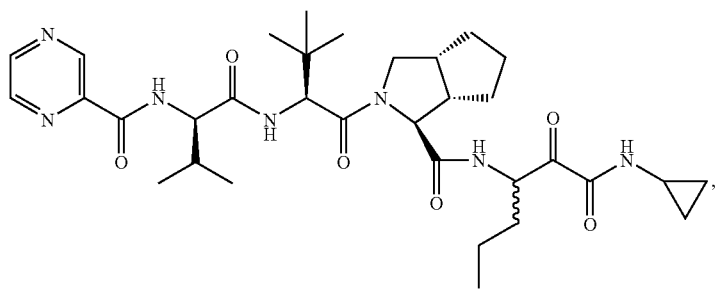
T
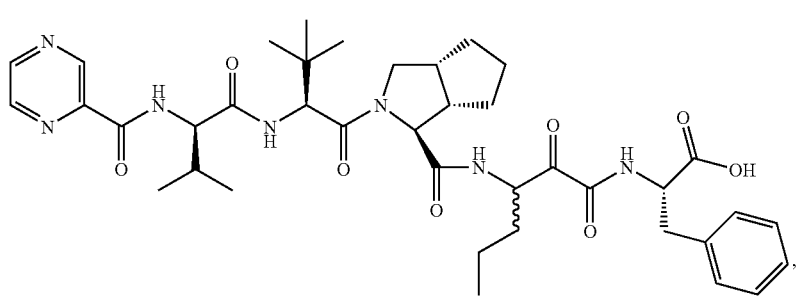
U
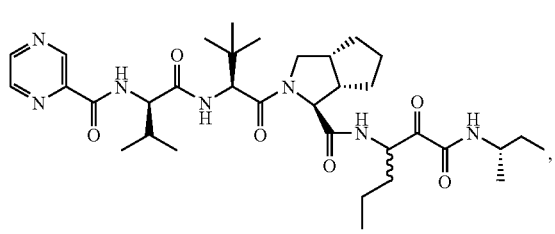
V
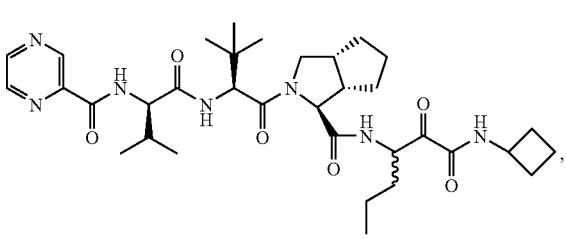
W
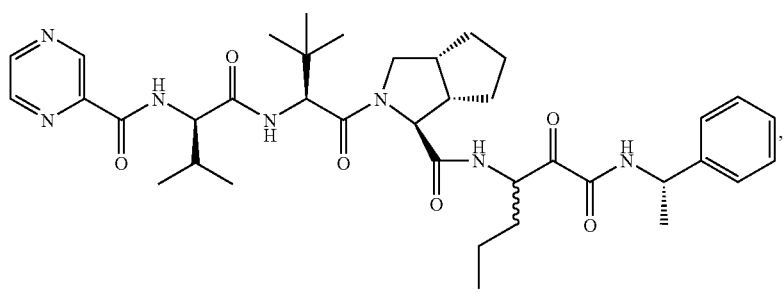
X
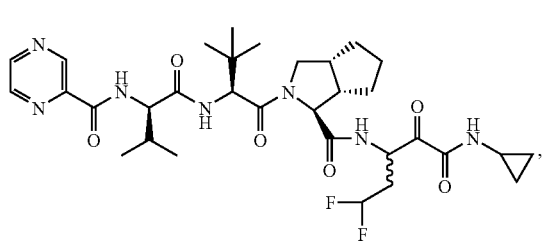
Y
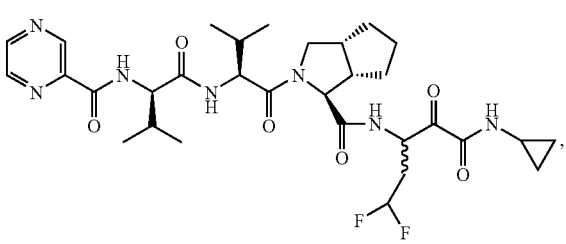
Z
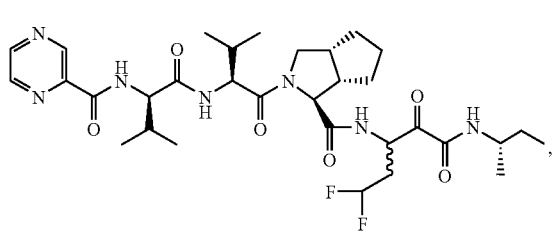
AA
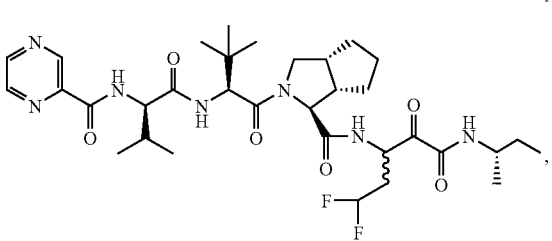

-continued
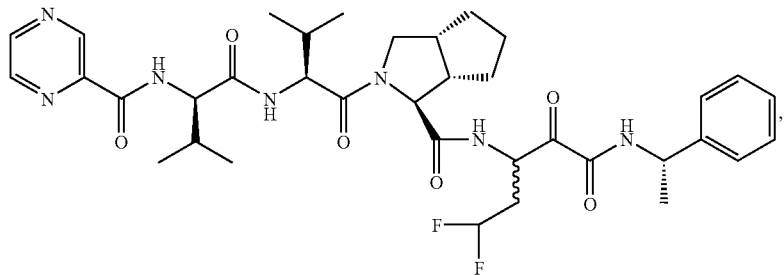
AB
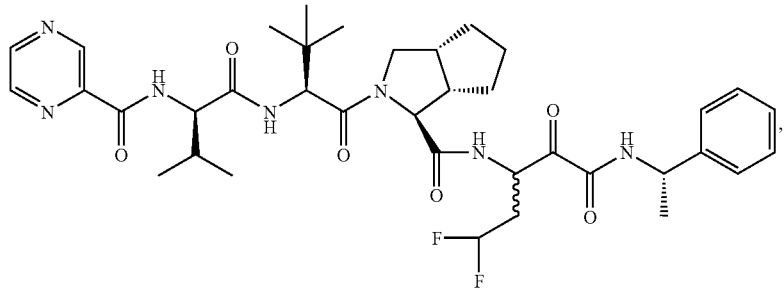
AC
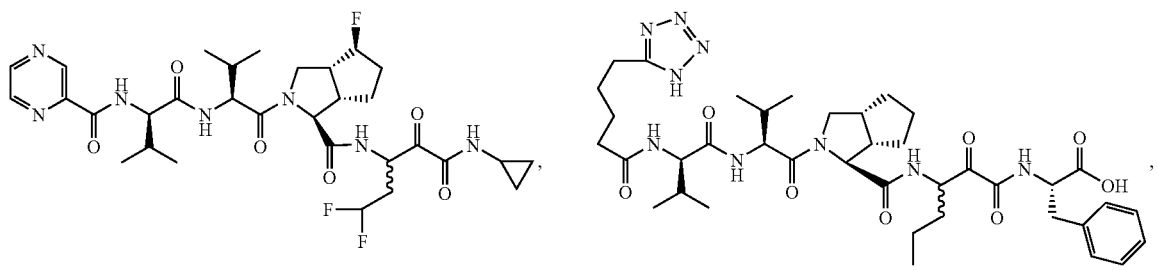
AD                                      AE
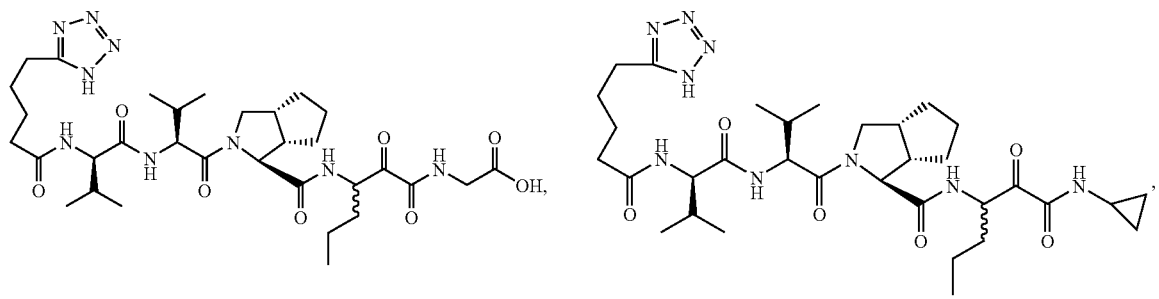
AF                                      AG
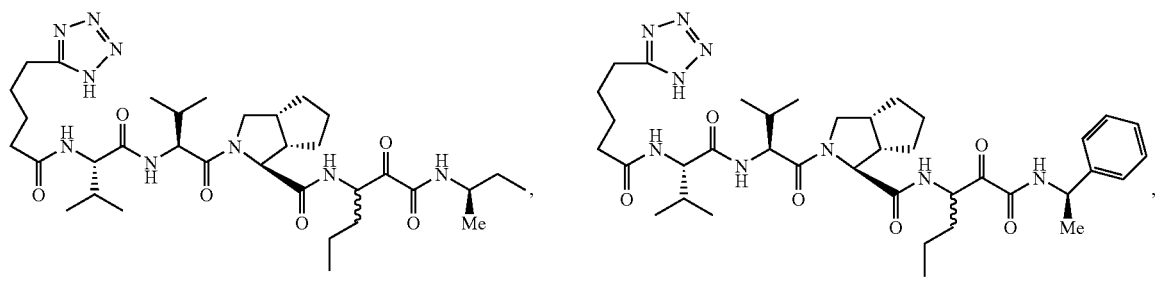
AH                                      AI -continued
AJ
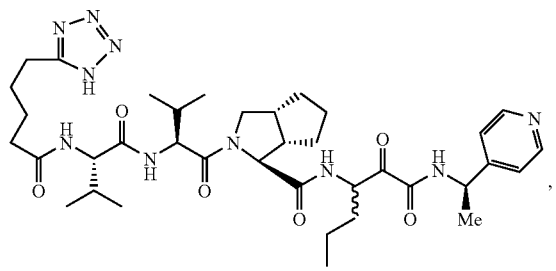
AK
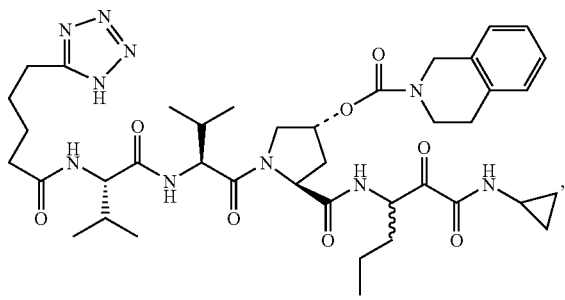
AL
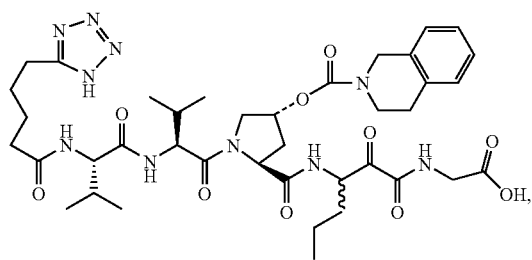
AM
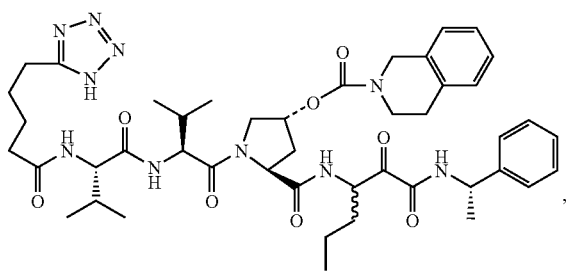
AN
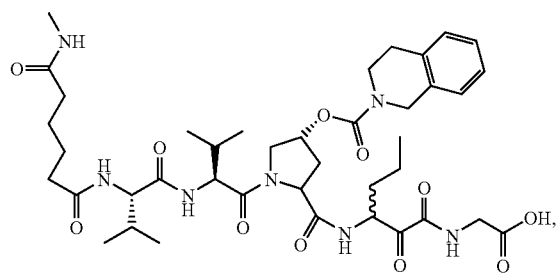
AO
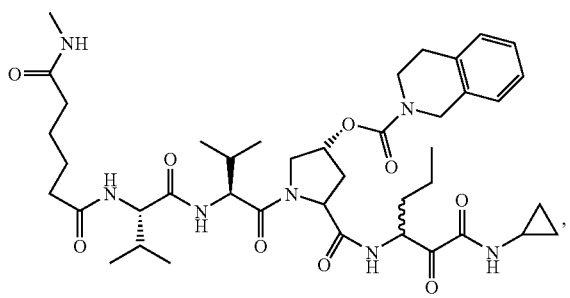
AP
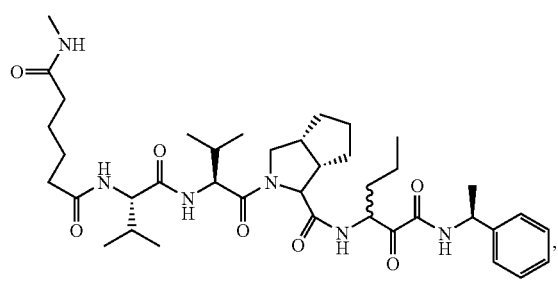
AQ
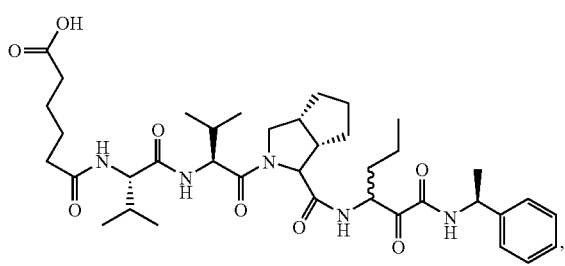
AR
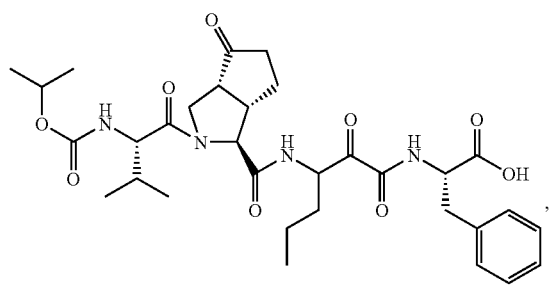
AS
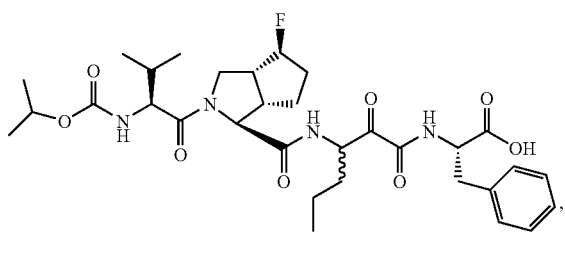

-continued
AT
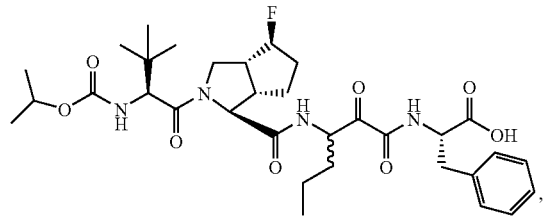
AU
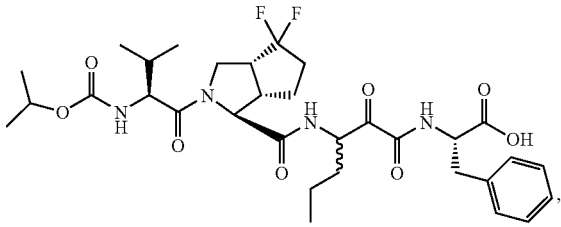
AV
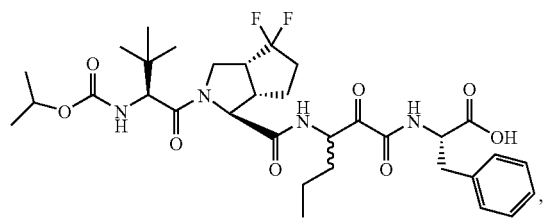
AW
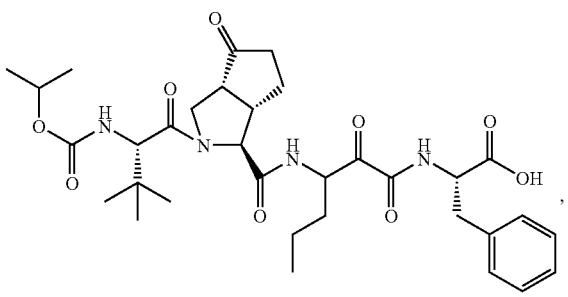
AX
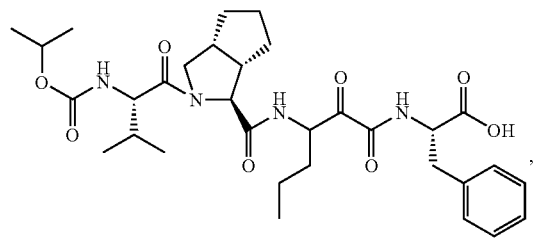
AY
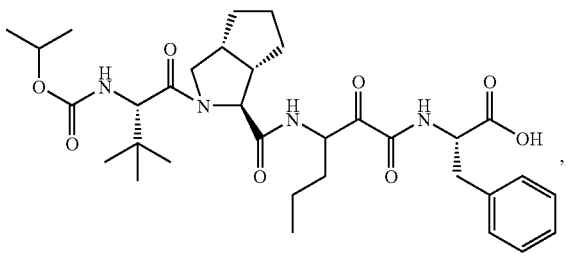
AZ
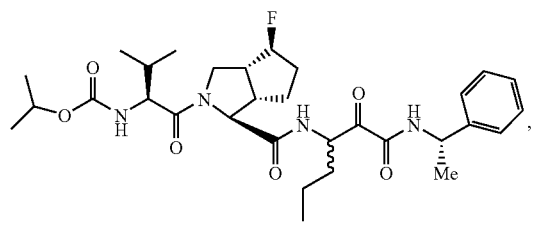
BA
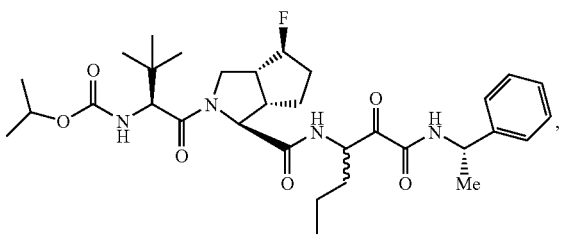
BB
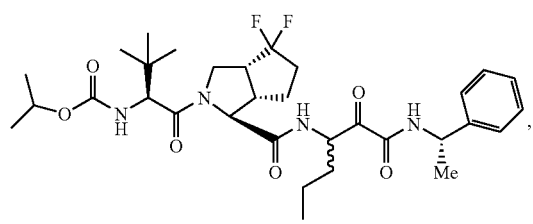
BC
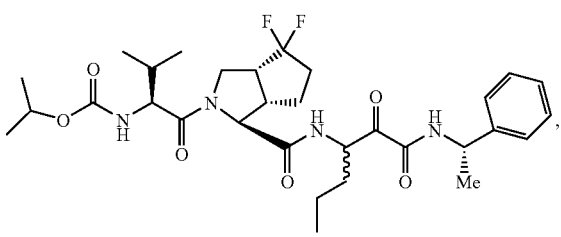

-continued
| BD | BE |
|---|---|
| 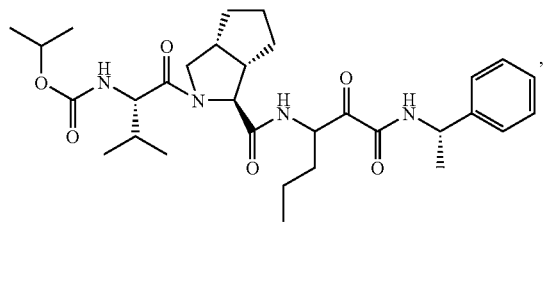 | 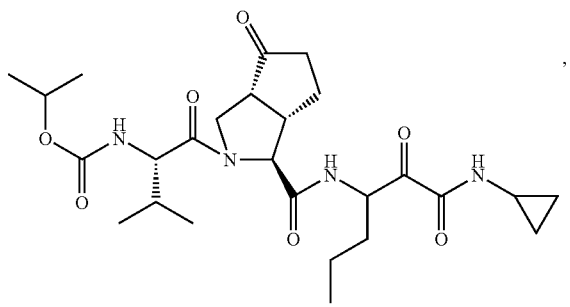 |
| BF | BG |
|---|---|
| 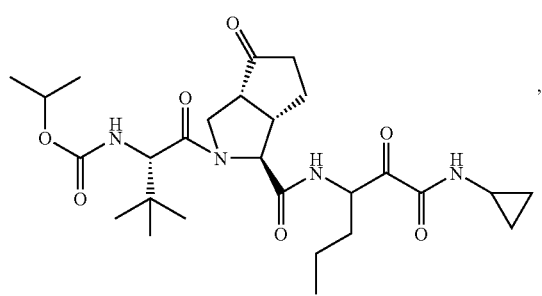 | 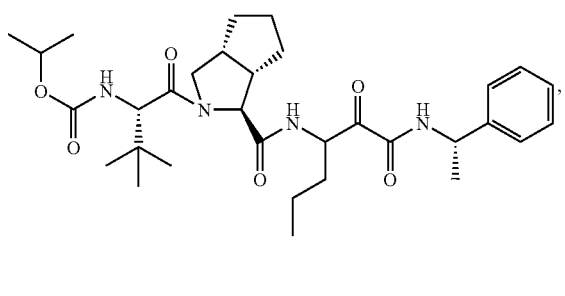 |
| BH | BI |
|---|---|
| 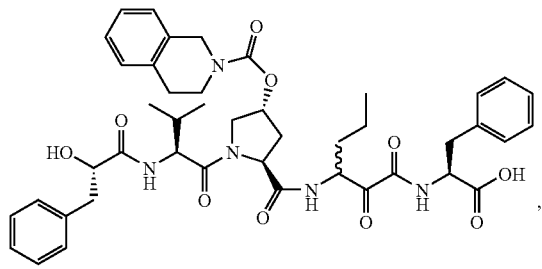 | 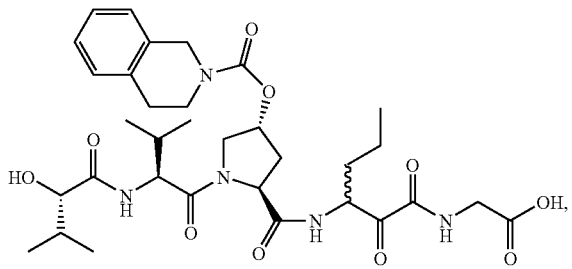 |
| BJ | BK |
|---|---|
| 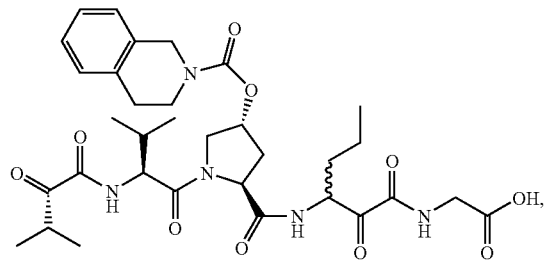 | 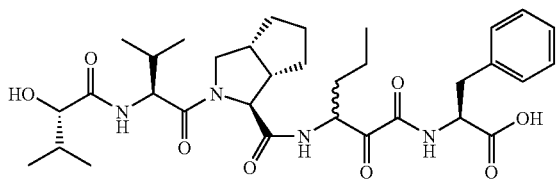 |
| BL | BM |
|---|---|
| 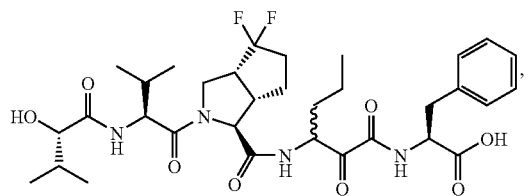 | 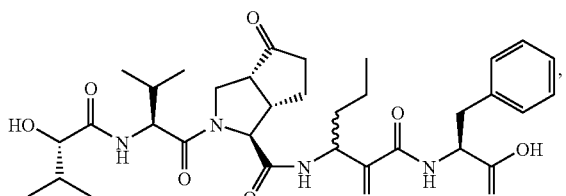 |

-continued
BN
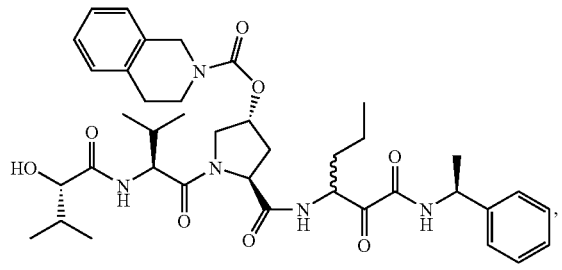
BO
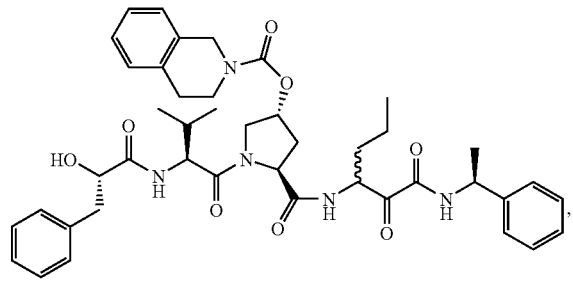
BP
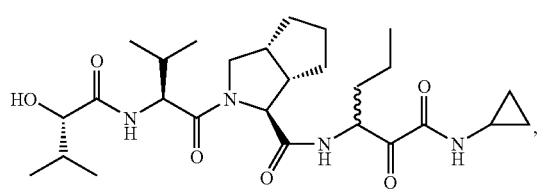
BQ
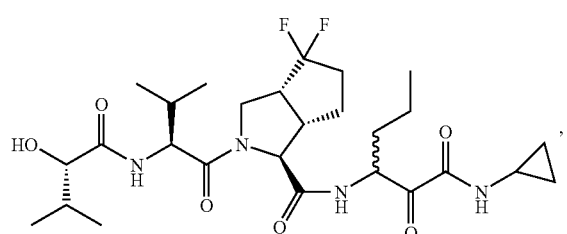
BR
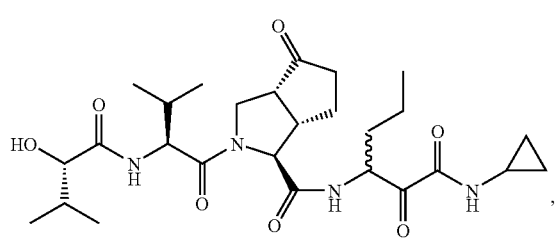
BS
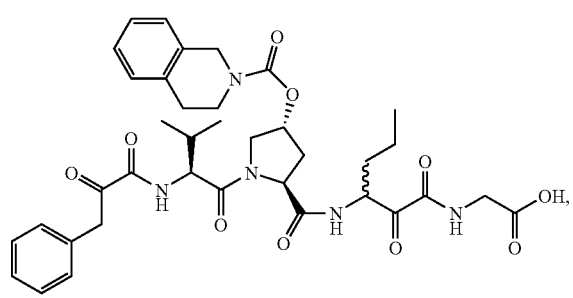
BT
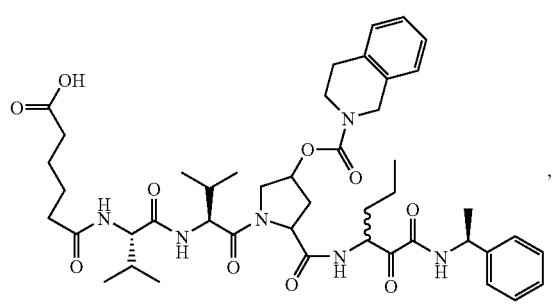
BU
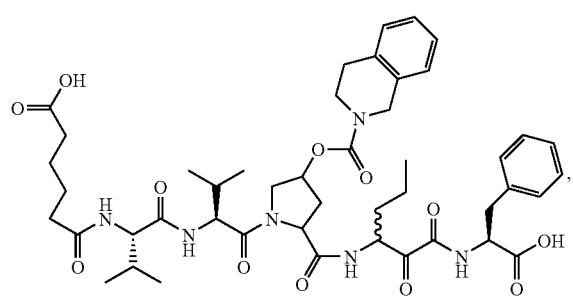
BV
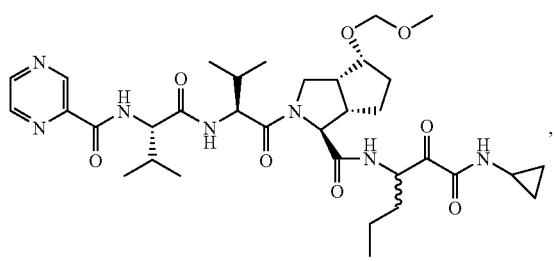
BW
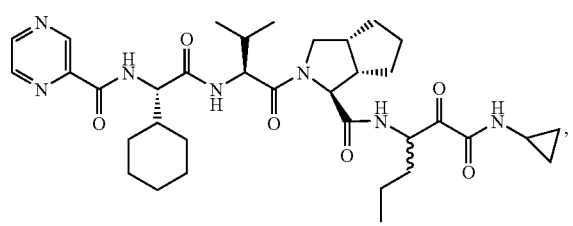

-continued
BX
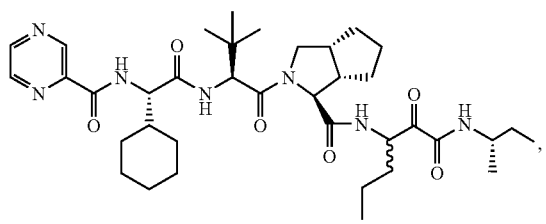
BY
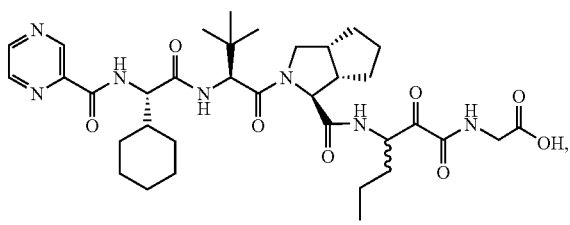
BZ
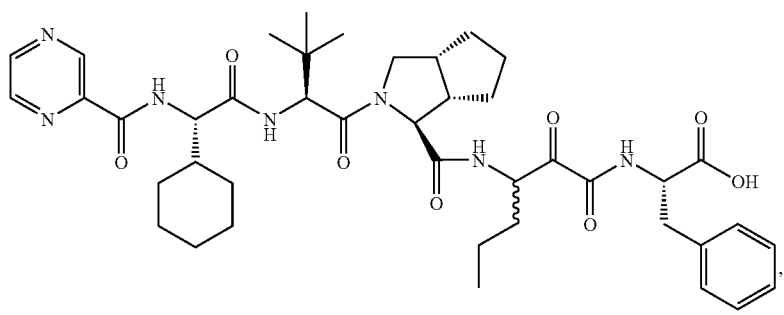
CA
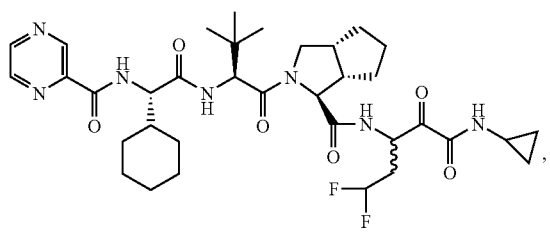
CB
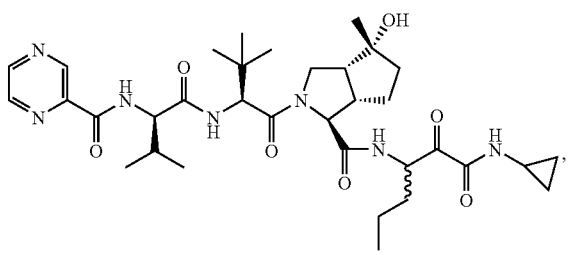
CC
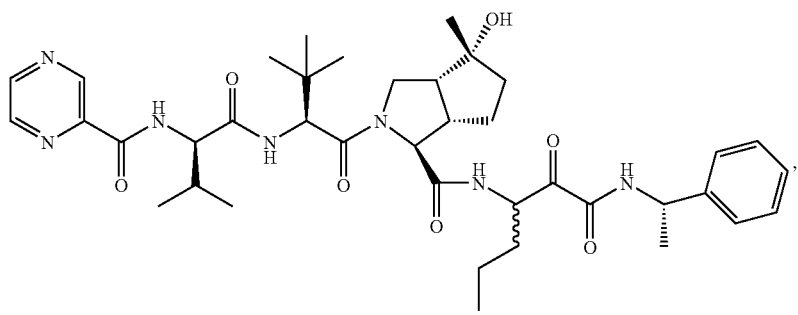
CD
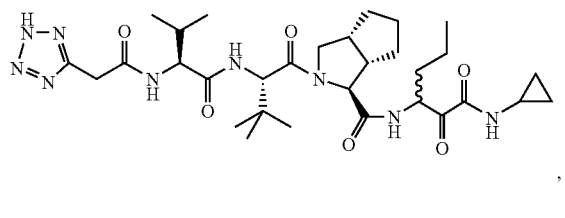
CE
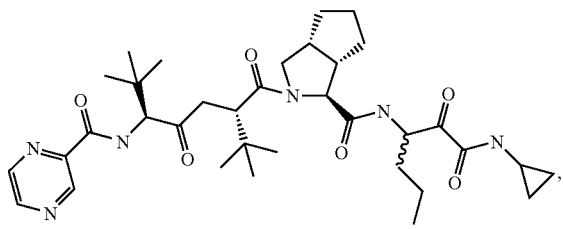

-continued
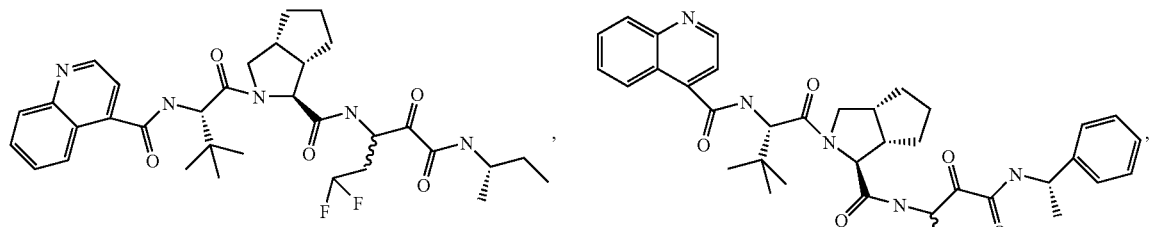
CF
CG
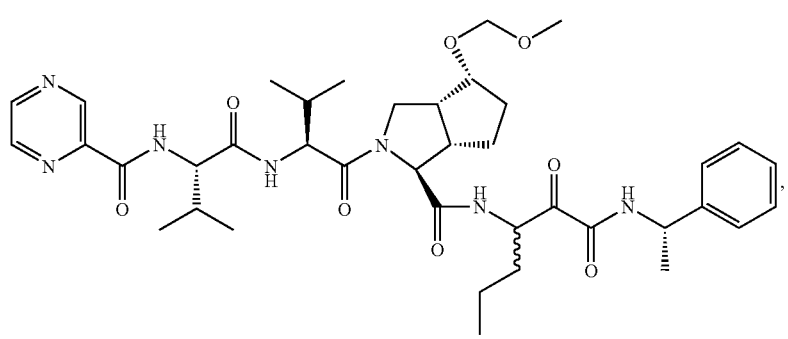
CH
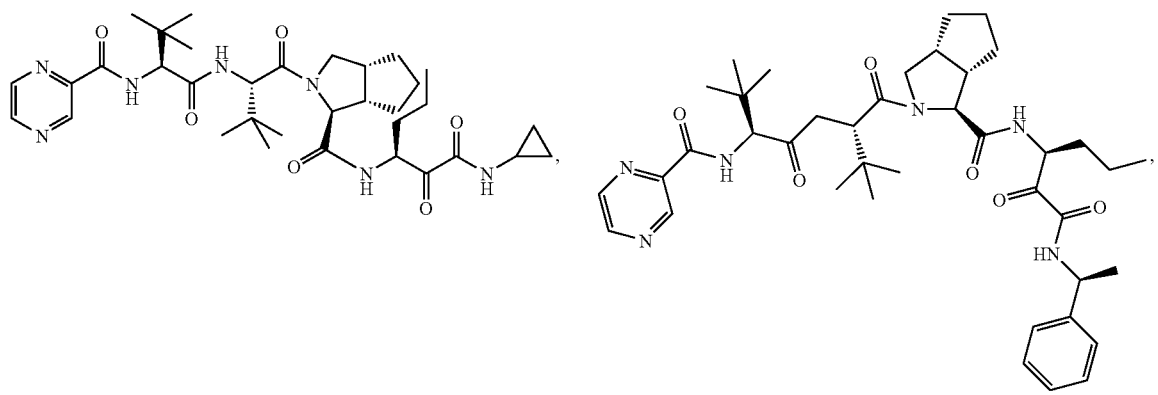
CI
CJ
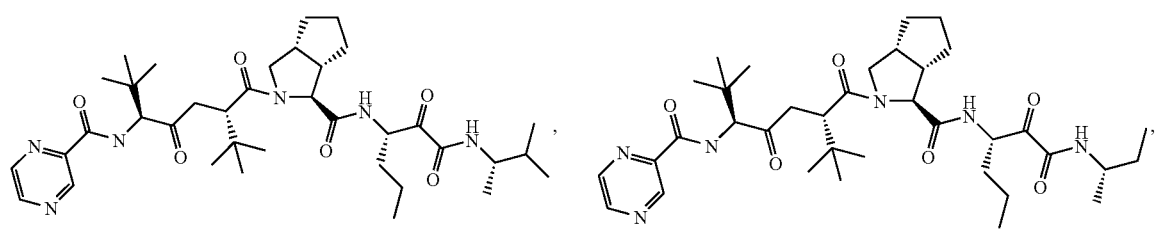
CK
CL
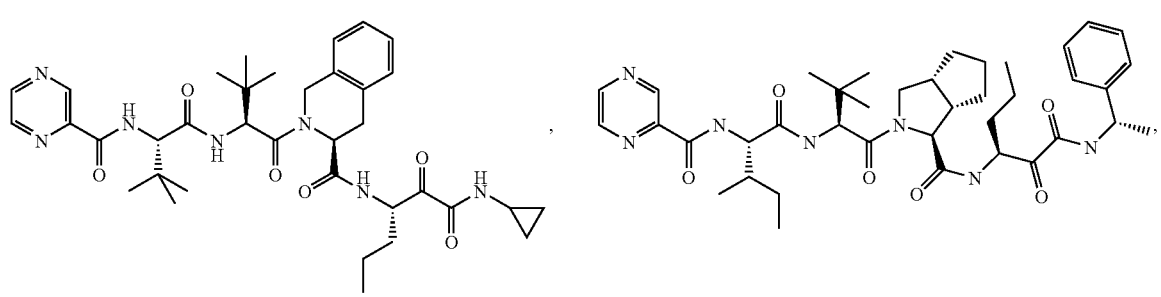
CM
CN -continued
CO
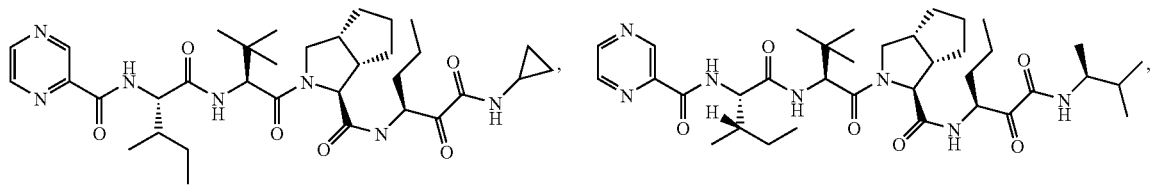
CP
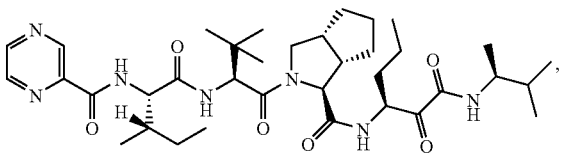
CQ
CR
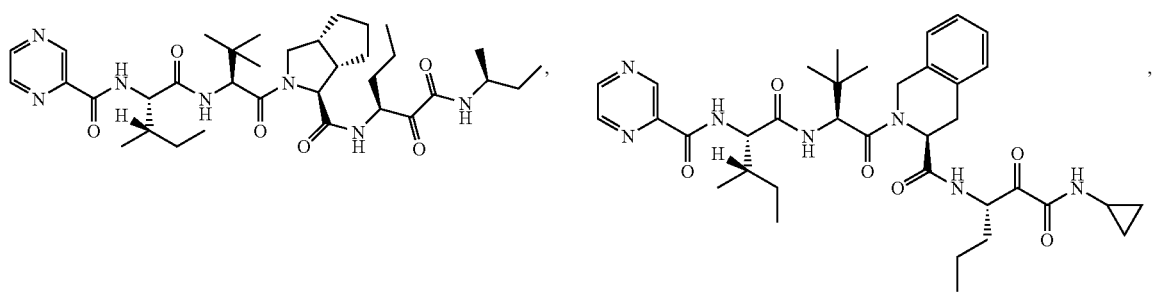
CS
CT
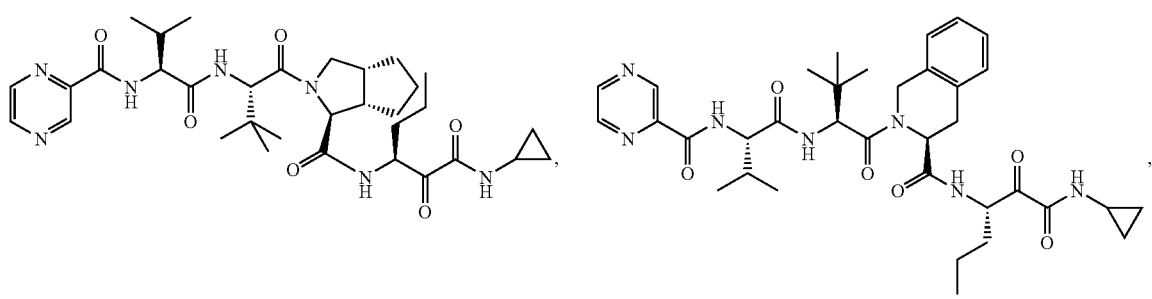
CU
CV
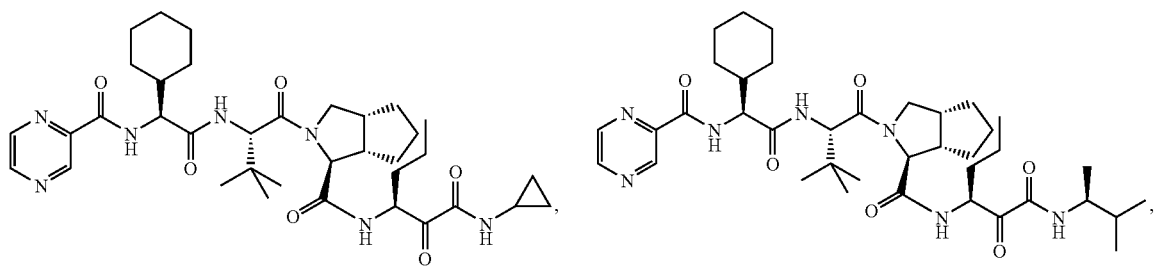
CW
CX
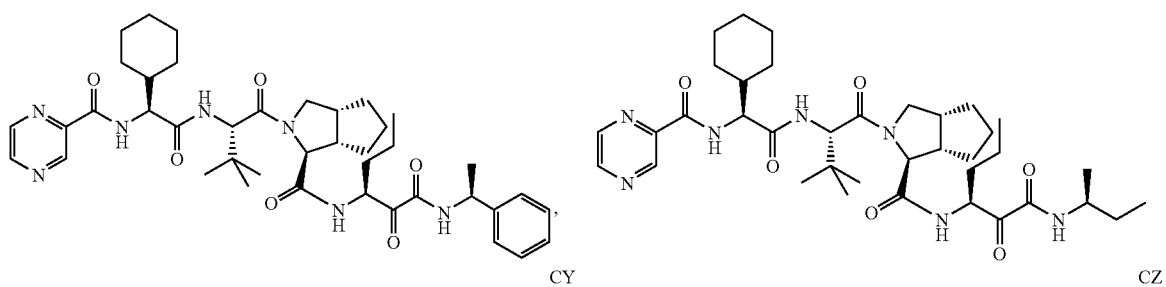
CY
CZ
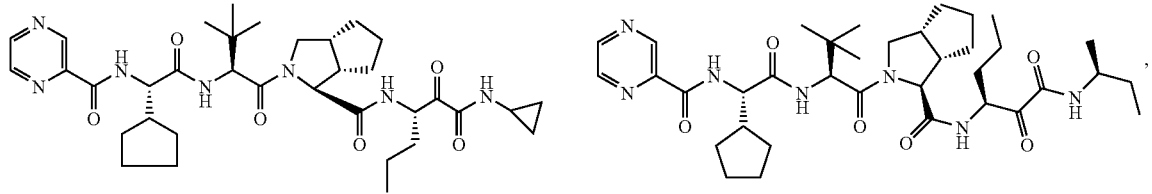

-continued
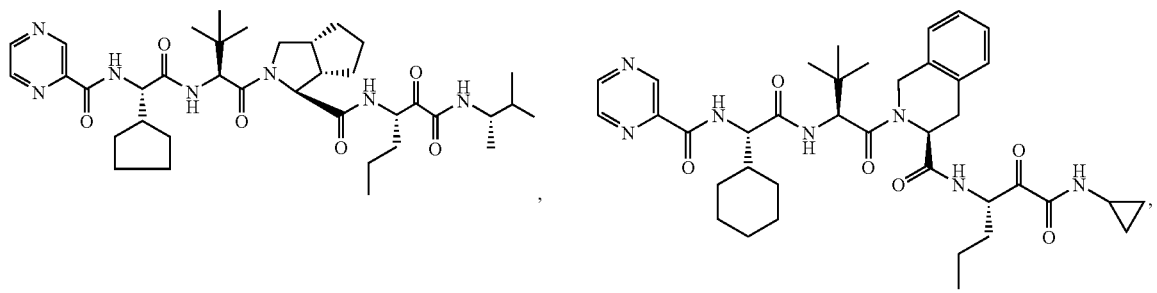
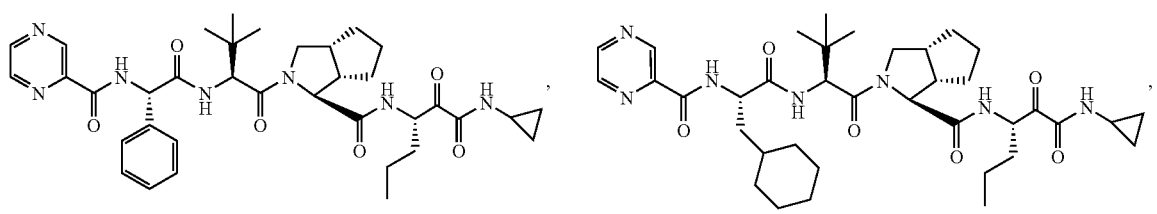
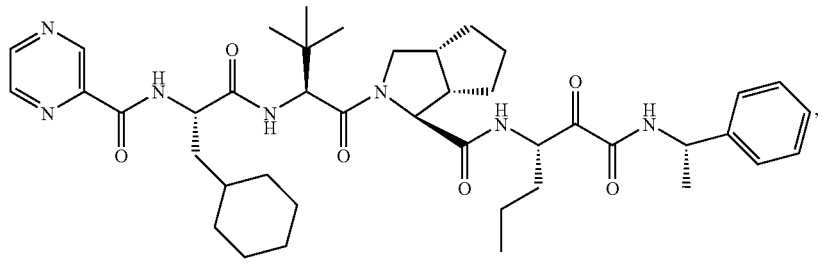
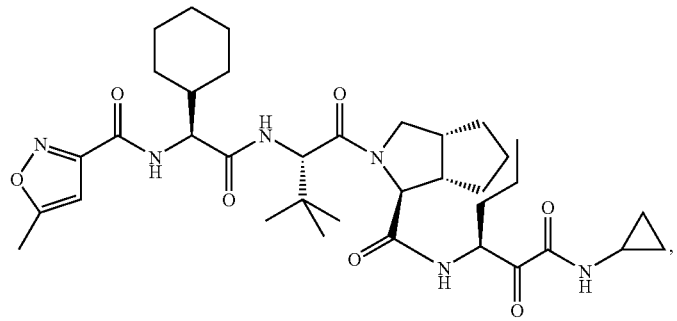
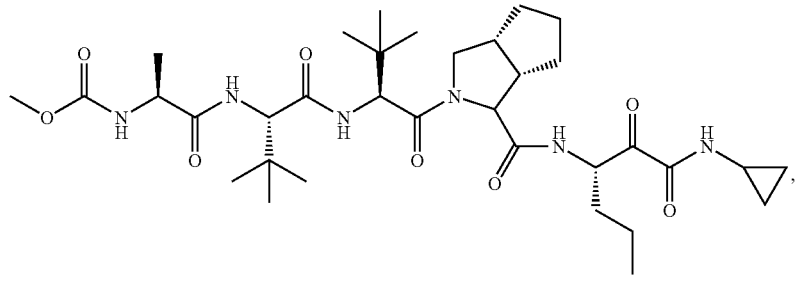
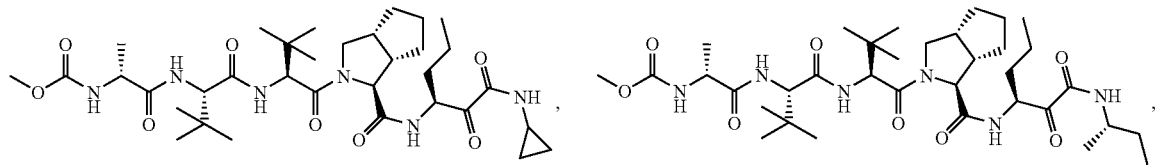

-continued
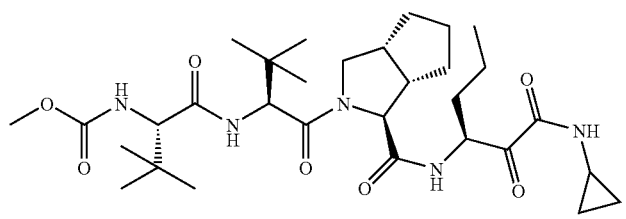
DJ
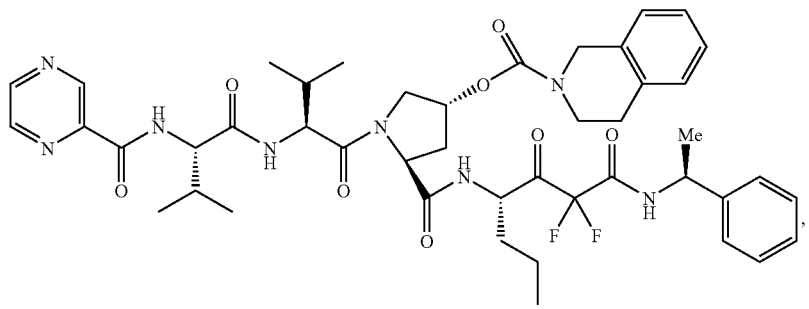
DK
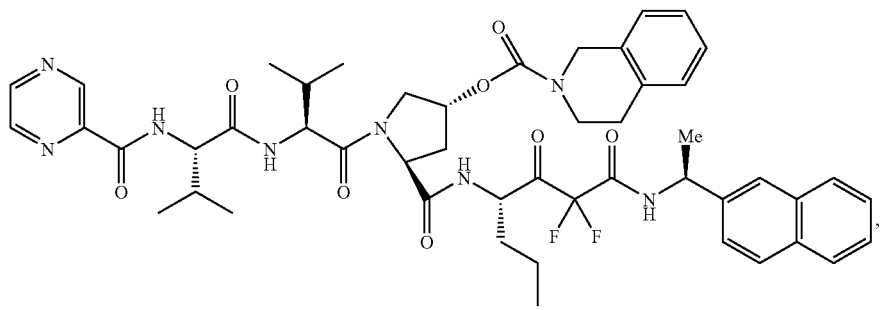
DL
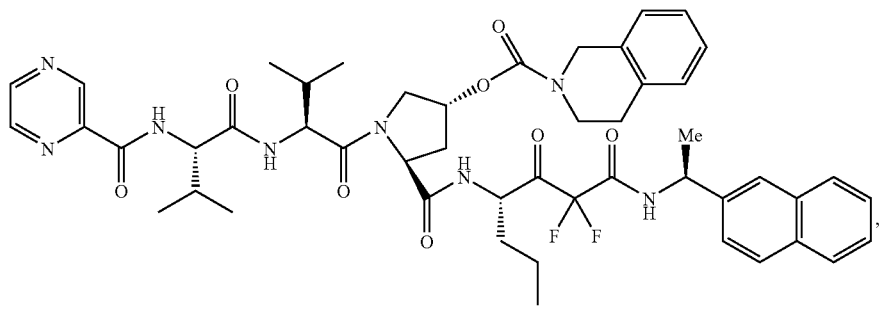
DM
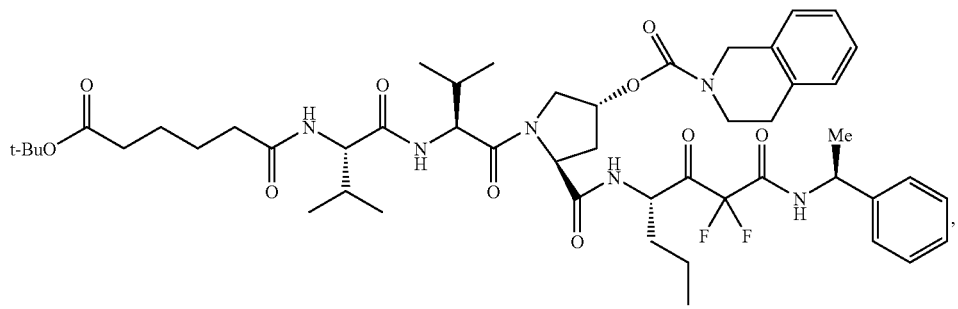
DN -continued
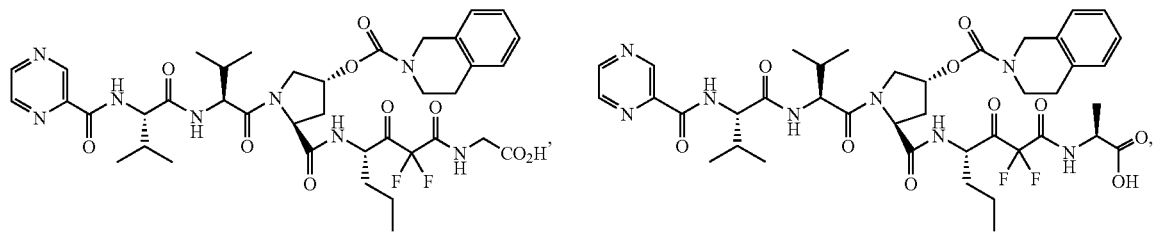
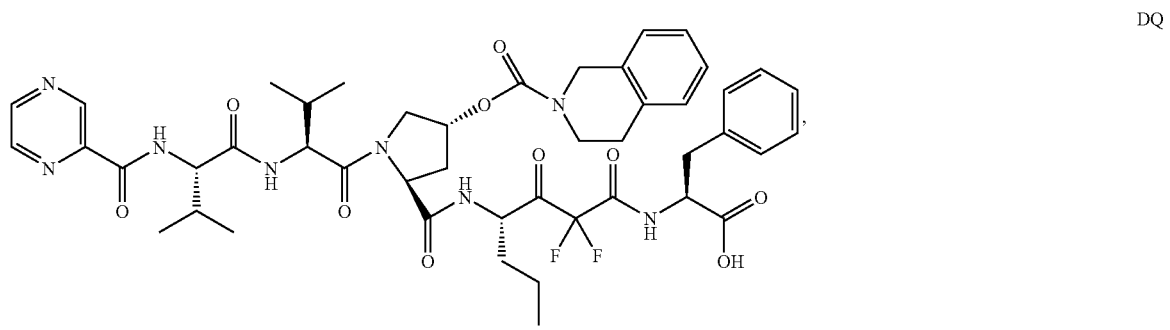
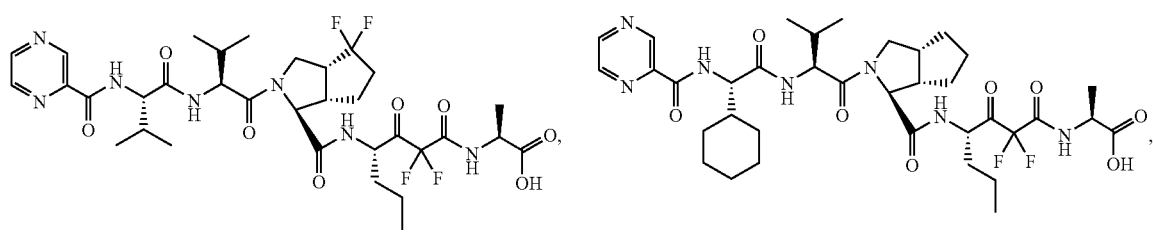
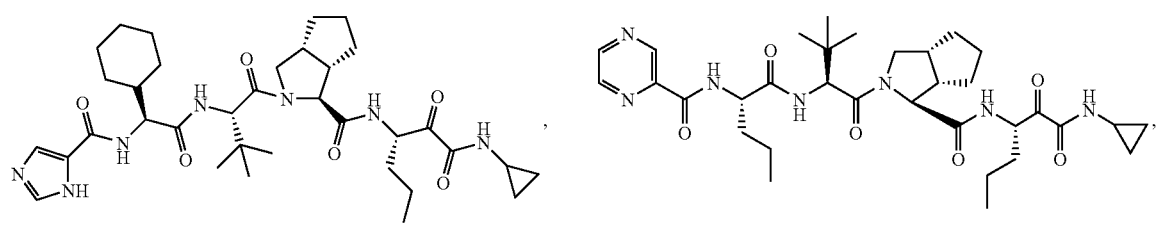
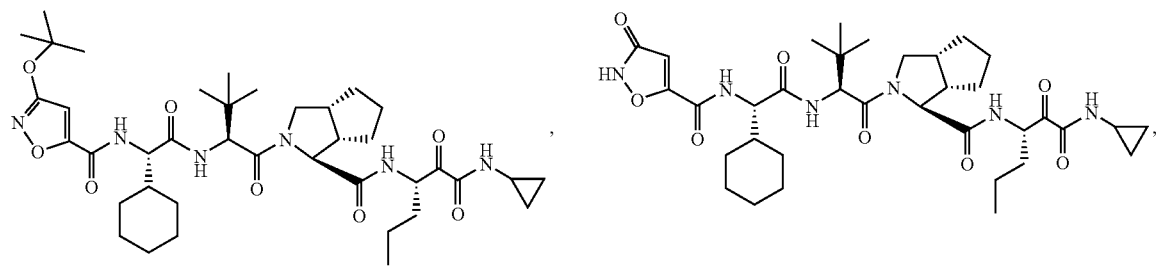

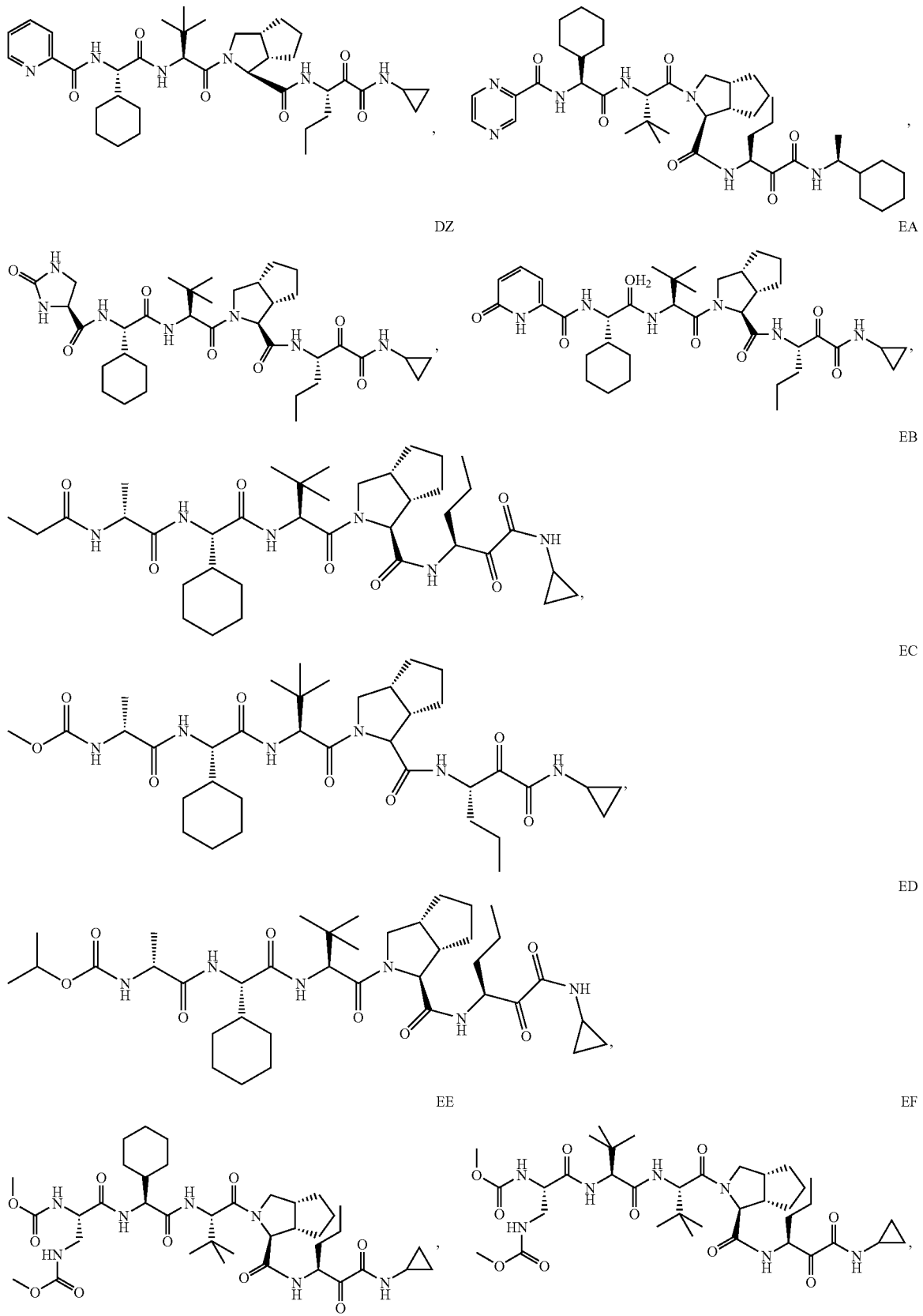

-continued
EG
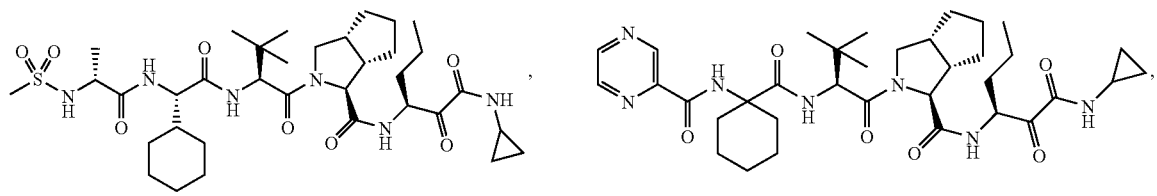
EH
EI
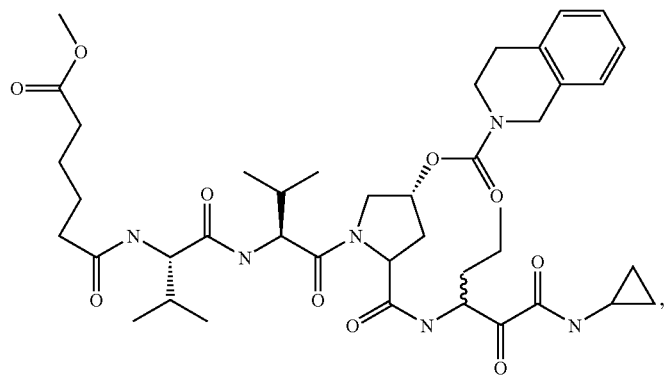
EJ
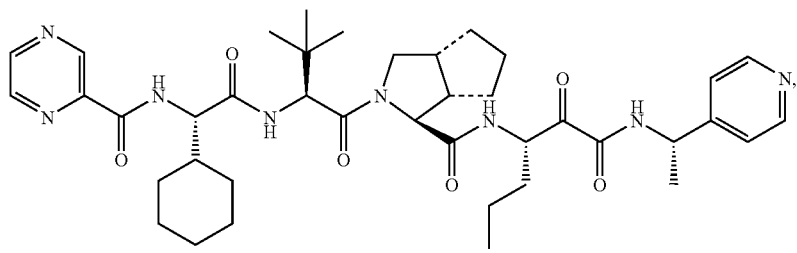
EK
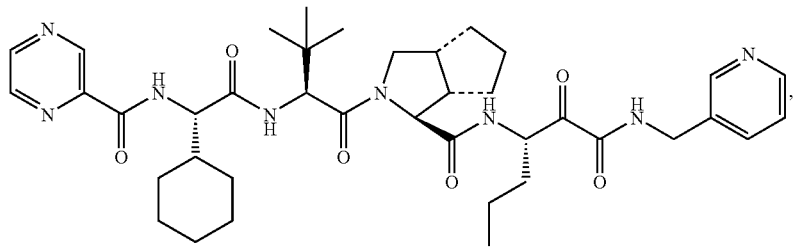
EL
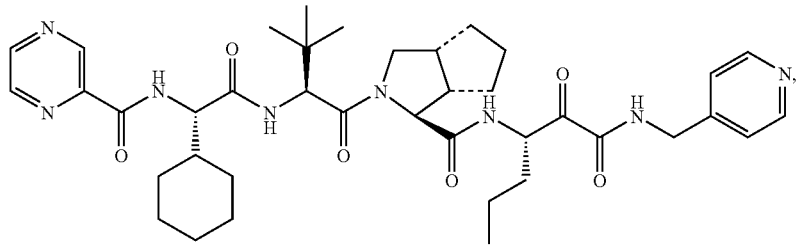
EM
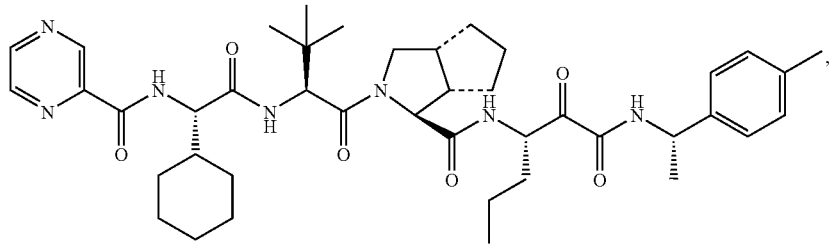

-continued
EN
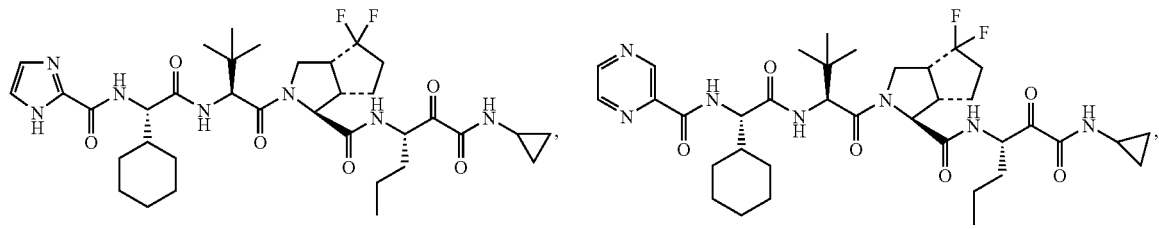
EO
EP
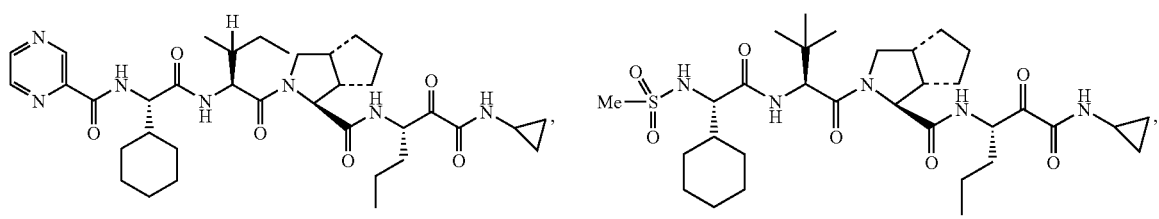
EQ
ER
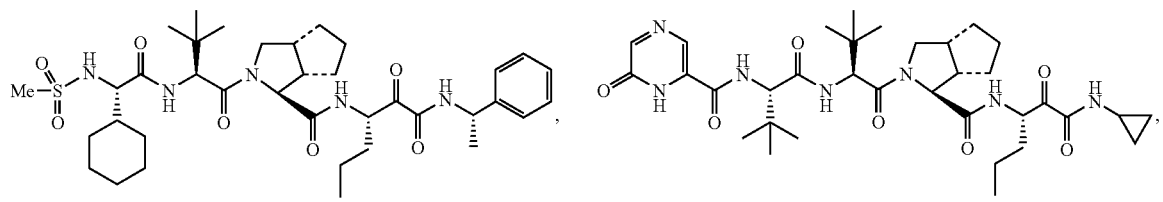
ES
ET
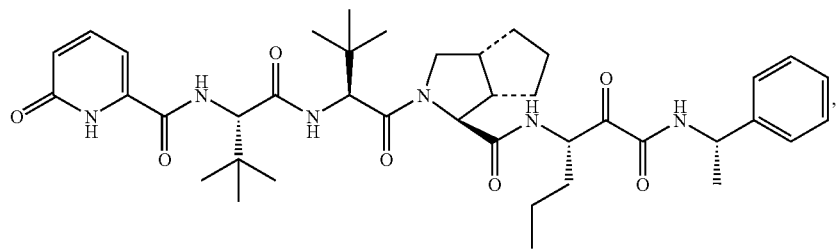
EU
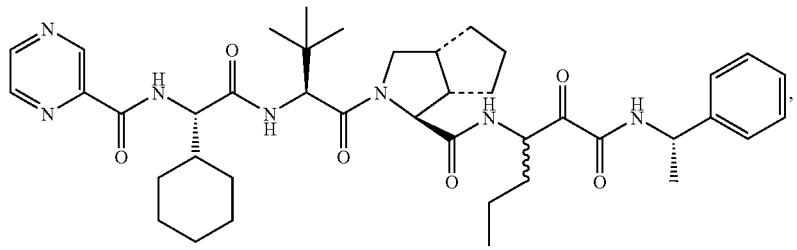
EV
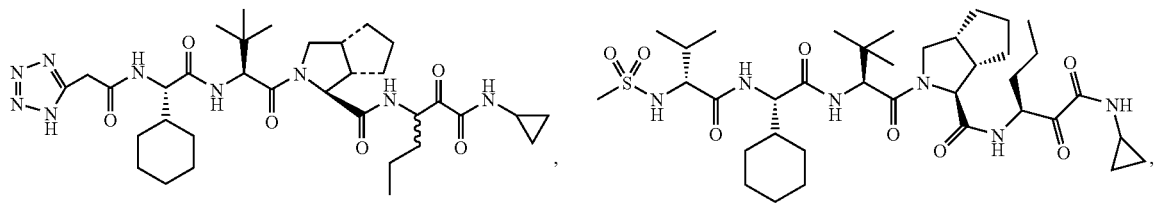
EW -continued
EX
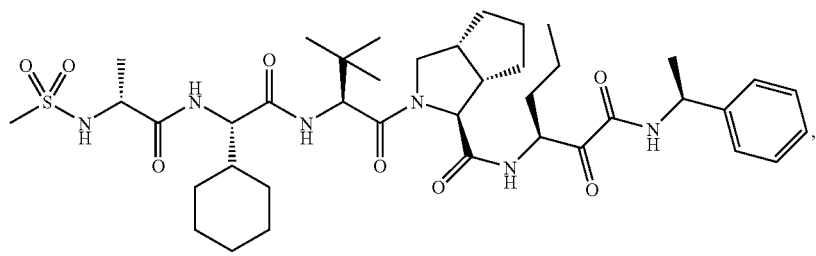
EY
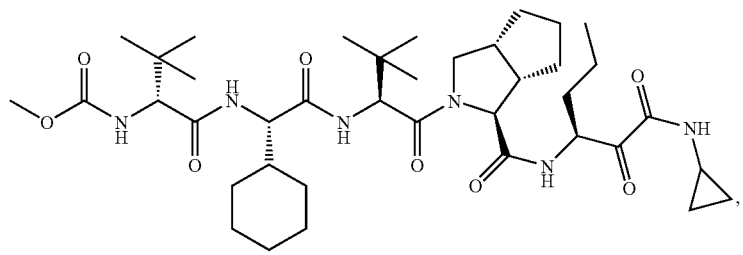
EZ
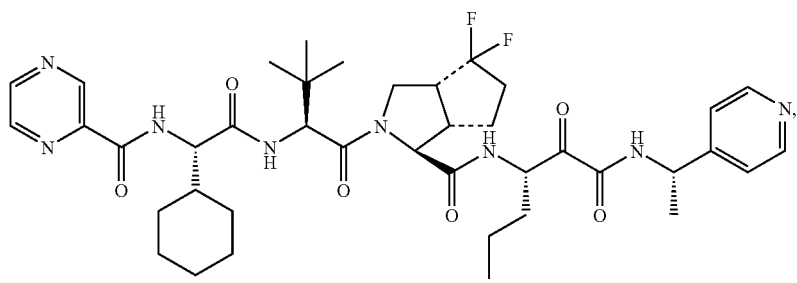
FA FB
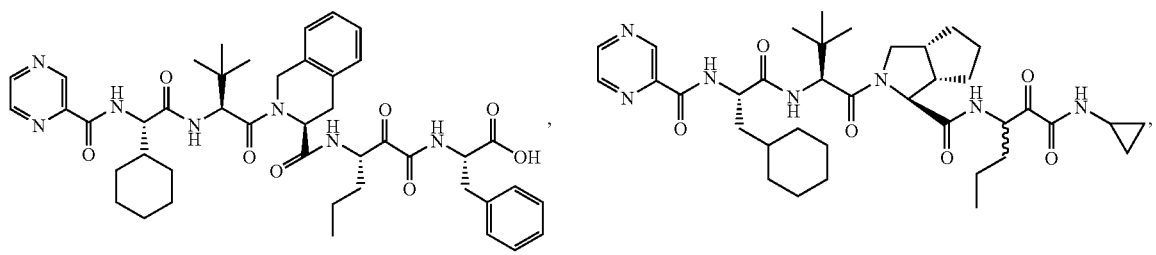
FC FD
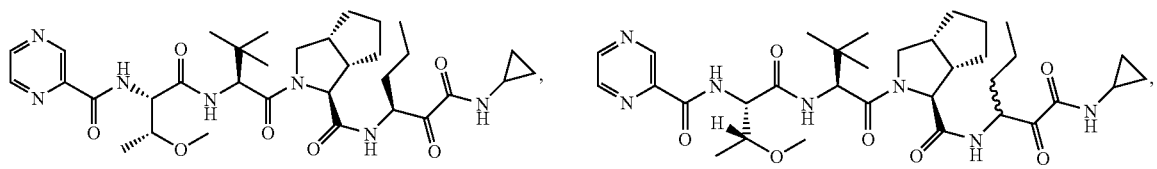
FE FF
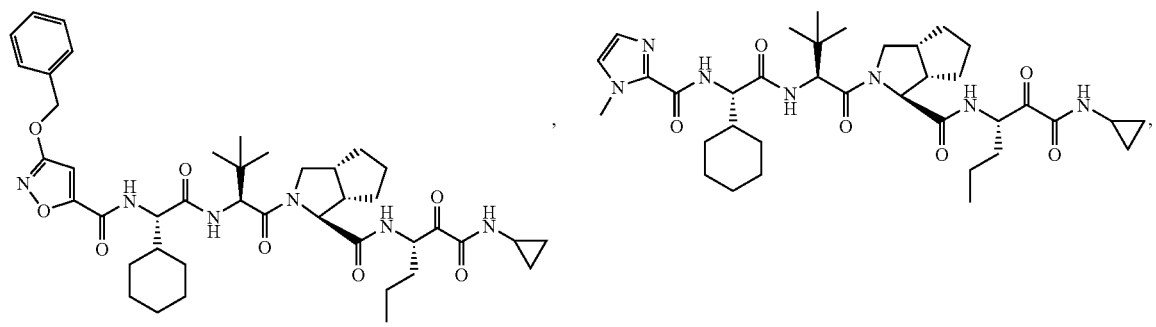

-continued

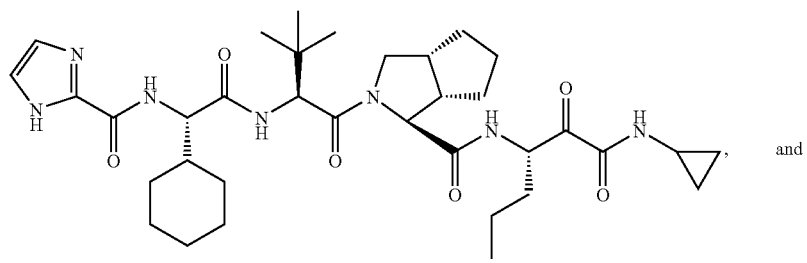 FG

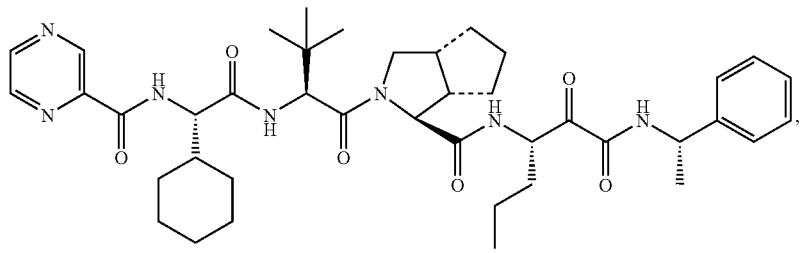 FH or a pharmaceutically acceptable salt or prodrug thereof, or a solvate of such a compound, its salt or its prodrug.

A preferred compound is one selected from the group consisting of S, U, BW, BX, BY, BZ, CE, CU, CW, CY, DZ, EA, EC, EJ, FH, EW, EO, EZ, FG and EN a pharmaceutically acceptable salt or prodrug thereof, or solvate of such compound, its salt or its prodrug.

Another preferred embodiment of the invention are selected from the following group of compounds:

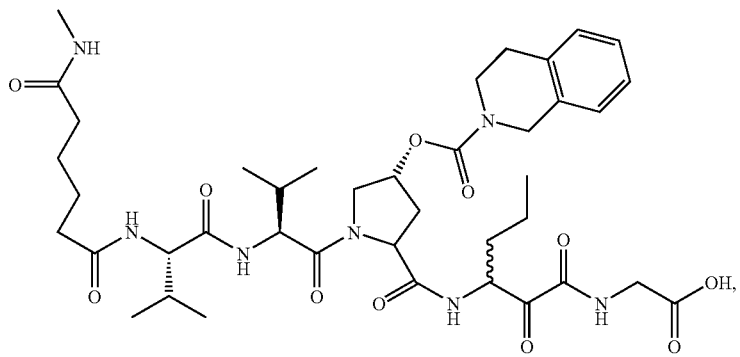 AN

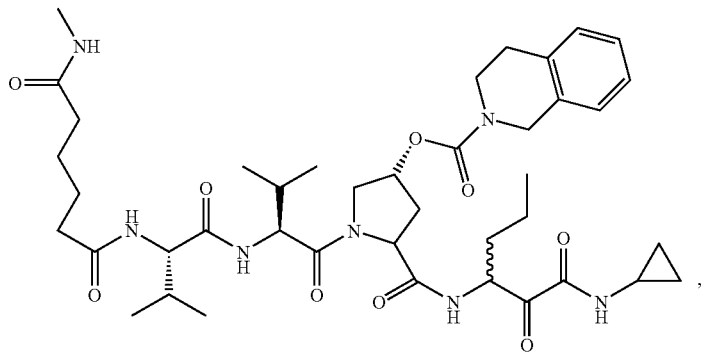 AO

-continued
AP
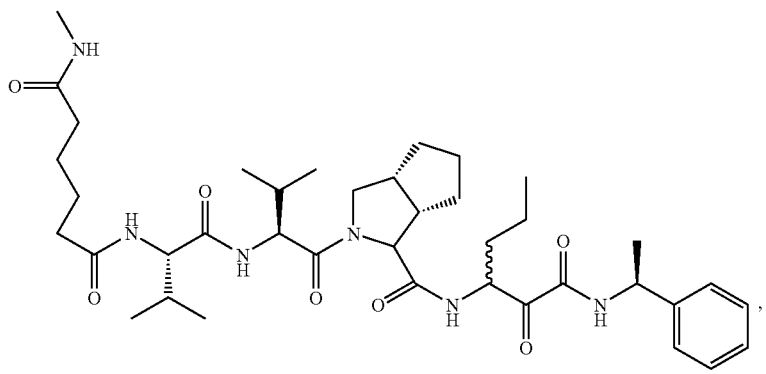
AQ
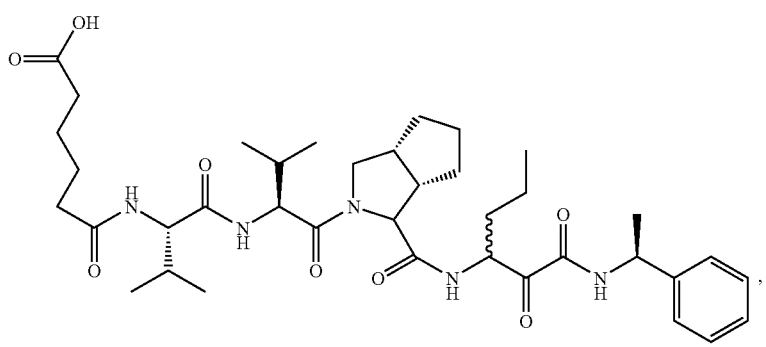
AR
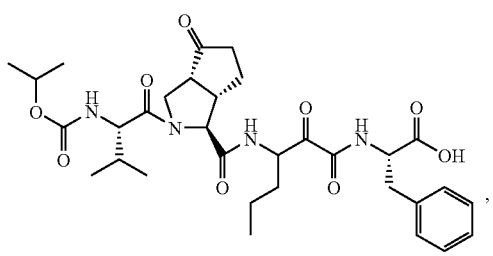
AS
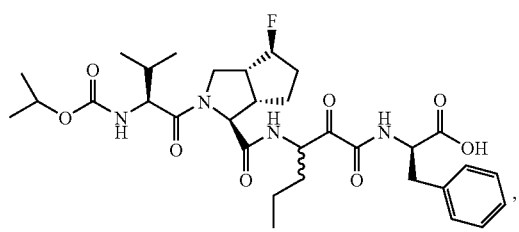
AT
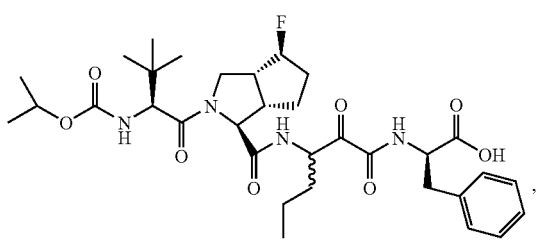
AU
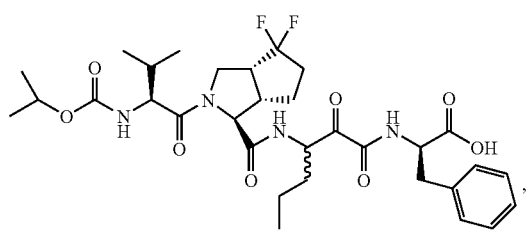
AV
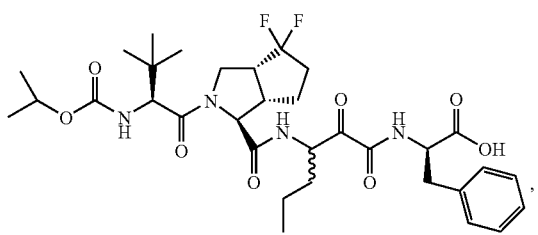
AW
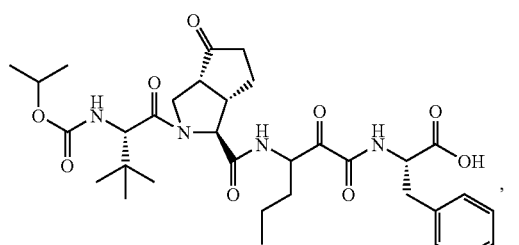

-continued
AX
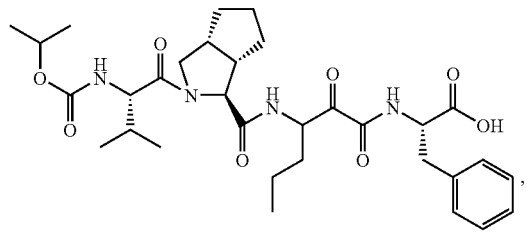,
AY
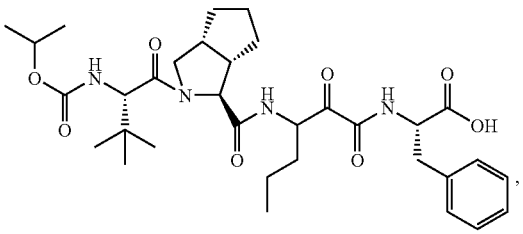,
AZ
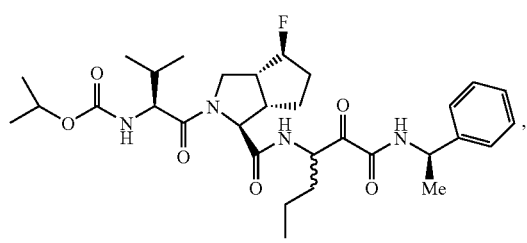,
BA
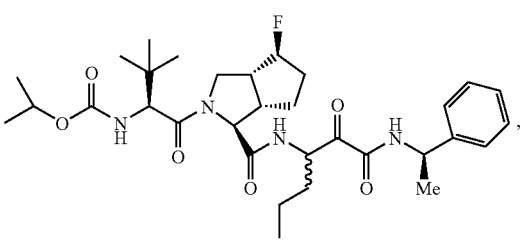,
BB
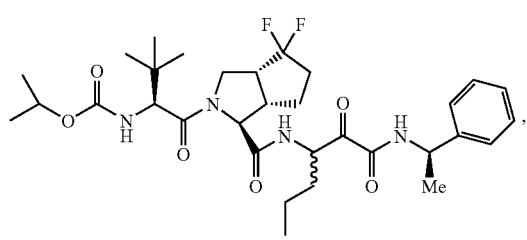,
BC
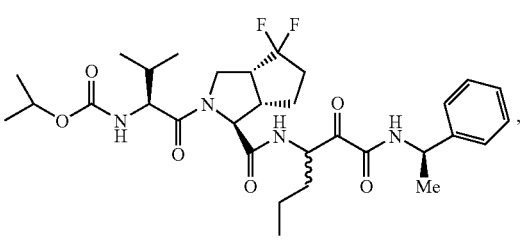,
BD
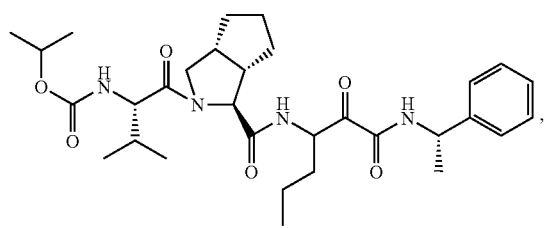,
BE
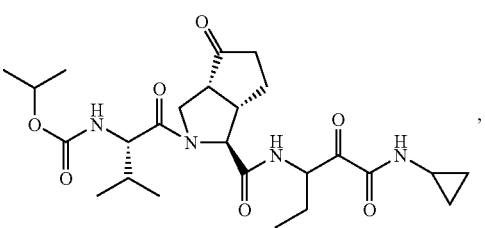,
BF
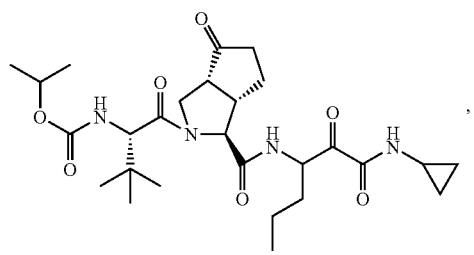,
BG
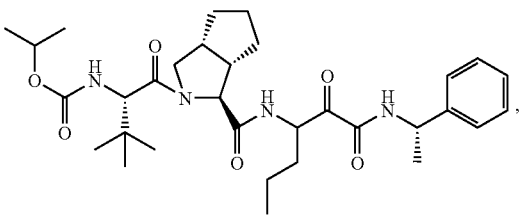,
BH
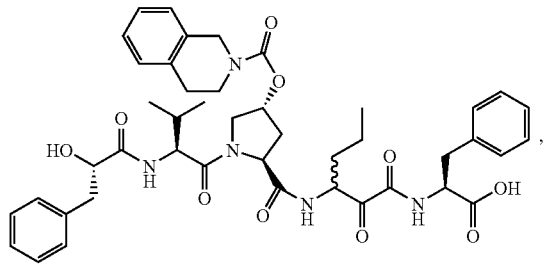,
BI
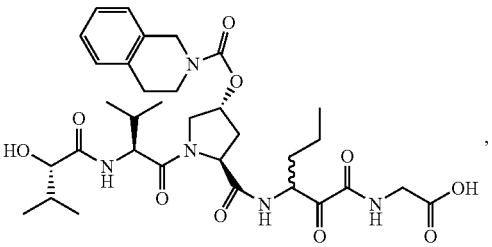, -continued
BJ
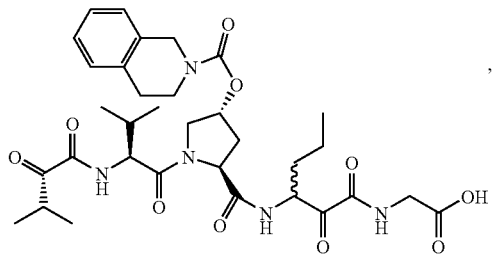
BK
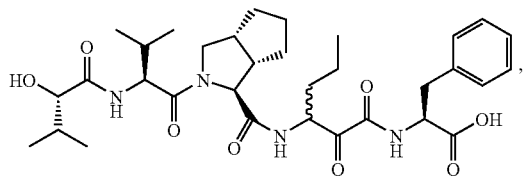
BL
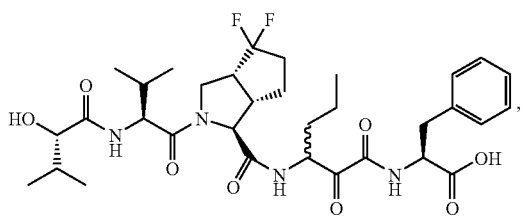
BM
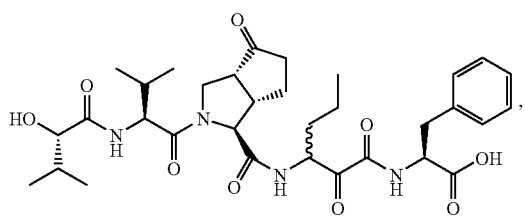
BN
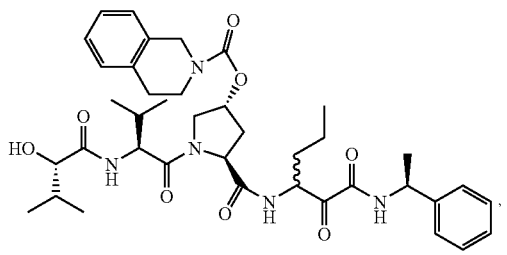
BO
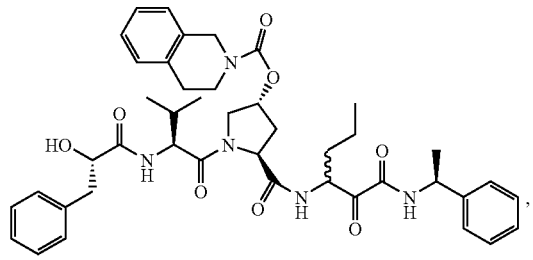
BP
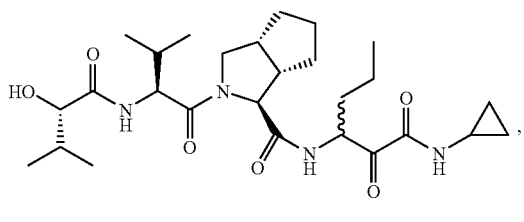
BQ
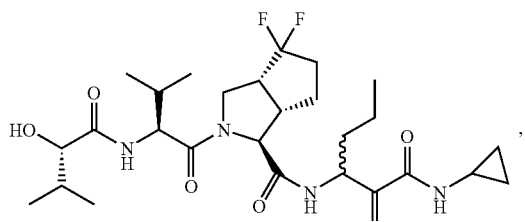
BR
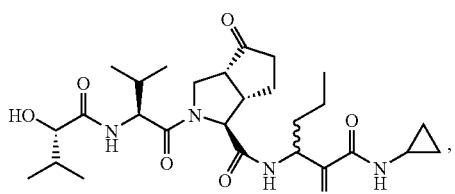
BS
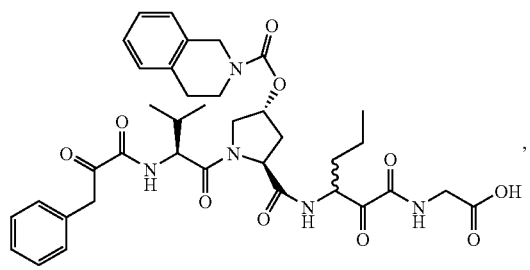

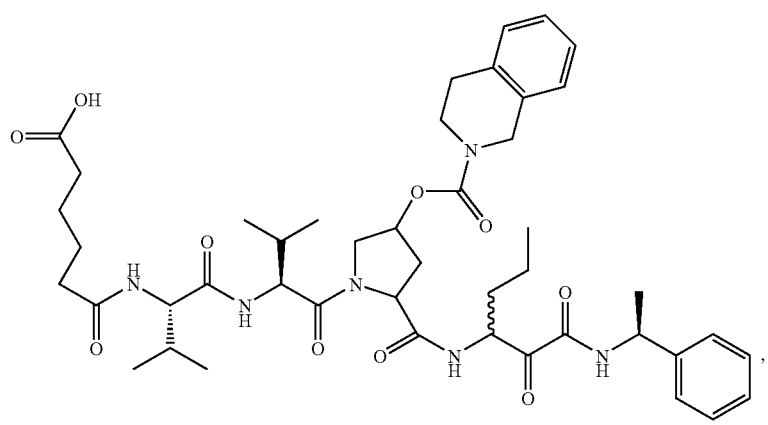
BT
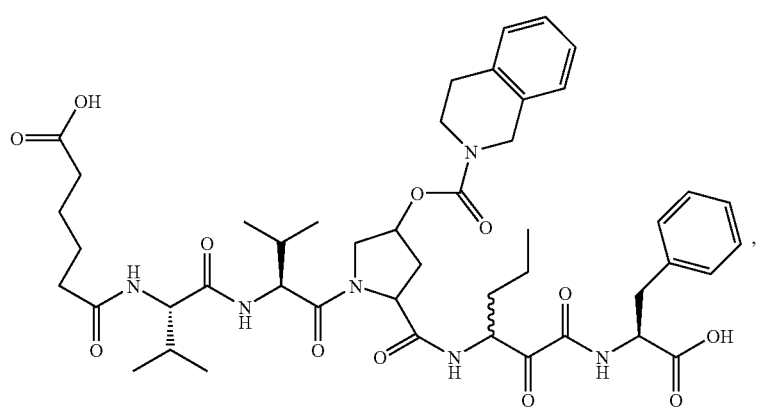
BU
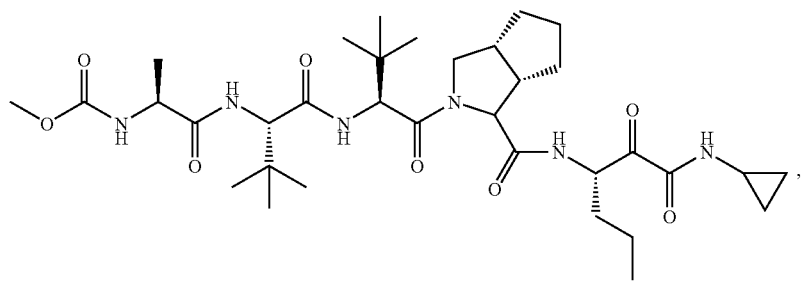
DG
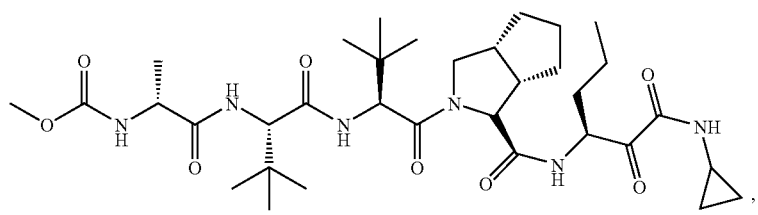
DH

-continued
DI
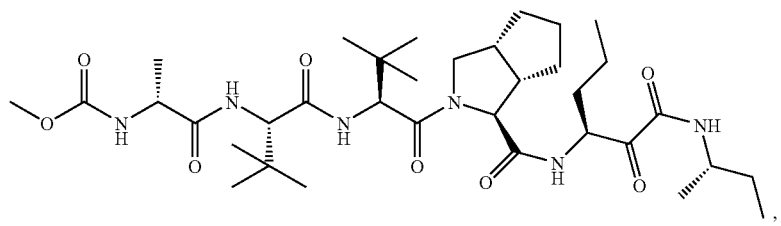
DJ
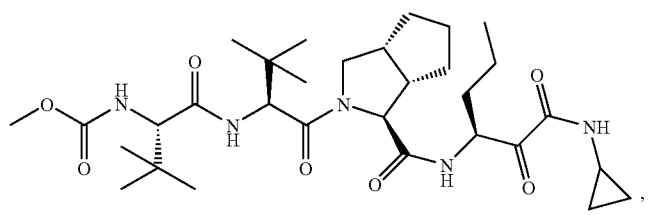
DN
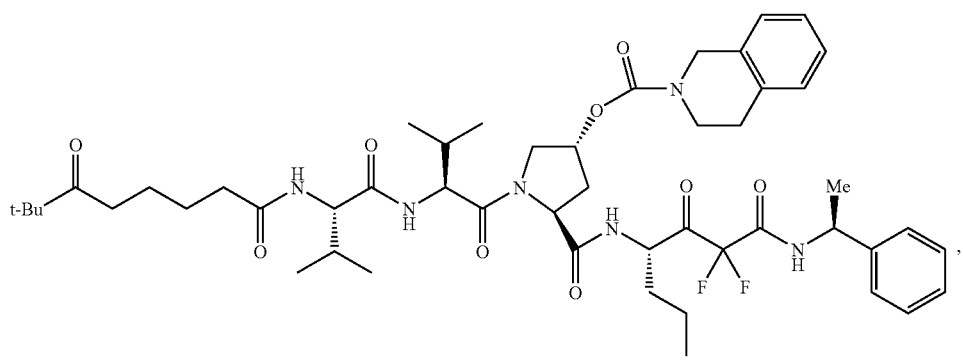
EB
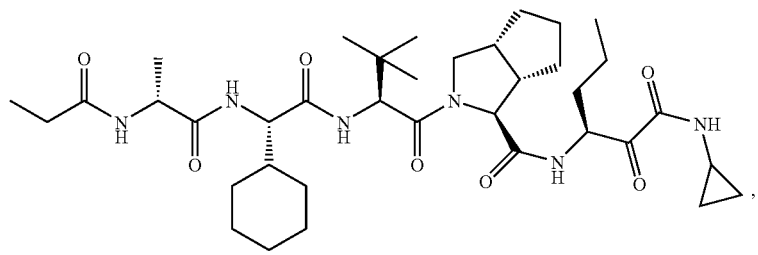
EC
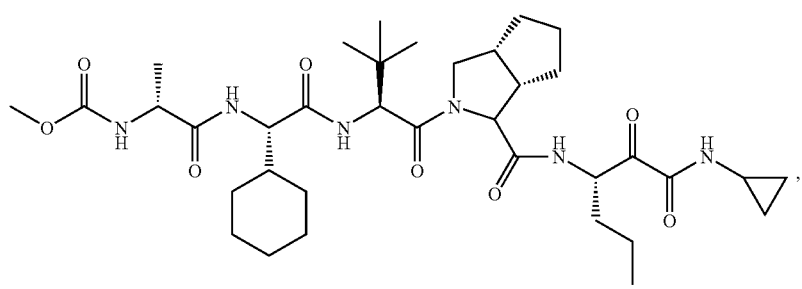

-continued
ED
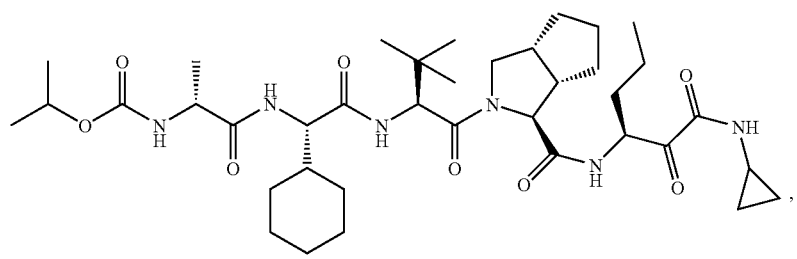
EE
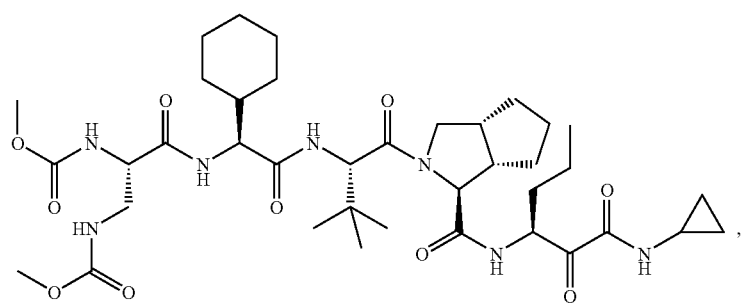
EF
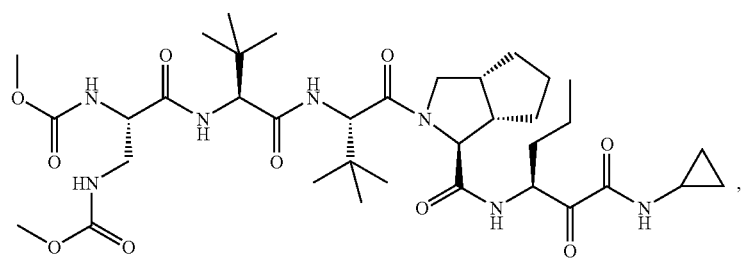
EG EH
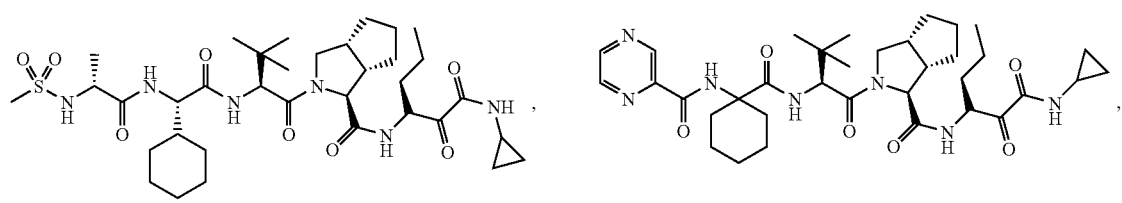
EI EQ
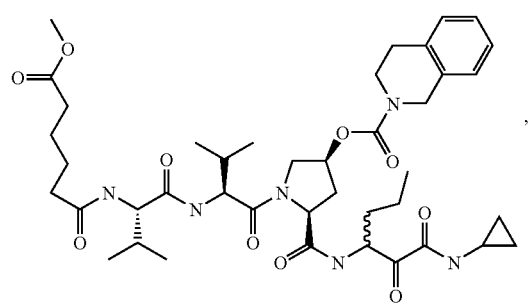
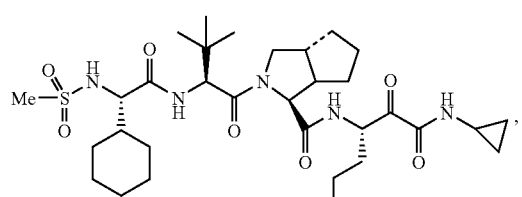

-continued

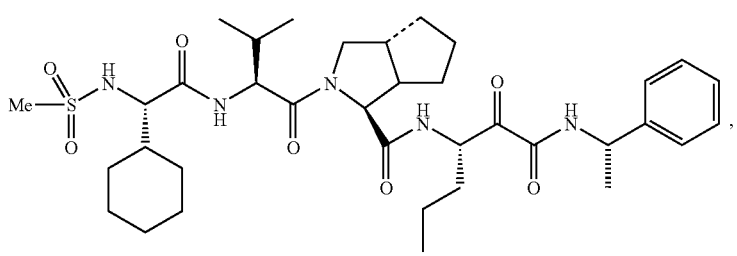
ER

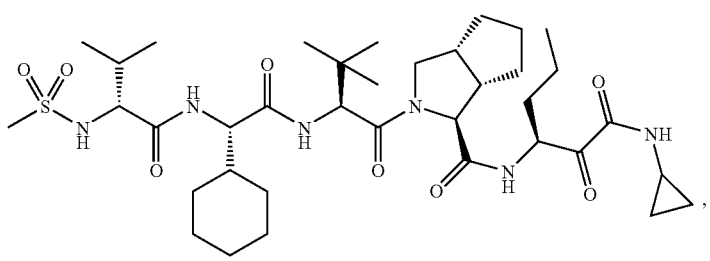
EW

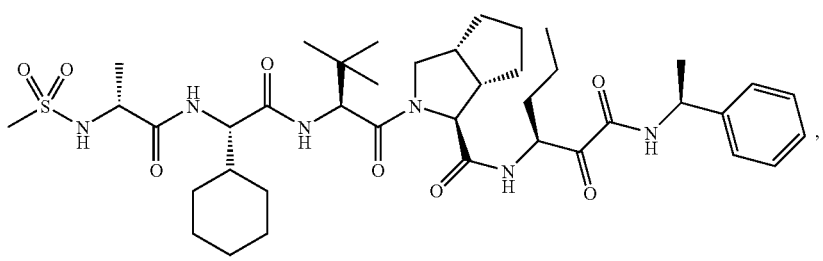
EX

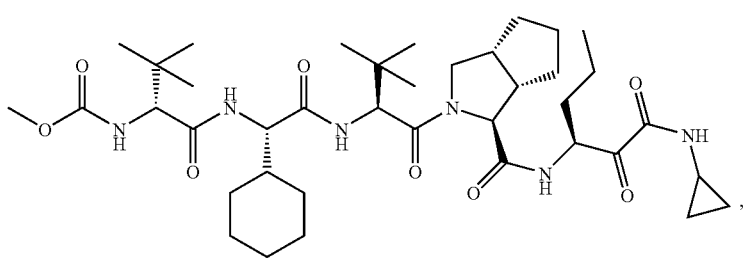
EY or a pharmaceutically acceptable salt or prodrug thereof, or a solvate of such a compound, its salt or its prodrug.

Another preferred embodiment of the invention is a compound of the formula

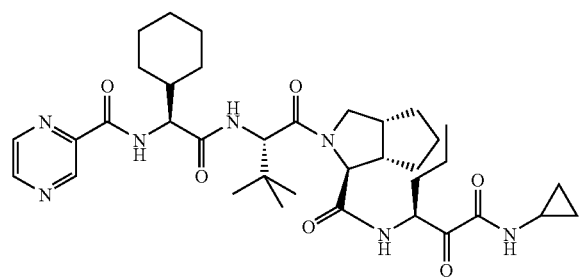

or a pharmaceutically acceptable salt or prodrug thereof, or a solvate of such a compound, its salt or its prodrug.

Another preferred embodiment of the invention is compound of formula 1 wherein:

$R^0$ is a bond;

$R^1$ is hydrogen;

$R^2$ is lower alkyl optionally substituted with 1 to 3 aliphatic group substituents; or lower cycloalky optionally substituted with 1 to 3 cyclic group substituents;

$R^3$ and $R^5$ are each independently methylene optionally substituted with 1 to 3 aliphatic group substituents;

$R^4$, $R^6$, $R^8$ and $R^{10}$ are hydrogen;

R⁷ is methylene substituted with cycloalkyl, lower alkyl or aryl;or or (1,1- or 1,2-)cycloalkenyl optionally substituted with cycloalkyl, lower alkyl or aryl;

R9 is lower alkyl optionally substituted with 1 to 3 aliphatic group substituents; or heteroaryl optionally substituted with 1 to 3 cyclic group substituents;

or heterocyclic optionally substituted with 1 to 3 cyclic group substituents;

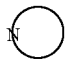

is monocyclic azaheterocyclyl, multicyclic azaheterocyclyl, or multicyclic azaheterocyclenyl optionally substituted with from 1 to 3 cyclic group substituents; and L is —C(O)—, —OC(O)—.

Another preferred embodiment of the invention is a compound selected from the group consisting of:

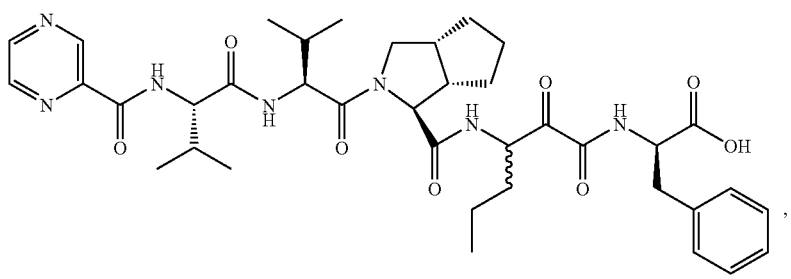

A

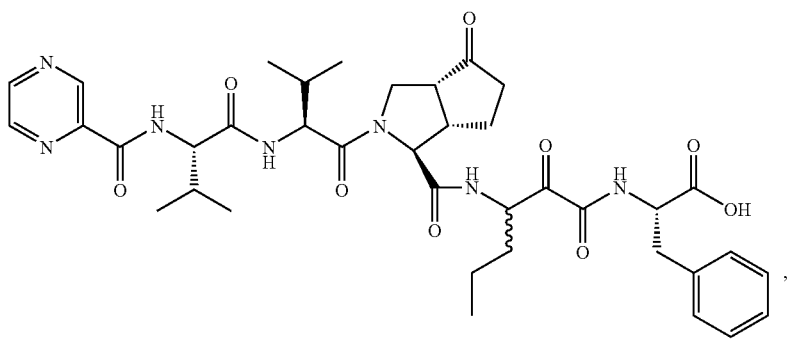

B

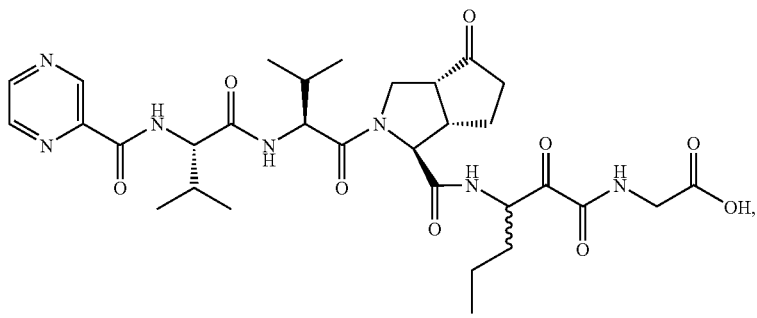

C

D
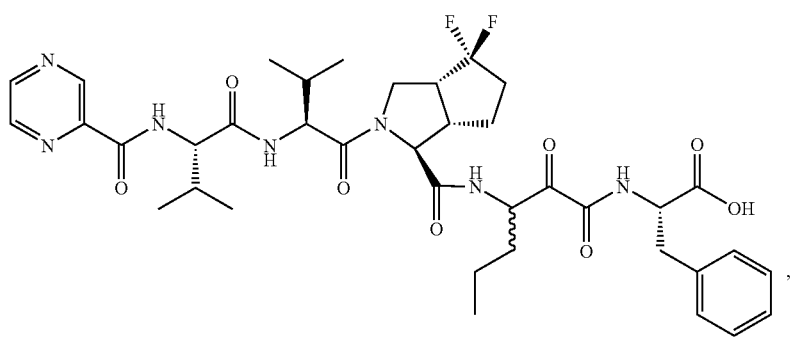
E
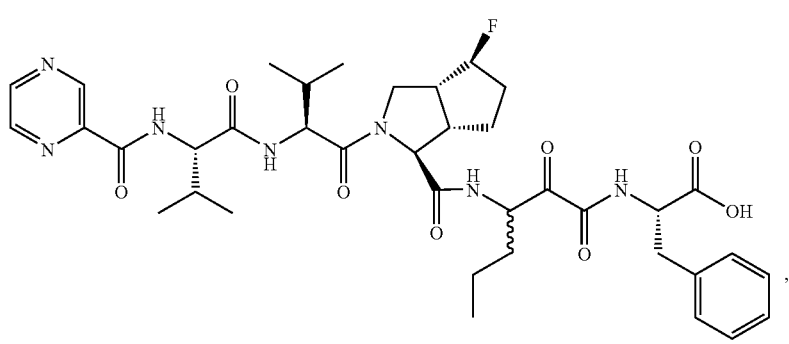
F
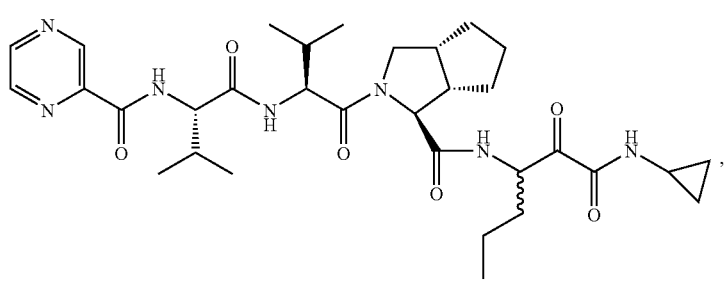
G 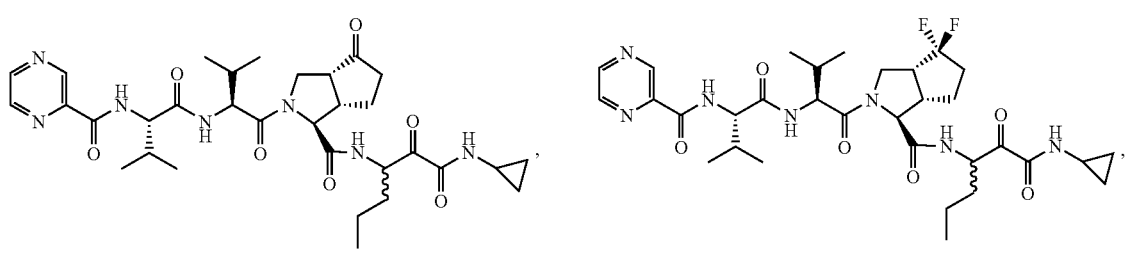 H
I
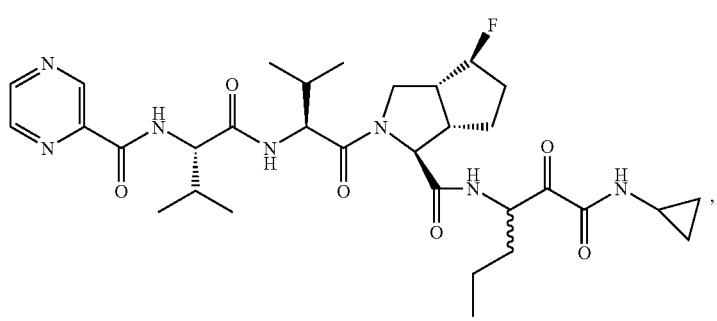

-continued
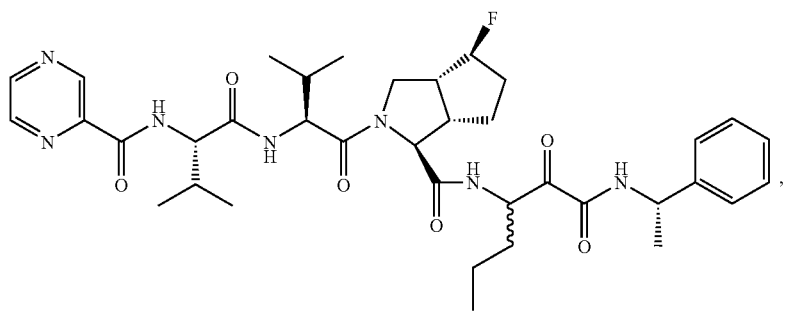
J
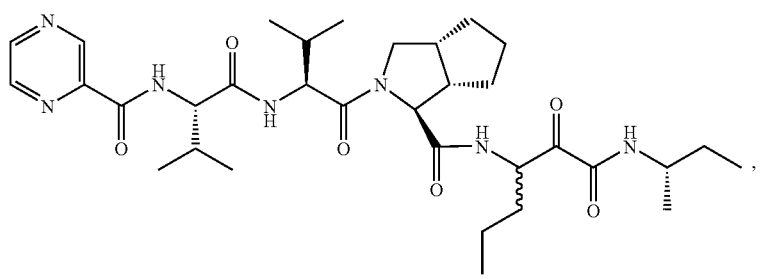
K
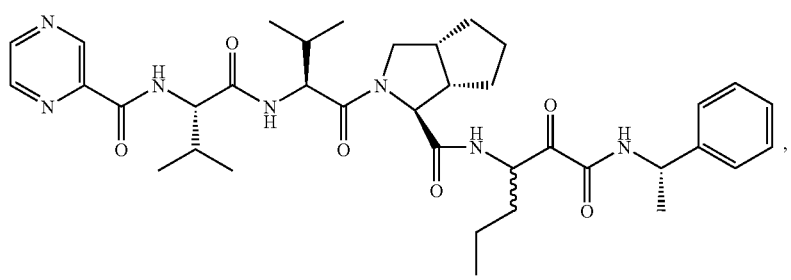
L
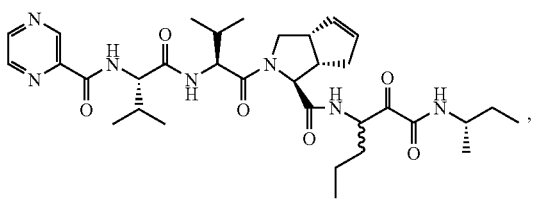
M
N
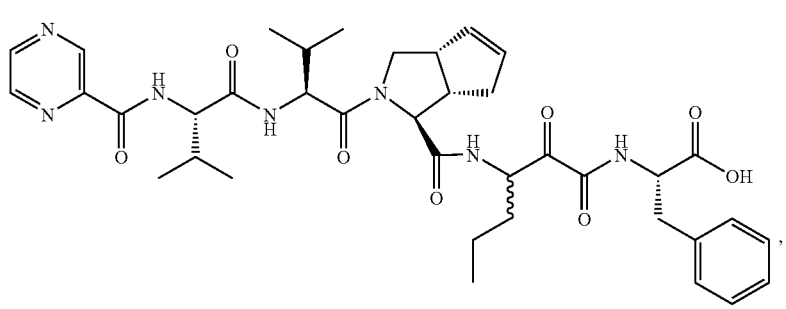
O -continued
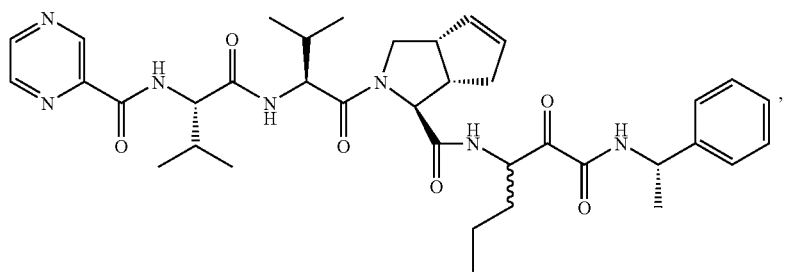
P
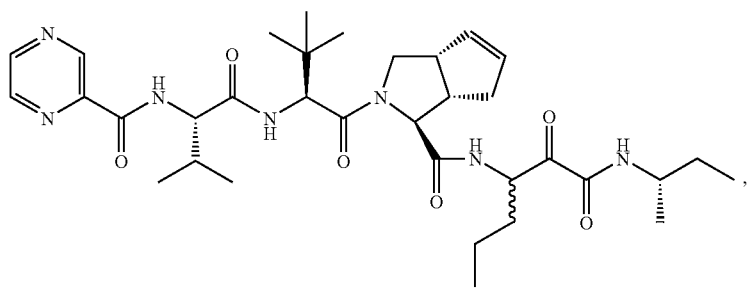
Q
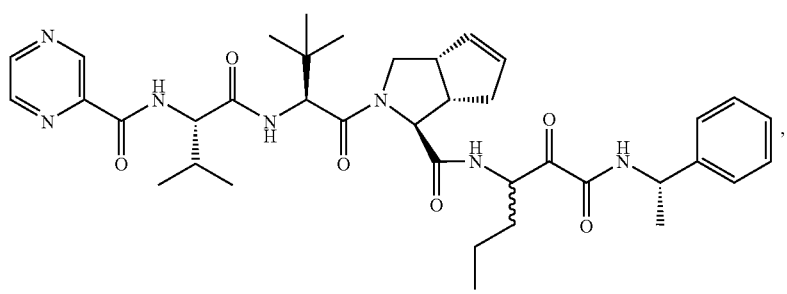
R
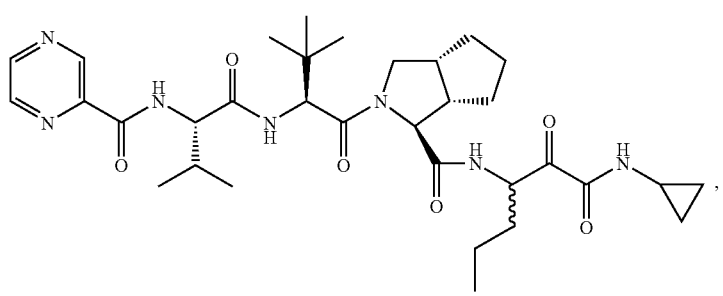
S
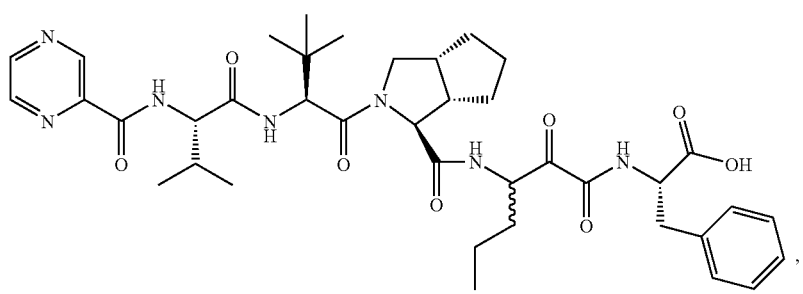
T -continued
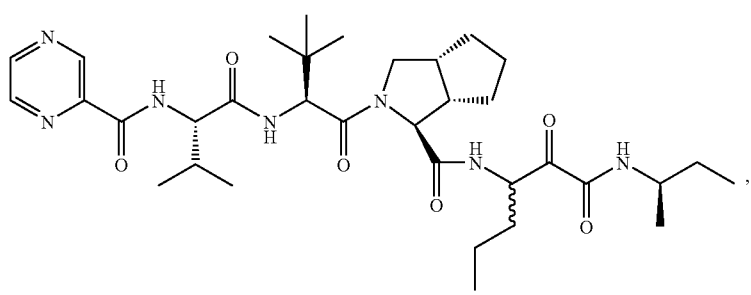
U
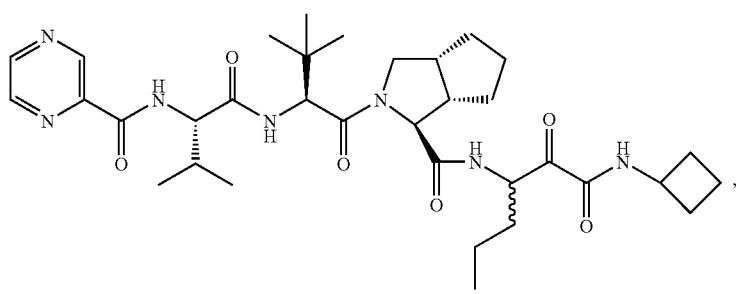
V
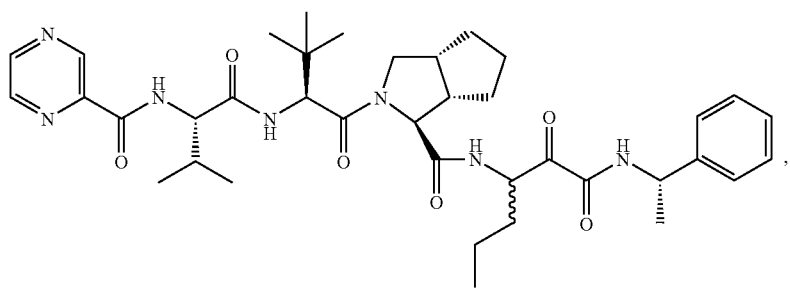
W
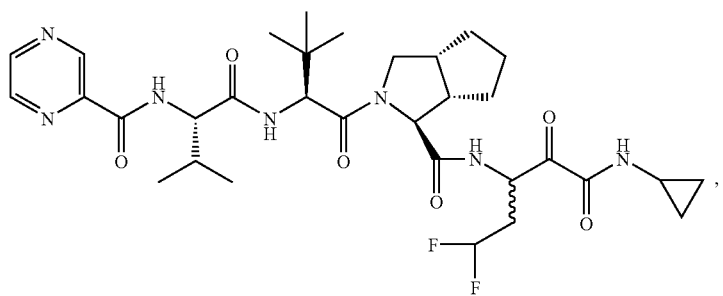
X
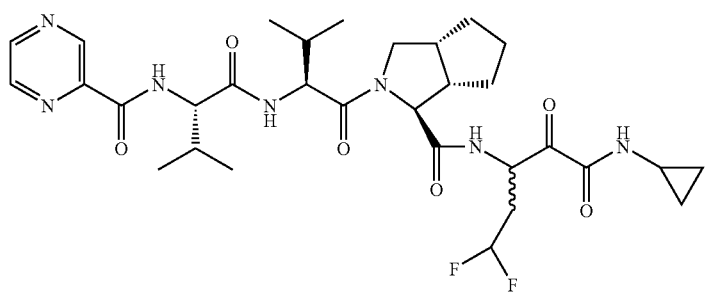
Y -continued
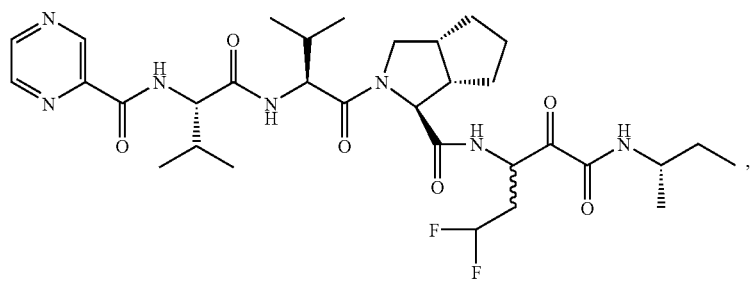
Z
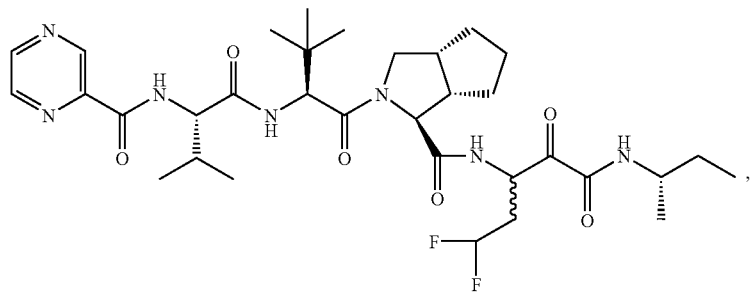
AA
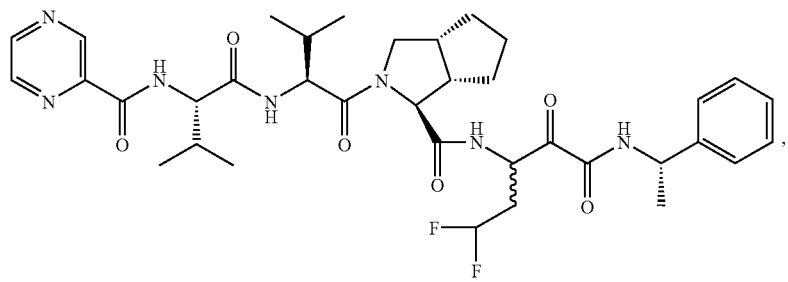
AB
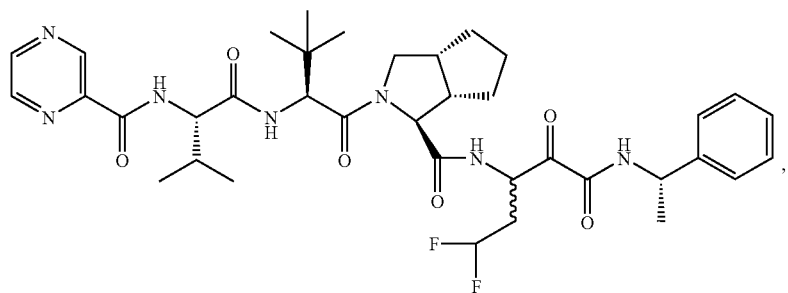
AC
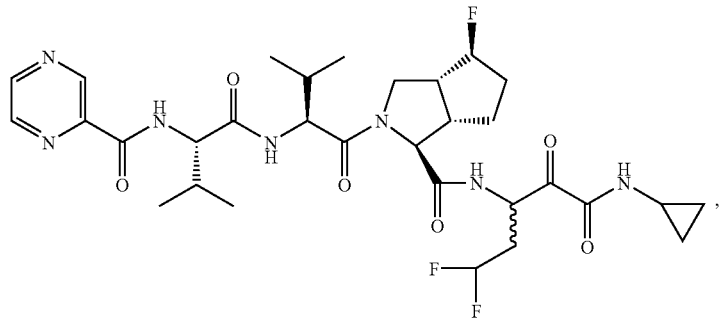
AD -continued
AE
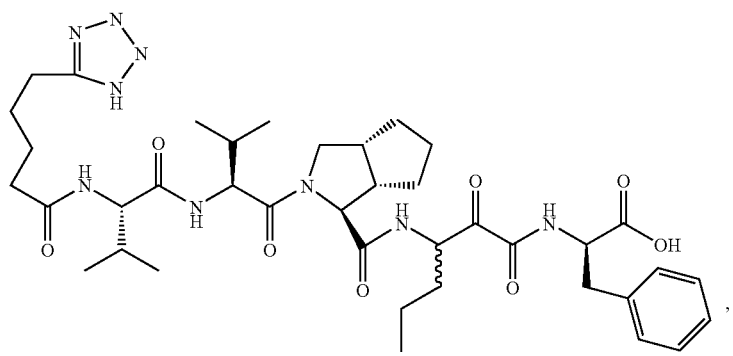
AF
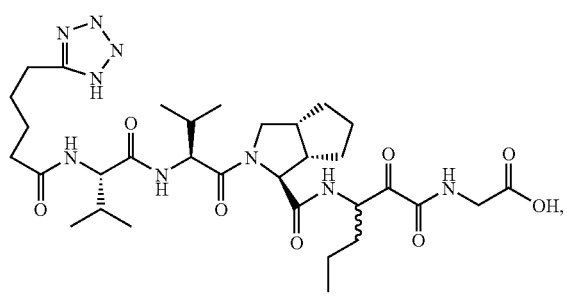
AG
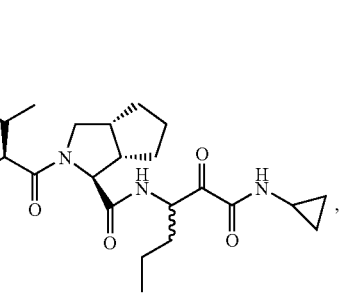
AH
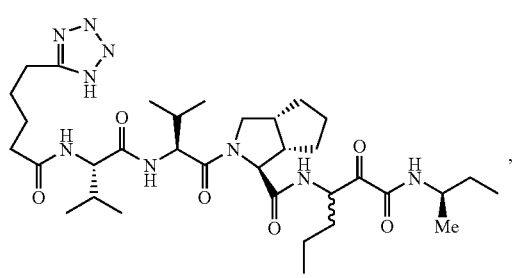
AI
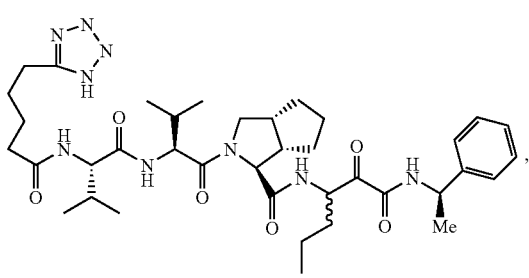
AJ
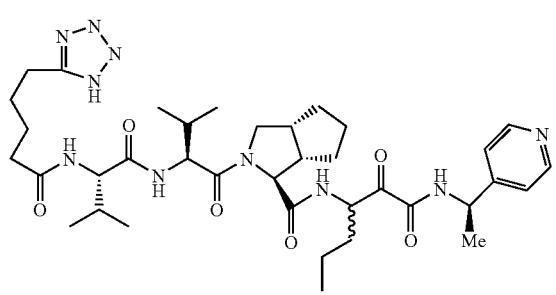
AK
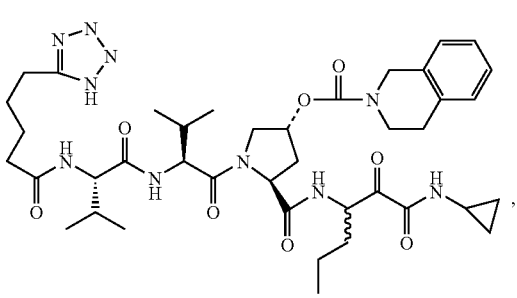
AL
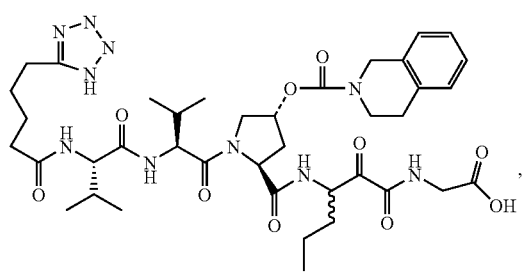
AM
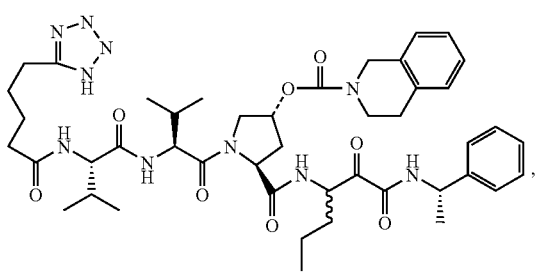

-continued
BV
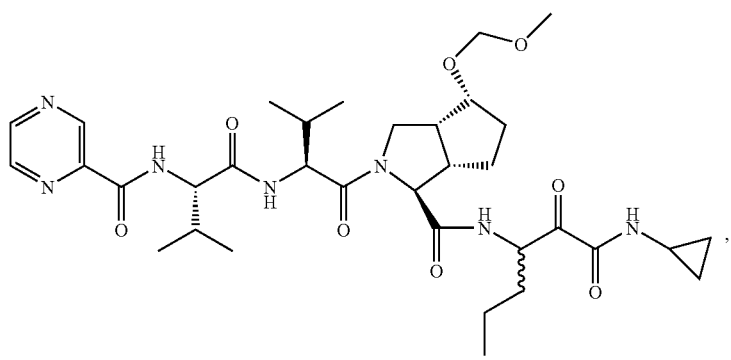
BW
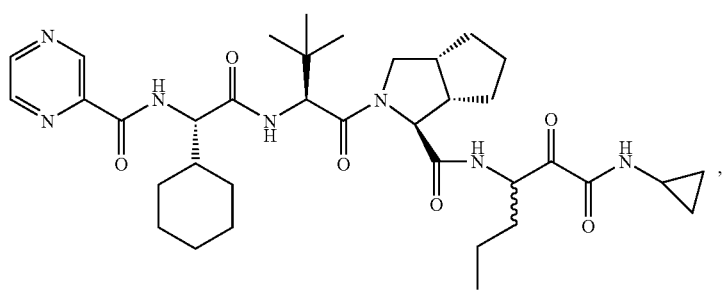
BX
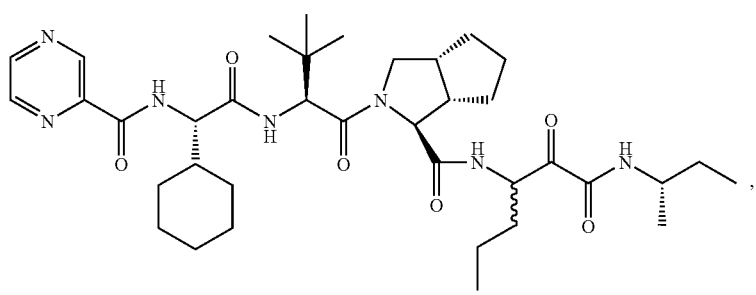
BY
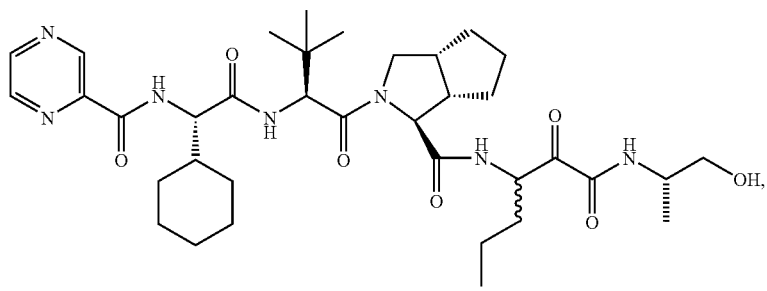
BZ
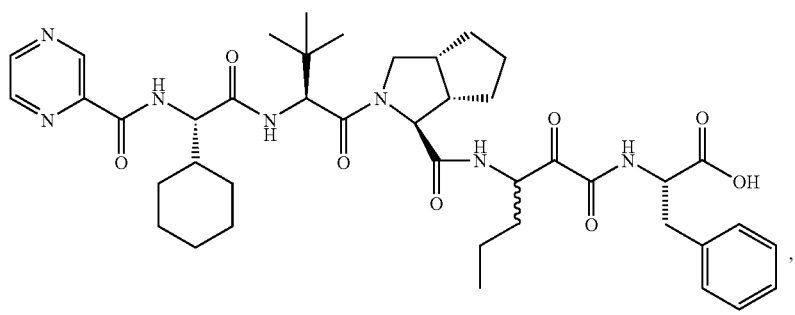

-continued
CA
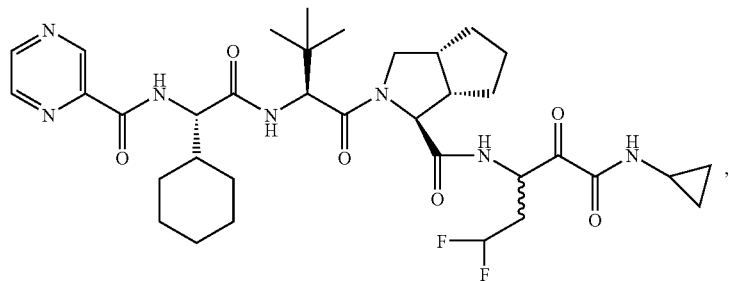
CB
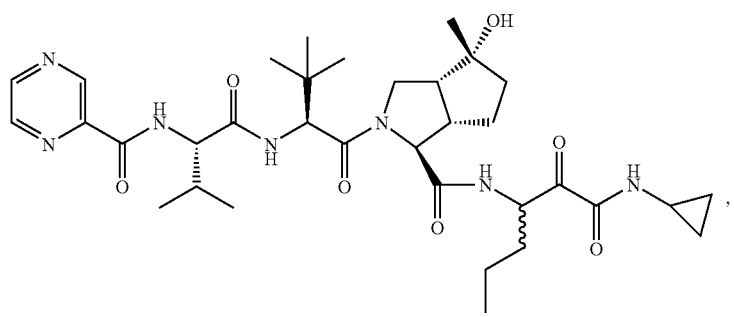
CC
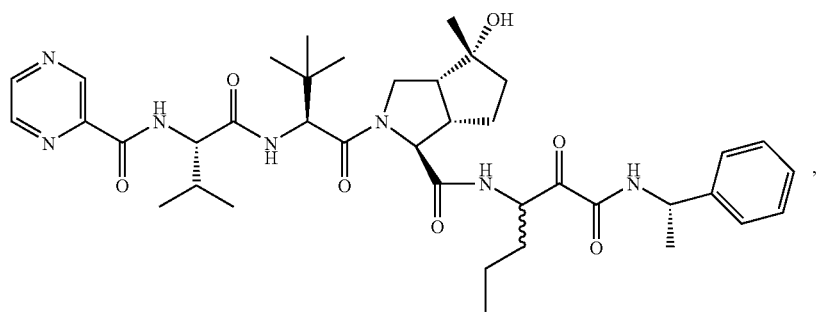
CD
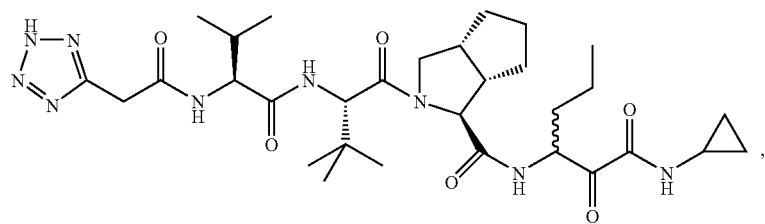
CE
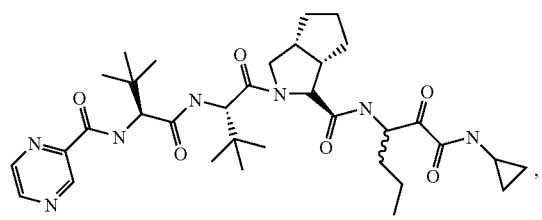
CF
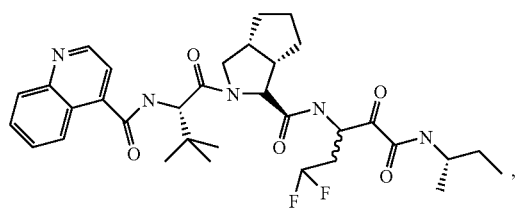

-continued
CG
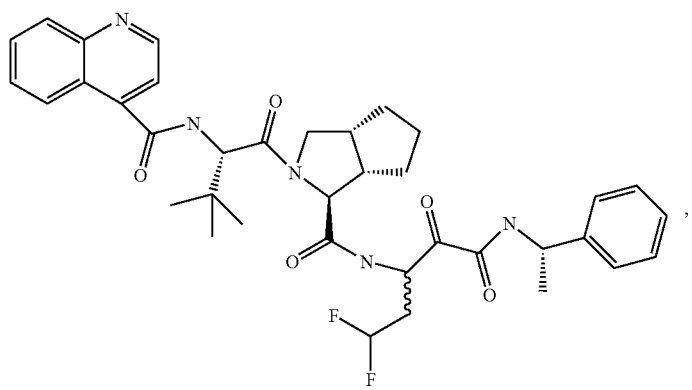
CH
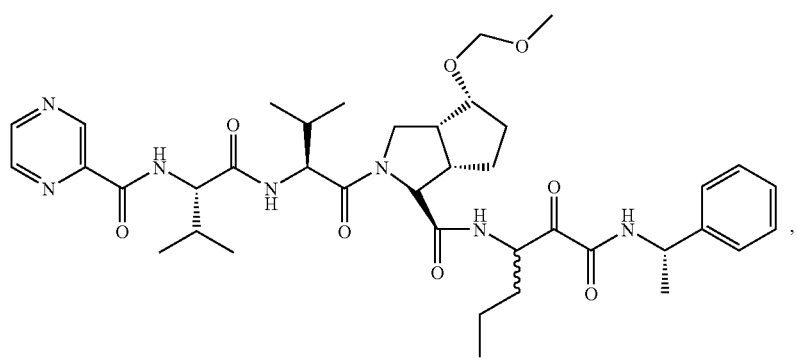
CI
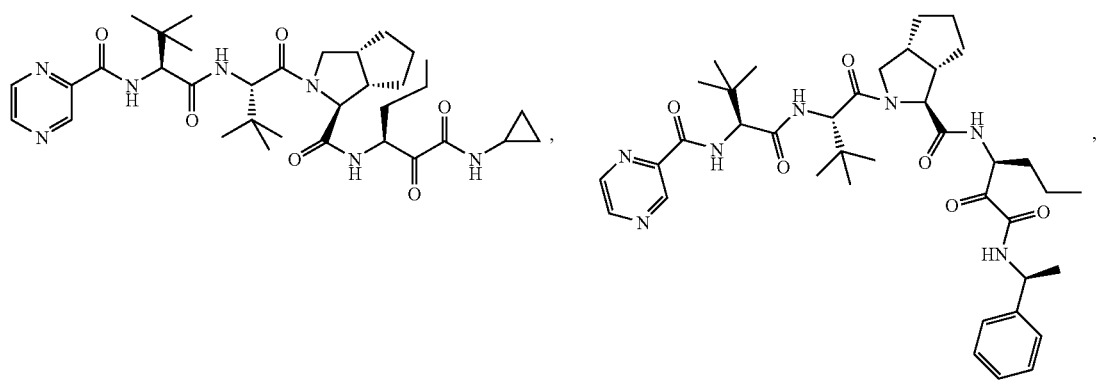
CJ
CK
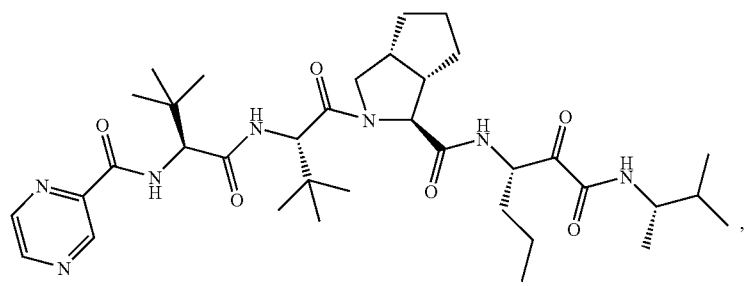

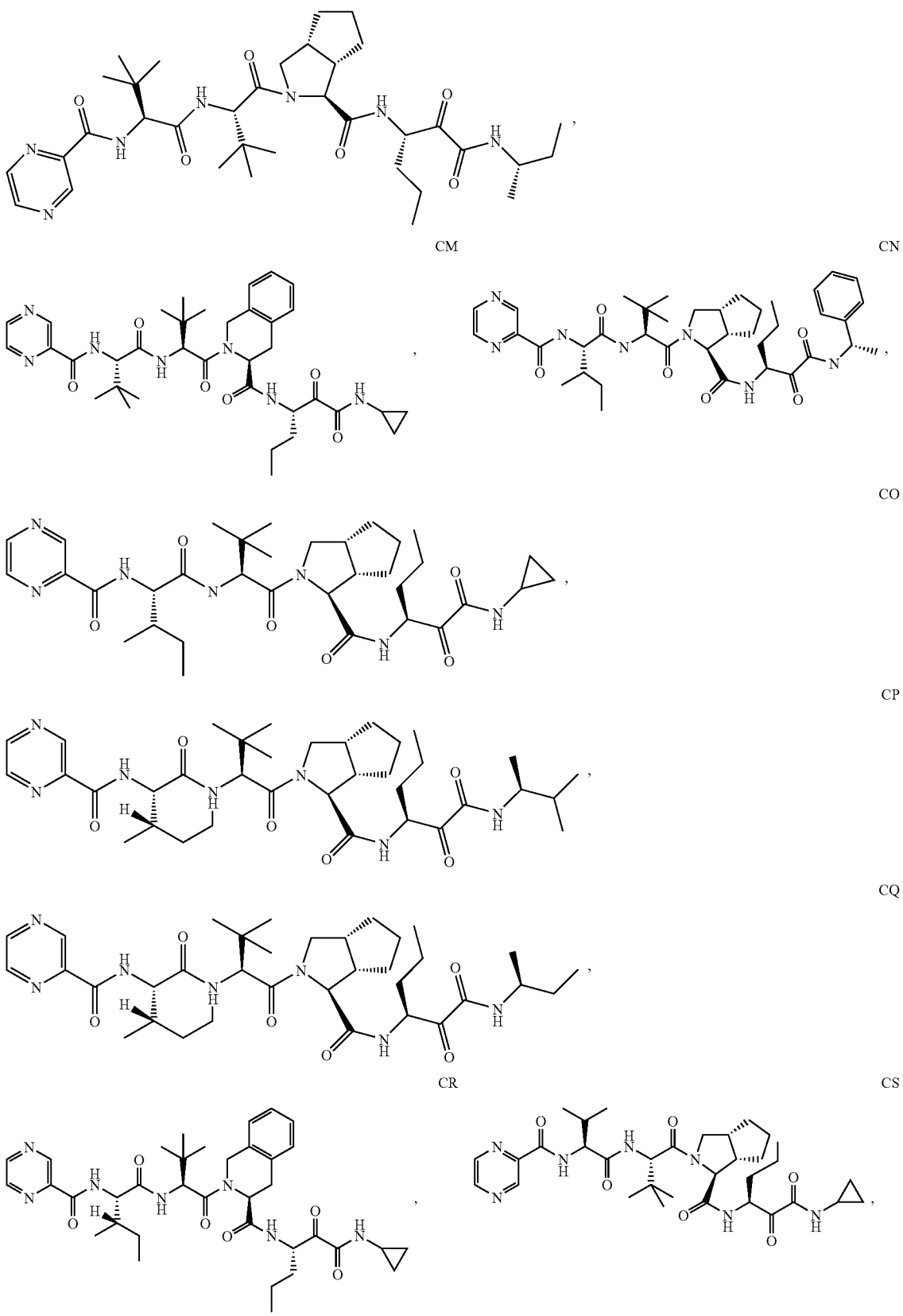

-continued
CT
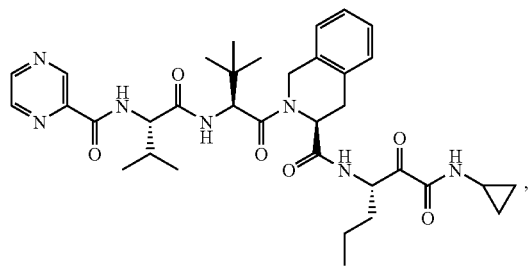
CU
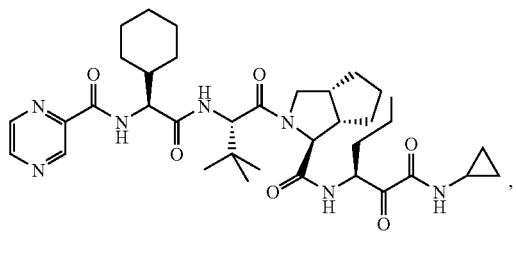
CV
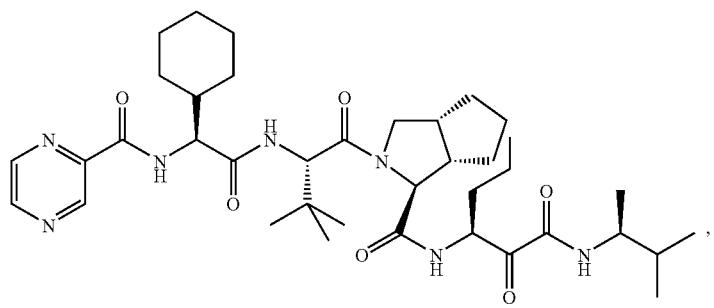
CW
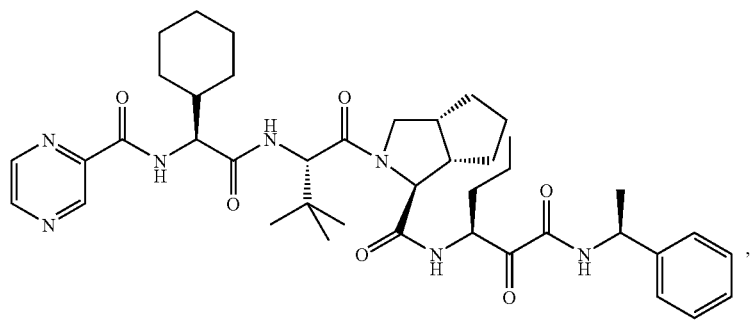
CX
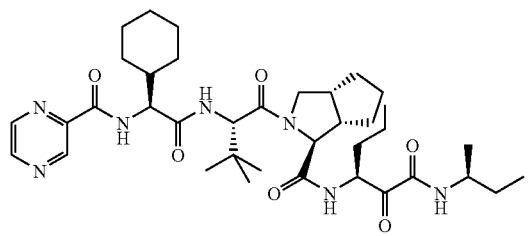
CY
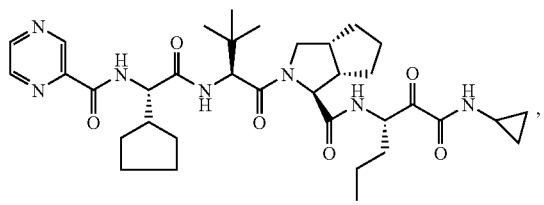
CZ
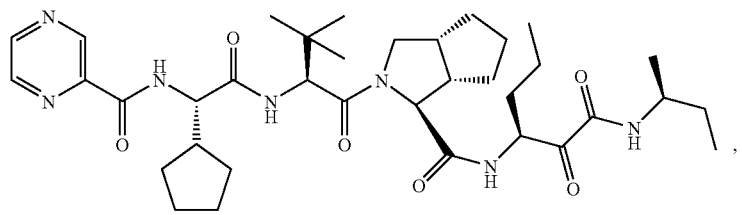

-continued
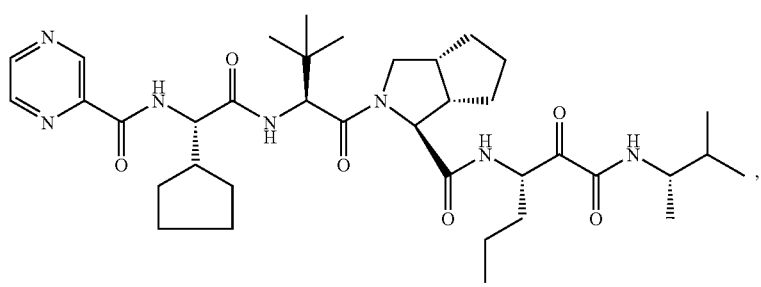
DA
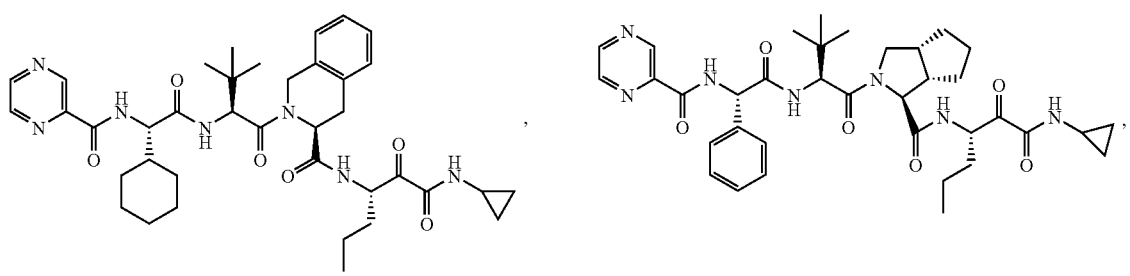
DB
DC
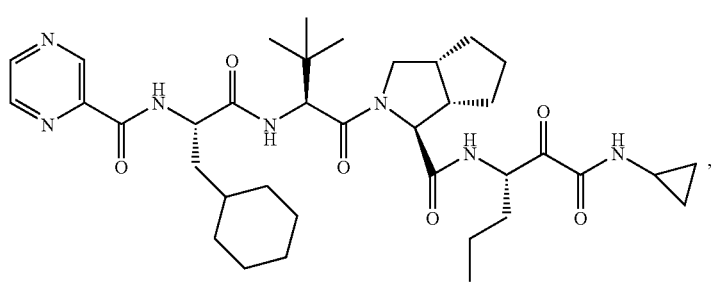
DD
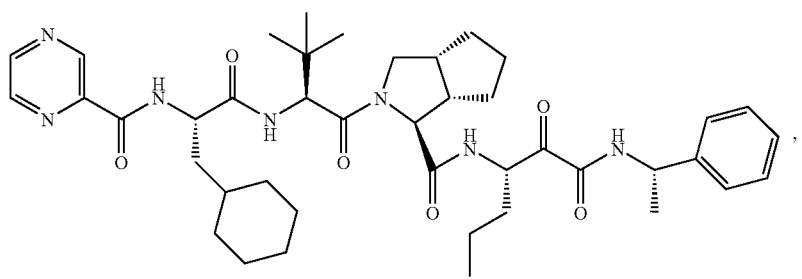
DE
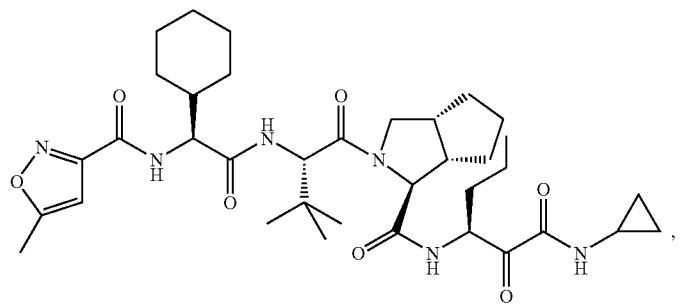
DF -continued
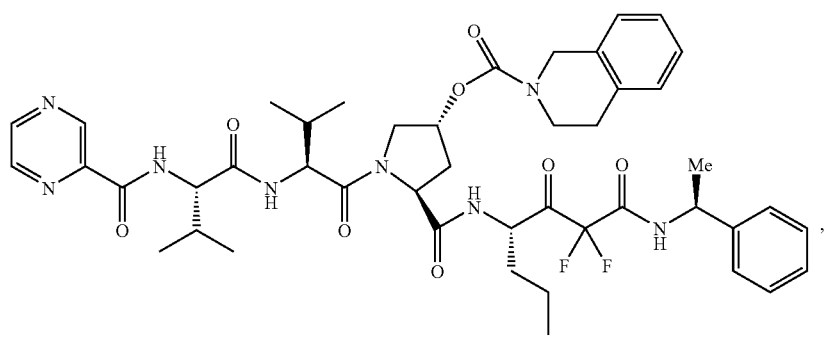
DK
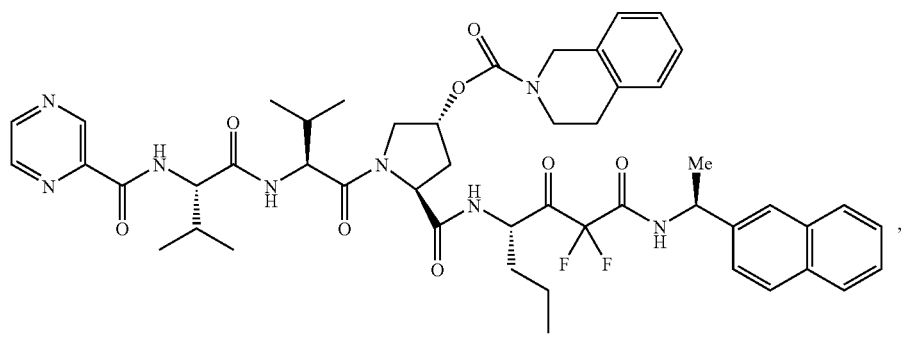
DL
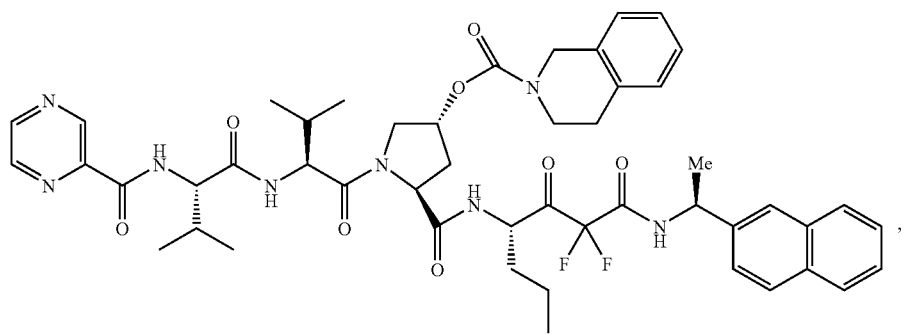
DM
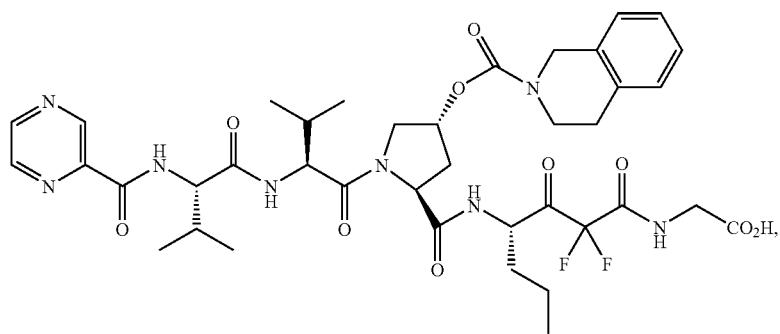
DO -continued
DP
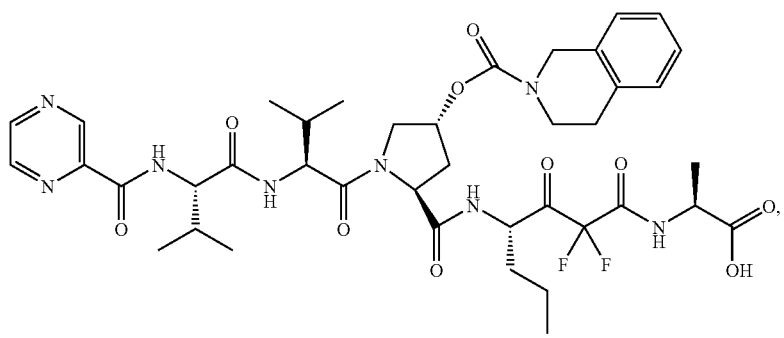
DQ
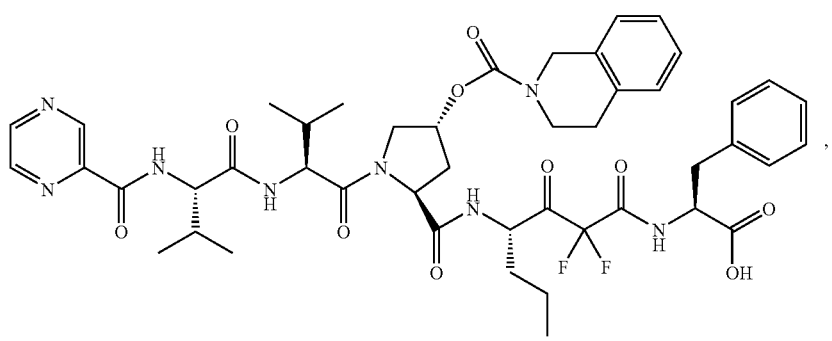
DR
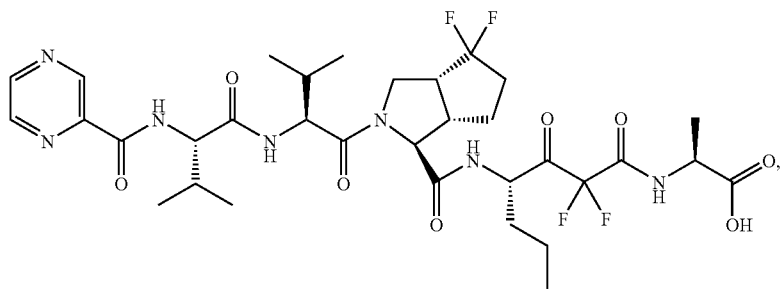
DS
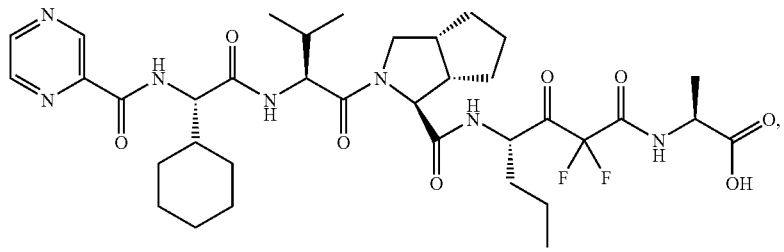
DT
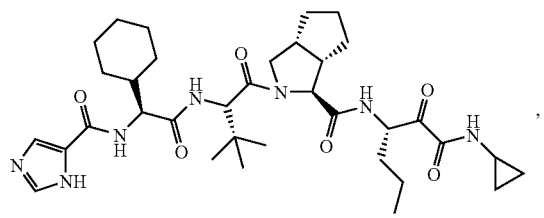
DU
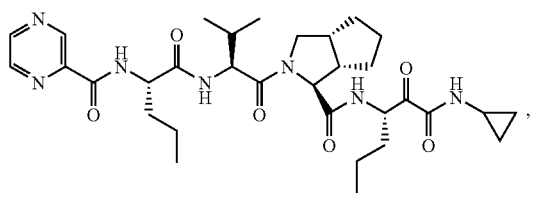

-continued
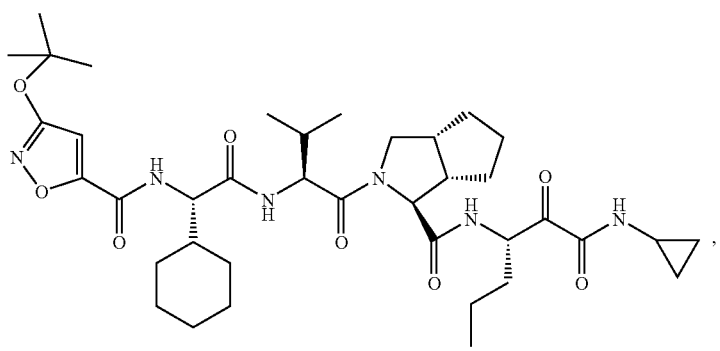
DV
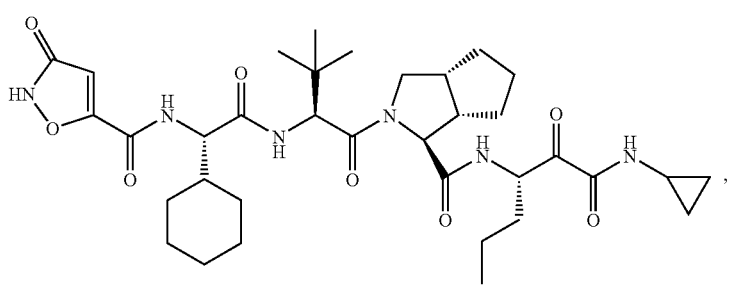
DW
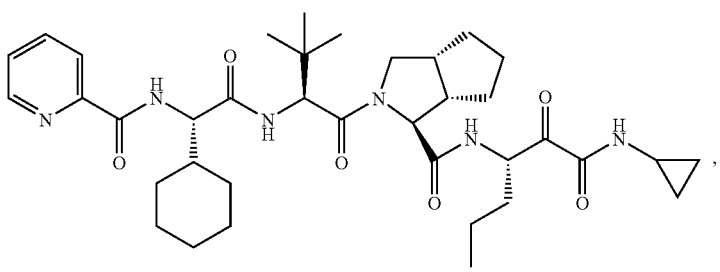
DX
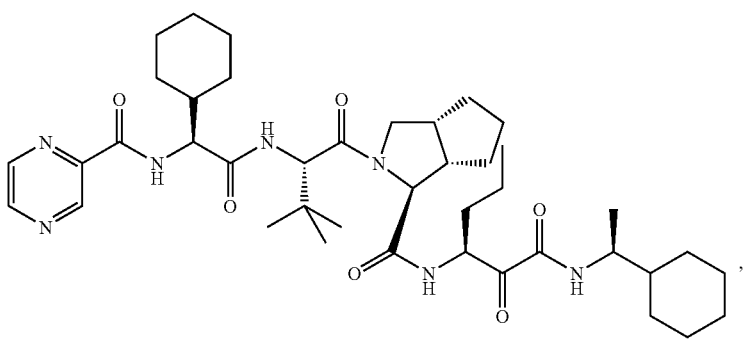
DY
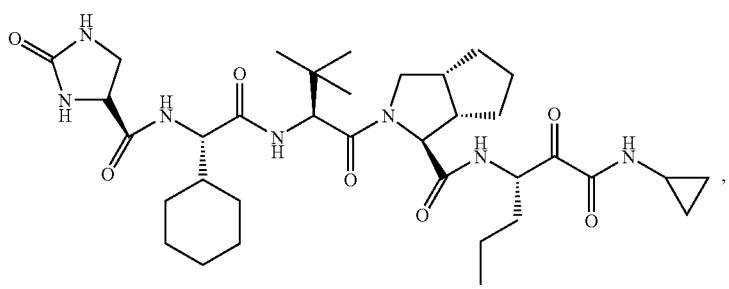
DZ -continued
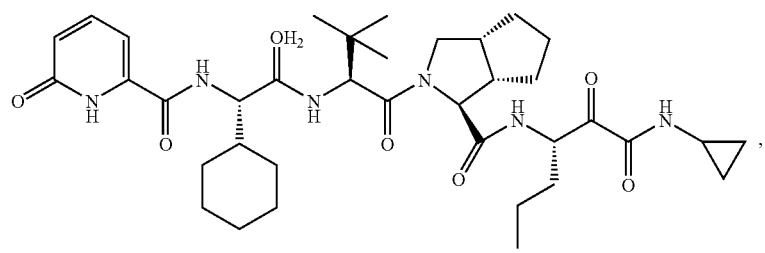
EA
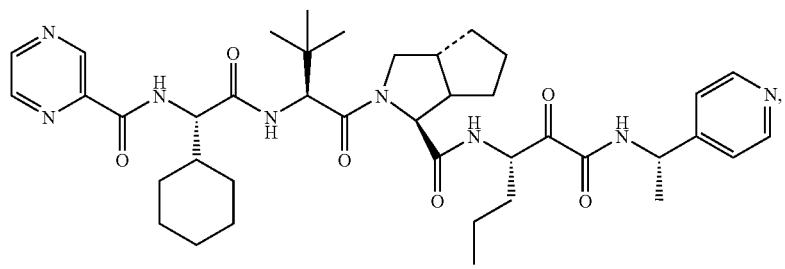
EJ
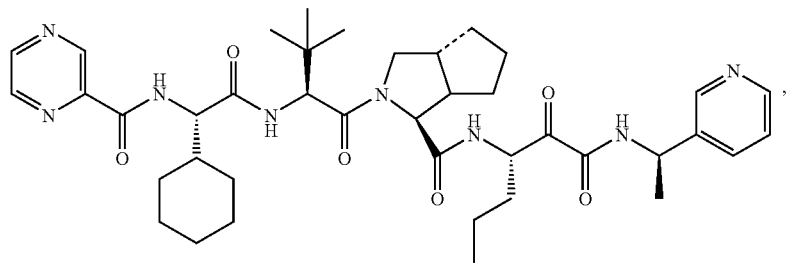
EK
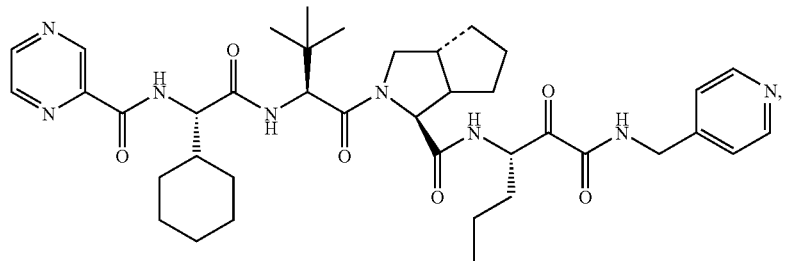
EL
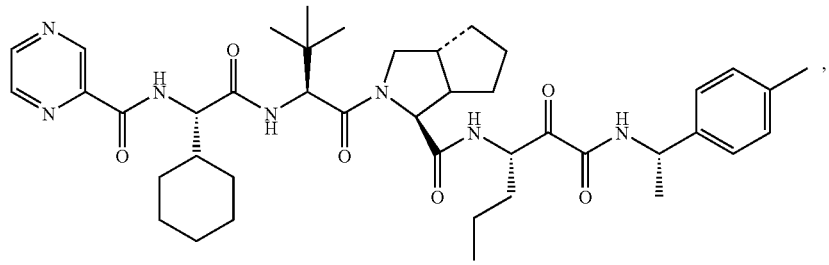
EM -continued
EN
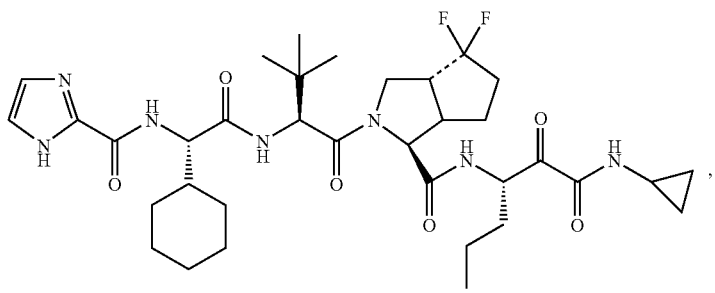
EO
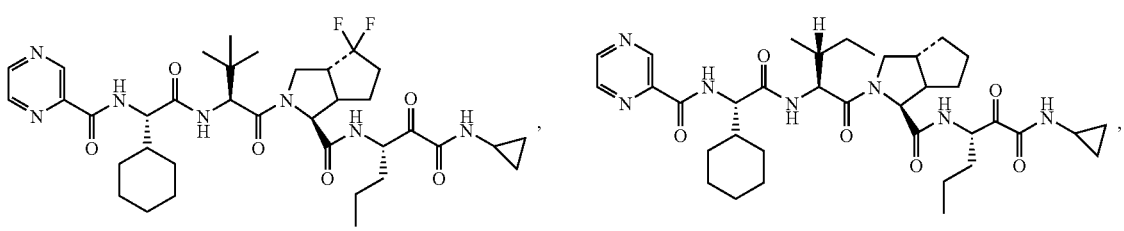
EP
ES
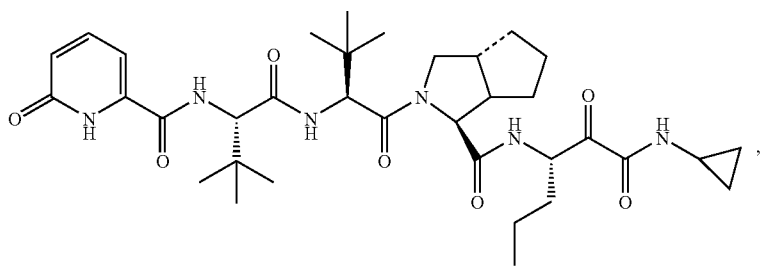
ET
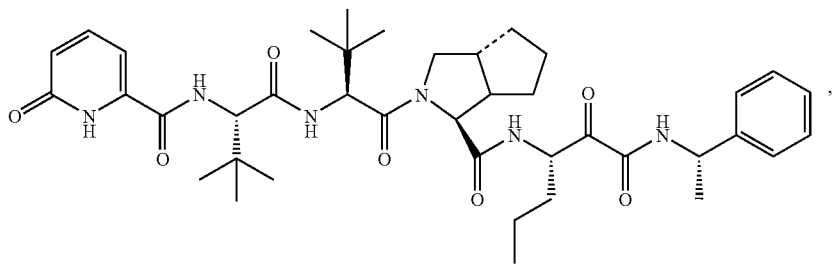
EU
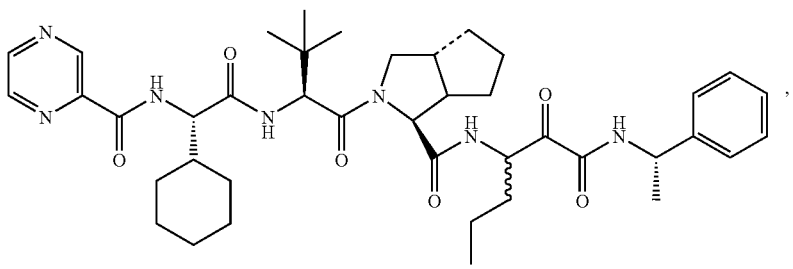

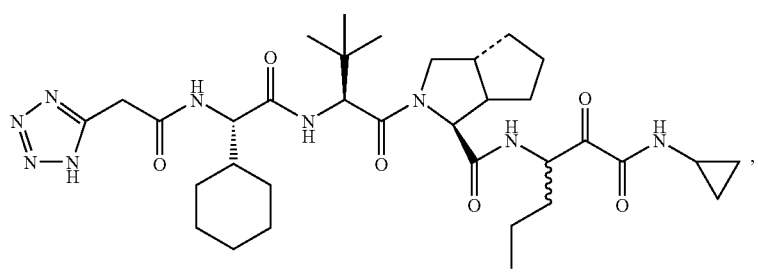
EV
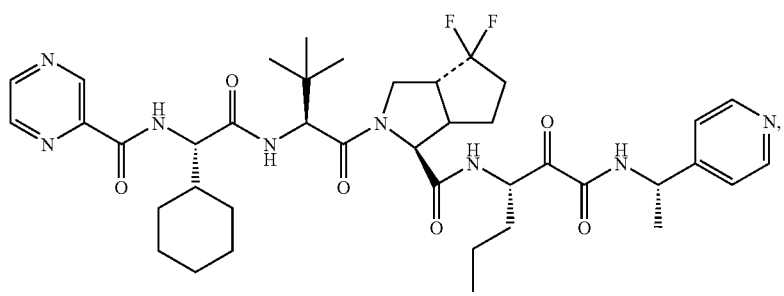
EZ
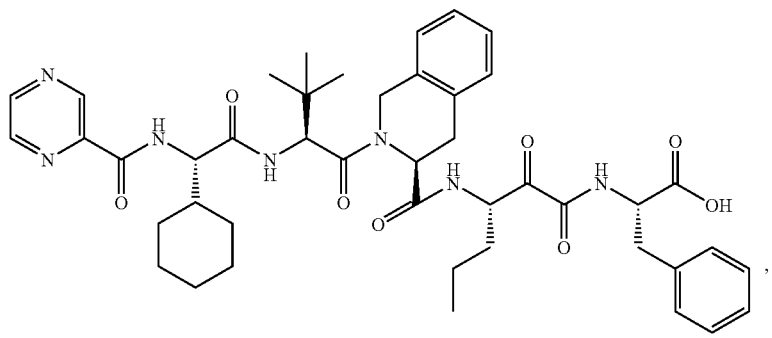
FA
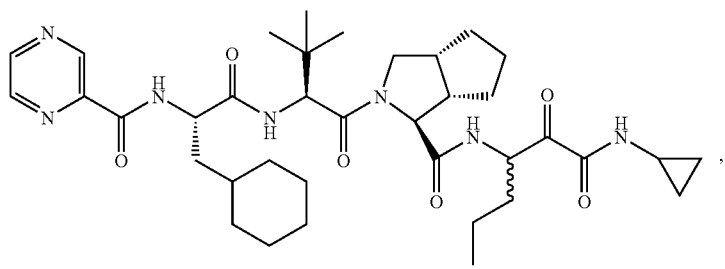
FB
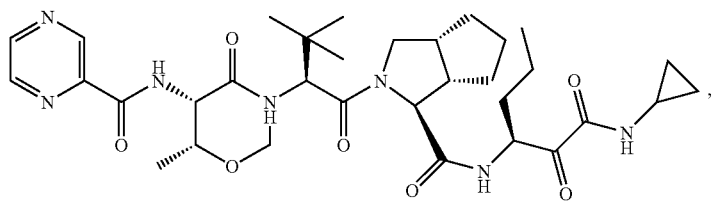
FC

-continued
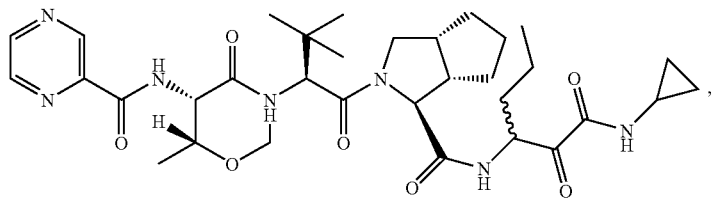
FD
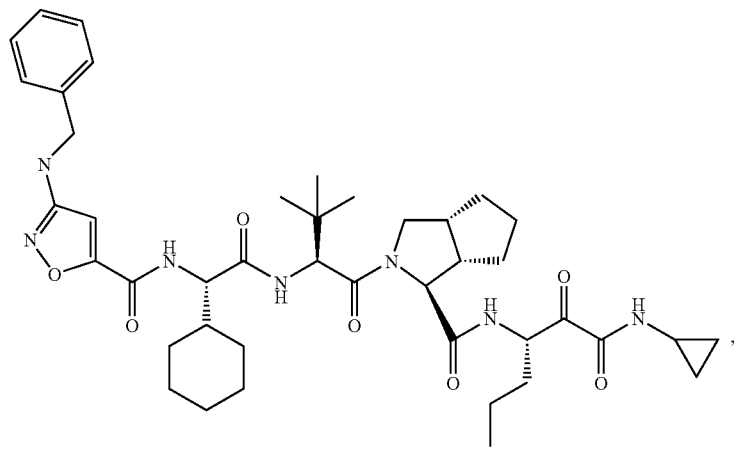
FE
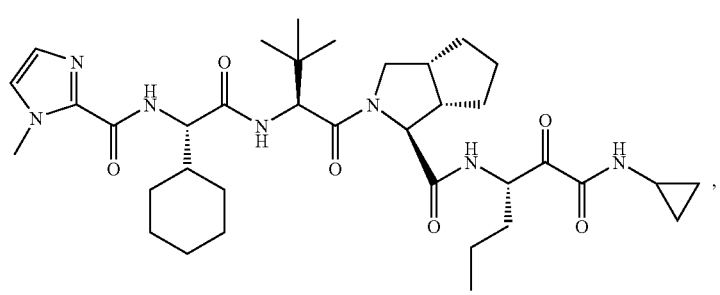
FF
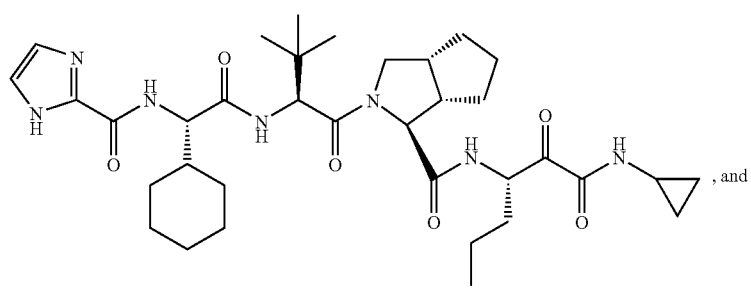
, and
FG
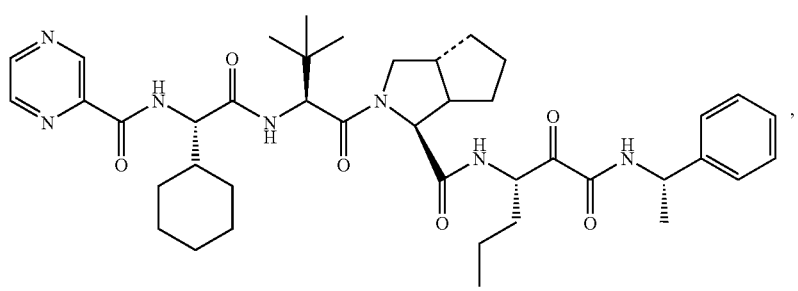
FH or a pharmaceutically acceptable salt or prodrug thereof, or a solvate of such a compound, its salt or its prodrug.

Another preferred embodiment of the invention is a compound of formula 1 wherein the optionally substituted aliphatic group, optionally substituted cyclic group or optionally substituted aromatic group of $R^9$ is substituted with at least one heteroaryl substituent.

Another preferred embodiment of the invention is a compound of formula 1 wherein the optionally substituted aromatic group of $R^9$ is optionally substituted heteroaryl.

Another preferred embodiment of the invention is a compound of formula 1 wherein the optionally substituted aliphatic group of $R^9$ is optionally substituted alkylheteroaryl.

Another preferred embodiment of the invention is a compound wherein the optionally substituted heteroary group of $R^9$ is pyrazinyl, tetrazolyl, quinolinyl, imidazolyl, isoxazolyl and pyradonyl, optionally substituted with a ring group substituent.

The compounds of the invention optionally are supplied as salts. Those salts that are pharmaceutically acceptable are of particular interest since they are useful in administering the foregoing compounds for medical purposes. Salts that are not pharmaceutically acceptable are useful in manufacturing processes, for isolation and purification purposes, and in some instances, for use in separating stereoisomeric forms of the compounds of this invention. The latter is particularly true of amine salts prepared from optically active amines.

Where the compound of the invention contains a carboxy group, or a sufficiently acidic bioisostere, base addition salts may be formed and are simply a more convenient form for use; and in practice, use of the salt form inherently amounts to use of the free acid form.

Also, where the compound of the invention contains a basic group, or a sufficiently basic bioisostere, acid addition salts may be formed and are simply a more convenient form for use; and in practice, use of the salt form inherently amounts to use of the free base form.

A preferred embodiment of a method according to the present invention is for treating a patient suffering from an HCV infection or physiological conditions related to the infection comprising administering to the patient a pharmaceutically effective amount of a compound of formula 1.

Another preferred embodiment of a therapeutic method according to the present invention is for treating a patient suffering from an HCV infection or physiological conditions related to the infection comprising administering a pharmaceutically effective amount of a compound of formula 1 in combination with a pharmaceutically effective amount of another anti-HCV therapeutic to the patient.

Another object of the present invention is to provide pharmaceutical compositions comprising, in addition to one or more HCV serine protease inhibitors, one or more interferons exhibiting anti-HCV activity and/or one or more compounds having anti HCV activity, including immunomodulatory compounds such as immunostimulatory cytokines exhibiting HCV antiviral activity, and a pharmaceutically acceptable carrier or diluent.

It is another object of the invention to provide a pharmaceutical composition which is effective, in and of itself, for utilization in a beneficial combination therapy because it includes a plurality of active ingredients which may be utilized in accordance with the invention.

The invention also provides kits or single packages combining two or more active ingredients useful in treating or preventing an HCV infection in a patient. A kit may provide (alone or in combination with a pharmaceutically acceptable diluent or carrier), the compound of formula 1 and the additional active ingredient (alone or in combination with diluent or carrier) other anti-HCV therapeutic.

Compounds of formula 1 may be prepared by the application or adaptation of known methods as used heretofore or described in the literature, or by methods according to this invention herein.

Another object of the present invention is to provide methods of treating or preventing a HCV infection in a patient in need thereof, comprising administering to said patient a pharmaceutically effective amount of a combination of one or more HCV serine protease inhibitors; one or more interferons exhibiting anti-HCV activity; and/or one or more compounds having anti-HCV activity, including immunomodulatory compounds such as immunostimulatory cytokines exhibiting HCV antiviral activity.

Another object of the present invention is the use of one or more HCV serine protease inhibitors in combination with one or more interferons exhibiting anti-HCV activity and/or one or more compounds having anti-HCV activity, including immunomodulatory compounds such as immunostimulatory cytokines exhibiting HCV antiviral activity, to prepare a medicament for treating or preventing a HCV infection in a patient in need thereof.

A further object of the present invention is a kit or pharmaceutical pack for treating or preventing HCV infection in a patient, wherein the kit or pharmaceutical pack comprises a plurality of separate containers, wherein at least one of said containers contains one or more HCV serine protease inhibitors, at least another of said containers contains one or more interferons or compounds that induce the production of an inteferon that exhibit anti-HCV activity (alone or in combination with a pharmaceutically acceptable carrier or diluent), and, optionally, at least another of said containers contains one or more compounds having anti-HCV activity (alone or in combination with a pharmaceutically acceptable carrier or diluent), including immunomodulatory compounds such as immunostimulatory cytokines exhibiting HCV antiviral activity.

Yet another object of the present invention is to provide a method of inhibiting hepatitis C virus replication in a cell, comprising contacting said cell, a hepatitis C virus serine protease inhibitor, and optionally an interferon or compounds that induce the production of an interferon that have anti-hepatitis C virus activity.

The amount of the HCV serine protease inhibitor(s), interferon(s), or anti-HCV compound(s) in any of the foregoing applications can be a pharmaceutically effective amount, a suboptimal anti-HCV effective amount, or combinations thereof, so long as the final combination of HCV protease inhibitor(s), interferon(s), and/or anti-HCV compound(s) comprises a pharmaceutically effective amount of compounds that is effective in treating or preventing HCV infection in a patient.

It is a further object of the invention to provide a method for preparing a chiral bicycloprolinate compound that is useful in preparing the compound of formula 1.

Preparation of Compounds of the Invention

The starting materials and intermediates of compounds of the invention may be prepared by the application or adaptation of known methods, for example methods as described in the Reference Examples or their obvious chemical equivalents.

Compounds of the invention may be prepared by the application or adaptation of known methods, by which is meant methods used heretofore or described in the literature, for example those described by R. C. Larock in Comprehensive Organic Transformations, VCH publishers (1989).

A compound of formula 1, wherein the variables and

moiety thereof are as described herein, may be prepared by treating a compound of formula 2, wherein the variables

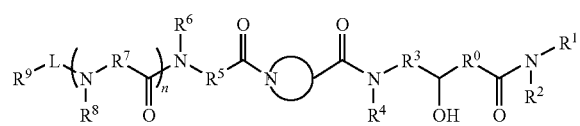

2

Oxidizing Agent ↓

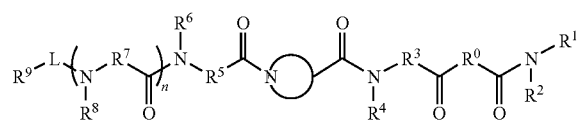

1 and

moiety thereof are as described herein, with an appropriate oxidizing agent and under appropriate conditions. A particular oxidizing agent is DMP reagent. Particular conditions include carrying out the oxidation in an appropriate organic solvent such as dichloromethane at about room temperature.

A compound of formula 2, wherein the variables and

moiety thereof are as described herein, may be prepared by coupling a compound of formula 3, wherein the variables and

moiety thereof are as described herein, and a compound of formula 4, wherein the

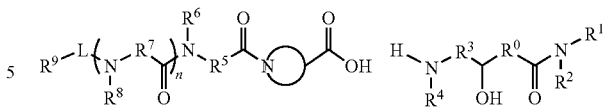

3

Coupling Agent and Conditions ↓

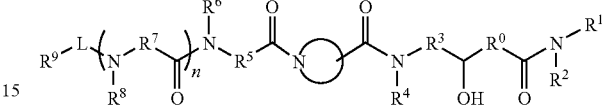

2 variables thereof are as described herein, with an appropriate coupling agent and under appropriate conditions. Particular coupling agent and conditions include using DIC and HOAt in an appropriate organic solvent such as DMF at about 0° C. or using PyBop and DIPEA in an appropriate organic solvent such as dichloromethane at about room temperature.

A compound of formula 3, wherein the variables and

moiety thereof are as described herein, may be prepared by coupling a compound of formula 5, wherein the variables thereof are as described herein, and a compound of formula 6, wherein $p^2$ is an acid

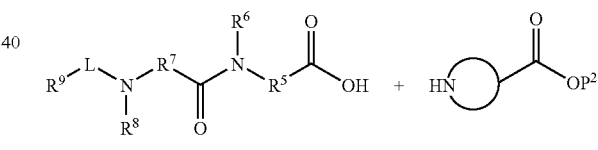

5  6

1. Coupling Agent and Conditions
2. Acid Deprotecting Agent and Conditions
↓

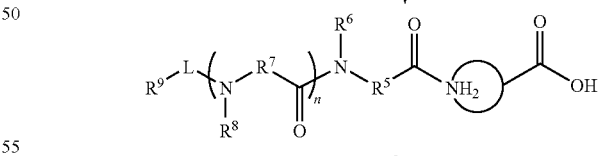

3 protecting group and the

moiety thereof is as described herein, with an appropriate coupling agent and under appropriate coupling conditions, followed by an appropriate deprotecting agent and under appropriate deprotecting conditions. Particular coupling agent and conditions include using DIC or DCC and HOAt in an appropriate organic solvent such as DMF or dichloromethane at about 0° C. to about room temperature. The deprotecting is carried out using an appropriate deprotecting agent that depends on the nature of the protecting agent, i.e., whether it is removable (labile) under acid, base, or hydrogenation conditions, and other reactive moieties in the compound undergoing deprotection, i.e., a deprotecting agent is chosen to carry out the deprotection without effecting the other reactive moieties unless a concomitant reaction is desired. A particular acid protecting agent is $C_1$ to $C_8$ lower alkyl; more particular methyl. A particular deprotecting agent is an inorganic base such as an alkali hydroxide; more particular NaOH. Particular deprotection conditions encompass carrying out the deprotection in an alcoholic solvent such as methanol or ethanol at about room temperature.

A compound of formula 5, wherein n is 0 and the other variables are as described herein, i.e., compound 5a, may be prepared by deprotecting a compound of formula 7,

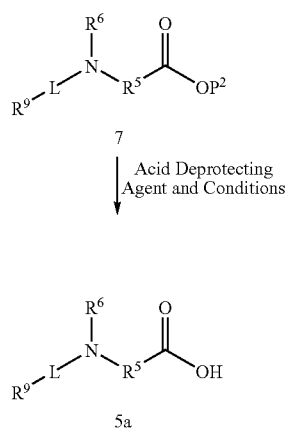

wherein $P^2$ is an acid protecting group and the other variables thereof are as described herein, with an appropriate deprotecting agent and under appropriate conditions. The deprotecting is carried out using an appropriate deprotecting agent that depends on the nature of the protecting agent, i.e., whether it is removeable (labile) under acid, base, or hydrogenation conditions, and other reactive moieties in the compound undergoing deprotection, i.e., a deprotecting agent is chosen to carry out the deprotection without effecting the other reactive moieties unless a concomitant reaction is desired. A particular acid protecting agent is $C_1$ to $C_8$ lower alkyl; more particular methyl. A particular deprotecting agent is an inorganic base such as an alkali hydroxide; more particular NaOH. Particular deprotection conditions encompass carrying out the deprotection in an alcoholic solvent such as methanol or ethanol at about room temperature.

A compound of formula 7, wherein the variables thereof are as described herein, may be prepared by acylating a compound of formula 8, wherein the variables thereof are as described herein, with a compound of formula 9, wherein M is a displaceable moiety and the other variables

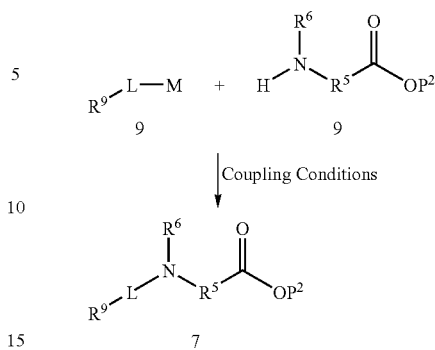

thereof are as described herein, under appropriate conditions. Particular coupling conditions use DIC or DCC and HOAt in an appropriate organic solvent such as DMF or dichloromethane at about 0° C. to about room temperature, or PyBop and DIPEA in an appropriate organic solvent such as DMF or dichloromethane at about room temperature; and preferably the latter conditions. A particular L is carbonyl. A particular M is hydroxy or N-oxysuccinimide.

A compound of formula 5, wherein n is 1 and the other variables are as described herein, i.e., compound 5b, may be prepared by deprotecting a compound of formula 10, wherein $P^2$ is an

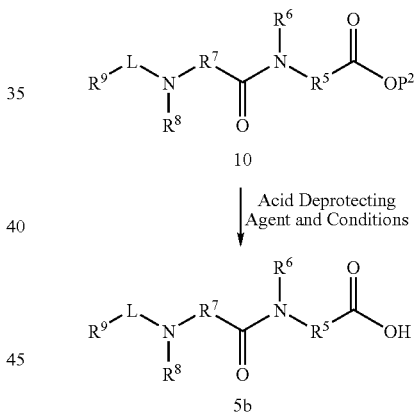

acid protecting group and the other variables thereof are as described herein, with an appropriate deprotecting agent and under appropriate conditions. The deprotecting is carried out using an appropriate deprotecting agent that depends on the nature of the acid protecting agent, i.e., whether it is removeable (labile) under acid, base, or hydrogenation conditions, and other reactive moieties in the compound undergoing deprotection, i.e., a deprotecting agent is chosen to carry out the deprotection without effecting the other reactive moieties unless a concomitant reaction is desired. A particular acid protecting agent is $C_1$ to $C_8$ lower alkyl; more particular methyl. A particular deprotecting agent is an inorganic base such as an alkali hydroxide; more particular NaOH. Particular deprotection conditions encompass carrying out the deprotection in an alcoholic solvent such as methanol or ethanol at about room temperature.

A compound of formula 10, wherein the variables thereof are as described herein, may be prepared by acylating a compound of formula 11, wherein the variables thereof are as described herein, with a compound of formula 9, wherein the variables thereof are as described herein,

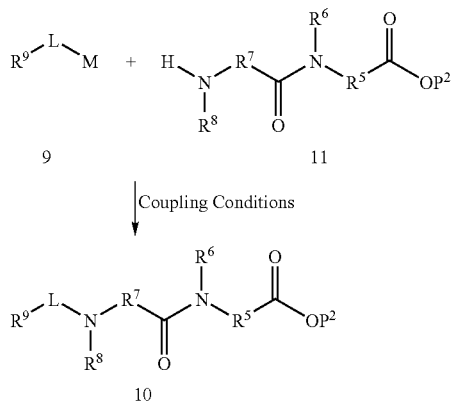

under appropriate conditions. Particular coupling conditions use DIC or DCC and HOAt in an appropriate organic solvent such as DMF or dichloromethane at about 0° C. to about room temperature, or PyBop and DIPEA in an appropriate organic solvent such as DMF or dichloromethane at about room temperature; and preferably the latter conditions. A particular L is carbonyl. A particular M is hydroxy or N-oxysuccinimide.

A compound of formula 11, wherein the variables are as described herein, may be prepared by deprotecting a compound of formula 12, wherein $P^1$ is an amine protecting group

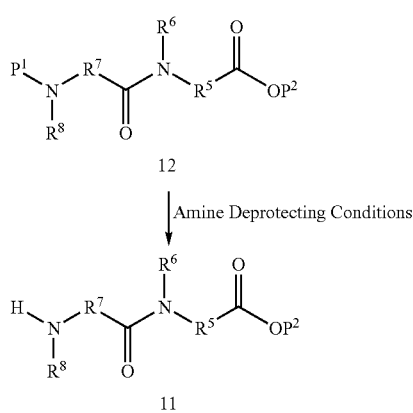

and the other variables thereof are as described herein, with an appropriate deprotecting agent and under appropriate conditions. The deprotecting is carried out using an appropriate deprotecting agent that depends on the nature of the amine protecting agent, i.e., whether it is removeable (labile) under acid, base, or hydrogenation conditions, and other reactive moieties in the compound undergoing deprotection, i.e., a deprotecting agent is chosen to carry out the deprotection without effecting the other reactive moieties unless a concomitant reaction is desired. A particular amine protecting agent is Cbz or BOC; more particular Cbz. A particular deprotecting agent is acid such as HCl or $H_2/Pd(OH)_2$; more particular $H_2/Pd(OH)_2$. Particular deprotection conditions encompass carrying out the deprotection in an alcoholic solvent such as methanol or ethanol or an alkyl alkanoate solvent such as ethyl acetate at about room temperature.

A compound of formula 12, wherein the variables thereof are as described herein, may be prepared by coupling a compound of formula 13, wherein the variables thereof are as described herein, with a compound of formula 14, wherein the variables thereof are as described herein,

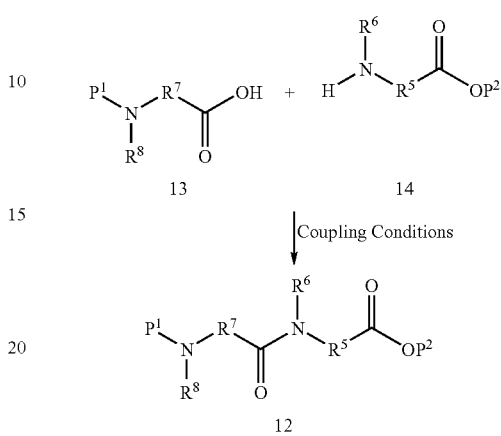

under appropriate conditions. Particular coupling conditions use HOAt/DIC and DIPEA in an appropriate organic solvent such as THF at about room temperature.

A compound of formula 4, wherein the variables are as described herein, may be prepared by deprotecting a compound of formula 15, wherein the variables thereof are

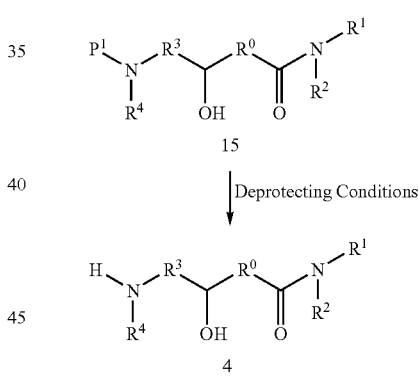

as described herein, with an appropriate deprotecting agent and under appropriate conditions. The deprotecting is carried out using an appropriate deprotecting agent that depends on the nature of the amine protecting agent, i.e., whether it is removeable (labile) under acid, base, or hydrogenation conditions, and other reactive moieties in the compound undergoing deprotection, i.e., a deprotecting agent is chosen to carry out the deprotection without effecting the other reactive moieties unless a concomitant reaction is desired. A particular amine protecting agent is Cbz or BOC; more particular Cbz. A particular deprotecting agent is an acid such as HCl or $H_2/Pd(OH)_2$; more particular $H_2/Pd(OH)_2$. Particular deprotection conditions encompass carrying out the deprotection in an alcoholic solvent such as methanol or ethanol or an alkyl alkanoate solvent such as ethyl acetate at about room temperature.

A compound of formula 15, wherein the variables thereof are as described herein, may be prepared by coupling a compound of formula 16, wherein the variables thereof are as described herein, with a compound of formula 17, wherein the variables thereof are as described herein,

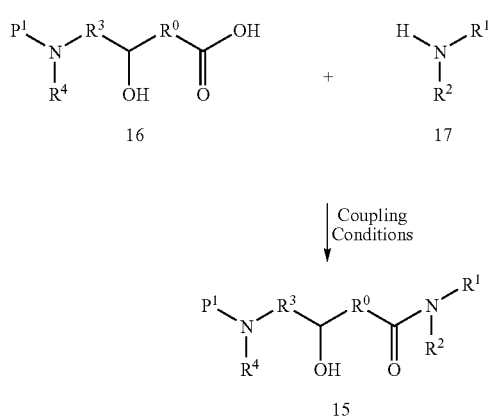

under appropriate conditions. A particular amine protecting agent is Cbz or BOC; more particular Cbz. Particular coupling conditions use HOBT, PyBop and DIPEA in an appropriate organic solvent such as dichloromethane at about 0° C. to about room temperature.

A compound of formula 16, wherein the variables are as described herein may be prepared by deprotecting a compound of formula 18, wherein the other variables thereof are

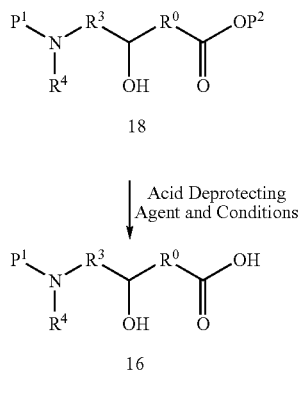

as described herein, with an appropriate deprotecting agent and under appropriate conditions. The deprotecting is carried out using an appropriate deprotecting agent that depends on the nature of the acid protecting agent, i.e., whether it is removeable (labile) under acid, base, or hydrogenation conditions, and other reactive moieties in the compound undergoing deprotection, i.e., a deprotecting agent is chosen to carry out the deprotection without effecting the other reactive moieties unless a concomitant reaction is desired. A particular amine protecting agent is Cbz. A particular acid protecting agent is $C_1$ to $C_8$ lower alkyl; more particular methyl. A particular deprotecting agent is an inorganic base such as an alkali hydroxide; more particular NaOH. Particular deprotection conditions encompass carrying out the deprotection in an alcoholic solvent such as methanol or ethanol at about room temperature.

A compound of formula 18, wherein $R^0$ is a bond and the other variables thereof are as described herein, may be prepared by protecting a compound of formula 20, wherein the variables thereof are as described herein, with a compound of formula 19, wherein the

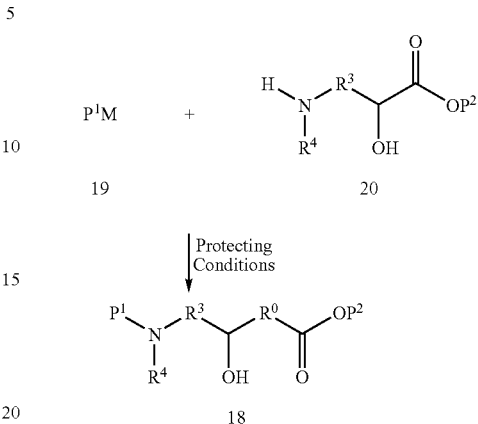

variables thereof are as described herein, under appropriate conditions. A particular amine protecting agent is Cbz or BOC. Particular coupling conditions use an appropriate organic solvent such as dichloromethane at about 0° C. to about room temperature.

A compound of formula 20, wherein $R^4$ is hydrogen and the other variables are as described herein, may be prepared by hydrogenating a compound of formula 21, wherein the

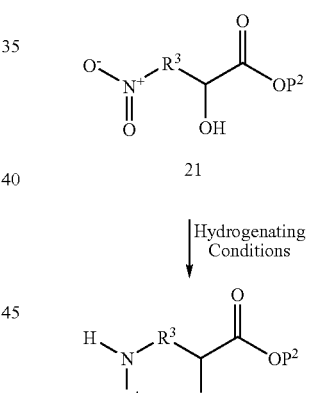

variables thereof are as described herein, with an appropriate hydrogenating agent and under appropriate conditions. A particular hydrogenating agent is $H_2/Pd(OH)_2$. Particular hydrogenating conditions encompass carrying out the hydrogenation in an alcoholic solvent such as methanol or ethanol or an alkyl alkanoate solvent such as ethyl acetate at about room temperature.

A compound of formula 20 wherein $R^4$ is optionally substituted aliphatic and the other variables are as described herein may be prepared by alkylating compound 20' wherein the variables are as described herein with compound 22 (alkylating agent) wherein $R^4$ is optionally substituted aliphatic and Q is a displaceable group such as a halides, tosylates or sulfonates, under appropriate conditions.

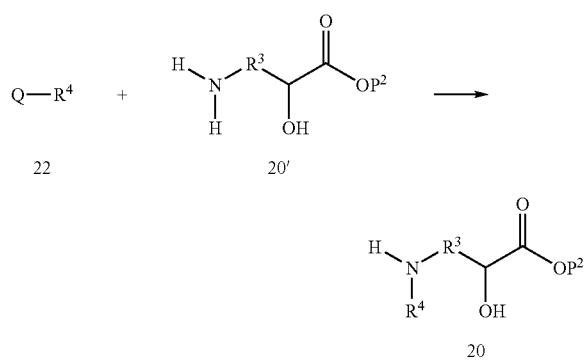

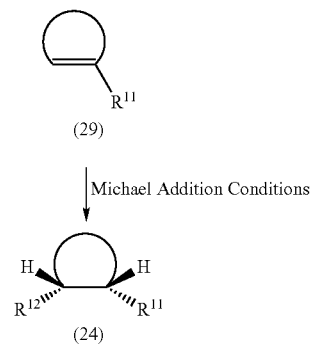

Appropriate alkylating agents include aliphatic (halides, tosylates or sulfonates). Appropriate alkylating conditions encompass carrying out to alkylation in an appropriate organic solvent such as an alcoholic solvent, e.g., methanol or ethanol, or etheric solvent, e.g., ether or tetrahydrofuran at about room temperature to about reflux.

A compound of formula 21, wherein the variables are as described herein, may be prepared by alkylating a compound of formula 22, wherein the variable thereof is as described herein, with a compound of formula 23, wherein the $R^3$'s independently are optionally

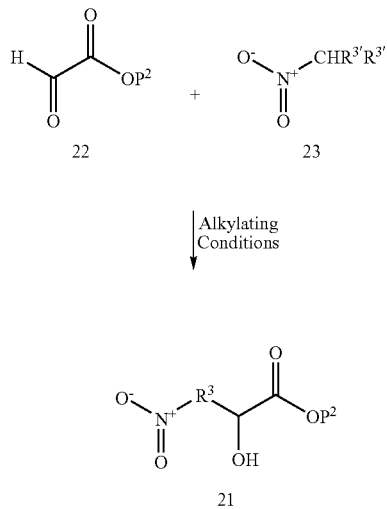

substituted aliphatic group, optionally substituted cyclic group or optionally substituted aromatic group as described herein, under appropriate conditions. Particular alkylating conditions encompass carrying out the alkylation using a strong base such as potassium t-butoxide in an alcoholic solvent such as methanol or ethanol at about room temperature.

A compound of formula 24 wherein the variables thereof are as described herein, may be prepared by effecting a Michael addition on a Michael acceptor of formula 29, wherein the variable thereof is as described herein, with an iminic glycinimide derivative.

Michael additions comprise appropriate aprotic polar solvents, alkali methyl hydroxide bases, and appropriate temperatures. For Michael additions, see Corey, E. J.; Noe, M. C.; Xu, F. *Tetrahedron Letter* 1998, 39, 5347. For the synthesis of chiral phase transfer catalysts, see Corey, E. J.; Noe, M. C.; Xu, F. *J. Am. Chem. Soc.* 1997, 119, 12414. Appropriate solvents include DCM, ACN, or THF depending on the reaction conditions. Appropriate bases include CsOH, NaOH, KOH, and LiOH. Appropriate temperatures range from about −78° C. to about 0° C., more particularly at about −60° C. Iminic glycinimides useful in the invention are described herein. A preferred iminic glycinimide is N-(diphenylmethylene)glycine tert-butyl ester. In addition, Michael addition conditions may be affected with or without a phase transfer catalyst (PTC) (chiral and nonchiral). A preferred PTC is O-[9]allyl-N-9-anthracenylmethylcinchonidium bromide.

A compound of formula 25, wherein the variables thereof are as described herein, may be prepared by imine cleavage and cyclizing of the compound of formula 24.

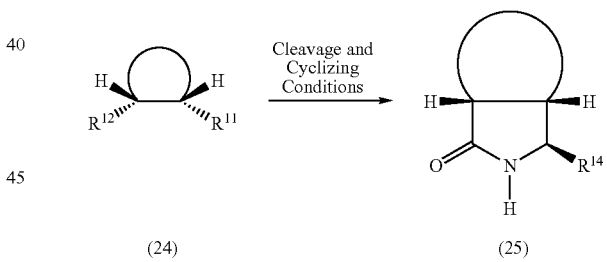

For cleavage and cyclization procedures, see Javidan, A.; Schfer, K.; Pyne, S. *Synlett* 1996, 100; Tatsukawa, A.; Dan, M.; Ohbatake, M.; Kawatake, K.; Fukata, T.; Wada, E.; Kanemase, S.; Kakei, S. *J. Org. Chem.* 1993, 58, 4221. Cleavage and cyclizing conditions include the use of polar solvents, acid reagents, and temperatures of about room temperature to about 150° C. Preferred conditions include the use of EtOH, AcONa and NH$_2$OH.HCl, and a temperature of about boiling point for the solvent used.

A compound of formula 26, wherein the variables thereof are as described herein, may be prepared by protecting the amide of the compound of formula 25, wherein the variables thereof are as described herein, with a suitable amide protecting group such as BOC. Other suitable protecting groups include CBz, —CO$_2$alkyl. Also see, Greene, T. W.; P. G. M. in *Protective Groups in Organic Synthesis*, Wiley, New York, 1991 for other amine protecting groups. Protecting conditions include the use of aprotic polar solvents, organic bases as catalysts, and temperatures of about 0° C.-100° C. Preferred conditions include the use of ACN, dimethyl amino pyridine, and a temperature of about room temperature.

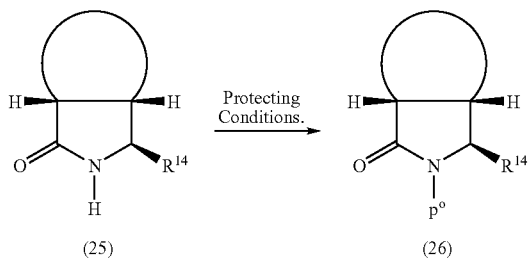

(25) (26)

A compound of formula 27, wherein the variables thereof are as described herein, may be prepared by reducing the protected compound of formula 26, wherein the variables thereof are as described herein.

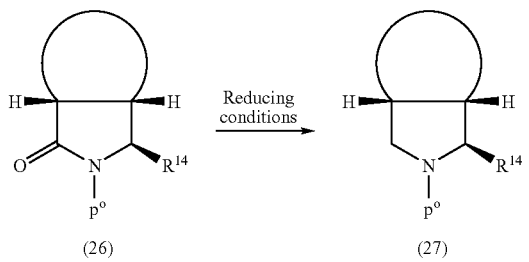

(26) (27)

Two reductions are, in fact, done. The first reduction is of the amide to a hemiaminal using DIBALH or superhydride [LiBEt$_3$H]. The second reduction is of the hemiaminal to the amine using Et$_3$SiH and BF$_3$·OEt$_2$. See Collado, I; Ezquerra, J.; Mateo, A. I.; Rubio, A., *J. Org. Chem.* 1998, 63 1995-2001 and Ezqueera, J.; Pedregal, C.; Yruretagoyena, B.; Rubio, A.; Carreno, M. C.; Escribano, A.; Garcia Ruano, J. L. *J. Org. Chem.* 1995, 60,2925 for reducing conditions. Other usual conditions for converting pyroglutamates into pyrrolidines is the use of BH$_3$.SMe$_2$.

A compound of formula 28, wherein the variables thereof are as described herein, may be prepared by deprotecting the compound of formula 27, wherein the variables thereof are as described herein.

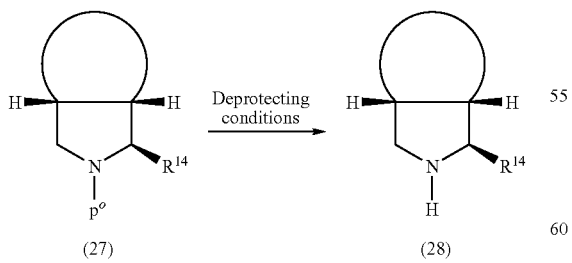

(27) (28)

See Gibson, P. G.; Bermeier, S. C.; Rapoport, H., *J. Org Chem.* 1994, 59, 3216-3218 for the conditions for selective removal of N—BOC protecting group in the presence of tert-butyl ester. One skilled in the art would know that the deprotecting conditions will dependent upon the choice of the protecting group. For example, if CBz is used, hydrogenation or basic conditions may be used. Preferably, if BOC is used, 1 N HCl in ethyl acetate may be used. See, Greene, T. W.; P. G. M. in *Protective Groups in Organic Synthesis*, Wiley, New York, 1991.

The person of ordinary skill in the art will appreciate that a compound of formula 3 may be prepared by coupling a compound of formula 5 with a compound of formula 28 under conditions described above herein.

Methods for preparing R$^3$, R$^5$ or R$^7$ as optionally substituted ethanediyl moieties include those known to those skilled in the art, e.g., those methods described in "The organic Chemistry of β-Lactams" edited by G. Georg, VCH Publishers, Inc. (1993), e.g., pages 240-241 and 303-305.

Schemes 1-11 that follow exemplify assorted methods for preparing an optionally substituted multicyclic azaheterocyclyl. The methods in the schemes below are also applicable to other optionally substituted multicyclic azaheterocyclyls comprising compatible like substituents.

SCHEME 1

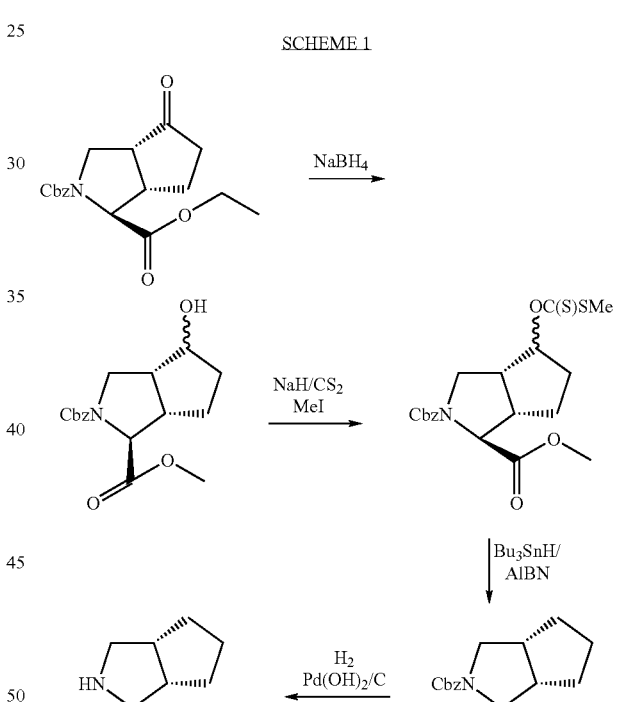

SCHEME 2

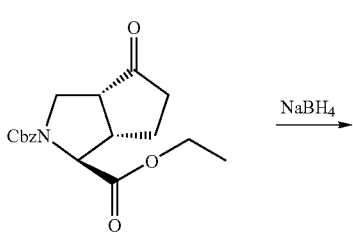

-continued
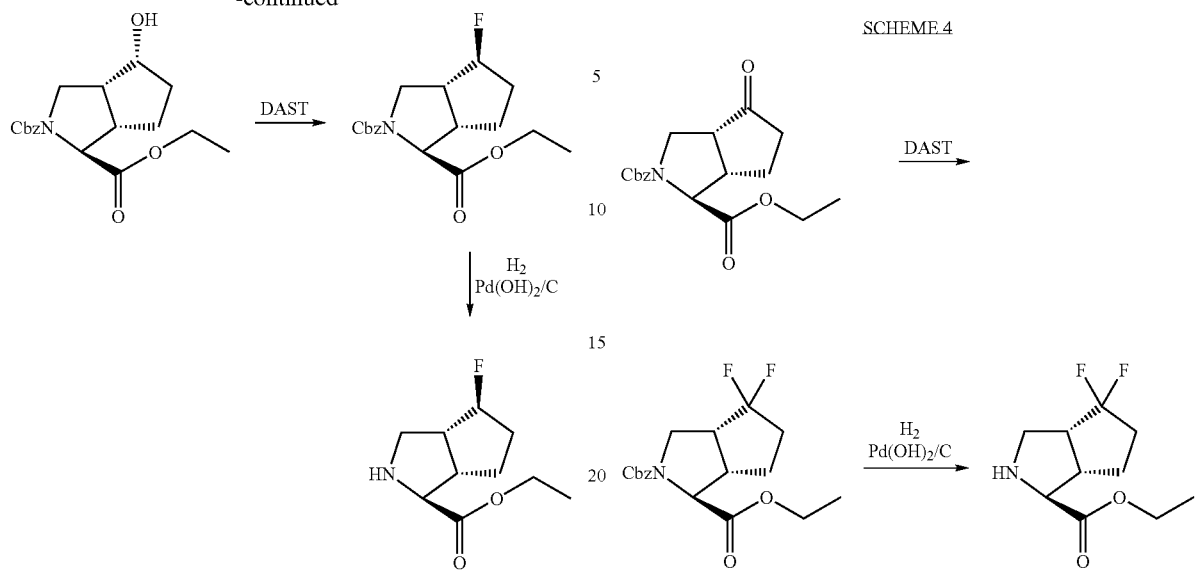
SCHEME 4
SCHEME 3
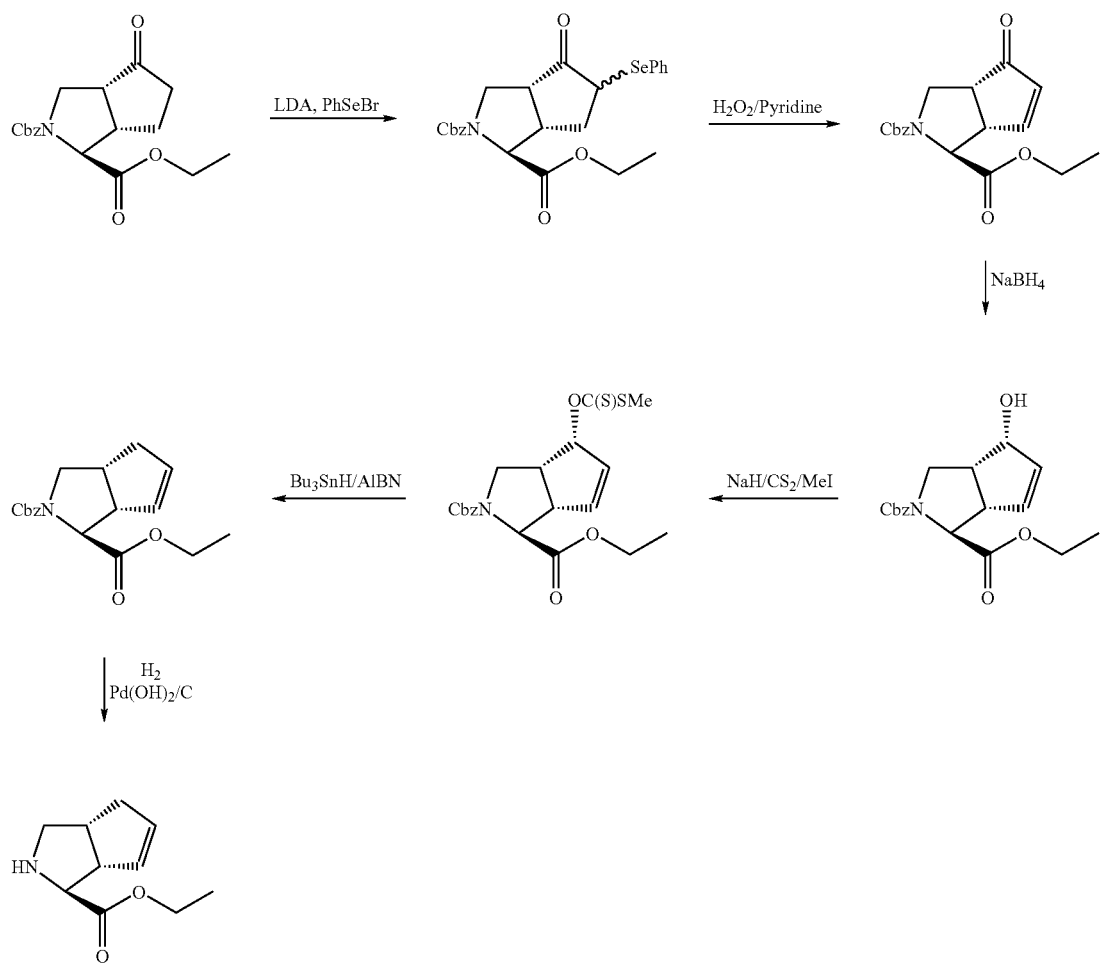

SCHEME 5
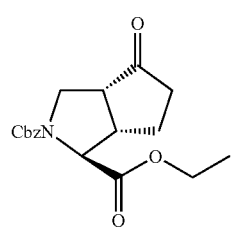
SCHEME 6
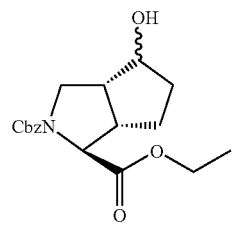
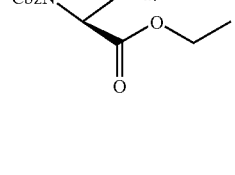
SCHEME 7
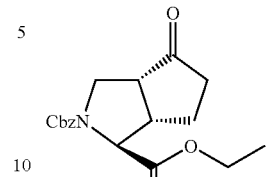
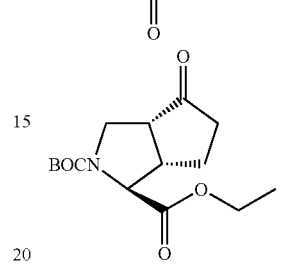
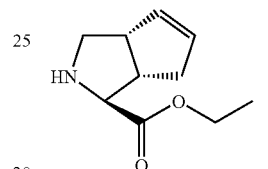
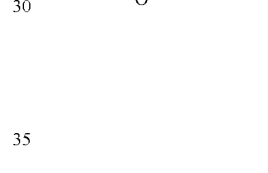
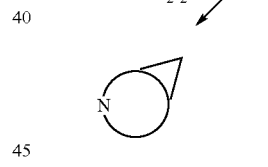
SCHEME 8
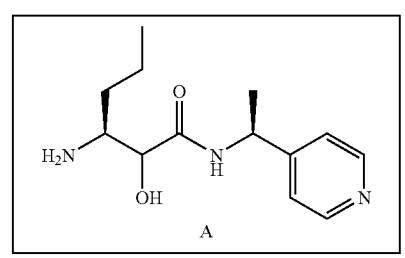
Scheme 9
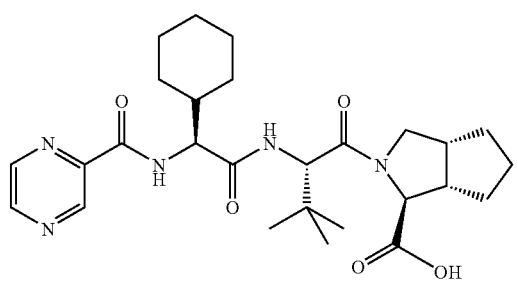

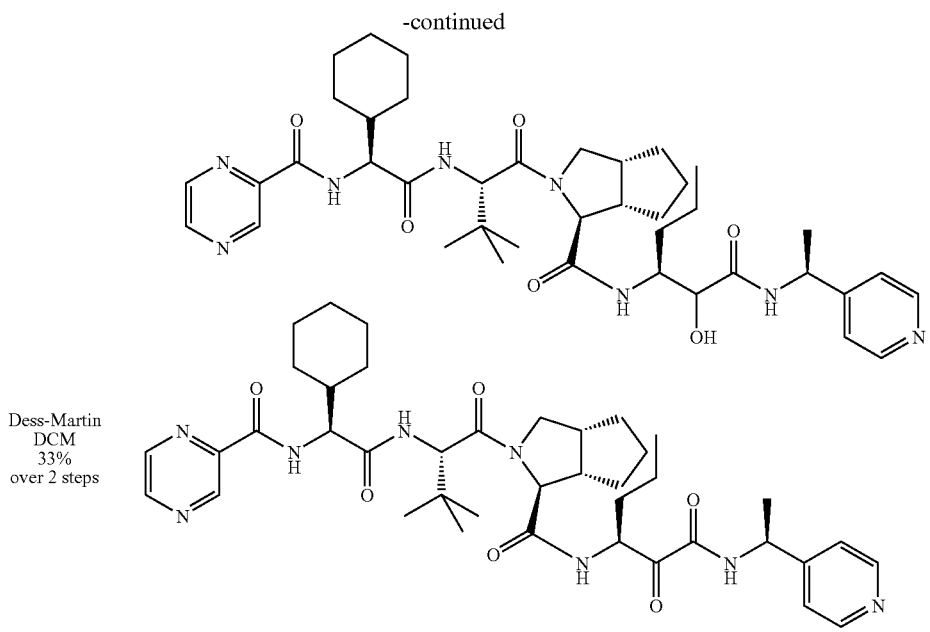
SCHEME 10
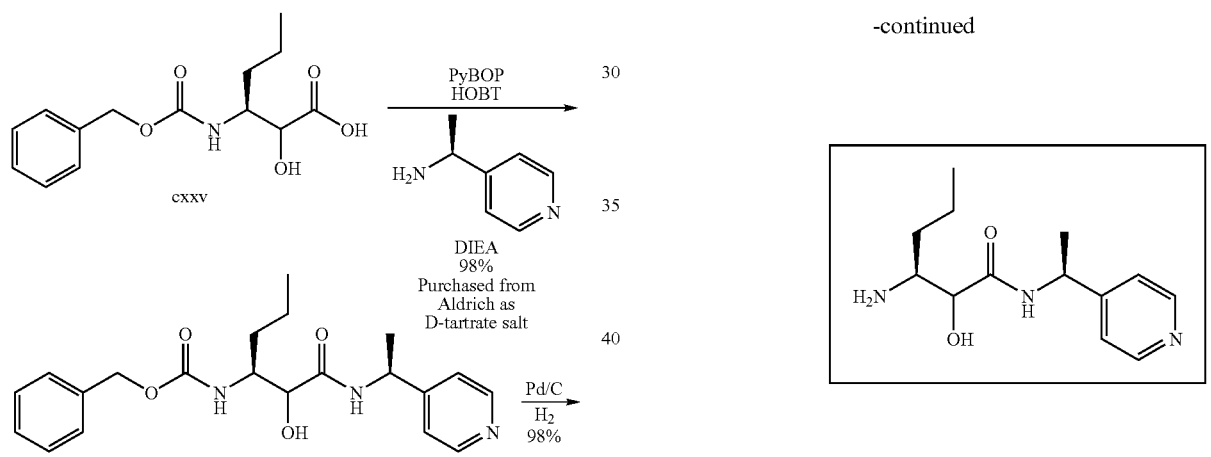
Scheme 11
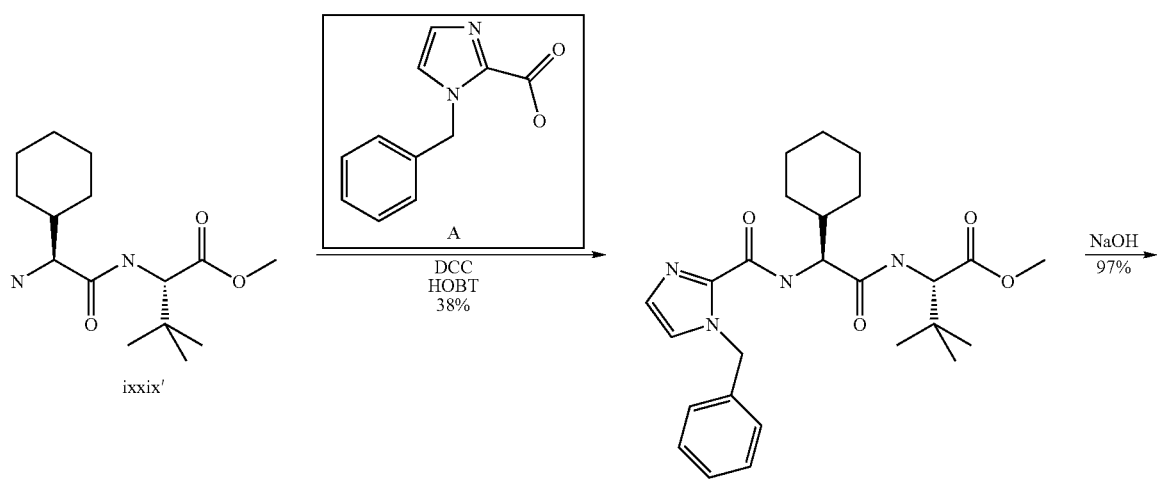

-continued
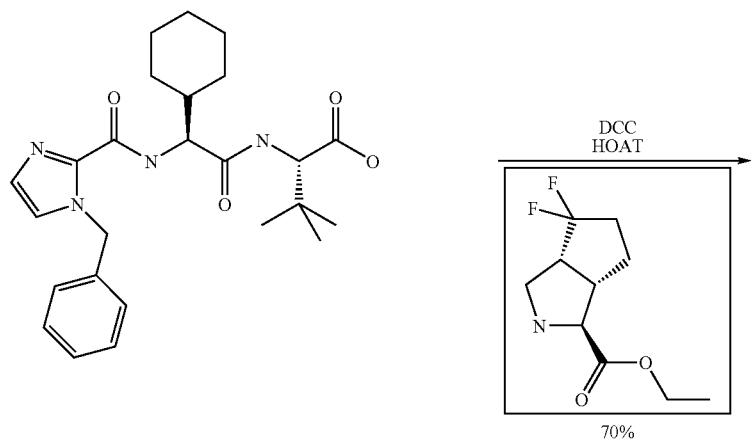
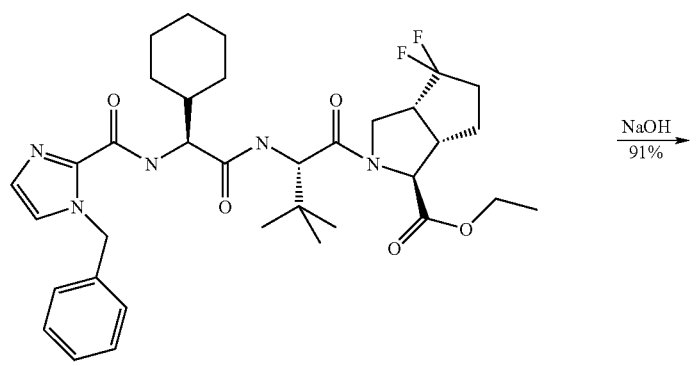
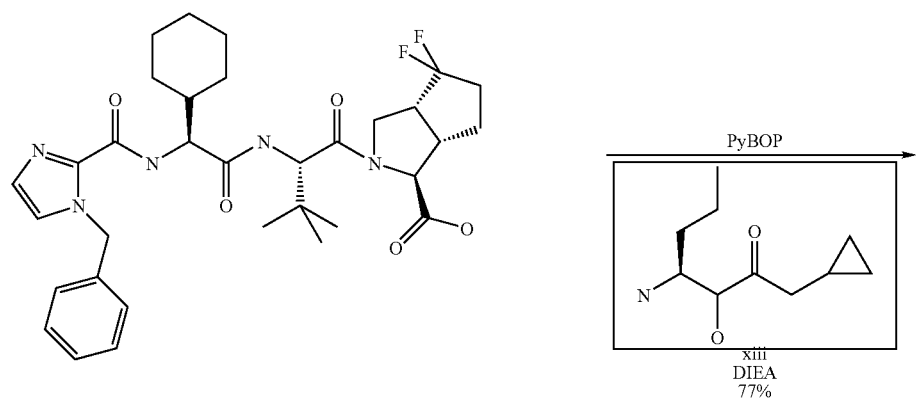
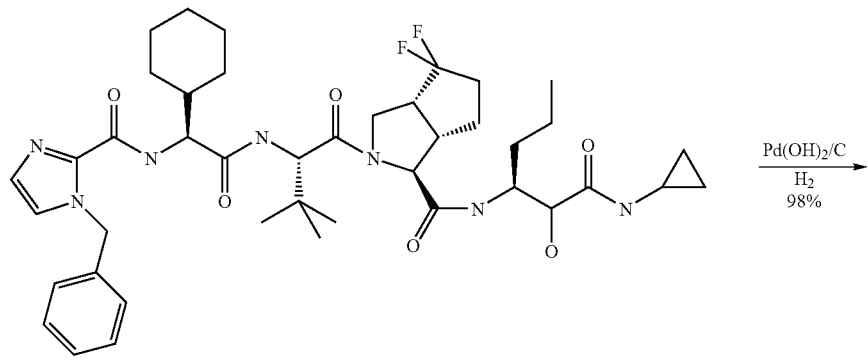

-continued

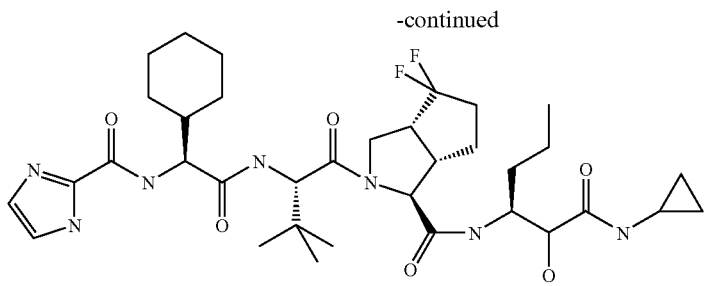

Dess-Martin
DCM
53%

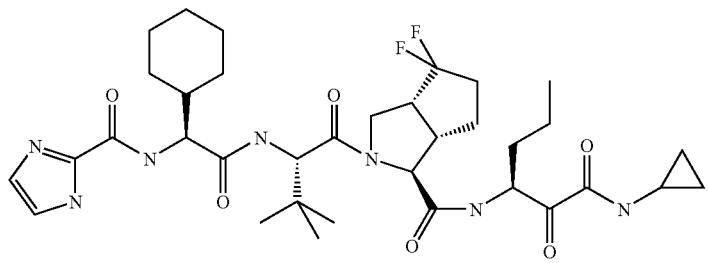

A compound of formula 1 including a group containing one or more nitrogen ring atoms, preferably imine (=N—), may be converted to the corresponding compound wherein one or more nitrogen ring atoms of the group are oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons (1991); J. F. W. McOmie in "Protective Groups in Organic Chemistry" Plenum Press, 1973.

A compound that is prepared as described herein may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired be further purified by various well techniques, such as recrystallization, reprecipitation or the various chromatography techniques, notably column chromatography or preparative thin layer chromatography.

According to a further feature of the present invention, compounds of the invention may be prepared by interconversion of other compounds of the invention.

As an example of the interconversion process, compounds of formula 1 containing sulphoxide linkages may be prepared by the oxidation of corresponding compounds containing —S— linkages. For example, the oxidation may conveniently be carried out by means of reaction with a peroxyacid, e.g., 3-chloroperbenzoic acid, preferably in an inert solvent, e.g., dichloromethane, preferably at or near room temperature, or alternatively by means of potassium hydrogen peroxomonosulphate in a medium such as aqueous methanol, buffered to about pH 5, at temperatures between about 0° C. and room temperature. This latter method is preferred for compounds containing an acid-labile group.

As another example of the interconversion process, compounds of formula 1 containing sulphone linkages may be prepared by the oxidation of corresponding compounds containing —S— or sulphoxide linkages. For example, the oxidation may conveniently be carried out by means of reaction with a peroxyacid, e.g., 3-chloroperbenzoic acid, preferably in an inert solvent, e.g., dichloromethane, preferably at or near room temperature.

It will be understood that designation of aromaticity with respect to aryls and heteroaryls herein includes any highly resonant unsaturated ring structure. Alternatively, placement of double bonds, where indicated, represents one potential structure for the depicted compound but will be understood to include other resonant states of the compound as well as protonated and charged species, only one of which may be shown.

It will be appreciated that compounds of the present invention may contain asymmetric centers. These asymmetric centers may independently be in either the R or S configuration. It will be apparent to those skilled in the art that certain compounds of the invention may also exhibit geometrical isomerism It is to be understood that the present invention includes individual geometrical isomers and stereoisomers and mixtures thereof, including racemic mixtures, of compounds according to the invention. Such isomers can be separated from their mixtures, by the application or adaptation of known methods, for example chromatographic techniques and recrystallization techniques, or they are separately prepared from the appropriate isomers of their intermediates.

For the purpose herein it is understood that tautermeric forms are included in the recitation of a given group, e.g., thioxo/mercapto or oxo/hydroxyl.

Acid additional salts are formed with the compounds of the invention in which a basic function such as an amino, alkylamino, or dialkylamino group is present. The pharmaceutically acceptable, i.e., nontoxic, acid addition salts are preferred. The salts chosen are chosen optimally to be compatible with the customary pharmaceutical vehicles and adapted for oral or parenteral administration. Acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution. Some suitable acids for use in the preparation of such salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acids, adipate, alginate, ascorbate, aspartate, benzenesulfonate,. benzoate, cyclopentanepropionate, digluconate, dodecylsulfate, bisulfate, butyrate, lactate, laurate, lauryl sulfate, malate, hydroiodide, 2-hydroxy-ethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphersulfonate, and others.

The acid addition salts of the compounds of this invention can be regenerated from the salts by the application or adaptation of known methods. For example, parent compounds of the invention can be regenerated from their acid addition salts by treatment with an alkali, e.g., aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g., hydrochloric acid.

Base addition salts may be formed where the compound of the invention contains a carboxy group, or a sufficiently acidic bioisostere. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, and the like.

Compounds of the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxan, tetrahydrofuran or methanol.

The starting materials and intermediates may be prepared by the application or adaptation of known methods, for example methods as described in the Reference Examples or their obvious chemical equivalents.

The compounds of the invention, their methods or preparation and their biological activity will appear more clearly from the examination of the following examples which are presented as an illustration only and are not to be considered as limiting the invention in its scope.

Samples were analyzed by TLC, NMR, RP-HPLC or EA.

The compounds of the invention, their methods or preparation and their biological activity will appear more clearly from the examination of the following examples which are presented as an illustration only and are not to be considered as limiting the invention in its scope.

Samples were analyzed by TLC, NMR, RP-HPLC or EA.

EXAMPLE 1

Compounds A-E

To a DCM solution (10 mL) of compound xi (310 mg, 0.39 mmol) is added TFA (4 mL). The reaction is stirred at about room temperature for 5 hours. At this point, the solvent is removed in vacuo. The resulting residue is purified by reverse phase HPLC to give 195 mg (68%) of compound A,

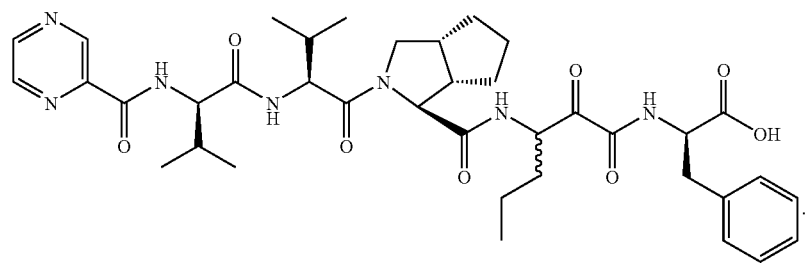

Following the above method and using the appropriate starting materials, the following consecutive compounds B-E are prepared:

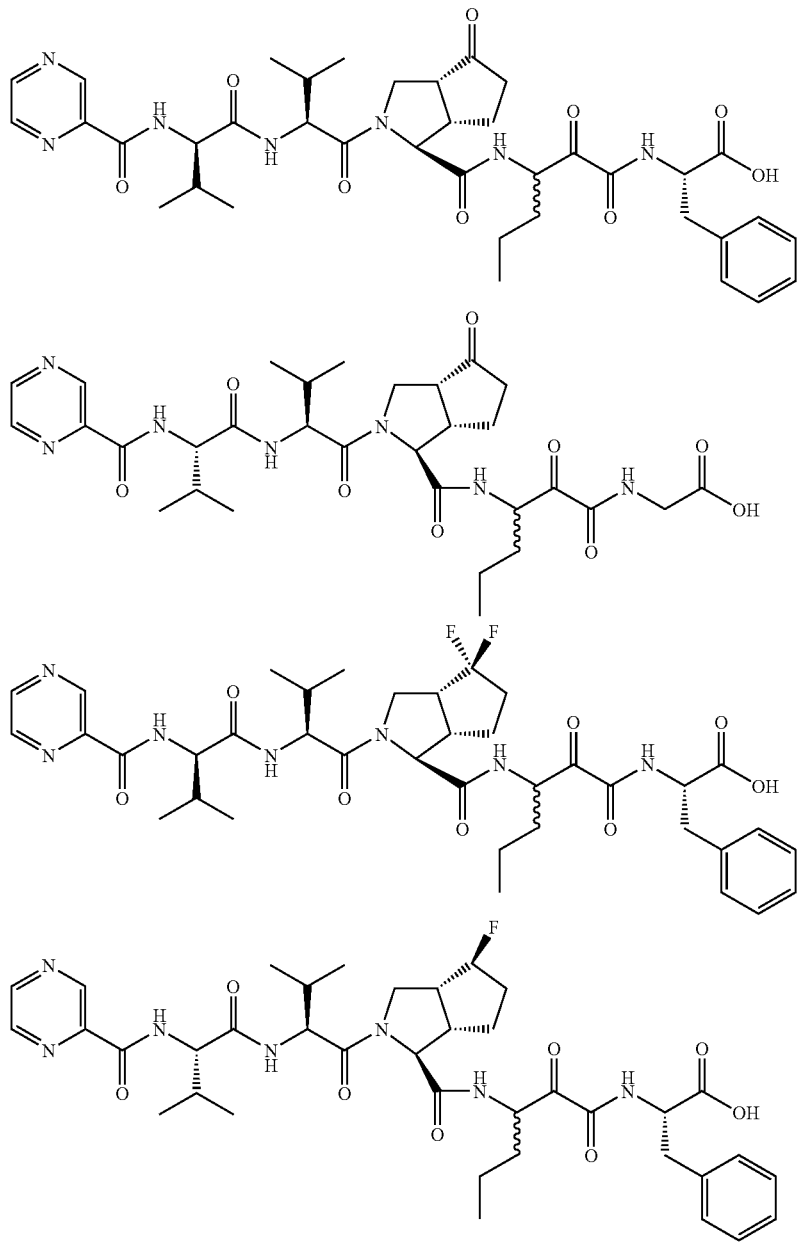

EXAMPLE 2

Compounds F-M

To a DCM solution (10 mL) of compound xii (350 mg, 0.56 mmol) is added DMP reagent reagent (307 mg, 0.73 mmol). The reaction is stirred at about room temperature for 2 hours and then quenched with 10% $Na_2SO_3$ for 30 minutes. The reaction mixture is then extracted with EtOAc (75 mL) and washed with brine. The organic layer is dried and concentrated in vacuo. The resulting residue is purified with silica gel chromatography (80-90% EtOAc/Hexanes) to give 248 mg (71%) of compound F

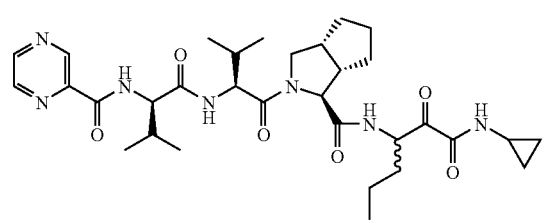

Following the above method and using the appropriate starting materials, the following consecutive compounds G-M are prepared:

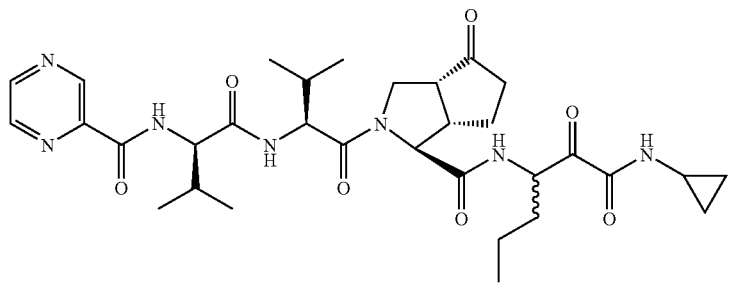
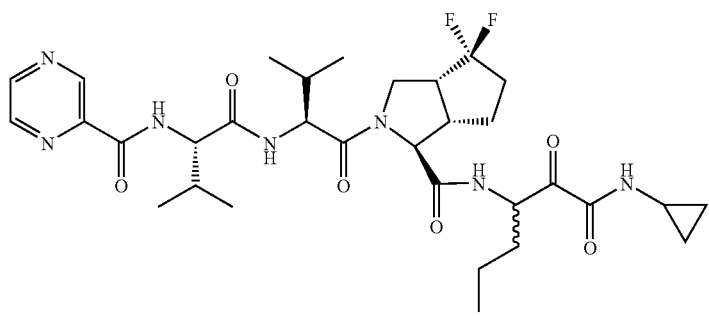
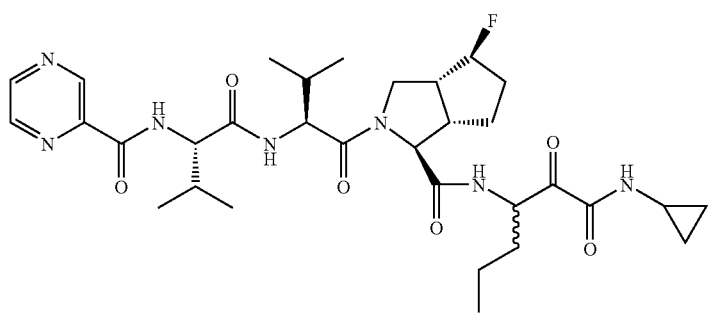
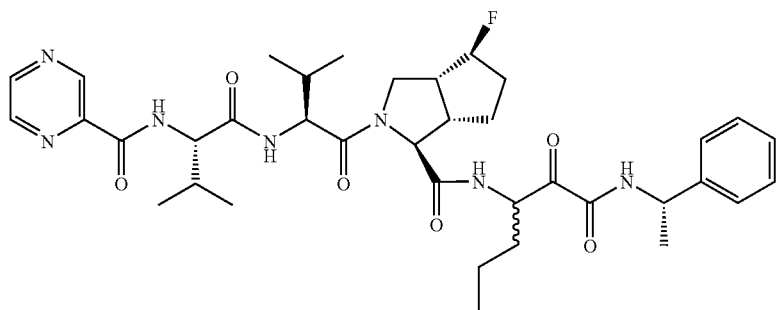
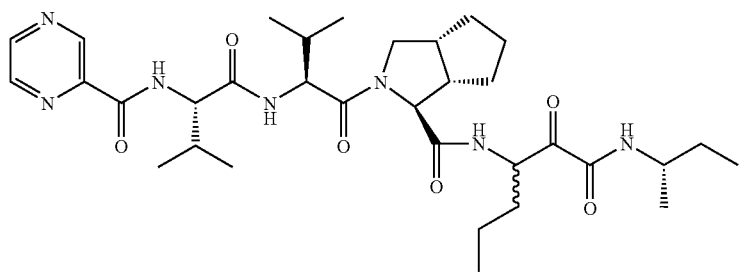

-continued

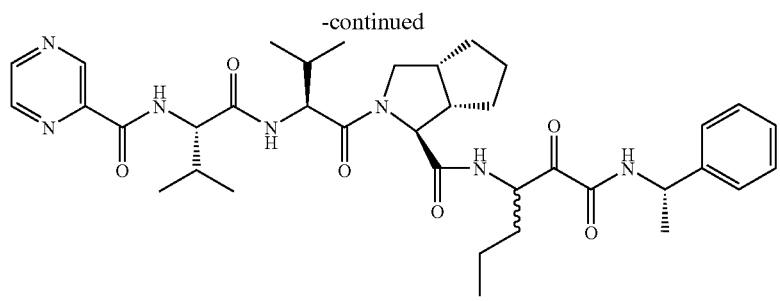

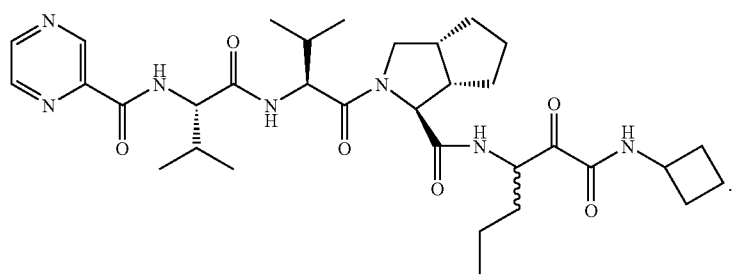

EXAMPLE 3

Compounds N-R

To a DCM solution (4 mL) of compound xix (~0.22 mmol) is added DMP reagent reagent (146 mg, 0.34 mmol). After stirring at about room temperature for 2 hours, the reaction is quenched with 10% $Na_2SO_3$. The reaction mixture is then diluted with DCM. The organic layer is separated and washed with 10% $Na_2SO_3$ twice and brine. The resulting organic layer is dried and concentrated in vacuo to give a residue, which is purified by silica gel chromatography (5% EtOH/EtOAc) to provide 78 mg (56%) of the desired compound N

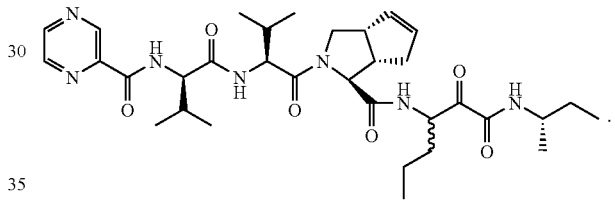

Following the above method and using the appropriate starting materials, the following consecutive compounds O-R are prepared:

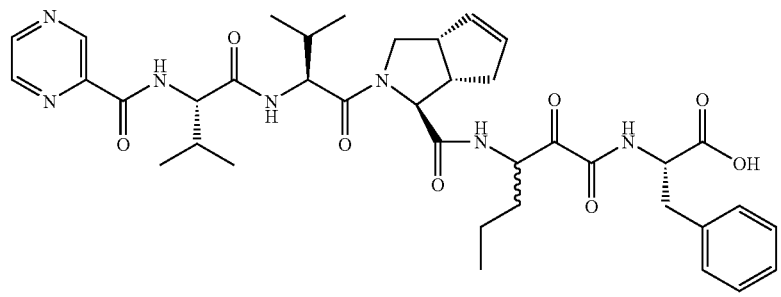

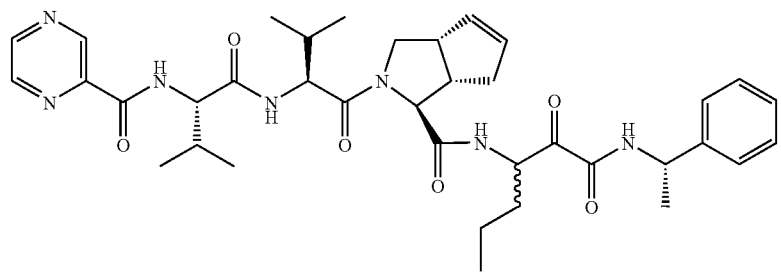

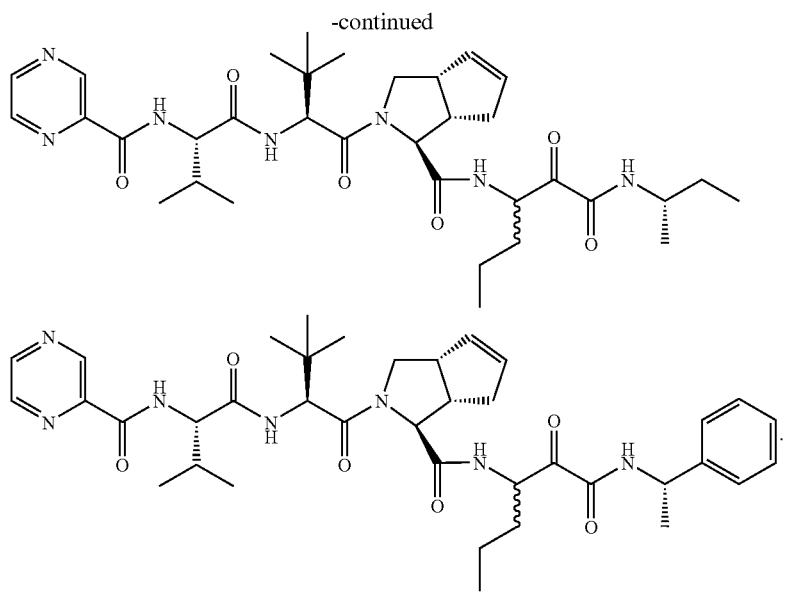

EXAMPLE 4

Compounds S-W

To a DCM solution (10 mL) of compound xxv (320 mg, 0.5 mmol) is added DMP reagent reagent (272 mg, 0.65 mmol). The reaction is stirred at about room temperature for 2 hours and quenched with 10% $Na_2SO_3$ for 20 minutes. The resulting mixture is then extracted with EtOAc. The organic layer is washed with brine, dried and concentrated in vacuo. The resulting residue is purified by silica gel chromatography (80% EtOAc/Hexanes) to give 170 mg (53%) of compound S,

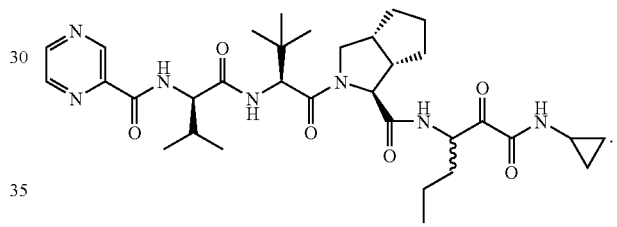

Following the above method and using the appropriate starting materials, the following consecutive compounds T-W are prepared:

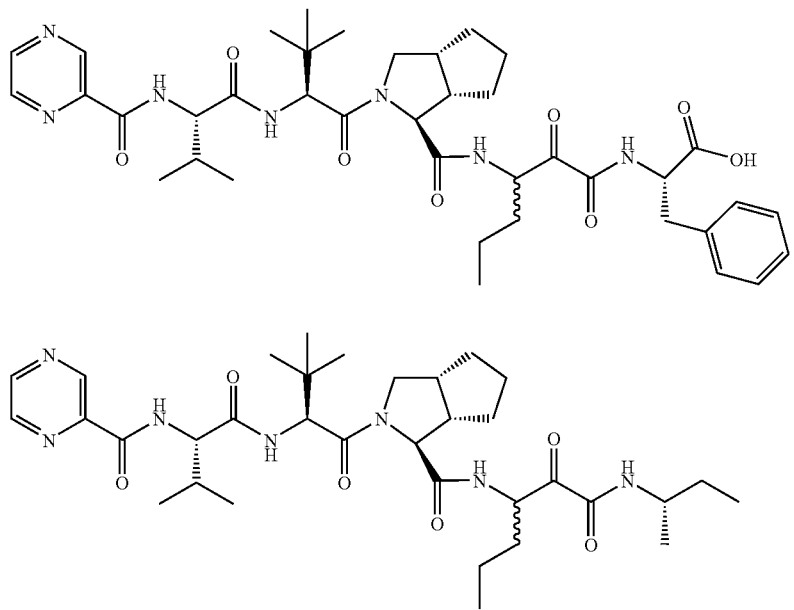

-continued

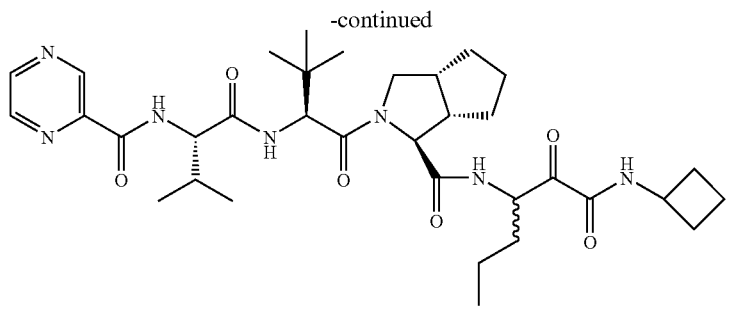

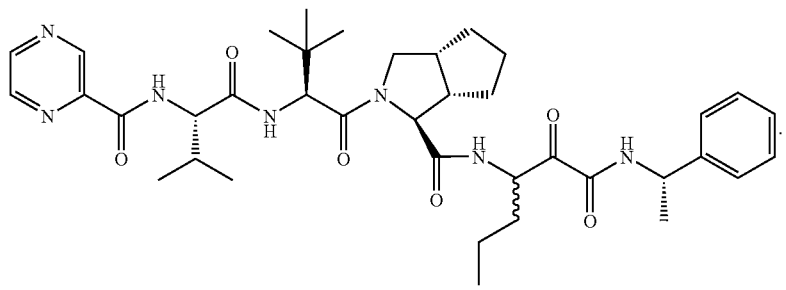

EXAMPLE 5

Compounds X-AD

To a DCM solution (20 mL) of compound xxvi (400 mg, 0.6 mmol) is added DMP reagent reagent (329 mg, 0.78 mmol). The reaction is stirred at about room temperature for 1.5 hours and quenched with 10% $Na_2SO_3$ for 20 minutes. The resulting mixture is then extracted with EtOAc. The organic layer is washed with brine, dried and concentrated in vacuo. The resulting residue is purified by silica gel chromatography (70-100% EtOAc/Hexanes) to give 210 mg (53%) of compound X,

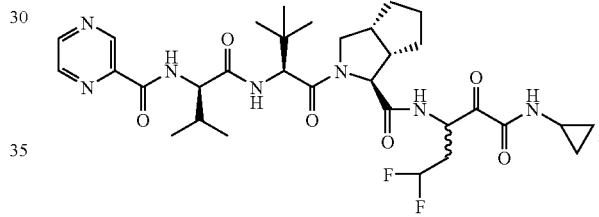

Following the above method and using the appropriate starting materials, the following consecutive compounds Y-AD are prepared:

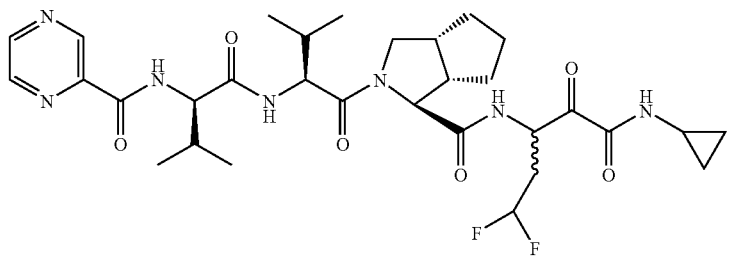

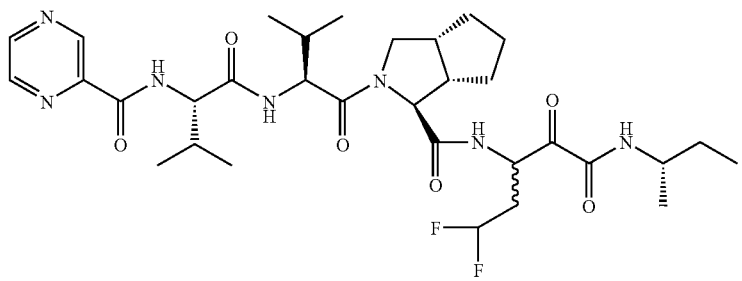

-continued
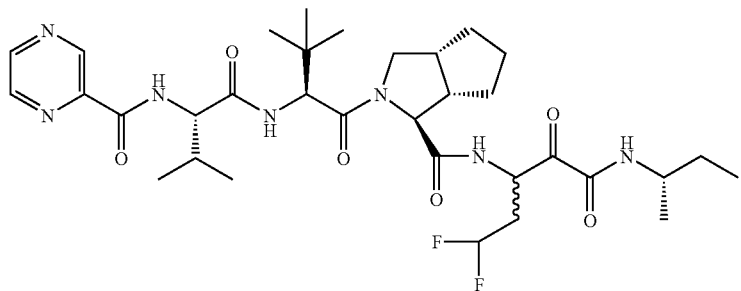
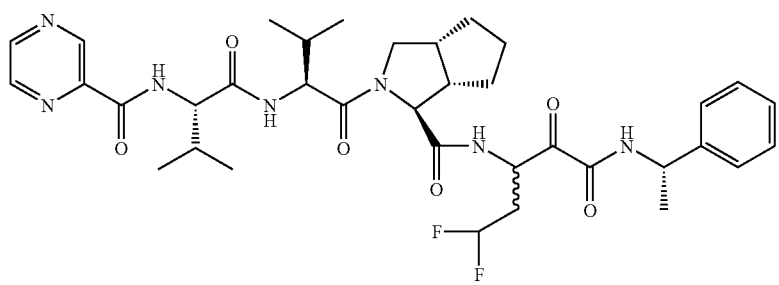
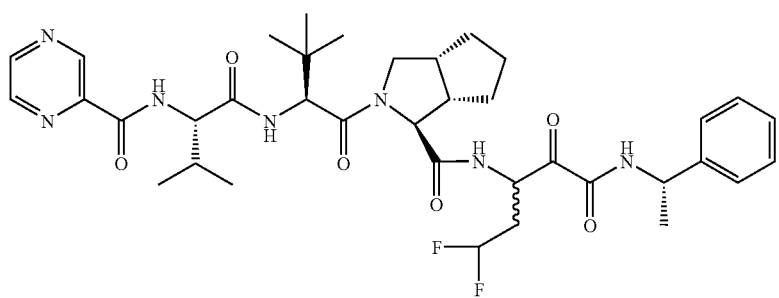
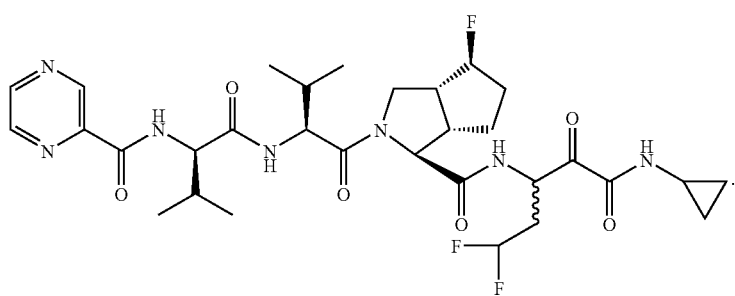

EXAMPLE 6

Compounds AE-AI

Compound xxxiii (150 mg; 0.076 mmol) is dissolved in 5 mL TFA and stirred for two days. The product is purified by RP-HPLC to yield 40 mg (33% yield) of compound AE,

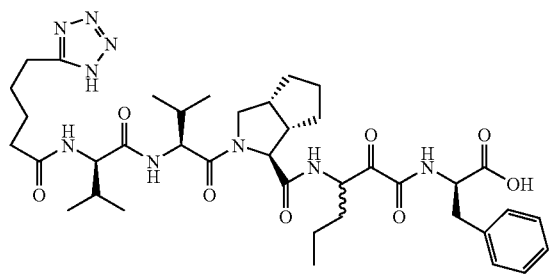

Following the above method and using the appropriate starting materials, the following consecutive compounds AF-AI are prepared:

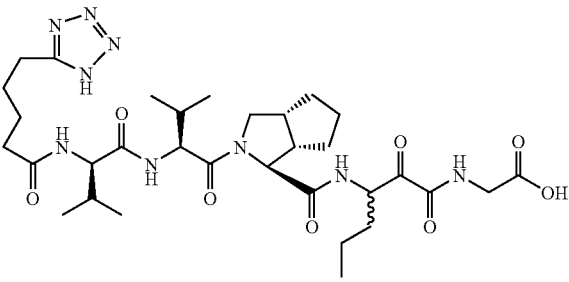

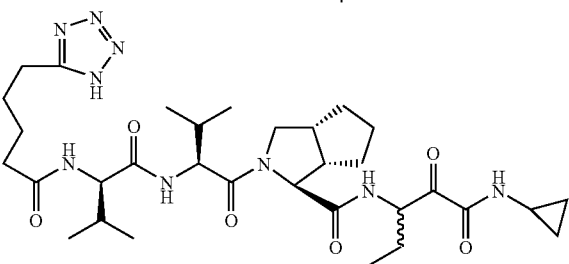

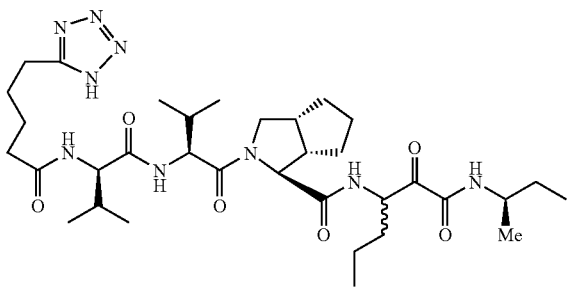

EXAMPLE 7

Compound AJ

Compound xxxviii (180 mg, 0.21 mmol) is dissolved in neat TFA (5 mL) and left for 3 day at about room temperature. At this point, the reaction mixture is concentrated in vacuo to give a residue, which is purified by reverse phase HPLC to give 50 mg (32%) of the compound AJ,

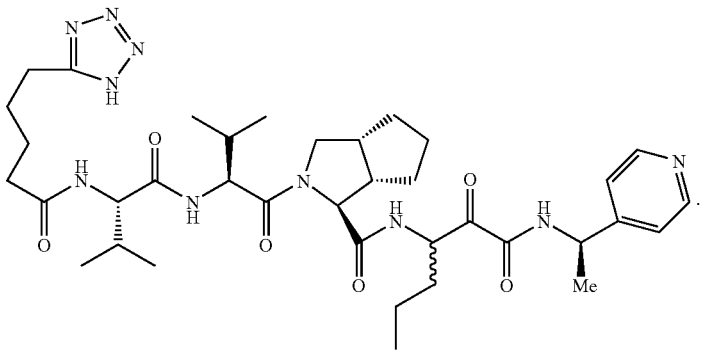

EXAMPLE 8

Compounds AK-AM

Compound xxxxiii (150 mg; 0.16 mmol) is dissolved in 4.5 mL TFA and stirred for three days. The product is purified by RP-HPLC to yield 70 mg (54% yield) compound AK,

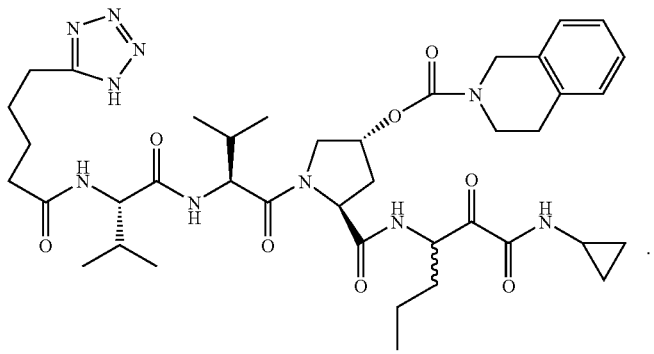

Following the above method and using the appropriate starting materials, the following consecutive compounds AL-AM are prepared:

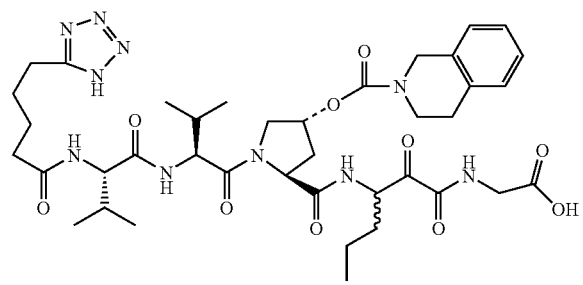

-continued

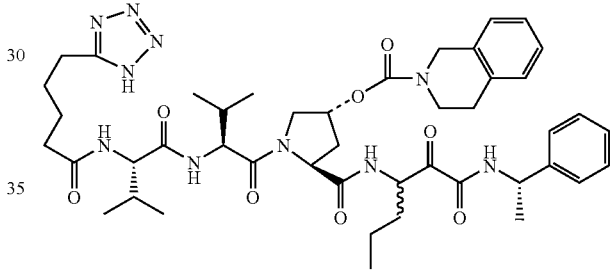

EXAMPLE 9

Compounds AN

Compound lii (80 mg) is dissolved in 3 mL TFA and 3 mL DCM. The mixture is stirred at about room temperature for 5 hours. The solvent is removed by evaporation. The resulting residue is purified by HPLC to yield 62 mg (83%) of compound AN,

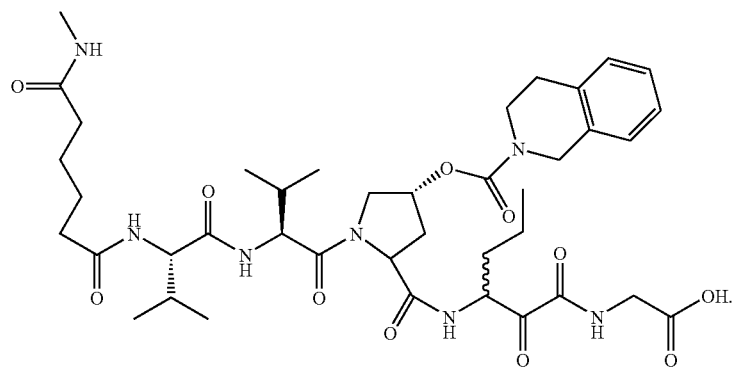

EXAMPLE 10
Compounds AO

Compound liii (160 mg; 0.2 mmol) is dissolved in 5 mL DCM and DMP reagent reagent (170 mg; 0.4 mmol) is added. The mixture is stirred at about room temperature for three hours. The solvent is removed by evaporation and the residue is dissolved in 50% acetonitrile/water and purified by RP-HPLC to yield 51 mg (32%) of compound AO,

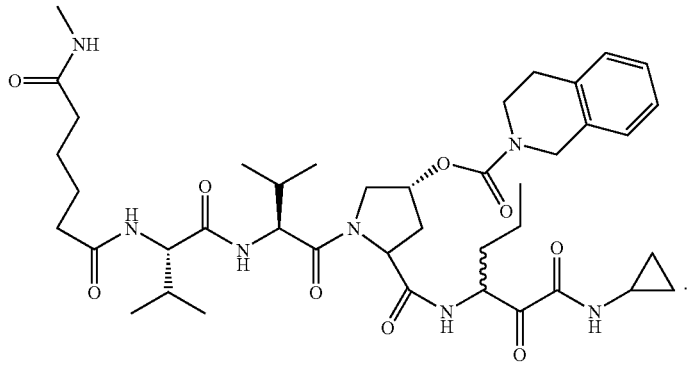

EXAMPLE 11
Compounds AP

Compound lix (162 mg; 0.22 mmol) is dissolved in 8 mL of DCM and DMP reagent reagent (189 mg; 0.44 mmol) is added. The mixture is stirred at about room temperature for 3 hours. The solvent is removed by evaporation and product is purified by RP-HPLC to yield 41 mg (25%) of compound AP,

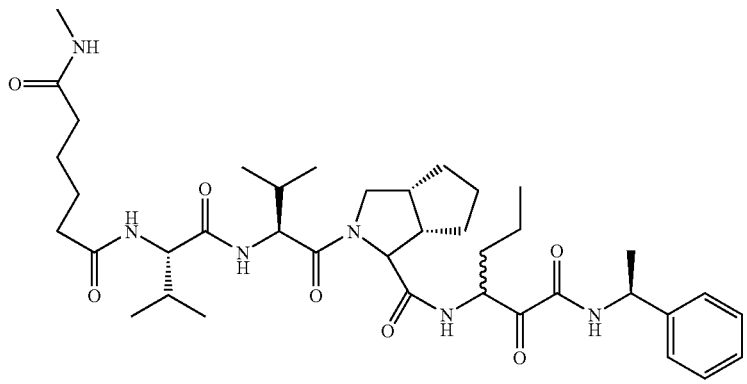

EXAMPLE 12
Compounds AQ

Compound lx (70 mg; 0.09 mmol) is dissolved in 5 mL TFA and 5 mL DCM. The mixture is stirred at about room temperature for 3 hours. The solvent is removed by vacuum and the residue is dissolved in 50% acetonitrile/water and lyophilized to yield compound AQ as a powder,

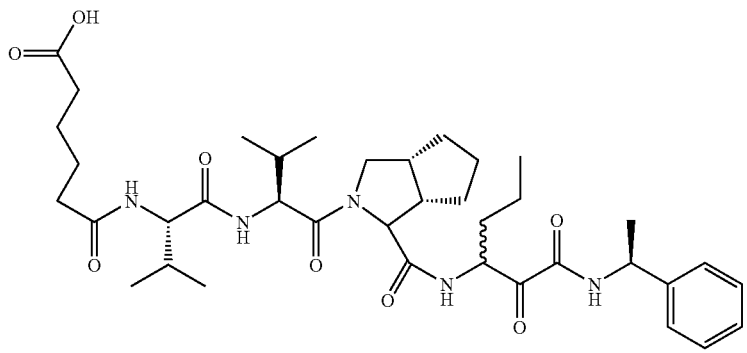

EXAMPLE 13

Compounds AR-BG

Compound lxvi (223 mg, 0.326 mmol) is stirred in a solution of TFA (5 mL) and DCM (5 mL) for 4 hours. TLC (silica gel: 2% MeOH/EtOAc) showed complete conversion to the slower product The solvent is removed under reduced pressure and the product lyophilized to give 198 mg (97%) compound AR,

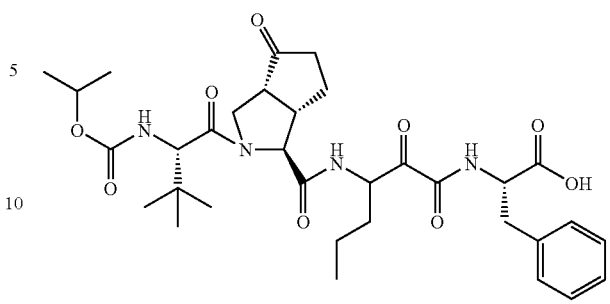

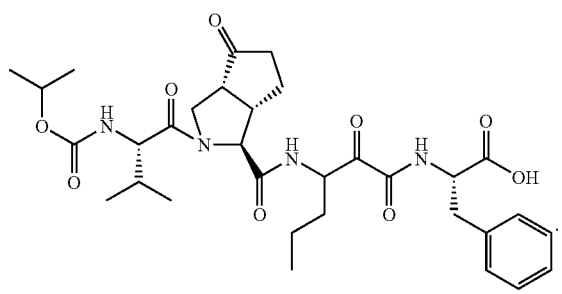

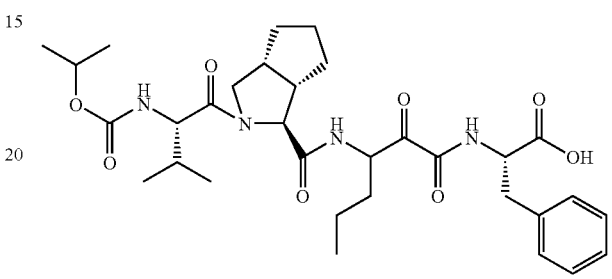

Following the above method and using the appropriate starting materials, the following consecutive compounds AS-BG are prepared:

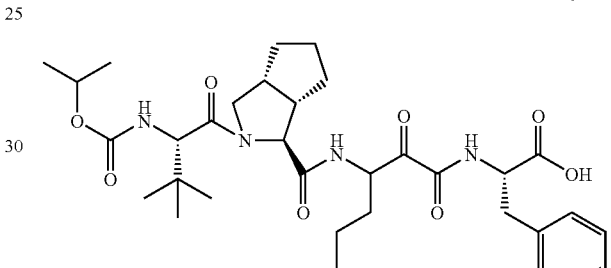

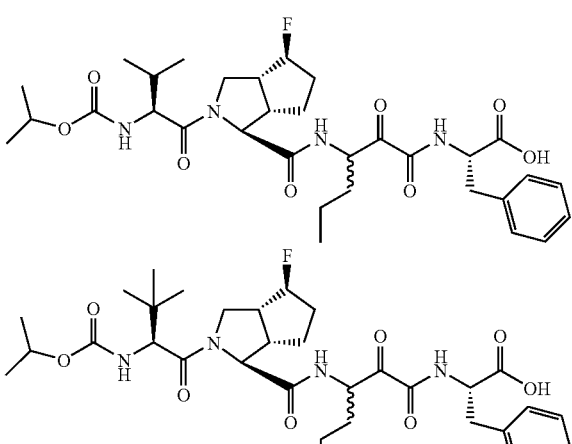

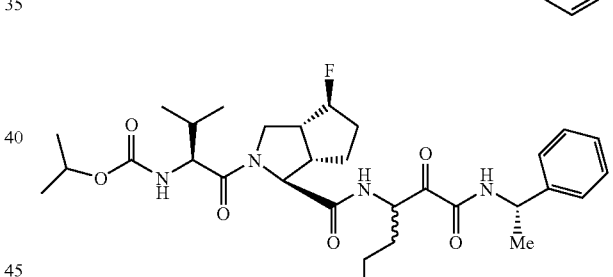

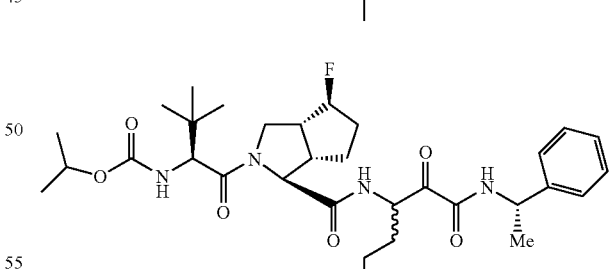

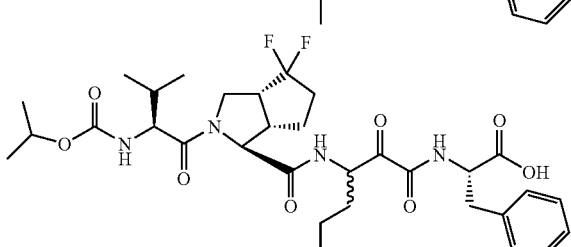

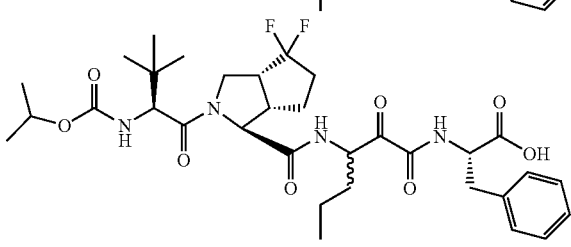

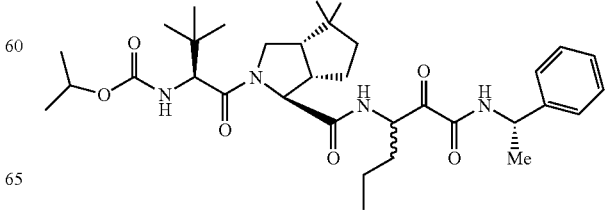

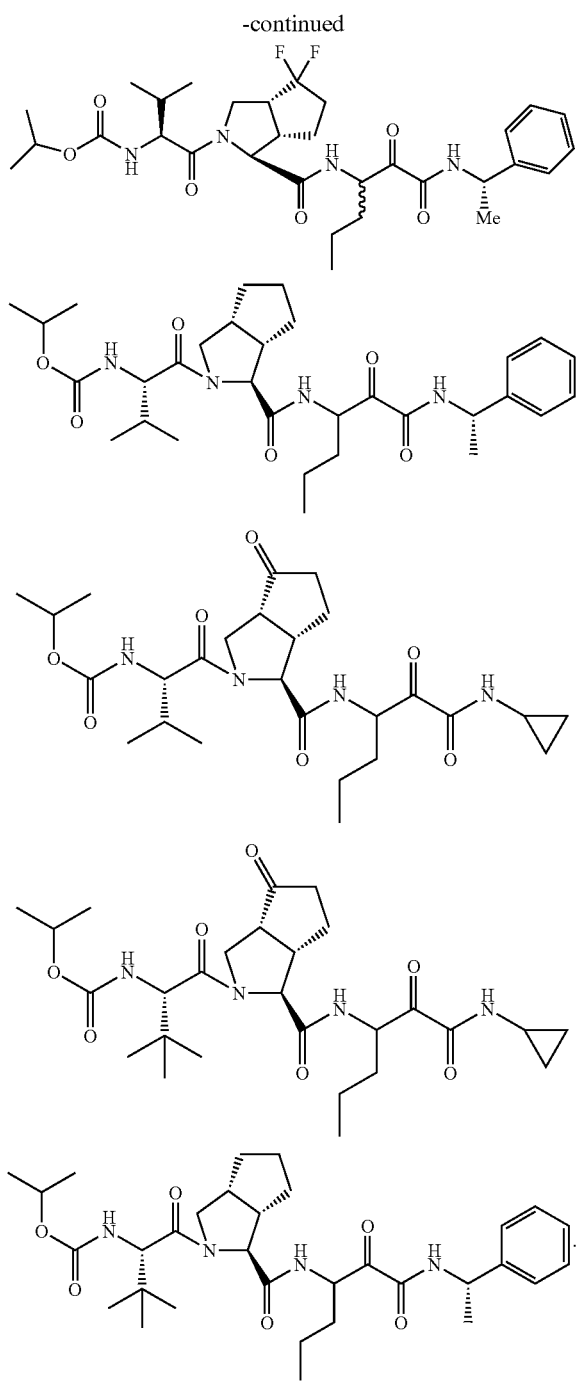

EXAMPLE 14

Compounds BH-BS

Compound lxxiii (150 mg, 0.15 mmol) is taken up in DCM (3 mL). To this solution is added TFA (1.5 mL). The resulting solution is stirred overnight. At this point, the reaction is concentrated in vacuo to give a residue. The residue is purified by reverse phase HPLC and lyophilized to give 60 mg (50%) of compound BH,

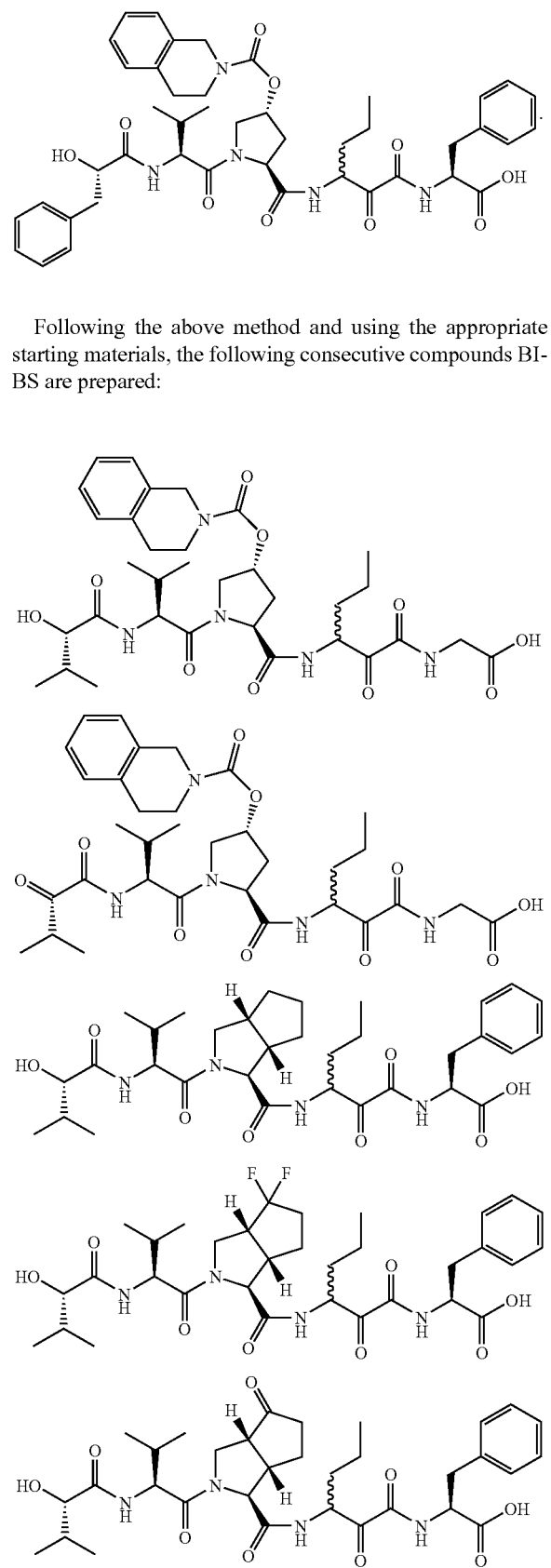

Following the above method and using the appropriate starting materials, the following consecutive compounds BI-BS are prepared:

-continued

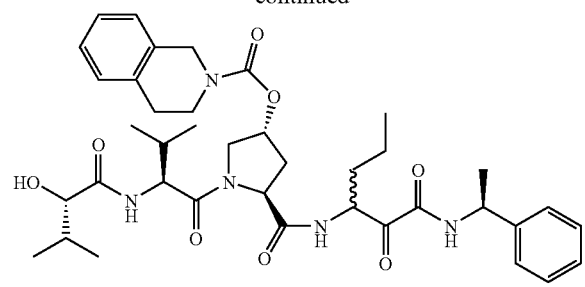

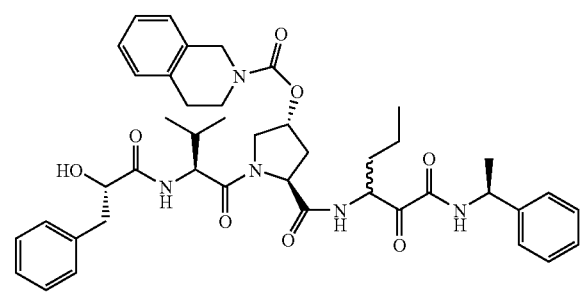

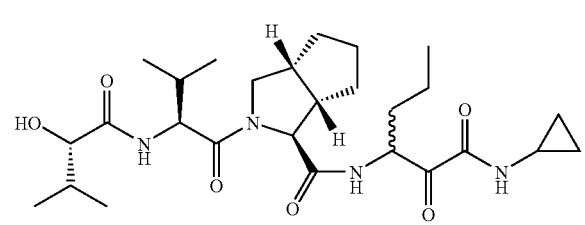

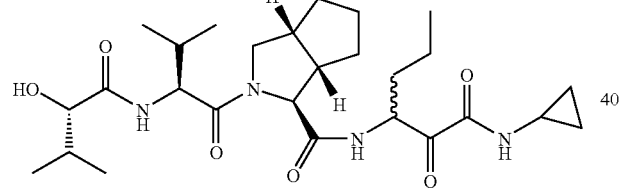

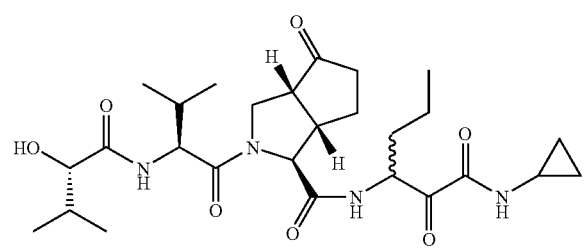

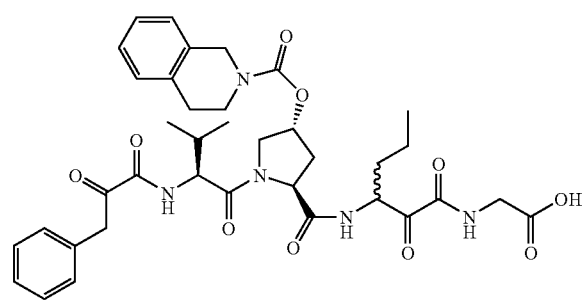

EXAMPLE 15

Compounds BT-BU

Following the method of Example 12 and using the appropriate starting materials, the following consecutive compounds BT-BU are prepared:

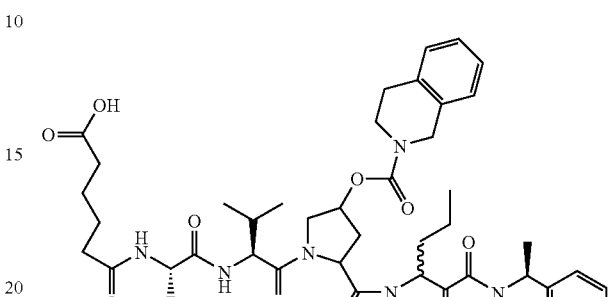

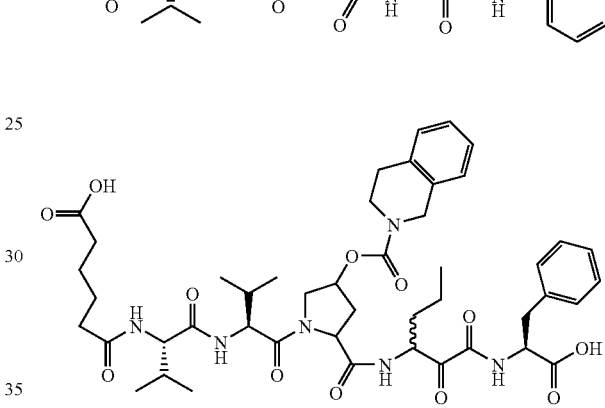

EXAMPLE 16

Compound BV

To a dichloromethane solution (4.2 mL) of compound lxxvii (143 mg, 0.21 mmol) is added DMP reagent reagent (165 mg, 0.39 mmol). The reaction is stirred at about room temperature for 2 hours and quenched with 10% $Na_2SO_3$ (aq.) for 20 minutes. The resulting mixture is extracted with EtOAc. The organic layer is washed with brine, dried over $MgSO_4$ and concentrated to a yellow oil. Purification by silica gel chromatography (5% EtOH/EtOAc) yielded 124 mg (79%) of compound BV,

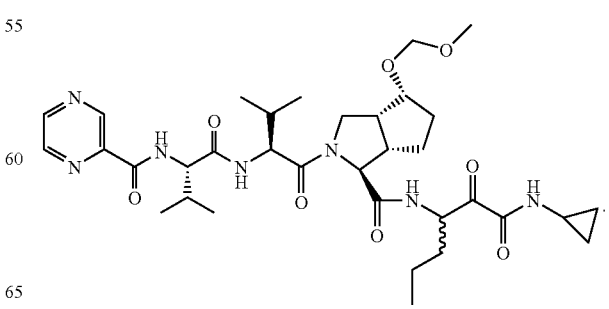

EXAMPLE 17

Compounds BW-CA

To a dichloromethane solution (20 mL) of compound lxxxix (420 mg, 0.62 mmol) is added DMP reagent reagent (342 mg, 0.81 mmol). The reaction is stirred at about room temperature for 1 hour and quenched with 10% Na₂SO₃ for 20 minutes. The resulting mixture is then extracted with EtOAc. The organic layer is washed with brine, dried and concentrated in vacuo. The resulting residue is purified by silica gel chromatography (80% EtOAc/Hexanes) to give 208 mg (50%) of compound BW,

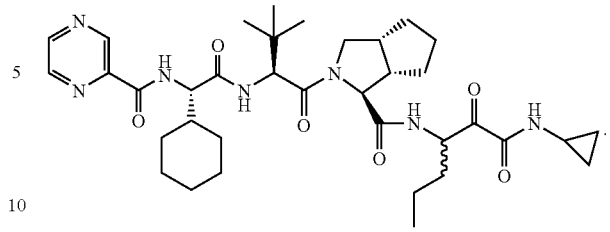

Following the above method but using the appropriate starting materials, the following consecutive compounds BX-CA are prepared:

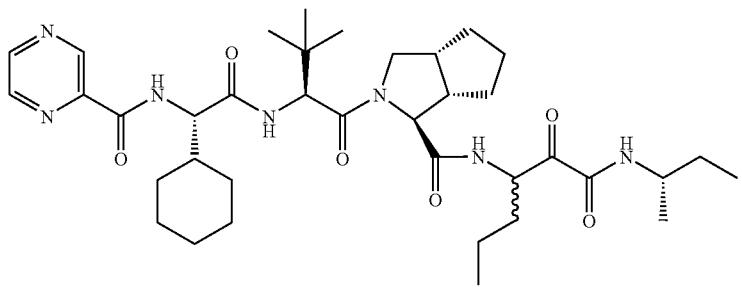

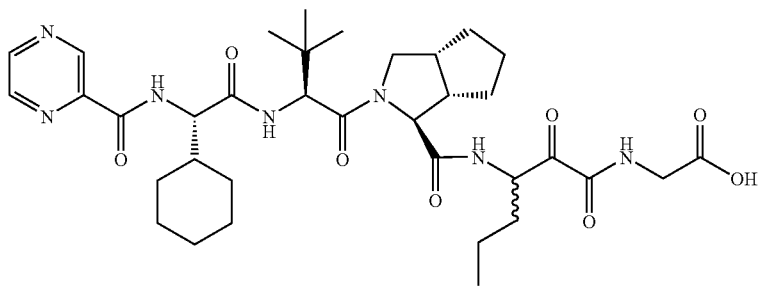

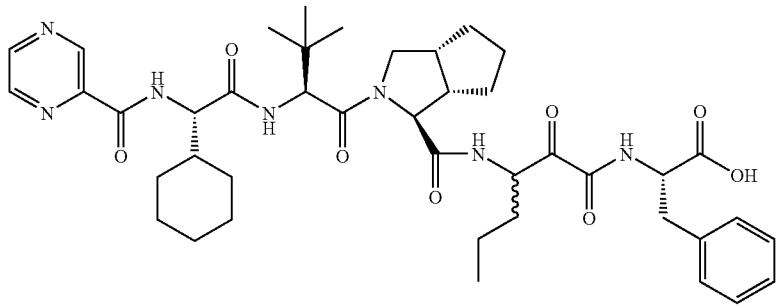

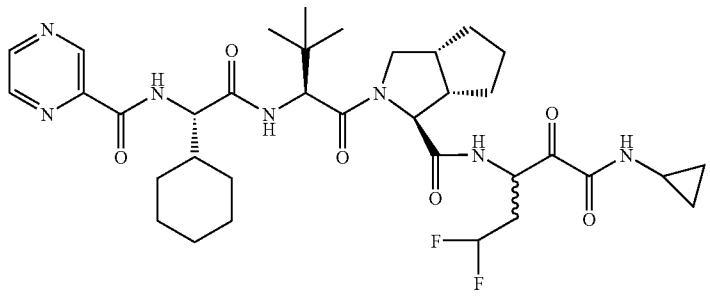

EXAMPLE 18

Compounds CB-CC

To a dichloromethane solution (6.5 mL) of compound lxxxvii (200 mg, 0.3 mmol) is added DMP reagent reagent (227 mg, 0.54 mmol). The reaction is stirred at about room temperature for 2 hours and quenched with 10% $Na_2SO_3$ (aq.) for 20 minutes. The resulting mixture is extracted with EtOAc. The organic layer is washed with brine, dried over $MgSO_4$ and concentrated to a yellow oil. Purification by silica gel chromatography (5% EtOH/EtOAc) yields 138 mg (70%) of compound CB,

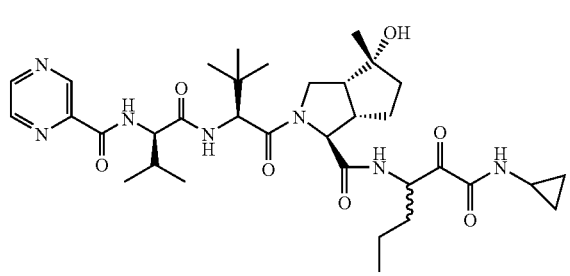

Following the above method but using the appropriate starting materials, the following compound CC is prepared:

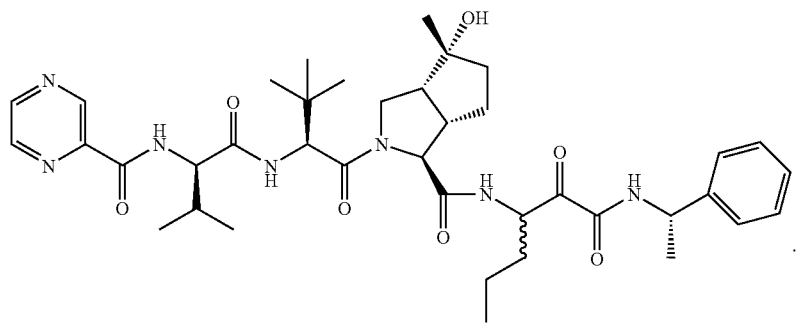

EXAMPLE 19

Compound CD

Compound lxxxxviii (40 mg, 0.05 mmol) is taken up in TFA (3 mL). The solution stirred over two nights and is concentrated. The residue is purified on reverse phase HPLC to give 25 mg (74%) of compound CD,

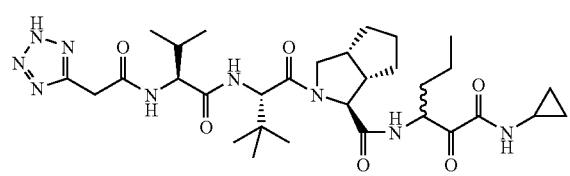

EXAMPLE 20

Compound CE

Following the method of Example 17 and using the appropriate starting materials, the following compound CE is prepared:

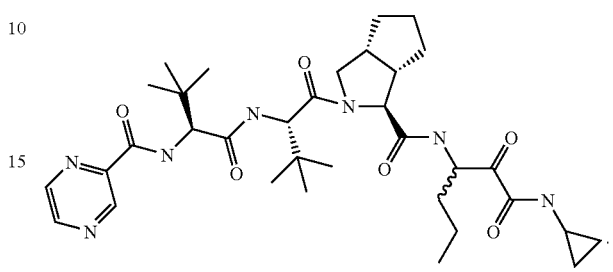

EXAMPLE 21

Compounds CF-CG

Following the method of Example 14 and using the appropriate starting materials, the following consecutive compounds CF-CG are prepared:

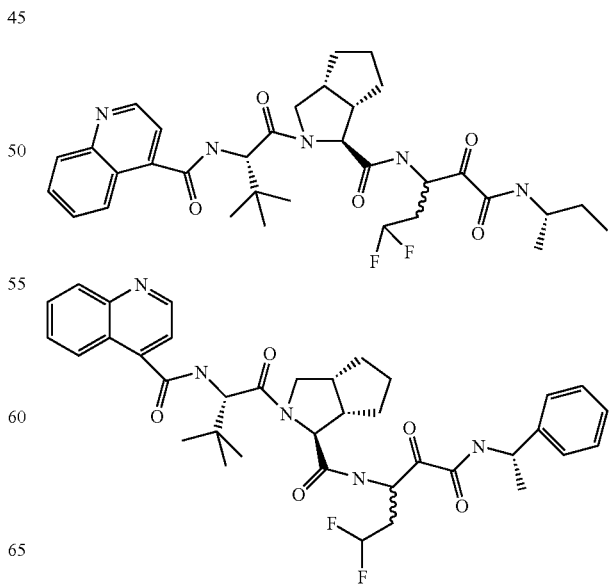

EXAMPLE 22

Compound CH

Following the method of Example 16 and using the appropriate starting materials, the following compound CH is prepared:

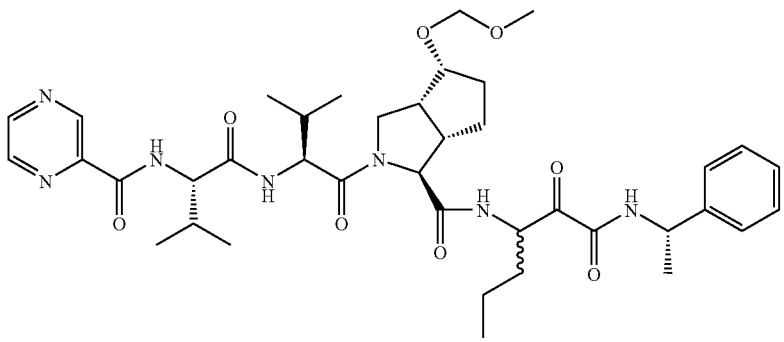

EXAMPLE 23

Compounds CI-CM

Compound cxi (490 mg, 0.75 mmol) is dissolved in DCM (6 mL). DMP reagent reagent (380 mg, 0.9 mmol) is added to this solution and stirred 1 hour. The reaction mixture is quenched with a 10% $Na_2SO_3$ solution, and then the organic phase is washed with saturated $NaHCO_3$ and brine. Following the concentration of the organic phase, the resultant residue is chromatographically purified by 70% EtOAc/hexanes to yield compound CI (325 mg, 66.4%).

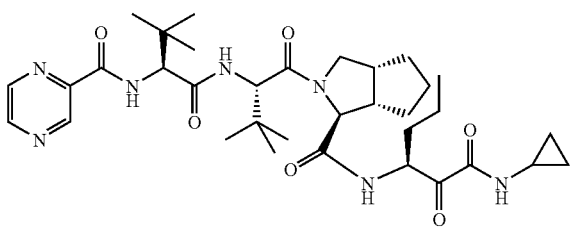

Following the above method for preparing the above compound and methods related to preparing the intermediate thereto, but using the appropriate starting materials the following consecutive compounds CJ-CM are prepared:

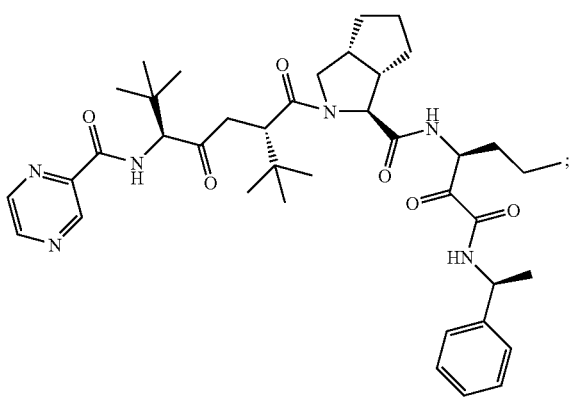

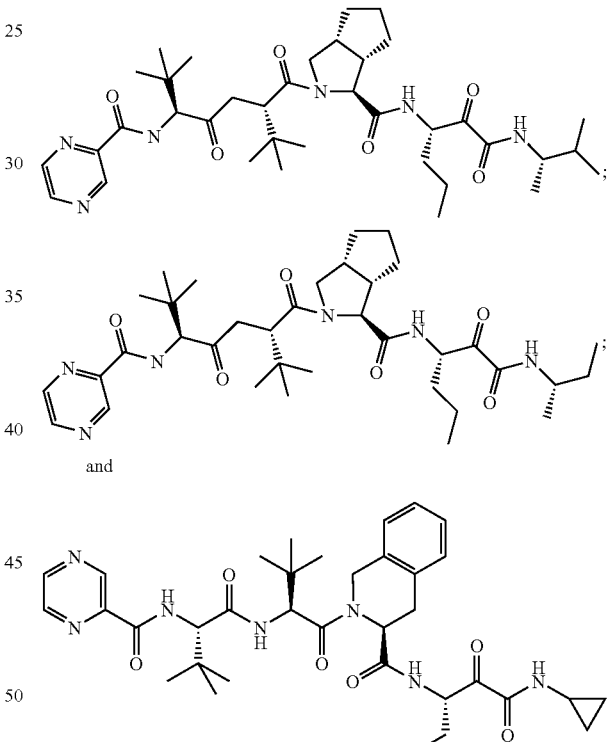

and

EXAMPLE 24

Compounds CN

To a DCM/THF solution (3 mL/3 mL) of compound cxviii (335 mg, 0.46 mmol) is added DMP reagent reagent (300 mg, 0.69 mmol). The reaction mixture is stirred at room temperature for 2 hours and quenched with 10% $Na_2SO_3$ (aq.) for 20 minutes. The resulting mixture is extracted with EtOAc. The organic phase is washed with brine, dried over $MgSO_4$ and concentrated to yield a yellow oil. Purification by silica gel chromatography (80% EtOAc/hexanes) yields compound CN (220 mg, 67%).

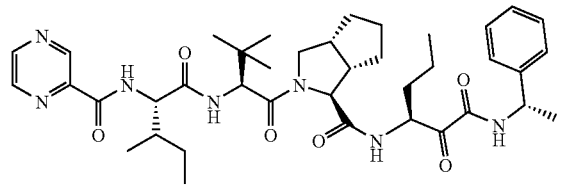

EXAMPLE 25

Compounds CO-CR

To a DCM/THF solution (1.5 mL/1.5 mL) of compound cxix (164 mg, 0.25 mmol) is added DMP reagent reagent (159 mg, 0.38 mmol). The reaction mixture is stirred at room temperature for 2 hours and quenched with 10% $Na_2SO_3$ (aq.) for 20 minutes. The resulting mixture is extracted with EtOAc. The organic phase is washed with brine, dried over $MgSO_4$ and concentrated to yellow oil. Purification by silica gel chromatography (70% EtOAc/hexanes) yields compound CO (100 mg, 61%).

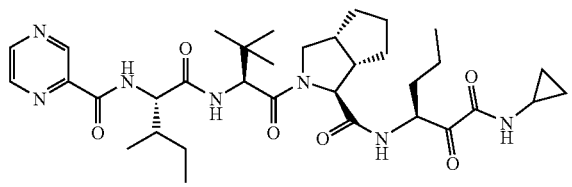

Following the above method for preparing the above compound and methods related to preparing the intermediate thereto, but using the appropriate starting materials the following consecutive compounds CP-CR are prepared:

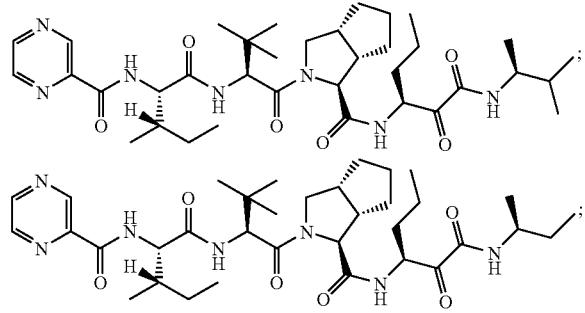

and

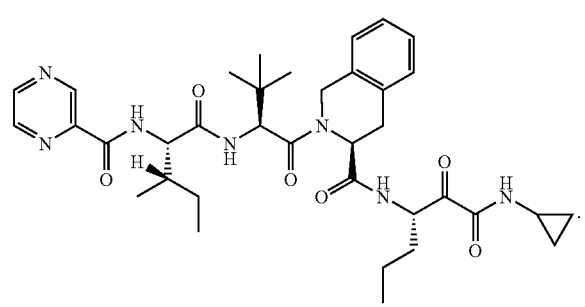

EXAMPLE 26

Compounds CS-CT

Compound cxx is dissolved in DCM (3 mL). DMP reagent reagent (180 mg, 0.41 mmol) is added to the solution, and then stirred for 1 hour. The reaction mixture is quenched with 10% $Na_2SO_3$, and then the organic phase is washed with saturated $NaHCO_3$ and brine. Following the concentration of the organic phase, the residue is chromatographically purified by 100% EtOAc to yield compound CS (95 mg, 43.7%).

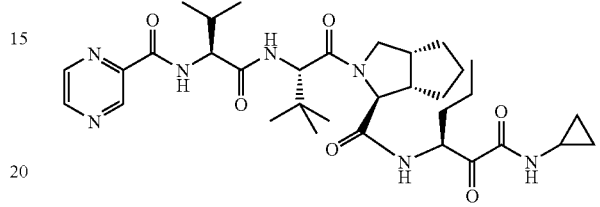

Following the above method for preparing the above compound and methods related to preparing the intermediate thereto, but using the appropriate starting materials the following compound CT is prepared:

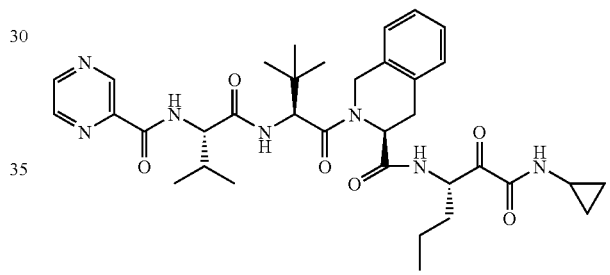

EXAMPLE 27

Compounds CU, EI, EK-EM, EO-EZ, and FA-FG

Compound cxxviii (356 mg, 0.52 mmol) is dissolved in DCM (5 mL). DMP reagent reagent (270 mg, 0.63 mmol) is added to this solution and stirred 1 hour. The reaction mixture is quenched with 10% $Na_2SO_3$, and then the organic phase is separated and washed with saturated $NaHCO_3$ and brine. Following the concentration of the organic solvent, the residue is chromatographically purified by 100% EtOAc to yield compound CU (200 mg, 56.3%). mp 225-235° C.

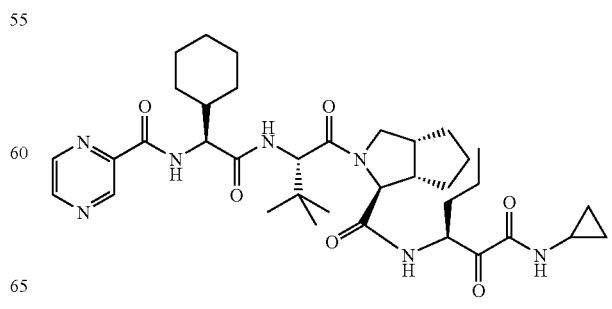

Following the above method for preparing the above compound and methods related to preparing the intermediate thereto, but using the appropriate starting materials the following consecutive compounds EI, EK-EM, EO-EZ and FA-FH are prepared:
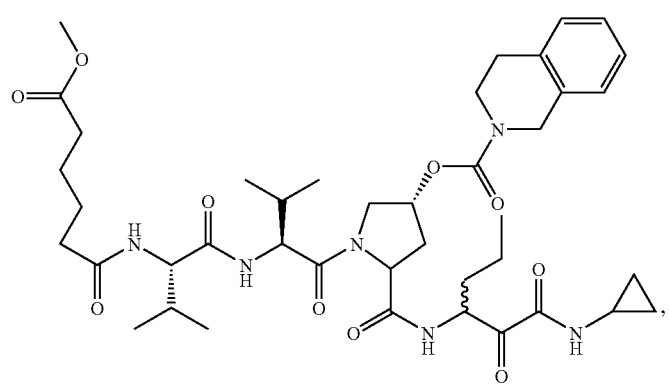
EI
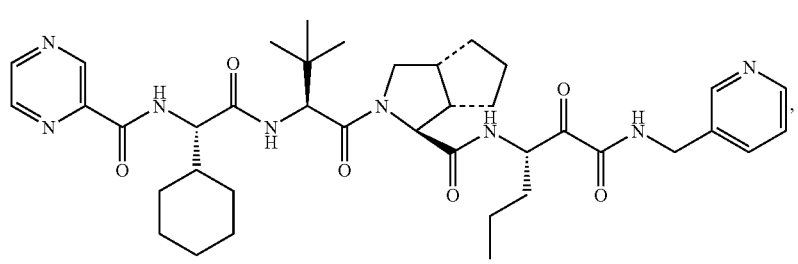
EK
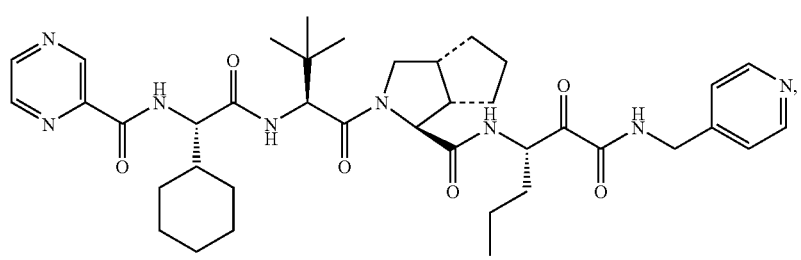
EL
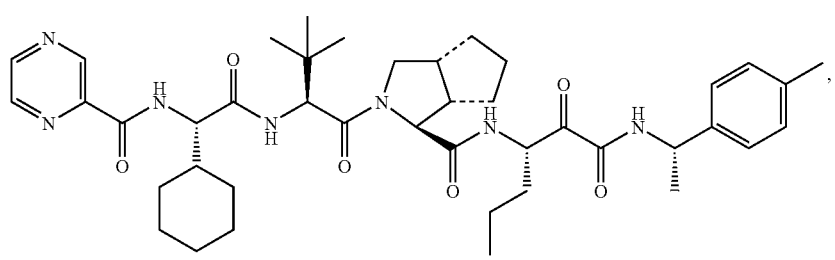
EM
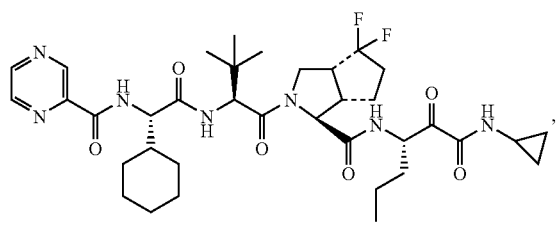
EO
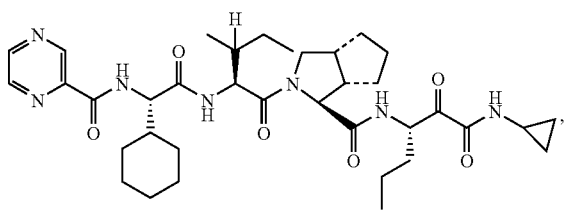
EP -continued
EQ
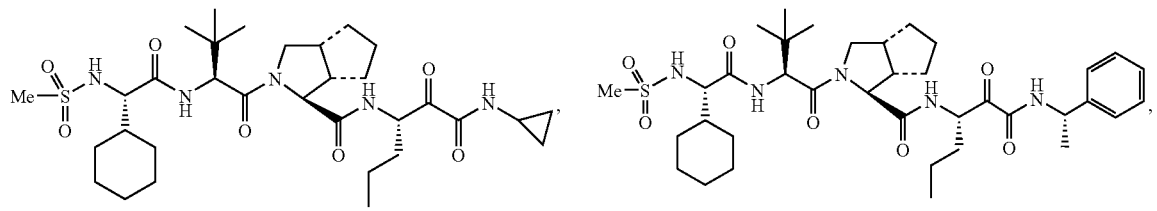
ER
ES
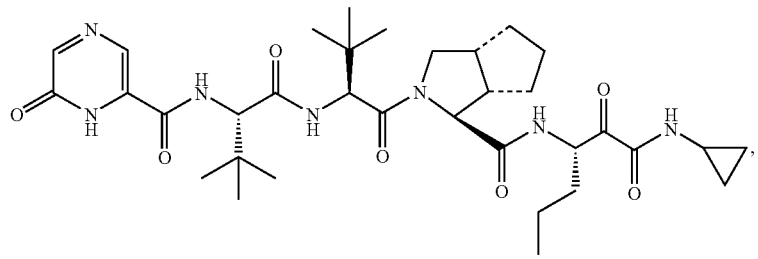
ET
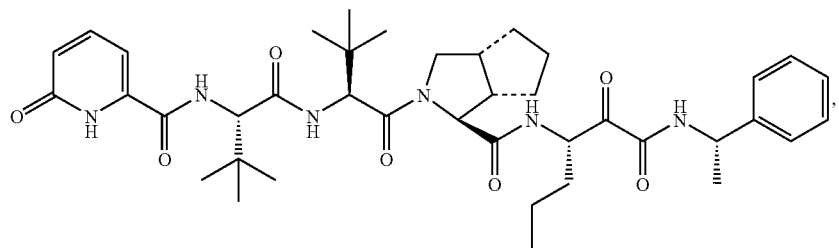
EU
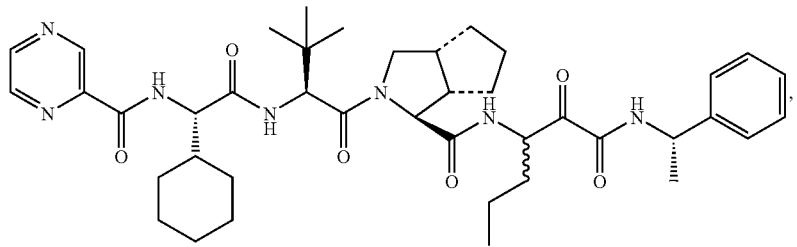
EV
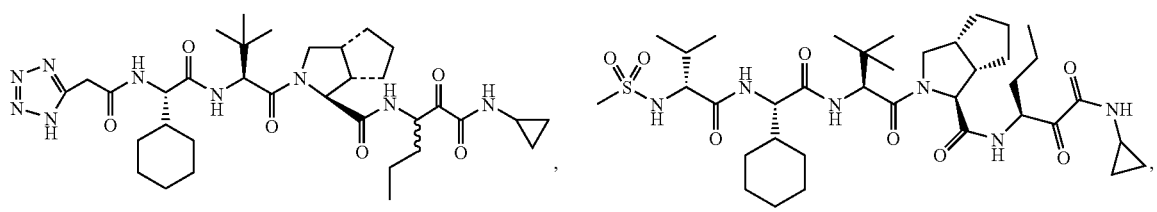
EW
EX
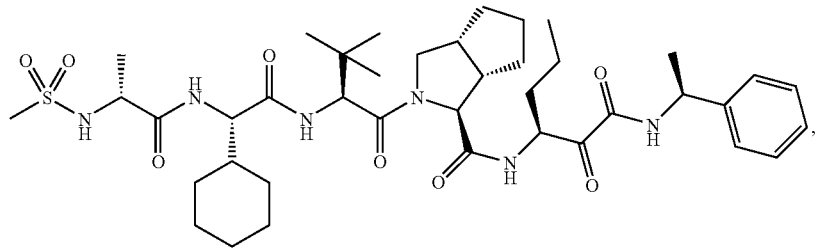

-continued
EY
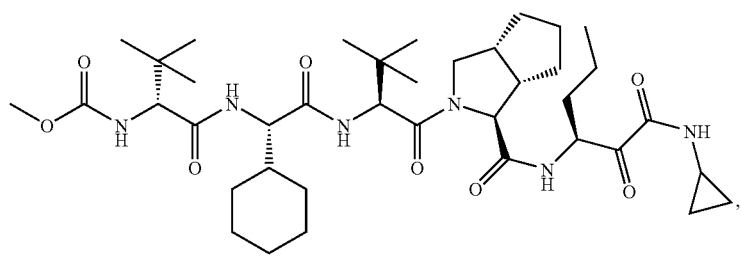
EZ
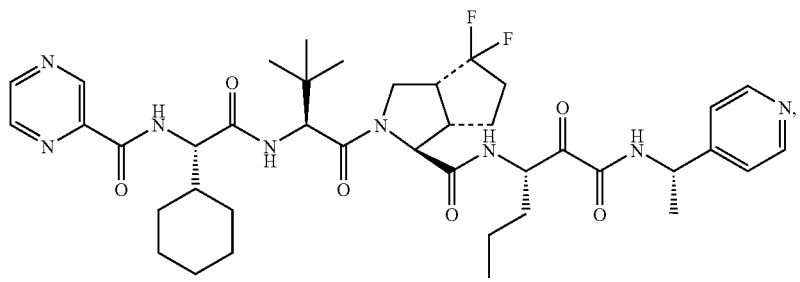
FA
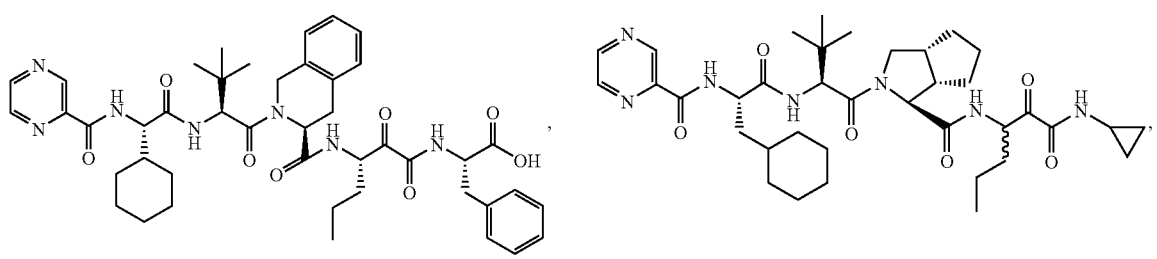
FB
FC
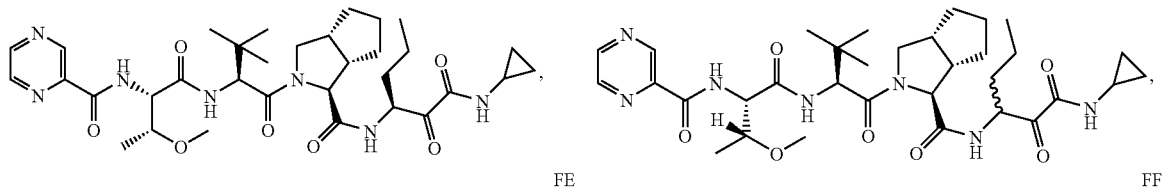
FD
FE
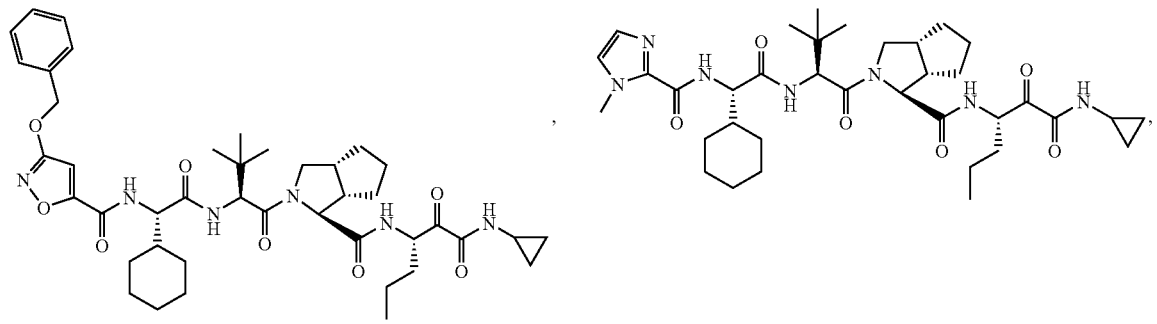
FF
FG
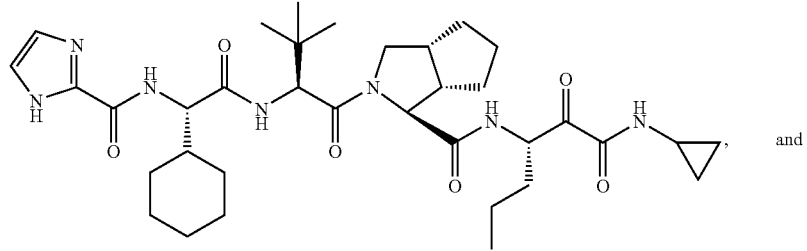
and -continued

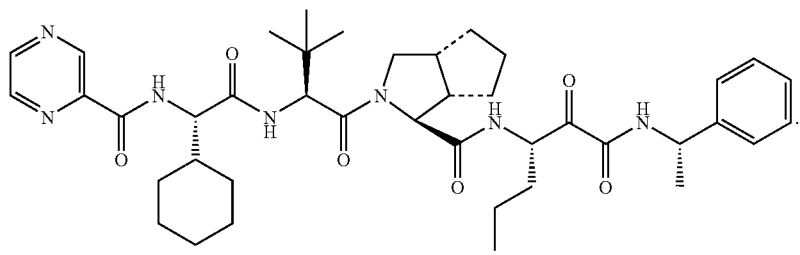

EXAMPLE 28
Compounds CV-DC

Compound cxxx (330 mg, 0.46 mmol) is dissolved in DCM (5 mL). DMP reagent reagent (240 mg, 0.56 mmol) is added to this solution and stirred 1 hour. The reaction mixture is quenched with a 10% Na$_2$SO$_3$, and the organic phase washed with saturated NaHCO$_3$ and brine.

Following the concentration of the organic phase, the resulting residue is chromatographically purified by b 100% EtOAc to yield compound cxxx (280 mg, 85.9%).

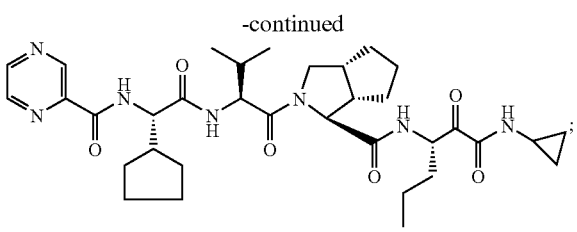

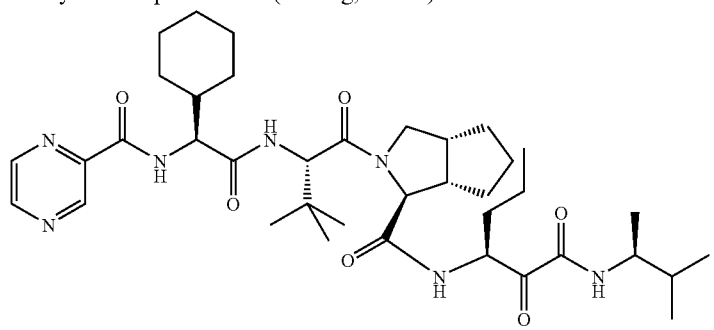

Following the above method for preparing the above compound and methods related to preparing the intermediate thereto, but using the appropriate starting materials the following consecutive compounds CW-DC are prepared:

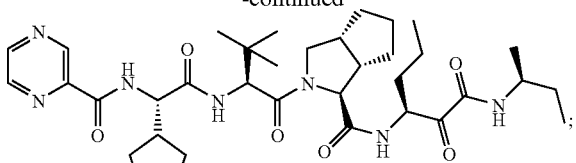

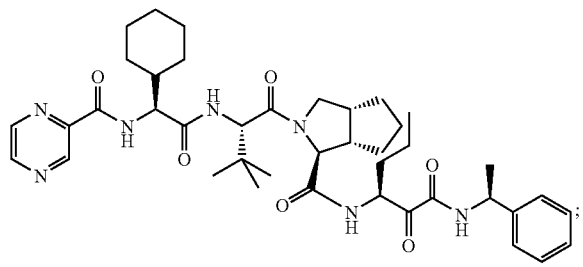

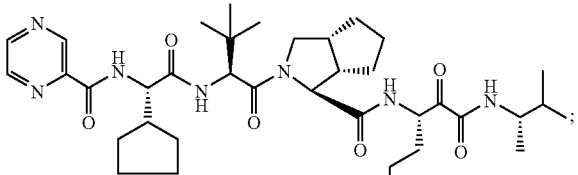

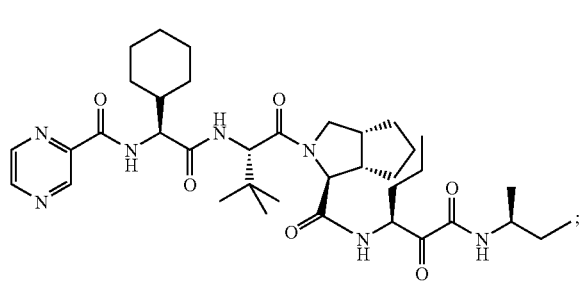

and

-continued

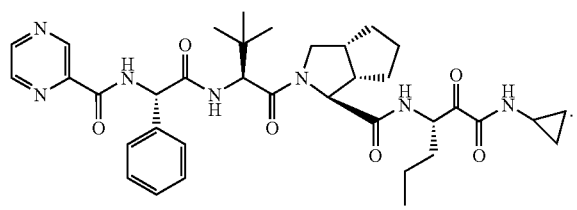

EXAMPLE 29

Compounds DD-DE

To a DCM solution (6 mL) of compound cxxxviii (400 mg, 0.57 mmol) is added DMP reagent reagent (362 mg, 0.85 mmol). The reaction mixture is stirred at room temperature for 2 hours and quenched with 10% $Na_2SO_3$ (aq.) for 20 minutes. The resulting mixture is extracted with EtOAc. The extracted organic phase is washed with brine, dried over $MgSO_4$ and concentrated to yield yellow oil. Purification by silica gel (70% EtOAc/hexanes) yields compound DD (201 mg, 51%).

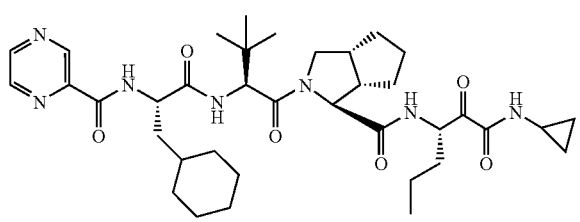

Following the above method for preparing the above compound and methods related to preparing the intermediate thereto, but using the appropriate starting materials the following compound DE is prepared:

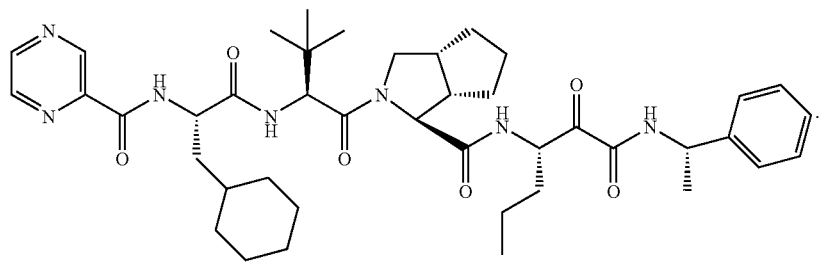

EXAMPLE 30

Compound DF

Compound cxxxxiii (165 mg, 0.24 mmol) is dissolved in DCM (5 mL). DMP reagent reagent (125 mg, 0.29 mmol) is added to the solution and stirred 1 hour. The reaction mixture is quenched with a 10% $Na_2SO_3$, and the organic phase washed with saturated $NaHCO_3$ and brine. Following the concentration of the organic phase, the resultant residue is purified chromatographically by 70% EtOAc/hexanes to yield compound DF (108 mg, 65.6%).

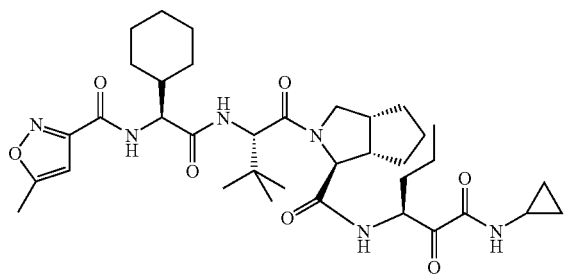

EXAMPLE 31

Compounds DG-DJ

To a solution of compound cil (0.350 g, 0.516 mmol) in DCM (15 mL) cooled by an ice bath is added DMP reagent reagent (0.281 g, 0.671 mmol). The mixture is stirred at room temperature for 2 hours, then quenched with 10% $Na_2SO_3$ solution and stirred for 20 minutes. The resulting mixture is extracted with DCM (3×20 mL) and the organic extract is dried ($MgSO_4$). After filtration to remove $MgSO_4$, the filtrate is concentrated and purified by column chromatography (70% Ethyl acetate/Hexanes) to yield the final compound DG (0.265 g, 76%) as white solid.

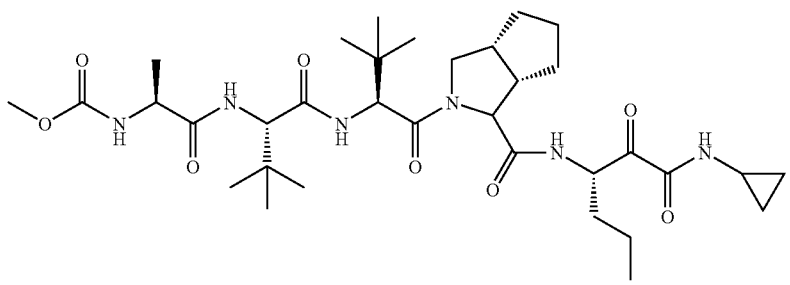

Following the above method for preparing the above compound and methods related to preparing the intermediate thereto, but using the appropriate starting materials the following consecutive compounds DH-DJ are prepared:

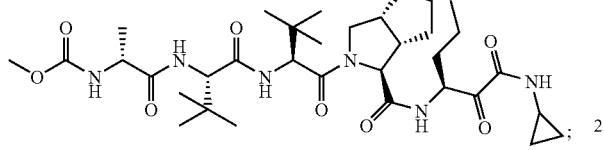

and

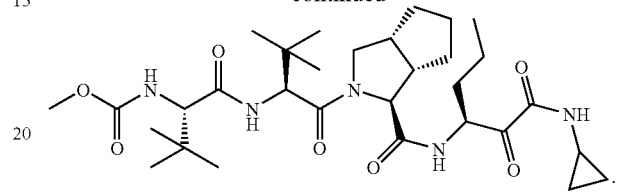

-continued

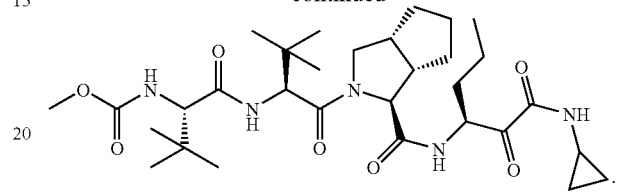

EXAMPLE 32

Compounds DK-DN

A DCM solution of compound clx (108 mg, 0.123 mmol) is treated with DMP reagent reagent (78 mg, 0.185 mmol). After stirring at room temperature for 1 hour, the reaction mixture is diluted with EtOAc (50 mL), and then quenched with 10% $Na_2SO_3$. After stirring for 30 minutes, the organic phase is separated and washed with $NaHCO_3$ and brine. The organic phase is dried and concentrated in vacuo to give a residue that is purified by silica gel chromatography (80% EtOAc/hexanes) to yield compound DK (84 mg, 78%).

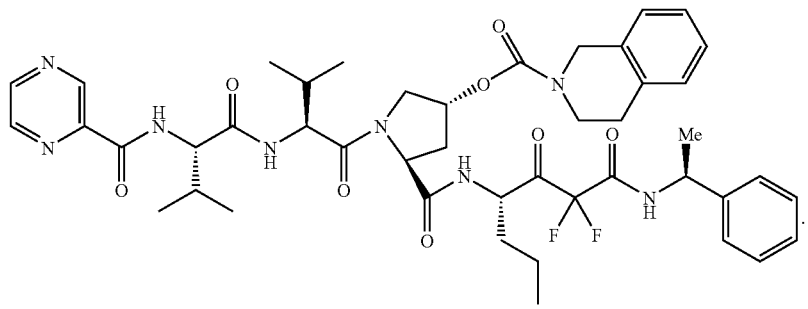

Following the above method for preparing the above compound and methods related to preparing the intermediate thereto, but using the appropriate starting materials the following compounds DL-DN are prepared.

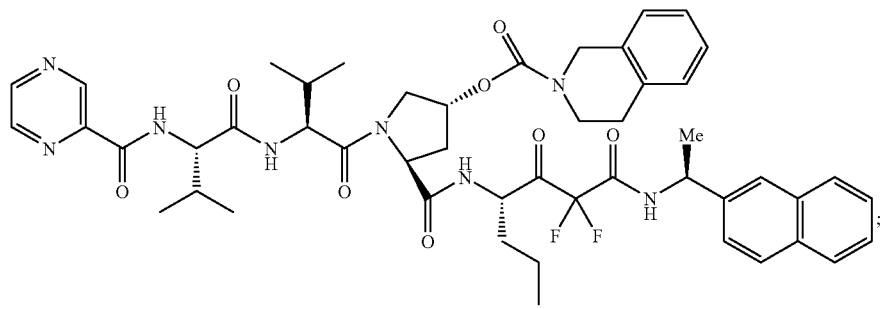

-continued

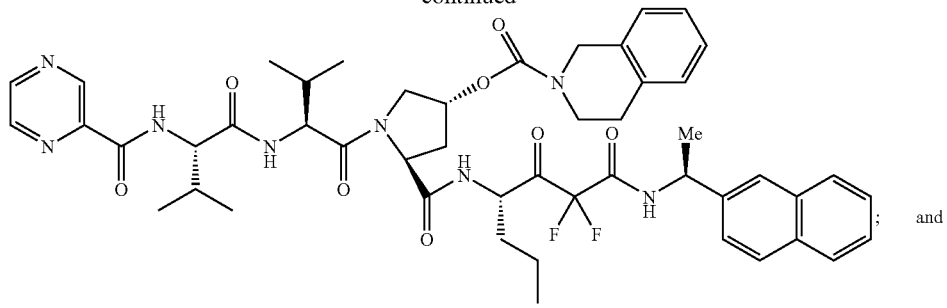

and

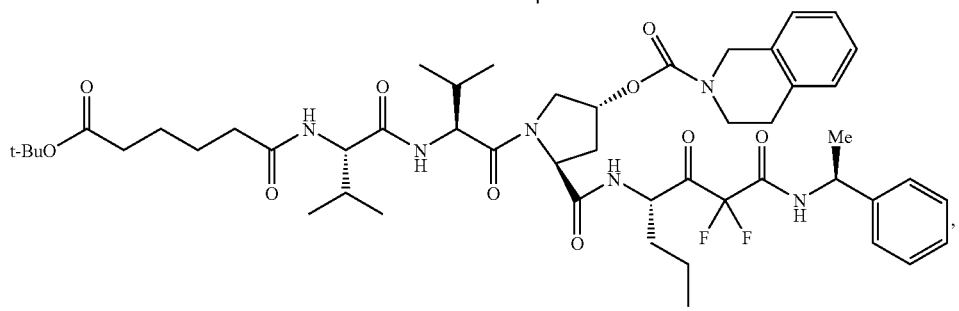

EXAMPLE 33

Compounds DO-DS

An EtOH solution (10 mL) of compound clxii (174 mg, 0.189 mmol) is hydrogenated using Pd/C (30% eq., 60 mg, 10% palladium content) for 2.5 hours. The catalyst is then filtered off. The resulting filtrate is concentrated in vacuo to yield a residue that is purified by semi-preparative reverse phase chromatography and lyophilized to afford compound DO in 70% yield.

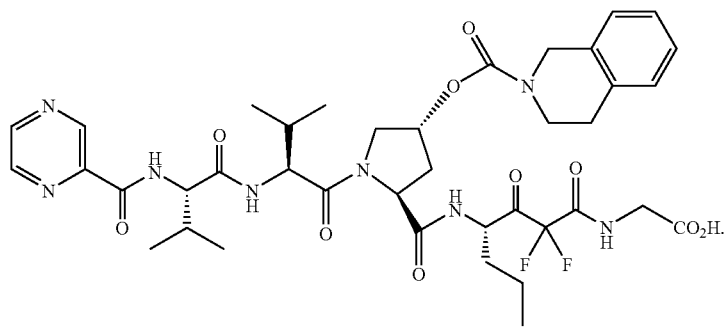

Following the above method for preparing the above compound and methods related to preparing the intermediate thereto, but using the appropriate starting materials the following consecutive compounds DP-DS are prepared.

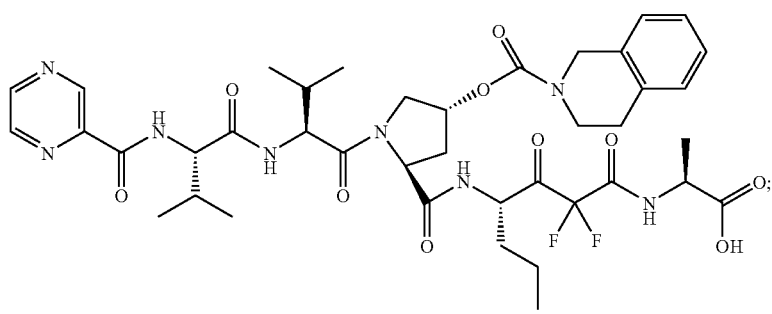

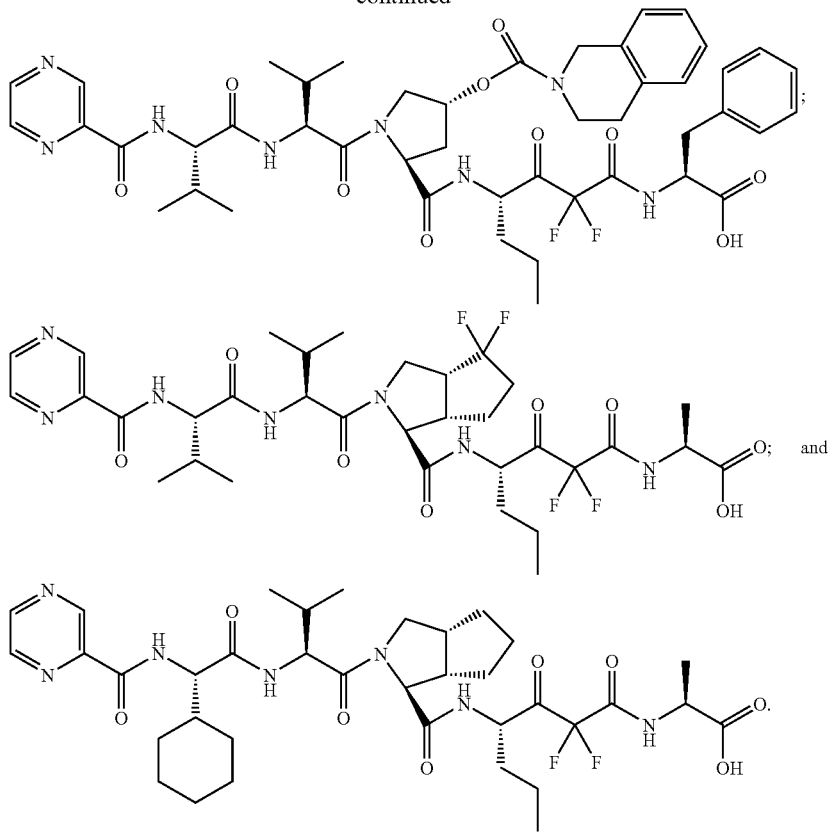

EXAMPLE 34

Compound CW

Compound clxiii (175 mg, 0.24 mmol) is taken up in DCM (3 mL). DMP reagent (120 mg, 0.28 mmol) is added to this solution and stirred 1 hour. The reaction is quenched with a 10% $Na_2SO_3$ and washed with saturated $NaHCO_3$ and brine. Purification by 70% EtOAc yields compound CW (134 mg, 75%).

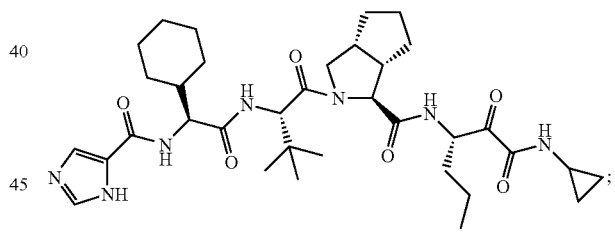

EXAMPLE 35

Compounds CY and DT-DX

To a DCM solution (15 mL) of clxxii (290 mg, 0.43 mmol) is added DMP reagent (239 mg, 0.56 mmol). The reaction is stirred at room temperature for 1 hour and quenched with 10% $Na_2SO_3$ for 20 minutes. The resulting mixture is then extracted with EtOAc. The organic layer is washed with brine, dried and concentrated in vacuo. The resulting residue is purified by silica gel chromatography (8-100% EtOAc/Hexanes) to give compound CY (151 mg, 52%).

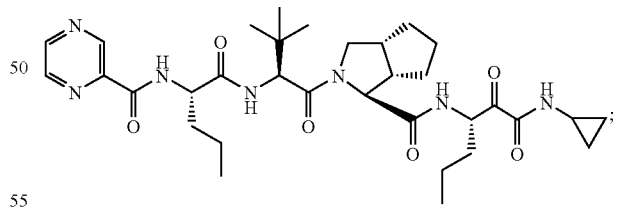

Following the above method for preparing the above compound and methods related to preparing the intermediate thereto, but using the appropriate starting materials the following consecutive compounds DT-DX are prepared.

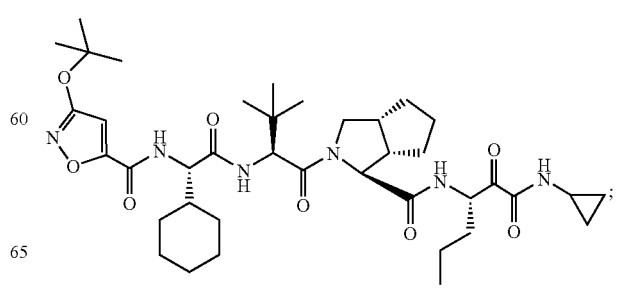

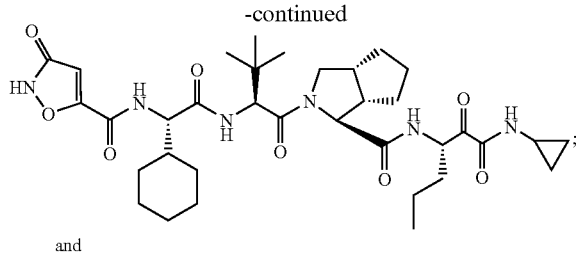

and

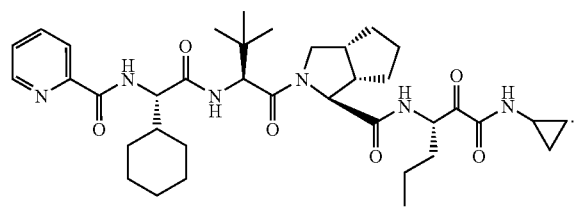

EXAMPLE 36

Compounds DY

Compound lxxxv (1.17 mmol) is taken up in DCM (5 mL). DMP reagent (545 mg, 1.3 mmol) is added to this solution and stirred 1 hour. The reaction is quenched with a P—Na$_2$SO$_3$ (1.5 mmol/g resin) and stirred one hour. P-TBD scavenger resin* (2.5 mmol/g resin) is added and stirred 45 minutes. The resulting mixture is filtered and purified by 50% EtOAc to give compound DY (440 mg, 50.2% over two steps).

*Reference for P-TBD scavenger resin: J. Parlow et al. *Tetrahedron*, 55, 6785-6796 (1999).

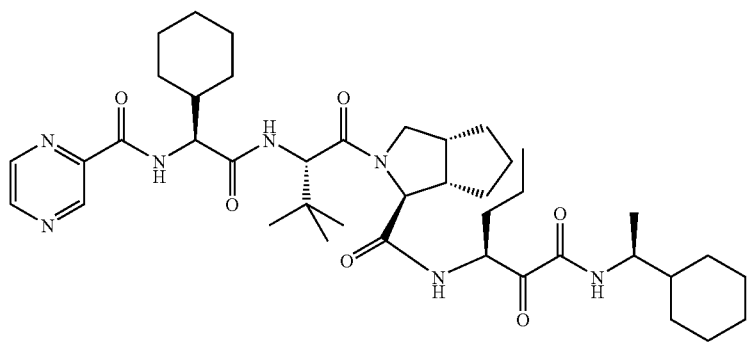

EXAMPLE 37

Compound DZ

The starting material compound clxxxi (94 mg, 0.14 mmole) is dissolved in a mixture of THF (10 mL) and DCM (20 mL). The DMP reagent (118 mg, 0.28 mmol) is then added. After stirring at room temperature for 2 hours. The reaction is dumped in a separatory funnel containing Dri Solv THF (120 mL). The reaction is washed with 10% Na$_2$SO$_3$ (50 mL), and then brine (75 mL). The organic layer is then separated, dried over MgSO$_4$ and the solvent removed under reduced pressure. After chromatography (silica gel: elution with 50% Dri Solv THF/EtOAc, and then 4% MeOH/THF). Fractions are checked by MS. Appropriate fractions are lyopholized to yield compound DZ (38.8 mg, 41%).

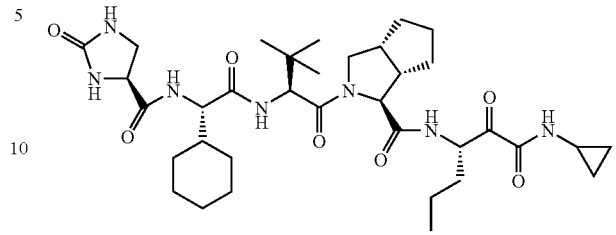

EXAMPLE 38

Compounds EA-EB

The starting compound clxxxxv (185 mg, 0.26 mmol) is dissolved in THF (20 mL). The DMP reagent (219 mg, 0.52 mmol) is then added. After stirring at room temperature for 1 hour. TLC shows complete conversion to ketone (5% MeOH/THF). The reaction is dumped in a separatory funnel containing Dri Solv THF (120 mL). The reaction is washed with 10% Na$_2$SO$_3$ (50 mL), and then brine (75 mL). The organic layer is then separated, dried over MgSO$_4$ and solvent removed by reduced pressure to yield a residue that is purified by chromatography (silica gel: elution with 50% Dri Solv THF/EtOAc, and then 4% MeOH/THF) and fractions are checked by UV and MS. The appropriate fractions are lyopholized to yield compound EA (159 mg, 88%).

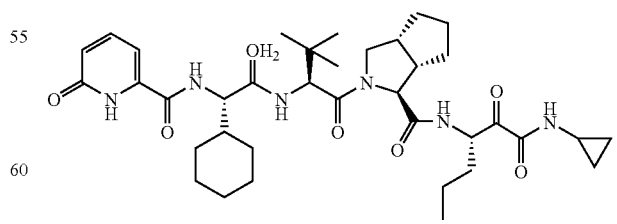

Following the above method for preparing the above compound and methods related to preparing the intermediate thereto, but using the appropriate starting materials the following compound EB is prepared:

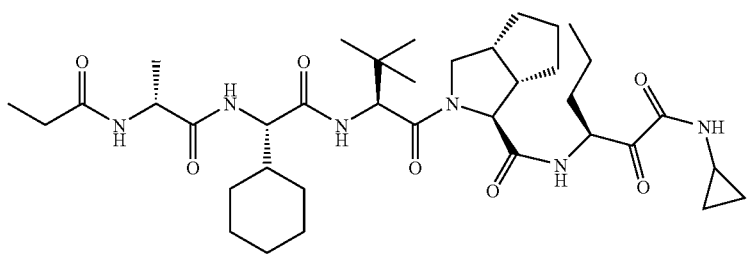

EXAMPLE 39

Compounds EC-ED

To a solution of compound clxxxxviii (0.341 g, 0.503 mmol) in DCM (15 mL) cooled in an ice bath is added DMP reagent (0.277 g, 0.654 mmol). The mixture is stirred at room temperature for 2 hours, then quenched with 10% $Na_2SO_3$ solution and stirred for 20 minutes. The resulting mixture is extracted with DCM (3×20 mL) and the organic extract is dried ($MgSO_4$). After filtration to remove $MgSO_4$, the filtrate is concentrated and purified by column chromatography (70% EtOAc/Hexane) to give compound EC (0.183 g, 54%) as white solid.

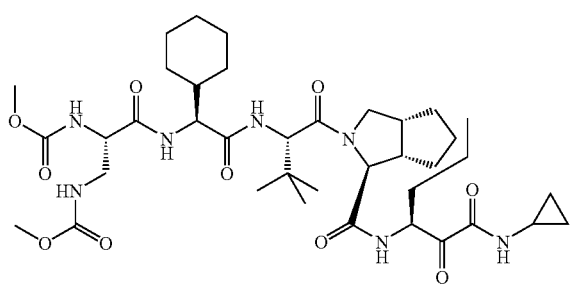

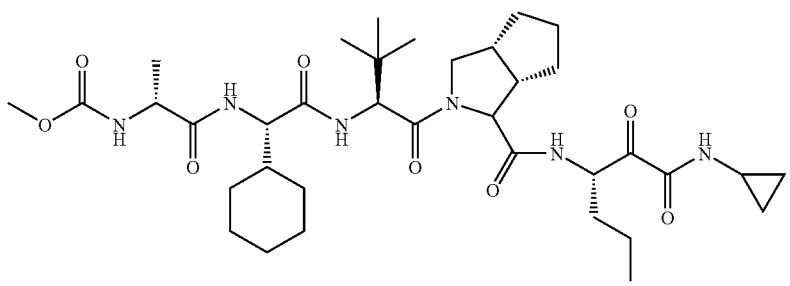

Following the above method for preparing the above compound and methods related to preparing the intermediate thereto, but using the appropriate starting materials the following compound ED is prepared:

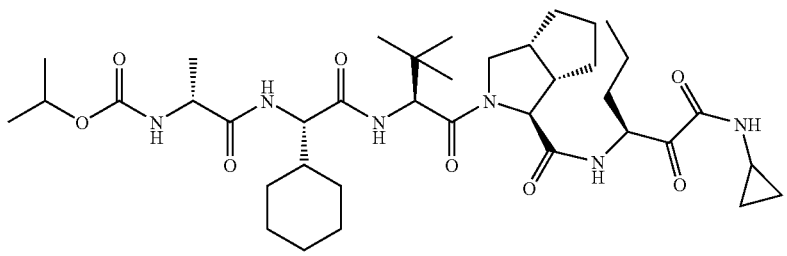

EXAMPLE 40

Compounds EE-EG

Compound ccii (290 mg, 0.37 mmol) is taken up in DCM (5 mL). DMP reagent (175 mg, 0.41 mmol) is added to this solution and stirred 1 hour. The reaction is quenched with P—$Na_2SO_3$ (1.5 mmol/g resin) and stirred 1 hour. Quenched DMP reagent is scavenged with P-TBD (2.5 mmol/g resin) and stirred 1 hour. The resulting mixture is filtered, rinsed with DCM, before being concentrated to a residue. The resulting residue is purified by 50% EtOAc/Hex to yield compound EE (440 mg, 28%).

Following the above method for preparing the above compound and methods related to preparing the intermediate thereto, but using the appropriate starting materials the following compounds EF-EG are prepared:

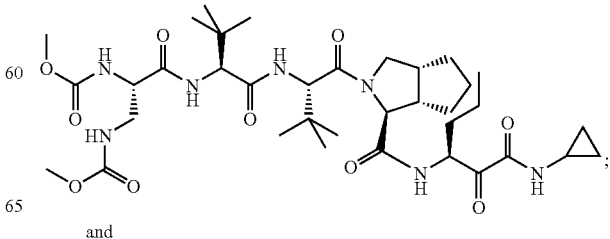

and

-continued

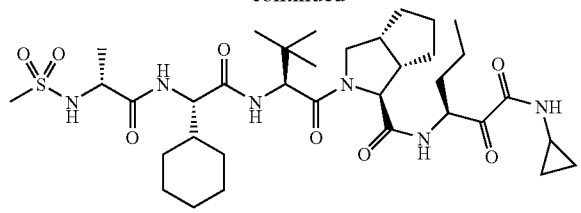

EXAMPLE 41

Compound EH

To a DCM solution (3 mL) of compound cciii (140 mg, 0.2 mmol) is added DMP reagent (133 mg, 0.3 mmol). The reaction is stirred at room temperature for 2 hours and quenched with 10% $Na_2SO_3$ (aq.) for 20 minutes. The resulting mixture is extracted with EtOAc. The organic layer is washed with brine, dried over $MgSO_4$, concentrated to a yellow oil that is purified by silica gel (70% EtOAc/hexane), and after lypholized to yield compound EH (50 mg, 38%).

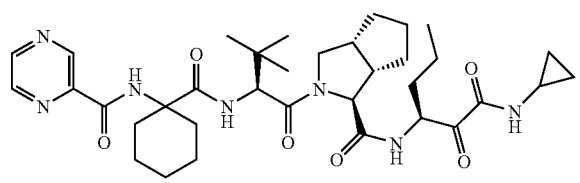

rated $NaHCO_3$, and brine. The organic phase is dried with $MgSO_4$, filtered, and concentrated to give the crude coupled intermediate cdix.

cdix

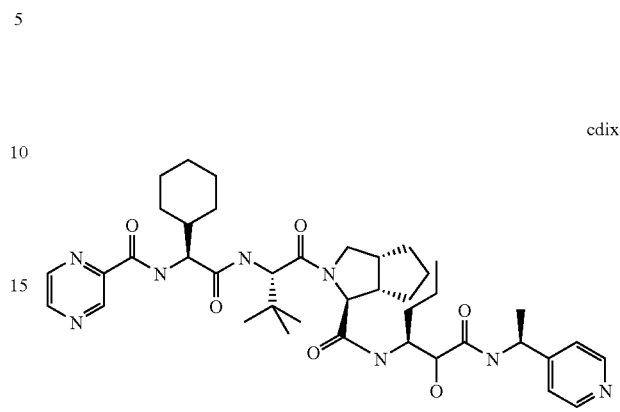

This intermediate cdix (~1 mmol) is taken up in DCM (10 mL). Dess-Martin Periodinane (466 mg, 1.1 mmol) is added to this solution. After stirring for 1 hour at room temperature, the reaction is quenched with a polymer bound $Na_2SO_3$ (740 mg, 1.5 mmol DMP/g resin) and stirred 45 minutes. Then, the reaction mixture is scavenged with polymer bound TBD resin (440 mg, 2.5 mmol DMP/g resin). The resulting mixture is stirred for 45 minutes and then filtered. Purification is achieved in 5% EtOH/EtOAc to yield compound EJ (245 mg, 32% over 2 steps). Literature reference for the work-up procedure can be found in Tetrahedron 55 (1999) 6785-6796.

EJ

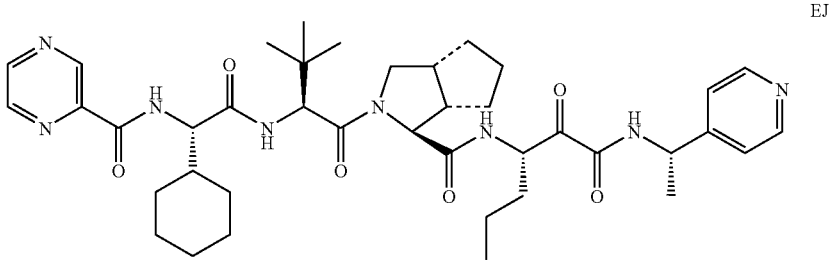

EXAMPLE 42

Compound EJ

Compound ixxxiii (520 mg, 1 mmol) is taken up in DCM (5 mL). PyBOP (624 mg, 1.2 mmol) is added to the above solution and stirred for 5 minutes. Compound cdviii (300 mg, 1.2 mmol) in THF (5 mL) is added drop-wise to this solution, followed by DIPEA (0.22 ml, 1.2 mmol). The reaction is stirred at room temperature overnight under nitrogen. At this point, the reaction is diluted with EtOAc, washed with satu-

EXAMPLE 43

Compound EN

Intermediate compound cdvii (415 mg, 0.59 mmol) is taken up in DCM (10 mL) and THF (10 mL). t-BuOH (300 uL) is added followed by Dess-Martin Periodinane (750 mg, 1.77 mmol). The reaction is stirred 50 minutes and then quenched with P—$Na_2SO_3$ (1.5 mmol DMP/g resin). After stirring for 20 minutes at room temperature, the reaction mixture is scavenged with P-TBD (2.5 mmol DMP/g resin). After stirring for 1 hour, the resulting mixture was filtered and concentrated. Product was purified by silica gel chromatography (50% to 70% EtOAc/Hexanes) to yield compound EN (220 mg, 53%).

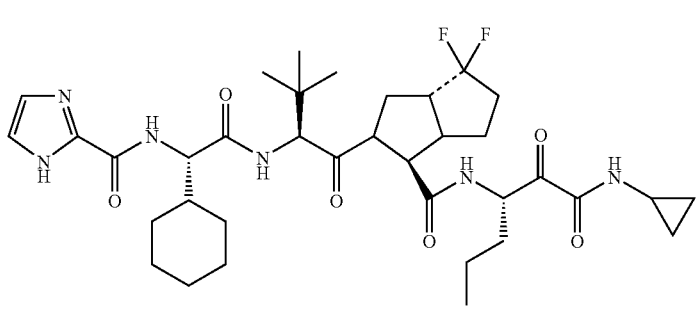

EN

Mass Spectra [M] were obtained for the following compounds as shown in Table 1 below.

TABLE 1

| LY# | Example | Mass Found |
|---|---|---|
|  | A | 733.3 |
|  | B | 747.2 |
|  | C | 657.2 |
|  | D | 769.4 |
|  | E | 733.4 |
|  | F | 625.4 |
|  | G | 639.3 |
|  | H | 661.4 |
|  | I | 643.4 |
|  | J | 707.3 |
|  | K | 641.3 |
|  | L | 689.3 |
|  | M | 639.3 |
|  | N | 639.4 |
|  | O | 731.4 |
|  | P | 687.4 |
|  | Q | 653.4 |
|  | R | 701.4 |
|  | S | 639.3 |
|  | T | 747.1 |
|  | U | 655.4 |
|  | V | 653.4 |
|  | W | 703.4 |
|  | X | 661.3 |
|  | Y | 647.3 |
|  | Z | 663.3 |
|  | AA | 667.4 |
|  | AB | 711.4 |
|  | AC | 725.4 |
|  | AD | 647.3 |
|  | AE | 779.4 |
|  | AF | 689.3 |
|  | AG | 671.4 |
|  | AK | 806.4 |
|  | AH | 687.5 |
|  | AI | 735.4 |
|  | AJ | 736.5 |
|  | AM | 870.4 |
|  | AN | 813.3 |
|  | AP | 724.4 |
|  | AQ | 653.4 |
|  | AR | 628.2 |
|  | AW | 642.2 |
|  | AX | 614.2 |
|  | AY | 628.3 |
|  | BD | 570.3 |
|  | BE | 520.2 |
|  | BF | 534.3 |
|  | BG | 584.3 |
|  | BU | 890.3 |
|  | BV | 685.4 |
|  | BW | 679.3 |
|  | BX | 695.3 |
|  | BY | 697.3 |

TABLE 1-continued

| LY# | Example | Mass Found |
|---|---|---|
|  | BZ | 787.4 |
|  | CA | 701.3 |
|  | CB | 669.4 |
|  | CC | 733.5 |
|  | CD | 643.3 |
|  | CE | 653.5 |
|  | CH | 749.4 |
|  | CI | 653.3 |
|  | CJ | 717.5 |
|  | CK | 683.4 |
|  | CL | 669.3 |
|  | CM | 675.2 |
|  | CN | 717.2 |
|  | CO | 653.3 |
|  | CP | 683.3 |
|  | CQ | 669.3 |
|  | CR | 675.2 |
|  | CT | 661.8 |
|  | CS | 639.3 |
|  | CU | 679.2 |
|  | CV | 709.3 |
|  | CW | 743.3 |
|  | CX | 695.3 |
|  | CY | 665.2 |
|  | CZ | 681.3 |
|  | DA | 695.3 |
|  | DB | 701.2 |
|  | DC | 673.3 |
|  | DD | 693.3 |
|  | DE | 757.4 |
|  | DF | 682.3 |
|  | DG | 676.3 |
|  | DH | 676.2 |
|  | DI | 692.5 |
|  | DJ | 605.2 |
|  | DK | 874.4 |
|  | DL | 924.5 |
|  | DM | 924.2 |
|  | DN | 952.7 |
|  | DO | 830 |
|  | DP | 842.5 |
|  | DT | 667.4 |
|  | DU | 639.2 |
|  | DV | 740.3 |
|  | DW | 684.2 |
|  | DX | 678.5 |
|  | DY | 749.3 |
|  | DZ | 685.3 |
|  | EA | 649.3 |
|  | EB | 700.3 |
|  | EC | 702.3 |
|  | ED | 730.3 |
|  | EE | 775.3 |
|  | EF | 749.3 |
|  | EG | 722.3 |
|  | EH | 665.2 |
|  | EI | 796.4 |

TABLE 1-continued

| LY# | Example | Mass Found |
|---|---|---|
|  | EJ | 744.3 |
|  | EK | 730.5 |
|  | EL | 730.5 |
|  | EM | 757.3 |
|  | EN | 703.5 |
|  | EO | 715.5 |
|  | EP | 679.2 |
|  | EQ | 651.3 |
|  | ER | 715.3 |
|  | ES | 668.5 |
|  | ET | 732.5 |
|  | EU | 743.3 |
|  | EV | 683.3 |
|  | EW | 750.4 |
|  | EX | 786.4 |
|  | EY | 744.5 |
|  | EZ | 780.4 |
|  | FB | 693.4 |
|  | FC | 655.3 |
|  | FD | 655.3 |
|  | FE | 774.4 |
|  | FF | 681.5 |
|  | FG | 667.5 |

High Resolution Mass Spectra (HRMS) of the following compounds were obtained as shown in Table 2.

TABLE 2

| Example | Molecular Formula (M + 1) | Calculated MS (M + 1) | Mass Found (M + 1) |
|---|---|---|---|
| L | C37H52N7O6 | 690.3979 | 690.3986 |
| M | C33H50N7O6 | 640.3822 | 640.3822 |
| Z | C32H48F2N7O6 | 664.3634 | 664.3627 |
| AB | C36H48F2N7O6 | 712.3634 | 712.3649 |
| CE | C34H52N7O6 | 654.3979 | 654.3967 |
| EN | C35H52N7O6F2 | 704.3947 | 704.3945 |
| EK | C37H63N6O8S | 751.4428 | 750.4350 (M) |
| EC | C36H59N6O8 | 703.4395 | 703.4382 |
| CA | C35H50N7O6F2 | 702.3790 | 702.3801 |
| EZ | C40H55N8O6F2 | 781.4213 | 781.4196 |
| EU | C36H52N7O6F2 | 716.3947 | 716.3929 |
| CY | C35H52N7O6 | 666.3979 | 666.3966 |
| BX | C37H58N7O6 | 696.4448 | 696.4432 |
| S | C33H50N7O6 | 640.3823 | 640.3831 |
| BW | C36H54N7O6 | 680.4136 | 680.4126 |
| CU | C36H54N7O6 | 680.4136 | 680.4128 |
| EJ | C40H57N8O6 | 745.4401 | 745.4417 |
| EM | C35H54N7O6 | 668.4136 | 668.4139 |
| None | C41H58N7O6 | 744.4448 | 744.4691 |

INTERMEDIATE EXAMPLE 1

Compound ii

To an ethanol solution (40 mL) of compound i (8.1 g, 24.4 mmol) is added NaBH4

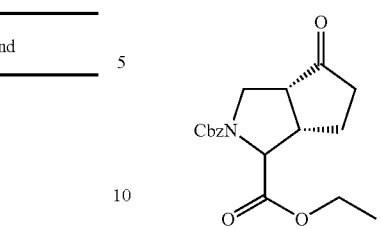

i (924 mg, 24.4 mmol) at –10° C. The reaction is stirred at that temperature for 30 minutes, and then quenched with AcOH (3 mL). The reaction mixture is diluted with EtOAc (250 mL), and washed with NaHCO3 and brine. The organic layer is dried and concentrated in vacuo to yield a residue that is purified by silica gel chromatography (50% EtOAc/Hexanes) to provide 7.85 g (97%) of compound ii,

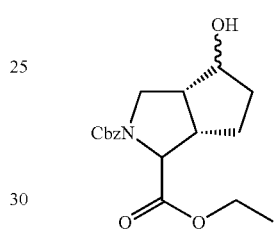

ii

INTERMEDIATE EXAMPLE 2

Compound iii

To a THF solution (70 mL) of compound ii (4.48 g, 13.4 mmol) is added at 0° C. of NaH (699 mg, 60%, 17.42 mmol). After stirring at that temperature for 40 minutes, neat MeI (1.25 mL, 20.1 mmol) is added. The reaction is stirred at about room temperature overnight. At this point, the reaction is quenched carefully with saturated solution of NH4Cl at 0° C. The reaction mixture is extracted with Et2O and EtOAc. The organic layer is washed with water, brine and dried with Na2SO4. The organic layer thus obtained is concentrated in vacuo to provide the xanthate compound iii,

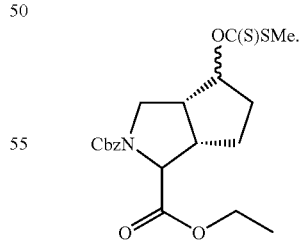

iii

INTERMEDIATE EXAMPLE 3

Compound iv

The xanthate compound iii (~13.4 mmol) is dissolved in toluene (100 mL). To this solution is added AIBN (216 mg, 1.34 mmol). The resulting solution is degassed with dry nitrogen and then treated with n-Bu₃SnH (5.4 mL, 20.1 mmol). The reaction mixture is heated at 90° C. for 3 hours. At this point, the reaction is cooled to room temperature and concentrated in vacuo. The resulting residue is purified with silica gel chromatography (15-20% EtOAc/Hexanes) to provide 2.8 g (66% overall from compound ii) of compound iv,

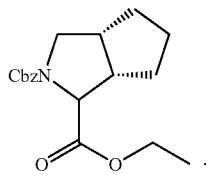

iv

INTERMEDIATE EXAMPLE 4
Compound v

To an ethanol solution (21 mL) of compound iv (1 g, 3.15 mmol) is added Pd(OH)₂/C (655 mg, 20%, 0.95 mmol) under a stream of nitrogen. The resulting reaction mixture is subjected to standard hydrogenation (1.5 atm). After 5 hours, the hydrogen source is removed and the reaction is filtered. The filtrates are concentrated in vacuo to provide the free amine compound v,

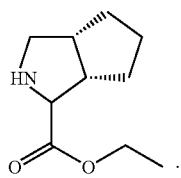

v

INTERMEDIATE EXAMPLE 5
Compound vi

To a DCM solution (10 mL) of compound vii (629 mg, 1.95 mmol) is added at about

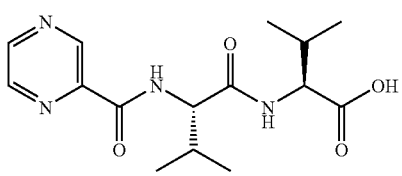

vii room temperature HOAt (265 mg, 1.95 mmol) and followed by 1 M DCC solution in DCM (1.95 mL, 1.95 mmol). After stirring for 30 minutes, a DCM solution (3 mL) of compound v (1.5 mmol) is added to the above HOAt-activated acid. The reaction is stirred at about room temperature overnight. At this point, the reaction is filtered through Celite. The filtrates are diluted with EtOAc (75 mL) and washed with water and brine. The organic layer is dried and concentrated in vacuo. The resulting residue is purified by silica gel chromatography (70-80% EtOAc/Hexanes) to afford 620 mg (85%) of compound vi,

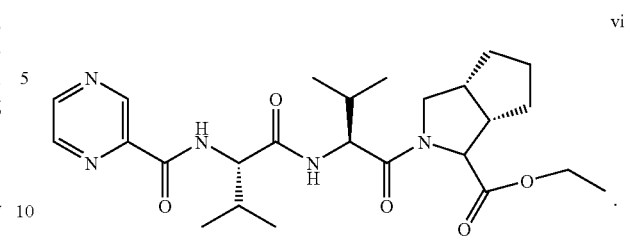

vi

INTERMEDIATE EXAMPLE 6
Compound viii

To an ethanol solution (10 mL) of compound vi (615 mg, 1.26 mmol) is added 2 N NaOH aqueous solution (1.26 mL, 2.52 mmol). The reaction is stirred overnight at about room temperature and then acidified to pH 3 using Dowex acidic resins. The solids are filtered off and the filtrates are concentrated in vacuo to give a residue that is redissolved in 1:1 CH₃CN/H₂O. This solution is subjected to lyophilization to provide 495 mg (85%) of compound viii,

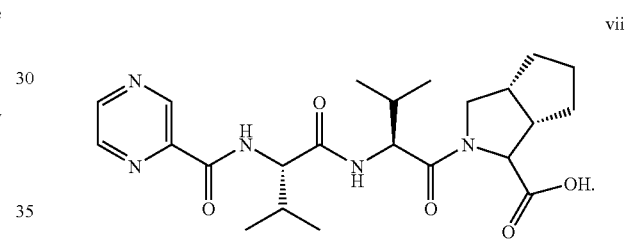

vii

INTERMEDIATE EXAMPLE 7
Compound ix

To a DCM solution (10 mL) of compound viii (230 mg, 0.5 mmol) is added PyBop (417 mg, 0.8 mmol). The reaction is stirred at about room temperature for 30 minutes. To this solution is then added a THF solution (5.25 mL) of compound x (263 mg, 0.75 mmol) and followed by

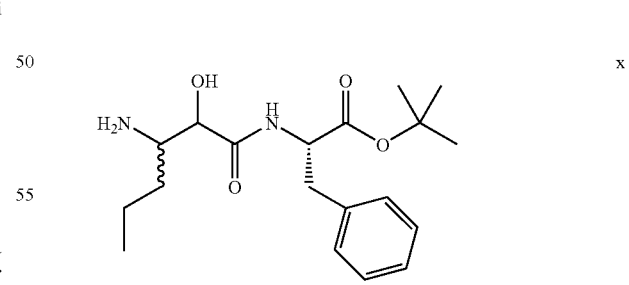

x

DIPEA (0.174 mL, 1 mmol). The reaction is stirred at about room temperature overnight and then quenched with water (30 mL) for 30 minutes. The reaction mixture is extracted with EtOAc (100 mL). The organic layer is washed with brine and dried and concentrated in vacuo to afford a residue that is purified via silica gel chromatography (5% EtOH/EtOAc) to give ~400 mg (100%) of compound ix, ix

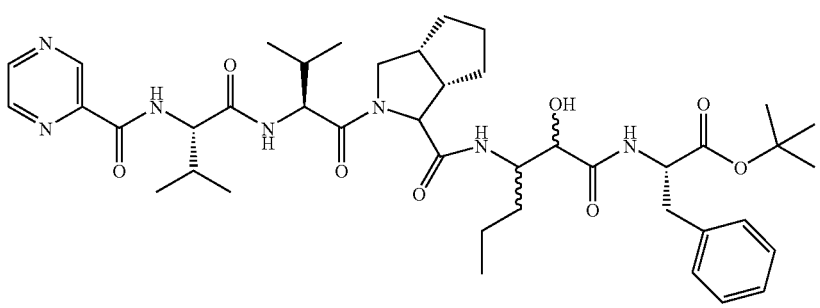

INTERMEDIATE EXAMPLE 8

Compound xi

To a DCM solution (10 mL) of compound ix (396 mg, 0.5 mmol) is added DMP reagent reagent (278 mg, 0.65 mmol). The reaction is stirred at about room temperature for 1 hour and then quenched with 10% $Na_2SO_3$ for 30 minutes. The reaction mixture is then extracted with EtOAc (75 mL) and washed with brine. The organic layer is dried and concentrated in vacuo. The resulting residue is purified with silica gel chromatography (70% EtOAc/Hexanes) to give 320 mg (81%) of compound xi, xiii

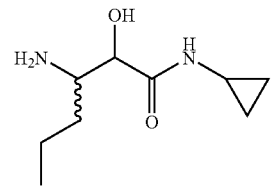

xi

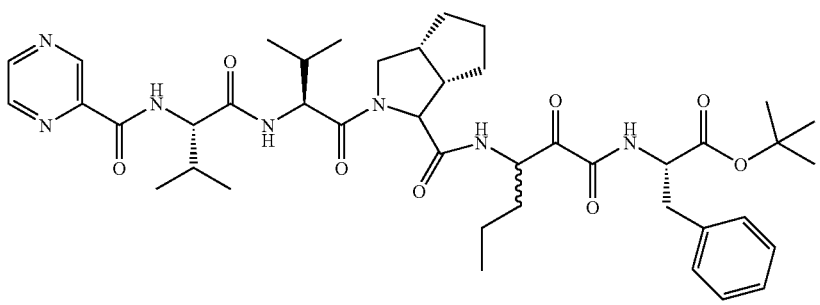

INTERMEDIATE EXAMPLE 9

Compound xii

To a DCM solution (10 mL) of compound viii (230 mg, 0.5 mmol) is added PyBop (417 mg, 0.8 mmol). The reaction is stirred at about room temperature for 30 minutes. To this solution is then added a THF solution (3.5 mL) of compound xiii (140 mg, 0.75 mmol) and followed by DIPEA (0.174 mL, 1 mmol). The reaction is stirred at about room temperature overnight and then quenched with water (30 mL) for 30 minutes. The reaction mixture is extracted with EtOAc (75 mL). The organic layer is washed with brine and dried and concentrated in vacuo to afford a residue that is purified via silica gel chromatography (5% EtOH/EtOAc) to give in quantitative yield compound xii, xii

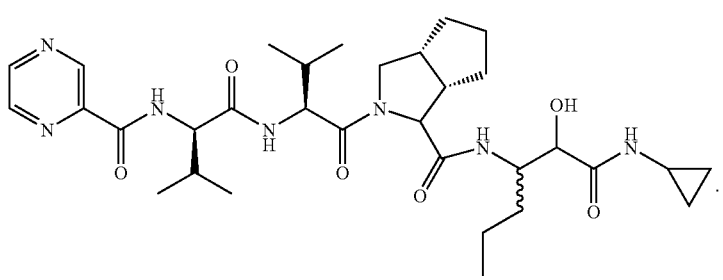

INTERMEDIATE EXAMPLE 10

Compound i'

To a methanol solution (30 mL) of compound i (5 g, 15.1 mmol) is added (BOC)₂O (3.3 g, 15.1 mmol) and H₂/Pd(OH)₂/C (1.6 g, 10% Pd content). The reaction is stirred at about room temperature for 2 hours and then filtered through Celite twice. The Celite bed is rinsed with DCM. The combined filtrates are concentrated in vacuo to yield an oily residue that is purified by silica gel chromatography (40% EtOAc/Hexanes) to give 3.8 g (85%) of compound i',

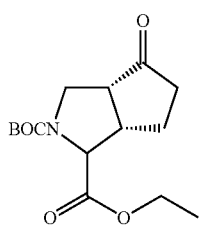

i'

INTERMEDIATE EXAMPLE 11

Compound ii'

To a methanol solution (111 mL) of compound i' (3.7 g, 12.5 mmol) is added at 0° C. NaBH₄ (0.805 g, 21 mmol). After stirring at 0° C. for 2.5 hours, the reaction solvent is evaporated slowly in vacuo to yield a residue that is diluted with EtOAc. This solution is then washed with water twice. The aqueous layer is extracted with EtOAc. The combined organic layers are dried with MgSO₄ and filtered and concentrated in vacuo to yield a residue that is purified with chromatography to provide 3.76 g (99%) of compound ii',

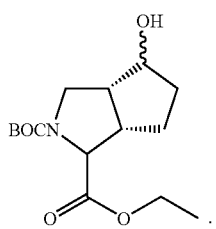

ii'

INTERMEDIATE EXAMPLE 12

Compound xiv

To a DCM solution (180 mL) of compound ii' (3.76 g, 12.3 mmol) is added at 0° C. DMAP (5 g, 40.1 mmol) and then followed by Tf₂O (4 mL, 23.7 mmol). The reaction is stirred at 0° C. for 1 hour and at about room temperature for additional 1.5 hours. The reaction mixture is then washed twice with 5% NaHCO₃ and dried with MgSO₄. The organic layer thus obtained is concentrated in vacuo to provide the crude triflate. The resulting triflate (2.7 g, 6 mmol) is dissolved in DCM (120 mL). To this solution is added DMAP (2.5 g, 20.5 mmol). The resulting reaction mixture is heated to reflux overnight At this point, the reaction is cooled to room temperature and washed with 5% NaHCO₃ twice. The reaction mixture is dried with MgSO₄ filtered and concentrated in vacuo to yield a brownish oily residue that is purified (1% MeOH/DCM) to give 500 mg (30%) of compound xiv,

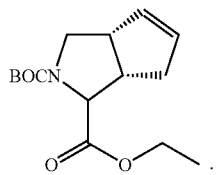

xiv

INTERMEDIATE EXAMPLE 13

Compound xv

Compound xiv (500 mg, 1.8 mmol) is dissolved in 4 N HCl in dioxane (6.75 mL). The reaction is stirred at about room temperature for ~4 hours. At this point, the solvent is removed in vacuo. The resulting residue is titrated with diethylether twice to give in almost quantitative yield the HCl salt of compound xv,

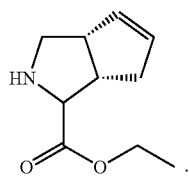

xv

INTERMEDIATE EXAMPLE 14

Compound xvi

To a THF solution (7 mL) of compound vii (579 mg, 1.8 mmol) is added HOAt (245 mg, 1.8 mmol) and DCC (1.8 mL, 1 M in DCM). A suspension is resulted. After stirring at about room temperature for 15 minutes, a THF solution (6 mL) of compound xv (1.8 mmol) and DIPEA (0.63 mL, 3.6 mmol) is added to the above suspension. Additional DIPEA (0.8 mL) is added later. The reaction mixture is stirred overnight at about room temperature. At that point, the white solids so formed are filtered off. The white solids are rinsed with THF. The combined filtrates and washings are concentrated in vacuo to give the crude product that is purified by silica gel chromatography (100% EtOAc) to provide 665 mg (76%) of compound xvi,

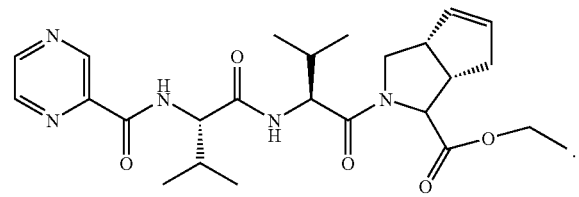

XVI

INTERMEDIATE EXAMPLE 15

Compound xvii

To an ethanol solution (8 mL) of 7 (665 mg, 1.37 mmol) is added 1 N aqueous NaOH (2.4 mmol) at 0° C. The reaction-is stirred overnight at about room temperature, and then acidified to pH 3 using Dowex acidic resins. The solids are filtered. The resulting filtrates are concentrated in vacuo to give a pale yellow residue that is redissolved in 1:1 $CH_3CN/H_2O$ and lyophilized to give 467 mg (74%) of compound xvii,

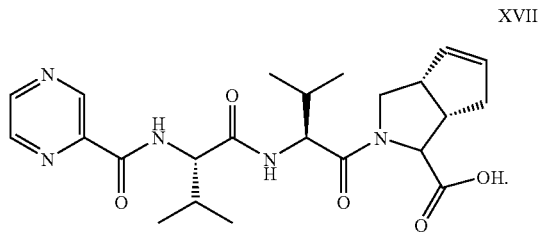

XVII

INTERMEDIATE EXAMPLE 16

Compound xix

A DCM solution (4 mL) of compound xvii (100 mg, 0.22 mmol) is treated with PyBop (207 mg, 0.4 mmol) at about room temperature for 20 minutes. At this point, the above solution is treated with a THF solution (2.6 mL) of compound xviii (65 mg, 0.32 mmol), followed by DIPEA

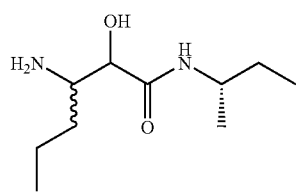

XVIII (0.076 mL). After stirring at about room temperature for 7 hours, the reaction is quenched with water. The reaction mixture is diluted with DCM (60 mL). The organic layer is separated and washed twice with brine and dried with $MgSO_4$. Upon filtration, concentrated and silica gel chromatography (5% EtOH/EtOAc), 148 mg (~100%) of compound xix is obtained.

INTERMEDIATE EXAMPLE 17

Compound xx

To a THF solution (100 mL) of N-Cbz-L-valine (14.4 g, 57.2 mmol) is added HOBT (7.72 g, 57.2 mmol) and EDCI (10.98 g, 57.2 mmol). After stirring at about room temperature for 20 minutes, a THF solution (50 mL) containing tert-L-Leucine methyl ester-hydrochloride (10.4 g, 57.2 mmol) and DIPEA (11.9 mL, 68.7 mmol) is added to the above solution. The reaction is stirring at about room temperature overnight. Upon standard aqueous work-up and silica gel chromatography (30% EtOAc/Hexanes) 14 g (64%) of compound xx is afforded.

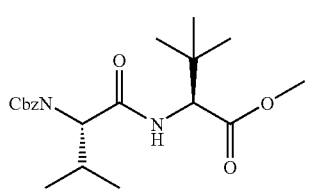

xx

INTERMEDIATE EXAMPLE 18

Compound xxi

To a methanol solution (80 mL) of xx (6.71 g, 17.7 mmol) is added (under a stream of $N_2$) Pd/C (1.88 g, 10% Pd content). The reaction vessel is subjected to hydrogenation (1 atm $H_2$) overnight at about room temperature. At this point, the reaction mixture is filtered through a pad of Celite and concentrated in vacuo to provide the corresponding crude free amine for next step. A THF solution of the amine (~17.7 mmol) is added to a THF (46 mL) and DMF (5 mL) solution containing 2-pyrazinecarboxylic acid (2.85 g, 23 mmol), Hobbit (3.12 g, 23 mmol) and EDCI (4.41 g, 23 mmol). To the resulting mixture is then added DIPEA (3.08 g, 17.7 mmol). The reaction is stirred overnight at about room temperature and then quenched with water. The reaction mixture is extracted with EtOAc. The organic layer is washed with brine and concentrated in vacuo to provide a residue that is purified by silica gel chromatography (40-50% EtOAc/Hexanes) to provide 3.9 g (63%) of compound xxi,

XIX

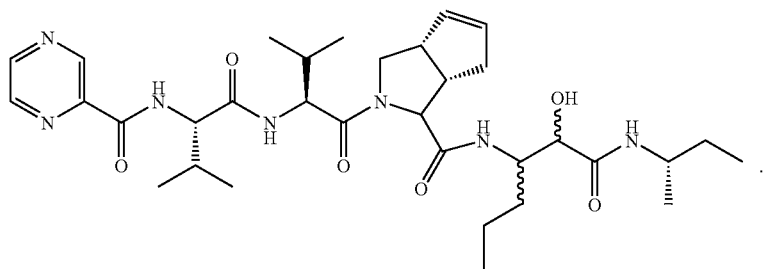

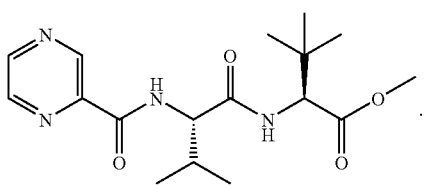

INTERMEDIATE EXAMPLE 19

Compound xxii

To a methanol solution (40 mL) of compound xxi (4.67 g, 13.34 mmol) is added 2 N NaOH (10 mL, 20 mmol). The reaction is stirred at about room temperature for 2 hours. At this time, an additional amount of 2 N NaOH (3.3 mL, 6.67 mmol) is added to the reaction mixture. After stirring at about room temperature overnight, the reaction is acidified to pH 3 using acidic resin. The reaction is then filtered and the filtrates are concentrated in vacuo to yield a residue that is dissolved in 1:1 $CH_3CN/H_2O$ for lyophilization. 4.15 g (93%) of compound xxii is obtained.

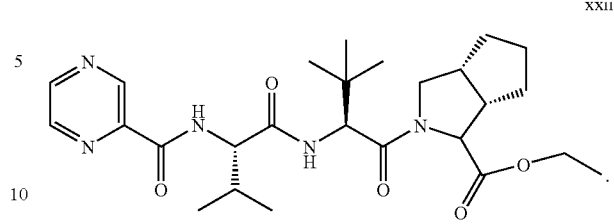

INTERMEDIATE EXAMPLE 21

Compound xxiv

An ethanol solution (20 mL) of compound xxiii (1.06 g, 2.11 mmol) is treated with 2 N NaOH (2.11 mL, 4.23 mmol). After stirring at about room temperature overnight, the reaction mixture is acidified to pH 3 with acidic resin. The solids are filtered off. The resulting filtrates are concentrated in vacuo to give a residue that is lyophilized to give ~1 g (100%) of compound xxiv,

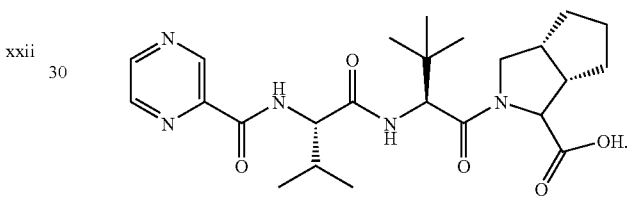

INTERMEDIATE EXAMPLE 20

Compound xxiii

A DCM solution (10 mL) of compound xxii (917 mg, 2.73 mmol) is treated with HOAt (371 mg, 2.73 mmol) and DCC (2.73 mL, 1 M, 2.73 mmol). After stirring for 30 minutes, the reaction mixture is treated with a THF solution (10 mL) of compound v (500 mg, 2.73 mmol). After stirring at about room temperature overnight, the white solids (urea) are filtered. The filtrates are concentrated in vacuo to give a residue that is purified by silica gel chromatography (60-70% EtOAc/Hexanes) to provide 1.06 g (77%) of compound xxiii,

INTERMEDIATE EXAMPLE 22

Compound xxv

A DCM solution (10 mL) of compound xxiv (236.7 mg, 0.5 mmol) is treated with PyBop (417 mg, 0.8 mmol). After stirring at about room temperature for 20 minutes, the reaction mixture is treated with a DMF solution (5.6 mL) of compound xiii (139.5 mg, 0.75 mmol), followed by DIPEA (0.174 mL, 1 mmol). After stirring at about room temperature for 8 hours, the reaction is quenched with water and extracted with EtOAc. The resulting organic layer is washed with brine and dried and concentrated in vacuo to give a residue that is purified by silica gel chromatography (5% EtOH/EtOAc) to afford ~320 mg (100%) of compound xxv,

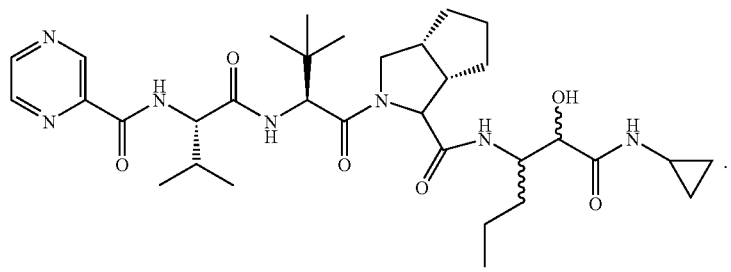

INTERMEDIATE EXAMPLE 23

Compound xxvi

A DCM solution (15 mL) of compound xxiv (355 mg, 0.75 mmol) is treated with PyBop (622 mg, 1.2 mmol). After stirring at about room temperature for 20 minutes, the reaction mixture is treated with a THF solution (10 mL) of compound xxvii' (156 mg, 0.75

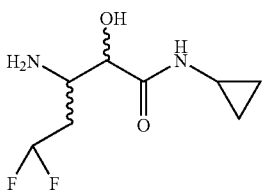

xxvii' mmol), followed by DIPEA (0.26 mL, 1.5 mmol). After stirring at about room temperature overnight, the reaction is quenched with water and extracted with EtOAc. The resulting organic layer is washed with brine and dried and concentrated in vacuo to give a residue that is purified by silica gel chromatography (2% EtOH/EtOAc) to afford ~400 mg (80%) of compound xxvi, The product is extracted from the aqueous solution with EtOAc (3×50 mL). The organic is combined, dried and concentrated to yield 4.25 g (68%) of methyl 5-tetrazol-5-ylpentanoate.

INTERMEDIATE EXAMPLE 26

Methyl 5-[N-(1,1-dimethylbenzyl)tetrazol-5-yl]pentanoate

Methyl 5-tetrazol-5-ylpentanoate (4.23 g, 23 mmol) and trichloroacetic acid (8.69 g, 53 mmol) are dissolved in 50 mL of $CHCl_3$. α-Methylstyrene (2.72, 23 mmol) is added to the solution dropwise, and the reaction mixture is allowed to stirred at about room temperature fore overnight. The reaction mixture is diluted with EtOAc to 200 mL, and organic layer is washed with 10% aqueous KOH and brine. The organic layer is dried, concentrated. The product is purified by flash column chromatography to yield 6.6 g (95%) methyl 5-[N-(1,1-dimethylbenzyl)tetrazol-5-yl]pentanoate.

INTERMEDIATE EXAMPLE 27

5-[N-(1,1-dimethylbenzyl)tetrazol-5-yl]pentanoic acid

Methyl 5-[N-(1,1-dimethylbenzyl)tetrazol-5-yl]pentanoate (6.6 g, 21.8 mmol) is dissolved in methanol (100 mL)

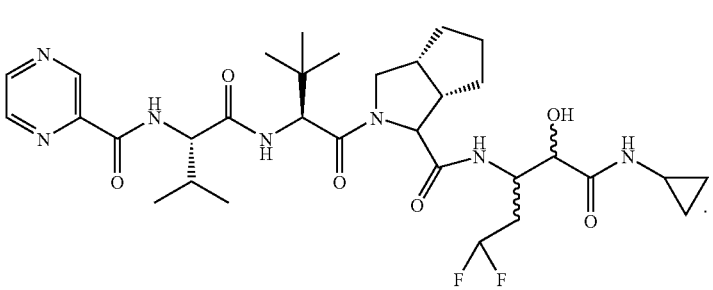

xxvi

INTERMEDIATE EXAMPLE 24

Methyl 5-cyanopentanoate

Potassium Cyanide (4 g, 61.44 mmol) is dissolved in 70 mL water and 200 mL methanol. To the solution 10 g (51.2 mmol) of methyl 5-bromopentanoate is added and the mixture is refluxed overnight. The reaction mixture is concentrated to dryness. To the residue, 100 mL of EtOAc is added to extract the product. The organic is washed with water three times, dried and concentrated to yield 5.37 g (74%) of methyl 5-cyanopentanoate as an oil.

INTERMEDIATE EXAMPLE 25

Methyl 5-tetrazol-5-ylpentanoate

Methyl 5-cyanopentanoate (4.8 g, 34 mmol) is dissolved in toluene, triethylammonium chloride (14 g, 102 mmol) and sodium azide (6.63, 102 mmol) is added. The mixture is heated to reflux for overnight. The reaction mixture is cooled to room temperature, water is added to extract (3×100 mL) methyl 5-tetrazol-5-ylpentanoate from the organic. To the aqueous phase, concentrate HCl is added to adjust pH to 2.

and 23 mL of 1 N aqueous NaOH is added. The mixture is stirred overnight and is concentrated to remove methanol. The residue is dissolved in water (100 mL) and the solution is neutralized by adding the same equivalent of 1 N aqueous HCl. The product is extracted with EtOAc (3×50 mL). The organic is dried and concentrated to yield 4.75 g (75%) 5-[N (1,1 dimethylbenzyl)tetrazol-5-yl]pentanoic acid.

INTERMEDIATE EXAMPLE 28

Compound xxviii

5-[N-(1,1-dimethylbenzyl)tetrazol-5-yl]pentanoic acid (4.75 g, 16.5 mmol) is dissolved in DCM (100 mL), 4.8 g (24.8 mmol) of EDCI and 6 mL of DIPEA are added. To the mixture, N-hydroxylsuccinimide (3.8 g, 33 mmol) is added. The reaction mixture is stirred for three hours at about room temperature. The mixture is diluted with DCM to 200 mL and the solution is washed with water three times. The organic is dried and concentrated to yield 4.79 g (75%) of compound xxviii,

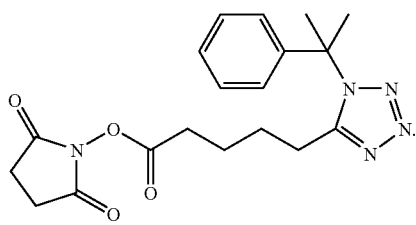

xxviii

INTERMEDIATE EXAMPLE 29

Compound xxix

The dipeptide H-Val-Val-OH (3.22 g, 14.9 mmol) is suspended in 50 mL of N,N-dimethylformamide (DMF) and 4.75 g (12.42 mmol) of compound xxviii is added followed the addition of 3.4 mL (18.63 mmol) of diisopropylethylamine (DIPEA). The mixture is warmed up to 40° C. and stirred overnight. The solvent is evaporated under high vacuum. The residue is dissolved in EtOAc and washed with 1 N HCl and brine to yield 5.52 g (91%) of compound xxix,

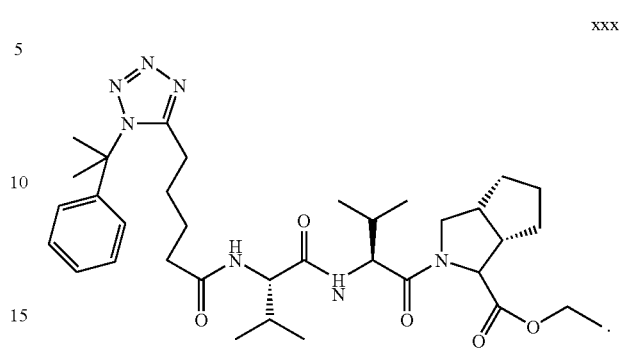

xxx

INTERMEDIATE EXAMPLE 31

Compound xxxi

Compound xxx (1.02 g, 1.57 mmol) is dissolved in 10 mL MeOH and 2 mL of 1 N aqueous NaOH is added. The mixture is stirred overnight The methanol is removed by evaporation and the residue is dissolved in water and neutralized with 2 mL HCl. Following extraction with EtOAc, 1.00 g (~100%) of compound xxxi is afforded.

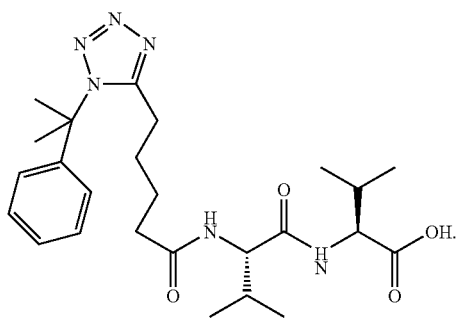

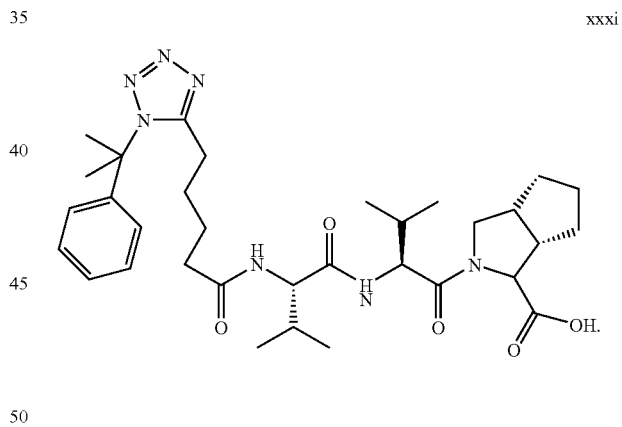

xxxi

INTERMEDIATE EXAMPLE 30

Compound xxx 1.6 g (3.29 mmol) of compound xxix is dissolved in 20 mL of DCM, 3.3 mL of 1 M solution of DCC in THF is added. To the mixture, 500 mg (2.73 mmol) of compound v is added. The mixture is stirred at about room temperature overnight. The mixture is diluted with EtOAc to 100 mL and washed with 1 N HCl, NaHCO₃ and brine. Purified by column chromatography (50% EtOAc/hexane) to yield 1.02 g (58%) compound xxx,

INTERMEDIATE EXAMPLE 32

Compound xxxii

Compound xxxi (300 mg, 0.48 mmol) and PyBop (300 mg, 0.58 mmol) are dissolved in 10 mL DCM. To the solution, compound x (201 mg, 0.58 mmol) is added and then DIPEA (104 µl) is added. The mixture is stirred at about room temperature overnight. The reaction mixture is then diluted with EtOAc to 100 mL and washed twice with 1 N HCl, twice with NaHCO₃ and thrice with brine. The organic is dried and concentrated. The residue is purified by column chromatography (100% EtOAc) to yield 450 mg (98%) of compound xxxii,

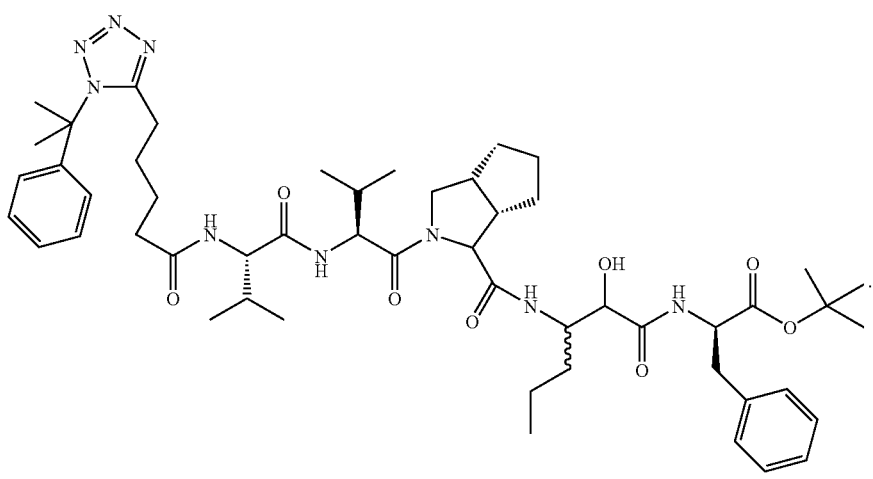

xxxii

INTERMEDIATE EXAMPLE 33
Compound xxxiii

Compound xxxii 360 mg (0.38 mmol) is dissolved in 8 mL DCM and 240 mg (0.57 mmol) of DMP reagent reagent is added. The mixture is stirred at about room temperature for three hours. The mixture is diluted with EtOAc to 50 mL and washed with brine three times. The product is purified by column chromatography (25% ethanol/EtOAc) to yield 300 mg (83%) of compound xxxiii, mL) of (s)-α-(4-pyridyl)ethylamine (410 mg, 3.36 mmol). This is followed by the addition of DIPEA (0.5 mL, 3.36 mmol). The reaction is stirred overnight at about room temperature. At this point, the reaction mixture is diluted with EtOAc. The whole is washed with saturated NaHCO₃ and brine. The organic layer thus obtained is dried and concentrated in vacuo. The resulting residue is purified by silica gel chromatography (5% EtOH/EtOAc) to provide 630 mg (58%) of compound xxxiv, xxxiii

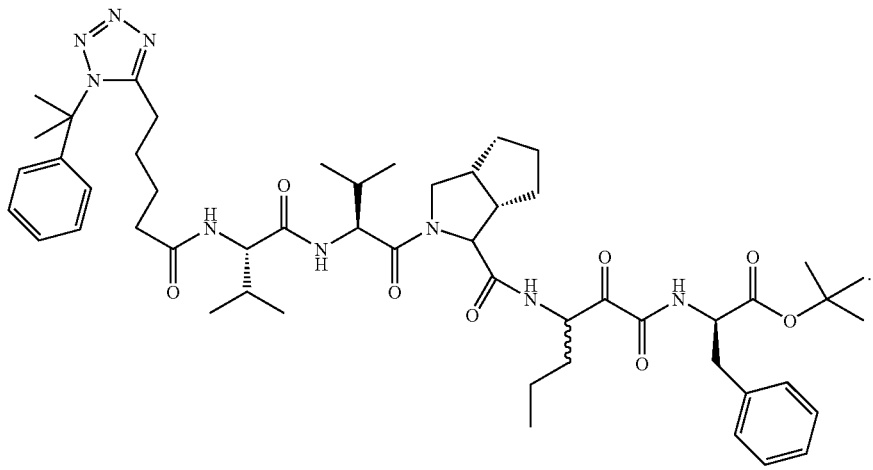

INTERMEDIATE EXAMPLE 34
Compound xxxiv xxxiv

To a DCM solution (10 mL) of xxxv (790 mg, 2.80 mmol) is added PyBop (1.7 g, xxxv

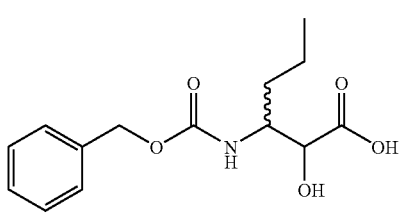

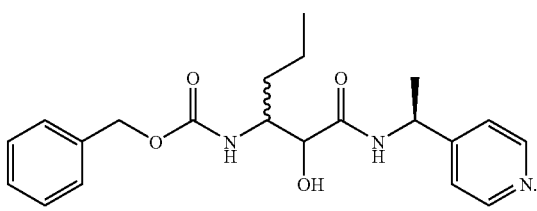

3.36 mmol) and Hobbit (450 mg, 3.36 mmol). The resulting solution is cooled to 0° C. and treated with a DCM solution (3

Note: (s)-α-(4-pyridyl)ethylamine is obtained from its D-tartrate salt by base wash (1 N NaOH) and subsequent EtOAc extraction. The recovery rate is 89%.

INTERMEDIATE EXAMPLE 35

Compound xxxvi

To a methanol solution (15 mL) of compound xxxiv (630 mg, 1.64 mmol) is added under $N_2$ Pd/C (150 mg, 10% palladium content). The reaction is stirred under $H_2$ overnight. The reaction mixture is filtered through a pad of Celite® 521. The filtrates are concentrated in vacuo to provide 420 mg (~100%) of compound xxxvi,

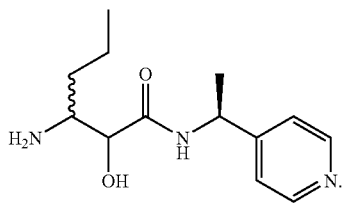

xxxvi

INTERMEDIATE EXAMPLE 36

Compound xxxvii

To a DCM solution (3 mL) of compound xxxi (270 mg, 0.43 mmol) is added PyBop (270 mg, 0.52 mmol). This is followed by addition of compound xxxvi (160 mg, 0.64 mmol) and DIPEA (0.09 mL, 0.52 mmol). The reaction is stirred at about room temperature overnight. At this point, the reaction is diluted with EtOAc and washed with 0.1N HCl, followed by saturated $NaHCO_3$ and brine. The resulting organic layer is dried and concentrated to give compound xxxvii (430 mg total mass) for next step xxxvii

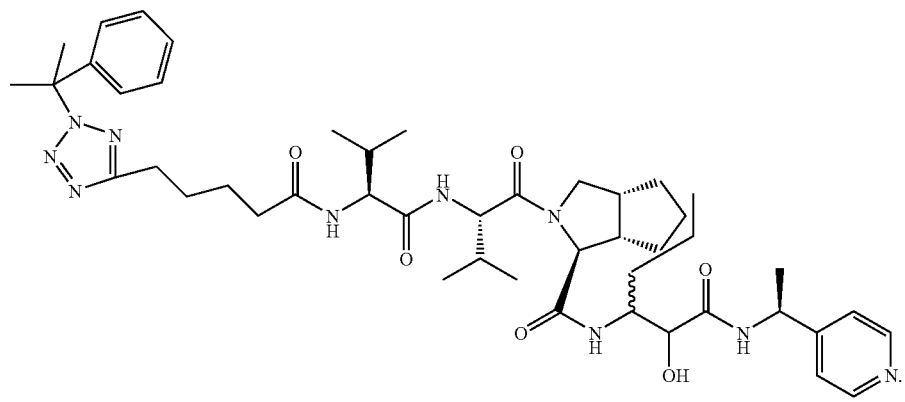

INTERMEDIATE EXAMPLE 37

Compound xxxviii

To a DCM solution (3 mL) of compound xxxvii (370 mg, 0.43 mmol) is added DMP reagent reagent (280 mg, 0.65 mmol). The reaction is stirred at about room temperature for 2 hours and then quenched with 10% $Na_2SO_3$. After stirring for 30 minutes, the reaction is extracted with EtOAc. The organic layer is washed with saturated $NaHCO_3$ and brine. The resulting organic layer is dried and concentrated in vacuo to give a residue that is purified by silica gel chromatography (5% EtOH/EtOAc) to provide 180 mg (49% for 2-steps) of compound xxxviii, xxxviii

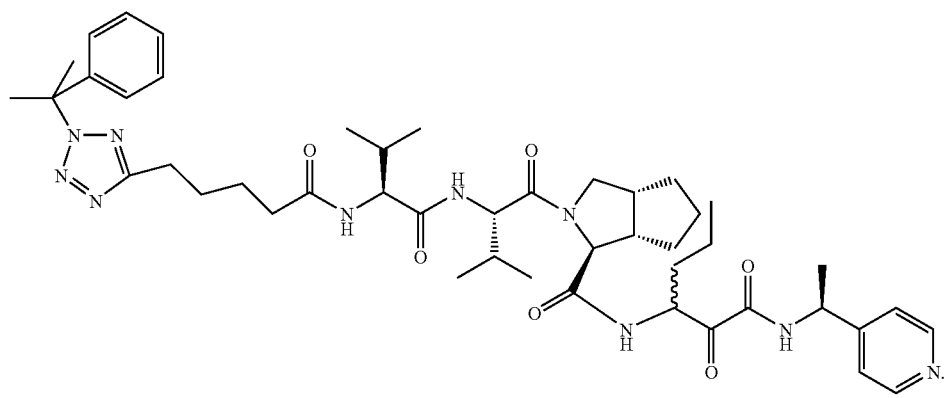

INTERMEDIATE EXAMPLE 38

Compound xxxx

Compound xxix (2.5 g, 5 mmol) is dissolved in 40 mL of DCM, 5.1 mL of 1 M solution of DCC in THF is added to the solution. To the mixture, 1.08 g (3.53 mmol) of compound xxxix is added. The mixture is stirred at about room temperature overnight.

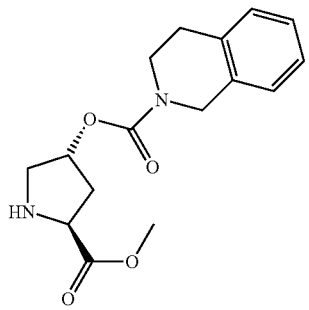

xxxix

The mixture is diluted with EtOAc to 100 mL, washed sequentially with 1 N HCl, NaHCO$_3$ and brine, and then purified by column chromatography (80% EtOAc/hexane) to yield 2.59 g (95%) of compound xxxx,

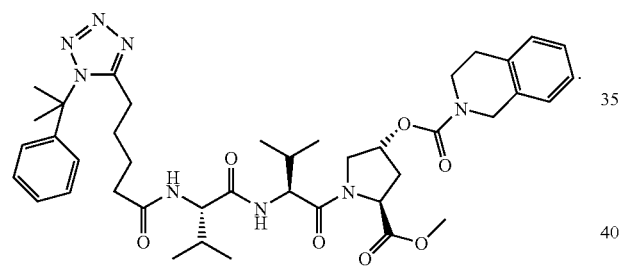

xxxx

INTERMEDIATE EXAMPLE 39

Compound xxxxi

Compound xxxx (2.59 g, 3.35 mmol) is dissolved in 20 mL MeOH and 4 mL of 1 N aqueous NaOH is added. The mixture is stirred overnight and then rotary evaporated to leave a residue. The residue is dissolved in water and neutralized with 2 mL HCl. The neutralized solution is then extracted with EtOAc to yield 2.49 g (~100%) of compound xxxxi,

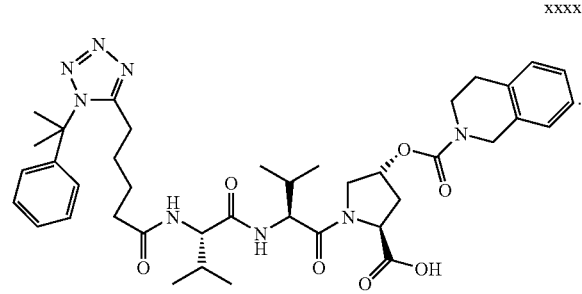

xxxxi

INTERMEDIATE EXAMPLE 40

Compound xxxxii

Compound xxxxi (847 mg, 1.16 mmol) and 724 mg (1.39 mmol) of PyBop are dissolved in 10 mL DCM. To the solution, compound xiii (260 mg, 1.39 mmol) is added and then followed by the addition of DIPEA (209 µl). The mixture is stirred at about room temperature overnight. The reaction mixture is then diluted with EtOAc to 100 mL and washed twice with 1 N HCl, twice with NaHCO$_3$ and thrice with brine. The organic is dried and concentrated. The residue is purified by column chromatography (5% ethanol/EtOAc) to yield 930 mg (86%) of compound xxxxii,

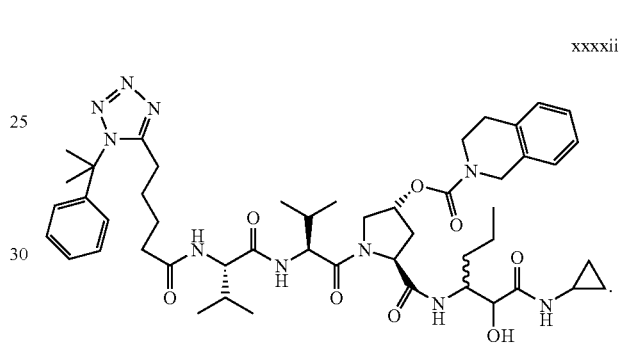

xxxxii

INTERMEDIATE EXAMPLE 41

Compound xxxxiii

Compound xxxxii (350 mg, 0.38 mmol) is dissolved in 10 mL DCM and 242 mg (0.57 mmol) of DMP reagent reagent is added. The mixture is stirred at about room temperature for three hours. The mixture is diluted with EtOAc to 50 mL and washed thrice with brine. The product is purified by column chromatography (100% EtOAc) to yield 180 mg (51%) of compound xxxiii,

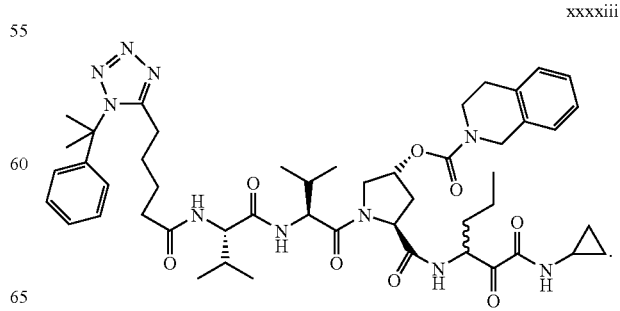

xxxxiii

INTERMEDIATE EXAMPLE 42

Compound xxxxv

H-Val-Val-OH (5 g, 23 mmol) is suspended in 100 mL DMF, compound xxxxiv

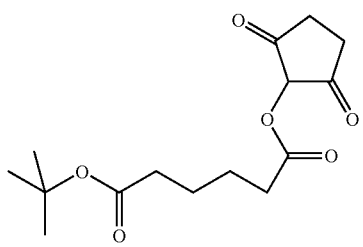

(8.3 g, 27.6 mmol) is added, and then 6.2 mL (35.5 mmol) of DIPEA is added. The mixture is stirred at 40° C. for two days. The solvent is removed under high vacuum and the residue is dissolved in 100 mL EtOAc and washed thrice with 1 N HCl and twice with brine. 9.14 g (99%) of compound xxxxv is afforded.

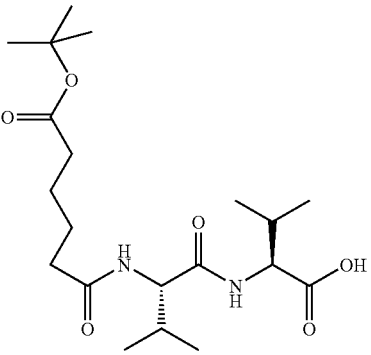

INTERMEDIATE EXAMPLE 43

Compound xxxxvi

Compound xxxxv (2.8 g, 7 mmol) and 954 mg (7 mmol) of HOAt is dissolved in 100 mL DCM. 7 mL of 1 M DCC/DCM is added. To the reaction mixture, compound xxxix (2.15 g) is added and the reaction mixture is stirred at about room temperature for overnight. The mixture is concentrated to dryness and the residue is dissolved in EtOAc and purified by column chromatography (100% EtOAc) to yield 4.57 g (95%) of compound xxxxvi,

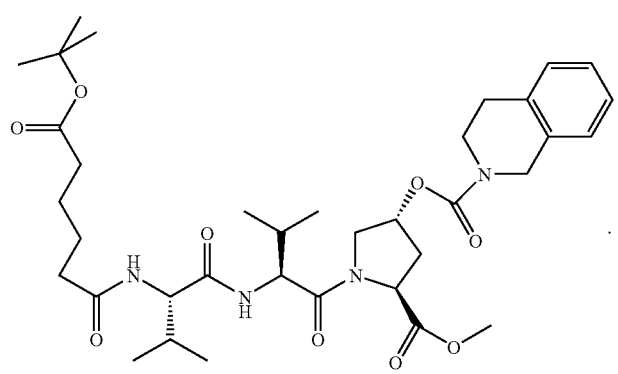

INTERMEDIATE EXAMPLE 44

Compound xxxxvii

Compound xxxxvi (4.57 g, 6.65 mmol) is dissolved in 10 mL TFA and 10 mL DCM. The mixture is stirred at about room temperature for 4 hours. The solvent is removed by vacuum and the residue is dissolved in 50:50 acetonitrile/water and lyophilized to yield as a powder compound xxxxvii,

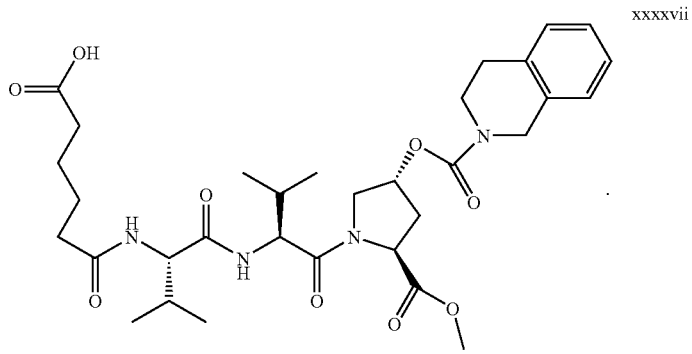

INTERMEDIATE EXAMPLE 45

Compound xxxxviii

Compound xxxxvii (1 g, 1.59 mmol) and 990 mg (2.28 mmol) of PyBop is dissolved in 20 mL DCM and 1.6 mL of 1 M methylamine in THF is added. The mixture is stirred at about room temperature for 4 hours. The reaction mixture is diluted to 100 mL with EtOAc and washed with 1 N HCl, NaHCO$_3$ and brine. The residue is purified by flash column chromatography (10% EtOH/EtOAc) to yield 1 g (98%) of compound xxxxviii,

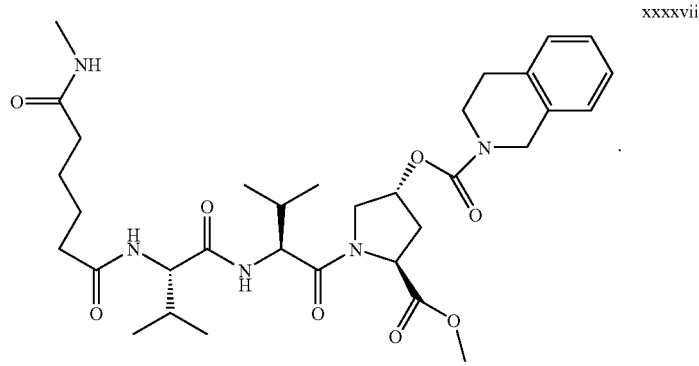

INTERMEDIATE EXAMPLE 46

Compound xxxxix

Compound xxxxviii (1 g, 1.55 mmol) is dissolved in 10 mL of MeOH and 2 mL 1 N NaOH is added. The mixture is stirred at about room temperature for overnight. The solvent is removed by evaporation. The residue is dissolved in water, neutralized and extracted with EtOAc to yield 960 mg (98%) of compound xxxxix,

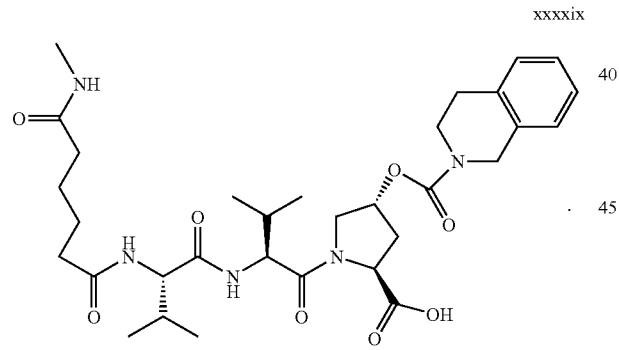

INTERMEDIATE EXAMPLE 47

Compound li

Compound xxxxix (315 mg, 0.5 mmol) and 312 mg (0.6 mmol) of PyBop are dissolved in 10 mL DCM. Compound 1 (56 mg, 0.6 mmol) and 108 μl of DIPEA is added. The mixture

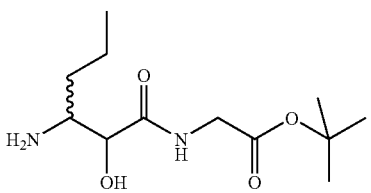

is stirred at about room temperature overnight, and is diluted to 100 mL with EtOAc and washed with 1 N HCl, NaHCO$_3$ and brine. Purified by column chromatography (15% EtOH/EtOAc) to yield 400 mg (92%) of compound li,

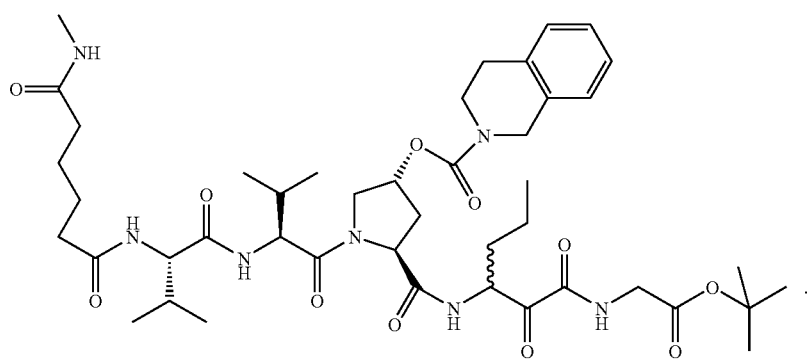

INTERMEDIATE EXAMPLE 48

Compound lii

Compound li (400 mg, 0.46 mmol) is dissolved in 10 mL of DCM and 292 mg (0.69 mmol) DMP reagent reagent is added. The mixture is stirred at about room temperature for 3 hours. The solvent is removed by evaporation and product is purified by RP-HPLC to yield 130 mg (32%) of compound lii,

INTERMEDIATE EXAMPLE 50

Compound liv

Compound xxxxv (755 mg, 1.88 mmol) and 255 mg (1.88 mmol) of HOAt are dissolved in 20 mL DCM. 1.88 mL of 1 M DCC/DCM is added. To the reaction mixture, compound v (288 mg) is added and the reaction mixture is stirred at about room temperature for 2 hours. The mixture is concentrated to dryness and the residue is dissolved in EtOAc and purified by column chromatography (80% EtOAc/Hexanes) to yield 800 mg (90%) of compound liv,

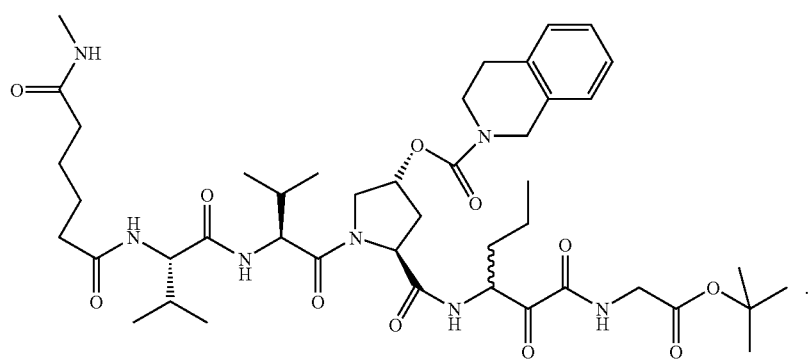

lii

INTERMEDIATE EXAMPLE 49

Compound liii

Compound xxxxix (210 mg, 0.33 mmol) and 208 mg (0.4 mmol) of PyBop are dissolved in 10 mL DCM. Compound xiii (154 mg, 0.83 mmol) is added to the solution followed by the addition of DIPEA (72 µl, 0.4 mmol). The mixture is stirred at about room temperature overnight. The reaction mixture is diluted to 100 mL with EtOAc, washed with 1 N HCl, NaHCO$_3$ and brine, and then purified by flash column chromatography (10% EtOH/EtOAc) to yield 250 mg (95%) of compound liii,

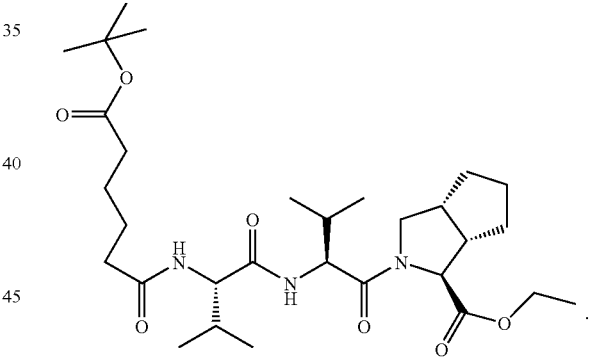

liv

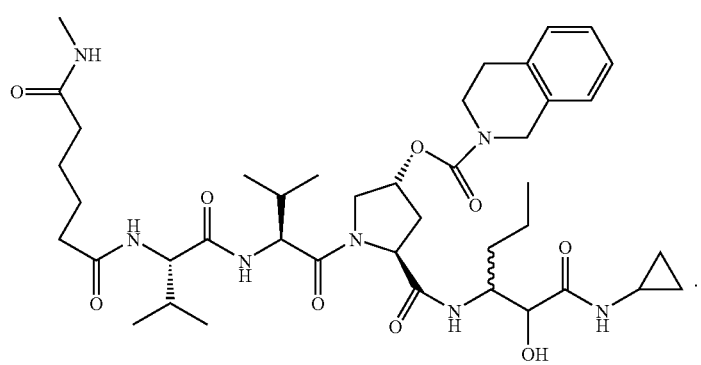

liii

INTERMEDIATE EXAMPLE 51

Compound lv

Compound liv (800 mg, 1.41 mmol) is dissolved in 10 mL MeOH and 2 mL NaOH is added. The mixture is stirred at about room temperature overnight. The solvent is removed by vacuum and the residue is dissolved in water and neutralized with 2 mL 1 N HCl. The product is extracted with EtOAc. Evaporation of the extraction solvent afforded 760 mg (~100%) lv,

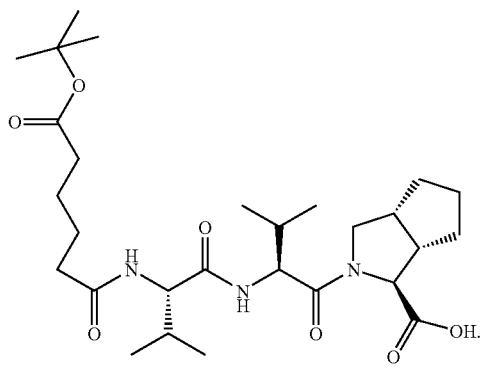

lv

INTERMEDIATE EXAMPLE 52

Compound lvii

Compound lv (760 mg, 1.41 mmol) and 880 mg (1.69 mmol) of PyBop are dissolved in 5 mL DCM. Compound lvi (530 mg, 2.12 mmol) is added to the solution and then 0.31

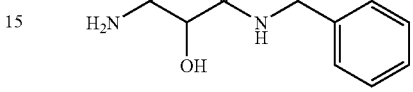

lvi of DIPEA is added. The mixture is stirred at about room temperature overnight. The reaction mixture is diluted to 100 mL with EtOAc, washed with 1 N HCl, NaHCO₃ and brine, and then purified by flash column chromatography (100% EtOAc) to yield 870 mg (80%) of compound lvii,

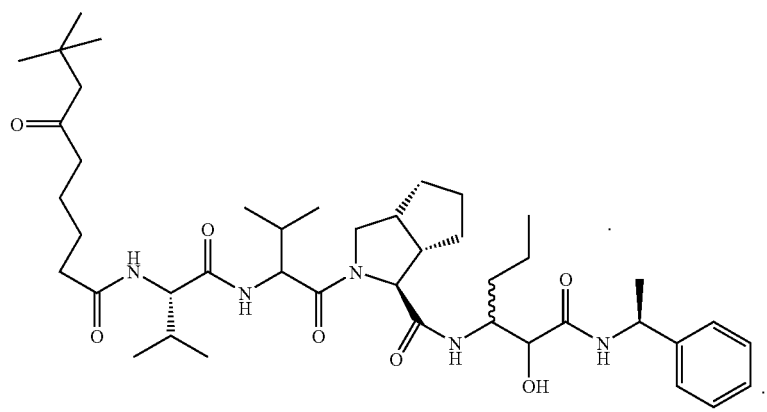

lvii

INTERMEDIATE EXAMPLE 53

Compound lviii

Compound lvii (350 mg, 0.45 mmol) is dissolved in 5 mL TFA and 5 mL DCM and the mixture is stirred at about room temperature for 3 hours. The solvent is removed by evaporation and the product is purified by RP-HPLC to yield 220 mg (69%) of compound lviii,

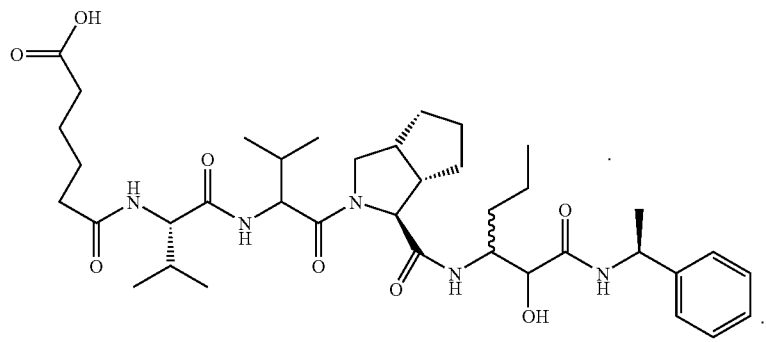

lviii

INTERMEDIATE EXAMPLE 54

Compound lix

Compound lviii (200 mg, 0.28 mmol) and 218 mg (0.42 mmol) of PyBop are dissolved in 5 mL DCM. Methylamine (0.28 mL of 2 M in TBF) is added. The mixture is stirred at about room temperature overnight. The mixture is diluted to 100 mL with EtOAc, washed with 1 N HCl, NaHCO$_3$ and brine, and then purified by column chromatography (15% EtOH/EtOAc) to yield 168 mg (79%) of lix, showed total conversion to a slower running spot. The reaction is carefully quenched with ice and then with a cold saturated solution of NH$_4$Cl (10 mL). The mixture is dumped in DCM (300 mL). The organic layer is washed once with saturated solution of NH$_4$Cl (60 mL) and twice with brine (60 mL). The organic layer is then separated, dried over MgSO$_4$ and concentrated in vacuo, to yield 3.5 g of compound ii (87%)

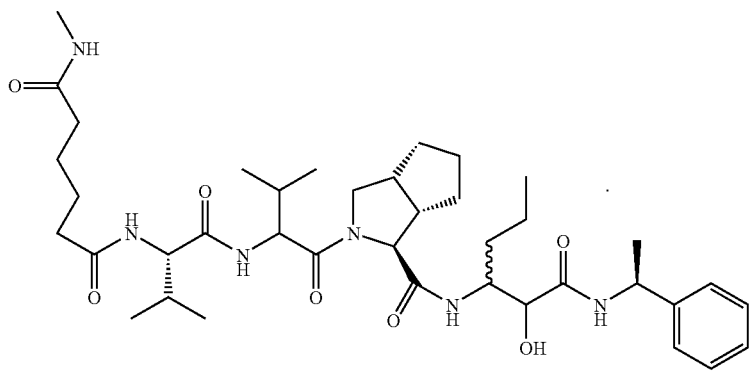

lix

INTERMEDIATE EXAMPLE 55

Compound lx

Compound lviii (200 mg, 0.26 mmol) is dissolved in 4 mL of DCM and 165 mg (0.39 mmol) of DMP reagent reagent is added. The mixture is stirred at about room temperature for 3 hours. The solvent is removed by evaporation. The residue is dissolved in 50% acetonitrile/water, and filtered purified by RP-HPLC to yield 140 mg (70%) of compound lx,

INTERMEDIATE EXAMPLE 57

Compound lxi

In a 250 mL round bottom flask equipped with a H$_2$ balloon, an ethanolic solution (50 mL) of compound ii (3.5 g, 10.5 mmol) is subjected to standard hydrogenation conditions [20% Pd(OH)$_2$/C (1.47 g, 2.1, mmol)] for 5 hours at about room temperature. The catalyst is filtered off through Celite and washed with DCM. The solvent is then removed under reduced pressure to yield 2 g (96%) of compound lxi, lx

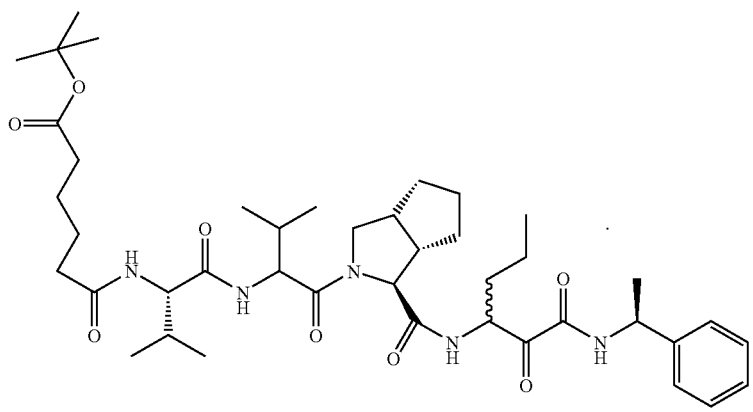

INTERMEDIATE EXAMPLE 56

Compound ii

A DCM (30 mL) and EtOH (30 mL) solution of compound i (4 g, 12.1 mmol), under N$_2$, is cooled down to −10° C. NaBH$_4$ (458 mg, 12.1 mmol) is added and the solution is stirred at −10° C. for 50 minutes. TLC (50% EtOAc/Hexane)

LXI

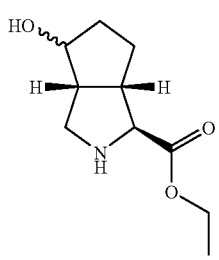

INTERMEDIATE EXAMPLE 58

Compound lxii

Under inert atmosphere, a solution of compound lxi (200 mg, 1 mmol), compound lxiii,

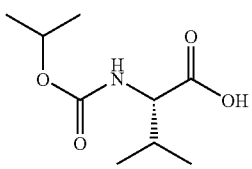

lxiii (233 mg, 1.1 mmol), HOAt (1-hydroxy-7-azabenzotriazole) (156 mg, 1.15 mmol) in anhydrous DMF (6 mL) is stirred for 20 minutes. The temperature is then taken down to 0° C., followed by the addition of DIC(0.18 mL, 1.15 mmol). The reaction is stirred overnight at about room temperature. The solution is diluted with EtOAc and then washed twice with 1 N HCl, twice with saturated aqueous NaHCO$_3$, and brine. The organic layer is separated dried over MgSO$_4$ and the solvent removed under reduced pressure. The residue is cleaned by chromatography (silica gel: 70% EtOAc/DCM) to give in 45% yield compound lxii.

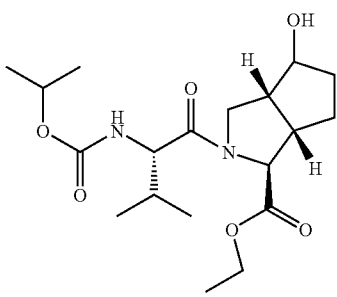

lxii

INTERMEDIATE EXAMPLE 59

Compound lxiv

A solution of compound lxii (777 mg, 2 mmol) in dioxane (6 mL) and 0.5 M NaOH (6 mL) is stirred for 5 hours at about room temperature. Examination by TLC (100% EtOAc) shows complete conversion to a spot at the origin. The reaction is cooled down with an ice bath followed by the addition of 1 N HCl (4 mL). Solid NaCl is then added and the whole mixture is extracted twice with EtOAc (2×150 mL). The organic extracts are then combined, dried over MgSO$_4$ and the solvent removed under reduced pressure to give compound lxiv in 92% yield.

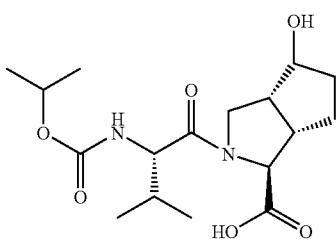

lxiv

INTERMEDIATE EXAMPLE 60

Compound lxv

Under an inert atmosphere, a solution of compound x (203 mg, 0.58 mmol), compound lxiv (276 mg, 0.775 mmol), HOAt (1-hydroxy-7-azabenzotriazole) (126 mg, 0.93 mmol) in anhydrous DMF (6 mL) is stirred for 20 minutes. The temperature is then taken down to 0° C., followed by the addition of DIC (0.14 mL, 0.93 mmol). The reaction is stirred overnight at about room temperature. The solution is diluted with EtOAc and then washed twice with 1 N HCl, twice with saturated aqueous NaHCO$_3$, and brine. The organic layer is separated dried over MgSO$_4$ and the solvent removed under reduced pressure. The residue is purified by chromatography (silica gel: 50% EtOAc/DCM to 80:19:1 EtOAC/DCM/MeOH) to give compound lxv in 62% yield.

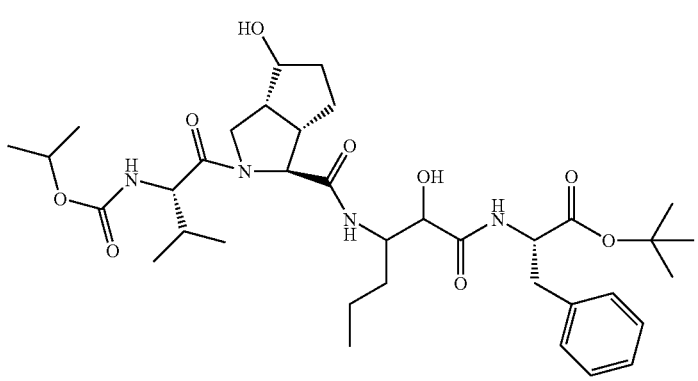

lxv

INTERMEDIATE EXAMPLE 61

Compound lxvi

Under an inert atmosphere, to a solution of compound lxv (287 mg, 0.42 mmol) in anhydrous DCM (15 mL) is added the DMP reagent reagent (605 mg, 1.43 mmol) The reaction is stirred for 2 hours at about room temperature. (Note.—The doubling of the amount of the DMP reagent reagent and the reaction time is to assure that both alcohol groups are completely oxidized to the corresponding keto groups). Examination by TLC (silica gel: 2% MeOH/EtOAc) shows complete conversion to the faster product. The reaction is diluted with DCM (150 mL) and then washed twice with a 10% aqueous sodium sulfite solution (2×50 mL), twice with saturated aqueous NaHCO$_3$, and with brine. The organic layer is separated dried over MgSO$_4$ and the solvent removed under reduced pressure. The residue is purified by chromatography (silica gel: 50% EtOAC/DCM to 80:19:1 EtOAC/DCM/MeOH) to give in 77% yield compound lxvi.

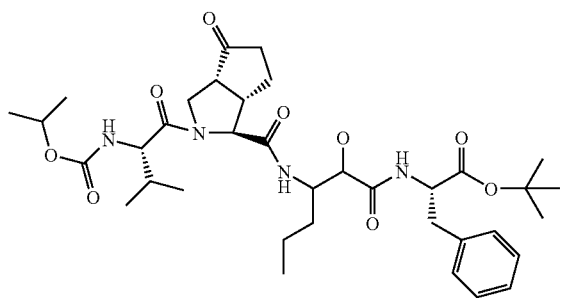

lxvi

INTERMEDIATE EXAMPLE 62

Compound lxvii

To a DCM solution (60 ml) of L-3 phenyl lactic acid (2 g, 12 mmol) is added PYBOP (7.5 g, 14.4 mmol). To this solution is added a DCM solution (20 mL) containing L-valine methyl ester HCl (2.4 g, 14.4 mmol) and DIPEA (2.6 mL, 14.4 mmol). The resulting reaction mixture is stirred overnight at about room temperature. At this point, the reaction is diluted with EtOAc (30 mL), washed with NaHCO$_3$ (30 mL) and brine (15 mL). The organic layer is dried over Na$_2$SO$_4$, filtered and concentrated. Purification is achieved in 50% EtOAc/Hex on silica gel to give 2.97 g (89%) of compound lxvii,

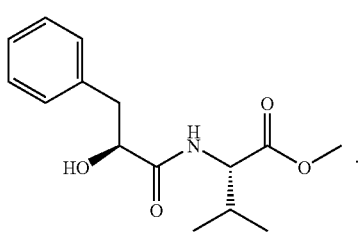

lxvii

INTERMEDIATE EXAMPLE 63

Compound lxviii

Compound lxvii (2.97 g, 10.6 mmol) is taken up in DCM (50 mL) and cooled with an ice bath. TBSCI (2.1 g, 13.8 mmol) is added to this solution followed by imidazole (0.94 g, 13.8 mmol). The resulting solution is stirred overnight. The reaction is then diluted with EtOAc (50 mL), washed with NaHCO$_3$ and brine. The organic layer is dried over Na$_2$SO$_4$, filtered and concentrated. Purification is achieved in 20% EtOAc/Hexane on silica gel to give 3.79 g (90%) of compound lxviii,

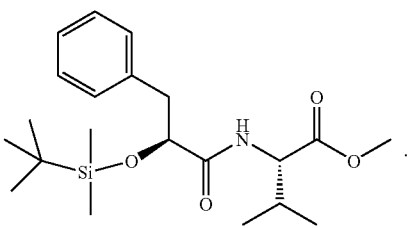

lxviii

INTERMEDIATE EXAMPLE 64

Compound lxix

To a methanol (50 ml) solution of compound lxviii (3.78 g, 9.6 mmol) is added 1 N aqueous NaOH (14.4 mL, 14.4 mmol). The resulting solution is stirred overnight. The solvent is partially removed in vacuo. The pH of the reaction mixture is then lowered to 3 using 1 N HCl aqueous solution. The solution is diluted with EtOAc and brine. The desired product is extracted with EtOAc (3×50 ml). The organic layers are combined, dried over Na$_2$SO$_4$, filtered and concentrated to give 3.5 g (96%) of compound lxix,

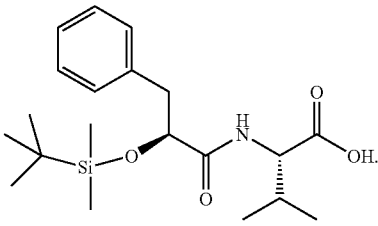

lxix

INTERMEDIATE EXAMPLE 65

Compound lxx

To a DCM (15 mL) solution containing compound lxix (1.1 g, 2.9 mmol) is added HOAt (0.44 g, 3.2 mmol) followed by a 1 M solution of DCC (3.2 mL, 3.2 mmol) in DCM. After sting at about room temperature for 20 minutes, a DCM (15 mL) solution of compound xxxix (970 mg, 3.2 mmol) is added. This reaction is stirred overnight under N$_2$. The reaction is then diluted with EtOAc (30 mL), filtered through a pad of silica gel, washed with 0.1 N HCl, NaHCO$_3$, and brine. The organic layer is dried over Na$_2$SO$_4$, filtered and concentrated in vacuo. Purification is achieved in 50% EtOAc/Hex on silica gel to give 1.5 g (77%) of compound lxx,

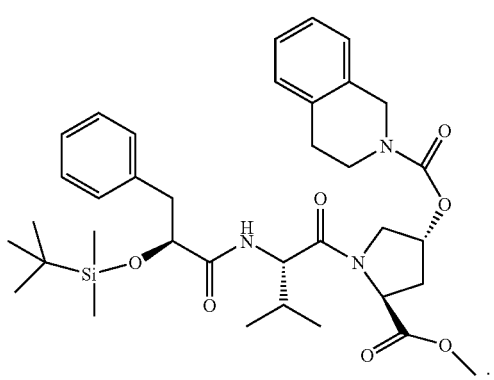

INTERMEDIATE EXAMPLE 66

Compound lxxi

To a methanol solution (30 mL) of compound xx (1.5 g, 2.4 mmol) is added 1 N aqueous NaOH (3.6 mL, 3.6 mmol). The resulting solution stirred overnight. At this point, the solvent is partially removed, and the pH of the reaction mixture is adjusted to 3 using 1 N aqueous HCl. The reaction is then diluted with EtOAc (50 mL) and brine (20 mL). The aqueous layer is extracted with EtOAc (3×50 mL). The organic layers are combined, dried over $Na_2SO_4$, filtered and concentrated to provide 1.3 g (92%) of compound lxxi,

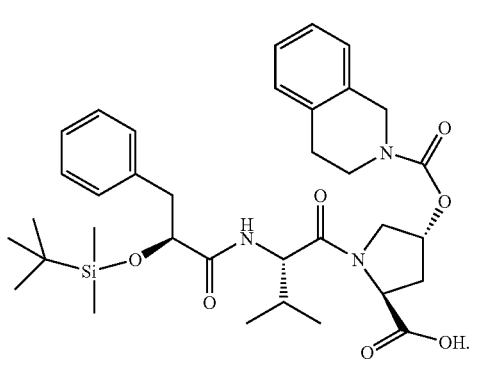

INTERMEDIATE EXAMPLE 67

Compound lxxii

To a solution of DCM (2 mL) containing compound lxxi (180 mg, 0.28 mmol) is added PyBOP (175 mg, 0.34 mmol) and DIPEA (0.06 mL, 0.34 mmol), followed by a DCM solution (3 nL) of compound x (150 mg, 0.41 mmol). The resulting solution is stirred overnight under $N_2$. The reaction is then diluted with EtOAc (30 mL), washed with $NaHCO_3$ and brine. The organic layer is dried over $Na_2SO_4$, filtered and concentrated. Purification is achieved in 100% EtOAc on silica gel to give 270 mg (98%) of compound lxxii,

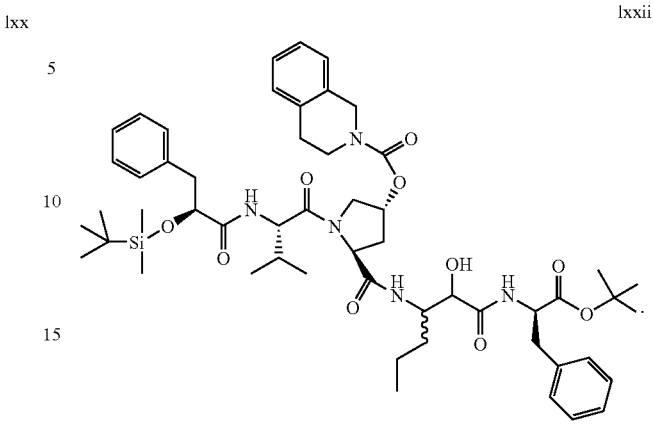

INTERMEDIATE EXAMPLE 68

Compound lxxiii

To a DCM (3 mL) solution of compound lxxii (270 mg, 0.27 mmol) is added DMP reagent reagent (140 mg, 0.33 mmol). After stirring at about room temperature for 1.5 hours, the reaction is quenched with 10% $Na_2SO_3$ (10 mL). The reaction is diluted with EtOAc (30 mL) and stirred for 10 minutes. The organic layer is washed with $NaHCO_3$ and brine. The organic layer is dried over $Na_2SO_4$, filtered and concentrated. Purification is achieved in 60% EtOAc/Hex. to give 150 mg (56%) of compound lxxiii,

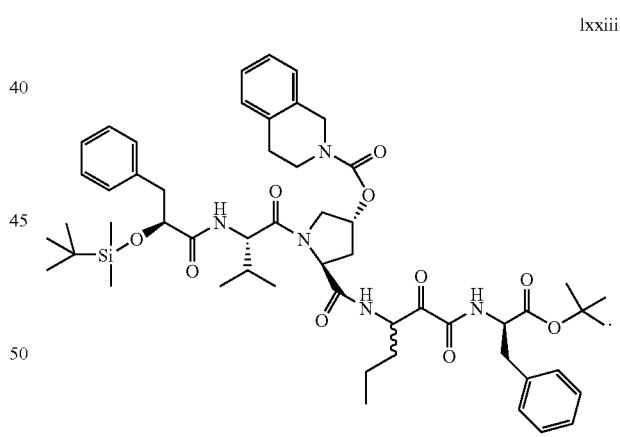

INTERMEDIATE EXAMPLE 69

Compound lxi

To an ethanol solution (50 mL) of compound ii (3.5 g, 10.5 mmol) is added under a stream of nitrogen $Pd(OH)_2/C$ (1.47 g, 20% Pd content, 2.1 mmol). The reaction is subjected to hydrogenation under 1 atm pressure. Upon completion, the catalysts are filtered through a pad of Celite and washed with dichloromethane. The filtrates are concentrated in vacuo to give 2 g (96%) of compound lxi.

INTERMEDIATE EXAMPLE 70

Compound lxxiv

To a DMF solution (60 mL) of compound vii (9.1 g, 28.2 mmol) is added HOAt (4 g, 29.4 mmol) and 1,3-disiopropylcarbodiiide (3.7 g, 29.4 mmol). After stirring at about room temperature for 30 minutes, a DMF solution (10 mL) of compound lxi (5.1 g, 25.6 mmol) is added to the above solution. The reaction is stirred at about room temperature overnight. At this point, the white solids are filtered off. The filtrates are concentrated in vacuo to give a residue that is purified by silica gel chromatography to give 9.5 g (67%) of compound lxxiv,

LXXIV

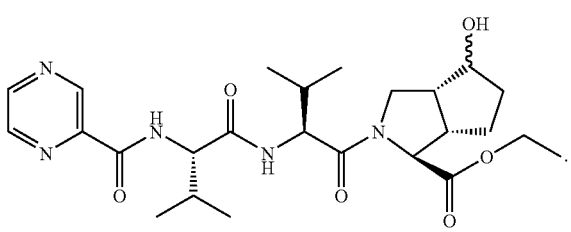

INTERMEDIATE EXAMPLE 71

Compound lxxv

To a solution of compound lxxiv (1.5 g, 3 mmol) in anhydrous THF (25 mL) is added EtiPr₂N (0.78 mL, 4.5 mmol) at about room temperature. The mixture is cooled to 0° C. and MOMCl (1.5 mL, 19.7 mmol) is added in a dropwise fashion. The reaction is allowed to warm to room temperature and stirred overnight. The solution is then diluted with ether and washed with water (3 times). The aqueous layers are extracted further by ether and all the organic layers are dried over MgSO₄ before being concentrated to afford a yellow oil. The desired isomer of compound lxxv is isolated by silica gel chromatography (EtOAc/Hexanes

LXXV

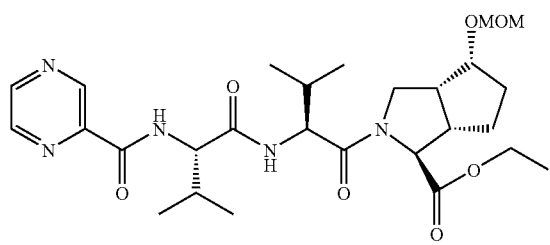

5/2) in 40% yield with clear separation of diastereomers.

INTERMEDIATE EXAMPLE 72

Compound lxxvi

To a solution of compound lxxv (502 mg, 0.9 mmol) in EtOH (5 mL) is added 2 N aqueous NaOH (0.9 mL, 1.8 mmol) dropwise at 0° C. The reaction is allowed to warm to room temperature and stirred overnight. Upon completion of the saponification, the solution is acidified to pH 3 with Dowex 50W8X-200 acidic resin. The solids are filtered off and the resulting filtrate is concentrated in vacio to give a oily residue that is lyophilized to give 370 mg (80%) compound lxxvi,

LXXVI

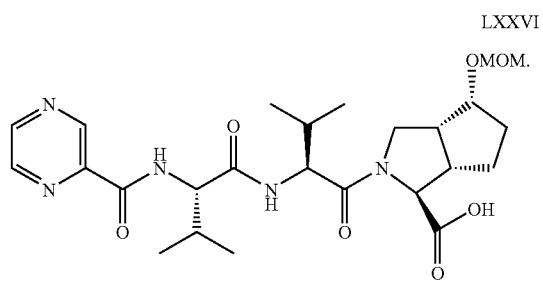

INTERMEDIATE EXAMPLE 73

Compound lxxvii

A dichloromethane solution (4 mL) of compound lxxvi (110 mg, 0.21 mmol) is treated with PyBOP (200 mg, 0.38 mmol). After stirring at about room temperature for 30 minutes, the reaction mixture is charged with a THF solution (3.2 mL) of compound xiii (60 mg, 0.32 mmol), followed by EtiPr₂N. After stirring overnight at about room temperature, the reaction is quenched with water and extracted with EtOAc. The resulting organic layer is washed with brine and dried over MgSO₄, before being concentrated to a yellow oil. Purification by silica gel chromatography (5% EtOH/EtOAc) yields 143 mg (100%) of compound lxxvii,

LXXVII

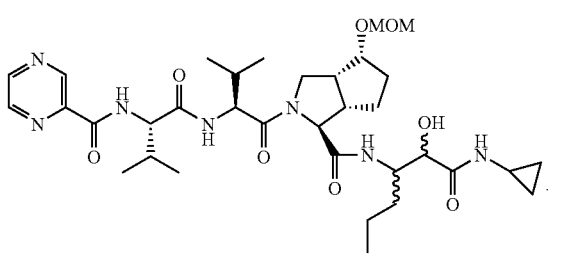

INTERMEDIATE EXAMPLE 74

Compound lxxviii

To a THF solution (50 mL) of H-Chg-OH 2 (5 g, 19.4 mmol) is added HOBt (2.63 g, 19.4 mmol) and EDCI (3.72 g, 19.4 mmol). After stiring at about room temperature for 20 minutes, a THF (19 mL) and DMF (10 mL) solution containing tert-L-Leucine methyl ester-hydrochloride (19.4 mmol) and DIPEA (6.75 mL, 38.8 mmol) is added to the above solution. The reaction is stirred at about room temperature overnight. Standard aqueous work-up and silica gel chromatography (15-20% EtOAc/Hexanes) affords 2.27 g (30%) of compound lxxviii,

INTERMEDIATE EXAMPLE 75

Compound lxxix

To a THF solution (12 mL) of compound lxxviii (2.27 g, 5.91 mmol) is added 4 N HCl solution in dioxane (7.38 mL, 29.5 mmol). The reaction is stirred at about room temperature overnight. At this point, the solvent is removed under reduced pressure to yield the compound lxxix that is used directly for next reaction.

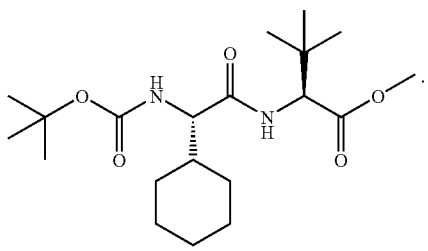

lxxviii

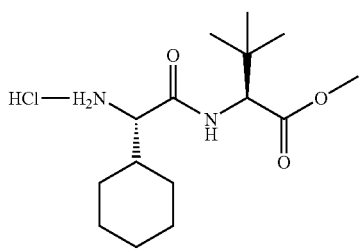

lxxix

INTERMEDIATE EXAMPLE 76

Compound lxxx

To a THF solution of compound lxxix (5.9 mmol) is added to a THF (20 mL) solution containing 2-pyrazinecarboxylic acid (878 mg, 7.08 mmol), HOBt (957 mg, 7.08 mmol) and EDCI (1.36 g, 7.08 mmol). To the resulting mixture is then added DIPEA (2.05 mL, 11.8 mmol). The reaction is stirred overnight at about room temperature and then quenched with water. The reaction mixture is extracted with EtOAc. The organic layer is washed with brine and concentrated in vacuo to provide a residue that is purified by silica gel chromatography (40-50% EtOAc/Hexanes) to provide 1 g (36%) of compound lxxx,

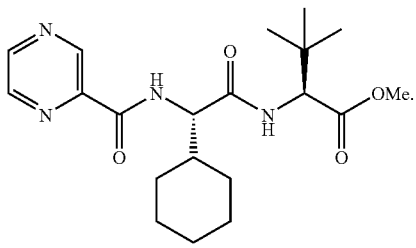

lxxx

INTERMEDIATE EXAMPLE 77

Compound lxxxi

To a methanol solution (20 mL) of compound lxxx (1 g, 2.56 mmol) is added 2 N NaOH 3.2 mL, 6.4 mmol). The reaction is stirred at about room temperature overnight. At this point, the reaction is acidified to pH 3 using 5 N HCl. The reaction is diluted with EtOAc (75 mL), and washed with water and brine. The organic layer thus obtained is dried and concentrated in vacuo to give a residue that is dissolved in 1:1 $CH_3CN/H_2O$ for lyophilization. A total of ~1 g (100%) of compound lxxxi is obtained.

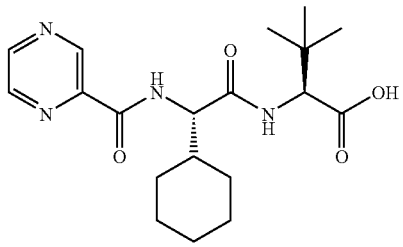

lxxxi

INTERMEDIATE EXAMPLE 78

Compound lxxxii

A dichloromethane solution (10 mL) of compound lxxxi (2.56 mmol) is treated with HOAt (348 mg, 2.56 mmol) and DCC (2.56 mL, 1M, 2.56 mmol). After stirring for 30 minutes, the reaction mixture is treated with a THF solution (5 mL) of compound v (2.56 mmol). After stirring at about room temperature overnight, the white solids (urea) are removed by filtration. The filtrates are concentrated in vacuo to give a residue that is purified by silica gel chromatography to provide 1.4 g (100%) of the compound lxxxii,

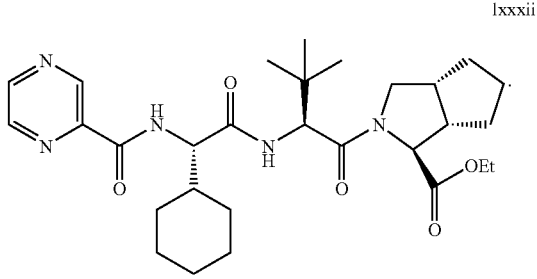

lxxxii

INTERMEDIATE EXAMPLE 79

Compound lxxxiii

An ethanol solution (15 mL) of compound lxxxii (1.4 g, 2.58 mmol) is treated with 2 N NaOH (2.58 mL, 5.17 mmol). After stirring at about room temperature overnight, the reaction mixture is acidified to pH 3 with acidic resin. The solids are filtered off. The resulting filtrates are concentrated in vacuo to give a residue that is lyophilized to give 1.32 g (~100%) of compound lxxxiii,

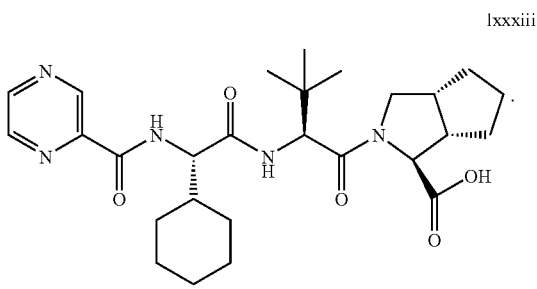

lxxxiii

INTERMEDIATE EXAMPLE 80

Compound lxxxiv

A dichloromethane solution (15 mL) of compound lxxxiii (360 mg, 0.7 mmol) is treated with PyBOP (582 mg, 1.12 mmol). After stirring at about room temperature for 20 minutes, the reaction mixture is treated with a THF solution (10 mL) of compound xiii (195.6 mg, 1.05 mmol), followed by DIPEA (0.25 mL, 1.40 mmol). After stirring overnight at about room temperature, the reaction is quenched with water and extracted with EtOAc. The resulting organic layer is washed with brine and dried and concentrated in vacuo to give a residue that is purified by silica gel chromatography (3% EtOH/EtOAc) to afford 420 mg (88%) of compound lxxxiv,

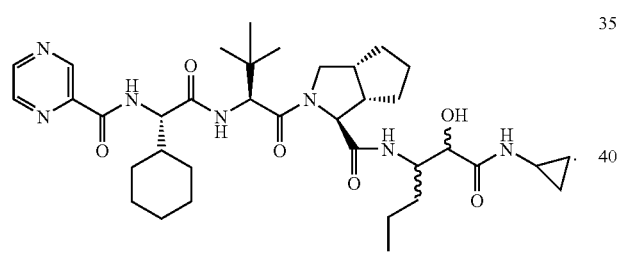

LXXXIV

INTERMEDIATE EXAMPLE 81

Compound ii'''

A mixture of anhydrous dichloromethane and ether (20 mL:20 mL) is cooled to −78° C. under $N_2$ (g). To the solution is added $TiCl_4$ (1 M in dichloromethane, 10 mL, 10 mmol) and then MeLi (1.4 M in ether, 7.1 mL, 10 mmol) is added subsequently with stirring for another 30 minutes at −78° C. A solution of compound i (2 g, 6 mmol) in 10 mL dichloromethane is added to the mixture dropwise at the same temperature over 15 minutes. The solution is slowly warmed up to −40° C. for 10 minutes and then stirred at 0° C. for 2 hours. The reaction is quenched by pouring the mixture into a water/ether mixture (1:1) and then the layers are allowed to separate. The aqueous layer is further extracted by ether twice. All organic layers is washed by water, brine and dried over $MgSO_4$ before being concentrated to a yellow oil. The desired compound ii''' is isolated by silica gel chromatography (EtOAc/Hexanes 2/1) in 83%

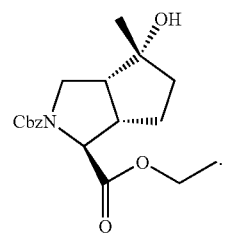

ii''''

INTERMEDIATE EXAMPLE 82

Compound lxi'

To the compound ii''' (1.7 g, 5 mmol) is added to 10 wt % Pd on C (0.53 g, 0.5 mmol), followed by addition of MeOH (17 mL). Hydrogen gas is flushed through the reaction mixture and hydrogen gas is maintained for reaction at 1 atm overnight. The reaction mixture is then filtered and concentrated to afford 929 mg (87%) of compound lxi' as a colorless oil.

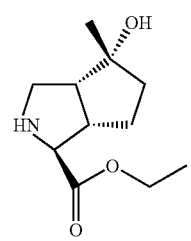

lxi'

INTERMEDIATE EXAMPLE 83

Compound lxxxv

To a THF solution (16 mL) of compound xxii (1 g, 3 mmol) is added at about room temperature HOAt (0.41 g, 3 mmol) and followed by 1 M DCC solution of dichloromethane (3 mL, 3 mmol). After stirring for 30 minutes at about room temperature, a dichloromethane solution (6 mL) of compound lxi' is added to the above HOAt-activated acid. The reaction is stirred at about room temperature overnight. At this point, the reaction is filtered through Celite. The filtrate is diluted with EtOAc (120 mL) and washed with water and then brine. The organic layer is dried and concentrated to an yellow oil which is purified by silica gel chromatography (100% EtOAc) to yield 1 g (65%) of compound lxxxv,

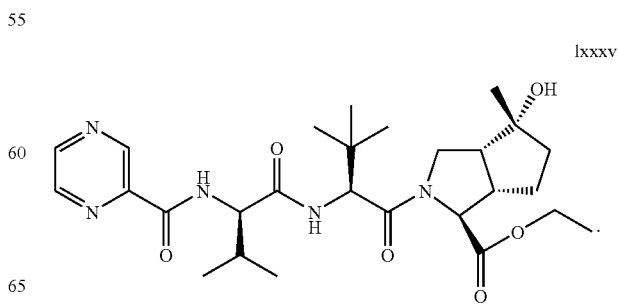

lxxxv

INTERMEDIATE EXAMPLE 84

Compound lxxxvi

To an ethanol solution (8 mL) of compound lxxxv (920 mg. 1.7 mmol) is added 2 N NaOH aqueous solution (1.7 mL, 3.4 mmol). The reaction is stirred overnight at about room temperature and then acidified to pH 3 by Dowes acidic resin. The solids are filtered off and the filtrate is concentrated to give a colorless oil, which is redissolved in 1:1 $CH_3CN/H_2O$ and lyophilized to provide 800 mg (93%) of compound lxxxvi. HPLC shows a single product peak.

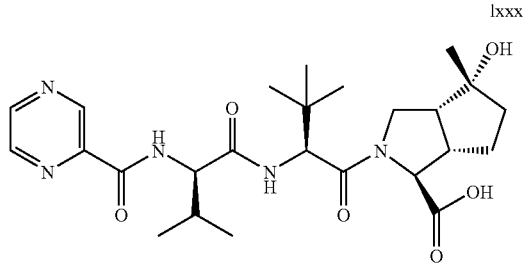

lxxxvi

INTERMEDIATE EXAMPLE 85

Compound lxxxvii

To a dichloromethane solution (4 mL) of compound lxxxvi (150 mg, 0.3 mmol) is added by PyBOP (250 mg, 0.47 mmol). The solution is stirred at about room temperature for 30 minutes. To this solution is then added a THF (4.5 mL) solution of compound xiii (84 mg, 0.45 mmol) followed by $EtiPr_2N$ (0.1 mL, 0.6 mmol). The reaction is stirred at about room temperature overnight and then quenched with water (25 mL) for 30 minutes. The mixture is then extracted with EtOAc. The resulting organic layer is washed with brine and dried over $MgSO_4$, before being concentrated to a yellow oil. Purification by silica gel chromatography (5% EtOH/EtOAc) yields 200 mg (100%) of compound lxxxvii,

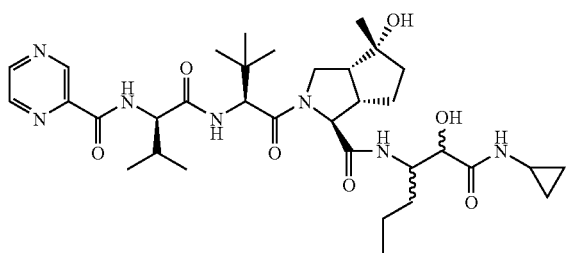

lxxxvii

INTERMEDIATE EXAMPLE 86

Compound lxxxix

Compound lxxxviii, N-Cbz-L-Valine, (2.5 g, 9.9 mmol) is taken up in THF (30 mL).

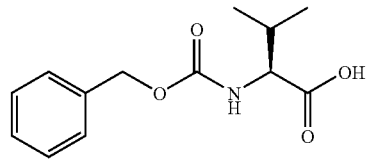

lxxxviii

EDCI (2.29 g, 11.9 mmol) and HOBT (1.62 g, 11.9 mmol) are added and the mixture stirred five minutes. L-tert-Leucine methyl ester hydrochloride (2.17 g, 11.9 mmol) is added in THF (23.9 mL) followed by DIPEA (2.1 mL). The reaction mixture is stirred overnight under nitrogen. The reaction mixture is diluted with ethyl acetate, washed with 1 N HCl, saturated sodium bicarbonate, and brine. The organic phase is dried over sodium sulfate, filtered and concentrated. The concentrate residue is purified in 25% ethyl acetate/hexane to afford 1.1 g (29%) of compound lxxxix,

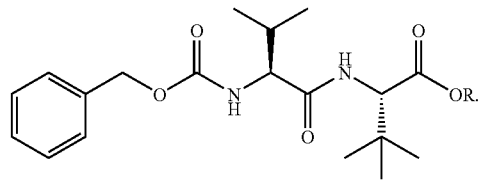

lxxxix

INTERMEDIATE EXAMPLE 87

Compound lxxxx

Compound lxxxix is hydrolyzed under standard conditions using methyl alcohol (0.3 M) and 1 N NaOH (1.5 eq) to afford 1.03 g (95%) of compound lxxxx,

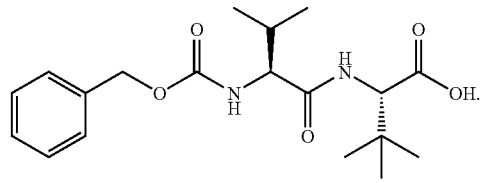

lxxxx

INTERMEDIATE EXAMPLE 88

Compound lxxxxi

Compound lxxxx (385 mg, 1.06 mmol) is taken up in dichloromethane (3 mL). DCC (1.4 mmol) is added followed by HOAt (190 mg, 1.4mmol). Compound v (260 mg, 1.4 mmol) is then added in dichloromethane (3 mL). The resulting mixture is stirred overnight under nitrogen. The reaction is diluted with ethyl acetate, filtered through silica gel, and concentrated. The residue is purified in 50% ethyl acetate/ hexane to afford 440 mg (80%) of compound lxxxxi,

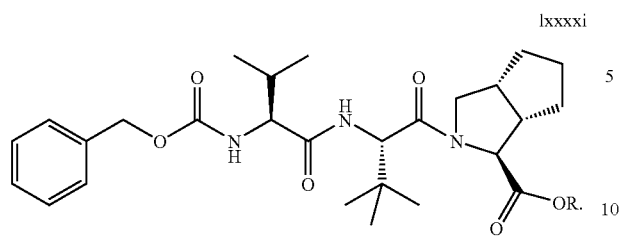

INTERMEDIATE EXAMPLE 89

Compound lxxxxii

Compound lxxxxi is hydrolyzed under standard conditions using ethyl alcohol (0.3 M) and 1 N NaOH (1.5 eq) to afford 390 mg of compound lxxxx.ii,

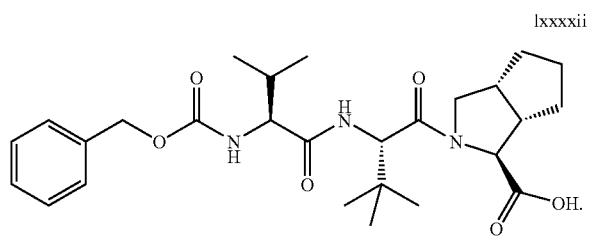

INTERMEDIATE EXAMPLE 90

Compound lxxxxiii

Compound lxxxxii (350 mg, 0.7 mmol) is taken up in dichloromethane (3 mL). PyBOP (480 mg, 0.91 mmol) is added followed by compound xiii (170 mg, 0.91 mmol). DIPEA (0.16 mL, 0.91 mmol) is added and reaction mixture stirred overnight. The reaction mixture is concentrated and purified in 100% ethyl acetate to afford 420 mg (90%) of compound lxxxxiii,

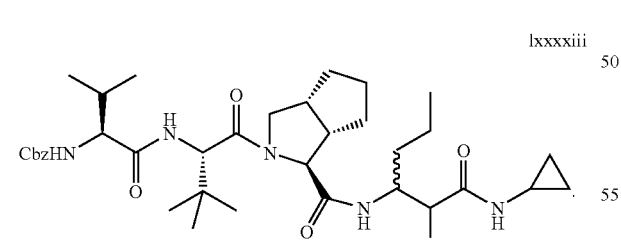

INTERMEDIATE EXAMPLE 91

Compound lxxxxiv

Compound lxxxxiii is hydrogenated using 10% Pd/C (1% mol) in methyl alcohol under hydrogen to afford 335 mg (100%) of compound lxxxiv,

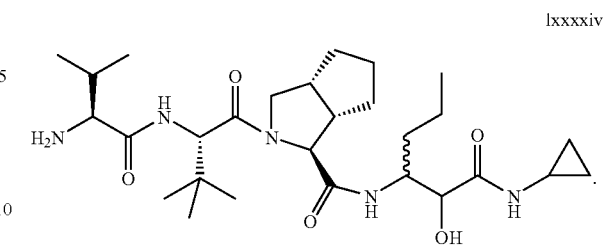

INTERMEDIATE EXAMPLE 92

Compound lxxxxv

Ethyl 1H-tetrazole-5-acetate (5 g, 32 mmol) is taken up in chloroform (80 mL). Trichlioroacetic acid (12.03 g, 73.65 mmol) is added followed by alpha methyl styrene (3.78 g, 32 mmol). The reaction mixture is stirred overnight. The next day, the solution is diluted with ethyl acetate, washed with 10% KOH and brine. The organic phase is dried over magnesium sulfate, filtered and concentrated to afford 8 g (96%) of the corresponding N-protected ethyl tetrazole-5-acetate. This material is subjected to standard hydrolysis conditions using ethyl alcohol (0.3 M) and 1 N NaOH (3 eq) to afford 7 g (99%) of compound lxxxxv,

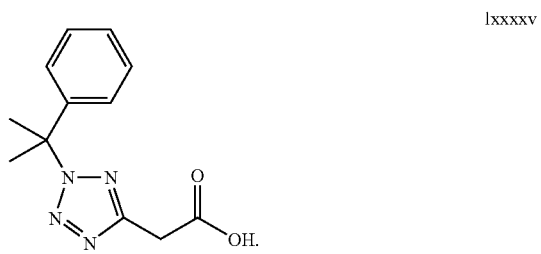

INTERMEDIATE EXAMPLE 93

Compound lxxxxvi

Compound lxxxxv (3.62 g, 14.7 mmol) is taken up in dichloromethane (50 mL). EDCI (4.32 g, 22.1 mmol) and DIPEA (5.1 mL, 29.4 mmol) are added and stirred for five minutes. N-hydroxy succinimide (3.38 g, 29.4 mmol) is added and stirred three hours. The reaction is diluted with dichloromethane and washed with water three times. The organic phase is dried over sodium sulfate, filtered and concentrated to afford 3.66 g (73%) of compound lxxxxvi,

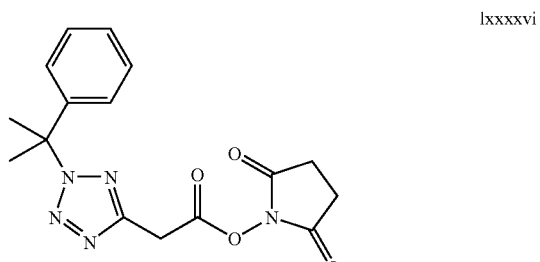

INTERMEDIATE EXAMPLE 94

Compound lxxxxvii

Compound lxxxxiv (335 mg, 0.62 mmol) and compound lxxxxvi (343 mg, 1 mmol) are taken up in dichloromethane (6 mL). DIPEA (0.17 mL, 1 mmol) is added and reaction mixture stirred overnight. The reaction is diluted with ethyl acetate, washed with saturated sodium bicarbonate, brine and concentrated. The residue is purified in 5% ethyl alcohol/ethyl acetate to give 80 mg (16%) of compound lxxxxvii,

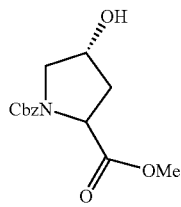

ic

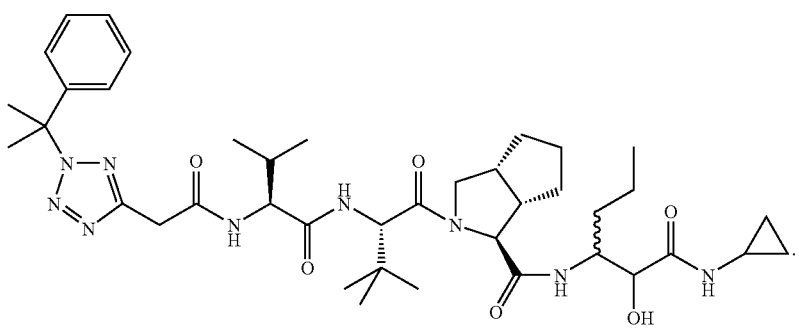

lxxxxvii

INTERMEDIATE EXAMPLE 95

Compound lxxxxviii

Compound lxxxxvii (80 mg, 0.11 mmol) is taken up in dichloromethane (3 mL). DMP reagent reagent (55 mg, 0.13 mmol) is added and stirred for one hour. The reaction mixture is diluted with ethyl acetate and quenched with 10% solution of sodium sulfite. The organic phase is washed with saturated sodium bicarbonate and brine. The organic phase is concentrated and the reulting residue is purified in 100% ethyl acetate to afford 40 mg (48%) of compound lxxxxvii, quantitative yield from compound c, N-Cbz-4-hydroxy Pro), is dissolved in DCM (25

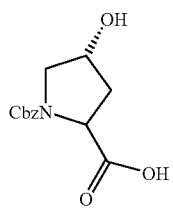

c

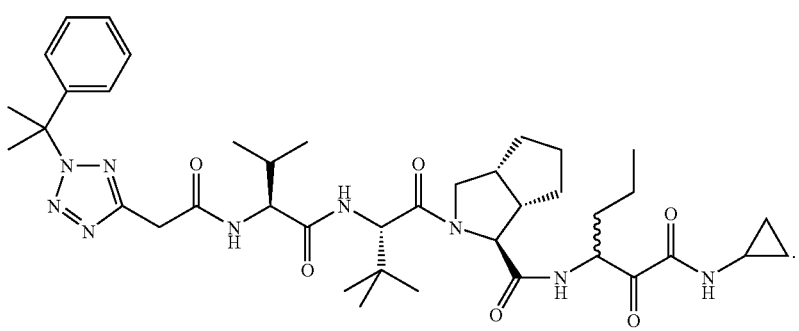

lxxxxviii

INTERMEDIATE EXAMPLE 96

Compound xxxix

Compound ic, N-Cbz-4-Hydroxy Pro methyl ester, (2.1 g, 7.9 mmol is prepared in mL). CDI (1.54 g, 9.5 mmol) and DIPEA (1.7 mL, 9.5 mmol) are added to the solution and stirred for 10 minutes. 1,2,3,4-Tetrahydroisoquinoline (TIQ) (1.2 mL, 9.5 mmol) is added drop-wise to the reaction mixture and stirred five hours. The organic phase is washed with water, 1 N HCl, and brine. Following the concentration of thee organic phase, the resultant residue is chromatographically purified by 40% EtOAc/Hexanes to yield compound ci, N-Cbz4-TIQcarbonyloxy-Pro methyl ester, (2.5 g, 75%).

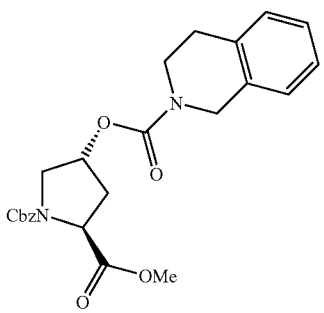

ci

Compound ci (2.5 g, 5.9 mmol) is dissolved in MeOH (75 mL). The solution is flushed with N$_2$ and Pd/C (10%, 300 mg) is added. The reaction mixture is flushed with H$_2$ and stirred overnight. The reaction mixture is filtered through Celite and concentrated to yield compound compound xxxix, 4-(TIQ-carbonyloxy)-Pro, methyl ester,(1.49 g, 83%).

INTERMEDIATE EXAMPLE 97

Compound vii

Compound cii, N-pyrazin-2-ylcarbonyl-Val-Val methyl ester, (10.9 g, 32.4 mmol) is

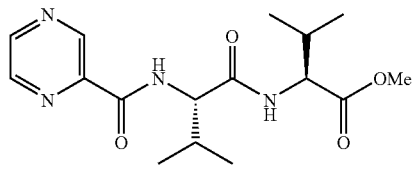

cii dissolved in THF (80 mL), and then aqueous NaOH (48.6 mL, 48.6 mmol) is added. The resulting mixture is stirred 48 hours, and then additional NaOH (16.3 mL, 16.3 mmol) is added and mixture is heated to 40° C. for three hours. The pH of the reaction mixture is then lowered to 3, and the acqueous phase extracted with EtOAc and then concentrated to yield crude compound vii, N-pyrazin-2-ylcarbonyl-Val-Val acid (10.6 g, 100%).

INTERMEDIATE EXAMPLE 98

Compound ciii

Compound cii (4.1 g, 12.7 mmol) is dissolved in DCM (20 mL). HOAt (1.73 g, 12.7 mmol) and DCC (12.7 mmol) are added to this solution, and the solution stirred for one hour. Compound xxxix (3.22 g, 10.6 mmol) is added to reaction mixture in DCM (10 mL). The resulting mixture is stirred overnight under N$_2$. The reaction mixture is filtered through silica gel and concentrated. The resulting residue is purified by silica gel chromatography (50% to 80% EtOAc/Hexanes gradient) to yield compound ciii, N-pyrazin-2-ylcarbonyl-Val-Val-4-(TIQcarbonyloxy)-Pro methyl ester, (5.27 g, 81.7%).

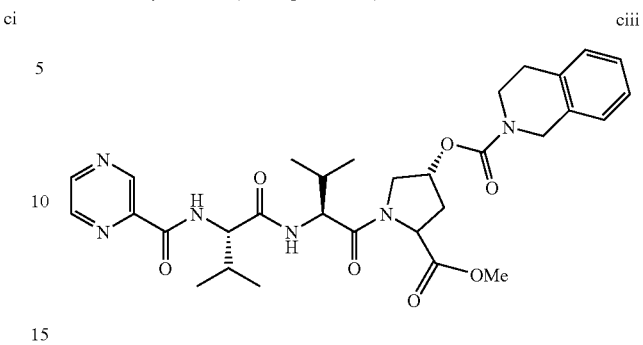

ciii

INTERMEDIATE EXAMPLE 99

Compound civ

Compound ciii (650 mg, 1.29 mmol) is dissolved in THF (5 mL). Aqueous NaOH (1.42 mL, 1.42 mmol) is added to the solution and then stirred overnight. The pH of the solution is lowered to 3, and the organic phase is isolated and concentrated to yield a residue. The residue is purifed using reverse phase HPLC in acetonitrile/water to yield compound civ, N-pyrazin-2-ylcarbonyl-Val-Val-4-(TIQcarbonyloxy)-Pro acid, (600 mg, 95%).

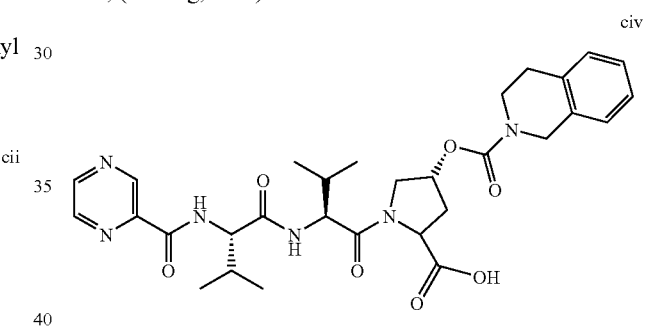

civ

INTERMEDIATE EXAMPLE 100

Compound cv

N-Boc-L-tert-Leucine (2.3 g, 10 mmol) and L-tert-Leucine methyl ester hydrochloride (2 g, 11 mmol) are combined in DMF (30 mL). HOAt (1.6 g, 11.5 mmol) is then added to the solution. The resulting mixture is stirred for 20 minutes under N$_2$ and then lowered to 0° C. whereupon DIC (1.8 mL, 11.5 mmol) and 2,4,6-collidine (1.45 mL, 11 mmol) are added. The resulting solution is stirred overnight with warming to room temperature. The reaction mixture is diluted with EtOAc, and the organic phase washed with 1 N HCl, saturated NaHCO$_3$ and brine. Following the concentration of the organic phase, the resultant residue is chromatographically purified by 20% -30% EtOAc/hexanes gradient to yield compound cv (3.3 g, 92%).

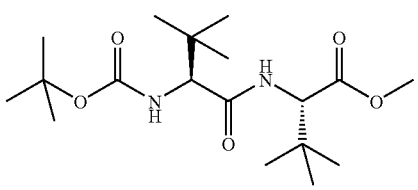

cv

INTERMEDIATE EXAMPLE 101

Compound cvi

Compound cv (3.3 g, 9.2 mmol) is hydrolyzed using dioxane (40 mL) and 0.5 N NaOH (37 mL, 18.4 mmol) to yield compound cvi (2.9 g, 92%).

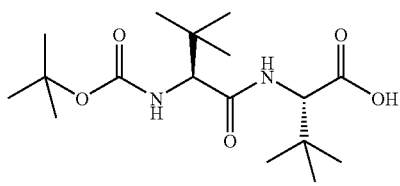

cvi

INTERMEDIATE EXAMPLE 102

Compound cvii

Compound cvi (2 g, 5.8 mmol) and compound v (1 g, 5.5 mmol) are dissolved in DMF (20 mL). HOAt (832 mg, 6.6 mmol) and DIC (1.1 mL, 6.6 mmol) are then added to the solution. The resulting solution is stirred overnight under N₂. The reaction mixture is diluted with EtOAc, and the organic phase washed with 1 N HCl, saturated NaHCO₃ and brine. Following the concentration of the organic phase, the resultant residue is chromatographically purified by 20%-30% EtOAc/hexanes gradient to yield compound cvii (2.4 g, 81%).

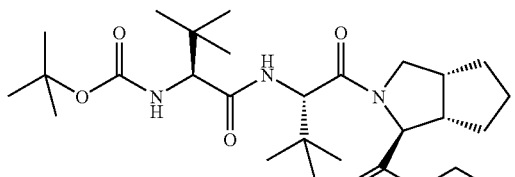

cvii

INTERMEDIATE EXAMPLE 103

Compound cviii

Compound cvii (2.4 g, 4.72 mmol) is dissolved in DCM (10 mL). TFA (10 mL) is added to the solution. The resulting solution is stirred for 4 hours. The reaction mixture is concentrated, dissolved in EtOAc, and then the organic phase is washed with 1 N NaOH and brine. The organic phase is concentrated to yield compound cviii (1.084 g, 56.1%).

cviii

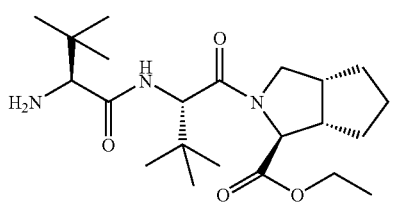

INTERMEDIATE EXAMPLE 104

Compound cix

2-Pyrazinecarboxylic acid (181 mg, 1.46 mmol) and compound cviii (541 mg, 1.325 mmol) are dissolved in DMF (15 mL). HOAt (207 mg, 1.52 mmol) and DIC (0.24 mL, 1.52 mmol) are added to the solution. The resulting solution is stirred overnight under N₂. The reaction mixture is diluted with EtOAc, and the organic phase washed with 1 N HCl, saturated. NaHCO₃ and brine. Following the concentration of the organic phase, the resultant residue is chromatographically purified by 20%-30%-35% EtOAc/hexanes gradient to yield compound cix (430 mg, 63%).

cix

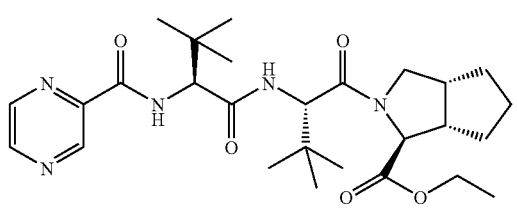

INTERMEDIATE EXAMPLE 105

Compound cx

Compound cix is hydrolyzed using EtOH (7 mL) and 1 N NaOH (4.7 mL, 4.7 mmol) to yield compound cx (700 mg, 91.6%).

cx

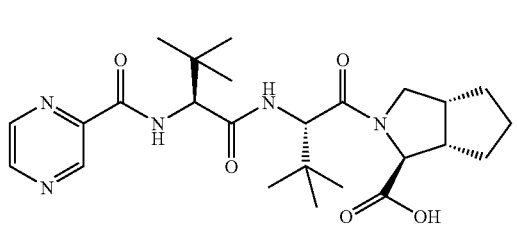

INTERMEDIATE EXAMPLE 106

Compound cxi

Compound cx (690 mg, 1.42 mmol) is dissolved in DCM (9 mL). PYBOP (890 mg, 1.7 mmol) is then added to the solution, followed by the addition of Compound xiii' (320 xiii'

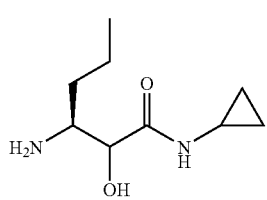

mg, 1.7 mmol). To the resulting mixture is added DIPEA (0.3 mL, 1.7 mmol). The reaction mixture is stirred overnight under N₂. The reaction mixture is then diluted with EtOAc, washed with saturated NaHCO₃, and brine. Following the concentration of the organic phase, the resultant residue is chromatographically purified by 100% EtOAc to yield compound cxi (490 mg, 52.7%).

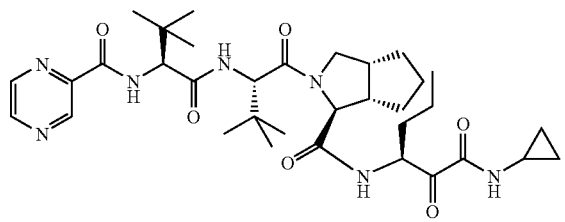

INTERMEDIATE EXAMPLE 107

Compound cxiv

Compound cxii (1.2 g, 3.06 mmol) is dissolved in MeOH (12 mL). After thoroughly

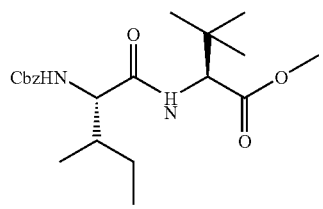

flushing with N₂, 10 wt % Pd(OH)₂ on carbon (0.6 g) is added and the mixture is hydrogenated for overnight, whereupon a complete reaction mixture is shown by TLC (30% EtOAc/hexanes). The solution is isolated from solid material by filtration and concentrated to the corresponding deprotected compound cxiiias a colorless oil (100%)

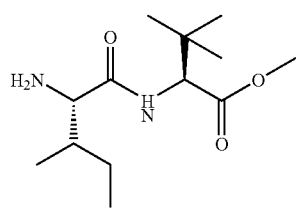

that is used in the next step without further purification.

2-Pyrazinecarboxylic acid (400 mg, 3.2 mmol, 1.1 eq) is dissolved in DCMP/THF (4 mL/4 mL), and then HOAt (440 mg, 3.2 mmol) and DCC (343 mL, 1 M in DCM) are added. After stiring at room temperature for 20 minutes, the compound cxiii (0.96 g, 3.2 mmol) obtained previously is dissolved in DCM (6.4 mL) and added to the activated mixture. After stirring overnight at room temperature, the reaction mixture is filtered through Celite and compound cxiv is purified by column chromatography (30% EtOAc/hexanes)

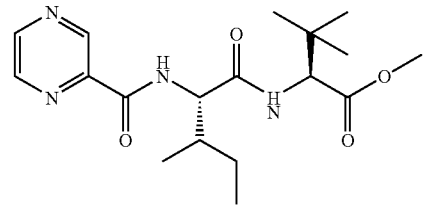

to yield a white solid (0.8 g, 80%).

INTERMEDIATE EXAMPLE 108

Compound cxv

Compound cxiv (0.8 g, 2.2 mmol) is dissolved in MeOH (10 mL), and then 2 N NaOH (aq) (3.3 mL, 6.6 mmol) is added. The solution is stirred at room temperature overnight, whereupon the completion of the reaction mixture is indicated by TLC (50% EtOAc/hexanes). Acidification to pH 3 by 5 N HCl and diluted with EtOAc is followed by extraction of the organic phase. The extracted organic phase is washed with brine and dried over MgSO₄ to yield compound cxv (0.74, 95%) upon concentration.

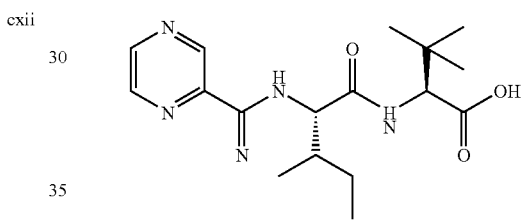

INTERMEDIATE EXAMPLE 109

Compound cxvi

To a DCM solution (6 mL) of compound cxv (0.74 g, 2.1 mmol) at room temperature is added HOAt (290 mg, 2.1 mmol), followed by the addition of 1 M DCC solution in DCM (2.2 mL, 2.2 mmol). After stirring for 30 minutes at room temperature, a THF solution (10.5 mL, 0.2 M) of compound v (2.1 mmol) is added to the above HOAt-activated acid.

The reaction mixture is stirred at room temperature overnight. At this point, the reaction mixture is filtered through celite. The filtrate is diluted with EtOAc (120 mL) and washed with water and brine. The organic phase is dried and concentrated to a yellow oil that is purified by silica gel chromatography (50% EtOAc/hexanes) to yield compound cxvi (0.714 g, 66%).

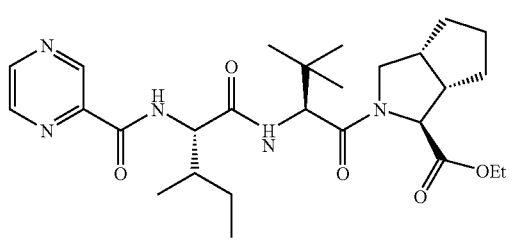

INTERMEDIATE EXAMPLE 110

Compound cxvii

To an EtOH solution of compound cxvi (0.7 g, 1.4 mmol) is added 2 N NaOH aqueous solution (2 mL, 4 mmol). The reaction mixture is stirred overnight at room temperature, then acidified to pH 3 by 5 N HCl and diluted with EtOAc is followed by extraction of the organic phase. The extracted organic phase is washed with brine and dried over $MgSO_4$ to yield compound cxvii (95%) upon concentration.

cxvii

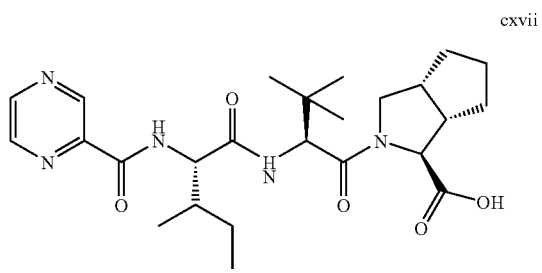

INTERMEDIATE EXAMPLE 111

Compound cxviii

To a DCM/THF solution (10 mL/2 mL) of compound cvii (300 mg, 0.6 mmol) is added PyBOP (416 mg, 0.8 mmol). The solution is stirred at room temperature for 30 minutes. To this solution is then added compound xxxvi' (200 mg, 0.8 mmol), followed by DIPEA xxxvi'

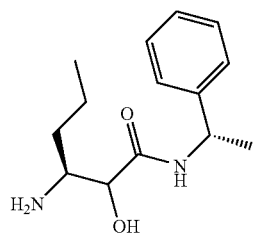

(0.22 mL, 1.2 mmol). The reaction mixture is stirred at room temperature overnight and then quenched with water (25 mL) for 30 minutes. The mixture is then extracted with EtOAc. The resulting organic phase is washed with brine and dried over $MgSO_4$, before being concentrated to yield a yellow oil. Purification by silica gel chromatography (3-5% EtOH/EtOAc) yields compound cxviii (335 mg, 76%).

cxviii

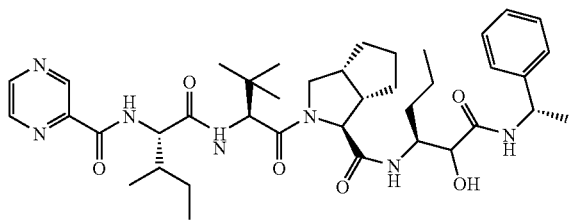

INTERMEDIATE EXAMPLE 112

Compound cxix

To a DCM solution (10 mL) of compound cxvid (340 mg, 0.6 mmol) is added PyBOP (470 mg, 0.9 mmol). The solution is stirred at room temperature for 30 minutes. To this solution is then added compound xiii' (170 mg, 0.9 mmol), followed by DIPEA (0.24 mL, 1.2 mmol). The reaction mixture is stirred at room temperature overnight and then quenched with water (25 mL) for 30 minutes. The mixture is then extracted with EtOAc. The resulting organic phase is washed with brine and dried over $MgSO_4$, before being concentrated to yellow oil. Purification by silica gel chromatography (3-5% EtOH/EtOAc) yields compound cxix (164 mg, 36%).

cxix

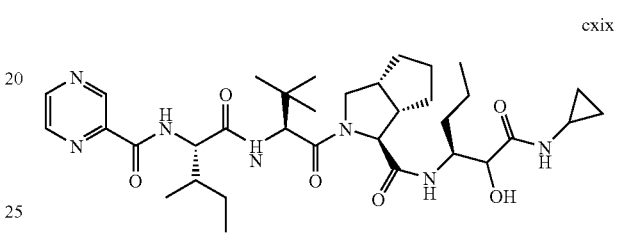

INTERMEDIATE EXAMPLE 113

Compound xx

N-Cbz-L-Valine (6.28 g, 25 mmol) is dissolved in DCM (30 mL). HOBT (3.38 g, 25 mmol) and DCC (25 mL, 1 M solution) are added to this solution and stirred five minutes. L-tert-Leucine methyl ester hydrochloride (25 mL, 1 M solution) is added to this mixture and stirred overnight under $N_2$. The reaction mixture is diluted with EtOAc, washed with 1 N HCl, saturated $NaHCO_3$, and brine. The organic phase is dried over $Na_2SO_4$, filtered and concentrated. The residue is chromatographically purified by 20%-30% EtOAc/hexanes to yield compound xx (2.96g, 31%).

INTERMEDIATE EXAMPLE 114

Compound xxi

Compound xx (2.95 g, 7.8 mmol) is hydrogenated using 10% Pd/C (800 mg) in MeOH (40 mL) under $H_2$ to yield the below corresponding free amine (1.9 g, 100%).

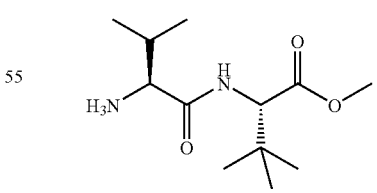

2-Pyrazine-carboxylic acid (970 mg, 7.8 mmol) is dissolved in DCM (20 mL). PyBOP (4.06 g, 7.8 mmol) is added to this solution. The free amine (1.9 g, 7.8 mmol) in DCM (15 mL) is added to the solution, and then DIPEA (1.36 mL, 7.8 mmol) is added. The resulting mixture is stirred overnight under $N_2$. The reaction mixture is diluted with EtOAc, and the organic phase is washed with saturated NaHCO₃ and brine. Following the concentration of the organic phase, the residue is chromatographically purified by 30%40% EtOAc/Hexanes to yield compound xxi (2.07 g, 75.8%).

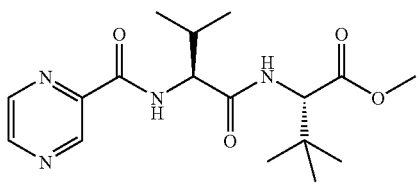

xxi

INTERMEDIATE EXAMPLE 115

Compound xxii

Compound xxi is hydrolyzed using MeOH (20 mL) and 1 N NaOH (3 eq) to yield compound xxii (1.82g, 93.9%).

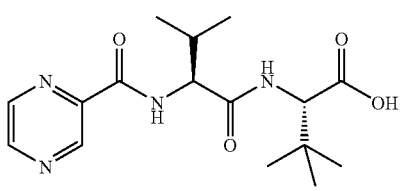

xxii

INTERMEDIATE EXAMPLE 116

Compound xxiii

Compound xxii (895 mg, 2.66 mmol) is dissolved in DCM (10 mL). DCC (3.2 mmol) is added to the solution, and then HOAt (435 mg, 3.2 mmol) is added. Compound v (3.2 mmol) in THF (16 mL) is then added. The resulting mixture is stirred overnight under N₂. The reaction mixture is diluted with EtOAc, filtered through silica gel, and concentrated. The resulting residue is chromatographically purified by 50% EtOAc/hexanes to yield compound xxiii (730 mg, 54.8%).

INTERMEDIATE EXAMPLE 117

Compound xxiv

Compound xxiii is hydrolyzed using EtOH (5 mL) and 1 N NaOH (1.5 eq) to yield compound xxiv (690 mg, 100%).

INTERMEDIATE EXAMPLE 118

Compound cxx

Compound xxiv (245 mg, 0.52 mmol) is dissolved in DCM (3 mL). PyBOP (330 mg, 0.62 mmol) is added to the solution, and then compound xiii' (120 mg, 0.62 mmol) is added. To the resulting mixture is added DIPEA (0.11 mL, 0.62 mmol). The reaction mixture is stirred overnight under N₂. The reaction mixture is diluted with EtOAc, and the organic phase washed with saturated NaHCO₃ and brine. Following the concentration of the organic phase, the residue is chromatographically purified by 5% EtOH/EtOAc to yield compound cxx (220 mg, 60%).

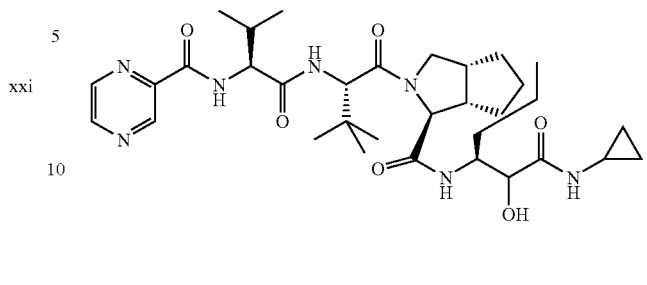

cxx

INTERMEDIATE EXAMPLE 119

Compound xiii'

Boc-NVA-OH (24.96 g, 114.9 mmol) is dissolved in THF (200 mL). CDI (22.35, 137.8

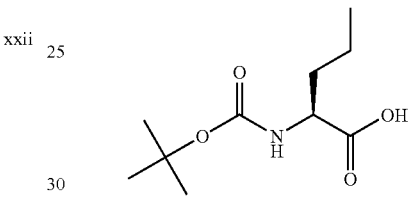

mmol) is added portion-wise to the solution, and the solution is stirred for 30 minutes. N,O-Dimethylhydroxylamine hydrochloride (12.33 g, 126.4 mmol) is dissolved in DMF (50 mL) and then DIPEA (22 mL, 126.4 mmol) is added to the solution. The DMF solution is allowed to stir at room temperature for 20 minutes and then added to THF solution. The resulting mixture is stirred over a weekend under N₂. The reaction mixture is concentrated in vacuo to 100 mL total volume. This organic phase is washed with 1 N HCl, saturated NaHCO₃ and brine. The organic phase is concentrated to yield crude compound cxxi (25.3 g).

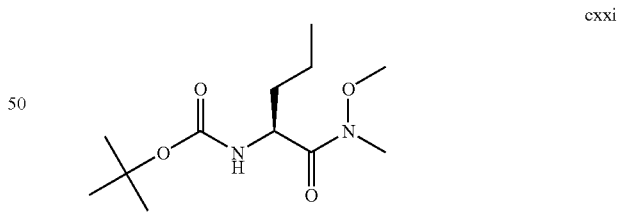

cxxi

LAH (107.3 mmol) is added to a dry 1-L round bottom flask under N₂ in a 1 M Et₂O solution. This solution is lowered to 0° C., and then compound cxxi (97.5 mmol) is added drop-wise in Et₂O (100 mL). Upon completion of the addition, the resulting mixture is stirred for 30 minutes. The reaction mixture is quenched at 0° C. by slowly adding EtOAc (50 mL), followed by slowly adding a 5% KHSO₄ (50 mL) solution. This mixture is stirred for 30 minutes. The organic phase is washed with 1 N HCl, saturated NaHCO₃, and brine. The organic phase is concentrated to yield crude compound cxxii (22.28 g).

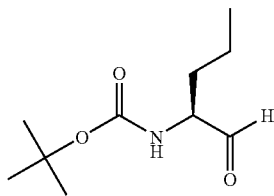
cxxii

Compound cxxii is dissolved in MeOH (100 mL). Na$_2$S$_2$O$_4$ (16.82 g, 96.6 mmol) is dissolved in water (100 mL and then added to solution of compound cxxii at 0° C. This mixture is stored in the refrigerator (5° C.) overnight. KCN (7.53 g, 115.9 mmol) in water (100 mL) is added to reaction mixture and stirred for 1.5 hours at room temperature. The compound is extracted with EtOAc (3×100 mL). The organic phase is washed with brine (3×50 mL), dried over MgSO$_4$, filtered and concentrated to yield crude compound cxxiii (15.86 g).

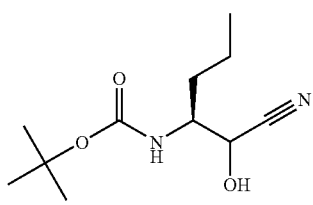
cxxiii

Compound cxxiii (15.86 g) is dissolved in dioxane (100 mL). Concentrated HCl (37%, 100 mL) is added to this solution followed by anisole (10 mL) and reflux is established (110° C.). The reaction stirred for 1.5 hours. When the reaction mixture is cooled to room temperature, the solvent is removed in vacuo to yield a dry paste. The residue is dried overnight under high vacuum to yield crude compound cxxiv.

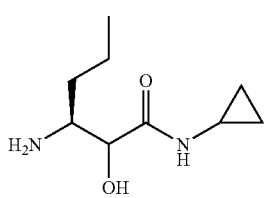
cxxiv

Compound cxxiv (69.6 mmol) is dissolved in DMF (60 mL) and THF (60 mL). N-(Benzyl-oxycarbonyloxy)succinimide (17.33 g, 69.6 mmol) is added to the mixture, followed by the addition of DIPEA (12.1 mL, 69.6 mmol). The reaction mixture is stirred overnight under N$_2$. The mixture is concentrated to a reduced volume (50 mL) and diluted with EtOAc. The organic phase is washed with 0.1 N HCl (2×100 mL) and brine to yield compound cxxv (17.5 g, 54.2% over five steps).

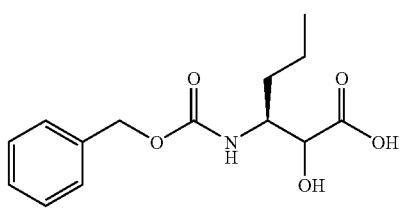
cxxv

Compound cxxv (5.66 g, 20.14 mmol) is dissolved in DCM (60 mL). PyBOP (12.57 g, 24.2 mmol) and HOBT (3.27 g, 24.2 mmol) are added to this solution and stirred five minutes. The resulting mixture is lowered to 0° C., and then cyclopropylamine (1.67 mL, 24.2 mmol) and DIPEA (4.2 mL, 24.2 mmol) are added. The reaction mixture is stirred overnight warning to room temperature. The reaction mixture is washed with 0.1 N HCl, saturated NaHCO$_3$, and brine. The organic phase is then concentrated and chromatographically purified using 70% EtOAc/Hexanes to yield compound cxxvi (3.18 g, 49.3%).

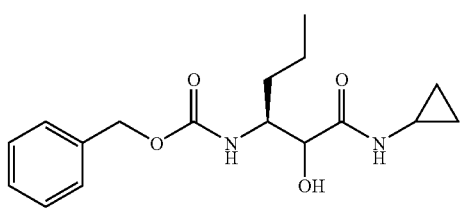
cxxvi

Compound cxxvi (3.18 g, 9.94 mmol) is hydrogenated using 10% Pd/C (600 mg) in MeOH (70 mL). The reaction mixture is stirred overnight under H$_2$, filtered through celite and concentrated to yield crude compound xiii' (2.1 g, 100%).

xiii'

INTERMEDIATE EXAMPLE 120

Compound cxxvii

N-Cbz-L-Cyclohexylglycine (3 g, 10.3 mmol) is dissolved in DCM (36 mL). HOAt (1.5 g, 11.28 mmol) and DCC (11.28 mL, 11.28 mmol) are added to this solution and stirred five minutes. L-tert-Leucine methyl ester hydrochloride (103 mL, 1 M solution, 10.3 mmol) is added to this mixture and stirred overnight under N$_2$. The reaction mixture is filtered through celite, rinsed with EtOAc and concentrated to a residue that is purified chromatographically using 20%-30% EtOAc/hexanes to yield compound cxxvii (2.2 g, 52%).

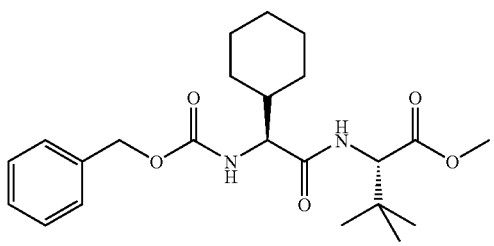

cxxvii

INTERMEDIATE EXAMPLE 121

Compound lxxix'

Compound cxxvii (2.2 g, 5.2 mmol) is hydrogenated using 20% Pd(OH)$_2$/C (1 g) in MeOH (15 mL) under H$_2$ to yield compound lxxix' (1.4 g, 98%).

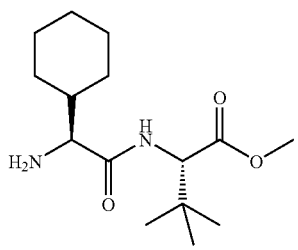

lxxix'

INTERMEDIATE EXAMPLE 122

Compound lxxx

2-Pyrazinecarboxylic acid (360 mg, 2.9 mmol) is dissolved in DCM (10 mL). PyBOP (1.81 g, 3.5 mmol) is added to the solution. Compound lxxix' (825 mg, 2.9 mmol) in THF (10 nL) is then added to the solution, followed by the addition of DIPEA (0.5 mL, 2.9 mmol). The resulting mixture is stirred overnight under N$_2$. The reaction mixture is diluted with EtOAc, and the organic phase washed with saturated NaHCO$_3$ and brine. The residue resulting from the concentration of the organic phase is chromatographically purified by 30% EtOAc/Hexanes to yield Compound lxxx (780 mg, 69%).

INTERMEDIATE EXAMPLE 123

Compound lxxxi

Compound lxxx is hydrolyzed using MeOH (10 mL) and 1 N NaOH (3 eq) to yield compound lxxxi (615 mg, 81.8%).

INTERMEDIATE EXAMPLE 124

Compound lxxxii

Compound lxxxi (610 mg, 1.6 mmol) is dissolved in DCM (10 mL). DCC (1.94 mL, 1.94 mmol) is then added to the solution, followed by the addition of HOAt (270 mg, 1.94 mmol). Compound v (1.94 mmol) in THF (19.4 mL) is then added to the solution. The resulting mixture is stirred over two nights under N$_2$. The reaction mixture is diluted with EtOAc, filtered through silica gel, and concentrated. The resulting residue is purified chromatographically by 40% EtOAc/hexanes to yield compound lxxxii (450 mg, 83.4%).

INTERMEDIATE EXAMPLE 125

Compound lxxxiii

Compound lxxxi is hydrolyzed using EtOH (10 mL) and 1 N NaOH (3 eq) to yield compound lxxxiii (650 mg, 99%).

INTERMEDIATE EXAMPLE 126

Compound cxxviii

Compound lxxxiii (400 mg, 0.78 mmol) is dissolved in DCM (5 mL). PyBOP (610 mg, 1.2 mmol) is added to the solution, followed by Compound xiii' (230 mg, 1.2 mmol). To the resulting mixture is added DIPEA (0.2 mL, 1.2 mmol). The reaction mixture is stirred overnight under N$_2$. The reaction mixture is diluted with EtOAc, and the organic phase washed with saturated NaHCO$_3$ and brine. Following the concentration of the organic phase, the residue is chromatographically purified by 100% EtOAc to 5% EtOH/EtOAc gradient to yield compound cxxviii (365 mg, 68.7%).

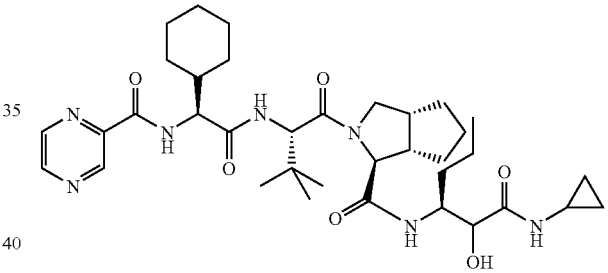

cxxviii

INTERMEDIATE EXAMPLE 127

Compound cxxx

Compound lxxxiii (365 mg, 0.7 mmol) is dissolved in DCM (5 mL). PYBOP (440 mg, 0.84 mmol) is added to the solution, followed by the addition of compound cxxix (0.84

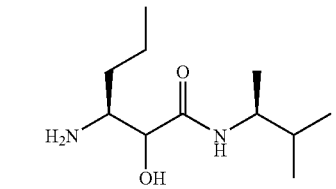

cxxix mmol) in THF (8.4 mL). To the resulting mixture is added DIPEA (0.1 mL, 0.84 mmol). The reaction mixture is stirred overnight under N$_2$. The reaction mixture is diluted with EtOAc, and the organic phase is washed with satutrated NaHCO$_3$ and brine. Following the concentration of the organic phase, the resulting residue is chromatographically purified by 100% EtOAc to yield compound cxxx (350 mg, 70%).

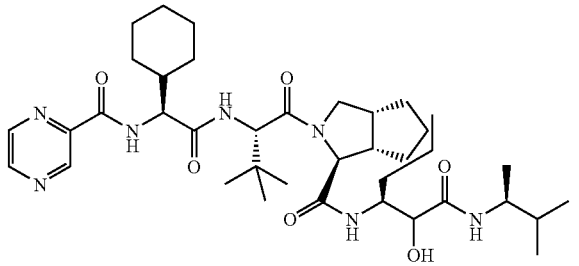

cxxx

INTERMEDIATE EXAMPLE 128

Compound cxxxi

Compound cxxv (2.54 g, 9.05 mmol) is dissolved in DCM (30 mL). PYBOP (5.65 g, 10.9 mmol) and HOBT (1.47 g, 10.9 mmol) are added to the solution and stirred five minutes. The resulting mixture is lowered to 0° C., whereupon (S)-(+)-3-Methyl-2-butylamine (1.27 mL, 10.9 mmol) and DIPEA (1.9 mL, 10.9 mmol) are added. The reaction mixture is stirred overnight with warming to room temperature. The organic phase is washed with 0.1 N HCl, saturated NaHCO$_3$ and brine. Following the concentration of the organic phase, the resultant residue is chromatographically purified by 30% EtOAc/hexanes to yield compound cxxxi (1.44 g, 45.5%).

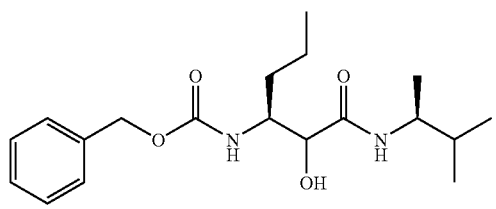

cxxxi

INTERMEDIATE EXAMPLE 129

Compound cxxix

Compound cxxxi (1.3 g, 3.7 mmol) is hydrogenated using 10% Pd/C (500 mg) in MeOH (40 mL). The reaction mixture is stirred overnight under H$_2$. The reaction mixture is filtered through celite and the organic phase concentrated to yield crude compound cxxix (800 mg, 100%).

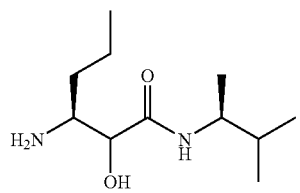

cxxix

INTERMEDIATE EXAMPLE 130

Compound cxxxiv

Compound cxxxii (1.6 g, 3.7 mmol) is dissolved in MeOH (12 mL). After thoroughly

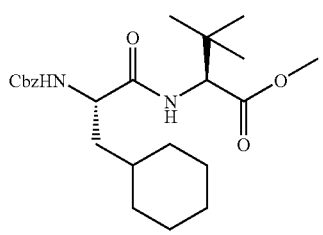

cxxxii flushing with N$_2$, 10 wt % Pd(OH)$_2$ on carbon (0.74 g) is added and the mixture is hydrogenated overnight, whereupon a complete reaction mixture is shown by TLC (30% EtOAc/hexanes). The solution is isolated from solid material by filtration and concentrated to yield compound cxxxiii as colorless oil (100%) that is used in the next

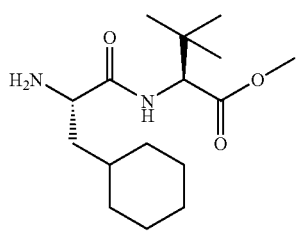

cxxxiii step without further purification. 2-Pyrazinecarboxylic acid (400 mg, 3.2 mmol, 1.1 eq) is dissolved in DCM/THF (4 mL/4 mL), and then HOAt (440 mg, 3.2 mmol) and DCC (3.3 mL, 1 M in DCM) is added. After stirring at room temperature for 20 minutes, compound cxxxiii (0.96 g, 3.2 mmol) obtained previously is dissolved in DCM (6.4 mL) and added to the activated mixture. After stirring over 2 days at room temperature, the reaction mixture is filtered through Celite, and concentrated to a residue that is purified by column chromatography (50% EtOAc/hexanes) to yield compound cxxxiv as a white solid (1.06 g, 83%).

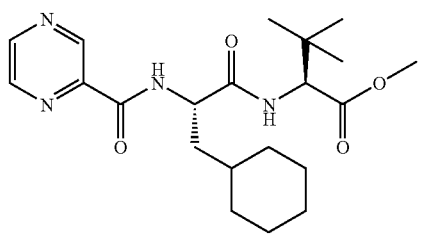

cxxxiv

INTERMEDIATE EXAMPLE 131

Compound cxxxv

Compound cxxxiv (1.06 g, 2.6 mmol) is dissolved in MeOH (10 mL), and then 2 N NaOH (aq) (4 mL, 8 mmol) is added. The solution is stirred at room temperature overnight, whereupon the completion of the hydrolysis is indicated by TLC (50% EtOAc/hexanes). The solution is acidified to pH 3 by 5 N HCl, diluted with EtOAc and then the organic phase is extracted. The extracted organic phase is washed with brine and dried over MgSO$_4$ to yield compound cxxxv (100%) upon concentration.

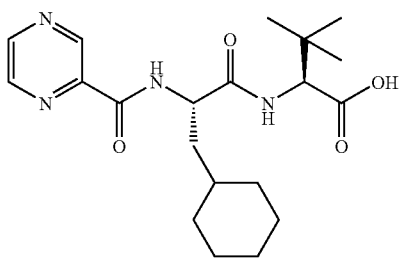

cxxxv

INTERMEDIATE EXAMPLE 132

Compound cxxxvi

To a DCM solution (8 mL) of compound cxxxv (1.44 g, 3.7 mmol) at room temperature is added HOAt (500 mg, 3.7 mmol), and then 1 M DCC solution in DCM (3.7 mL, 3.7 mmol) is added. After stirring for 30 minutes at room temperature, a THF solution (18.5 mL, 0.2 M) of compound v (3.7 mmol) is added to the above HOAt-activated acid. The reaction mixture is stirred at room temperature overnight. The reaction mixture is filtered through Celite. The filtrates are diluted with EtOAc (120 mL) and washed with water and brine. The organic phase is dried and concentrated to yield yellow oil that is purified by silica gel chromatography (70% EtOAc/hexanes) to yield compound cxxxvi (1 g, 71%).

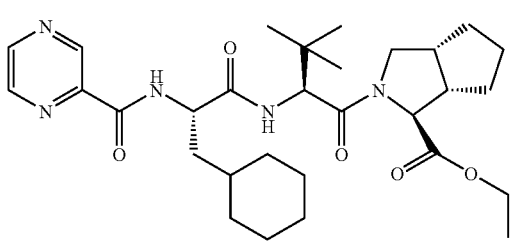

cxxxvi

INTERMEDIATE EXAMPLE 133

Compound cxxxvii

To an EtOH solution (8 mL) of compound cxxxvi (1 g, 1.8 mmol) is added 2 N NaOH aqueous solution (2.7 mL, 5.4 mmol). The reaction mixture is stirred overnight at room temperature, then acidified to pH 3 by 5 N HCl, diluted with EtOAc, and then the organic phase is extracted. The extracted organic phase is washed with brine and dried over MgSO$_4$ to yield compound cxxxvii (88%) upon concentration.

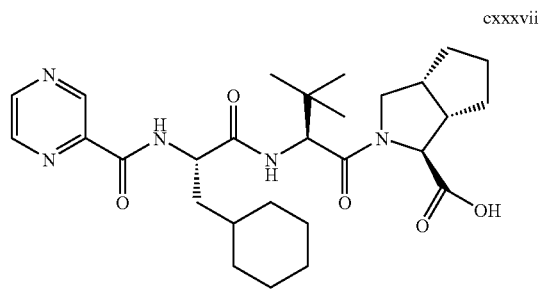

cxxxvii

INTERMEDIATE EXAMPLE 133

Compound cxxxviii

To a DCM solution (10 mL) of compound cxxxvii (350 mg, 0.6 mmol) is added PyBOP (450 mg, 0.86 mmol). The solution is stirred at room temperature for 30 minutes. To this solution is then added compound xiii' (160 mg, 0.86 mmol) followed by DIPEA (0.23 mL, 1.3 mmol). The reaction mixture is stirred at room temperature overnight and then quenched with water (25 mL) for 30 minutes. The mixture is then extracted with EtOAc. The extracted organic phase is washed with brine and dried over MgSO$_4$, before being concentrated to yield yellow oil. Purification by silica gel chromatography (5% EtOH/tOAc) yields compound cxxxviii (407 mg, 88%).

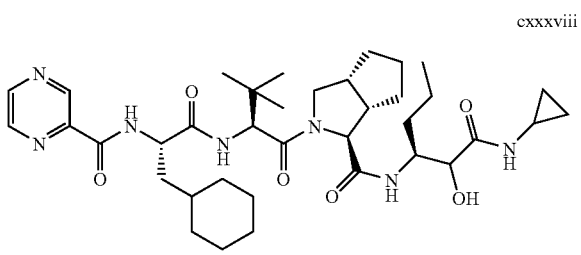

cxxxviii

INTERMEDIATE EXAMPLE 134

Compound cxxxix

5-Methylisoxazole-3-carboxylic acid (200 mg, 2.05 mmol) is dissolved in DCM (5 mL). PyBOP (1.07 g, 2.05 mmol) is added to the solution. Compound lxxix' (582 mg, 2.05 mmol) in DCM (5 mL) is added to the solution, followed by the addition of DIPEA (0.36 mL, 2.05 mmol). The resulting mixture is stirred overnight under N$_2$. The reaction mixture is diluted with EtOAc, and the organic phase washed with saturated NaHCO$_3$ and brine. The organic phase is concentrated, and the resultant residue is purified chromato-graphically by 30% EtOAc/hexanes to yield Compound cxxxix (495 mg, 61.4%).

INTERMEDIATE EXAMPLE 135

Compound cxxxx

Compound cxxxix is hydrolyzed using MeOH (10 mL) and 1 N NaOH (3 eq) to yield compound cxxxx (430 mg, 90%).

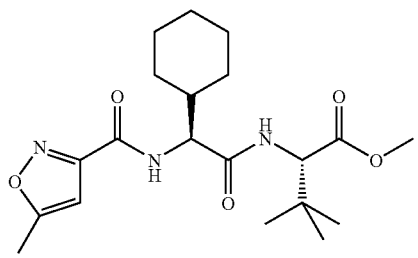

cxxxix

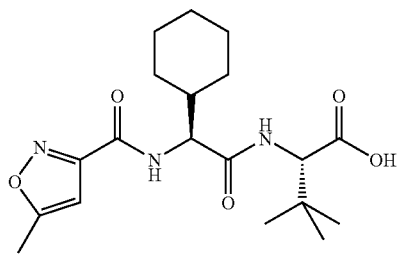

cxxxx

INTERMEDIATE EXAMPLE 136

Compound cxxxxi

Compound cxxxx (380 mg, 1 mmol) is dissolved in DCM (5 mL). DCC (1.2 mmol) is then added to the solution, followed by the addition of HOAt (165 mg, 1.2 mmol). Compound v (1.2 mmol) is then added in THF (12 mL). The resulting mixture is stirred overnight under $N_2$. The reaction mixture is diluted with EtOAc, filtered through silica gel, and concentrated. The resultant residue is chromatographically purified by 35% EtOAc/hexanes to yield compound cxxxxi (320 mg, 58%).

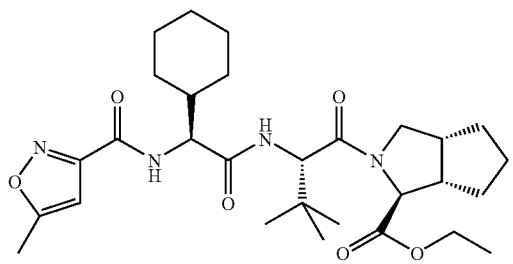

cxxxxi

INTERMEDIATE EXAMPLE 137

Compound cxxxxii

Compound cxxxxi is hydrolyzed using EtOH (10 mL) and 1 N NaOH (3 eq) to yield compound cxxxxii (730 mg, 94.3%).

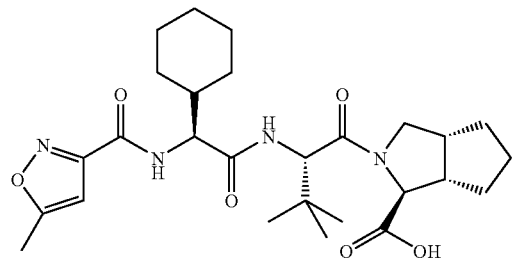

cxxxxii

INTERMEDIATE EXAMPLE 138

Compound cxxxxiii

Compound cxxxxii (240 mg, 0.46 mmol) is dissolved in DCM (5 mL). PyBOP (295 mg, 0.56 mmol) is then added to the solution, followed by the addition of Compound xiii' (110 mg, 0.56 mmol). To the resulting mixture is added DIPEA (0.1 mL, 0.56 mmol). The reaction mixture is stirred over two nights under $N_2$. The reaction mixture is diluted with EtOAc, and the organic phase washed with saturated $NaHCO_3$ and brine. Following the concentration of the organic phase, the resultant residue is chromatographically purified by 90% EtOAc/hexanes to yield Compound cxxxxiii (168 mg, 53%).

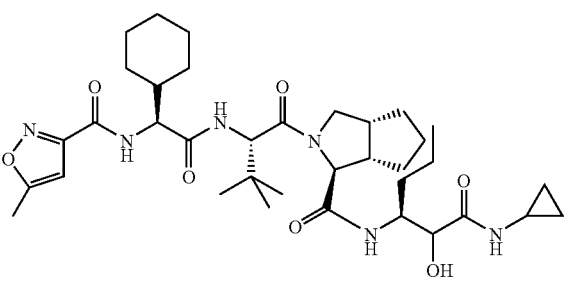

cxxxxiii

INTERMEDIATE EXAMPLE 139

Compound cxxxxiv

To a solution of NaOH (2N, 42.1 mL, 84.2 mmol) at 5° C. is added L-alanine (5.00 g, 56.1 mmol). After stirring for 10 minutes, methyl chloroformate (6.5 mL, 84.2 mmol) and NaOH (2 N, 42.1 mL, 84.2 mmol) are added dropwise simultaneously. The solution is stirred in ice bath for 2 hours, then at room temperature for 1 hour. The mixture is washed with $Et_2O$ (2×50 mL), the aqueous layer is neutralized to pH ~2 with 5 N HCl, and extracted with EtOAc (3×50 mL). The extracted organic phase is washed with brine, dried by $MgSO_4$ and concentrated to yield compound cxxxxiv,

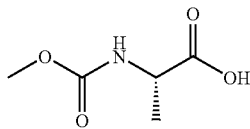

N-carbomethoxy-L-alanine, (4.54 g, 54%) as colorless oil.

INTERMEDIATE EXAMPLE 140

Compound cxxxxvi

A solution of compound cxxxxv (3.57 g, 9.44 mmol) in THF at 5° C. is treated with HOAt

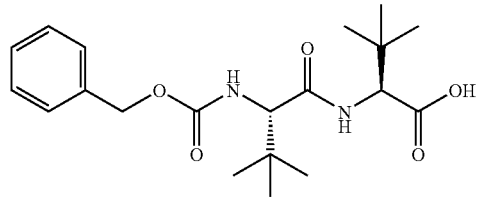

(1.28 g, 9.44 mmol), and then DCC (9.50 mL, 9.50 mmol) is added. After stirring in ice bath for 45 minutes, a solution of compound v (104 mL, 10.4 mmol) in THF is added. The mixture is stirred at room temperature overnight. The mixture is cooled to 5° C. and quenched with saturated NaHCO₃. After filtration to remove the precipitated DCU, the mixture is dissolved in EtOAc (100 mL), washed with saturated NaHCO₃, brine, and then dried by MgSO₄ and concentrated to a residue purified by silica column chromatography (25% EtOAc/Hexanes) to yield compound cxxxxvi (2.91 g, 57%) as gummy foam.

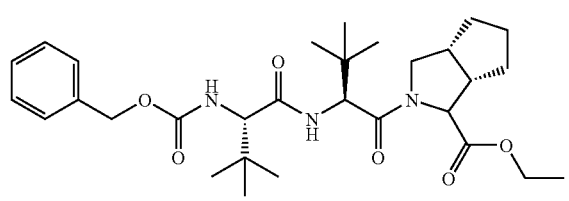

INTERMEDIATE EXAMPLE 141

Compound cviii

To a solution of compound cxxxxvi in MeOH (25 mL) cooled by an ice bath under a stream of $N_2$ is added slowly Pd/C. The mixture is hydrogenated at 1 atm overnight. The catalyst is removed by filtration, the filtrate is combined with 5 mL DMF and dried under vacuum to yield compound cviii.

INTERMEDIATE EXAMPLE 142

Compound cxxxxvii

To a solution of compound cxxxxiv (0.298 g, 2.03 mmol) and HOAt (0.276 g, 2.03 mmol) in THF cooled in ice bath is treated with DCC (2.05 mL, 2.05 mmol). After stirring in an ice bath for 0.5 hour, a solution of compound cviii in THF is added, and then DIPEA (0.39 mL, 2.2 mmol) is added. The mixture is stirred at room temperature overnight, then cooled in an ice bath, and quenched with saturated NaHCO₃. The precipitated DCU is filtered and the filtrate is dissolved in EtOAc (100 mL). The organic phase is washed with saturated NaHCO₃, brine, and then dried by MgSO₄. After removal of the organic solvent, the residue is purified by silica column chromatography (60% EtOAc/Hexanes) to yield compound cxxxxvii (0.47 g, 48%) as gummy foam.

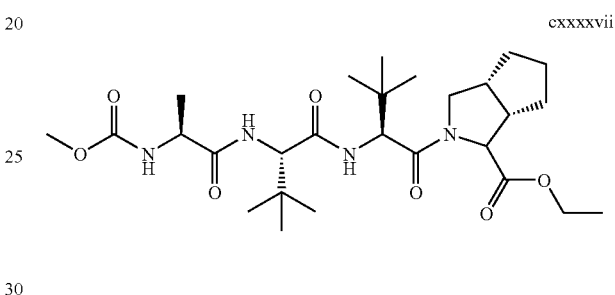

INTERMEDIATE EXAMPLE 143

Compound cxxxxviii

To a solution of compound cxxxxvii (0.47 g, 0.847 mmol) in EtOH (5 mL) at 5° C. is added NaOH (2 N, 1.31 mL, 2.62 mmol). The mixture is stirred at room temperature for 4 hours. The solution is acidified to pH ~2 with HCl (1N) and the EtOH is removed by rotary evaporation. The mixture is extracted with EtOAc (3×30 mL) and the combined extract is washed with brine, and then dried by MgSO₄. The solvent is removed and the residue is dried under vacuum to yield compound cxxxxviii (0.366 g, 82%) as gummy foam.

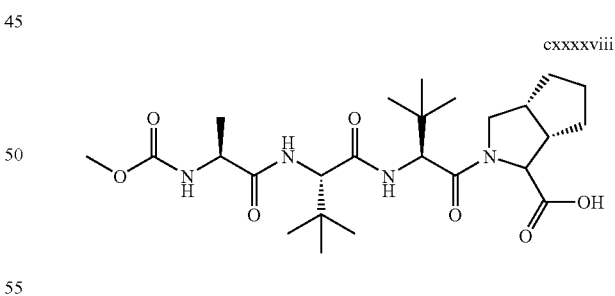

INTERMEDIATE EXAMPLE 144

Compound cil

A solution of compound cxxxxviii (0.366 g, 0.718 mmol) in DCM is cooled in an ice bath and treated with PyBop (0.599 g, 1.15 mmol). After stirring at room temperature for 0.5 hour, the mixture is cooled by an ice bath and treated with a solution of compound xiii' (0.200 g, 1.08 mmol) in THF and DIPEA (0.250 mL, 1.44 mmol). The mixture is stirred at room temperature overnight and then quenched with NH₄Cl solution. The solvent is concentrated and the mixture is dissolved in EtOAc (100 mL). The organic phase is washed with saturated NaHCO₃, brine, and then dried by MgSO₄. After removal of the organic solvent, the residue is purified by column chromatography (5% EtOH/EtOAc) to yield compound cil (0.35 g, 72%)

reaction mixture is further refluxed for 30 minutes. The reaction mixture is cooled to room temperature and diluted with DCM (200 mL). The organic phase is washed with 1 N KHSO₄. The organic phase is concentrated and dried in vacuo to yield a residue that is purified by silica gel chromatography (20% EtOAc/Hexane) to yield compound cl (2.78 g, 57%).

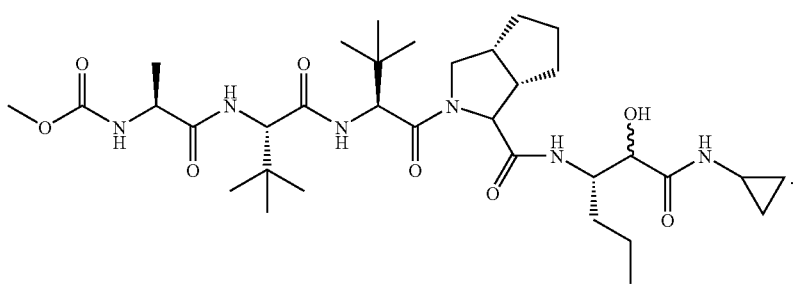

cii

INTERMEDIATE EXAMPLE 145

Compound cxxi

To a THF solution (85 mL) of N-Boc-Nva-OH (compound 1) (8.68 g, 40 mmol) is added CDI (7.79 g, 48 mmol). After stirring at room temperature for 30 minutes, the above solution is treated with a DMF solution (25 mL) containing N,O-dimethyl-hydroxylamine hydrochloride (4.25 g, 44 mmol) and DIPEA (7.66 mL, 44 mmol). The reaction mixture is stirred overnight at room temperature. The reaction mixture is then concentrated in vacuo. The resulting residue is diluted with EtOAc (300 mL). This solution is washed sequentially with 0.1 N HCl (50 mL), saturated NaHCO₃ (3×50 mL) and brine. The organic phase is concentrated in vacuo to yield a residue that is purified with silica gel chromatography (40% EtOAc/Hexanes) to compound cxxi (9.38 g, 94%).

INTERMEDIATE EXAMPLE 146

Compound cxxii

To a diethyl Et₂O solution (50 mL) of compound cxxi (9.38 g, 31.9 mmol) cooled to 0° C. is added (slowly) LAH (34.7 mL, 1 M, 34.7 mmol). The temperature of the reaction flask is maintained below 5° C. during LAH addition. Upon completion of the addition, EtOAc (20 mL) is added to the reaction to quench the excess LAH. Aqueous KHSO₄ (5%, 20 mL) is then added in a dropwise fashion in order to keep the temperature below 5° C. The organic phase is separated and then washed sequentially with 1 N HCl (3×30 mL), saturated NaHCO₃ (3×30 mL) and brine. The organic phase is concentrated and dried in vacuo to yield crude compound cxxii (5.18 g, 69%).

INTERMEDIATE EXAMPLE 147

Compound cl

To a THF (25 mL) suspension of Zn (2.75 g, 42 mmol) is added at reflux 0.2 mL of EtOC(O)CF₂Br. This is followed by slowly adding a THF solution (25 mL) of compound cxxii (3.05 g, 15.0 mmol) and EtOC(O)CF₂Br (4.84 mL, 37.5 mmol). Upon completion of the addition of both reagents, the

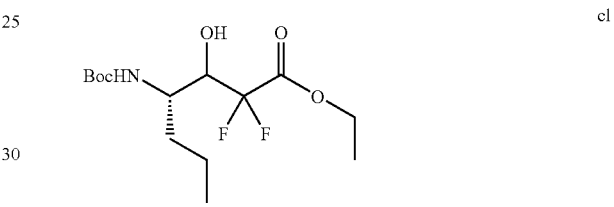

cl

This preparation is essentially the same as that disclosed by Thaisrivongs et al., *J. Med. Chem.*, 29, 2080-2087 (1986).

INTERMEDIATE EXAMPLE 148

Compound cli

A THF solution (40 mL) of compound cl (2.78 g, 8.53 mmol) is treated with 1 N NaOH (12.8 mL, 12.8 mmol). After stirring at room temperature overnight, thie solvent is partially removed in vacuo. The remaining reaction mixture is diluted with water (50 mL) and lyophilized to yield crude compound cli (2.82 g, >100%) as its sodium salt.

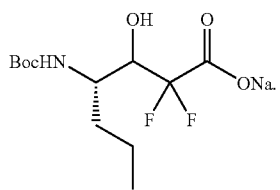

cli

This preparation is essentially the same as that disclosed by Thaisrivongs et al., *J. Med. Chem.*, 29, 2080-2087 (1986).

INTERMEDIATE EXAMPLE 149

Compound clii

A DCM solution (10 mL) of the crude compound cli (516 mg, 1.61 mmol) is treated with HOBT (436 mg, 3.23 mmol) and DIC (0.328 mL, 2.09 mmol). After stirring at room temperature for 30 minutes, the reaction mixture is treated with a DCM solution (5 mL) containing glycine benzylester-TsOH salt (815 mg, 2.42 mmol) and DIPEA (0.422 mL, 2.42 mmol). After stirring at room temperature for 12 hours, the reaction mixture is quenched with water and extracted with EtOAc. The organic phase is dried and concentrated in vacuo and purified by silica gel chromatography (40% EtOAc/hexanes) to yield compound clii (495 mg, 69%).

$^1$H NMR of compound clii (400 MHz, CDCl$_3$): δ 7.29-7.21 (i, 5H), 5.16 (bs, 2H), 4.89 (bs, 1H), 4.20-3.90 (m, 4H), 3.80 (bs, 1H), 1.75-1.42 (m, 4H), 1.38 (s, 9H), 0.87 (m, 3H).

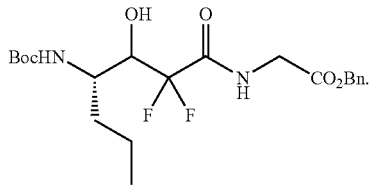

clii

Starting from crude compound cli, compounds cliii (83%) and cliv (50%) are prepared in an identical method to that described for compound clii.

$^1$H NMR of compound cliii (400 Mz, CDCl$_3$): δ 7.49 (bs, 1H), 7.34-7.24 (m, 5H), 5.13 (AB q, J=12.2 Hz, J'=23.9 Hz, 2H), 4.88 (bd, J=8.8 Hz, 1H), 4.53 (m, 1H), 3.98-3.91 (m, 2H), 3.82 (m, 1H), 1.65-1.20 [m, 16H, including singlet at 1.37 (9H)], 0.86 (t, J=7.3 Hz, 3H).

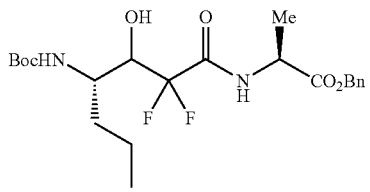

cliii $^1$H NMR of compound cliv (400 MHz, CDCl$_3$): δ 7.60-7.0 (m, 10H), 5.30-5.00 (m, 2H), 5.00-4.75 (m, 2H), 4.15-3.70 (m, 3H), 3.30-3.00 (m, 2H), 1.75-1.20 [m, 13H, including singlet at 1.36 (9H)], 0.86 (bs, 3H).

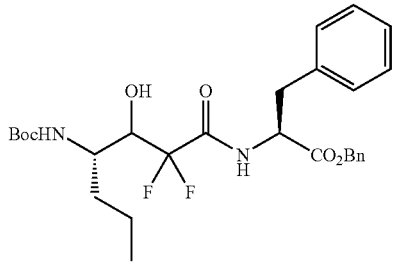

cliv

INTERMEDIATE EXAMPLE 150

Compound clv

To a DCM (10 mL) and THF (5 mL) solution of the crude compound cli (1 g, 3.13 mmol) is added HOBT (634 mg, 4.69 mmol) and EDCI (781 mg, 4.07 mmol), and then (s)-α-methylbenzylamine (0.604 mL, 4.69 mmol). The reaction mixture is stirred overnight at room temperature and then quenched with water. The reaction mixture is extracted with EtOAc. The organic phase is washed with brine and dried by Na$_2$SO$_4$. The organic phase is concentrated in vacuo to yield a residue that is purified by silica gel chromatography (20% EtOAc/hexanes) to yield compound clv (459 mg, 37%). $^1$H NMR of compound clv(400 MHz, CDCl$_3$): δ 7.32-7.21 (m, 6H), 5.00 (m, 1H), 4.75 (m, 1H), 3.94 (m, 2H), 3.70 (ma, 1H), 1.65-1.15 [m, 16H, including doublet at 1.51 (J=6.8 Hz, 3H), singlet at 1.39 (9H)], 0.82 (m, 3H).

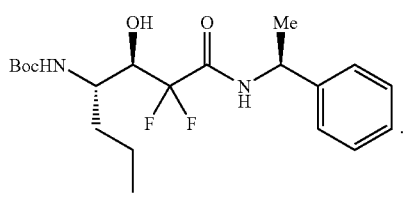

clv

INTERMEDIATE EXAMPLE 151

Compound clvi

Compound clv (220 mg, 0.55 mmol) is dissolved in 4 N HCl in dioxane (10 mL). The reaction mixture is stirred at room temperature for 2 hours and then concentrated in vacuo to give the crude compound clvi (~100%) as its HCl salt.

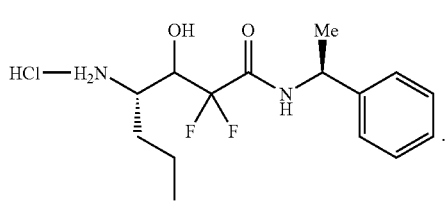

clvi

Following the procedure described for preparing compound clvi, compounds clvii, clviii, and clix are prepared in almost quantitative yield from the crude compound cli.

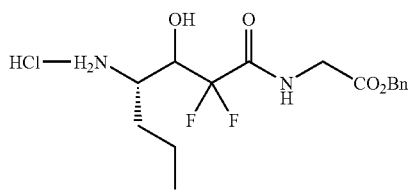

clvii

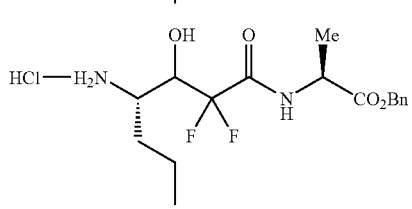

clviii

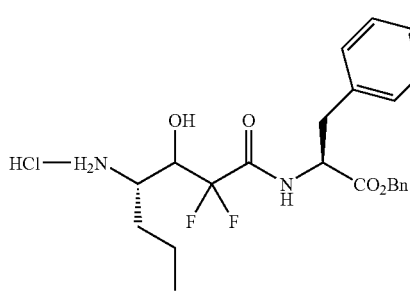

clix

INTERMEDIATE EXAMPLE 152

Compound clx

A DCM solution (4 mL) of the HCl salt of compound vii (96 mg, 0.144 mmol) is treated with PyBOP (120 mg, 0.23 mmol) and DIPEA (0.1 mL, 0.576 mmol). After stirring at room temperature for 30 minutes, the solution is treated with a THF solution (4 mL) containing compound clv (0.288 mmol) and DIPEA (0.2 mL, 1.152 mmol). The reaction mixture is stirred at room temperature overnight. The reaction mixture is then diluted with EtOAc (50 mL), and the organic phase then washed with $NaHCO_3$ and brine. The organic phase is concentrated in vacuo and the residue purified by silica gel chromatography (80% EtOAc/hexanes) to yield compound clx (113 mg, 89%).

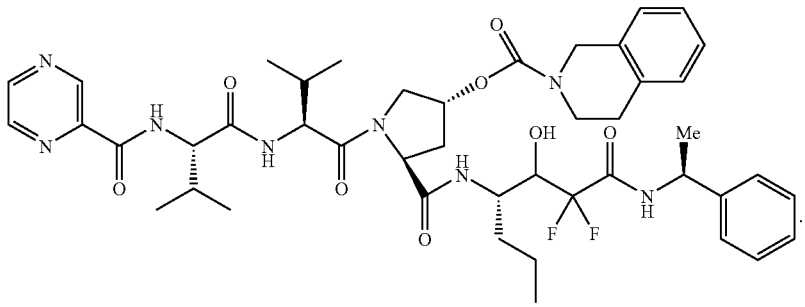

INTERMEDIATE EXAMPLE 153

Compound clxi

A DCM solution (6 mL) of compound vii (140 mg, 0.235 mmol) is treated with PyBOP (196 mg, 0.376 mmol) for 30 minutes. A THF solution (6 mL) of compound clvii (~0.47 mmol) and DIPEA (0.327 mL, 1.88 mmol) is then added to the above solution. The reaction mixture is stirred at room temperature overnight and quenched with water (30 minutes). The reaction mixture is extracted with EtOAc (50 mL). The organic phase is washed with $NaHCO_3$ and brine. The combined aqueous layers are back extracted with EtOAc (50 mL). The combined organic phases are dried and concentrated in vacuo. The resultant residue is purified by silica gel chromatography (80-100 EtOAc/hexanes) to yield compound clxi (104 mg, 48%).

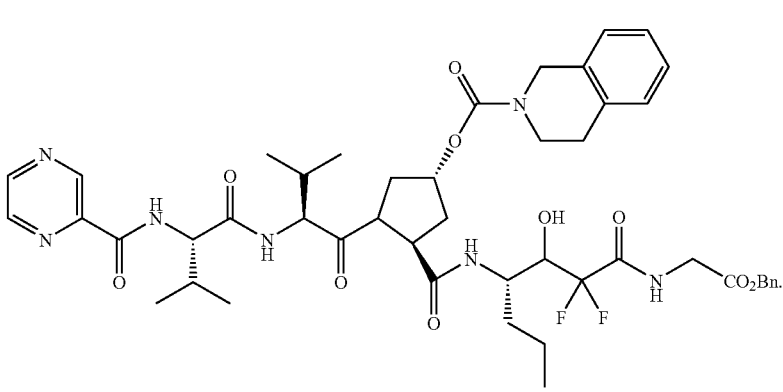

INTERMEDIATE EXAMPLE 154

Compound clxii

To a DCM solution (10 mL) of compound clxi (280 mg, 0.304 mmol) is added DMP reagent reagent (193 mg, 0.456 mmol). The reaction mixture is stirred at room temperature for 3 hours and quenched with 10% $Na_2SO_3$. The organic phase is washed with $NaHCO_3$ and brine. The resulting organic phase is dried and concentrated in vacuo to yield a residue that is purified with silica gel chromatography (80-100% EtOAc/hexanes) to yield compound clxii (271 mg, 97%).

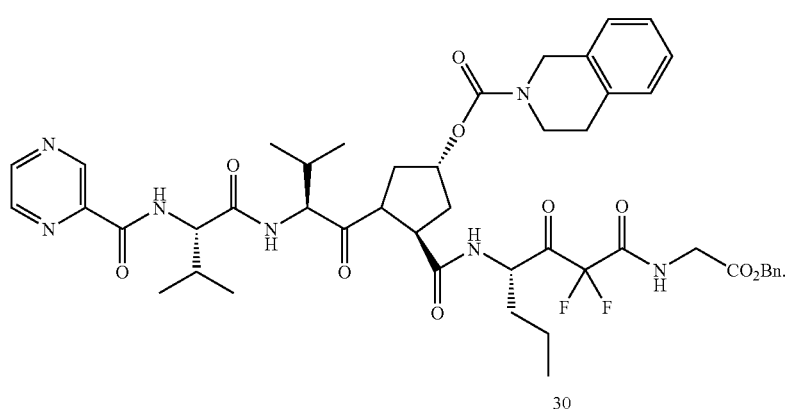

clxii

INTERMEDIATE EXAMPLE 155

Compound clxiii

Compound lxxxiii (220 mg, 0.43 mmol) is taken up in DCM (5 mL). PyBOP (270 mg, 0.51 mmol) is added to the DCM solution and stirred 5 minutes. Compound xxxvi' (0.51 mmol) in THF (5.1 mL) is added drop-wise to this solution. DIPEA (0.09 mL, 0.51 mmol) is added to reaction mixture and stirred overnight under $N_2$. The next day, the reaction mixture is diluted with EtOAc, washed with saturated $NaHCO_3$, washed with brine. Purification by 70% to 90% EtOAc/Hexane gradient yields compound clxiii (180 mg, 56%).

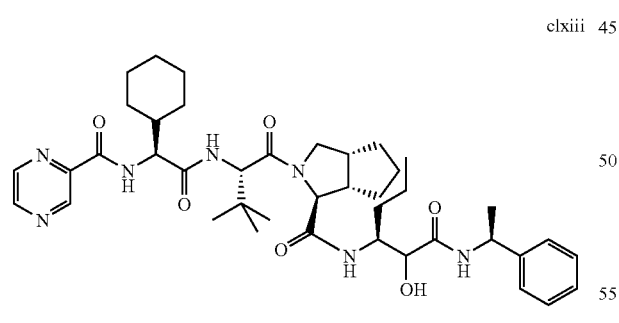

clxiii

INTERMEDIATE EXAMPLE 156

Compound clxiv

Compound cxxv (2.09 g, 7.4 mmol) is taken up in DCM (20 mL). PyBOP (4.64 g, 8.9 mmol) and HOBt (1.2 g, 8.9 mmol) are added to this solution and stirred five minutes. The resulting mixture is lowered to 0° C where S(−)-α-Methylbenzylamine (1.15 mL, 8.9 mmol) and DIPEA (1.55 mL, 8.9 mmol) are added. The reaction is stirred overnight with warming to room temperature. The reaction mixture is washed with 0.1 N HCl, sat $NaHCO_3$, and brine. Purification by 30% EtOAc/Hexanes yields compound clxiv (1.6 g, 56.3%).

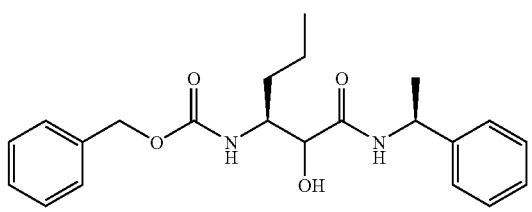

clxiv

INTERMEDIATE EXAMPLE 157

Compound xxxvi'

Compound clxiv (1.48 g, 3.8 mmol) is hydrogenated using 10% Pd/C (300 mg) in MeOH (50 mL). The reaction mixture stirred overnight under $H_2$. The reaction mixture is filtered through celite and concentrated to give compound xxxvi' (895 mg, 94.2%).

INTERMEDIATE EXAMPLE 158

Compound clxvi

To a DCM solution (15 mL) of compound clxv (2 g, 8.2 mmol) is added HOAt (1.34 g,

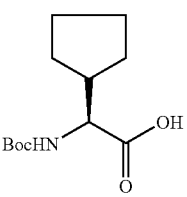

clxv 9.84 mmol) and DCC (9.84 mL, 1 M, 9.84 mmol). After stirring at room temperature for 20 minutes, a THF solution (9.84 mL) containing tert-L-Leucine methyl ester-hydrochloride (9.84 mmol) and DIPEA (1.72 mL, 9.84 mmol) is added to the above solution. Then DMAP (1 g, 8.2 mmol) is added at room temperature. The reaction is stirred at room temperature overnight. Following standard aqueous work-up and silica gel chromatography (20% EtOAc/Hexanes), compound clxvi (1.75 g, 58%) is obtained.

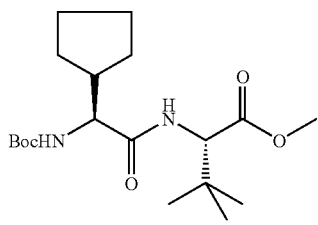

clxvi

INTERMEDIATE EXAMPLE 159

Compound clxvii

To a THF solution (35 mL) of compound clxvi (1.75 g, 4.73 mmol) is added 4 N HCl solution in dioxane (11.8 mL, 47.3 mmol). The reaction is stirred at room temperature overnight. At this point, the solvent is removed under reduced pressure to yield crude clxvii (~100%), which is redissolved in DMF and used directly in the next reaction.

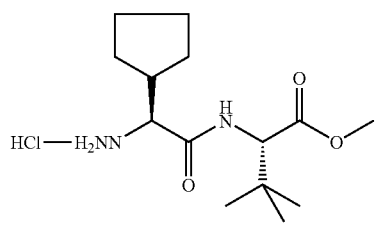

clxvii

INTERMEDIATE EXAMPLE 160

Compound clxviii

To a DCM solution (15 mL) containing 2-pyrazinecarboxylic acid (447 mg, 3.6 mmol), PyBOP (1.87 g, 3.6 mmol) is added a DMF solution (15 mL) of compound clxvii (811 mg, 3 mmol). To the resulting mixture is then added DIPEA (0.63 mL, 3.6 mmol). The reaction is stirred overnight at room temperature and then quenched with water. The reaction mixture is extracted with EtOAc. The organic layer is washed with brine and concentrated in vacuo to provide a residue that is purified by silica gel chromatography (40% EtOAc/Hexanes) to yield compound clxviii (0.93 g, 82%).

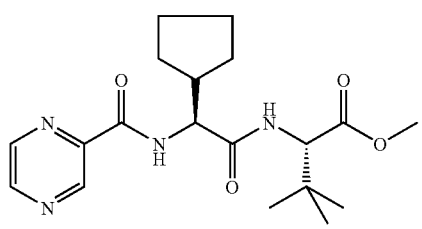

clxviii

INTERMEDIATE EXAMPLE 161

Compound clxix

To a MeOH solution (10 mL) of compound clxviii (0.93 g, 2.47 mmol) is added 2 N NaOH (3.71 mL, 7.41 mmol). The reaction is stirred at room temperature overnight. Then the reaction is acidified to pH 3 using 1 N HCl. The reaction is diluted with EtOAc (75 mL), and washed with water and brine. The organic layer thus obtained is dried and concentrated in vacuo to give compound clxix (~100%).

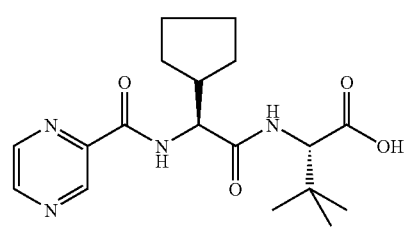

clxix

INTERMEDIATE EXAMPLE 162

Compound clxx

A DCM solution (10 mL) of compound clxix (2.47 mmol) is treated with HOAt (436 mg, 3.21 mmol) and DCC (3.2 mL, 1 M, 3.2 mmol). After stirring for 30 minutes, the reaction mixture is treated with a THF solution (13.6 mL) of compound v (499 mg, 2.72 mmol). After stirring at room temperature overnight, white solids (urea) are filtered. The filtrates are concentrated in vacuo to give a residue that is purified by silica gel chromatography to yield compound clxx (0.99 g, 76%).

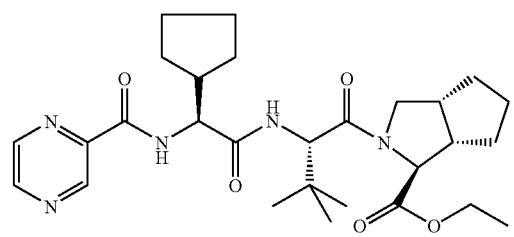

clxx

INTERMEDIATE EXAMPLE 163

Compound clxxi

An EtOH solution (20 mL) of compound clxx (0.99 g, 1.88 mmol) is treated with 2 N NaOH (2.81 mL, 5.63 mmol). After stirring at room temperature overnight, the reaction mixture is acidified to pH 3 with 1 N HCl. The reaction mixture is extracted with EtOAc (75 mL). The organic layer is dried and concentrated in vacuo to give compound clxxi (772 mg, 82%).

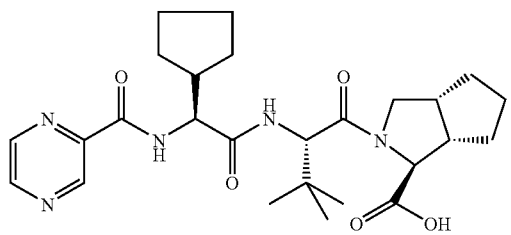

INTERMEDIATE EXAMPLE 164

Compound clxxi

A DCM solution (10 mL) of compound clxxi (290 mg, 0.58 mmol) is treated with PyBOP (484 mg, 0.93 mmol). After stirring at room temperature for 20 minutes, the reaction mixture is treated with a THF solution (7.5 mL) of compound xiii' (140 mg, 0.75 mmol), followed by DIPEA (0.13 mL, 0.75 mmol). After stirring overnight at room temperature, the reaction is quenched with water and extracted with EtOAc. The resulting organic layer is washed with brine and dried and concentrated iin vacuo. The resulting residue is purified by silica gel chromatography (5% EtOH/EtOAc) to yield compound clxxii 290 mg (75%).

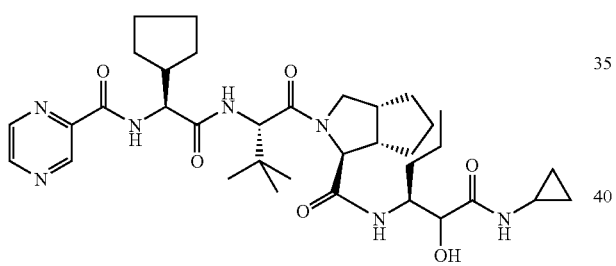

INTERMEDIATE EXAMPLE 165

Compound clxxiv

Compound lxxxiii (600 mg, 1.17 mmol) is taken up in DCM (4 mL). PyBOP (670 mg, 1.3 mmol) is added, stirred five minutes, and cooled to 0° C. Compound clxxiii (333 mg, 1.3

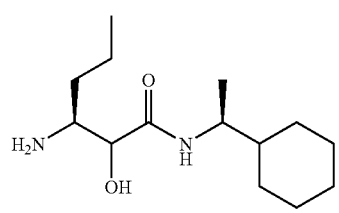

mmol) in THF (13 mL) is added drop-wise to this solution. DIPEA (0.23 mL, 1.3 mmol) is added to reaction mixture and allowed to warm to ambient temperature with stirring for two nights. The next day, the reaction is concentrated and purified by 2% EtOH/EtOAc to give crude compound clxxiv (900 mg, excess of 100%).

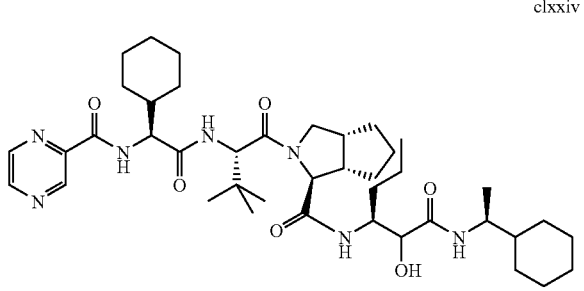

INTERMEDIATE EXAMPLE 166

Compound clxxxv

Compound cxxv (3.01 g, 10.7 mmol) is taken up in DCM (30 mL) and the temperature lowered to −78° C. PyBOP(6.1 g, 11.7 mmol) and HOBT (1.58 g, 11.7 mmol) are added to this solution followed by (S)-(+)-1-cyclohexylethylamine, compound clxxv, (1.74 mL, 11.7 mmol) and DIPEA (2.1 mL, 11.7 mmol). The resulting mixture stirred overnight at room temperature. The next day, the reaction mixture is diluted with EtOAc, washed with 0.1 N HCl, saturated NaHCO$_3$, and brine. The product is purified in 40% EtOAc/Hex to give 2 g (47.8%) of compound clxxvi.

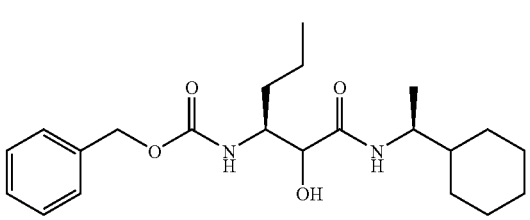

INTERMEDIATE EXAMPLE 167

Compound clxii

Compound clxxvi (2 g, 5.13 mmol) is hydrogenated using 10% Pd/C (500 mg) in MeOH (40 mL). The reaction mixture stirred overnight under H$_2$. The reaction mixture is filtered through celite and concentrated to give compound clxxiii (1.31 g, 99.8%).

INTERMEDIATE EXAMPLE 168

Compound clxxix:

In a round bottom flask under inert atmosphere, compound clxxvii [(S)-(−)-2-oxo 1,5

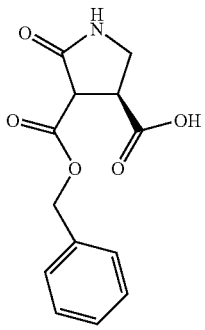

clxxvii

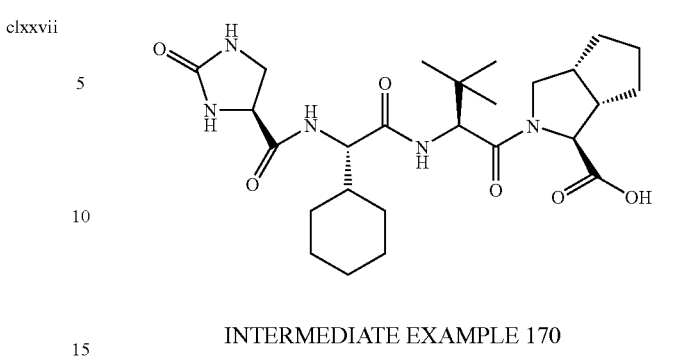

INTERMEDIATE EXAMPLE 170

Compound clxxxi imidazoline dicarboxylic acid 1-benzyl ester] (290 mg, 1.1 mmol) is dissolved in anhydrous DMF (6 mL). HOAt (151 mg, 1.2 mmol) is added and the reaction is stirred at room temperature for 25 minutes. The reaction is then cooled down in an ice bath. DIC (0.2 mL, 0.16 g, 1.2 mmol) is then added followed by the addition of compound clxxviii (1 mmol, 435 mg.) in anhydrous DMF (4 mL). The rtertion is allowed to rise slowly to room temperature and stirred for 2 days. The reaction is then dumped in a separatory funnel containing 120 mL of EtOAc and washed 2× with 1 N HCl (50 mL) and 1× brine. The organic layer is separated, dried over $MgSO_4$. The solvent evaporated under reduced pressure and the residue purified by chromatography on silica gel (load in DCM and elute with 30% then 50% EtOAc/DCM then 2% MeOH(EtOAc) to yield product clxxix (434 mg, 64%).

In a round bottom flask under inert atmosphere, compound clxxx (279 mg, 0.54 mmol) is dissolved in anhydrous DMF (6 mL). HOAt (82 mg, 0.65 mmol) is added and the reaction is stirred at room temperature for 25 minutes. The reaction is then cooled down in an ice bath. DIC (0.11 mL, 0.65 mmol) is then added, followed by the addition of compound xiii' (0.7 mmol) in anhydrous DMF (4 mL). The reaction is allowed to rise slowly to room temperature and stirred for 21 hours. The reaction is then dumped in a separatory funnel containing 120 mL of EtOAc and washed 2× with 1 N HCl (50 mL) and 1× brine. The organic layer is separated, dried over MgSO4. The solvent evaporated by reduced pressure and the product cleaned by chromatography on silica gel (load in DCM and elute with 50% EtOAc/Hexane, then 3% MeOH/EtOAc, then 20% EtOH/EtOAc). After removal of solvent, the residue is redissolved in Dri Solv THF and filtered to remove any silica gel. Removal of the solvent then yields compound clxxxi (434 mg, 64% yield).

clxxix

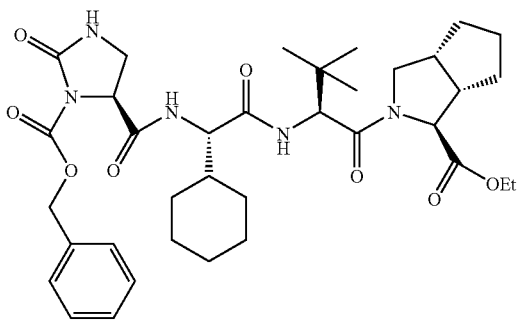

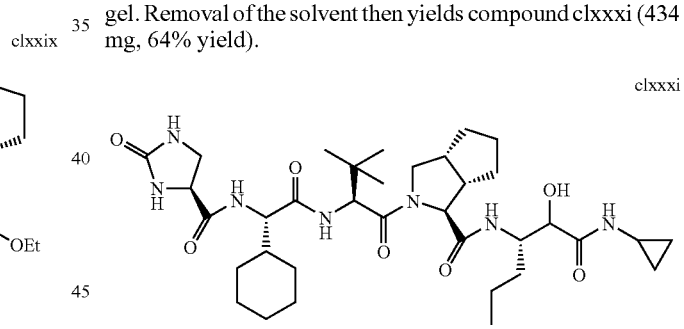

clxxxi

INTERMEDIATE EXAMPLE 169

Compound clxxx

INTERMEDIATE EXAMPLE 171

Compound clxxxiii

The starting material clxxix (434 mg, 0.64 mmol) is dissolved in Dioxane (6 mL) and 0.5 M aqueous NaOH solution (4 mL, 3 eq.). The reaction is run overnight. TLC in 100% EtOAc (using PMA stain) shows in addition to the expected acid product at the origin, a faster running product. The reaction mixture is acidified to pH 2 with 1 N HCl, and then extracted 2× with EtOAc. Solid NaCl is added to the aqueous solution to facilitate the extraction. The organic extracts are then combined, dried over $MgSO_4$ and evaporated under reduced pressure. MS indicates that the CBZ group is removed by the hydrolysis. The resulting compund clxxx (quantitative yield) is used as is in the next step.

In a round bottom flask under inert atmosphere, 6-hydroxy picolinic

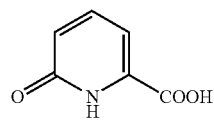

(153 mg, 1.1 mmol) is dissolved in anhydrous DMF (6 mL). HOAt (151 mg, 1.2 mmol) is added and then thereaction is stirred at room temperature for 25 minutes. The reaction is then cooled down in an ice bath. DIC (0.2 mL, 0.16 g, 1.2 mmol) is then added followed by the addition of the compound clxxxii (1.0 mmol, 435 mg.) in anhydrous DMF (4 mL). The

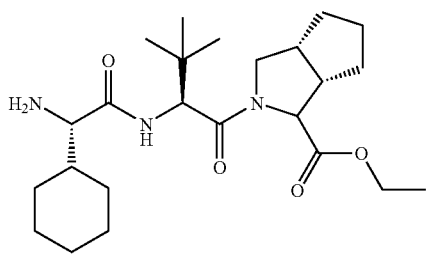

clxxxii reaction is allowed to rise slowly to room temperature and stirred for 2 days. The reaction is then dumped in a separatory funnel containing 120 mL of EtOAc and washed 2× with 1 N. HCl (50 mL) and 1× with brine. The organic layer is separated, dried over MgSO$_4$. The solvent is evaporated by reduced pressure and the product purified by chromatography on silica gel (load in DCM, elute with 30%, then 50% EtOAc/DCM, and then 2% MeOH/EtOAc) to yield compound clxxxiii collected (314 mg, 56%).

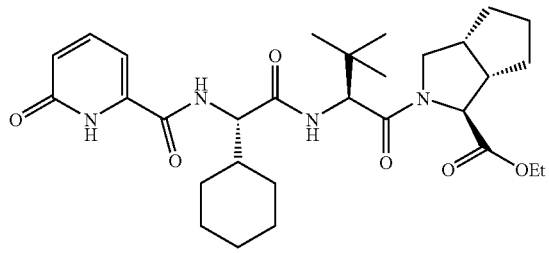

INTERMEDIATE EXAMPLE 172

Compound clxxxiv

The starting material clxxxiii (314 mg, 0.56 mmol) is dissolved in dioxane (5 mL) and 0.5 M NaOH (3.4 mL, 3 eq). The reaction is run overnight TLC in 100% EtOAc (using UV) shows complete conversion to the slow running acid product at the origin. The reaction is acidified to pH 2 with 1 N HCl, and then extracted 2× with EtOAc. Solid NaCl is added to the aqueous to facilitate the extraction. The organic extracts are then combined, dried over MgSO$_4$, and then evaporated under reduced pressure to yield compound clxxxiv (0.5 mmol, 89%) that is used as is in the next step.

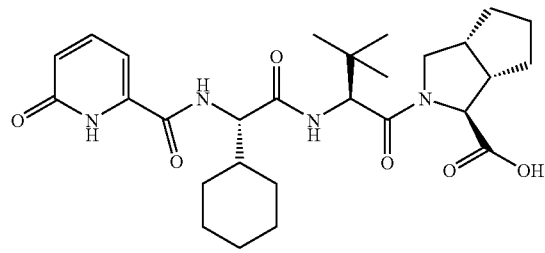

clxxxiv

INTERMEDIATE EXAMPLE 173

Compound clxxxv

In a round bottom flask under inert atmosphere, acid compound clxxxiv (265 mg, 0.5 mmol) is dissolved in anhydrous DMF (6 mL). HOAT (75.6 mg, 0.6 mmol) is added and the reaction is stirred at room temperature for 25 minutes. The reaction is then cooled down in an ice bath. DIC (0.1 mL, 0.6 mmol) is then added followed by the addition of the compound xiii' (0.65 mmol) in anhydrous DMF (4 mL). The reaction is allowed to rise slowly to room temperature and stirred for 21 hours. The reaction is then dumped in a separatory funnel containing EtOAc (120 mL) and washed 2× with 1 N HCl (50 mL) and 1× with brine. The organic layer is separated, dried over MgSO$_4$. The solvent is evaporated by reduced pressure and the product purified by chromatography on silica gel (load in DCM, elute with 50% EtOAc/Hexane, then pure EtOAc, and then 4% MeOH/EtOAc) to yield product compound clxxxv (185 mg, 52%).

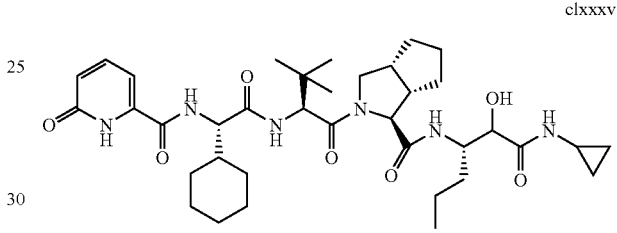

clxxxv

INTERMEDIATE EXAMPLE 174

Compound cxxxxiv'

To a solution of D-alanine (5 g, 56.1 mmol) in 1 N NaOH (152 mL, 152 mmol) at 0° C. is added a solution of MeOC(O)Cl (6.5 mL, 84.2 mmol) in diethyl ether (30 mL). The mixture is stirred in ice bath for 3 hours and then adjusted to pH 9 with 1 N NaOH. After stirring at room temperature for 1 hour, the mixture is washed with ether (3×50 mL), acidified to pH ~2 with 5 N HCl, extracted with EtOAc (5×50 mL). The organic extract is washed with water, brine, and then dried (MgSO$_4$). The solvent is removed to yield compound cxxxiv, N-methoxycarbonyl-D-alanine, as colorless oil (6.48 g, 79%).

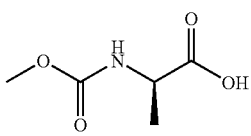

cxxxiv

INTERMEDIATE EXAMPLE 175

Compound clxxxvi

To a solution of N-methoxycarbonyl-D-alanine (0.193 g, 1.31 mmol) and HOAt (0.177 g, 1.31 mmol) in DCM (10 mL) cooled in ice bath is treated with DCC (1.31 mL, 1.31 mmol). After stirring in an ice bath for 0.5 hour, a solution of prepared compound clxxxii (0.88 mmol) in THF (8.8 mL) is added.

The mixture is warmed up to room temperature and stirred overnight, then cooled in ice bath, and quenched with saturated NaHCO₃ solution. The precipitates are filtered and the filtrate is taken up in EtOAc (100 mL). The organic layer is washed with saturated NaHCO₃ solution, brine, and then dried (MgSO₄). After removal of the solvent, the residue is purified by silica column chromatography (60% EtOAc/Hexane) to yield compound clxxxvi as gummy foam (0.321 g, 68%).

clxxxvi

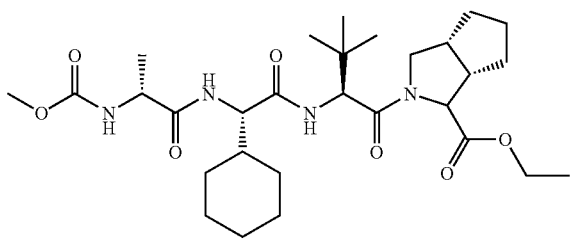

INTERMEDIATE EXAMPLE 176

Compound clxxxvii

To a solution of compound clxxxvi (0.321 g, 0.597 mmol) in EtOH (5 mL) at 5° C. is added 2 N NaOH (1.05 mL, 2.1 mmol). The mixture is stirred at room temperature for 4 hours. The solution is acidified to pH ~2 with 1 N HCl and EtOH is removed by rotary evaporation. The mixture is extracted with EtOAc (3×30 mL) and the combined extract is washed with brine, and then dried (MgSO₄). Solvent is removed and the residue is dried under vacuum to give compound clxxxvii as gummy foam (0.235 g, 77%).

clxxxvii

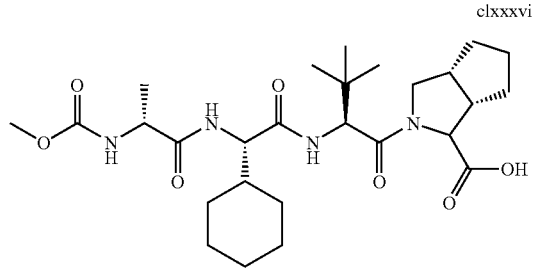

INTERMEDIATE EXAMPLE 177

Compound clxxxviii

A solution of compound clxxxvii (0.363 g, 0.712 mmol) in DCM (10 mL) is cooled in an ice bath and treated with PyBOP (0.594 g, 1.14 mmol). After stirring at room temperature for 0.5 hour, the mixture is cooled in ice bath and treated with a solution of compound xiii' (1.1 mmol) in THF (11 mL) and DIPEA (0.249 mL, 1.42 mmol). The mixture is stirred at room temperature overnight and quenched with NH₄Cl solution. The solvent is concentrated and the mixture is taken up in EtOAc (100 mL). The organic layer is washed with saturated NaHCO₃ solution, brine, and then dried (MgSO₄). After removal of the solvent, the residue is purified by column chromatography (5% EtOH/EtOAc) to give clxxxviii (0.341 g, 71%).

INTERMEDIATE EXAMPLE 178

Compound clxxxix

Diaminopropionic acid (3 g, 28.7 mmol) is taken up in 1 M NaOH (86.2 mL, 86.2 mmol) and cooled to 0° C., and then MeOC(O)Cl (5.54 mL, 71.75 mmol) is added in Et₂O (25 mL). The resulting mixture stirred overnight warming to room temperature. The reaction mixture pH is lowered to 2 and aqueous layer is extracted 3× with EtOAc. Extracts are combined and dried over Na₂SO₄, filtered and concentrated to yield compound clxxxix (3.09 g, 48.9%).

clxxxix

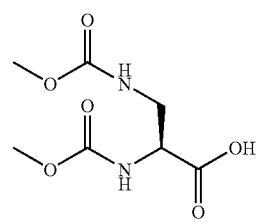

INTERMEDIATE EXAMPLE 179

Compound cc

Compound clxxxix (340 mg, 1.55 mmol) is taken up in DCM (4 mL). DCC (1.7 mmol) and HOAt (235 mg, 1.7 mmol) are added followed by compound clxxi (1.7 mmol) in DCM (3.4 mL). The reaction mixture stirred overnight. The next day, the reaction mixture is filtered through a pad of silica and concentrated. Purification is achieved in 75% EtOAc/Hex to give compound clxxxx (715 mg, 72.4%).

clxxxx

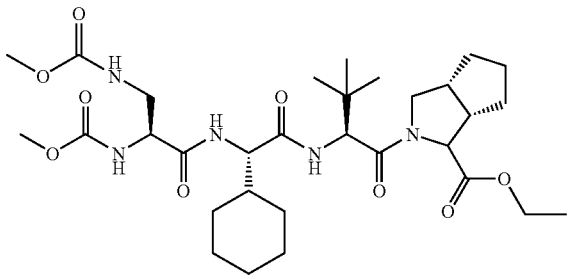

INTERMEDIATE EXAMPLE 180

Compound clxxxxi

Compound clxxxx (715 mg, 1.12 mmol) is hydrolyzed under standard conditions using EtOH (4 mL) and 1 N NaOH (3 eq) to yield compound clxxxxi (600 mg, 88.0%).

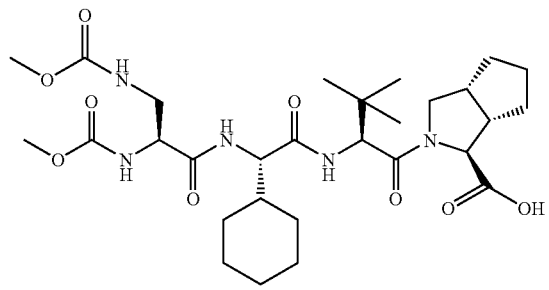

INTERMEDIATE EXAMPLE 181

Compound clxxxxii

Compound clxxxxi (550 mg, 0.9 mmol) is taken up in DCM (8 mL). PyBOP (675 mg, 1.3 mmol) is added followed by compound xiii' (1.3 mmol) in THF (1.3 mL). DIPEA (0.23 mL, 1.3 mmol) is added and the resulting solution stirred overnight. The next day, the reaction is diluted with EtOAc, washed with saturated NaHCO₃, and then brine, before being concentrated to yield a residue. The resulting residue is purified by 5% EtOH/EtOAc to yield compound clxxxxii (290 mg, 41.5%).

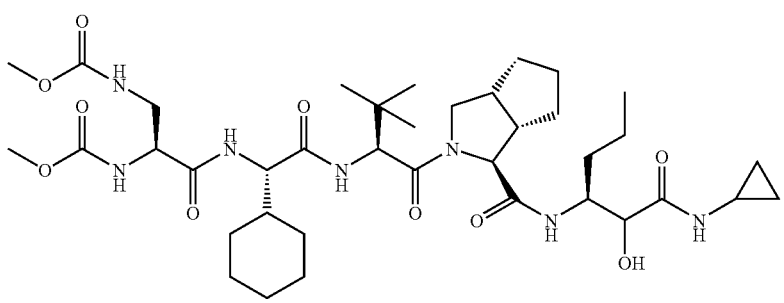

INTERMEDIATE EXAMPLE 182

Compound clxxxxii

Cbz-cyclohexyglycine-tert-leucine methyl ester (7.36 g, 17.6 mmol) is hydrolyzed under standard conditions using MeOH (60 mL) and 1 N NaOH (52.8 mL, 3 eq) to yield intermediate clxxxxii (92%).

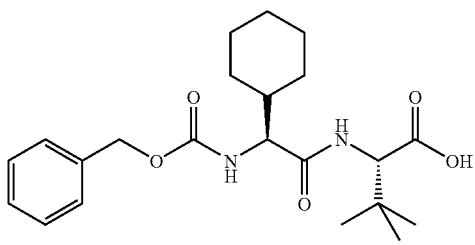

INTERMEDIATE EXAMPLE 183

Compound clxxxxiv

Compound clxxxxiii (3.82 g, 9.46 mmol) is taken up in DCM (30 mL). DCC (11.35 mmol) in DCM (11.35 mL) is added, followed by the addition of HOAt (1.54 g, 11.35 mmol). The resulting mixture stirred five minutes and compound v (9.46 mmol) in THF (40 mL) is added. The resulting mixture is stirred overnight. The next day, the reaction mixture is diluted with EtOAc, washed with 1 N HCl, saturated NaHCO₃, and then brine, before being concentrated to yield a residue. The reulting reside is purified by 20% to 30% gradient on silica gel to give compound clxxxxiv (3.03 g, 56.3%).

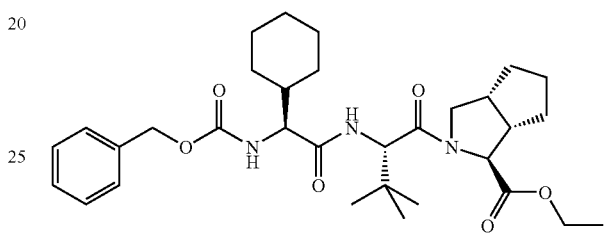

INTERMEDIATE EXAMPLE 183

Compound clxxxii

Compound clxxxxiv (3.03 g, 5.33 mmol) is hydrogenated using 10% Pd/C (500 mg) in MeOH (30 mL) under H₂ for 4 hours to yield compound clxxxii (2.3 g, 99%).

INTERMEDIATE EXAMPLE 184

Compound clxxxxv

To a solution of 1-amino-1-cyclohexanecarboxylic acid (2.86 g, 20 mmol) in MeOH (40 mL) is added dropwise SOCl₂ (3 mL) at 0° C. The mixture is slowly warmed up to room temperature and then refluxed for 5 hours. Et2O is then added to the clear solution and the precipitate is isolated. The solid is further dried over vacuum to yield compound clxxxxv (95%) as white powder.

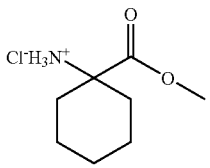

clxxxxv

INTERMEDIATE EXAMPLE 185

Compound clxxxxvi

2-Pyrazinecarboxylic acid (1 g, 8 mmol, 1 eq) is dissolved in DCM (15 mL) with addition of HOAt (1.1 g, 8 mmol) and DCC (8 mL, 1 M) in DCM. After stirring at room temperature for 20 minutes, compound clxxxxv (1.3 g, 8 mmol) is added to the activated mixture. DIPEA (2 mL, 12 mmol) is added subsequently, followed by DMAP (1.5 g, 12 mmol). After stiring over 3 days at room temperature, the reaction mixture is filtered through celite, concentrated and the desired product clxxxxvi is purified by column chromatography (50% EtOAc/hexane) as yellow oil (2.1 g, 100%).

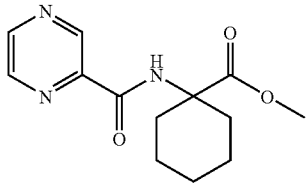

clxxxxvi

INTERMEDIATE EXAMPLE 186

Compound clxxxxvii

Compound clxxxxvi (1.06 g, 2.6 mmol) is dissolved in MeOH (30 mL) with addition of 2 N NaOH (aq) (12 mDL, 24 mmol). The solution is stirred at room temperature overnight before TLC (50% EtOAc/hexane) indicates complete hydrolysis. The solution is then acidified to pH 3 by 5 N HCl and diluted with EtOAc and followed by extraction of the organic layer. The organic layer is subsequebtly washed with brine and dryed over MgSO$_4$ to yield compound clxxxvii (84%) upon concentration.

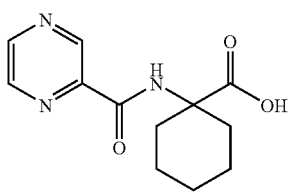

clxxxxvii

INTERMEDIATE EXAMPLE 187

Compound clxxxxviii

Compound clxxxvii (1.6 g, 6.4 mmol) is dissolved in DCM (18 mDL) and then HOAt (0.96 g, 7 mmol) and DCC (7 mL, 1 M in DCM) are subsequently at room temperature. After stirring at room temperature for 20 minutes, L-tert-leucine methyl ester hydrochloride (7 mL, 1 M in THF) is added to the activated mixture. DIPEA (1.2 mL, 7 mmol) is added subsequently, followed by DMAP (1.2 g, 9.8 mmol). After stirring over 3 days at room temperature, the reaction mixture is filtered through celite, purified by column chromatography and concentrated to yield compound clxxxxviii (60% EtOAc/hexane) as white solid (1.74 g, 72%).

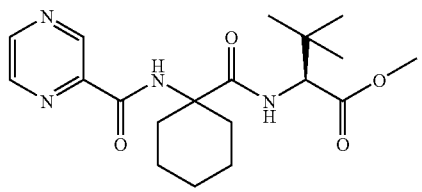

clxxxxix

INTERMEDIATE EXAMPLE 188

Compound cic

Compound clxxxxviii (1.74 g, 4.6 mmol) is dissolved in MeOH (22 mL) with addition of 2 N NaOH (aq) (7 mL, 14 mmol). The solution is stirred at room temperature overnight before TLC (50% EtOAc/hexane) indicated complete hydrolysis. The solution is acidified to pH 3 by 5 N HCl and diluted with EtOAc and then the organic layer is extracted. The organic layer is washed with brine and dried over MgSO$_4$ and then concentrated to yield compound cic (100%).

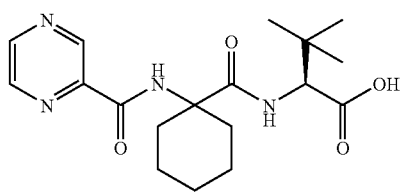

cic

INTERMEDIATE EXAMPLE 189

Compound cc

To a DCM solution (15 mL) of compound cic (1.5 g, 4.1 mmol) at room temperature is added HOAt (610 mg, 4.5 mmol), followed by 1 M DCC solution in DCM (4.5 mL, 4.5 mmol). After stirring for 30 minutes at room temperature, then a THF solution (20 mL, 0.2 M) of compound v (4 mmol) is added. The reaction is stirred at room temperature overnight. Then, the reaction is filtered through celite. The filtrate is concentrated to a yellow oil which is purified by silica gel chromatography (50% EtOAc/hexane) to yield compound cci (660 mg, 32%).

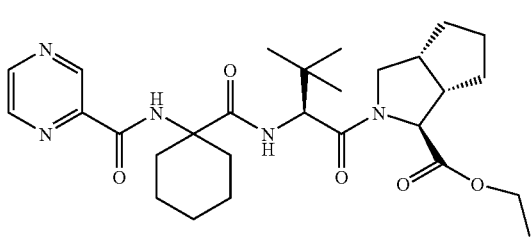

cc

INTERMEDIATE EXAMPLE 190

Compound cci

To an EtOH solution (6 mL) of compound cc (600 mg, 1.13 mmol) is added 2 N NaOH (1.7 mL, 3.4 mmol). The reaction is stirred for 2 hours at room temperature, then acidified to pH 3 by 5 N HCl. The mixture is then diluted with EtOAc, followed by extraction of the organic layer. Subsequently, the organic layer is washed with brine and then dried over $MgSO_4$ to yield compound cci (92%) upon concentration.

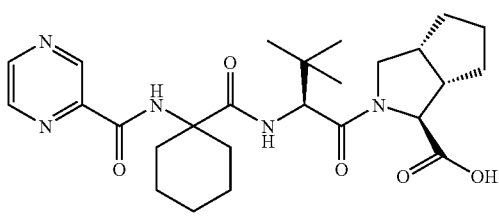

cci

INTERMEDIATE EXAMPLE 191

Compound ccii

To a DCM solution (8 mL) of ccii (310 mg, 0.62 mmol) is added PyBOP (420 mg, 0.8 mmol). The solution is stirred at room temperature for 30 minutes. To this solution is then added compound xiii' (8 mL, 0.1 M) in THF, followed by the addition of DIPEA (0.23 mL, 1.3 mmol). The reaction is stirred at room temperature overnight and then quenched with water (25 mL) for 30 minutes. The mixture is then extracted with EtOAc. The resulting organic layer is washed with brine and then dried over $MgSO_4$, before being concentrated to yield a yellow oil. Purification by silica gel chromatography (3% EtOH/EtOAc) yields compound ccii (140 mg, 33%).

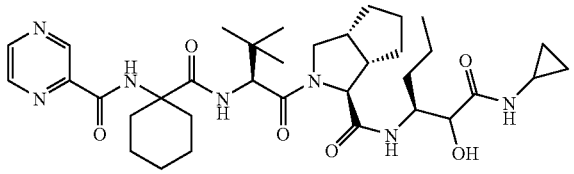

ccii

INTERMEDIATE EXAMPLE 192

Compound ccxiv

To a solution of compound cciii, tert-butyl (N-diphenylmethylene)-glycine ester, (6 g, 0.0206 mmol) and chiral PTC (1.08 g, 0.00206 mmol) in dry D-wi (48 mL), under $N_2$ atmosphere, at −60° C., is added $CsOH.H_2O$ (6.9 g, 0.0412 mmol). To the reaction mixture is added dropwise 1-carboxy-1-cyclopentene methyl ester (5.2 mL, 0.0412 mmol) in 10 mL of DCM. The mixture is stirred for 4 days at −60° C., then diluted with 200 mL of $Et_2O$ and 15 mL of saturated $NH_4Cl$ aqueous solution is added. Phases are separated and the organic phase is washed with 15 mL water and 15 mL brine. The aqueous phases are extracted with 100 mL of $Et_2O$. The organics phases are joined and dried over $Na_2SO_4$. Crude product is obtained by removal of the solvent dissolved in 100 mL of EtOH and then $NH_2OH.HCl$ (1.43 g, 0.0206 mmol) and NaOAc (1.68 g, 0.0206 mmol) are added. The mixture is refluxed for 48 hours. Then the solvent is removed and the crude residue obtained is directly purified by flash chromatography eluting with 30%-50% EtOAc/hexane to yield compound cciv (65%) as a white solid. $C_{12}H_{19}NO_3$ (MW=225.29); MS: m/z ($M^++1$)=226.5. Enantiomeric excess: 18% ee, determined by Chiral HPLC.

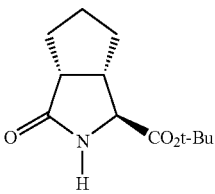

cciv

INTERMEDIATE EXAMPLE 193

Compound ccv

To a solution of compound cciv (2 g, 0.0088 mmol) in 60 mL of ACN is added a catalytic amount of DMAP (0.216 g, 0.0017 mmol) and a solution of di-tert-butyl-d-carbonate (2.49 g, 0.011 mmol) in 30 mL of ACN. The mixture is stirred for 14 hours at room temperature, then diluted with 100 mL of DCM, and washed with saturated $NaHCO_3$ (10 mL) and with brine (10 mL). The organic phase is dried over $Na_2SO_4$. Evaporation of the solvent yields a crude product that is purified on a silica gel column eluting with 15% EtOAc/hexane to give compound ccv (86%) as white solid. $C_{17}H_{27}NO_5$ MW=325,40 MS: m/z ($M^++1$)=326.2

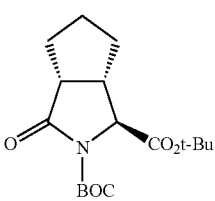

ccv

INTERMEDIATE EXAMPLE 194

Compound ccvi

To a solution of compound ccv (1.7 g, 0.0052 mmol) in 50 mTL of THF (0.14 M) at −78° C., is added DIBAL-H (7.8 mL, 0.0078 mmol). The mixture is stirred for 1 hour, then 10 mL of MeOH are added. The mixture is diluted with 25 mL of EtOAc and 25 mL of saturated aqueous solution of sodium tartrate, and then stirred at room temperature for an hour. The phases are separated and the aqueous phase is extracted once with 50 mL of EtOAc. The organic phases are combined and dried over $Na_2SO_4$. Evaporation of solvent gave a crude residue that is used without any purification. The crude is dissolved in 25 mL of DCM, $Et_3Si$ (0.84 mL, 0.0052 mmol) is added, and then the mixture is cooled to −78° C. before the dropwise addition of $BF_3OEt_2$ (0.71 mL, 0.0061 mmol). After 30 minutes $Et_3Si$ (0.84 mL) and $BF_3OEt_2$ (0.71 mL) are added and the mixture stirred for 2 hours to −78° C. The reaction is then quenched with saturated aqueous $NaHCO_3$ (10 mL) and extracted with DCM (2×20 mL). The organic phases are combined and dried over $Na_2SO_4$. Evaporation of solvent gives a crude residue that is purified by flash chromatography eluting with 13% EtOAc/hexane to yield compound ccvi (87%). $C_{17}H_{29}NO_4$ MW=311,42 MS: m/z $(M^++1)$=312.6

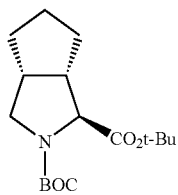

ccvi

INTERMEDIATE EXAMPLE 195

Compound ccvii

Compound ccvi (0.5 g, 0.0016 mmol) is dissolved in 8 mL of 1 N HCl in EtOAc (prepared by bubbling dry HCl into dry EtOAc then diluting to 1 N with additional EtOAc). The mixture is stirred for 6 hours at room temperature. Solvent is removed in vacuo and the resulting precipitate is dissolved in $Et_2O$. After stirring the mixture for 15 minutes, the solvent is removed under reduced pressure. The resulting white solid is washed with $Et_2O$ and the compound ccvii (0.27 g, 80% yield) is isolated by filtration. $C_{12}H_{21}NO_2$ MW 211,15 MS: m/z $(M^++1)$=212.6

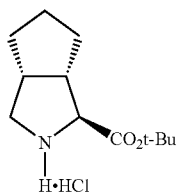

ccvii

INTERMEDIATE EXAMPLE 196

Compound v

To a solution of compound ccxvi (0.230 g, 0.74 mmol) in DCM (3.7 mL) is added TFA (2.85 mL). The mixture is stirred overnight, then solvent is removed iit vacuo to dryness and the residue is dissolved in EtOH (7.5 mL). The mixture is cooled at 0° C. and $SOCl_2$ (0.22 mL, 2.96 mmol) is added dropwise and then refluxed for 2 hours. EtOH is removed at reduced pressure and the residue dissolved in DCM (10 mL). The resulting solution is washed twice with a saturated aqueous solution of $NaHCO_3$ (5 mL). Phases are separated and the organic phase is dried over $Na_2SO_4$ and solvent removed in vacuo to yield compound v (80%) as oil. $C_{10}H_{17}NO_2$ M.W.: 183.25 MS: m/z $(M^++1)$=184.2

INTERMEDIATE EXAMPLE 197

Compound cd

1-Benzylimidazole (6 g, 37.9 mmol) is taken up in $Et_2O$ (180 mL). The resulting solution is lowered to −60° C. and treated with n-BuLi (1.6 M, 24 mL). The reaction is stirred for 30 minutes and then $CO_2$ is bubbled through mixture for 15 minutes. The precipitate is filtered, rinsed with $Et_2O$ and then taken up in $H_2O$. This aqueous solution is acidified to pH 3 with 5 N HCl. The desired product, cd, is isolated after lyophilization as a white solid.

cd

INTERMEDIATE EXAMPLE 198

Compound cdi

A DCM solution (100 mL) of compound i (9.25 g, 27.9 mmol) is treated at 0° C. with DAST (9.2 mL, 69.8 mmol). After stirring at room temperature overnight, the reaction is quenched with ice and extracted with DCM (200 mL). The organic layer is washed with brine and concentrated. in vacuo. The residue is purified with silica gel chromatography (30% EtOAc/hexanes) to yield 8.5 g (86%) of the desired fluorinated intermediate. A portion of this intermediate (4.5 g, 14.2 mmol) is dissolved in EtOH (75 mL). This solution is subjected to standard hydrogenation conditions using $Pd(OH)_2/C$ (2.98 g, 20% Pd content, 4.26 mmol). After stirring overnight at room temperature, the reaction mixture is filtered through Celite. The filtrates are concentrated in vacuo to yield compound cdi (2.5 g, 96%).

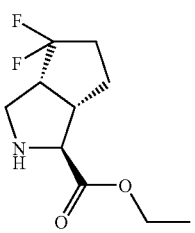

cdi

INTERMEDIATE EXAMPLE 199

Compound cdii

To a solution of compound cd (890 mg, 4.4 mmol) taken up in DCM (15 mL). HOBT (595 mg, 4.4 mmol) and DCC (4.4 mmol, 1 M in DCM) are added and stirred for 20 minutes. A DCM solution (15 mL) of lxxix' (990 mg, 3.5 mmol) is added to this mixture. The resulting mixture is stirred overnight under nitrogen. The reaction mixture is diluted with EtOAc, washed with saturated NaHCO$_3$ and brine. The organic layer is concentrated in vacuo to give a residue, which is purified in 30% EtOAc/Hexanes to yield compound cdii (666 mg, 41%).

cdii

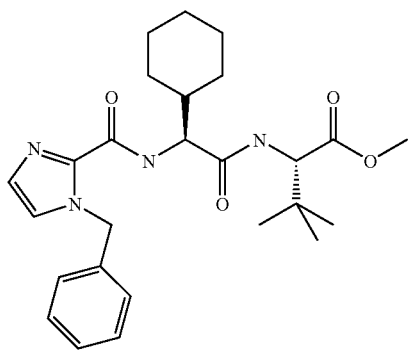

INTERMEDIATE EXAMPLE 200

Compound cdiii

Compound cdiii is prepared from compound cdii under standard hydrolysis conditions using methyl alcohol (10 mL) and 1 N NaOH (3 eq). 565 mg of compound cdiii are recovered (88%).

cdiii

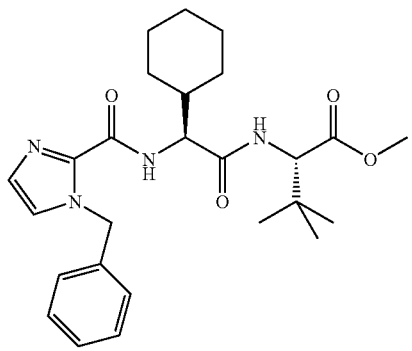

INTERMEDIATE EXAMPLE 201

Compound cdiv

Compound cdiii (1.24 mmol) is taken up in DCM (5 mL). DCC (1.6 mmol, 1 M DCM) is added followed by HOAT (1.6 mmol). The resulting mixture is stirred 20 minutes and

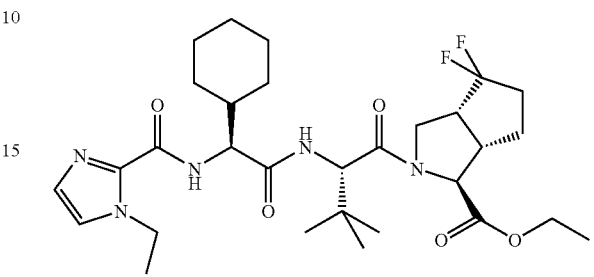

compound cdi (1.6 mmol) is added dropwise in THF (8 mL). The reaction is stirred overnight. The reaction is filtered and rinsed with EtOAc. The combined organic layer is washed with saturated NaHCO$_3$, brine, dried over MgSO$_4$, and concentrated. Purification is achieved in 30% EtOAc/Hexanes to yield compound cdiv (565 mg, 70%).

cdiv

INTERMEDIATE EXAMPLE 202 cdv

Compound cdv (565 mg, 0.86 mmol) is prepared from compound cdiv under standard hydrolysis conditions using ethyl alcohol (10 mL) and 1 N NaOH (3 eq). 490 mg (91%) of compound cdv is recovered.

cdv

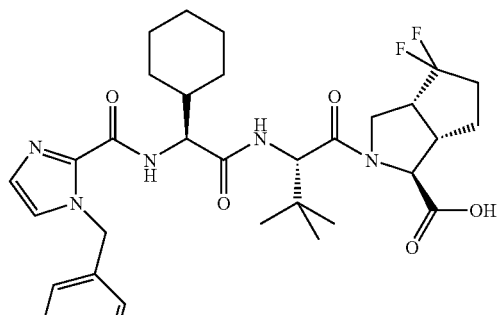

INTERMEDIATE EXAMPLE 203 cdvi

Compound cdv (490 mg, 0.78 mmol) is taken up in DCM (10 mL). PyBOP (520 mg, 1 mmol) is added to DCM solution followed by a THF solution (10 mL) of xiii (186 mg, 1 mmol). DIEA (0.18 mL, 1 mmol) is added to the reaction mixture and stirred overnight under nitrogen. The next day, the reaction is diluted with EtOAc, washed with saturated NaHCO₃ and brine. Purification is achieved in 100% EtOAc to yield compound cdvi (478 mg, 77%).

cdvi

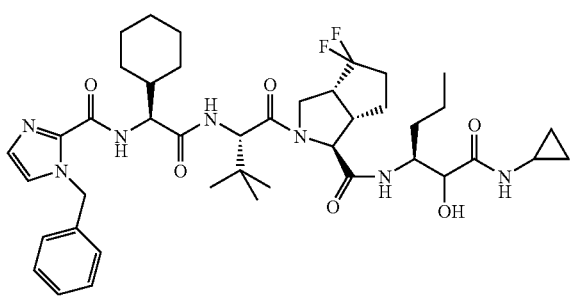

INTERMEDIATE EXAMPLE 204 cdvii

Compound cdvi (478 mg, 0.6 mmol) is hydrogenated using Pd(OH)₂/C (20% dry basis, 100 mg) in MeOH (40 mL). The reaction mixture is stirred overnight under hydrogen. At this point, the reaction mixture is filtered through Celite and concentrated to yield compound cdvii (417 mg, 98%).

cdvii

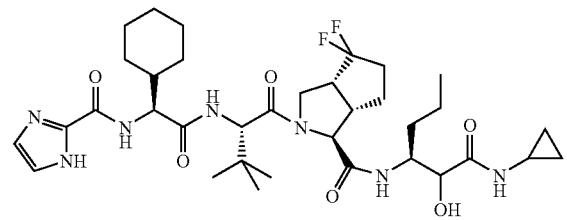

INTERMEDIATE EXAMPLE 205 cdx

Compound cxxv (Purchased from Albany Molecular Research Inc., 1.5 g, 5.2 mmol) is taken up in DCM (15 mL). PyBOP (2.7 g, 5.2 mmol) and HOBT (700 mg, 5.2 mmol) are added to this solution. A THF solution (15 mL) of (−)-alpha-(4-pyridyl)ethyl amine (640 mg, 5.2 mmol) is added to above solution, followed by DIEA (0.93 ml, 5.2 mmol). [The (−)-alpha-(4-pyridyl)ethyl amine is obtained from the tartrate salt of (−)-alpha-(4-pyridyl)ethyl amine (Aldrich) by stirring with 1 N NaOH (2 eq) for 1 hour followed by extraction with EtOAc (3×) 70% recovery]. The reaction is stirred overnight at room temperature. The reaction mixture is washed with saturated NaHCO₃, and brine. The product is purified in 5% EtOH/EtOAc to yield 2 g (99%) of intermediate compound cdx.

cdx

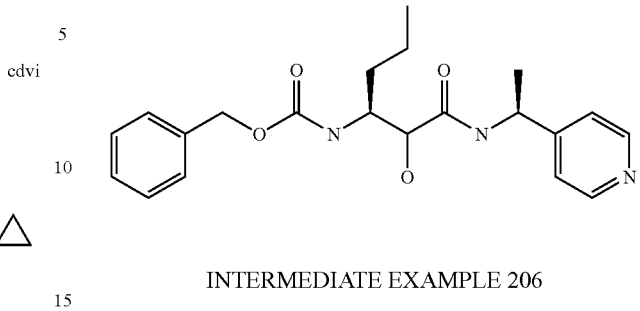

INTERMEDIATE EXAMPLE 206 cdviii

Compound cdx (2 g, 5.2 mmol) is hydrogenated using 10% Pd/C (500 mg) in MEOH (50 mL). The reaction mixture is stirred overnight under hydrogen. The product is filtered through celite and concentrated to give compound cdviii (1.3 ,g 98%).

cdviii

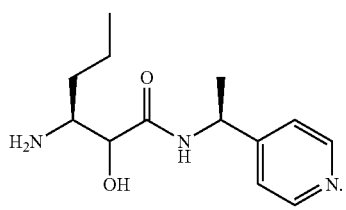

Pharmacology

Compounds according to the invention as described herein as being useful for being able to inhibit HCV protease, and thus, are also useful for inhibiting HCV replication.

Accordingly, an invention herein is directed to a method of inhibiting HCV protease comprising contacting an anti-HCV protease inhibitory amount of a compound of formula 1 with a composition comprising HCV protease.

Yet another invention herein is directed to a method of inhibiting replication of HCV comprising contacting HCV with an effective amount of a compound of formula 1. Furthermore, another invention herein is directed to a method of treating a patient suffering from or subject to an HCV infection comprising administering to the patient a pharmaceutically effective amount of compound of formula 1. References herein to treating an HCV infection should be understood to include prophylactic therapy to prevent or inhibit the infection as well as the treatment of an established acute or chronic HCV infection or physiological conditions associated with HCV infection to essentially cure the patient of the infection, inhibit the degree (amount) of infection or ameliorate the physiological conditions associated therewith. "Effective amount" is meant to describe an amount of the compound of the present invention effective within the scope of reasonable biological judgement, suitable for use in contact with the cells of humans and other mammals without undue toxicity, irritation, allergic response and the like, and are commensurate with a reasonable benefit/risk ratio in treating an HCV infection and thus producing the desired therapeutic effect.

Physiological conditions discussed herein include some, but not all, of the possible clinical situations where an anti- HCV treatment is warranted. Those experienced in this field are well aware of the circumstances requiring either an anti-HCV treatment.

A particular aspect of the invention provides for a compound according to the invention to be administered in the form of a pharmaceutical composition, though the compound may be administered alone. "Pharmaceutical composition" means a composition comprising a compound of formula 1 and at least one component selected from the group comprising pharmaceutically acceptable carriers, diluents, coatings, adjuvants, excipients, or vehicles, such as preserving agents, fillers, disintegrating agents, wetting agents, emulsifying agents, emulsion stabilizing agents, suspending agents, isotonic agents, sweetening agents, flavoring agents, perfuming agents, coloring agents, antibacterial agents, antifungal agents, other therapeutic agents, lubricating agents, adsorption delaying or promoting agents, and dispensing agents, depending on the nature of the mode of administration and dosage forms. The compositions may be presented in the form of tablets, pills, granules, powders, aqueous solutions or suspensions, injectable solutions, elixirs or syrups. Examplary suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Examplary antibacterial and antifungal agents for the prevention of the action of microorganisms include parabens, chlorobutanol, phenol, sorbic acid, and the like. Examplary isotonic agents include sugars, sodium chloride and the like. Examplary adsorption delaying agents to prolong absorption include aluminum monosterate and gelatin. Examplary adsorption promoting agents to enhance absorption include dimethyl sulphoxide and related analogs. Examplary carriers, diluents, solvents, vehicles, solubilizing agents, emulsifiers and emulsion stabilizers, include water, chloroform, sucrose, ethanol, isopropyl alcohol, ethyl carbonate, ethyl acetate, benzyl alcohol, tetrahydrofurfuryl alcohol, benzyl benzoate, polyols, propylene glycol, 1,3-butylene glycol, glycerol, polyethylene glycols, dimethylformamide, Tween® 60, Span® 80, cetostearyl alcohol, myristyl alcohol, glyceryl mono-stearate and sodium lauryl sulfate, fatty acid esters of sorbitan, vegetable oils (such as cottonseed oil, groundnut oil, corn germ oil, olive oil, castor oil and sesame oil) and injectable organic esters such as ethyl oleate, and the like, or suitable mixtures of these substances. Examplary excipients include lactose, milk sugar, sodium citrate, calcium carbonate, dicalcium phosphate phosphate. Examplary disintegrating agents include starch, alginic acids and certain complex silicates. Examplary lubricants include magnesium stearate, sodium lauryl sulphate, talc, as well as high molecular weight polyethylene glycols.

Other therapeutic agents may be used in combination with a compound of the present invention, including other anti-HCV agents. Some Examplary known anti-HCV agents include immunomodulatory agents, such as α-, β- or γ-interferons; pegylated derivatized interferon-α compounds, other antiviral agents such as ribavirin and amantadine; other inhibitors of hepatitis C protease; inhibitors of other targets in the HCV life cycle including the helicase, polymerase, metalloprotease, internal ribosome entry, or broad-spectrum antiviral compounds such as VX-497, an inhibitor of cellular inosine monophosphate dehydrogenase, IMPDH, covered by U.S. Pat. No. 5,807,876; or combinations thereof. Therapeutic agents used in combination with a compound of the present invention may be administered separately, simultaneously or sequentially.

The choice of material in the pharmaceutical composition other than the compound of formula 1 is generally determined in accordance with the chemical properties of the active compound such as solubility, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets.

The pharmaceutical compositions may be presented in assorted forms such as tablets, pills, granules, powders, aqueous solutions or suspensions, injectable solutions, elixirs or syrups. "Liquid dosage form" means the dose of the active compound to be administered to the patient is in liquid form, for example, pharmaceutically acceptable emulsions, solutions, suspensions, syrups and elixirs. In addition to the active compounds, the liquid dosage forms may contain inert diluents commonly used in the art, such solvents, solubilizing agents and emulsifiers.

Solid compositions may also be employed as fillers in soft and hard-filled gelatin capsules using such excipients as lactose or milk sugar as well as high molecular weight polyethylene glycols, and the like.

When aqueous suspensions are used they can contain emulsifying agents or agents which facilitate suspension.

The oily phase of the emulsion pharmaceutical composition may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier that acts as a stabilizer. It is also preferred to include both an oil and a fat. Together, the emulsifier(s) with or without stabilizer(s) make up the emulsifying wax, and the way together with the oil and fat make up the emulsifying ointment base which forms the oily dispersed phase of the cream formulations.

If desired, the aqueous phase of the cream base may include, for example, a least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound that enhances absorption or penetration of the active ingredient through the skin or other affected areas.

The choice of suitable oils or fats for a formulation is based on achieving the desired cosmetic properties. Thus the cream should preferably be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

In practice, a compound/pharmaceutical compositions of the present invention may be administered in a suitable formulation to humans and animals by topical or systemic administration, including oral, inhalational, rectal, nasal, buccal, sublingual, vaginal, colonic, parenteral (including subcutaneous, intramuscular, intravenous, intradermal, intrathecal and epidural), intracisternal and intraperitoneal. It will be appreciated that the preferred route may vary with for example the condition of the recipient.

"Pharmaceutically acceptable dosage forms" refers to dosage forms of the compound of the invention, and includes, for example, tablets, dragees, powders, elixr, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

"Formulations suitable for oral administration" may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tables may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compounds moistened with an inert liquid diluent. The tablets may optionally be coated or scored and may be formulated so as to provide slow or controlled release of the active ingredient therein.

Solid compositions for rectal administration include suppositories formulated in accordance with known methods and containing at least one compound of the invention.

If desired, and for more effective distribution, the compounds can be microencapsulated in, or attached to, a slow release or targeted delivery systems such as a biocompatible, biodegradable polymer matrices (e.g., poly(d,l-lactide coglycolide)), liposomes, and microspheres and subcutaneously or intramuscularly injected by a technique called subcutaneous or intramuscular depot to provide continuous slow release of the compound(s) for a period of 2 weeks or longer. The compounds may be sterilized, for example, by filtration through a bacteria retaining filter, or by incorporating sterilizing agents in the form of sterile solid compositions which can be dissolved in sterile water, or some other sterile injectable medium immediately before use.

"Formulations suitable for nasal or inhalational administration" means formulations which are in a form suitable to be administered nasally or by inhalation to a patient. The formulation may contain a carrier, in a powder form, having a particle size for example in the range 1 to 500 microns (including particle sizes in a range between 20 and 500 microns in increments of 5 microns such as 30 microns, 35 microns, etc.) Suitable formulations wherein the carrier is a liquid, for administration as for example a nasal spray or as nasal drops, include aqueous or oily solutions of the active ingredient Formulations suitable for aerosol administration may be prepared according to conventional methods and may be delivered with other therapeutic agents. Inhalational therapy is readily administered by metered dose inhalers.

"Formulations suitable for oral administration" means formulations which are in a form suitable to be administered orally to a patient. The formulations may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

"Formulations suitable for parenteral administration" means formulations that are in a form suitable to be administered parenterally to a patient. The formulations are sterile and include emulsions, suspensions, aqueous and non-aqueous injection solutions, which may contain suspending agents and thickening agents and anti-oxidants, buffers, bacteriostats and solutes which render the formulation isotonic, and have a suitably adjusted pH, with the blood of the intended recipient.

"Formulations suitable for rectal or vaginal administrations" means formulations that are in a form suitable to be administered rectally or vaginally to a patient. The formulation is preferably in the form of suppositories that can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

"Formulations suitable for systemic administration" means formulations that are in a form suitable to be administered systemically to a patient. The formulation is preferably administered by injection, including transmuscular, intravenous, intraperitoneal, and subcutaneous. For injection, the compounds of the invention are formulated in liquid solutions, preferably in physiologically compatible buffers such as Hank's solution or Ringer's solution. In addition, the compounds may be formulated in solid form and redissolved or suspended immediately prior to use. Lyophilized forms are also included. Systematic administration also can be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, or suppositories. For oral administration, the compounds are formulated into conventional oral administration forms such as capsules, tablets, and tonics.

"Formulations suitable for topical administration" means formulations that are in a form suitable to be administered topically to a patient. The formulation may be presented as a topical ointment, salves, powders, sprays and inhalants, gels (water or alcohol based), creams, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

"Solid dosage form" means the dosage form of the compound of the invention is solid form, for example capsules, tablets, pills, powders, dragees or granules. In such solid dosage forms, the compound of the invention is admixed with at least one inert customary excipient (or carrier) such as sodium citrate or dicalcium phosphate or (a) fillers or extenders as for example starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, (i) lubricants, as for example, talc, calcium stearate, magnesium stearate, solid polyethylene glycols, sodium lauryl sulfate, () opacifying agents, (k) buffering agents, and agents which release the compound(s) of the invention in a certain part of the intestinal tract in a delayed manner.

Actual dosage levels of active ingredient(s) in the compositions of the invention may be varied so as to obtain an amount of active ingredient(s) that is (are) effective to obtain a desired therapeutic response for a particular composition and method of administration for a patient. A selected dosage level for any particular patient therefore depends upon a variety of factors including the desired therapeutic effect, on the route of administration, on the desired duration of treatment, the etiology and severity of the disease, the patient's condition, weight, sex, diet and age, the type and potency of each active ingredient, rates of absorbtion, metabolism and/or excretion and other factors.

Total daily dose of the compounds of this invention administered to a patient in single or divided doses may be in amounts, for example, of from about 0.001 to about 100 mg/kg body weight daily and preferably 0.01 to 10 mg/kg/day. For example, in an adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. The percentage of active ingredient in a composition may be varied, though it should constitute a proportion such that a suitable dosage shall be obtained. Dosage unit compositions may contain such amounts of such submultiples thereof as may be used to make up the daily dose. Obviously, several unit dosage forms may be administered at about the same time. A dosage may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. It goes without saying that, for other patients, it will be necessary to prescribe not more than one or two doses per day.

The formulations can be prepared in unit dosage form by any of the methods well known in the art of pharmacy. Such methods include the step of bringing into association the active ingredient with the carrier that constitutes one or more accessory ingredients. In general the formulations are prepared by uniformly and intimately bringing into association the active ingredient with liquid carriers or finely divided solid carriers or both, and then, if necessary, shaping the product.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compounds within the scope of the present invention exhibit marked pharmacological activities according to tests described in the literature and below, which tests results are believed to correlate to pharmacological activity in humans and other mammals.

In Vitro Enzyme Assay Procedure

Inhibition of HCV NS3 Serine Protease

HCV NS3 protease domain was expressed and purified as described previously (Vertex, PCT publication WO98/17679; which is incorporated herein by reference). The chromogenic peptide substrate, EDVV AbuC-p-nitroanilide, and the NS4A cofactor fragment (-KKGSVVIVGRIVLSGK-) for NS3 protease was custom synthesized by American Peptide Corn (Ca). The compounds of this invention were tested for their ability to inhibit HCV NS3 protease activity using a spectrophotometric assay with EDVV AbuC-p-nitroanilide as substrate. The assay was run in a 96-well microtiter plate using a SpectraMax 250 reader (Molecular Devices, Sunnyvale, Calif.) with kinetic capability. Cleavage of EDVV AbuC-p-nitroanilide (500 µM) substrate by purified HCV NS3 protease (0.5 µM) was performed at 30° C. in the buffer containing 30 µM NS4A fragment, 46 mM Hepes, pH 8.0, 92 mM NaCl, 18% glycerol, 5 mM DTT, and 7.5% DMSO in the absence or presence of the testing compound. The reaction was monitored for pNA (p-nitroaniline) release at 405 nm.

The determination of the kinetic parameters including Vmax, $K_m$ and $V_{max}/K_m$ is performed under the conditions as described above. Ki values are calculated from rate vs. [inhibitor] plots, at fixed concentrations of enzyme and substrate, by a nonlinear least squares fit of the data to the equation of Morrison for tight binding competitive inhibition [J. F. Morrison, *Biochim. Biophys. Acta.*, 185, 269-286 (1969)]. The Prism program (GraphPad Software, Inc.) is used for this procedure.

The HCV serine protease inhibitors disclosed herein can be used in combination with other molecules that directly exhibit or indirectly elicit anti-HCV activity either prophylactically in patients at risk for contracting HCV infection, or to treat patients that are already infected. The term "anti-HCV activity" refers to the capacity of a molecule, when present, to completely inhibit or reduce accumulation of HCV virions compared to HCV virion accumulation in the absence of such molecule, and/or the capacity of a molecule to reduce or ameliorate conditions or symptoms associated with HCV infection or pathogenesis in patients. Molecules having anti-HCV activity include those that disrupt one or more steps in HCV infection or replication, as well as those that evoke immunomodulating and antiproliferative actions in host cells. Molecules having anti-HCV activity can inhibit HCV-specific replicative events such as, but not limited to, HCV-directed nucleic acid or protein synthesis. Stages of HCV replication at which molecules having anti-HCV activity can act include cell entry (e.g., attachment; penetration); uncoating and release of the HCV genome; replication of the HCV genome (e.g., replication of either strand of the viral RNA genome; transcription of viral messenger RNA); translation of HCV proteins; posttranslational modification of HCV proteins (e.g., proteolytic cleavage; glycosylation); intracellular transport of viral proteins; assembly of virion components; and release of viral particles (e.g., budding). Classes of molecules having anti-viral activity include, but are not limited to, soluble receptor decoys and antireceptor antibodies; ion channel blockers, capsid stabilizers, and fusion protein inhibitors; inhibitors of viral polymerases, reverse transcriptase, helicase, primase, or integrase; antisense oligonucleotides and ribozymes; immunomodulating and immunostimulating agents, including cytokines such as interferons, as well as peptide agonists, steroids, and classic drugs such as levamisole; inhibitors of regulatory proteins; protease inhibitors; assembly protein inhibitors; and antiviral antibodies and cytotoxic lymphocytes. The term "anti-HCV effective amount" or "pharmaceutically effective amount" refers to an amount of a compound, or combination of compounds as disclosed herein, effective in reducing or ameliorating conditions or symptoms associated with HCV infection or associated pathogenesis in patients, or in reducing viral levels in vitro or in vivo. In vitro applications include the Replicon Assay system, described below, where such amounts are effective in reducing HCV replicon RNA accumulation and/or the accumulation of proteins encoded by genes contained therein.

Compounds having anti-HCV activity contemplated for use in the compositions and methods of combination therapy disclosed herein include, but are not limited to, immunomodulatory molecules, including immunostimulatory cytokines, and other compounds known to have HCV antiviral activity, such as various antiviral nucleosides and nucleotides.

Immunomodulatory molecules contemplated for use in combination with the HCV serine protease inhibitors disclosed herein include, but are not limited to, interferon-alpha 2B (Intron A, Schering Plough); Rebatron (Schering Plough, Interferon-alpha 2B+Ribavirin); pegylated interferon alpha (Reddy, K. R. et al. Efficacy and safety of pegylated (40-kd) interferon alpha-2a compared with interferon alpha-2a in noncirrhotic patients with chronic hepatitis C. *Hepatology* 33, 433-438 (2001)); consensus interferon (Kao, J. H., Chen, P. J., Lai, M. Y. & Chen, D. S. Efficacy of consensus interferon in the treatment of chronic hepatitis C. *J. Gastroenterol. Hepatol.* 15, 1418-1423 (2000)); interferon-alpha 2A (Roferon A; Roche); lymphoblastoid or "natural" interferon; interferon tau (Clayette, P. et al. IFN-tau, a new interferon type I with antiretroviral activity. *Pathol. Biol. (Paris)* 47, 553-559 (1999)); interleukin 2 (Davis, G. L., Nelson, D. R. & Reyes, G. R. Future options for the management of hepatitis C. *Seminars in Liver Disease* 19, 103-112 (1999)); Interleukin 6 (Davis, G. L., Nelson, D. R. & Reyes, G. R. Future options for the management of hepatitis C. *Seminars in Liver Disease* 19, 103-112 (1999)); Interleukin 12 (Davis, G. L., Nelson, D. R. & Reyes, G. R. Future options for the management of hepatitis C. *Seminars in Liver Disease* 19, 103-112 (1999)); Ribavirin; and compounds that enhance the development of a type 1 helper T cell response (Davis, G. L., Nelson, D. R. & Reyes, G. R. Future options for the management of hepatitis C. *Seminars in Liver Disease* 19, 103-112 (1999)). Interferons may ameliorate viral infections by exerting direct antiviral effects and/or by modifying the immune response to infection. The antiviral effects of interferons are often mediated through inhibition of viral penetration or uncoating, synthesis of viral RNA, translation of viral proteins, and/or viral assembly and release.

Compounds that stimulate the synthesis of interferon in cells (Tazulakhova, E. B., Parshina, O. V., Gusev, T. S. & Ershov, F. I. Russian Experience in Screening, Analysis, and Clinical Application of Novel Interferon Inducers. *J. Interferon Cytokine Res.* 21, 65-73)) include, but are not limited to, double stranded RNA, alone or in combination with tobramycin, and Imiquimod (3M Pharmaceuticals) (Sauder, D. N. Immunomodulatory and pharmacologic properties of imiquimod. *J. Am. Acad. Dermatol.* 43, S6-11 (2000)).

Other compounds known to have, or that may have, HCV antiviral activity by virtue of non-immunomodulatory mechanisms include, but are not limited to, Ribavirin (ICN Pharmaceuticals); inosine 5'-monophosphate dehydrogenase inhibitors (VX497, being developed by Vertex Pharmaceuticals); amantadine and rimantadine (Younossi, A. M. and Perillo, R. P. The roles of amantadine, rimantadine, ursodeoxycholic acid, NSAIDs, alone or in combination with alpha interferons, in the treatment of chronic hepatitis C. *Seminars in Liver Disease* 19, 95-102 (1999)); LY217896 (U.S. Pat. No. 4,835,168) (Colacino, J. M. et al. Evaluation of the anti-influenza virus activities of 1,3,4-thiadiazol-2-ylcyanamide (LY217896) and its sodium salt. *Antimicrobial Agents & Chemotherapy* 34, 2156-2163 (1990)); and 9-Hydroxyimino-6-methoxy-1,4a-dimethyl-1,2,3,4,4a,9,10,10a-octahydro-phenanthrene-1-carboxylic acid methyl ester; 6-Methoxy-1,4a-dimethyl-9-(4-methyl-piperazin-1-ylimino)-1,2,3,4,4a,9,10,10a-octahydro-phenanthrene-1-carboxylic acid methyl ester-hydrochloride; 1-(2-Chloro-phenyl)-3-2,2-diphenyl-ethyl)-urea (U.S. Pat. No. 6,127,422).

Formulations, doses, and routes of administration for the foregoing molecules are either taught in the references cited below, or are well-known in the art as disclosed, for example, in F. G. Hayden, in *Goodman & Gilman's The Pharmacological Basis of Therapeutics*, Ninth Edition, Hardman et al., Eds., McGraw-Hill, New York (1996), Chapter 50, pp. 1191-1223, and the references cited therein. Alternatively, once a compound that exhibits HCV antiviral activity has been identified, a pharmaceutically effective amount of that compound can be determined using techniques that are well-known to the skilled artisan. Note, for example, Benet et al., in *Goodman & Gilman's The Pharmacological Basis of Therapeutics*, Ninth Edition, Hardman et al., Eds., McGraw-Hill, New York (1996), Chapter 1, pp. 3-27, and the references cited therein. Thus, the appropriate forumulations, dose(s) range, and dosing regimens, of such a compound can be easily determined by routine methods.

The drug combinations of the present invention can be provided to a cell or cells, or to a human patient, either in separate pharmaceutically acceptable formulations administered simultaneously or sequentially, formulations containing more than one therapeutic agent, or by an assortment of single agent and multiple agent formualtions. However administered, these drug combinations form an anti-HCV effective amount of components.

A large number of other immunomodulators and immunostimulants that can be used in the methods of the present invention are currently available and include: AA-2G; adamantylamide dipeptide; adenosine deaminase, Enzon; adjuvant, Alliance; adjuvants, Ribi; adjuvants, Vaxcel; Adjuvax; agelasphin-11; AIDS therapy, Chiron; algal glucan, SRI; algammulin, Anutech; Anginlyc; anticellular factors, Yeda; Anticort; antigastrin-17 immunogen, Ap; antigen delivery system, Vac; antigen formulation, IDBC; antiGnRH immunogen, Aphton; Antiherpin; Arbidol; azarole; Bay-q-8939; Bay-r-1005; BCH-1393; Betafectin; Biostim; BL-001; BL-009; Broncostat; Cantastim; CDRI-84-246; cefodizime; chemokine inhibitors, ICOS; CMV peptides, City of Hope; CN-5888; cytokine-releasing agent, St; DHEAS, Paradigm; DISC TA-HSV; J07B; I01A; I01Z; ditiocarb sodium; ECA-10-142; ELS-1; endotoxin, Novartis; FCE-20696; FCE-24089; FCE-24578; FLT-3 ligand, Immunex; FR-900483;

FR-900494; FR-901235; FTS-Zn; G-proteins, Cadus; gludapcin; glutaurine; glycophosphopeptical; GM-2; GM-53; GMDP; growth factor vaccine, EntreM; H-BIG, NABI; H-CIG, NABI; HAB439; *Helicobacter pylori* vaccine; herpes-specific immune factor; HIV therapy, United Biomed; HyperGAM+CF; ImmuMax; Immun BCG; immune therapy, Connective; immunomodulator, Evans; immunomodulators, Novacell; imreg-1; imreg-2; Indomune; inosine pranobex; interferon, Dong-A (alpha2); interferon, Genentech (gamma); interferon, Novartis (alpha); interleukin-12, Genetics Ins; interleukin-15, Immunex; interleukin-16, Research Cor; ISCAR-1; J005X; L-644257; licomarasminic acid; LipoTher; LK-409; LK-410; LP-2307; LT (R1926); LW-50020; MAF, Shionogi; MDP derivatives, Merck; met-enkephalin, TNI; methylfurylbutyrolactones; MIMP; mirimostim; mixed bacterial vaccine, Tem; MM-1; moniliastat; MPLA, Ribi; MS-705; murabutide; murabutide, Vacsyn; muramyl dipeptide derivative; muramyl peptide derivatives myelopid; -563; NACOS-6; NH-765; NISV, Proteus; NPT-16416; NT-002; PA-485; PEFA-814; peptides, Scios; peptidoglycan, Pliva; Perthon, Advanced Plant; PGM derivative, Pliva; Pharmaprojects No. 1099; No. 1426; No. 1549; No. 1585; No. 1607; No. 1710; No. 1779; No. 2002; No. 2060; No. 2795; No. 3088; No. 3111; No. 3345; No. 3467; No. 3668; No. 3998; No. 3999; No. 4089; No. 4188; No. 4451; No. 4500; No. 4689; No. 4833; No. 494; No. 5217; No. 530; pidotimod; pimelautide; pinafide; PMD-589; podophyllotoxin, Conpharm; POL-509; poly-ICLC; poly-ICLC, Yamasa Shoyu; PolyA-PolyU; Polysaccharide A; protein A, Berlox Bioscience; PS34WO; *Pseudomonas* MAbs, Teijin; Psomaglobin; PTL-78419; Pyrexol; pyriferone; Retrogen; Retropep; RG-003; Rhinostat; rifamaxil; RM-06; Rollin; romurtide; RU40555; RU41821; *Rubella* antibodies, ResCo; S-27609; SB-73; SDZ-280-636; SDZ-MRL-953; SK&F-107647; SL04; SL05; SM-4333; Solutein; SRI-62-834; SRL-172; ST-570; ST-789; staphage lysate; Stimulon; suppressin; T-150R1; T-LCEF; tabilautide; temurtide; Theradigm-HBV; Theradigm-HPV; Theradigm-HSV; TBF, Pharm & Upjohn; THF, Yeda; thymalfasin; thymic hormone fractions; thymocartin; thymolymphotropin; thymopentin; thymopentin analogues; thymopentin, Peptech; thymosin fraction 5, Alpha; thymostimulin; thymotrinan; TMD-232; TO-115; transfer factor, Viragen; tuftsin, Selavo; ubenimex; Ulsastat; ANGG−; CD4+; Collag+; COLSF+; COM+; DA-A+; GAST−; GF-TH+; GP-120−; IF+; IF-A+; IF-A-2+; IF-B+; IF-G+; IF-G-1B+; EL-2+; IL-12+; IL-15+; IM+; LHRH−; LIPCOR+L LYM-B+; LYM-NK+; LYM-T+; OPI+; PEP+; PHG-MA+; RNA-SYN−; SY-CW−; TH-A-1+; TH-5+; TNF+; UN.

Representative nucleoside and nucleotide compounds useful in the present invention include, but are not limited to: (+)-cis-5-fluoro-1-[2-(hydroxy-methyl)-[1, 3-oxathiolan-5-yl]cytosine; (−)-2'-deoxy-3'-thiocytidine-5'-triphosphate (3TC); (−)-cis-5-fluoro-1-[2-(hydroxy-methyl)-[1,3-oxathiolan-5-yl]cytosine (FFC); (−) 2',3', dideoxy-3'-thiacytidine [(−) -SddC]; 1-(2'-deoxy-2'-fluoro-beta-D-arabinofuranosyl)-5-iodocytosine (FIAC); 1-(2'-deoxy-2'-fluoro-beta-D-arabinofuranosyl)-5-iodocytosine triphosphate (FIACIP); 1-(2'-deoxy-2'-fluoro-beta-D-arabinofuranosyl)-5-methyluracil (FMAU); 1-beta-D-ribofuranosyl-1,2,4-triazole-3-carboxamide; 2',3'-dideoxy-3'-fluoro-5-methyl-dexocytidine (FddMeCyt); 2',3'-dideoxy-3'-chloro-5-methyl-dexocytidine (ClddMeCyt); 2',3'-dideoxy-3'-amino-5-methyl-dexocytidine (AddMeCyt); 2',3'-dideoxy-3'-fluoro-5-methyl-cytidine (FddMeCyt); 2',3'-dideoxy-3'-chloro-5-methyl-cytidine (ClddMeCyt); 2',3'-dideoxy-3'-amino-5-methyl-cytidine (AddMeCyt); 2',3'-dideoxy-3'-fluorothymidine (FddThd); 2',3'-dideoxy-beta-L-5-fluorocytidine (beta-L-FddC); 2',3'-dideoxy-beta-L-5-thiacytidine; 2',3'-dideoxy-beta-L-5-cytidine (beta-L-ddC); 9-(1,3-dihydroxy-2-propoxymethyl) guanine; 2'-deoxy-3'-thia-5-fluorocytosine; 3'-amino-5-methyl-dexocytidine (AddMeCyt); 2-amino-1,9-[(2-hydroxymethyl-1-(hydroxymethyl)ethoxy]methyl]6H-purin-6-one (gancyclovir); 2-[2-(2-amino-9H-purin-9y)ethyl]-1,3-propandil diacetate (famciclovir); 2-amino-1,9 dihydro-9-[(2-hydroxy-ethoxy)methyl]6H-purin-6-one (acyclovir); 9-(4-hydroxy-3-hydroxymethyl-but-1-yl)guanine (penciclovir); 9-(4-hydroxy-3-hydroxymethyl-but-1-yl)-6-deoxy-guanine diacetate (famciclovir); 3'-azido-3'-deoxythymidine (AZT); 3'-chloro-5-methyl-dexocytidine (ClddMeCyt); 9-(2-phosphonyl-methoxyethyl)-2',6'-diaminopurine-2',3'-dideoxyriboside; 9-(2-phosphonylmethoxyethyl)adenine (PMEA); acyclovir triphosphate (ACVTP); D-carbocyclic-2'-deoxyguanosine (CdG); dideoxy-cytidine; dideoxy-cytosine (ddC); dideoxy-guanine (ddG); dideoxy-inosine (ddI); E-5-(2-bromovinyl)-2'-deoxyuridine triphosphate; fluoro-arabinofuranosyl-iodouracil; 1-(2'-deoxy-2'-fluoro-1-beta-D-arabinofuranosyl)-5-iodo-uracil (FIAU); stavudine; 9-beta-D-arabinofuranosyl-9H-purine6-amine monohydrate (Ara-A); 9-beta-D-arabinofuranosyl-9H-purine-6-amine-5'-monophosphate monohydrate (Ara-AMP); 2-deoxy-3'-thia-5-fluorocytidine; 2',3'-dideoxy-guanine; and 2',3'-dideoxy-guanosine.

Synthetic methods for the preparation of nucleosides and nucleotides useful in the present invention are well known in the art as disclosed in *Acta Biochim Pol.*, 43, 25-36 (1996); *Swed. Nucleosides Nucleotides* 15, 361-378 (1996); *Synthiesis* 12, 1465-1479 (1995); *Carbohzyd. Chem.* 27, 242-276 (1995); *Chem. Nucleosides Nucleotides* 3, 421-535 (1994); *Ann. Reports in Med. Chem.*, Academic Press; and *Exp. Opin. Invest. Drugs* 4, 95-115 (1995).

The chemical reactions described in the references cited above are generally disclosed in terms of their broadest application to the preparation of the compounds of this invention. Occasionally, the reactions may not be applicable as described to each compound included within the scope of compounds disclosed herein. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional will be applicable to the preparation of the corresponding compounds of this invention. In all preparative methods, all starting materials are known or readily preparable from known starting materials.

While nucleoside analogs are generally employed as antiviral agents as is, nucleotides (nucleoside phosphates) must sometimes have to be converted to nucleosides in order to facilitate their transport across cell membranes. An example of a chemically modified nucleotide capable of entering cells is S-1-3-hydroxy-2-phosphonylmethoxypropyl cytosine (HPMPC, Gilead Sciences). Nucleoside and nucleotide compounds of this invention that are acids can form salts. Examples include salts with alkali metals or alkaline earth metals, such as sodium, potassium, calcium, or magnesium, or with organic bases or basic quaternary ammonium salts.

Immunomodulators and immunostimulants useful in the combination therapy methods of the present invention can be administered in amounts lower than those conventional in the art. For example, interferon alpha is typically administered to humans for the treatment of HCV infections in an amount of from about 1×10⁶ units/person three times per week to about 10×10⁶ units/person three times per week (Simon et al., *Hepatology* 25: 445-448 (1997)). In the methods and compositions of the present invention, this dose can be in the range of from about 0.1×10⁶ units/person three times per week to about 7.5×10⁶ units/person three times per week; more preferably from about 0 5×10⁶ units/person three times per week to about 5×10⁶ units/person three times per week; most preferably from about 1×10⁶ units/person three times per week to about 3×10⁶ units/person three times per week. Due to the enhanced hepatitis C virus antiviral effectiveness of immunomodulators and immunostimulants in the presence of the HCV serine protease inhibitors of the present invention, reduced amounts of these immunomodulators/immunostimulants can be employed in the methods and compositions disclosed herein. Similarly, due to the enhanced hepatitis C virus antiviral effectiveness of the present HCV serine protease inhibitors in the presence of immunomodulators and immunostimulants, reduced amounts of these HCV serine protease inhibitors can be employed in the methods and compositions disclosed herein. Such reduced amounts can be determined by routine monitoring of hepatitis C virus titers in infected patients undergoing therapy. This can be carried out by, for example, monitoring HCV RNA in patients' serum by slot-blot, dot-blot, or RT-PCR techniques, or by measurement of HCV surface or other antigens. Patients can be similarly monitored during combination therapy employing the HCV serine protease inhibitors disclosed herein and other compounds having anti-HCV activity, for example nucleoside and/or nucleotide antiviral agents, to determine the lowest effective doses of each when used in combination.

In the methods of combination therapy disclosed herein, nucleoside or nucleotide antiviral compounds, or mixtures thereof, can be administered to humans in an amount in the range of from about 0.1 mg/person/day to about 500 mg/person/day; preferably from about 10 mg/person/day to about 300 mg/person/day; more preferably from about 25 mg/person/day to about 200 mg/person/day; even more preferably from about 50 mg/person/day to about 150 mg/person/day; and most preferably in the range of from about 1 mg/person/day to about 50 mg/person/day.

Doses of compounds can be administered to a patient in a single dose or in proportionate multiple subdoses. In the latter case, dosage unit compositions can contain such amounts of submultiples thereof to make up the daily dose. Multiple doses per day can also increase the total daily dose should this be desired by the person prescribing the drug.

The regimen for treating a patient suffering from a HCV infection with the compounds and/or compositions of the present invention is selected in accordance with a variety of factors, including the age, weight, sex, diet, and medical condition of the patient, the severity of the infection, the route of administration, pharmacological considerations such as the activity, efficacy, pharmacokinetic, and toxicology profiles of the particular compounds employed, and whether a drug delivery system is utilized. Administration of the drug combinations disclosed herein should generally be continued over a period of several weeks to several months or years until virus titers reach acceptable levels, indicating that infection has been controlled or eradicated. Patients undergoing treatment with the drug combinations disclosed herein can be routinely monitored by measuring hepatitis viral RNA in patients' serum by slot-blot, dot-blot, or RT-PCR techniques, or by measurement of hepatitis C viral antigens, such as surface antigens, in serum to determine the effectiveness of therapy. Continuous analysis of the data obtained by these methods permits modification of the treatment regimen during therapy so that optimal amounts of each component in the combination are administered, and so that the duration of treatment can be determined as well. Thus, the treatment regimen/dosing schedule can be rationally modified over the course of therapy so that the lowest amounts of each of the antiviral compounds used in combination which together exhibit satisfactory anti-hepatitis C virus effectiveness are administered, and so that administration of such antiviral compounds in combination is continued only so long as is necessary to successfully treat the infection.

The present invention encompasses the use of the HCV serine protease inhibitors disclosed herein in various combinations with the foregoing and similar types of compounds having anti-HCV activity to treat or prevent HCV infections in patients. For example, one or more HCV serine protease inhibitors can be used in combination with: one or more interferons or interferon derivatives having anti-HCV activity; one or more non-interferon compounds having anti-HCV activity; or one or more interferons or interferon derivatives having anti-HCV activity and one or more non-interferon compounds having anti-HCV activity. When used in combination to treat or prevent HCV infection in a human patient, any of the presently disclosed HCV serine protease inhibitors and foregoing compounds having anti-HCV activity can be present in a pharmaceutically or anti-HCV effective amount. By virtue of their additive or synergistic effects, when used in the combinations described above, each can also be present in a subclinical pharmaceutically effective or anti-HCV effective amount, i.e., an amount that, if used alone, provides reduced pharmaceutical effectiveness in completely inhibiting or reducing the accumulation of HCV virions and/or reducing or ameliorating conditions or symptoms associated with HCV infection or pathogenesis in patients compared to such HCV serine protease inhibitors and compounds having anti-HCV activity when used in pharmaceutically effective amounts. In addition, the present invention encompasses the use of combinations of HCV serine protease inhibitors and compounds having anti-HCV activity as described above to treat or prevent HCV infections, where one or more of these inhibitors or compounds is present in a pharmaceutically effective amount, and the other(s) is(are) present in a subclinical pharmaceutically effective or anti-HCV effective amount(s) owing to their additive or synergistic effects. As used herein, the term "additive effect" describes the combined effect of two (or more) pharmaceutically active agents that is equal to the sum of the effect of each agent given alone. A syngergistic effect is one in which the combined effect of two (or more) pharmaceutically active agents is greater than the sum of the effect of each agent given alone.

EXAMPLE 42

Current standard therapy for hepatitis C virus (HCV) infection is treatment with the immunomodulator alpha-interferon (Chronic Hepatitis C: Current Disease Management, U.S. Department of Health and Human Services, National Institutes of Health, 1999). This therapy is ineffective in most HCV patients, who show either no response or a relapse even after prolonged interferon therapy. Additionally, there are severe side effects associated with interferon therapy.

In view of the pressing need for new, more effective antiviral drugs to treat HCV infected patients, the present inventors have developed a series of compounds that inhibit the serine protease of HCV (a complex of HCV viral proteins NS3 and NS4A). These compounds can be used alone, together with one another, and in combination with other classes of compunds to treat or prevent HCV infection. This example describes the testing of three representative HCV serine protease inhibitors, i.e., Compound CU, Compound EP, and Compound EC, alone and in combination with individual members of a set of interferons (interferon alpha-2B (Schering-Plough), interferon alpha-2A (PBL Biomedical Laboratories, New Brunswick, N.J.), interferon beta (Research Diagnostics Inc, Flanders, N.J.), and ovine-interferon tau (Research Diagnostics Inc, Flanders, N.J.)) in an HCV subgenomic RNA replicon assay (Replicon Assay) to determine if the two compounds act in concert to diminish HCV RNA accumulation. The Replicon Assay measures the amount of HCV subgenomic RNA (replicon RNA) remaining in replicon cells (Lohmann et al. *Science* 285:110-113 (1999)) after two days of drug treatment relative to the amount of replicon RNA in untreated cells. In this assay, the potency of compounds as HCV antiviral drugs is directly proportional to the level of inhibition of replicon. RNA accumulation.

The two drugs are tested in combinations in the in vitro Replicon Assay system to determine whether, when used together, they exhibit additive or synergistic anti-HCV activity. The Replicon Assay is employed as a surrogate model for in vitro HCV infection to evaluate the combined effects of the immunomodulator, for example interferon-alpha 2B ((Intron A); Schering Plough), and the HCV serine protease inhibitor, for example Compound CU. As shown below, the results demonstrate that there is a clear synergistic anti-HCV effect of these two types of drugs as measured using formal mathematical determinations of synergy to analyze their capacity to reduce HCV RNA levels in the Replicon Assay.

The Replicon Assay

The Replicon Assay employing a cell line containing the self-replicating HCV subgenomic RNA (replicon) is described in Lohmann et al. *Science* 285:110-113 (1999). The Genbank accession number for the sequence of the replicon used in the experiments described herein is listed in this reference as AJ242654. This paper discloses methods for in vitro transcription of RNA from the replicon cDNA, transfection of the replicon RNA into Huh7 cells by electroporation, and selection of cells containing the replicon RNA using the antibiotic G418. Huh7 cells are a hepatoma cell line obtained from Dr. William Mason at Fox Chase Cancer Research Center (Philadelphia). These cells are publicly available from Fox Chase, and have been extensively described in the scientific literature (Nakabayashi et al. *Cancer Res.* 42:3858-3863 (1982)). In the experiments described herein, all of the template DNA is removed from the in vitro transcribed replicon RNA preparation prior to electroporation of this RNA into Huh7 cells by multiple treatment with DNase (three sequential treatments).

The Replicon Assay is performed as described in detail below. Briefly, Replicon cells are placed in 96 well trays at a density of 10,000 cells per well and incubated 37° C. The cells are incubated in DMEM (Dulbecco's Minimal Essential Media) supplemented with 10% fetal bovine serum, glutamine, nonessential amino acids, and the antibiotic G418 (0.25 mg/ml). After overnight incubation, the medium is replaced with DMEM containing 2% fetal bovine serum and various concentrations of the serine protease inhibitor, such as Compound CU, and/or an interferon such as interferon-alpha 2B (Intron A, Schering Plough). Each compound is tested at six to eight different concentrations. For one extreme of the range of concentrations, high concentrations of the compounds that will result in almost complete inhibition of replicon RNA accumulation after two days of treatment are selected. From these starting concentrations, serial dilutions are made so that the concentration ranges tested in the Replicon Assay include concentrations at which the compounds are highly effective, as well as concentrations at which there is no significant effect. Each HCV serine protease inhibitor concentration is tested without any added interferon, as well as with the addition of six to eight different interferon doses. Similarly, interferon is tested without any added HCV serine protease inhibitor. After a 48-hour incubation with the compounds, the medium is removed from the plates, and total cellular RNA is extracted from the cells using the RNeasy-96 kit manufactured by Qiagen Inc. (Valencia, Calif.). This RNA is then analyzed by quantitative RT-PCR, or TaqMan® (Applied Biosystems, Foster City Calif.). The TaqMan® RT-PCR target is the neomycin resistance gene in the replicon RNA. The plates are configured so that there are 5 replicates of each drug treatment sample, and 16 replicates of the untreated samples. This permits greater statistical confidence in the quantitative RT-PCR data.

Analysis of the Replicon Assay data yields two values that are useful in assessing the potency of potential HCV antiviral agents. At each compound concentration tested, the level of inhibition in replicon RNA accumulation caused by the compound during two days of treatment relative to the amount of replicon RNA in untreated cells is determined. This is reported as percent inhibition. When a series of data points generated by treatments of cells at a range of concentrations has been obtained, $IC_{50}$ values, i.e., the compound concentration at which HCV replicon RNA accumulation is diminished 50% by the compound, are generated. Through repeated testing of the HCV serine protease inhibitors in the Replicon Assay, it is determined that the $IC_{50}$ has a percent coefficient of variation (% CV or 100% x standard deviation in the $IC_{50}$/mean $IC_{50}$) of about 20%. The $IC_{50}$ is the value used to rank individual compounds tested in this assay based on their potency as HCV antiviral agents. Simple $IC_{50}$ determinations are inadequate to assess the utility of compounds used in combination. The most effective analysis of the array of data generated using all the combinations of different interferons and serine protease inhibitors requires evaluation of the percent inhibitions as shown in Table 7 using mathematical methods described below that are designed to determine if combination treatments are agonistic, additive, or synergistic.

Details of the Replicon Assay are as follows:

Procedure for Quantitative Analysis of HCV Replicon RNA in the HCV Replicon Assay Using TaqMan®® RT-PCR The Replicon Assay is used to measure the capacity of potential HCV antiviral compounds to inhibit the accumulation of a HCV subgenomic RNA replicon molecule in a Huh7 cell line (Lohmann et al. Replication of Subgenomic Hepatitis C Virus RNAs in a Hepatoma Cell Line. *Science* 285, 110-113 (1999)). This assay comprises three operational components: (1) Replicon cell maintenance, assay plate set up, and compound application; (2) Extraction of total cellular RNA from replicon cells; and (3) Real time RT-PCR (TaqMa®) to measure the mount of replicon RNA in each sample. The Replicon Assay requires at least 4 days to perform; however, the process can be interrupted and samples frozen between steps. Each assay component is described below.

1. Replicon Cell Maintenance, Assay Plate Setup, and Compound Application 1.1 Replicon Cell Line Maintenance The cell line used in the Replicon Assay is produced as described in Lohmann et al. (Replication of Subgenomic Hepatitis C Virus RNAs in a Hepatoma Cell Line. *Science* 285, 110-113 (1999)). After 150 cm² cell culture flasks (Costar) containing Replicon cells are incubated at 37° C. and 5% $CO_2$ and become confluent, the cells are diluted 1:10, v/v, into fresh 150 cm² cell culture flasks. The medium is DMEM containing 10% fetal bovine serum (PBS), 1× non-essential amino acids (NEAA), 1× Glutamine (Glu), and 0.25 mg/ml G418. Three serial passages are performed, each time allowing the cells to become confluent, followed by dilution of the cells into fresh 150 cm² cell culture flasks. These cells, referred to as "original cells," are then aliquoted and stored for future use in the Replicon Assay. TaqMan®-based analysis is performed to determine the number of HCV replicon genomes per cell, which reveals the presence of ~150 copies of the replicon per cell. This is based on the ratio of copies of replicon RNA to two times the copies of the human apoB gene (number of haploid genomes).

1.1.1 Original cells are stored in liquid $N_2$. For cells used in the Replicon Assay, after 20 serial passages, cells are abandoned, and a fresh lot is revived from liquid $N_2$ storage.

1.2 Plating of cells in 96-Well Trays for the Replicon Assay 1.2.1. For preparation of 96-well plates, a 75% confluent 75 cm² flask of replicon-containing cells are trypsmized, and resuspended in 10 ml Medium A. Trypsinization is performed by removing the medium, adding 1 ml of trypsin-EDTA 0.25%, w/v, and then removing the trypsin-EDTA. After 5-10 minutes the cells release from the flask and are resuspended in medium.

1.2.2. Cells are counted using a hemacytometer, and the cell concentration is adjusted to $10^5$ cells/ml.

1.2.3. Each well is seeded with a 100 µl cell suspension using an Impact2 multi-channel pipette (Matrix), never plating more than four 96-well plates from a single cell suspension.

1.2.4. 96-well plates are incubated at 37° C. overnight.

1.3. Compound Dilution and Application to Replicon Cell Trays 1.3.1. HCV serine protease inhibitor compounds are dissolved in dimethylsulfoxide (DMSO) to a final concentration of 20 mM. Interferons are suspended in phosphate buffered saline solution containing 0.1% w/v bovine serum albumin.

1.3.2. The 20 mM compound solution is diluted to 1 mM with DMSO.

1.3.3. 50 µl of compound dissolved in DMSO are added to 10 ml Medium B (the compound concentration is 5 mM, and the DMSO concentration is now 0.5%), or 20 µl of 1 mM compound and 30 µl DMSO are added to 10 ml Medium B (compound concentration 2 µM.)

1.3.4. Compound dilution to final concentration is completed by mixing compound/Medium B solution with Medium C (contains 0.5% DMSO). Serial one to five dilutions of the compound are made with Medium C in a 2 ml polypropylene 96-well block to obtain the desired final concentrations of compound.

1.3.5. The cell plate is removed from the 37° C. incubator and labeled on the top right corner of the lid and the right side of the base. The medium is poured off of the 96-well plates.

1.3.6. 100 µl compound/medium solutions from each well of the 96-well dilution block are added to the 96well cell plate using an Impact2 Pipette.

1.3.7. 100 µl medium C are added to all the untreated wells according to Table 3 for testing compounds at either 1, 3, or 6 different concentrations. "Untx" refers to mock-treated cells (DMSO added at the same concentration as in treated cells); "Con." refers to compound concentration.

TABLE 3

| | Compound 1 | | | | | | Compound 2 | | | | | |
|---|---|---|---|---|---|---|---|---|---|---|---|---|
| | 1 | 2 | 3 | 4 | 5 | 6 | 7 | 8 | 9 | 10 | 11 | 12 |

2 compounds, 6 concentrations, 5 replicates

| | | | | | | | | | | | | |
|---|---|---|---|---|---|---|---|---|---|---|---|---|
| A | | untx | untx | untx | untx | untx | untx | untx | untx | untx | untx | |
| B | | con. 1 | con. 1 | con. 1 | con. 1 | con. 1 | con. 1 | con. 1 | con. 1 | con. 1 | con. 1 | |
| C | | con. 2 | con. 2 | con. 2 | con. 2 | con. 2 | con. 2 | con. 2 | con. 2 | con. 2 | con. 2 | |
| D | | con. 3 | con. 3 | con. 3 | con. 3 | con. 3 | con. 3 | con. 3 | con. 3 | con. 3 | con. 3 | |
| E | | con. 4 | con. 4 | con. 4 | con. 4 | con. 4 | con. 4 | con. 4 | con. 4 | con. 4 | con. 4 | |
| F | | con. 5 | con. 5 | con. 5 | con. 5 | con. 5 | con. 5 | con. 5 | con. 5 | con. 5 | con. 5 | |
| G | | con. 6 | con. 6 | con. 6 | con. 6 | con. 6 | con. 6 | con. 6 | con. 6 | con. 6 | con. 6 | |
| H | | untx | untx | untx | untx | untx | untx | untx | untx | untx | untx | |

4 compounds, 3 concentration, 5 replicates

| | | | | | | | | | | | | |
|---|---|---|---|---|---|---|---|---|---|---|---|---|
| A | | untx | untx | untx | untx | untx | untx | untx | untx | untx | untx | |
| B | | con. 1 | con. 1 | con. 1 | con. 1 | con. 1 | con. 1 | con. 1 | con. 1 | con. 1 | con. 1 | |
| C | | con. 2 | con. 2 | con. 2 | con. 2 | con. 2 | con. 2 | con. 2 | con. 2 | con. 2 | con. 2 | |
| D | | con. 3 | con. 3 | con. 3 | con. 3 | con. 3 | con. 3 | con. 3 | con. 3 | con. 3 | con. 3 | |
| E | | con. 1 | con. 1 | con. 1 | con. 1 | con. 1 | con. 1 | con. 1 | con. 1 | con. 1 | con. 1 | |
| F | | con. 2 | con. 2 | con. 2 | con. 2 | con. 2 | con. 2 | con. 2 | con. 2 | con. 2 | con. 2 | |
| G | | con. 3 | con. 3 | con. 3 | con. 3 | con. 3 | con. 3 | con. 3 | con. 3 | con. 3 | con. 3 | |
| H | | untx | untx | untx | untx | untx | untx | untx | untx | untx | untx | |

| | Compound 3 | | | | | | Compound 4 | | | | | |
|---|---|---|---|---|---|---|---|---|---|---|---|---|
| | 1 | 2 | 3 | 4 | 5 | 6 | 7 | 8 | 9 | 10 | 11 | 12 |

16 compounds, 1 concentration, 4 replicates.

| | | | | | | | | | | | | |
|---|---|---|---|---|---|---|---|---|---|---|---|---|
| A | | untx | cpd 1 | cpd 2 | cpd 3 | cpd 4 | cpd 5 | cpd 6 | cpd 7 | cpd 8 | untx | |
| B | | untx | cpd 1 | cpd 2 | cpd 3 | cpd 4 | cpd 5 | cpd 6 | cpd 7 | cpd 8 | untx | |
| C | | untx | cpd 1 | cpd 2 | cpd 3 | cpd 4 | cpd 5 | cpd 6 | cpd 7 | cpd 8 | untx | |
| D | | untx | cpd 1 | cpd 2 | cpd 3 | cpd 4 | cpd 5 | cpd 6 | cpd 7 | cpd 8 | untx | |

TABLE 3-continued

| | | | | | | | | | |
|---|---|---|---|---|---|---|---|---|---|
| E | untx | cpd 9 | cpd 10 | cpd 11 | cpd 12 | cpd 13 | cpd 14 | cpd 15 | cpd 16 | untx |
| F | untx | cpd 9 | cpd 10 | cpd 11 | cpd 12 | cpd 13 | cpd 14 | cpd 15 | cpd 16 | untx |
| G | untx | cpd 9 | cpd 10 | cpd 11 | cpd 12 | cpd 13 | cpd 14 | cpd 15 | cpd 16 | untx |
| H | untx | cpd 9 | cpd 10 | cpd 11 | cpd 12 | cpd 13 | cpd 14 | cpd 15 | cpd 16 | untx |

12 compounds, 1 concentration, 5 replicates.

| | | | | | | | | | |
|---|---|---|---|---|---|---|---|---|---|
| A | untx | untx | untx | untx | untx | untx | untx | untx | untx | untx |
| B | cpd 1 | cpd 1 | cpd 1 | cpd 1 | cpd 1 | cpd 7 | cpd 7 | cpd 7 | cpd 7 | cpd 7 |
| C | cpd 2 | cpd 2 | cpd 2 | cpd 2 | cpd 2 | cpd 8 | cpd 8 | cpd 8 | cpd 8 | cpd 8 |
| D | cpd 3 | cpd 3 | cpd 3 | cpd 3 | cpd 3 | cpd 9 | cpd 9 | cpd 9 | cpd 9 | cpd 9 |
| E | cpd 4 | cpd 4 | cpd 4 | cpd 4 | cpd 4 | cpd 10 | cpd 10 | cpd 10 | cpd 10 | cpd 10 |
| F | cpd 5 | cpd 5 | cpd 5 | cpd 5 | cpd 5 | cpd 11 | cpd 11 | cpd 11 | cpd 11 | cpd 11 |
| G | cpd 6 | cpd 6 | cpd 6 | cpd 6 | cpd 6 | cpd 12 | cpd 12 | cpd 12 | cpd 12 | cpd 12 |
| H | untx | untx | untx | untx | untx | untx | untx | untx | untx | untx |

1.4. The Plates are Incubated for 48 Hours at 37° C., and then Subjected to RNA Extraction.

TABLE 4

Summary of equipment and supplies used for cell culture and compound set up

| | | |
|---|---|---|
| 8 channel Impact2 Pipette, 1250 μl | cat no 2004 | Matrix |
| 2 ml polypropylene deep-well block, 96-well, sterile | cat no 4222 | Matrix |
| 25 ml Reagent Reservoirs, Sterile | cat no. 8096 | Matrix |
| 1250 μl X-tra long pipet tips | cat no. 8255 | Matrix |
| 96-well plate | cat no. 3595 | Costar |
| Hemacytometer | Bright line improved Neubauer 0.1 mm deep | Reichert |
| DMEM | cat no. 51444-79P | JRH |
| L-glutamine (Glu) | cat no. 12403-010 | GIBCO-BRL |
| Non-essential amino acids (NEAA) | cat no. 11140-050 | GIBCO-BRL |
| Fetal Bovine Serum (FBS) | cat no. 16250-078 | GIBCO-BRL |
| G418 | cat no. 55-0273 | Invitrogen |
| DMSO | cat no. D-2650 | Sigma |
| Medium A | DMEM, 10% FBS, 1× NEAA, 1× Glu, 0.25 mg/ml G418 | |
| Medium B | DMEM, 2% FBS, 1× NEAA, 1× Glu | |
| Medium C | DMEM, 2% FBS, 1× NEAA, 1× Glu, 0.5% DMSO | |
| Trypsin-EDTA 0.25% | GIBCO-BRL | |

2. Extraction of Total Cellular RNA from Replicon Cells 2.1 Introduction

The goal of the procedure is to extract RNA from in vitro tissue culture samples so that the viral or cellular RNA is quantitatively recovered and pure enough to be analyzed by quantitative HCV RT-PCR assay.

To permit detection of variations in the efficiency of the RNA extraction, standard amounts of bovine viral diarrhea virus (BVDV), an RNA virus with some similarity to HCV, are added to each cell sample before RNA extraction. Thus, the level of BVDV RNA detected in the final multiplex RT-PCR reaction should be consistent among all wells within the variability limits associated with the Replicon Assay. This RNA extraction efficiency internal control is discussed further in the TaqMan® section, below.

The RNA extraction approach used is the RNeasy-96 method manufactured by Qiagen Inc. (Valencia, Calif.). This method employs 96 silica-based mini-columns that are positioned in an array compatible with 96-well tissue culture operations. The RNA extraction technology is a modification of the Boom method, in which all cellular proteins and nucleic acid, including nucleases, are first denatured with a strong chaotropic salt (guanidinium thiocyanate). In this environment, nucleic acids have a strong affinity for silica, the material in the mini-column discs; however, proteins and other contaminants do not bind to silica, and pass through the columns. After washing the columns with chaotropic/ethanol solutions, the samples are partially dried, and the nucleic acid is then released from the column in a small volume of water.

To reduce variability in recovering HCV RNA, care is taken with the column washing and partial drying conditions. The presence of a small amount of ethanol on a column will contaminate the final RNA and interfere with the RT-PCR detection system-L Caution is required in all phases of this procedure because the starting samples may be biohazardous, the chaotropic salt is highly caustic, and as a thiocyanate, it can generate poisonous cyanide gas if allowed to come in contact with acidic environments.

TABLE 5

Summary of Equipment and Supplies Needed for HCV RNA Extraction Procedures

| | | |
|---|---|---|
| RNeasy 96 Kit (24) | cat no. 74183 | Qiagen |
| QIAvac 96 manifold | cat no. 19504 | Qiagen |
| Centrifuge 4-15C, for 2×96 plates, 6000× g | cat no. 81010 | Qiagen |
| plate rotor for 2×96 plates | cat no. 81031 | Qiagen |
| 200 Proof Ethyl Alcohol | | |
| 8 channel Impact2 Pipette, 250 μl | cat no 2002 | Matrix |
| 8 channel Impact2 Pipette, 1250 μl | cat no 2004 | Matrix |
| 2 ml polypropylene deep-well block, 96-well, sterile | cat no 4222 | Matrix |
| 25 ml Reagent Reservoirs, Sterile | cat no. 8096 | Matrix |

TABLE 5-continued

Summary of Equipment and Supplies Needed
for HCV RNA Extraction Procedures

| | | |
|---|---|---|
| 1250 µl X-tra long pipet tips | cat no. 8255 | Matrix |
| 200 µl pipet tips | cat no. 7275 | Matrix |
| serum free MEM medium | cat no. 11095-80 | GIBCOBRL |

2.2 Procedure:

2.2.1 Cell Lysis 2.2.1.1. Prepare lysis buffer. For one 96-well plate, add 150 µl β-mercaptoethanol (β-ME) and 1 µl BVDV stock (vortex stock before adding) to 15 ml RLT buffer (a component of the RNeasy kit, Qiagen). This stock is prepared by infecting MDBK cells (bovine kidney cells, #CCL-22, available from the American Type Culture Collection, Manassas Va.) with BVDV and harvesting the culture at peak cytopathic effect (CPE). This stock has an infectious titer of approximately $1 \times 10^7$ pfu/ml. This gives BVDV a threshold cycle ($C_t$) of about 22 in the TaqMan® assay. The BVDV stock is stored in a −80° C. freezer.

2.2.1.2. Cells are washed with 150 µl serum-free MEM medium (program 4 on 8 channel electronic pipette P1250: Fill 1250, Disp 150×8). 150 µl lysis buffer are added to each well (same program).

2.2.1.3. RNA is extracted immediately, or cells are frozen at −80° C.

2.2.2. Preparation of reagents and materials for RNA extraction.

2.2.2.1. Note the lot # of the RPE and RNeasy 96 Kit.

2.2.2.2. RPE: 720 ml of 100% ethanol are added. to one bottle of RPE (Qiagen), and mixed well; RPE bottles are always shaken well before use.

2.2.2.3. 70% Ethanol: 150 ml diethylpyrocarbonate (DEPC) water are added to 350 ml 100% ethanol and mixed well.

2.2.3. Preparation of RNA with RNeasy 96 kit 2.2.3.1. Frozen samples are thawed at room temperature for 40 min. At the same time, one column of Extraction Controls is thawed for each plate (Extraction Controls: The RNeasy Extraction Controls are a set of 8 tubes all connected together. Inside of each tube is 170 µl of cell lysate with a certain ratio of HCV positive and negative cells. From the top to the bottom are two each of a low, medium, high, and zero number controls, respectively. (See section 2.3 of the protocol below.)

2.2.3.2. The samples are mixed by pipetting 100 µl up and down five times. The entire sample is transferred into columns 1-10 of the 2 ml Matrix square-well block (program 1 on P250: Mix 100×5, Fill 170, Purge).

2.2.3.3. 150 µl of the replicon standard is transferred into column 11(no samples in column 12).

2.2.3.4. 150 µl of 70% ethanol (EtOH) are added to each sample (program 4 on P1250: Fill 1250, Disp 150).

2.2.3.5. An RNeasy 96 plate labelled with the appropriate plate number is placed in the vacuum manifold. Mix and transfer the lysate/EtOH to the RNeasy 96 plate (program 1 on P1250: Mix 200, Times 5, Fill 330, and Purge). Any unused wells are sealed with transparent tape (supplied by Qiagen), usually column 12.

2.2.3.6. Vacuum (approximately 800 mbar) is applied to load the sample onto the mini-columns.

2.2.3.7. The RNeasy-96 plate is washed with 1000 µl of RW1 buffer (Qiagen)/well (program 2 on P1250: Fill 1000, Disp 1000).

2.2.3.8. Vacuum is applied to the filter through the RW1 buffer, and the flow-through is emptied.

2.2.3.9. The RNeasy-96 plate is washed with 1000 µl of RPE buffer/well (program 2 on P1250).

2.2.3.10. Vacuum is applied to filter through the RPE buffer.

2.2.3.11. Repeat Step 2.2.3.9

2.2.3.12. Vacuum is applied to the filter through the RPE buffer, keeping the vacuum applied for 3 min.

2.2.3.13. Dry the RNeasy 96 plate: The RNeasy-96 plate is placed in a collection microtube rack (supplied by Qiagen), covered with the supplied AirPore tape, and the unit is centrifuged for 10 min at 6000× g (Qiagen Sigma centrifuge; 4-15° C.).

2.2.3.15. Elute the RNA from the RNeasy 96-well plate: The RNeasy-96 plate is transferred onto the top of a new collection microtube rack. 70 µl of RNase-free water are added to the middle of each well (program 3 on P1250: Fill 850, Disp 70).

2.2.3.16. Incubate 1 min at room temperature, and then place a fresh AirPore tape over the plate.

2.2.3.17. The unit is then centrifuged for 4 min at 6000× g in a Sigma 4-15° C. centrifuge. The eluted volume measures between 28 µl and 50 µl.

2.2.3.18. The RNeasy-96 plate is discarded, and the collection tube rack is sealed with the Qiagen-provided caps (8 per strip).

2.2.3.19. The eluted RNA is stored at −80° C. or immediately analyzed in the TaqMan® assay.

2.3 Extraction Controls Preparation

Day 1

2.3.1.1. Plate out $2.5 \times 10^7$ replicon-producing cells in a 150 cm$^2$ tissue culture flask (T-150).

2.3.1.2. Plate out $2.0 \times 10^6$ Huh7 cells in a 75 cm$^2$ tissue culture flask (T-75).

2.3.1.3 Incubate overnight at 37° C.

Day 2

2.3.1.4. Lyse the cells with lysis buffer.

2.3.1.5. Remove the supernatant from the Huh7 and replicon-producing cells, and wash the monolayer with 10 ml serum-free medium (MEM).

2.3.1.6. Add 30 ml of lysis buffer (with 1 µl of BVDV stock/15 ml of lysis buffer) to the Huh7 Cells, mix by repeated pipetting, and place the cell lysate in a 50 ml conical-bottomed tissue culture centrifuge tube.

2.3.1.7. Add 10.5 ml of lysis buffer to the replicon-producing cells, mix by repeated pipetting, and place the cell lysate in a 15 ml conical-bottomed tissue culture centrifuge tube.

2.3.2. For the HIGH Extraction Standard: Aliquot 170 µl of the replicon-producing cells cell lysate into rows 5 and 6 of two Matrix 0.75 ml tube racks.

2.3.3. For the MEDIUM Extraction Standard: Add 1.0 ml of the replicon-producing cells cell lysate to 9 ml of the Huh7 lysate, and mix well. Aliquot 170 µl of this mixture to rows 3 and 4 of two Matrix 0.75 ml tube racks.

2.3.4. For the LOW Extraction Standard: Add 50 µL of the replicon-producing cells cell lysate to 10 ml of the Huh7 lysate, and mix well. Aliquot 170 µl of this mixture to rows 1 and 2 of two Matrix 0.75 ml tube racks.

2.3.5. ZERO Extraction Control: Aliquot 170 µL of the Huh7 cell lysate to rows 7 and 8 of two Matrix 0.75 ml tube racks.

2.3.6. Store controls at −90° C.

3. TaqMan® RT-PCR and Data Analysis 3.1 Introduction: Real-time quantitative RT-PCR is used to measure the amount of HCV replicon RNA in each sample. This technology is also referred to as the PCR-based 5' nuclease assay, and TaqMan®. The analytic instrument is the Applied Biosystems 7700 Prism Sequence Detection System (Applied Biosystems, Foster City, Calif.). This instrument is essentially a time-multiplexed laser-induced fluorescence spectrograph coupled with a thermal cycler. It monitors the accumulation of PCR amplicon in each well of a 96-well sample tray throughout the course of the PCR process.

3.2. Use of BVDV Internal Control: As mentioned in the previous section, an internal positive control is incorporated into every sample. This serves as a measure of RNA extraction efficiency, and shows if the sample contains contaminants that inhibit TaqMan® PCR. BVDV is mixed with the chaotropic cell lysis buffer prior to applying the lysis buffer to the cells. Although the positive control is in every sample, the BVDV internal positive control assay is only performed when the HCV replicon RNA assay data fall outside of expected limits, suggesting that there could be a problem with the samples. The 7700 is capable of simultaneously monitoring the accumulation of two different PCR amplicons in the same tube by using detection probes labeled with two different fluorescent reporter dyes ("multiplexing"). Specific criteria that elicit a TaqMan® analysis for the BVDV internal positive control of a sample plate are described in the section on data analysis (3.6).

3.3 HCV Replicon RNA TaqMan® probe and primers. Because of the expected genetic stability and general lack of RNA secondary structure in the neomycin resistance gene (neo) encoded in the replicon, primers and a probe that bind in that region are employed. This segment of the replicon RNA extends from bases 342-1193 of the 8001 base pair replicon (SEQ ID NO: 1):

```
 301 gtgcttgcga gtgcccgggg aggtctcgta gaccgtgcac catgagcacg aatcctaaac
 361 ctcaaagaaa aaccaaacgt aacaccaacg ggcgcgccat gattgaacaa gatggattgc
 421 acgcaggttc tccggccgct tgggtggaga ggctattcgg ctatgactgg gcacaacaga
 481 caatcggctg ctctgatgcc gccgtgttcc ggctgtcagc gcaggggcgc ccggttcttt
 541 ttgtcaagac cgacctgtcc ggtgccctga atgaactgca ggacgaggca gcgcggctat
 601 cgtggctggc cacgacgggc gttccttgcg cagctgtgct cgacgttgtc actgaagcgg
 661 gaagggactg gctgctattg ggcgaagtgc cggggcagga tctcctgtca tctcaccttg
 721 ctcctgccga gaaagtatcc atcatggctg atgcaatgcg gcggctgcat acgcttgatc
 781 cggctacctg cccattcgac caccaagcga aacatcgcat cgagcgagca cgtactcgga
 841 tggaagccgg tcttgtcgat caggatgatc tggacgaaga gcatcagggg ctcgcgccag
 901 ccgaactgtt cgccaggctc aaggcgcgca tgcccgacgg cgaggatctc gtcgtgaccc
 961 atggcgatgc ctgcttgccg aatatcatgg tggaaaatgg CCGCTTTTCT GGATTCATCG
                                                                forward primer
1021 aCTGTGGCCG GCTGGGTGTG Gcggaccgct atcaggacat agcgttggct acccgtgata
          TaqMan ® probe
1081 ttgctgaaga gcTTGGCGGC GAATGGGctg accgcttcct cgtgctttac ggtatcgccg
                          reverse primer
1141 ctcccgattc gcagcgcatc gccttctatc gccttcttga cgagttcttc tgagtttaaa
```

3.4. Procedures 3.4. 1. Method for Preparing 1× Master Mixtures for NEO and BVDV RT-PCR

TABLE 6

Summary of equipment and supplies for preparing RT-PCR 10-plate Master Mix

| | Order No. | Supplier |
|---|---|---|
| Equipment and supplies | | |
| 0.5-10 µl pipette | 22 47 005-1 2000 Series | Eppendorf |
| 2-20 µl pipette | 22 47 015-9 2000 Series | Eppendorf |
| 10-100 µl pipette | 22 47 020-5 2000 Series | Eppendorf |
| 50-200 µl pipette | 22 47 025-6 2000 Series | Eppendorf |
| 100-1000 µl pipette | 22 47 030-2 2000 Series | Eppendorf |
| 1250 µl Matrix tips | cat no. 8255 | Matrix |
| 200 µl Matrix tips | cat no. 7275 | Matrix |
| 10 µl ART tips | cat no. 2140 | Molecular Bioproducts |
| 20 µl ART tips | cat no. 2149P | Molecular Bioproducts |
| 100 µl ART tips | cat no. 2065E | Molecular Bioproducts |
| 200 µl ART tips | cat no. 2069 | Molecular Bioproducts |

TABLE 6-continued

Summary of equipment and supplies for preparing RT-PCR 10-plate Master Mix

|  | Order No. | Supplier |
| --- | --- | --- |
| 1000 µl ART tips | cat no. 2079E | Molecular Bioproducts |
| Electronic pipette, Impact2 | cat no. 2001 | Matrix |
| 1.5 ml RNase-free microfuge tubes | cat no. 12450 | Ambion |
| 14 ml Polypropylene tubes | cat no. 352059 | Falcon |
| 25 ml reagent reservoir | cat no. 8096 | Matrix |
| 96-well reaction plate | cat no. N801-0560 | Applied Biosystems |
| optical cap strips | cat no. N801-0935 | Applied Biosystems |
| Disposable Sterile Gowns | cat no. 9515-E | Baxter |
| Reagents |  |  |
| Acid | 0.1 N HCl | Fisher |
| RNAseZap | cat no. 9780 | Ambion |
| RNAse away | cat no. 7005 | Molecular Bioproducts |
| 10-pak, EZ RT-PCR core reagents kit, 5× reaction buffer, 25 mM Manganese Acetate, deoxy NTPs | cat no. 403028 | Applied Biosystems |
| VIC NEO probe, 2 µM (=10×), 550 µl per aliquot | cat no. 450003, custom, 5'-VIC-CTG TGG CCG GCT GGG TGT GG-TAMRA-3' (SEQ ID NO: 2) | Applied Biosystems |
| VIC BVDV probe, 2 µM (=10×), 550 µl per aliquot (Vertex) | cat no. 450003, custom, 5'-VIC-CCC TCG TCC ACG TGG CAT CTC GA-TAMRA-3' (SEQ ID NO: 3) | Applied Biosystems |
| NEO forward primer, 3 µM (=10×) forward/reverse primer mix, 550 µl per aliquot | cat no. 4304972, custom, 5'-CCG CTT TTC TGG ATT CAT CG-3' (SEQ ID NO: 4) | Applied Biosystems |
| NEO reverse primer, 3 µM (=10×) forward/reverse primer mix, 550 µl per aliquot | cat no. 4304972, custom, 5'-CCC ATT CGC CGC CAA-3' (SEQ ID NO: 5) | Applied Biosystems |
| BVDV forward primer, 3 µM (=10×) forward/reverse primer mix, 550 µl per aliquot | custom, 5'-CAG GGT AGT CGT CAG TGG TTC G-3' (SEQ ID NO: 6), 1.0 µM scale w/gel purification | Oligos etc |
| BVDV reverse primer, 3 µM (=10×) forward/reverse primer mix, 550 µl per aliquot | custom, 5'-GGC CTC TGC AGC ACC CTA TC-3' (SEQ ID NO: 7), 1.0 µM scale w/gel purification | Oligos etc |
| NEO RNA standards | In vitro transcribed RNA from a plasmid containing the neo gene portion of the HCV replicon RNA using T7 RNA polymerase. The in vitro transcribed RNA is quantitated based on known molecular weight of the transcripts and the UV-absorbance of the purified transcript solution. This RNA is diluted, aliquoted, and stored at −80° C. Individual aliquots are thawed for each TaqMan ® assay. |  |
| RNA samples to be tested isolated from HCV replicon cells (section 2 of this Protocol), 10 µl/96-well plate |  |  |
| Nuclease-Free Water (Not DEPC Treated) | cat no. 9930 | Ambion |

3.4.2. Preparation of Reagents for Master mix 3.4.2.1. Clean the bench according to the two steps below, and wipe the pipettes with RNAse away.
RNAse Zap (Ambion, Austin, Tex.)
RNAse Away (Molecular Bioproducts, San Diego, Calif.)

3.4.2.2. Open core EZ RT-PCR reagents (Applied Biosystems) and put the 5× buffer on ice, thaw frozen reagents at room temperature for about 15 minutes, and then put them on ice. One EZ RT-PCR reagents kit can be used to analyze two 96-well RNA extractions.

3.4.2.3. Take one tube of 2 µM VIC probe (NEO or BVDV, 550 µl per tube) from −20° C. and put on ice.

3.4.2.4. Take one tube 3 µM forward/reverse primer mix (NEO or BVDV, 550 µl per tube) from −20° C. and put on ice.

3.4.2.5. Take one tube (30 µl) of standards RNA transcript ($10^8$ copies/10 µl) from −80° C. and place on ice.

3.4.2.6. Take one tube of room temperature Ambion water.

3.4.3. Assembly of Master Mixture for One 96-Well Plate Reaction.

3.4.3.1. Use a 1 ml pipette to transfer 5× buffer (Applied Biosystems) to a 14 ml tube; total volume added is 1100 µl.

3.4.3.2. Use a 1 ml pipette to add 25 mM $Mn(OAc)_2$ (Applied Biosystems) to a 14 ml tube; total volume added is 660 µl.

3.4.3.3. Use a 200 µl pipette to add 165 µl of 10 mM DATP to the 14 ml tube. Do the same for 10 mM dCTP, 20 mM dUTP, and 10 mM dGTP.

3.4.3.4. Use a 1 ml pipette to add 550 µl 10×3 µM forward/reverse primer mix.

3.4.3.5. Use a 1 ml pipette to add 550 µl 10×2 µM probe.

3.4.3.6. Use a 1 ml pipette to add 220 µl rTth DNA polymerase (Applied Biosystems).

3.4.3.7. Use a 100 µl pipette to add 55 µl AmpErase UNG (Applied Biosystems).
3.4.3.8. Use a 1 ml pipette to add 605 µl Ambion $H_2O$ to the 14 ml tube; the final volume is 4400 µl total.
3.4.3.9. Transfer the 4400 µl master mix to a 25 ml reagent reservoir.
3.4.3.10. Dispense 40 µl per well for all 96 wells using an 8-channel pipette.
3.4.3.11. Transfer 10 µl of extracted unknown samples to wells of the reaction plate using an 8-channel pipette, column by colulmn, column 1 through column 11. Cap each column after transfer.
3.4.3.12. Add 270 µl Ambion $H_2O$ to the 30 µl $10^8$ copies/10 µl RNA transcript for use in the standard curve and mix. There are now $10^7$ copies of the HCV replicon quantitation standard RNA/10 µl.

3.4.4. Setting Up the ABI 7700 for Each Run
3.4.4.1 Before each run, reboot the computer for the ABI 7700 and rebuild the desktop.
3.4.4.2 Close and remove any redundant programs from the hard drive; overuns data to trash.
3.4.4.3 Open Sequence Detector v1.7 program (SDS software).
3.4.4.5 Open the "Replicon Assay Runs" folder.
3.4.4.6 Open the "Replicon Assay" template plate. The thermal cycler conditions programmed into the template are as follows:
Stage 1: 50° C. for 2 min.
Stage 2: 60° C. for 30 min.
Stage 3: 95° C. for 5 min.
Stage 4: 95° C. for 15 sec.
Stage 5: 60° C. for 60 sec.
Cycle repeat number of stages 4-5: 40.
Template instrument:diagnosis: advanced options:
Select views: display mse.
Select views: display best fit.
Select miscellaneous: reference dye ROX.
3.4.4.7 "Save" (not "save as") the file in the "Replicon Assay Runs" folder.
3.4.4.8 Show setup: hit RUN 3.5 Preparing the ABI7700 Data After a Run Using SDS Software.
3.5.1. The assay plates are removed from the ABI7700 and discarded without ever being opened. This greatly reduces laboratory problems with PCR cross contamination.
3.5.2. The data are analyzed using the Sequence Detector System software V1.7.
3.5.3. The threshold levels are initially set using default settings.
3.5.4. Data rejection criteria: Data points or series of whole plates can be rejected. If there has been a significant deviation from protocol, reagent failure or mishap, or ABI 7700 run failure, data can be discarded. For rejection of any data points from an apparently normal run, one or more of these criteria must be met.
3.5.4.1. Threshold cycle calculations. Normally use the default values for the SDS software. If the Ct of the most concentrated sample is less than 15, then change the threshold value stop limit as needed to a lower value so that the Ct of the highest concentration sample is greater than the stop value. Update calculations after making this change.
3.5.3.2. Consider rejecting an entire abnormal TaqMan® run as indicated by a deviation from the mean values for the slope and y-axis intercept of the line generated by analysis of the neo RNA standards. The acceptable ranges for those values are:
Slope values should be between 3.0 and 3.6
y-intercept cycles should be between 36 and 41 cycles.
3.5.4.3. Aberrant individual TaqMan® wells as indicated by extreme Rn/ΔRn can be deleted prior to data analysis so that they do not affect the SDS software calculations.
3.5.4.4. Examine and record the no-template control Ct values and confirm that they are >7.0 Ct (>100×) higher than the Ct for any compound treated sample.
3.5.5. The HCV RNA standards Ct values are compared with previous results.
3.5.6. The HCV RNA standard curve is compared with previous results.
3.5.7. If aberrant amplification is evident in individual wells, those wells are identified and noted.
3.5.8. The "results" file is exported and transferred from the 7700 computer to another computer for analysis using Microsoft Excel.
3.5.9. Any of the following changes in reagent preparations or dilution used is reported.
New probe or primer synthesis from vendor.
New probe or primer dilution and aliquots.
New standards RNA transcript preparation.
New standards RNA transcript dilution and aliquots.
New BVDV viral preparation.
New column 11 standards preparation.

3.6 TaqMan® Data Analysis.
3.6.1. Copy and paste TaqMan® HCV Ct number and copy number from the TaqMan® results file into the appropriate cells of the Replicon Assay data analysis Microsoft Excel macro, and run the macro.
3.6.2. Copy the TaqMan® results table from the macro sheet onto another sheet, input compound serial number and lot number.
3.6.3 From this excel sheet, the mean, standard deviation, and percentage CV of Compound inhibition activity, as well as HCV copy number, HCV Ct number, and BVDV Ct number (if available), of all dilution points in 5 replicates and no-compound control, will be calculated.
3.6.4. Criteria for data rejection and implementation of BVDV Control TaqMan®. Check all the calculations. Data points or series of whole plates can be rejected. If there is a significant deviation from protocol, reagent failure or mishap, or ABI 7700 run failure, data can be discarded. For rejection of any data points from an apparently normal run, then one or more of these criteria must be met. The standard deviation of percentage inhibition should be less than 30% in active compounds. The % CV of HCV copy number should be less than 30%. The standard deviation of HCV Ct of all samples should be less than 0.5; this is usually about 0.1 to 0.3 in most samples. If the HCV Ct standard deviation is more than 0.5, then go back to the raw data table, and check the Ct numbers of 5 replicates. If the Ct number of any one well is 2 Ct different from the average Ct number of 5 replicates, then this well should omitted from the analysis. If more than 3 wells (not on same column) have unusual Ct numbers, then the BVDV TaqMan® internal control assay should be carried out. If the BVDV data show irregularity, then the compound should be tested again.
3.6.5. $IC_{50}$ calculation: Copy and paste the data of average inhibition and standard deviation into a sigmoid dose response with a variable slope calculator that uses non-linear regression methods. Using this tool, calculate the $IC_{50}$ by using both of two methods: fixing the top at 100% inhibition only, or fixing the top at 100% inhibition and the bottom at 0% inhibition. The method that gives the clearest fit is then reported for each compound. The most reliable $IC_{50}$ comes from the calculation having the lowest standard error. If $IC_{50}$s calculated from these two curve fit options show more than one fold difference, or if the $IC_{50}$ SD is greater than the $IC_{50}$, the compound should be tested again at adjusted concentrations.

Calculation of the Effect of HCV Serine Protease Inhibitors in Combination with Interferons The effect of a HCV serine protease inhibitor (HSPI) and an interferon in combination can be assessed in the Replicon Assay by generating a dose response curve for the HSPI in the presence of various levels of interferon, or by determining a dose response curve for an interferon in the presence of various levels of HSPI. The goal is to assess whether there is more or less inhibition of viral RNA accumulation than would be expected if the two drugs produce additive effects on the RNA. More specifically, the additivity definition of Lowe ((1928) Die Quantitation Probleme der Pharmakologic, *Ergebn. Physiol.*, 27, 47-187) is used. This is defined as follows. Let $D_{E,INF}$ be the concentration of interferon that results in effect E, and let $D_{E,HSPI}$ be the concentration of protease inhibitor that results in effect E.

$$1 = \frac{D_1}{D_{E,INF}} + \frac{D_2}{D_{E,HSPI}} \tag{1}$$

Then no interaction or Lowe additivity is defined by the following relationship, where the combination of concentration $D_1$ of INF and $D_2$ of HSPI produces the effect E.

Figure 2:
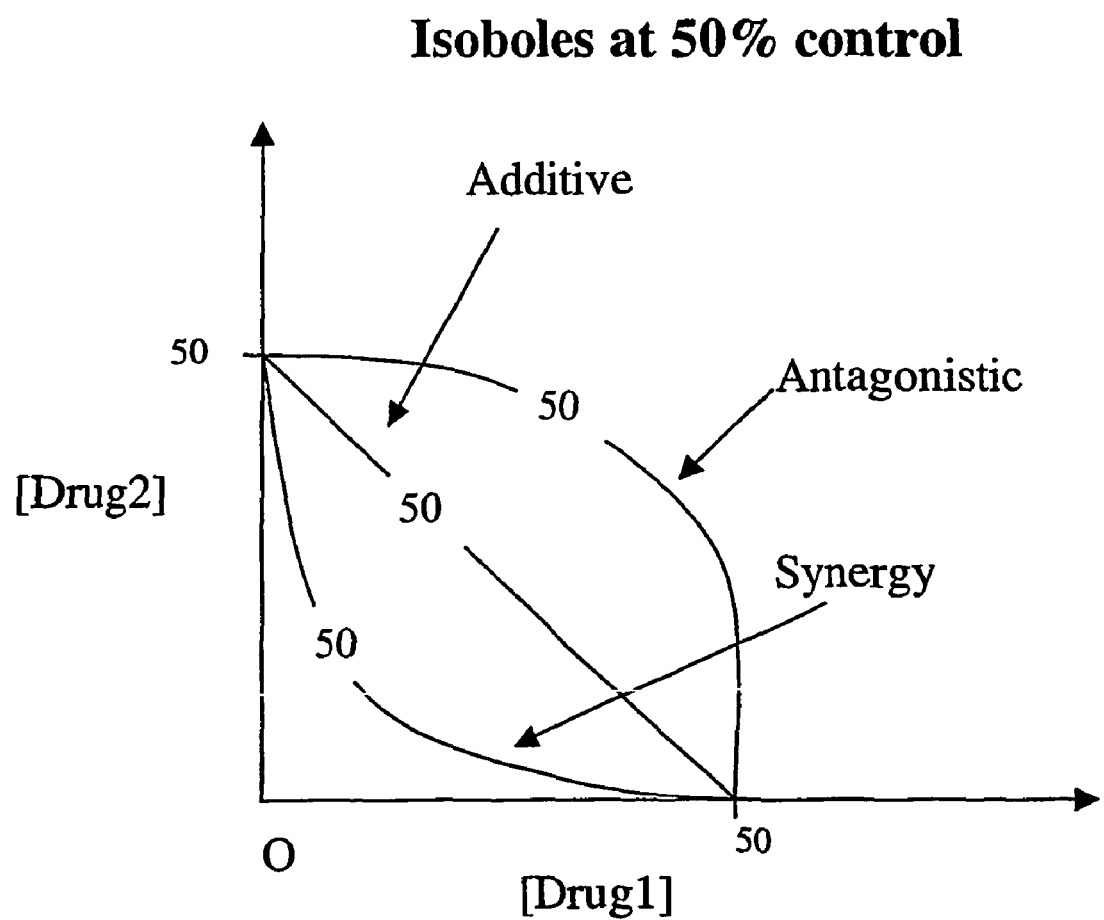
FIG. 2 graphically shows the isobol concavity exhibited by compounds used in combination that are antagonistic, additive, and synergistic according to the synergy calculation methods of Greco, Park and Rustom ((1990) Application of a New Approach for the Quantitation of Drug Synergism to the Combination of cis-Diamminedichloroplatinum and 1-β-D-Arabinofuranosylcytosine, *Cancer Research*, 50, 5318-5327).

The degree of synergy or antagonism is expressed in terms of iso-effect curves or Isobols. The combination (D1,D2) is a point on a graph where the axes are the concentrations of interferon and HSPI (FIG. 2). All such combinations that produce an effect level E form the E effect Isobol. It is necessarily the case that $(D_{E,INF},0)$ and $(0, D_{E,HSPI})$ are points on the Isobol. The Isobols are straight lines connecting points $(D_{E,INF},0)$ and $(0, D_{E,HSPI})$ when the additivity relationship (1) is satisfied.

Concave-up Isobols indicate synergy, and concave-down Isobols indicate antagonism. Following the guidelines of Berenbaum, M. C. ((1985) The expected effect of a combination of agents: the general solution. *J. Theor. Biol.*, 114, 413-431), and Greco, Park and Rustom ((1990) Application of a New Approach for the Quantitation of Drug Synergism to the Combination of cis-Diamminedichloroplatinum and 1-β-D-Arabinofuranosylcytosine, *Cancer Research*, 50, 5318-5327), add a term to (1) to account for synergy or antagonism. The equation defines a response surface that can be fit to the percent control values at all treatment combinations. Contour plots from this fitted response surface are the Isobols.

The response surface model assumes a sigmoidal dose response for each compound defined by (2).

$$E = \frac{E_{max}}{1 + \left(\frac{[Drug]}{IC50}\right)^m} + B \tag{2}$$

The concentrations that give a specified level of activity E alone are given by (3)

$$D_{E,INF} = IC50_{INF}\left(\frac{E-B}{E_{max}-E+B}\right)^{1/m_{INF}} \tag{3}$$

-continued
$$D_{E,HSPI} = IC50_{HSPI}\left(\frac{E-B}{E_{max}-E+B}\right)^{1/m_{310}}$$

To satisfy the model of Greco et al. (1990), the combined action of the drugs must then satisfy equation (4) for every combination of drugs that produces response level E.

$$1 = \frac{[INF]}{IC50_{INF}\left(\frac{E-B}{E_{max}-E+B}\right)^{1/m_{INF}}} + \frac{[HSPI]}{IC50_{HSPI}\left(\frac{E-B}{E_{max}-E+B}\right)^{1/m_{310}}} + \frac{\alpha[INF][HSPI]}{IC50_{INF}IC50_{HSPI}\left(\frac{E-B}{E_{max}-E+B}\right)^{1/2m_{INF}}\left(\frac{E-B}{E_{max}-E+B}\right)^{1/2m_{310}}} \tag{4}$$

Figure 3:
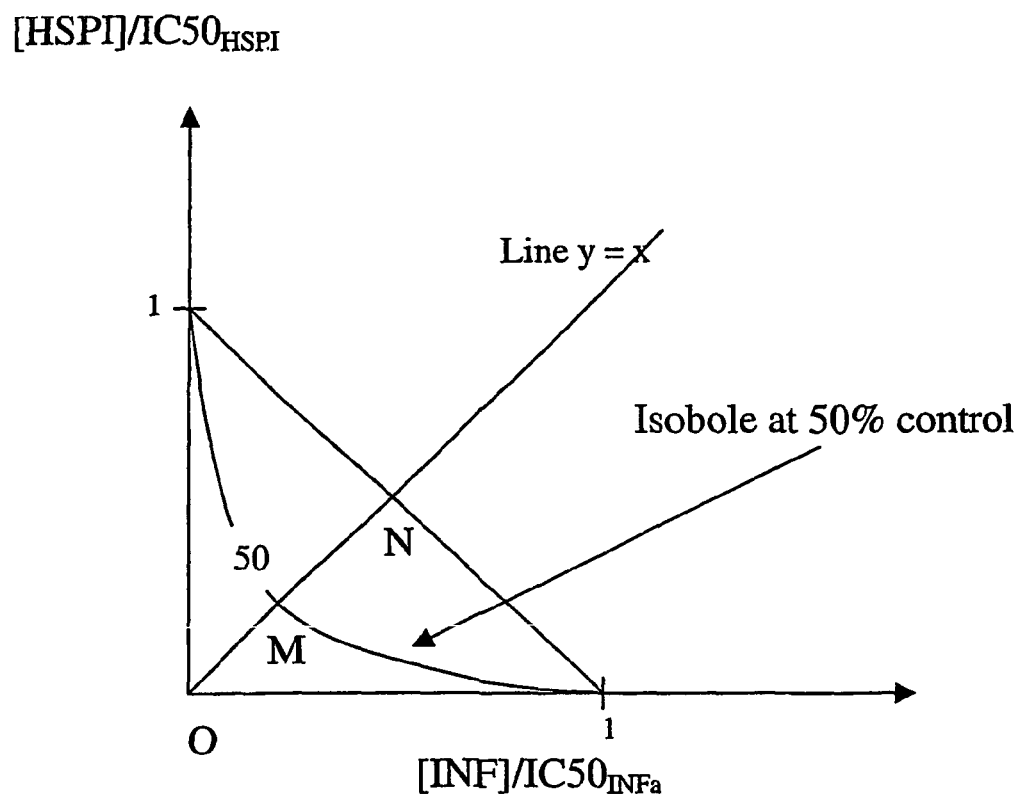
FIG. 3 shows the geometric relationship between a and the amount of curvature in the isobol. A hypothetical isobol at the E=50% effect level is displayed with a straight line isobol that would be expected under additivity. M is the point of intersection of the line y=x and the hypothetical isobol. N is the point of intersection of the line y=x and the straight line isobol. O is the origin (0,0). S gives a measure of the amount of curvature in the isobol, where S=ON/OM. ON is the distance from O to N and OM is the distance from O to M. The parameter α is related to S by the equation $\alpha=4(S^2-S)$.

The parameter α measures the amount of interaction. A zero value of alpha means no interaction or additivity since the equation reduces to (1) when α=0. Given $IC_{50}$s, Hill slopes (m), maximum value (Emax), and minimum value (B), this equation can be solved to give the effect that results from any treatment combination [INF] and [HSPI]. Therefore, this equation defines a response surface. Given an experiment where [INF] and [HSPI] are varied, the parameters can be chosen using nonlinear weighted least squares regression. The parameter a can be related to a synergy measure S (Hewlett, P. S. (1969) Measurement of potencies of drug mixtures. *Biometrics*, 25, 477-487), which is taken directly from the Isobols at a 50% effect. S is the ratio, of the distance from the origin to the Isobol defining additivity, to the distance from the origin to Isobol of the fitted data, along the line at 45 degrees from the axes. (S=ON/OM see FIG. 3). The relationship is $\alpha=4(S^2-S)$.

The method discussed in Greco et al. (1990), above, for fitting the response surface and determining synergy parameter α with its significance level is followed in assessing the degree of synergy in a series of experiments testing HSPIs in combination with several different interferons. However, there is a need to weight observations with lower counts more than those with higher counts. The counts relate directly to the percent control, which is the effect E. Using methods described in Carroll, R. J. and Rupert, D. ((1988) (*Transformation and Weighting in Regression*, Chapman and Hall, New York), the well to well variability can be seen to increase with the square of the mean percent control value. Therefore, the observations are weighted by one over the fitted percent control value (E) squared. The variance and weighting used to analyze these experiments is consistent with variability relationships observed by researchers investigating methods for analyzing Radioligand assays (Finney, D. J., (1976), Radioligand Assay, *Biometrics*, 32,721-740, and Dudley, R. A. Edwards, P., Ekins, R. P., McKinzie, I. G. M., Raab, G. M., Rodbard, D. and Rodgers, R. P. C. (1985), Guidelines for Immunoassay Data Processing, *Clinical Chemistry*, 31/8, 1264-1271).

Results

In an initial experiment, HCV serine protease inhibitor Compound CU is tested over a concentration range from 3 µM to 0.0123 µM, i.e., a 244-fold range. The interferon-alpha 2B concentrations vary from 30 units per sample to 0.0096 units per sample, i.e., a 3125-fold range. As shown in Table 7, when used as a single drug treatment, Compound CU exhibits an $IC_{50}$ of 0.48 µM, and the interferon $IC_{50}$ is 2.19 U. Within the precision of the Replicon Assay, which is approximately 20%, addition of interferon-alpha 2B results in an increase in the inhibition of replicon RNA accumulation in a dose-dependent manner. For example, treatment of cells with 0.333 µM Compound CU results in 28% inhibition of replicon RNA accumulation. Treatment of cells with a combination of 0.333 µM Compound CU, which is 71% of the $IC_{50}$ dose (0.469 µM) and 0.24 U of interferon-alpha 2B, which is 11% of the interferon-alpha 2B $IC_{50}$ (2.05 µM) results in a 49% inhibition of replicon RNA accumulation. Thus, 71% of one $IC_{50}$ dose in combination with 11% of the other results in 49% inhlbition of replicon RNA accumulation. Using an intuitive approach to determining if a combination treatment is synergistic or additive or antagonistic, one could predict that if effect of combination treatment were only additive, one would expect the combined fractions of the two $IC_{50}$ doses needed to obtain a 49% inhibition of replicon RNA accumulation to be 98%. Our experimental results demonstrate that the level of inhibition of replicon RNA accumulation is achieved using 71% plus 11%, i.e. 82% of the $IC_{50}$ dose rather than 98%, as predicted for additive effects of combination treatment. Thus at these concentrations of compounds, the effect appears to be synergistic because smaller fractional doses of the $IC_{50}$ dose of each compound are used to obtain 49% inhibition of HCV replicon RNA than would be required of either compound alone, where 98% of the $IC_{50}$ doses would be needed. The results of this combination treatment are shown in Table 8 and graphically in FIG. 1.

TABLE 7

Inhibition of replicon RNA accumulation after 48 hour treatment with Compound CU and interferon-alpha 2B, individually or in combination

| Compound CU (conc.) | Interferon-alpha 2B(units) | | | | | | |
|---|---|---|---|---|---|---|---|
| | 30 U | 6 U | 1.2 U | 0.24 U | 0.048 U | 0.0096 U | 0 U |
| 3 µM | 99% | 99% | 99% | 99% | 98% | 98% | 98% |
| 1 µM | 99% | 98% | 96% | 95% | 92% | 93% | 88% |
| 0.333 µM | 94% | 87% | 66% | 49% | 33% | 27% | 28% |
| 0.1111 µM | 93% | 79% | 46% | 29% | 12% | 15% | 11% |
| 0.0370 µM | 92% | 78% | 44% | 21% | 2% | 7% | 8% |
| 0.0123 µM | 92% | 78% | 44% | 20% | 19% | 19% | 5% |
| 0 µM | 89% | 73% | 38% | 16% | 8% | 12% | 0% |

These initial results, derived as stated earlier via use of the in vitro Replicon Assay and a simple additivity analysis of the data generated by that assay, demonstrate that combination treatment of replicon cells with an HCV serine protease inhibitor and an interferon yields at least an additive antiviral effect, and likely a synergistic antiviral effect.

Figure 4:
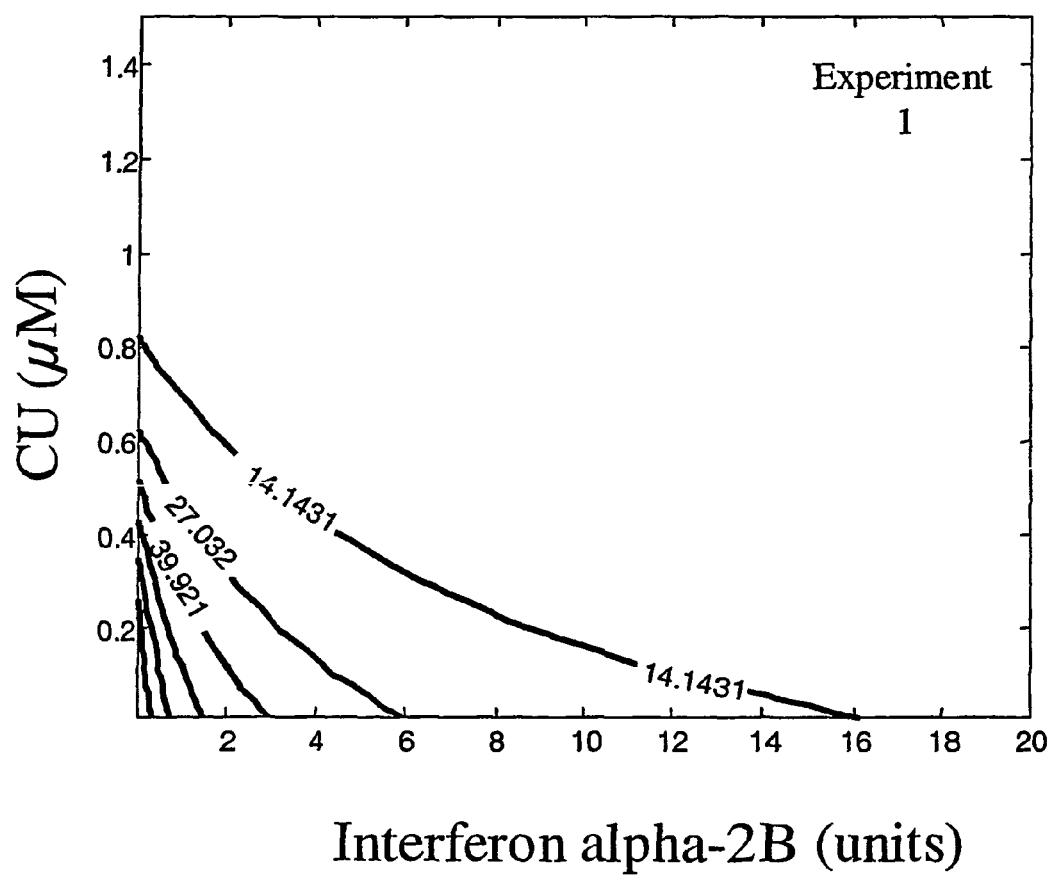
FIG. 4 shows the isobol calculations using the method of Greco et al., supra, for the combination of compound CU and interferon alpha-2B (Schering-Plough) using 6 dilutions of each compound in Experiment 1
Figure 5:
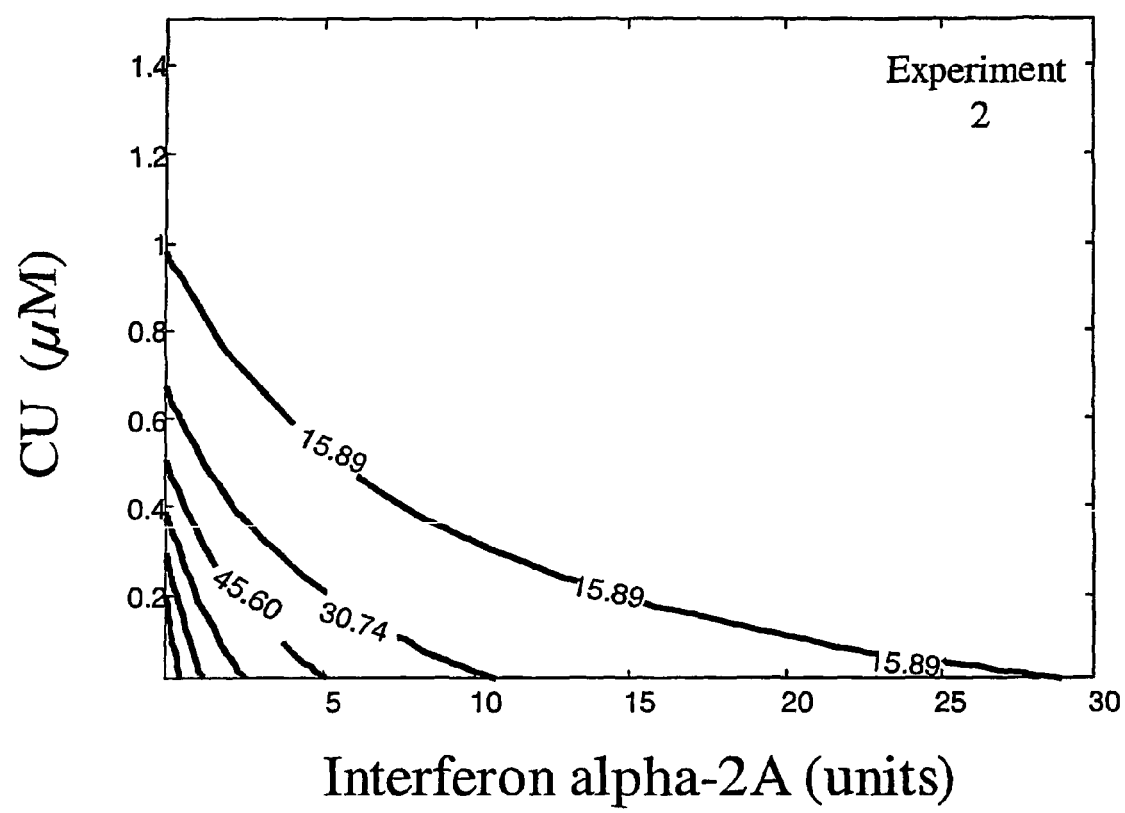
FIG. 5 shows the isobol calculations using the method of Greco et al., supra, for the combination of compound CU and interferon alpha-2A using 6 dilutions of each compound in Experiment 2.
Figure 6:
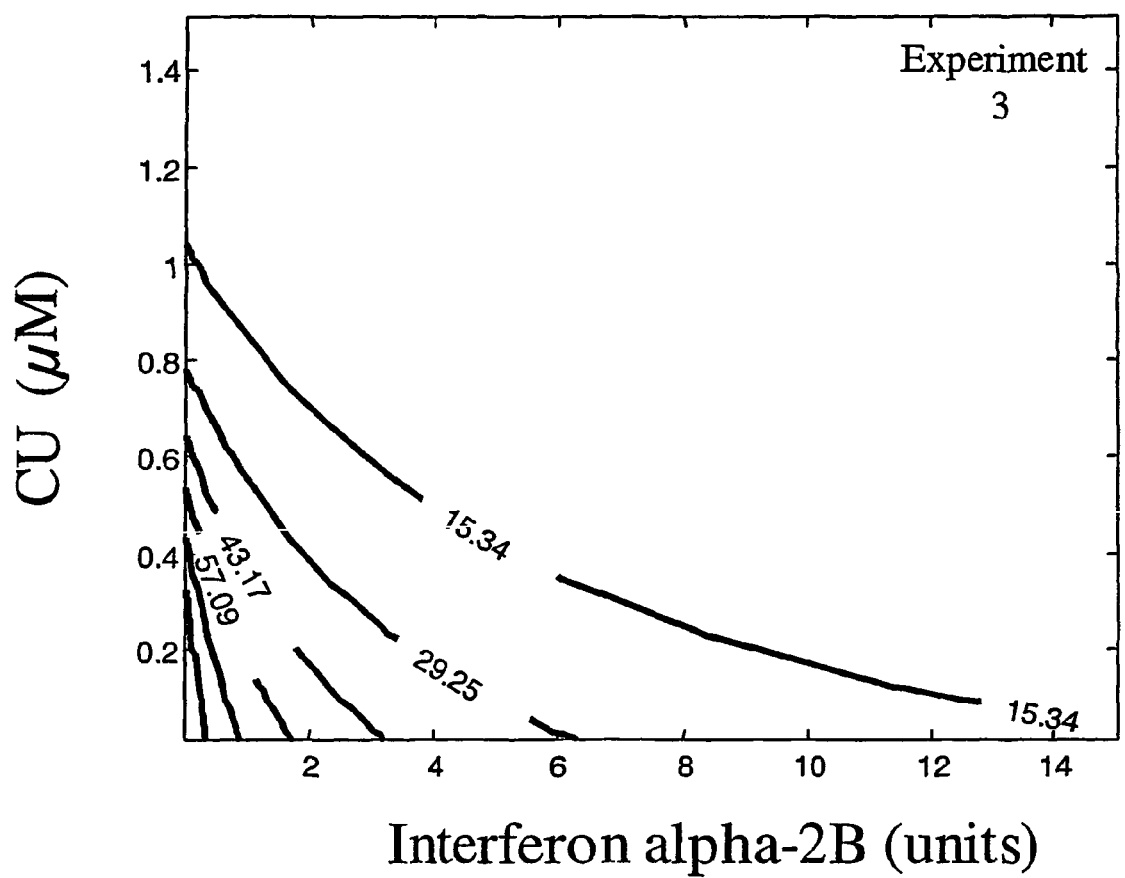
FIG. 6 shows the isobol calculations using the method of Greco et al., supra, for the combination of compound CU and interferon alpha-2B (Schering-Plough) using 8 dilutions of each compound in Experiment 3.
Figure 7:
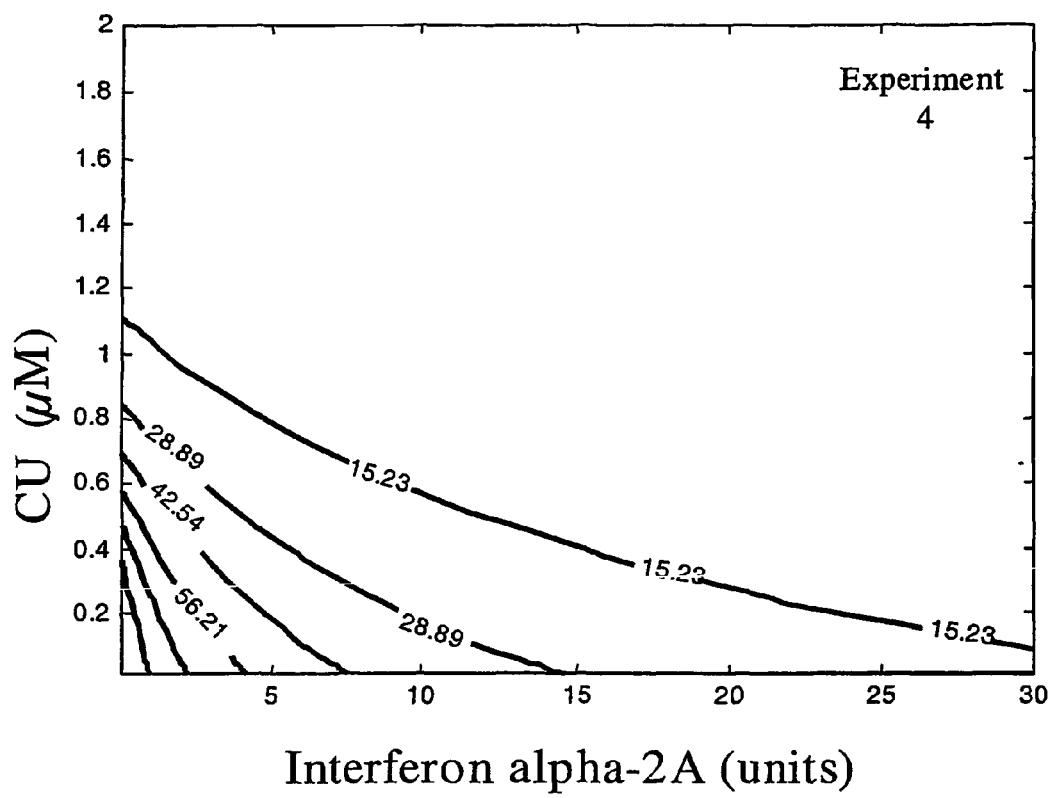
FIG. 7 shows the isobol calculations using the method of Greco et al., supra, for the combination of compound CU and interferon alpha-2A using 8 dilutions of each compound in Experiment 4.
Figure 8:
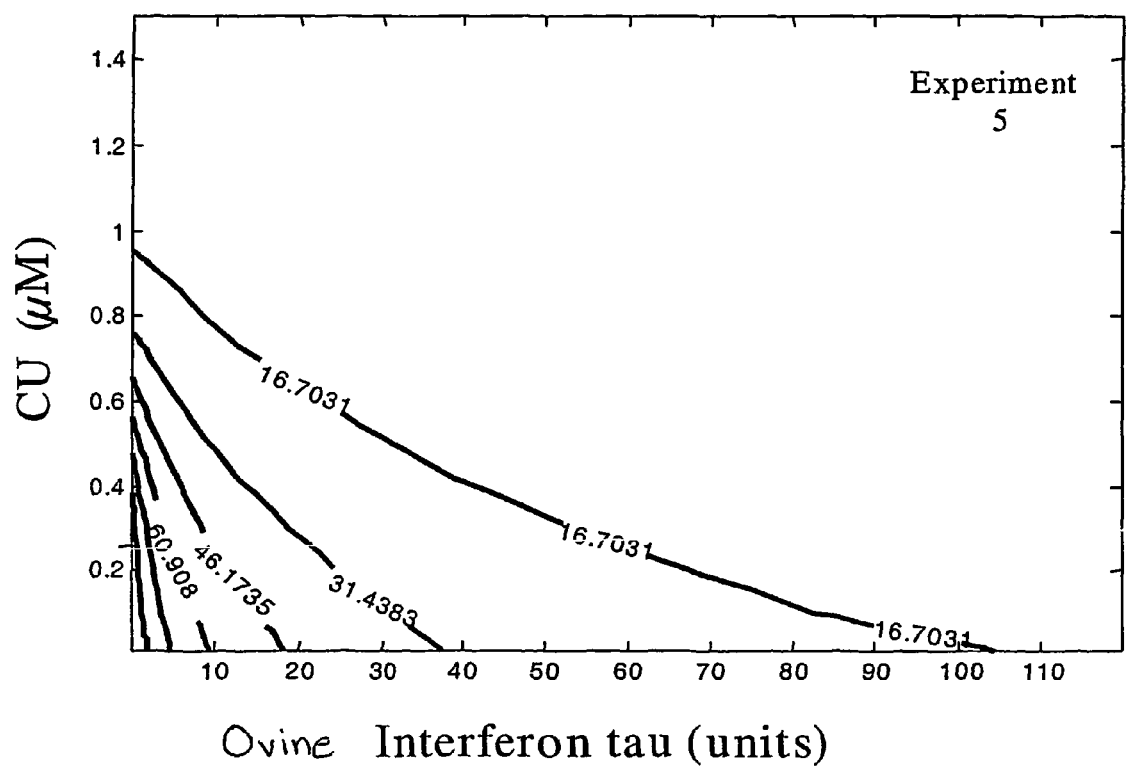
FIG. 8 shows the isobol calculations using the method of Greco et al., supra, for the combination of compound CU and ovine interferon tau using 8 dilutions of each compound in Experiment 5.
Figure 9:
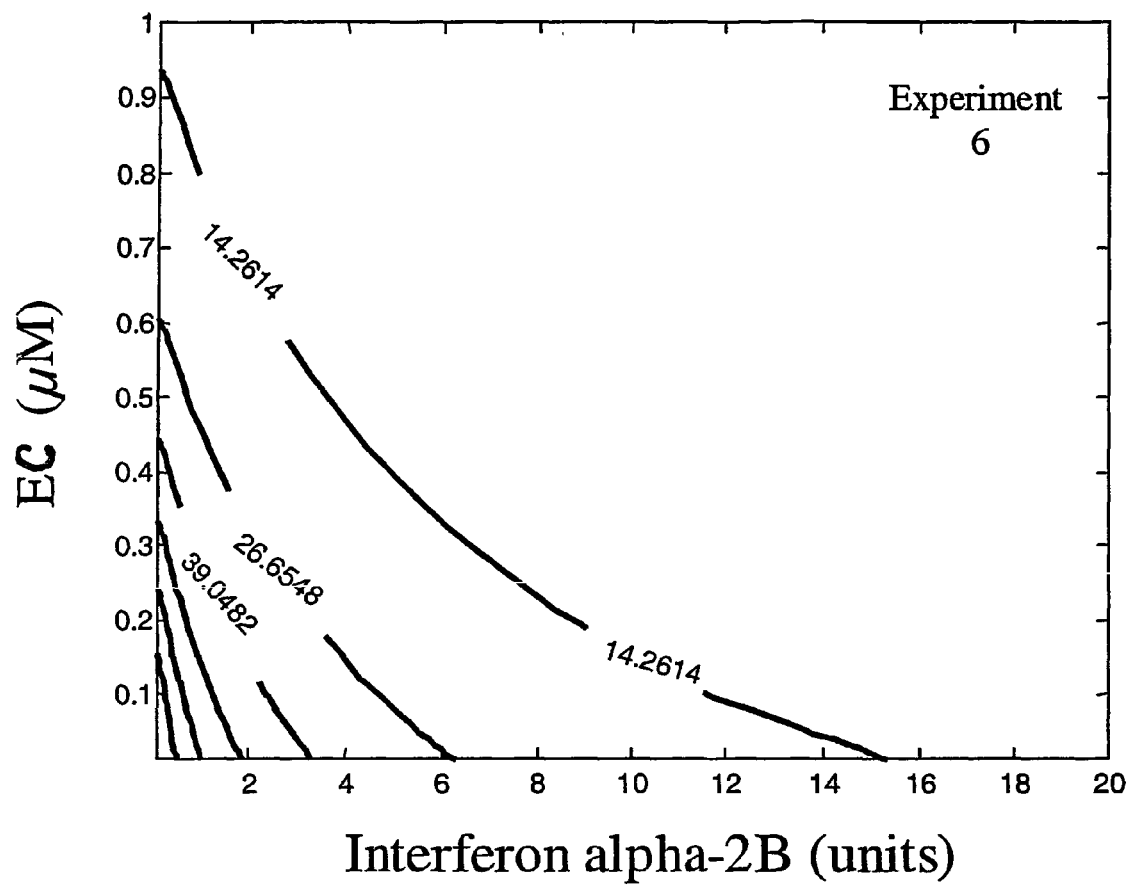
FIG. 9 shows the isobol calculations using the method of Greco et al., supra, for the combination of compound EC and interferon alpha-2B (Schering-Plough) using 8 dilutions of each compound in Experiment 6.
Figure 10:
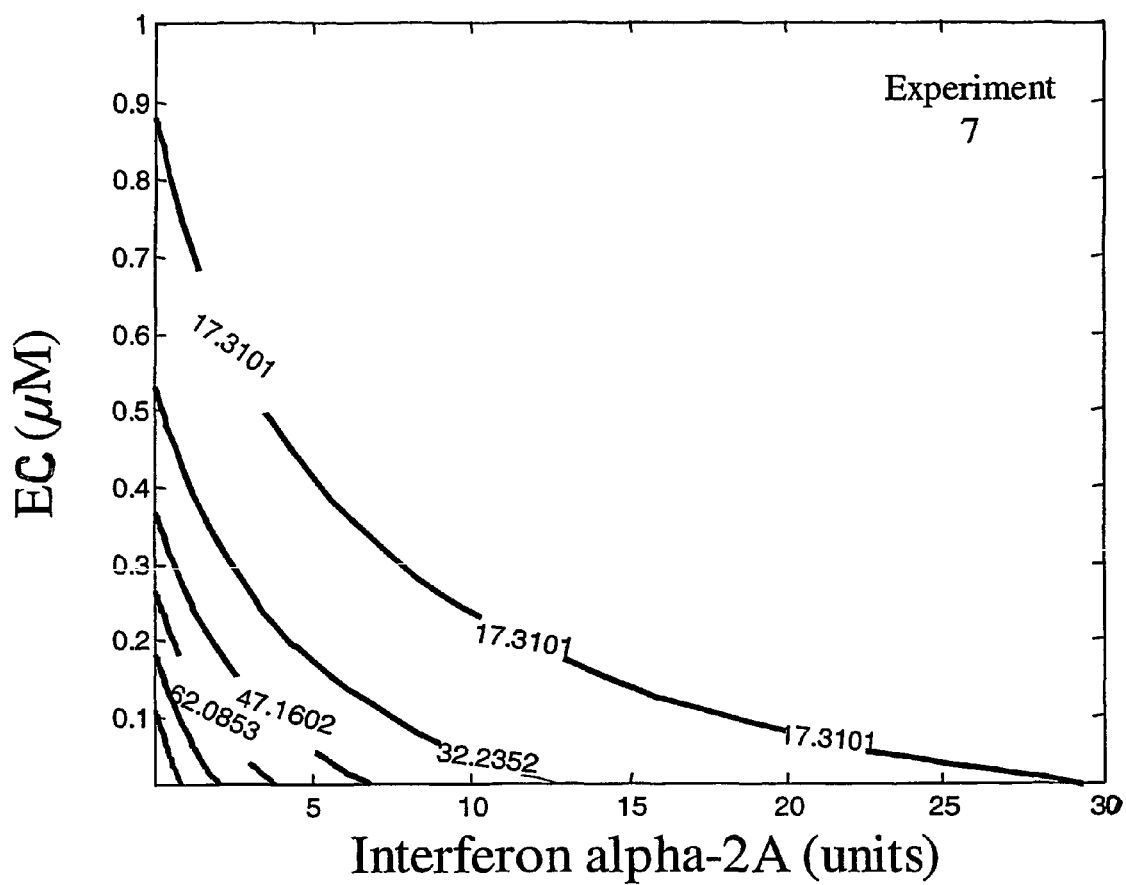
FIG. 10 shows the isobol calculations using the method of Greco et al., supra, for the combination of compound EC and interferon alpha-2A using 8 dilutions of each compound in Experiment 7.
Figure 11:
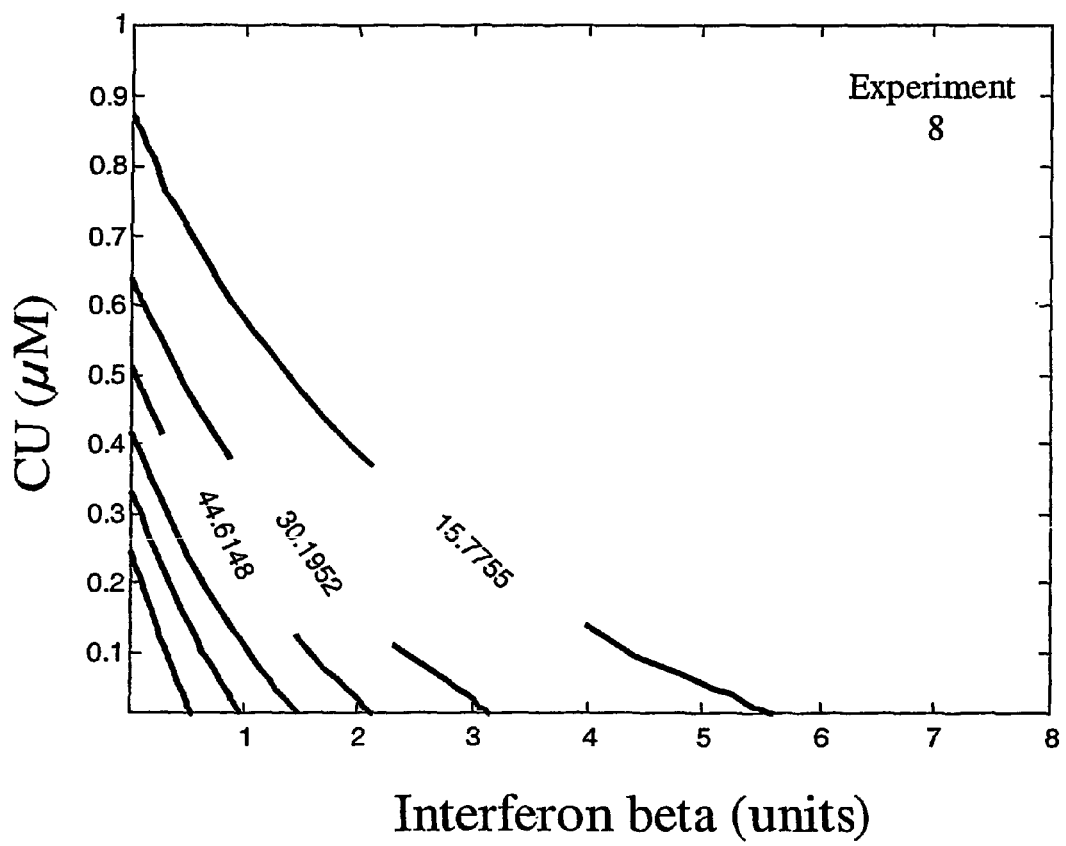
FIG. 11 shows the isobol calculations using the method of Greco et al., supra, for the combination of compound CU and interferon beta using 8 dilutions of each compound in Experiment 8.
Figure 12:
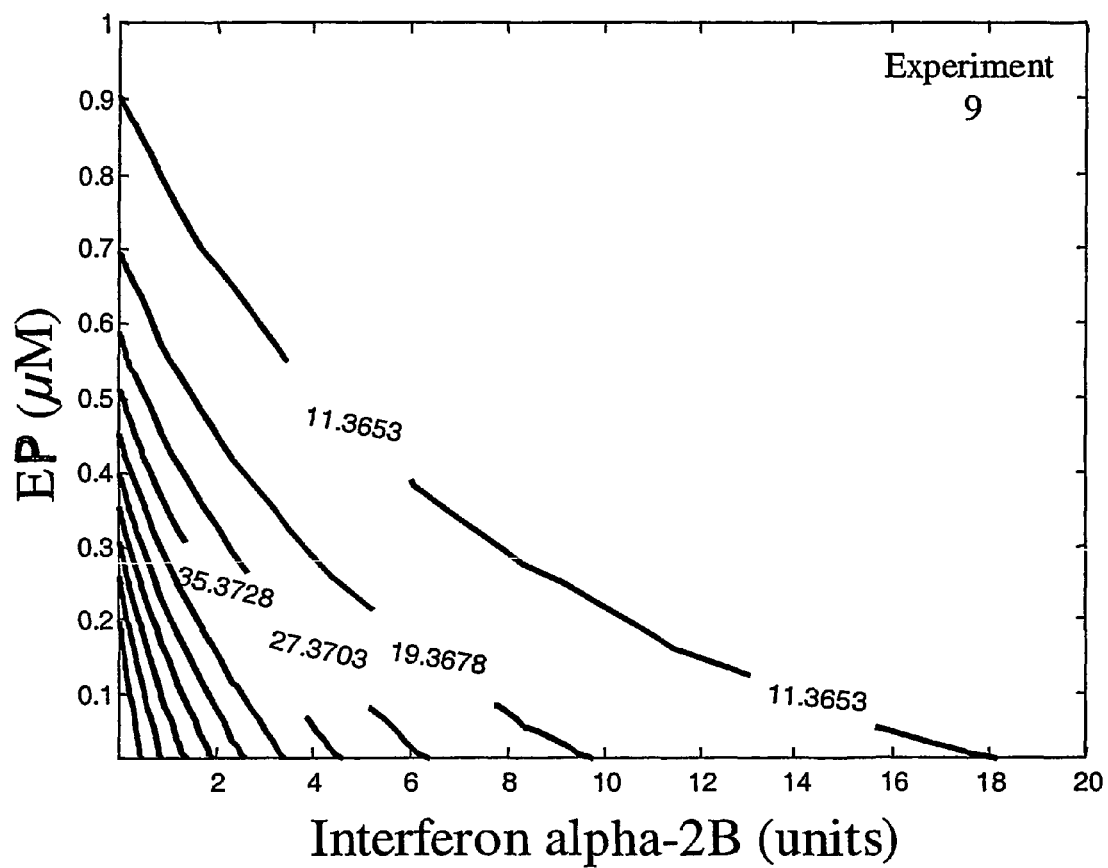
FIG. 12 shows the isobol calculations using the method of Greco et al., supra, for the combination of compound EP and interferon alpha-2B (Schering-Plough) using 8 dilutions of each compound in Experiment 9.
Figure 13:
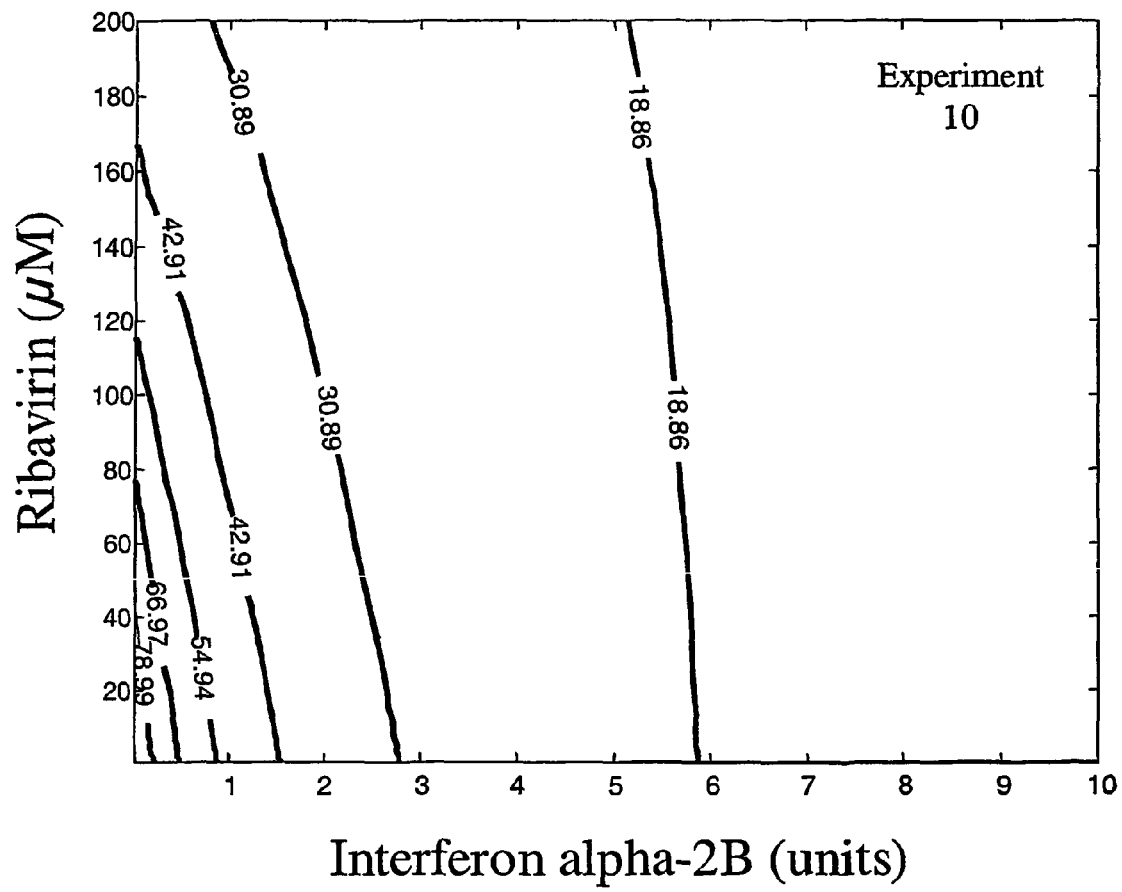
FIG. 13 shows the isobol calculations using the method of Greco et al., supra, for the combination of Ribavirin and interferon alpha-2B (Schering-Plough) using 8 dilutions of each compound in Experiment 10.

The foregoing data have been reanalyzed using the formal mathematical tools described above to determine if the relationship between HCV serine protease inhibitor CU and interferon alpha-2B is synergeistic, additive, or antagonistic. The reanalyzed data are shown numerically in Table 8, and graphically in FIG. 4.

Table 8 summarizes further results obtained in the Replicon Assay after treatment of replicon-containing cells for 48 hours with various HCV serine protease inhibitors of the present invention and several different interferons, individually or in combination. We point out that the standard deviation of values measured for inhibition of HCV replicon RNA in the Replicon Assay is ~20%. Compounds are tested over a broad concentration range and at lower compound concentrations that cause no significant inhibition of HCV replicon RNA concentration. Because of the ~20% standard deviation of the assay, some data points will generate negative numbers. Negative inhibition numbers indicate in a particular experiment there is on average more HCV replicon RNA molecules in the compound treated samples than in the mock treated samples.

TABLE 8

INHIBITION OF REPLICON RNA ACCUMULATION AFTER 48 HOUR TREATMENT WITH HCV SERINE PROTEASE INHIBITORS AND DIFFERENT INTERFERONS, INDIVIDUALLY OR IN COMBINATION

| EXPERIMENT 1 | | | | | | | |
|---|---|---|---|---|---|---|---|
| Compound | IFN alpha-2B (units) | | | | | | |
| CU (µM) | 30.00 | 6.00 | 1.20 | 0.24 | 0.048 | 0.0096 | 0.000 |
| 0.000 | 89% | 73% | 38% | 16% | 8% | 12% | 0% |
| 0.012 | 92% | 78% | 44% | 20% | 19% | 19% | 5% |
| 0.037 | 92% | 78% | 44% | 21% | 2% | 7% | 8% |
| 0.111 | 93% | 79% | 46% | 29% | 12% | 15% | 11% |
| 0.333 | 94% | 87% | 66% | 49% | 33% | 27% | 28% |
| 1.000 | 99% | 98% | 96% | 95% | 92% | 93% | 88% |
| 3.000 | 99% | 99% | 99% | 99% | 98% | 98% | 98% |

TABLE 8-continued

INHIBITION OF REPLICON RNA ACCUMULATION AFTER 48 HOUR
TREATMENT WITH HCV SERINE PROTEASE INHIBITORS AND DIFFERENT
INTERFERONS, INDIVIDUALLY OR IN COMBINATION

EXPERIMENT 2

| Compound | IFN alpha-2A (units) | | | | | | |
|---|---|---|---|---|---|---|---|
| CU (µM) | 30 | 6 | 1.2 | 0.24 | 0.048 | 0.0096 | 0 |
| 0 | 86% | 61% | 27% | 4% | −7% | 5% | 0% |
| 0.0123 | 87% | 66% | 17% | −23% | 8% | 8% | 10% |
| 0.37 | 85% | 62% | 13% | −2% | 0% | −1% | 1% |
| 0.1111 | 87% | 68% | 37% | 20% | −6% | 12% | 10% |
| 0.333 | 92% | 77% | 58% | 41% | 26% | 25% | 44% |
| 1 | 98% | 96% | 90% | 86% | 84% | 83% | 85% |
| 3 | 99% | 99% | 98% | 98% | 98% | 98% | 98% |

EXPERIMENT 3

| Interferon alpha-2B (units) | Compound CU (µM) | | | | | | | | |
|---|---|---|---|---|---|---|---|---|---|
| | 3 | 1.5 | 0.75 | 0.375 | 0.1875 | 0.0938 | 0.0469 | 0.0234 | 0 |
| 0 | 98% | 93% | 62% | 23% | 12% | −2% | −4% | −2% | 0 |
| 0.049 | 98% | 95% | 70% | 39% | 12% | 2% | 6% | 9% | 3% |
| 0.123 | 98% | 95% | 70% | 43% | 15% | 7% | 2% | 5% | 2% |
| 0.307 | 98% | 95% | 73% | 46% | 16% | 14% | 7% | 19% | −3% |
| 0.768 | 98% | 95% | 82% | 56% | 43% | 34% | 28% | 32% | 28% |
| 1.920 | 98% | 98% | 87% | 71% | 51% | 54% | 49% | 52% | 45% |
| 4.8 | 99% | 98% | 92% | 82% | 74% | 71% | 69% | 71% | 59% |
| 12.0 | 99% | 98% | 96% | 89% | 87% | 85% | 85% | 85% | 80% |
| 30.0 | 99% | 99% | 98% | 95% | 93% | 92% | 92% | 93% | 89% |

EXPERIMENT 4

| Interferon alpha-2A (units) | Compound CU (µM) | | | | | | | | |
|---|---|---|---|---|---|---|---|---|---|
| | 3 | 1.5 | 0.75 | 0.375 | 0.1875 | 0.0938 | 0.0469 | 0.0234 | 0 |
| 0 | 98% | 94% | 74% | 38% | 17% | 3% | −1% | 6% | 0% |
| 0.049 | 98% | 93% | 60% | 22% | 29% | 21% | −9% | −6% | 6% |
| 0.123 | 98% | 93% | 67% | 29% | 21% | 12% | 3% | 2% | −8% |
| 0.307 | 98% | 93% | 66% | 29% | 22% | 4% | −3% | −4% | 10% |
| 0.768 | 98% | 95% | 67% | 46% | 24% | 21% | 20% | 9% | 15% |
| 1.920 | 98% | 96% | 73% | 48% | 43% | 44% | 27% | 33% | 29% |
| 4.8 | 98% | 97% | 82% | 61% | 61% | 59% | 52% | 55% | 43% |
| 12.0 | 99% | 98% | 91% | 75% | 76% | 72% | 71% | 74% | 73% |
| 30.0 | 99% | 98% | 96% | 89% | 86% | 85% | 84% | 84% | 83% |

EXPERIMENT 5

| Ovine Interferon tau (units) | Compound CU (µM) | | | | | | | | |
|---|---|---|---|---|---|---|---|---|---|
| | 3 | 1.5 | 0.75 | 0.375 | 0.1875 | 0.0938 | 0.0469 | 0.0234 | 0 |
| 0.0 | 98% | 95% | 65% | 24% | −1% | −14% | −14% | −12% | 0 |
| 0.9375 | 97% | 95% | 72% | 41% | 17% | 11% | 12% | 6% | 17% |
| 1.875 | 97% | 95% | 71% | 40% | 31% | 18% | 18% | 11% | 4% |
| 3.75 | 98% | 96% | 75% | 44% | 38% | 25% | 34% | 18% | 17% |
| 7.5 | 98% | 96% | 82% | 61% | 42% | 37% | 25% | 26% | 36% |
| 15 | 98% | 97% | 84% | 64% | 59% | 61% | 56% | 51% | 53% |
| 30 | 98% | 98% | 90% | 79% | 72% | 68% | 65% | 68% | 68% |
| 60 | 98% | 98% | 93% | 87% | 80% | 80% | 74% | 77% | 82% |
| 120 | 98% | 98% | 95% | 92% | 86% | 87% | 86% | 86% | 87% |

EXPERIMENT 6

| Interferon-alpha 2B (units) | Compound EC (µM) | | | | | | | | |
|---|---|---|---|---|---|---|---|---|---|
| | 3 | 1.5 | 0.75 | 0.375 | 0.1875 | 0.0938 | 0.0469 | 0.0234 | 0 |
| 0 | 96% | 93% | 81% | 56% | 29% | 23% | 19% | 1% | 0 |
| 0.0492 | 96% | 92% | 80% | 60% | 31% | 15% | 19% | 29% | 6% |
| 0.1229 | 96% | 94% | 78% | 58% | 32% | 13% | 20% | 20% | 4% |

TABLE 8-continued

INHIBITION OF REPLICON RNA ACCUMULATION AFTER 48 HOUR
TREATMENT WITH HCV SERINE PROTEASE INHIBITORS AND DIFFERENT
INTERFERONS, INDIVIDUALLY OR IN COMBINATION

| 0.3072 | 97% | 95% | 82% | 60% | 38% | 32% | 34% | 42% | 23% |
| 0.768  | 97% | 95% | 87% | 66% | 43% | 41% | 46% | 43% | 25% |
| 1.92   | 98% | 97% | 90% | 73% | 62% | 51% | 54% | 58% | 47% |
| 4.8    | 98% | 97% | 94% | 87% | 76% | 73% | 78% | 76% | 69% |
| 12.0   | 98% | 98% | 96% | 92% | 86% | 86% | 86% | 85% | 84% |
| 30.0   | 98% | 98% | 96% | 96% | 93% | 92% | 92% | 95% | 91% |

EXPERIMENT 7

| Interferon-alpha-2A | Compound EC (μM) | | | | | | | |
|---|---|---|---|---|---|---|---|---|
| (units) | 3.0 | 1.5 | 0.75 | 0.375 | 0.1875 | 0.0938 | 0.0469 | 0.02344 | 0 |
| 0      | 96% | 92% | 81% | 47% | 28% | 17% | −1%  | −8%  | 0    |
| 0.0492 | 96% | 93% | 78% | 58% | 21% | 8%  | −12% | 10%  | −17% |
| 0.1229 | 95% | 93% | 79% | 64% | 14% | 5%  | 14%  | 7%   | −22% |
| 0.3072 | 95% | 91% | 80% | 64% | 22% | 15% | 5%   | 2%   | −5%  |
| 0.768  | 96% | 95% | 81% | 64% | 34% | 21% | 19%  | 20%  | 4%   |
| 1.92   | 96% | 95% | 88% | 78% | 44% | 41% | 19%  | 33%  | 21%  |
| 4.8    | 97% | 95% | 91% | 85% | 60% | 58% | 60%  | 53%  | 49%  |
| 12.0   | 97% | 97% | 95% | 91% | 77% | 72% | 76%  | 70%  | 71%  |
| 30.0   | 98% | 98% | 97% | 94% | 91% | 86% | 85%  | 85%  | 84%  |

EXPERIMENT 8

| Interferon-beta (units) | Compound CU (μM) | | | | | | | |
|---|---|---|---|---|---|---|---|---|
| | 3.0 | 1.5 | 0.75 | 0.375 | 0.1875 | 0.0938 | 0.0469 | 0.02344 | 0 |
| 0      | 97% | 95% | 77% | 34% | 16% | 6%  | −7%  | 0%  | 0   |
| 0.2344 | 98% | 97% | 83% | 49% | 31% | 19% | −21% | −7% | 1%  |
| 0.4688 | 98% | 96% | 84% | 56% | 39% | 27% | 10%  | −3% | 21% |
| 0.9375 | 98% | 97% | 91% | 73% | 54% | 42% | 31%  | 15% | 30% |
| 1.875  | 98% | 98% | 95% | 80% | 65% | 58% | 65%  | 60% | 60% |
| 3.75   | 98% | 98% | 97% | 92% | 86% | 81% | 77%  | 73% | 79% |
| 7.5    | 99% | 98% | 98% | 96% | 93% | 93% | 93%  | 90% | 92% |
| 15.0   | 99% | 99% | 99% | 97% | 97% | 96% | 97%  | 95% | 96% |
| 30.0   | 99% | 99% | 99% | 99% | 98% | 99% | 98%  | 98% | 97% |

EXPERIMENT 9

| Interferon-alpha-2B | Compound EP (μM) | | | | | | | |
|---|---|---|---|---|---|---|---|---|
| (units) | 8 | 4 | 2 | 1 | 0.5 | 0.25 | 0.125 | 0.0625 | 0 |
| 0      | 94% | 96% | 96% | 92% | 64% | 36% | 23% | 8%  | 0   |
| 0.0492 | 95% | 96% | 96% | 91% | 67% | 25% | 28% | 8%  | 3%  |
| 0.1229 | 95% | 97% | 96% | 91% | 65% | 44% | 4%  | 11% | 4%  |
| 0.3072 | 95% | 97% | 96% | 91% | 71% | 46% | 20% | 8%  | 20% |
| 0.7680 | 96% | 97% | 97% | 93% | 75% | 49% | 36% | 24% | 24% |
| 1.92   | 96% | 97% | 97% | 94% | 82% | 67% | 49% | 52% | 54% |
| 4.8    | 96% | 98% | 97% | 96% | 90% | 79% | 75% | 75% | 70% |
| 12     | 97% | 98% | 98% | 97% | 94% | 89% | 89% | 87% | 83% |
| 30     | 97% | 98% | 98% | 98% | 96% | 94% | 94% | 95% | 92% |

EXPERIMENT 10

| Interferon-alpha-2B | Ribavirin (μM) | | | | | | | |
|---|---|---|---|---|---|---|---|---|
| (units) | 200 | 80 | 32 | 12.8 | 5.12 | 2.048 | 0.8192 | 0.3277 | 0 |
| 0      | 85% | 62% | 43% | 3%  | −8% | −17% | −22% | −6% | 0   |
| 0.0492 | 87% | 66% | 48% | 44% | 11% | −4%  | −10% | 11% | −7% |
| 0.1229 | 84% | 64% | 53% | 40% | 26% | −12% | −5%  | 11% | −9% |
| 0.3072 | 86% | 70% | 62% | 44% | 28% | 1%   | 6%   | 14% | 7%  |
| 0.7680 | 90% | 80% | 72% | 65% | 38% | 30%  | 28%  | 44% | 29% |
| 1.92   | 93% | 85% | 77% | 76% | 61% | 57%  | 58%  | 50% | 46% |
| 4.8    | 96% | 92% | 87% | 83% | 82% | 74%  | 71%  | 77% | 72% |
| 12     | 97% | 95% | 93% | 91% | 90% | 89%  | 90%  | 89% | 85% |
| 30     | 98% | 97% | 96% | 95% | 94% | 94%  | 93%  | 95% | 94% |

As shown in FIGS. 4-13, which graphically depict the data in Table 8 plotted using the above-described mathematical method for measuring synergy, the Isobol curves for all combinations of HCV serine proteae inhibitors and interferons tested are concave-up, indicating that the antiviral effect of the treatments in the Replicon Assay is synergistic. These results are tabulated in Table 9, which shows relative levels of synergy for combination treatment and $IC_{50}$ values for antiviral compounds used individually. The key elements in Table 9 are the α values, and the p-values for the determinations. The α term is a measure of the maximum inflection of the Isobols for each combination treatment. An α value of zero indicates additivity, a negative value indicates antagonism, and as is the case in the combination treatments with the HCV serine protease inhibitors and interferons shown above, a value greater than one indicates synergy. The larger the α parameter, the greater the synergy. As shown in Table 9 for the combinations of HCV serine protease inhibitors and interferons, even ignoring significance levels in each experiment, a t test based on the 9 experiments for the average alpha value being 0 (no interaction) has a p-value of 0.00014, indicating that the results are highly significant.

The calculation of synergy based on the method of Greco Rustom ((1990) Application of a New Approach for the Quantitation of Drug Synergism to the Combination of cis-Diamminedichloroplatinum and 1-β-D-Arabinofuranosylcytosine, *Cancer Research,* 50, 5318-5327) used in this analysis is an ideal tool for evaluation of the kind of experimental data that can be generated using the HCV Replicon Assay. There are other methods that are applied to studies of antiviral compounds such as Pritchard and Shipman (Prichard, M. N., and Shipman, C. Jr., (1990) "A three-dimensional model to analyze drug-drug interactions (review)," Antiviral Res. 14: 181-206). Application of their synergy calculation method to the data shown in Table 8 also indicates combination treatment of the replicon cells with an HCV serine protease inhibitor and interferon will result in a synergistic inhibition of HCV replicon RNA accumulation (data not shown).

further emphasizes the significance of the combination treatments disclosed herein employing the present HCV serine protease inhibitors in combination with interferons in that these treatments clearly produce synergy, while the standard combination therapy in use for HCV (interferon alpha-2B in combination with Ribavirin) is not synergistic in the Replicon Assay.

The foregoing comparison of combination treatments employing the present HCV serine protease inhibitors plus interferons versus Ribavirin plus interferon in the Replicon Assay clearly indicates that the former are synergistic, while the latter is not. The experimental results obtained using the Replicon Assay indicate that a much lower dose of interferon would be efficacious if the interferon is used in combination with a HCV serine protease inhibitor than is needed when interferon alpha-2B is used in combination with Ribavirin. The Replicon Assay is a useful model system in which to test potential anti-HCV compounds, and is currently widely relied upon as an effective predictor of compound anti-HCV activity. Note, for example, Blight et al. (2000) Efficient Initiation of HCV RNA Replication in Cell Culture. *Science* 8; 290:1972-1974, and Chung et al. (2001) Hepatitis C virus replication is directly inhibited by IFN-α in a full-length binary expression system. *Proc. Nat. Acad. Sci. U.S.A.* 98(17):9847-52. Ribavirin alone is marginally effective in reducing the accumulation of HCV replicon RNA in the Replicon Assay (Table 8, Experiment 10 and last line of Table 9). This result is in apparent conflict with in vivo studies where, when used by itself, Ribavirin has no significant therapeutic value for the treatment of HCV. In contrast, in the Replicon Assay, correcting for cytotoxicity as discussed below, Ribavirin has an $IC_{50}$ of 145 μM. This result can be explained by recognizing that the Replicon Assay permits evaluation of high Ribavirin concentrations that would not be possible in human therapy due to in vivo cytotoxicity (Chutaputti A. (2000) Adverse effects and other safety aspects of the hepatitis C antivirals. *Journal of Gastroenterology and Hepatology.* 15 Suppl:E156-63).

TABLE 9

RELATIVE LEVELS OF SYNERGY FOR COMBINATION TREATMENT AND $IC_{50}$ VALUES FOR ANTIVIRAL COMPOUNDS USED INDIVIDUALLY

| | HCV Serine Protease Inhibitor (HSPI) | Interferon | $IC_{50}$ INF (units) | $IC_{50}$ HSPI (μM) | α (SE)[1] | P-value α > 0 |
|---|---|---|---|---|---|---|
| Experiment 1 | Compound CU | IFN alpha-2B | 2.05 | 0.469 | 0.477 (0.09) | <0.0001 |
| Experiment 2 | Compound CU | IFN alpha-2A | 3.72 | 0.446 | 0.770 (0.12) | <0.0001 |
| Experiment 3 | Compound CU | IFN alpha-2B | 2.36 | 0.587 | 0.730 (0.08) | <0.0001 |
| Experiment 4 | Compound CU | IFN alpha-2A | 5.67 | 0.633 | 0.438 (0.08) | <0.0001 |
| Experiment 5 | Compound CU | IFN tau | 13.22 | 0.605 | 0.328 (0.07) | <0.0001 |
| Experiment 6 | Compound EC | IFN alpha-2B | 2.53 | 0.384 | 0.516 (0.10) | <0.0001 |
| Experiment 7 | Compound EC | IFN alpha-2A | 5.50 | 0.312 | 1.24 (0.20) | <0.0001 |
| Experiment 8 | Compound CU | IFN beta | 1.82 | 0.466 | 0.551 (0.09) | <0.0001 |
| Experiment 9 | Compound EP | IFN alpha-2B | 3.06 | 0.426 | 0.490 (0.12) | <0.0001 |
| Experiment 10 | Ribavirin | IFN alpha-2B | 1.22 | 145 | −0.24 (0.067) | 0.0004 |

[1](SE) Standard Error

Figure 14:
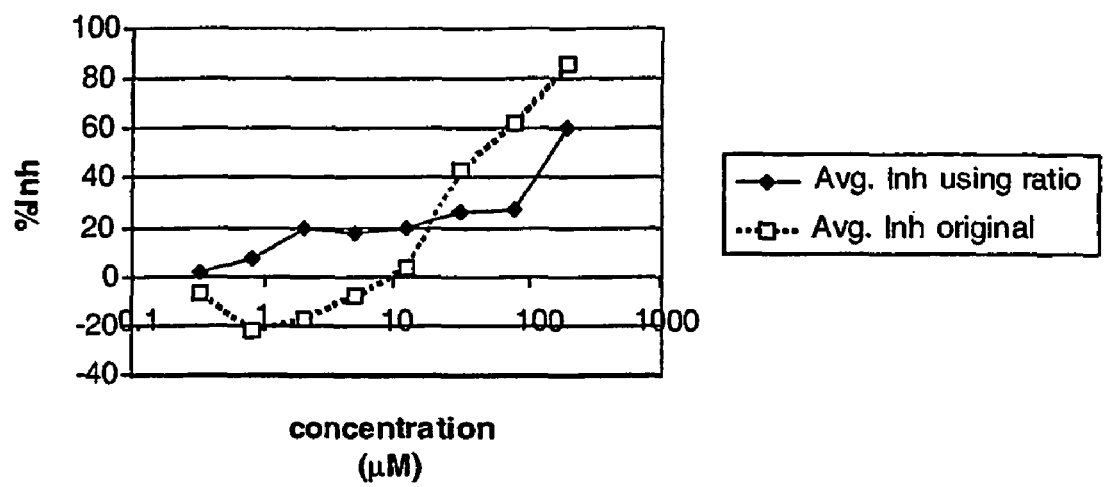
FIG. 14 shows inhibition of HCV replicon RNA accumulation caused by treatment of replicon cells with either (A)
Figure 14:
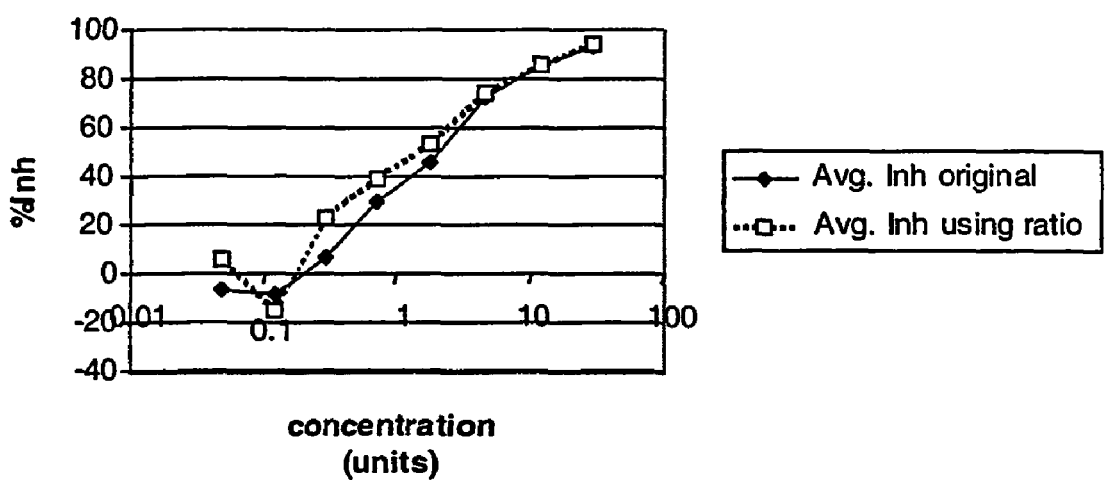

Another measure for evaluating the synergistic nature of anti-HCV drug treatment using the present HCV serine protease inhibitors and interferons is to use the same methods described above to evaluate the current standard combination therapy for HCV, i.e., interferon alpha-2B in combination with Ribavirin in the Replicon Assay. The last line of Table 9 shows that the α parameter for a mixture of interferon alpha-2B and Ribavirin is a negative number, indicating that there is a small amount of antagonism between these two drugs. This This evaluation necessarily requires assessment of the cytotoxicity of Ribavirin. Such toxicity occurs in patients and in cellular assays (Shiffman M. L., Verbeke S. B., Kimball P. M. (2000) Alpha interferon combined with ribavirin potentiates proliferative suppression but not cytokine production in mitogenically stimulated human lymphocytes. *Antiviral Research.* 48(2):91-9). In the experiments disclosed herein, Ribavirin cytotoxicity in the Replicon Assay is observed and measured in two ways. In both the XTT metabolic assay to determine replicon cell viability (Roehm N. W., Rodgers G. H., Hatfield S. M., Glasebrook A. L. (1991) An improved colorimetric assay for cell proliferation and viability utilizing the tetrazolium salt XTT. *Journal of Immunol. Methods.* 142 (2):257-65) and in the TaqMan® quantitiative RT-PCR assay that measures glyceraldehyde-3-phosphate dehydrogenase (GAPDH) mRNA levels in treated versus untreated cells in the Replicon Assay (Drink N., Szamel M., Young A. R., Wittern K. P., Bergemann J. (2000) Comparative quantification of IL-1beta, IL-10, IL-10r, TNFalpha and IL-7 mRNA levels in UV-irradiated human skin in vivo. *Inflammation Research.* 49(6):290-6), significant Ribavirin-induced cytotoxicity is observed, but is corrected for as follows. It is assumed that the level of GAPDH mRNA, which is a constitutively expressed housekeeping gene, is the same in all viable cells. It is known from measurements of GAPDH mRNA levels in cells treated with the transcription inhibitor actinomycin D that the half life of GAPDH mRNA is only a few hours (data not shown). Thus, it is postulated, as done by others using TaqMan® technology to determine the levels of particular mRNAs in human cells, that GAPDH mRNA levels are proportional to viable cell numbers (VCN) in any given sample, with the relationship of $VCN=2^{(40-Ct_{GAPDH\,mRNA})}$. The VCN is computed for each of the Replicon Assay sample wells, and then we divide the HCV Replicon RNA copy number for a specific well by the VCN for that well. Once computed, this ratio is used instead of the HCV copy number to compute inhibition ("Avg. Inh using ratio"; FIG. 14.A). Without correcting the Replicon Assay data for this cytotoxicity, such cytotoxicity is read as false positive inhibition of HCV RNA replicon accumulation. In the Replicon Assay, it is assumed that the measured inhibition of HCV RNA replicon accumulation is the sum of the actual inhibition of HCV RNA replicon accumulation and the apparent inhibition of HCV RNA replicon accumulation due to cytotoxicity. It is furthermore assumed that, based on the close correlation of the XTT and TaqMan® GAPDH mRNA measures of cytotoxicity, the inhibition of accumulation of GAPDH mRNA caused by compounds tested in the Replicon Assay is a reliable measure of apparent inhibition of HCV RNA replicon accumulation due to cytotoxicity. Thus, the true anti-HCV activity of a compound in the Replicon Assay corrected for general cytotoxicity can be estimated by dividing the number of HCV replicon RNA molecules measured in each sample by the VCN, thus normalizing to the number of viable cells in each sample. Using this method, FIG. 14.A shows an estimate of true Ribavirin anti-HCV activity in the Replicon Assay ("Avg. Inh using ratio"). The estimate of the $IC_{50}$ for Ribavirin is best calculated using this method. In FIG. 14.A, "Avg. Inh original" shows the uncorrected $IC_{50}$ for Ribavirin, which is approximately 80 μM, whereas the corrected $IC_{50}$ value calculated from the "Avg. Inh using ratio" curve is approximately 145 μM. Note that the difference between corrected and measured inhibition of HCV RNA replicon accumulation as a result of interferon alpha-2B treatment (FIG. 14.B) is insignificant in view of the ~20% % CV of the Replicon Assay. Like interferon alpha-2B, the HCV serine protease inhibitors tested in the present example exhibit no significant cytotoxicity at the concentrations employed. This is determined using XTT assays, in which the $TC_{50}$ values for the various compounds are: CU=64.7 μM, EP>10 μM, and EC>50 μM. These $TC_{50}$ values are 20-140 fold greater than the $IC_{50}$ values shown in Table 9. Thus, cytotoxicity of these compounds has no significant effect on HCV RNA accumulation in the Replicon Assay within the precision of the assay because such cytotoxicity occurs only at HCV serine protease inhibitor concentrations significantly greater than those tested in the Replicon Assay.

Conclusions Regarding the Efficacy of HCV Serine Protease Inhibitors and Interferons, Individually and in Combination The anti-HCV activities of the present HCV serine protease inhibitors and various interferons when used alone in the HCV Replicon Assay are shown in the columns and lines of the individual experiments making up Table 8 that employ only one antiviral agent. Table 9 lists the $IC_{50}$ values measured for each antiviral compound when tested alone. The foregoing results, derived via use of the in vitro Replicon Assay, also demonstrate that combination treatment of replicon cells with HCV serine protease inhibitors of the present invention and various interferons yields synergistic antiviral effects. It is fully expected that these effects will translate into in vivo effectiveness.

Combination therapy employing HCV serine protease inhibitors of the present invention possesses several major advantages over single drug therapy. First, by making treatment possible with lower doses of the individual drugs than would be possible if used alone, one would expect a reduction in toxicity and side effects associated with treatment. This is especially important in the case of interferon therapy, where the side effects are severe, and have been shown to be proportional to the dose administered to patients. The foregoing data indicate that a dose of HCV serine protease inhibitor such as CU at the $IC_{95}$ level could be combined with a dose of interferon alpha, for example at the $IC_{50}$ level, and the result would be much more effective therapy than could be achieved with the HCV serine protease inhibitor alone without the adverse side effects caused by high doses of interferon alpha. A second major benefit of combination therapy is that because the two drugs act independently, there is less chance of development of mutant HCV strains that resist treatment. Development of resistance is a major concern with RNA viruses like HCV. Because of their high rate of mutation, such viruses can rapidly adapt to environmental stresses. A third benefit of combination therapy may be reduced cost, due to the need for lower amounts of therapeutic agents required for effective treatment.

Additional immunomodulators that can be employed in the methods disclosed herein include, for example, alpha interferon 2A, consensus interferon, tau interferon, interferon+ Ribavirin (Rebatron), pegylated interferon, and promoters of interferon gene expression. It is fully anticipated that the anti-HCV activity of these compounds will be improved when used in combination with HCV serine protease inhibitors such as those disclosed herein. As interferons are known to be active in vivo and in the Replicon Assay, it is expected that the present HCV serine protease inhibitors will also be active in vivo, and more importantly, be capable of eliciting synergistic activity when used in combination with interferons, immune system stimulators thereof, or other compounds having HCV antiviral activity that act by a mechanism other than inhibition of the HCV serine protease.

The best current therapy for HCV employs interferon alpha and the nucleoside analog Ribavirin. This treatment is only marginally effective, and results in significant side effects that diminish patient compliance (Chronic Hepatitis C: Current Disease Management, U.S. Department of Health and Human Services, National Institutes of Health, 1999). Additionally, in -transplant patients, it is not clear the Ribavirin-interferon combination works, and may in fact be worse than interferon alone (Chronic Hepatitis C: Current Disease Management, U.S. Department of Health and Human Services, National Institutes of Health, 1999).

The results presented above demonstrate a synergistic combination effect when interferons are used with a new class of HCV antivirals, the serine protease inhibitors of the present invention. We fully expect that the in vitro results disclosed herein will lead to more effective treatment of HCV patients than is currently possible using interferon alone. Sub-therapeutic doses of interferon could mobilize the patient's immune system to better fight the virus, and the serine protease inhibitor could attack the virus directly, dealing the virus a two-pronged attack via different mechanisms of action. Treatment of HCV infection could thus be achieved at reduced cost to the patient in terms of both diminished side effects and lower payments for necessary pharmaceutical agents as less of both drugs would be needed for effective HCV antiviral therapy.

The present invention may be embodied in other specific forms without departing from the spirit or essential attributes thereof.

What is claimed is:

1. A compound of the formula

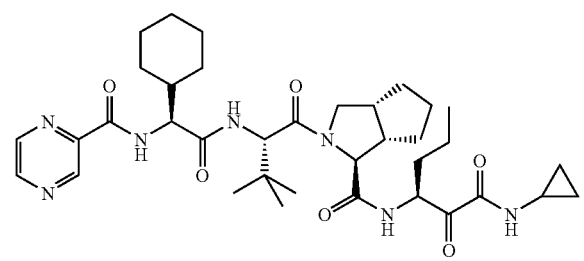

or a pharmaceutically acceptable salt or prodrug thereof.

2. A compound of the formula

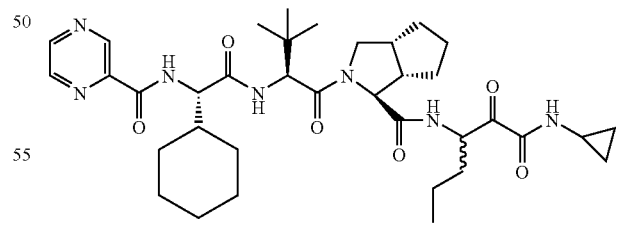

or a pharmaceutically acceptable salt or prodrug thereof.

3. A pharmaceutical composition comprising a pharmaceutically acceptable amount of the compound of claim 1 and a pharmaceutically acceptable carrier.

4. A pharmaceutical composition comprising a pharmaceutically acceptable amount of the compound of claim 2 and a pharmaceutically acceptable carrier.

5. A compound of the formula
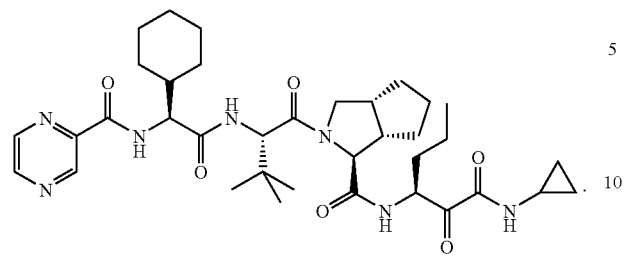
6. A pharmaceutically acceptable salt of a compound of the formula
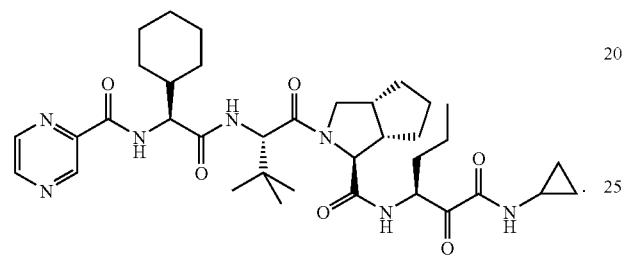
7. A compound of the formula
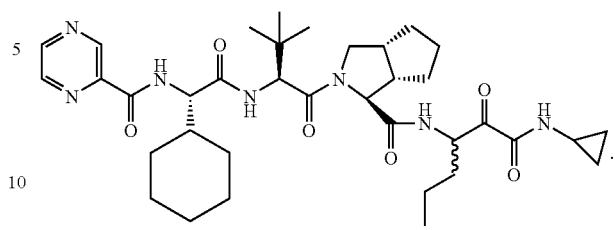
8. A pharmaceutically acceptable salt of a compound of the formula
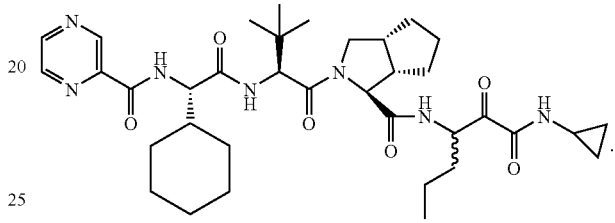
* * * * *

SEQUENCE LISTING

<160> NUMBER OF SEQ ID NOS: 7

<210> SEQ ID NO 1
<211> LENGTH: 900
<212> TYPE: DNA
<213> ORGANISM: Unknown
<220> FEATURE:
<223> OTHER INFORMATION: HCV Replicon RNA TaqMan probe and primers

<400> SEQUENCE: 1

```
gtgcttgcga gtgccccggg aggtctcgta gaccgtgcac catgagcacg aatcctaaac      60
ctcaaagaaa aaccaaacgt aacaccaacg ggcgcgccat gattgaacaa gatggattgc     120
acgcaggttc tccggccgct tgggtggaga ggctattcgg ctatgactgg gcacaacaga     180
caatcggctg ctctgatgcc gccgtgttcc ggctgtcagc gcaggggcgc ccggttcttt     240
ttgtcaagac cgacctgtcc ggtgccctga atgaactgca ggacgaggca gcgcggctat     300
cgtggctggc cacgacgggc gttccttgcg cagctgtgct cgacgttgtc actgaagcgg     360
gaagggactg gctgctattg ggcgaagtgc cggggcagga tctcctgtca tctcaccttg     420
ctcctgccga gaaagtatcc atcatggctg atgcaatgcg gcggctgcat acgcttgatc     480
cggctacctg cccattcgac caccaagcga acatcgcat cgagcgagca cgtactcgga     540
tggaagccgg tcttgtcgat caggatgatc tggacgaaga gcatcagggg ctcgcgccag     600
ccgaactgtt cgccaggctc aaggcgcgca tgcccgacgg cgaggatctc gtcgtgaccc     660
atggcgatgc ctgcttgccg aatatcatgg tggaaaatgg ccgcttttct ggattcatcg     720
actgtggccg gctgggtgtg gcggaccgct atcaggacat agcgttggct acccgtgata     780
ttgctgaaga gcttggcggc gaatgggctg accgcttcct cgtgctttac ggtatcgccg     840
ctcccgattc gcagcgcatc gccttctatc gccttcttga cgagttcttc tgagtttaaa     900
```

<210> SEQ ID NO 2
<211> LENGTH: 20
<212> TYPE: DNA
<213> ORGANISM: Unknown
<220> FEATURE:
<223> OTHER INFORMATION: HCV Replicon RNA TaqMan probe and primers

<400> SEQUENCE: 2

```
ctgtggccgg ctgggtgtgg                                                   20
```

<210> SEQ ID NO 3
<211> LENGTH: 23
<212> TYPE: DNA
<213> ORGANISM: Unknown
<220> FEATURE:
<223> OTHER INFORMATION: HCV Replicon RNA TaqMan probe and primers

```
-continued

<400> SEQUENCE: 3
ccctcgtcca cgtggcatct cga                                              23

<210> SEQ ID NO 4
<211> LENGTH: 20
<212> TYPE: DNA
<213> ORGANISM: Unknown
<220> FEATURE:
<223> OTHER INFORMATION: HCV Replicon RNA TaqMan probe and primers

<400> SEQUENCE: 4
ccgcttttct ggattcatcg                                                  20

<210> SEQ ID NO 5
<211> LENGTH: 15
<212> TYPE: DNA
<213> ORGANISM: Unknown
<220> FEATURE:
<223> OTHER INFORMATION: HCV Replicon RNA TaqMan probe and primers

<400> SEQUENCE: 5
cccattcgcc gccaa                                                       15

<210> SEQ ID NO 6
<211> LENGTH: 22
<212> TYPE: DNA
<213> ORGANISM: Unknown
<220> FEATURE:
<223> OTHER INFORMATION: HCV Replicon RNA TaqMan probe and primers

<400> SEQUENCE: 6
cagggtagtc gtcagtggtt cg                                               22

<210> SEQ ID NO 7
<211> LENGTH: 20
<212> TYPE: DNA
<213> ORGANISM: Unknown
<220> FEATURE:
<223> OTHER INFORMATION: HCV Replicon RNA TaqMan probe and primers

<400> SEQUENCE: 7
ggcctctgca gcaccctatc                                                  20
```